United States Patent
Li et al.

(10) Patent No.: US 11,739,076 B2
(45) Date of Patent: Aug. 29, 2023

(54) COMPOUND OR ITS SALT THEREOF TARGETING FIBROBLAST ACTIVATION PROTEIN, ITS PREPARATION METHODS AND ITS USES THEREOF

(71) Applicant: Institute of Nuclear Energy Research Atomic Energy Council, R.O.C., Taoyuan (TW)

(72) Inventors: Ming-Hsin Li, Taoyuan (TW); Sheng-Nan Lo, Taoyuan (TW); Shih-Ying Lee, Taoyuan (TW); Su-Jung Chen, Taoyuan (TW); Shih-Wei Lo, Taoyuan (TW); Wei-Lin Lo, Taoyuan (TW); Ming-Wei Chen, Taoyuan (TW)

(73) Assignee: INSTITUTE OF NUCLEAR ENERGY RESEARCH ATOMIC ENERGY COUNCIL, R.O.C., Taoyuan (TW)

( * ) Notice: Subject to any disclaimer, the term of this patent is extended or adjusted under 35 U.S.C. 154(b) by 0 days.

(21) Appl. No.: 17/690,390

(22) Filed: Mar. 9, 2022

(65) Prior Publication Data

US 2023/0159495 A1    May 25, 2023

(30) Foreign Application Priority Data

Oct. 28, 2021   (TW) .................. 11014002.2

(51) Int. Cl.
  *C07D 401/14*   (2006.01)
(52) U.S. Cl.
  CPC ........ *C07D 401/14* (2013.01); *C07B 2200/07* (2013.01)

(58) Field of Classification Search
  None
  See application file for complete search history.

(56) References Cited

U.S. PATENT DOCUMENTS

2020/0330624 A1   10/2020   Yang et al.

FOREIGN PATENT DOCUMENTS

| CN | 111991570 A | 11/2020 |
| CN | 112409414 A | 2/2021 |
| EP | 2804859 B1 | 6/2019 |
| WO | 2019154859 A1 | 8/2019 |
| WO | 2019154886 A1 | 8/2019 |

OTHER PUBLICATIONS

Lindner et al.; "Development of Quinoline-Based Theranostic Ligands for the Targeting of Fibroblast Activation Protein"; Apr. 6, 2018; The Journal of Nuclear Medicine; Germany.
Loktev et al.; "A Tumor-Imaging Method Targeting Cancer-Associated Fibroblasts"; Apr. 6, 2018; The Journal of Nuclear Medicine; Germany.
Loktev et al.; Development of Fibroblast Activation Protein-Targeted Radiotracers with Improved Tumor Retention; Mar. 8, 2019; The Journal of Nuclear Medicine; Germany.

*Primary Examiner* — Samantha L Shterengarts
(74) *Attorney, Agent, or Firm* — Locke Lord LLP; Tim Tingkang Xia, Esq.

(57) ABSTRACT

The present disclosure relates to a compound or its salt thereof targeting fibroblast activation protein, its preparation methods and uses, especially the compound represented by formula (I) D-R1-R2-A-R' or its salt thereof, and its preparation methods and its uses.

13 Claims, 13 Drawing Sheets

|   | retention time (min) | peak area (μAU*min) | peak height (μAU) | percentage of total peak area (%) |
|---|---|---|---|---|
| 1 | 8.170 | 27183 | 3760 | 0.22 |
| 2 | 8.992 | 10976 | 887 | 0.09 |
| 3 | 9.853 | 2661 | 762 | 0.02 |
| 4 | 10.022 | 11834448 | 815023 | 95.92 |
| 5 | 10.556 | 151446 | 16385 | 1.23 |
| 6 | 10.884 | 88262 | 10955 | 0.72 |
| 7 | 11.026 | 106868 | 12002 | 0.87 |
| 8 | 14.140 | 45110 | 2803 | 0.37 |
| 9 | 14.469 | 70569 | 4189 | 0.57 |

| | retention time (min) | peak area (µAU*min) | peak height (µAU) | percentage of total peak area (%) |
|---|---|---|---|---|
| 1 | 7.967 | 48442 | 7089 | 0.33 |
| 2 | 8.126 | 77401 | 8629 | 0.53 |
| 3 | 8.341 | 52382 | 5627 | 0.36 |
| 4 | 8.567 | 20285 | 2287 | 0.14 |
| 5 | 8.800 | 31588 | 3249 | 0.22 |
| 6 | 9.364 | 41334 | 3052 | 0.28 |
| 7 | 10.038 | 87118 | 10105 | 0.59 |
| 8 | 10.199 | 14018904 | 994823 | 95.70 |
| 9 | 10.806 | 225864 | 15294 | 1.54 |
| 10 | 11.865 | 45384 | 1941 | 0.31 |

COMPOUND OR ITS SALT THEREOF TARGETING FIBROBLAST ACTIVATION PROTEIN, ITS PREPARATION METHODS AND ITS USES THEREOF

REFERENCE TO RELATED APPLICATIONS

The present application is based on, and claims priority from, Taiwan application number 110140022 filed Oct. 28, 2021, the disclosure of which is hereby incorporated by reference herein in its entirety.

TECHNICAL FIELD

The present invention relates to a compound or its salt thereof targeting fibroblast activation protein, and its preparation methods and uses, especially the compound represented by formula (I) D-R1-R2-A-R' or its salt thereof, and its preparation methods and its uses.

BACKGROUND OF RELATED ARTS

The tumor microenvironment has an impact on tumor growth and is more complex than normal cells. In addition to malignant tumor cells, malignant tumors also contain stromal cells composed of vascular cells, immune cells, and fibroblasts. A variety of tumors, such as breast cancer, colorectal cancer, and pancreatic cancer, account for more than 90% of stromal cells. The fibroblasts in the composition are also called cancer-associated fibroblasts (CAFs) and involved in growth, migration and progress of the tumors. In the activated state, tumor-associated fibroblasts can migrate, proliferate, produce extracellular matrix, and exhibit different markers, such as α-smooth muscle actin (α-SMA), platelet-derived growth factor-β (Platete derived growth factor-β, PDGF-β) and fibroblast activation protein (FAP).

FAP is composed of 760 amino acids, of which 6 amino acids are in the cell membrane, 20 amino acids are involved in penetrating the membrane, and the remaining part is outside the membrane to form the β-propeller and enzyme active area. It belongs to the dipeptidyl peptidase (dipeptidyl peptidase 4, DPP4) family and is a type II membrane glycoprotein. It has the activities of dipeptidyl peptidase and endopeptidase. The amino acids involved in enzyme activity are serine (S624), aspartate (D702) and histidine (H734), so they belong to serine protease in the classification of enzymes, thereby acting on the substrate of FAP (prodrugs activated by FAP activity at the tumor site) or inhibitors (selectively inhibiting enzyme activity) have become important targets for targeting FAP.

The design of prodrugs is often combined with cytotoxic molecules, such as melitin, doxorubicin or thapsigargin, but there are no successful clinical results. In addition, inhibitors developed on the basis of $NH_2$-Xaa-Pro have large differences in specificity. Among them, Val-boro-Pro (PT-100, talabostat) has excellent preclinical test results, but even the effect of combined use with chemotherapy drugs at the human clinical stage is still not obvious. Therefore, in addition, the boric acid-based inhibitor MIP-1232 is combined with iodine for imaging, and the quinoline structure-based inhibitor, FAPI-01 combined with I-125, is used due to the deiodinase reaction and low intracellular accumulation of radioactivity, so the development is not good. Compared with FAPI-01, the inhibitors FAPI-02 is modified with 1,4,7,10-tetraazacyclododecane-1,4,7,10-tetraacetic acid (doclecanetetraacetic acid, DOTA) as the metal chelating group, have better pharmacokinetic properties and bio-chemical properties. In order to increase the retention time of the inhibitor in the tumor, the structure of FAPI-02 is modified to FAPI-04 with 2 fluorine atoms, so that the binding ratio of FAP and DDP4 is changed from 45(FAPI-02) to 750(FAPI-04).

Therefore, FAPI-04 has better selectivity than FAPI-02. However, in order to prolong the retention time of inhibitors in tumors, subsequent modifications of potential structures such as FAPI-21 and FAPI-46 based on FAPI-04 has developed. After modification, the ratio of tumor to other normal tissues (blood, liver, muscle and small intestine) is increased, and a larger amount of inhibitor can be accumulated in the tumor within 10 minutes after administration. However, FAPI-21 are highly accumulated in the oral mucosa, salivary glands and thyroid glands but FAPI-46 does not. Even though FAPI-46 has excellent tumor uptake and high tumor-to-tissue ratio, this series of inhibitors still cannot effectively prolong the tumor retention time. Therefore, there is still a need for technologies and new inhibitors that can prolong tumor retention.

EP2804859B uses a structure-activity correlation method to disclose specific and selective FAP-binding quinoline series molecules. This inhibitor can be used as a medicine for the treatment and/or prevention of FAP-related diseases in humans or animals, and is not limited to proliferative diseases. The in vitro test confirmed that most of the invented compounds in the cited case have an IC50 (inhibition of 50% biological activity) of less than 1 mM, which is 10 times lower than the reference compounds in the cited case. The higher IC50 of the proteins of other subtypes of FAP shows that the invented compounds have high selectivity and specificity. However, there is no more data to prove the retention time in animals and the accumulation status on FAP-related tumors.

US20200330624A1 discloses a reagent for imaging and radiotherapy. The reagent can target a subtype FAP for imaging and treatment of a subtype FAP related diseases. Using tumor cells expressing FAP-α and not expressing FAP-α for verification, it can be seen from the biological distribution results that the quinoline reagents cited in the case increase to 12 hours after administration, and the cumulative amount of reagents is only ⅓ (4.57±0.54% ID/g) of the highest amount (12.89±1.45% ID/g). The reagent of the cited case is quickly discharged from the animal body after it enters the animal body. It can be seen that the circulation time in the blood and the tumor accumulation time are short.

Compounds such as FAPI-01, FAPI-02, FAPI-04, FAPI-13, FAPI-21 and FAPI-46 are FAP inhibitors developed successively based on quinoline-based structures. The inhibitors are individually matched radionuclide FAPI-01 combined with $^{125}$I; FAPI-02 combined with $^{68}$Ga or $^{177}$Lu; FAPI-04 combined with $^{68}$Ga, $^{90}$Y or $^{177}$Lu; FAPI-21 combined with $^{68}$Ga or $^{177}$Lu; FAPI-46 combined with $^{68}$Ga, $^{90}$Y or $^{177}$Lu. The inhibitors in animal tumor models or the accumulation of tumor location in cancer patients is evaluated. Among them, FAPI-04 is often used with $^{68}$Ga in current clinical trials, and FAPI-46 is a modified FAP quinoline inhibitor with relatively better binding effect. In living tumor animal experiments, $^{68}$Ga-FAPI-46 showed 30% higher tumor accumulation than $^{68}$Ga-FAPI-04 at 1 hour after administration, the highest absorption value of $^{177}$Lu-FAPI-46 (1 hour after administration) at the tumor increases by 33% compared with $^{177}$Lu-FAPI-04 (4 hours after administration), and the accumulation of the drug at both tumors decreased to 2-3% ID/g after the drug is distributed to 24 hours. Therefore, FAPI-04 or FAPI-46 are both FAP inhibitor for short biological circulation (Loktev et al. J Nucl Med. 2018 September; 59(9):1423-1429. Lindner et al. J Nucl Med. 2018 September; 59(9):1415-1422. Loktev et al. J Nucl Med. 2019 October; 60(10):1421-1429. WO2019/154886 A1; WO 2019/154859 A1).

CN112409414 discloses that a compound is a 6-coordinated combination of 6 FAP quinoline inhibitor molecules containing isonitrile structure and a radioisotope Tc-99m to form a tumor imaging agent. The animal data shows that the drug has the largest accumulation in the tumor 1 hour after administration. The drug has the largest accumulation, and the accumulation is decreased in the 4th hour after administration, so it belongs to the FAP inhibitor of short biological cycle.

CN111991570A discloses that a FAP quinoline inhibitor molecule is combined with Tc-99m as a FAP-α specific tumor diagnostic imaging agent. The tumor animal test data shows that there is the highest tumor accumulation at 0.5 hours after administration, and then the accumulation of the tumor is reduced with increasing time, so it belongs to the FAP inhibitor of short biological cycle.

At present, quinoline FAP inhibitors are mostly molecules with short biological cycles. Although they accumulate rapidly in tumors, the accumulation of quinoline FAP inhibitors in tumors decreases with increasing distribution time. Therefore, if higher radioactive accumulation in tumors is required, the injection amount and demand of inhibitors will also increase. Therefore, the biological radiation dose in the organism produced by a single administration also increases. However, the lower the biological radiation dose caused by a single administration is the better. Therefore, there is a need for FAP inhibitors that long circulate in the body to reduce radiation dose by a single administration and increase the accumulation of radioactivity in the tumor.

SUMMARY

In view of the need for long-circulating fibroblast activation protein (FAP) inhibitors in organisms, one purpose of the present disclosure is to solve the problem that quinoline-like fibroblast activation protein inhibitors are mostly molecules of short biological cycles.

According to the purpose of the present disclosure, there is provided a compound or its salt thereof targeting fibroblast activation protein, as well as a preparation method and use thereof, especially a compound represented by formula (I) D-R1-R2-A-R' or its salt, preparation method and use thereof, wherein the compound represented by formula (I) D-R1-R2-A-R' or its salt thereof can increase the circulating time of the FAP inhibitor in the blood, and also increase the inhibitor accumulated in the tumor.

A compound represented by formula (I) D-R1-R2-A-R' or its salt thereof is provided, wherein A is a group represented by

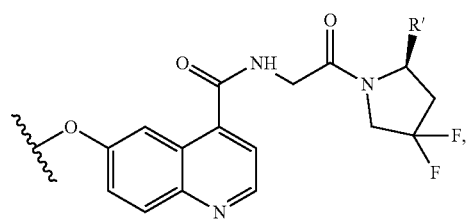

A is connected to R2 by forming an ether bond (—O—) therebetween, A is connected to R', R2 is connected to R1, R1 is connected to D; R' is a group represented by any structure selected from the group consisting of a cyano group (—CN), a methyl group (—CH$_3$) and an alkynyl group (—CCH); R2 is a group represented by any structure selected from a set of R2-I, a set of R2-II, a set of R2-III, a set of R2-IV or a set of R2-V; R1 is a group represented by any structure selected from a set of R1-I, a set of R1-II, a set of R1-III, a set of R1-IV or a set of R1-V; D structure is a group represented by a polycarboxylic macrocyclic ring structure selected from the group consisting of

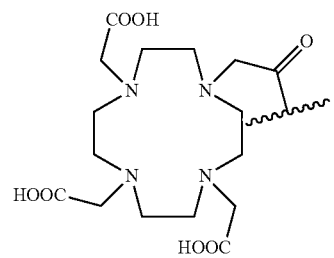 [SMILES: *C(=O)CN1CCN(CC(=O)O)CCN(CC(=O)O)CCN(CC(=O)O)CC1]

(DOTA) or

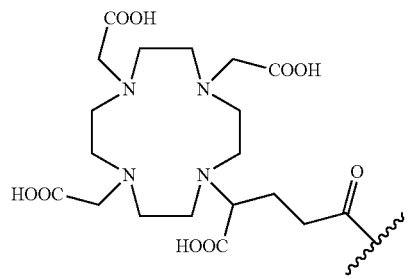 [SMILES: *C(=O)CCC(C(=O)O)N1CCN(CC(=O)O)CCN(CC(=O)O)CCN(CC(=O)O)CC1]

(DOTAGA) and is connected to any structure selected from the set of R1-I, the set of R1-II, the set of R1-III, the set of R1-IV or the set of R1-V to form an amide bond, and is bonded to a positively charged trivalent metal ion M, wherein M is a positive trivalent metal ion selected from the group consisting of $^{111}$In, $^{68}$Ga, $^{67}$Ga, $^{90}$Y or $^{177}$Lu.

wherein R2 is selected from the set of R2-I, R1 is selected from the set of R1-I, wherein the set of R2-I includes R2-I-1, R2-I-2, R2-I-3, R2-I-4, wherein the set of R1-I includes R1-I-1, R1-I-2, R1-I-3, R1-I-4, R1-I-5, R1-I-6, R1-I-7, R1-I-8, R1-I-9, R1-I-10, R1-I-11 R1-I-12, R1-I-13, R1-I-14, R1-I-15, R1-I-16; p in the set of R2-I refers to an integer represented by the number of units of —CH$_2$—; a carboxyl group (—COOH) in any structure of R2-I-1, R2-I-2, R2-I-3 and R2-I-4 is connected to an amino group of an amide terminal (—C(O)NH$_2$) of any structure selected from the set of R1-I to form an amide bond, the p is an integer of 2, 3, 4, 5, 6, or 7 in the structures of R2-I-1, R2-I-2, R2-I-3 or R2-I-4,

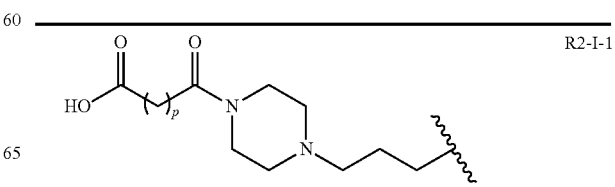

-continued

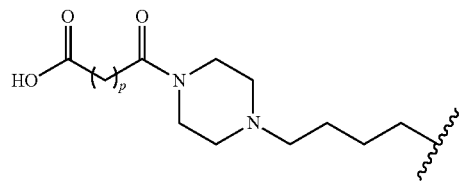
R2-I-2

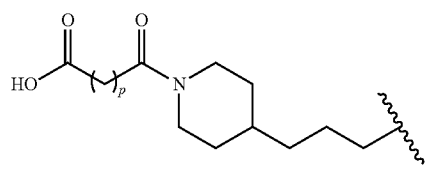
R2-I-3

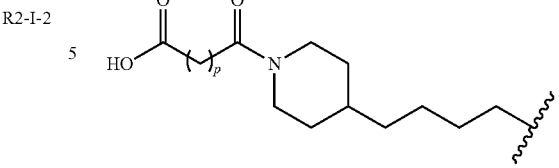
R2-I-4 a symbol "*" in any structure of the set of R1-I indicates a position of an optically active carbon having an R or S configuration of an optical structural isomer; an amide-terminated amino group (—C(O)NH$_2$) of any structure in the set of R1-I is connected to the carboxyl group (—COOH) of any molecule selected from the set of R2-I to form an amide bond;

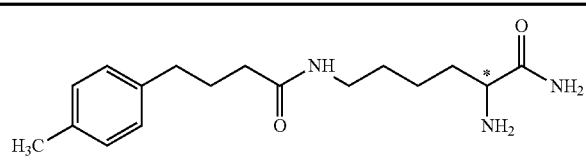
R1-I-1

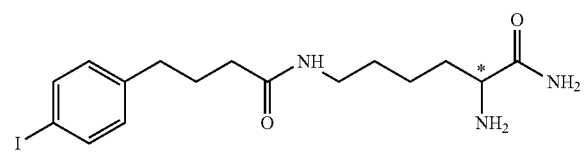 [SMILES: NC(=O)C(N)CCCCNC(=O)CCCc1ccc(I)cc1]
R1-I-2

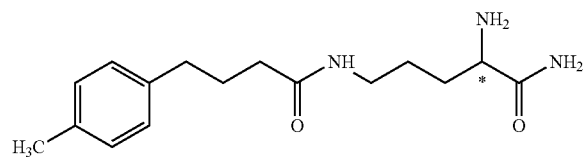 [SMILES: Cc1ccc(CCCC(=O)NCCCC(N)C(N)=O)cc1]
R1-I-3

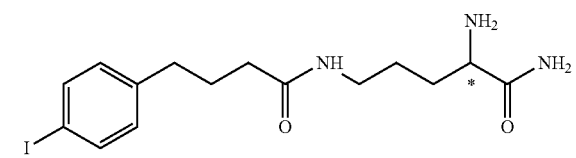 [SMILES: NC(=O)C(N)CCCNC(=O)CCCc1ccc(I)cc1]
R1-I-4

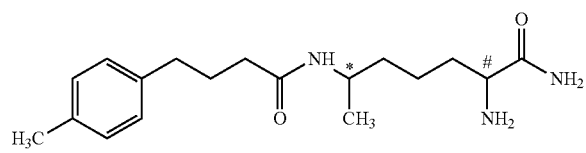 [SMILES: Cc1ccc(CCCC(=O)NC(C)CCCC(N)C(N)=O)cc1]
R1-I-5

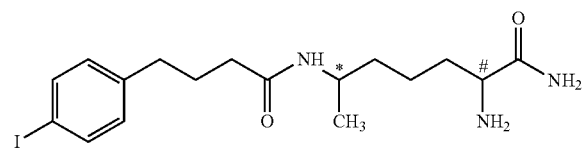 [SMILES: CC(CCCC(N)C(N)=O)NC(=O)CCCc1ccc(I)cc1]
R1-I-6

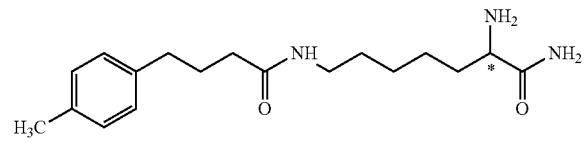 [SMILES: Cc1ccc(CCCC(=O)NCCCCCC(N)C(N)=O)cc1]
R1-I-7

-continued

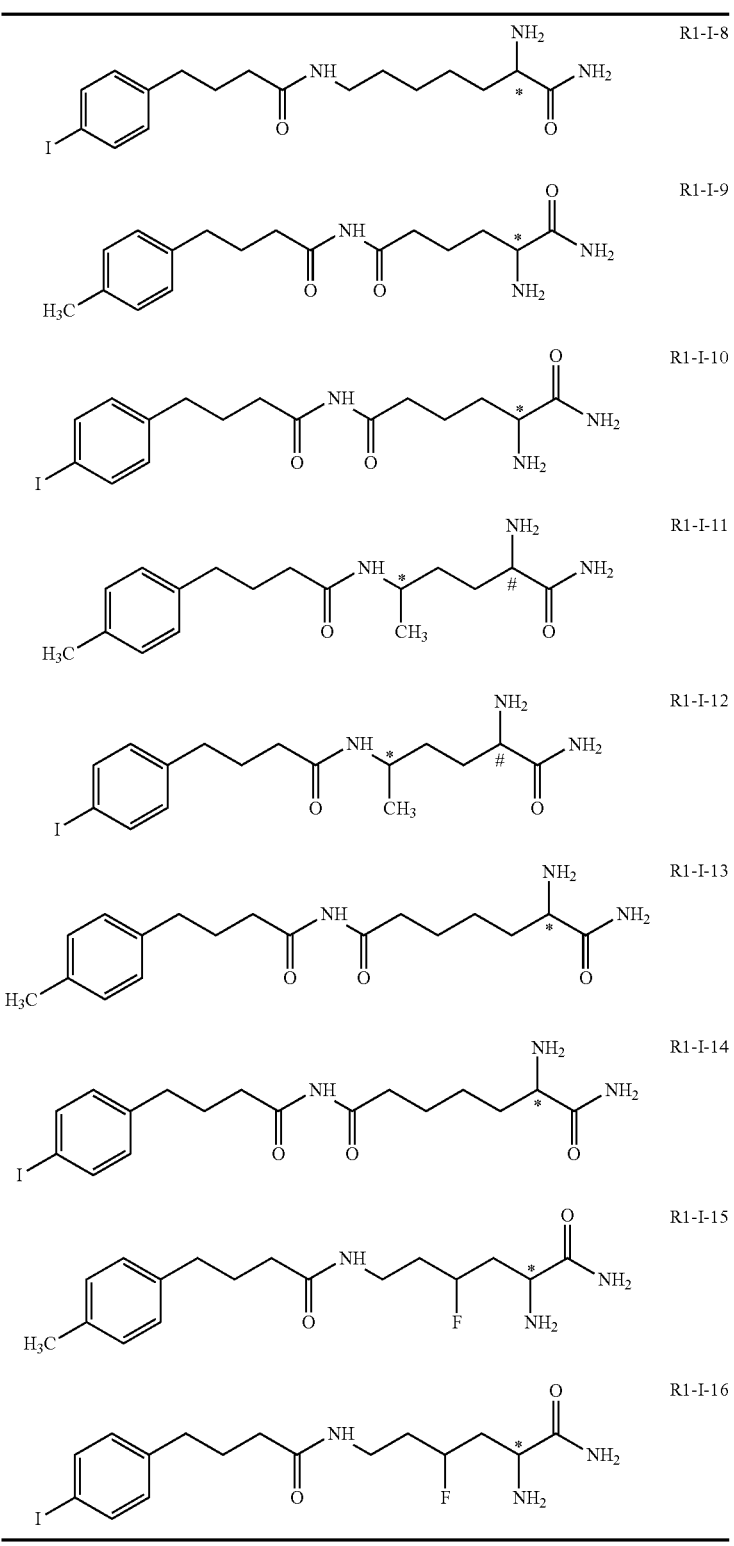

an amino group (—NH₂) that is connected to the optically active carbon of any structure in the set of R1-I is connected to the D structure to form an amide bond.

Or wherein R2 is selected from the set of R2-II, R1 is selected from the set of R1-II, wherein the set of R2-II includes R2-II-1, R2-II-2, R2-II-3, R2-II-4, R2-II-5, R2-II-6, R2-II-7, R2-II-8, R2-II-9, R2-II-10, R2-II-11, R2-II-12, R2-II-13, R2-II-14, R2-II-15, R2-II-16, R2-II-17, R2-II-18, R2-II-19, R2-II-20, R2-II-21, R2-II-22, R2-II-23, R2-II-24, wherein the set of R1-II includes R1-II-1, R1-II-2, R1-II-3, R1-II-4, R1-II-5, R1-II-6, R1-II-7, R1-II-8, R1-II-9, R1-II-10, R1-II-11, R1-II-12, R1-II-13, R1-II-14, R1-II-15, R1-II- 16, R1-II-17, R1-II-18, R1-II-19, R1-II-20, R1-II-21, R1-II-22, R1-II-23, R1-II-24, R1-II-25, R1-II-26, R1-II-27, R1-II-28; a symbol "*" in any structure of the set of R2-II indicates a position of an optically active carbons having an R or S configuration of an optical structural isomer; an amino group (—$NH_2$) of any structure in the set of R1-II is connected to the carboxyl group (—COOH) of any structure in the set of R1-II to form an amide bond,
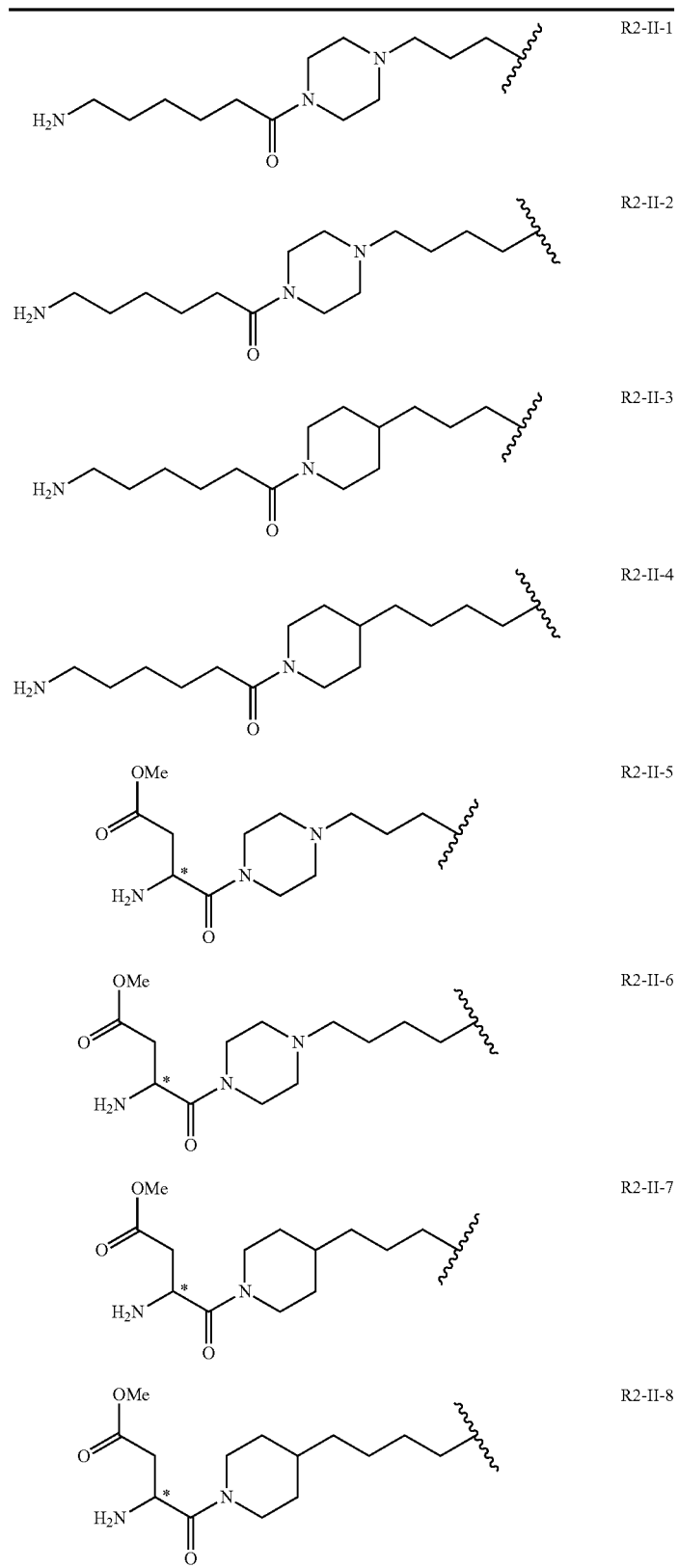

-continued
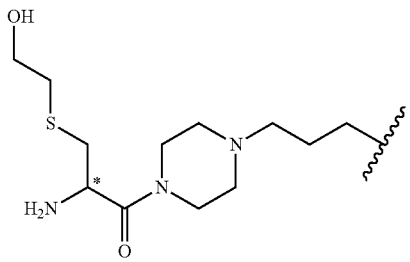 [SMILES: *CCCN1CCN(C(=O)C(N)CSCCO)CC1]
R2-II-9
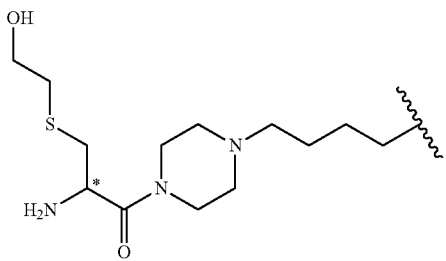
R2-II-10
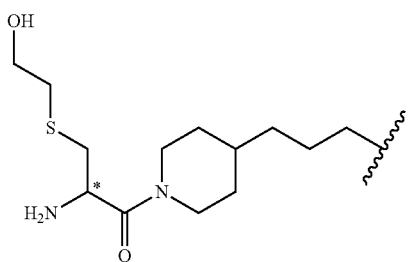 [SMILES: *CCCC1CCN(C(=O)C(N)CSCCO)CC1]
R2-II-11
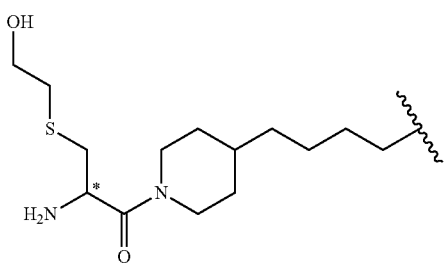
R2-II-12
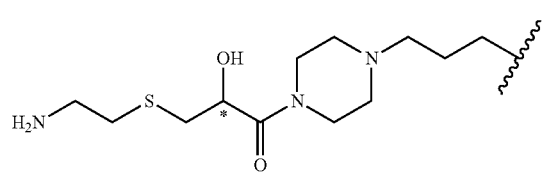 [SMILES: *CCCN1CCN(C(=O)C(O)CSCCN)CC1]
R2-II-13
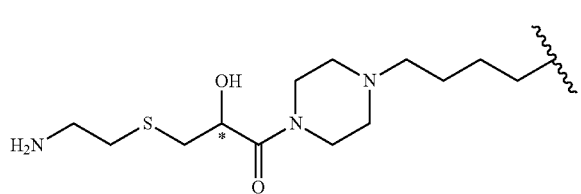
R2-II-14
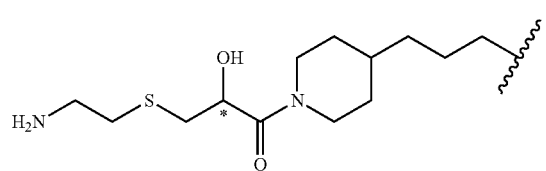 [SMILES: *CCCC1CCN(C(=O)C(O)CSCCN)CC1]
R2-II-15

-continued
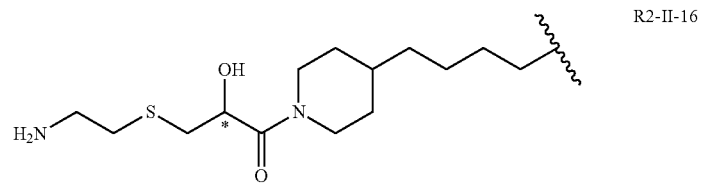
R2-II-16
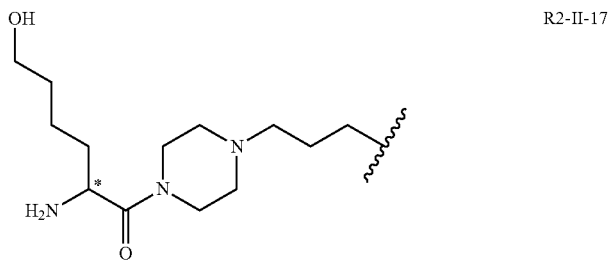
R2-II-17
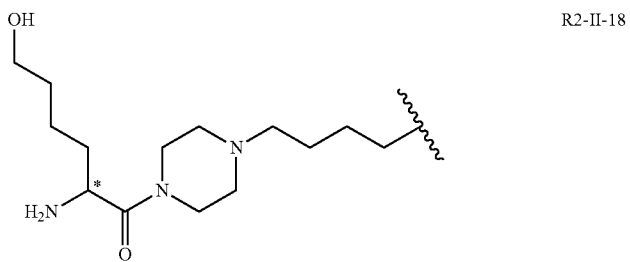
R2-II-18
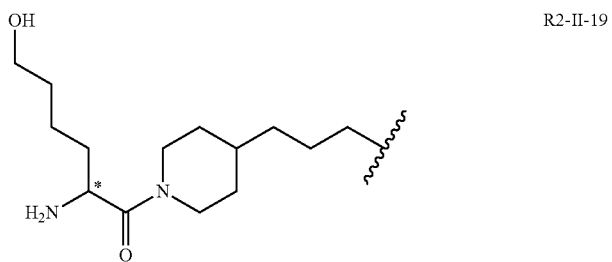
R2-II-19
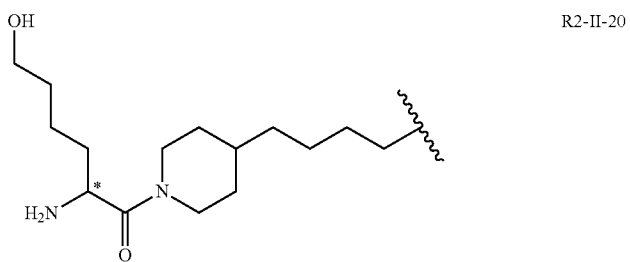
R2-II-20
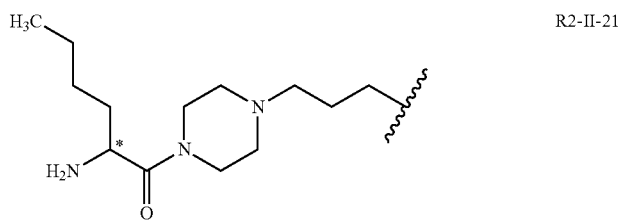
R2-II-21

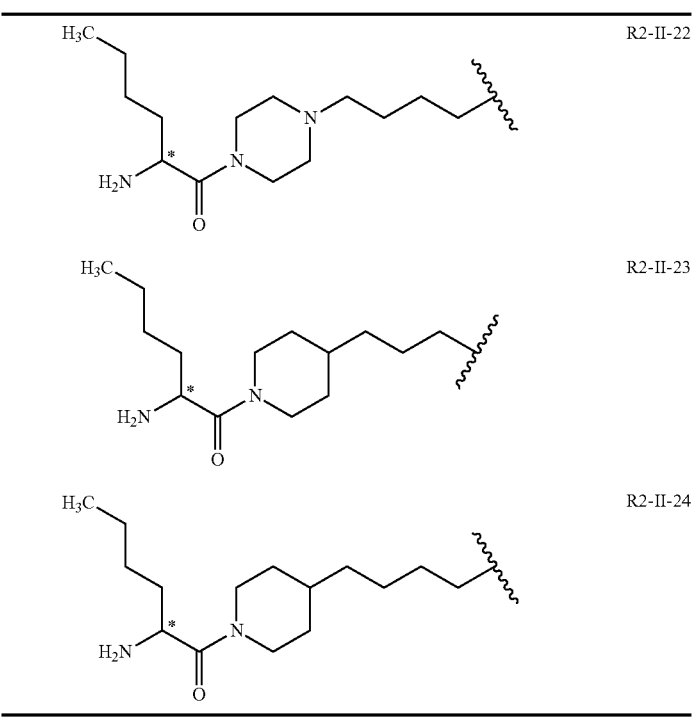
a symbol "*" and "#" in any structure of the set of R1-II indicates a position of an optically active carbon having an R or S configuration of an optical structural isomer; the carboxyl group (—COOH) of any structure in the set of R1-II is connected to an amino group of any molecule selected from the set of R2-II to form an amide bond;
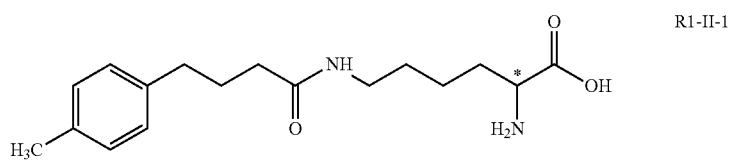
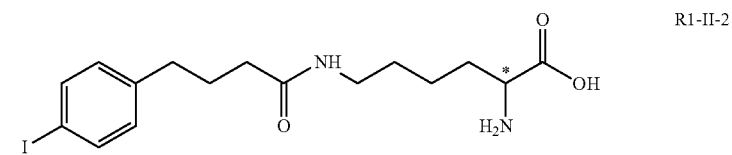
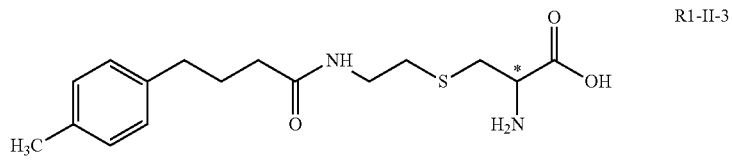
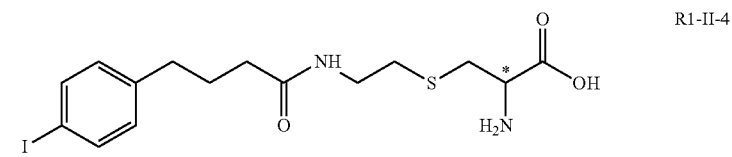

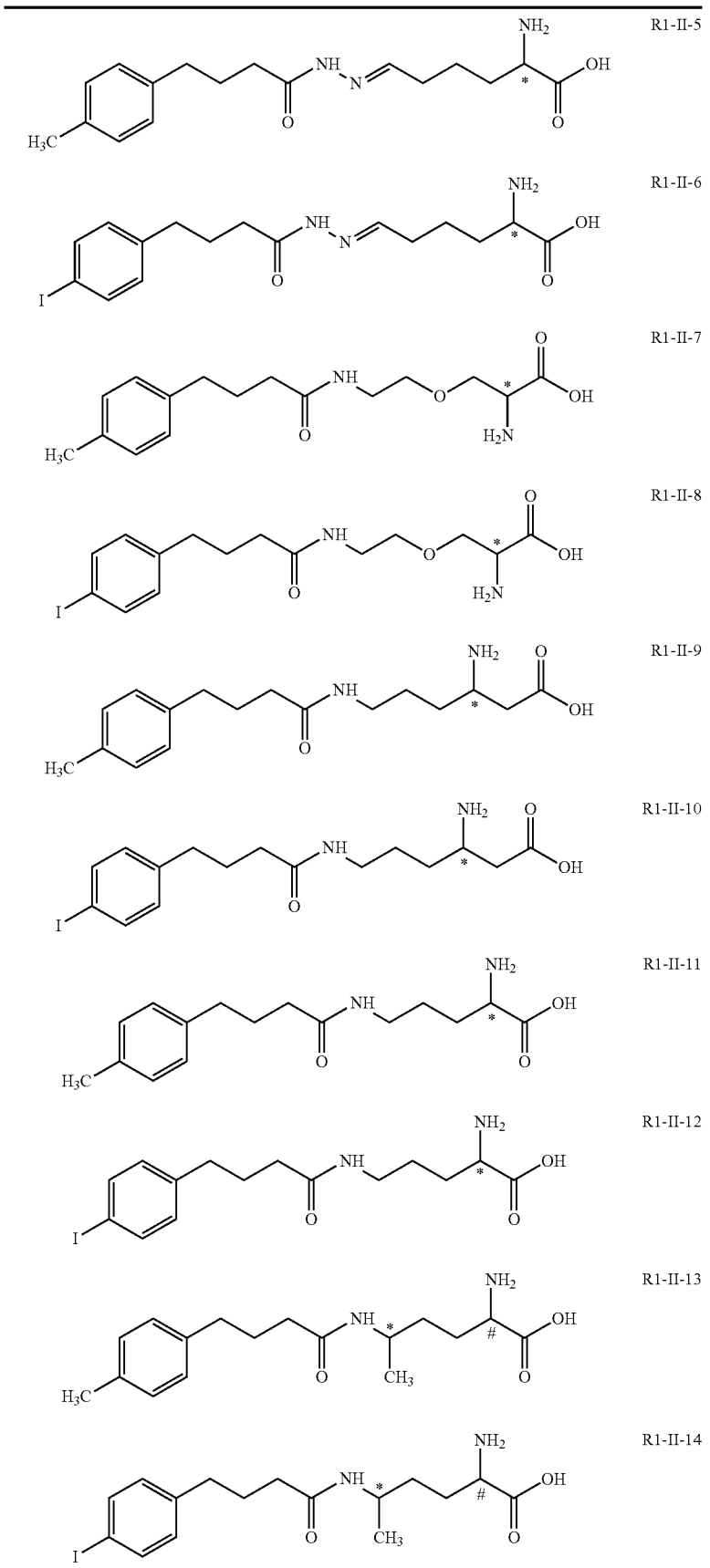

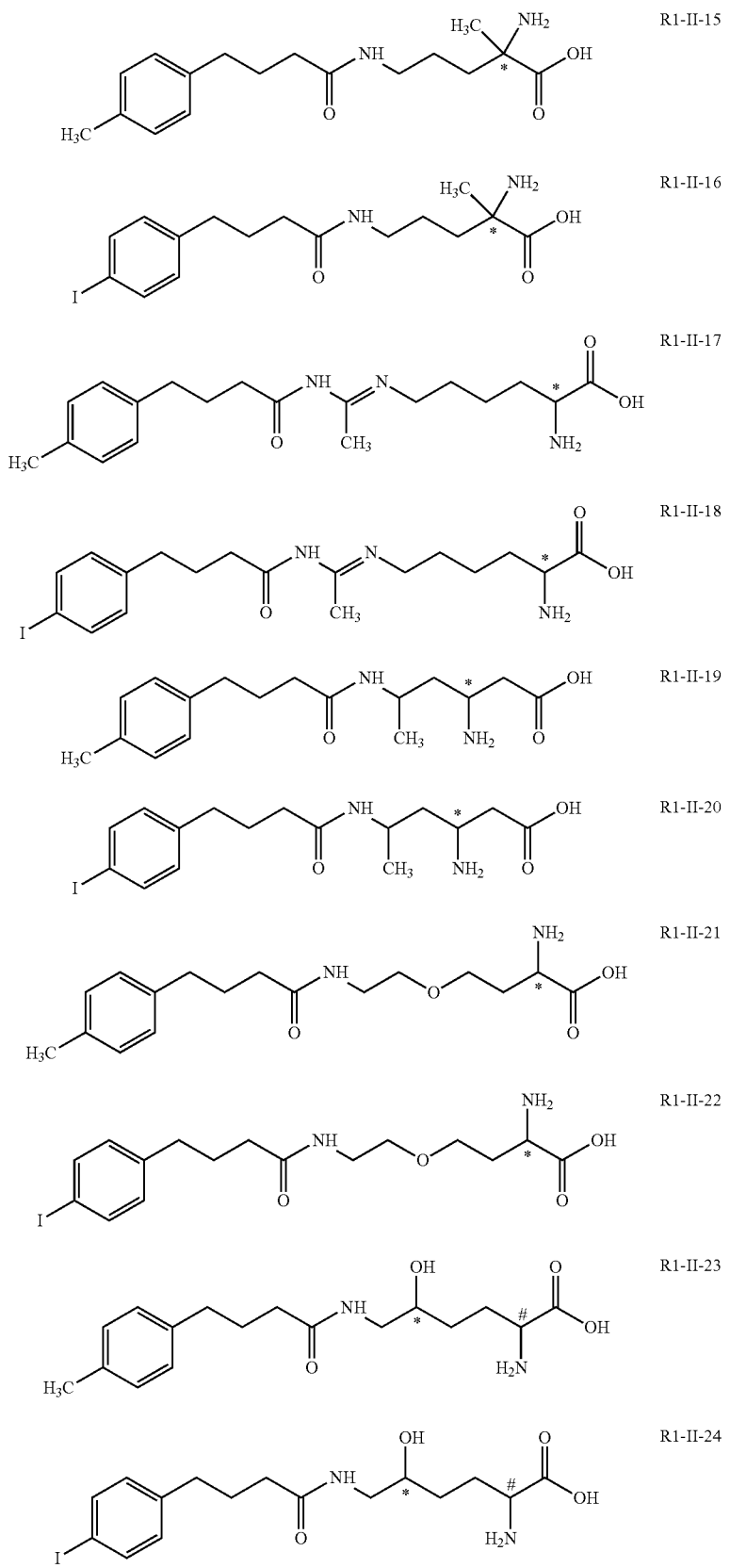

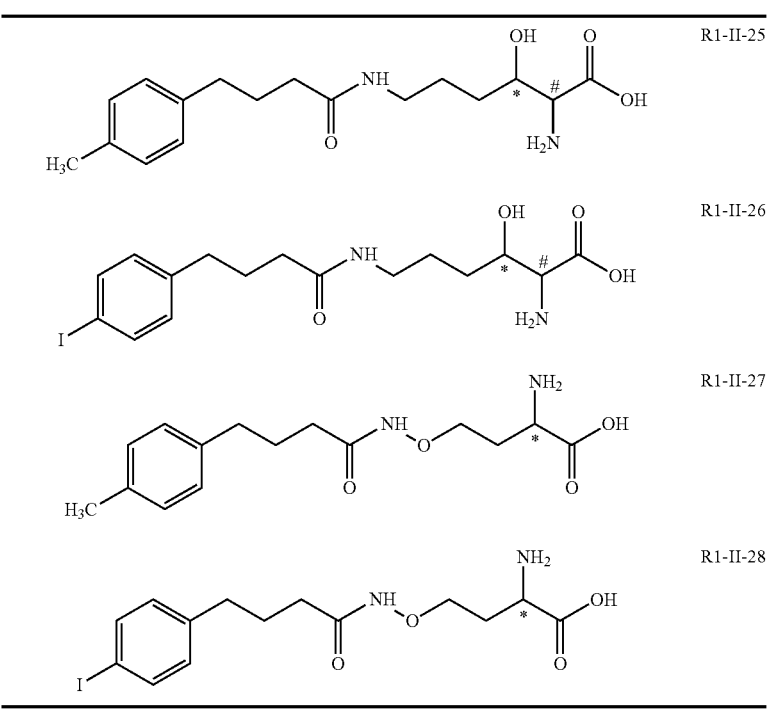

an amino group (—NH₂) of any structure in the set of R1-II is connected to the D structure to form an amide bond.

Or wherein R2 is selected from the set of R2-III, R1 is selected from the set of R1-III, wherein the set of R2-III includes R2-III-1, R2-III-2, R2-III-3, R2-III-4, R2-III-5, R2-III-6, R2-III-7, R2-III-8, R2-III-9, R2-III-10, R2-III-11, R2-III-12, R2-III-13, R2-III-14, R2-III-15, R2-III-16, R2-III-17, R2-III-18, R2-III-19, R2-III-20, wherein the set of R1-III includes R1-III-1, R1-III-2, R1-III-3, R1-III-4, R1-III-5, R1-III-6, R1-III-7, R1-III-8, R1-III-9, R1-III-10, R1-III-11, R1-III-12; a symbol "*" in any structure of the set of R2-III indicates a position of an optically active carbon having an R or S configuration of an optical structural isomer; a maleimide group of any structure in the set of R2-III is connected to a thiol group (—SH) of any structure in the set of R1-III to form a sulfide bond,

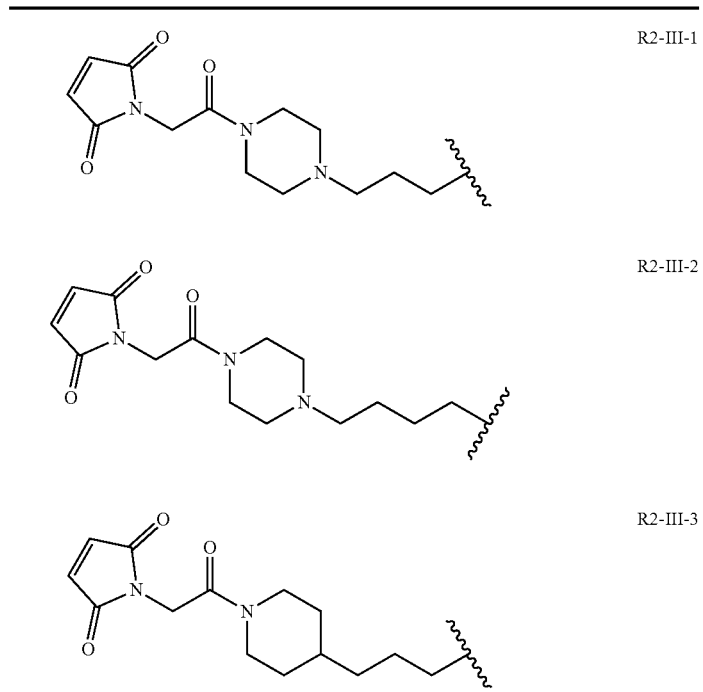

-continued
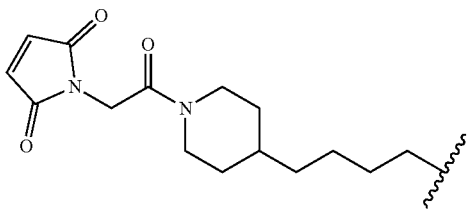
R2-III-4
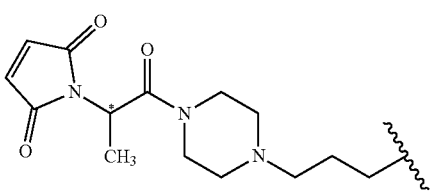
R2-III-5
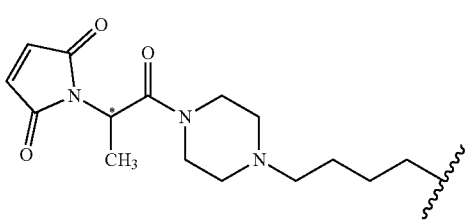 [SMILES: *CCCCN1CCN(C(=O)*(C)N2C(=O)C=CC2=O)CC1]
R2-III-6
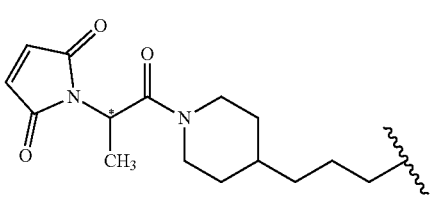 [SMILES: *CCCC1CCN(C(=O)*(C)N2C(=O)C=CC2=O)CC1]
R2-III-7
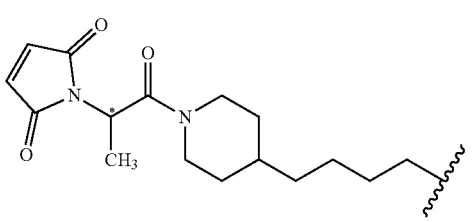 [SMILES: *CCCCC1CCN(C(=O)*(C)N2C(=O)C=CC2=O)CC1]
R2-III-8
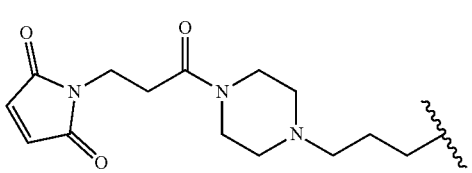 [SMILES: *CCCN1CCN(C(=O)CCN2C(=O)C=CC2=O)CC1]
R2-III-9
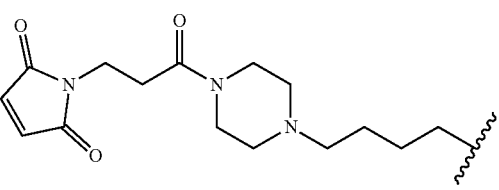 [SMILES: *CCCCN1CCN(C(=O)CCN2C(=O)C=CC2=O)CC1]
R2-III-10
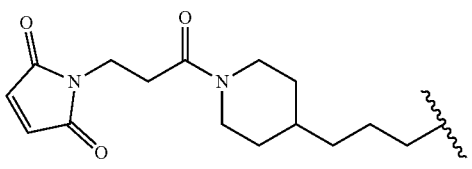
R2-III-11

-continued
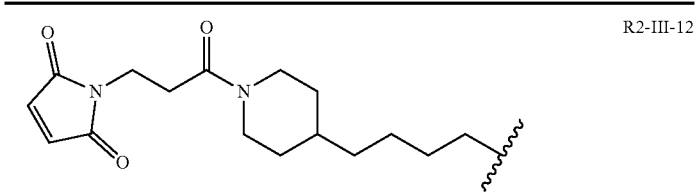 R2-III-12
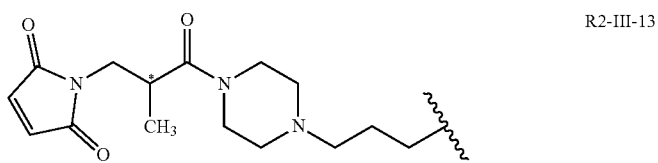 R2-III-13
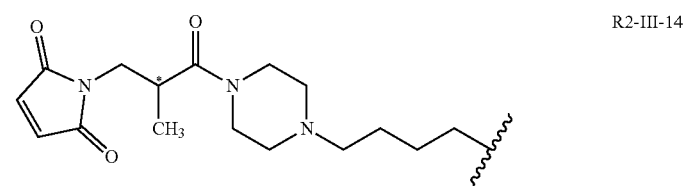 R2-III-14
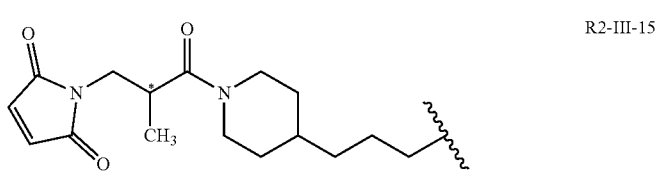 R2-III-15
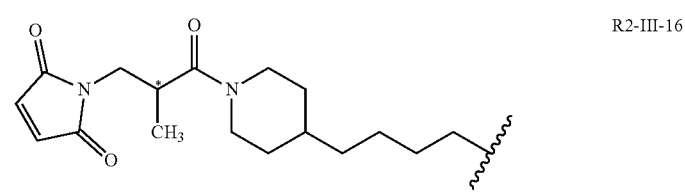 R2-III-16
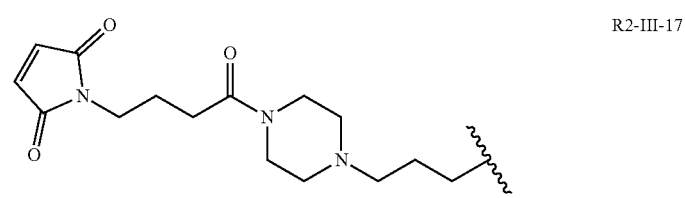 R2-III-17
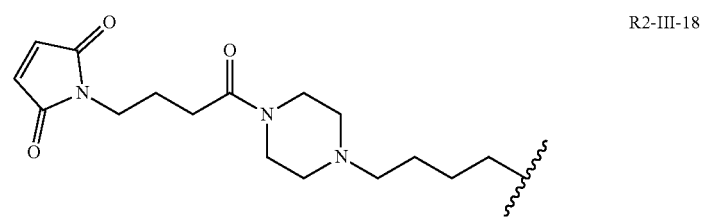 R2-III-18
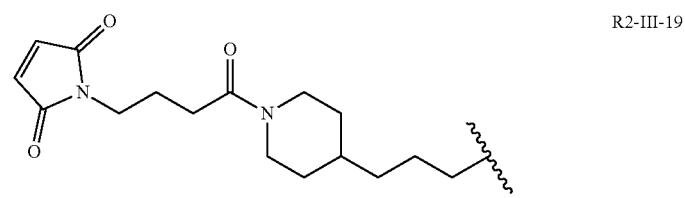 R2-III-19

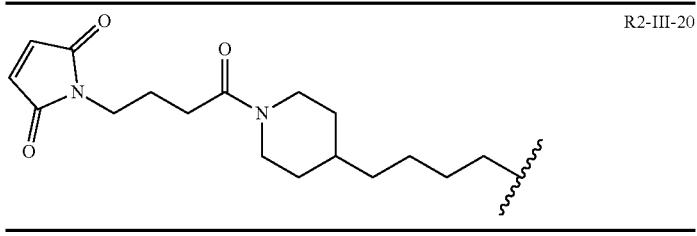
a symbol "*" in any structure of the set of R1-III indicates a position of an optically active carbon having an R or S configuration of an optical structural isomer; a thiol group (—SH) of any structure in the set of R1-III is connected to the maleimide group of any structure selected from the set of R2-III to form an amide bond;
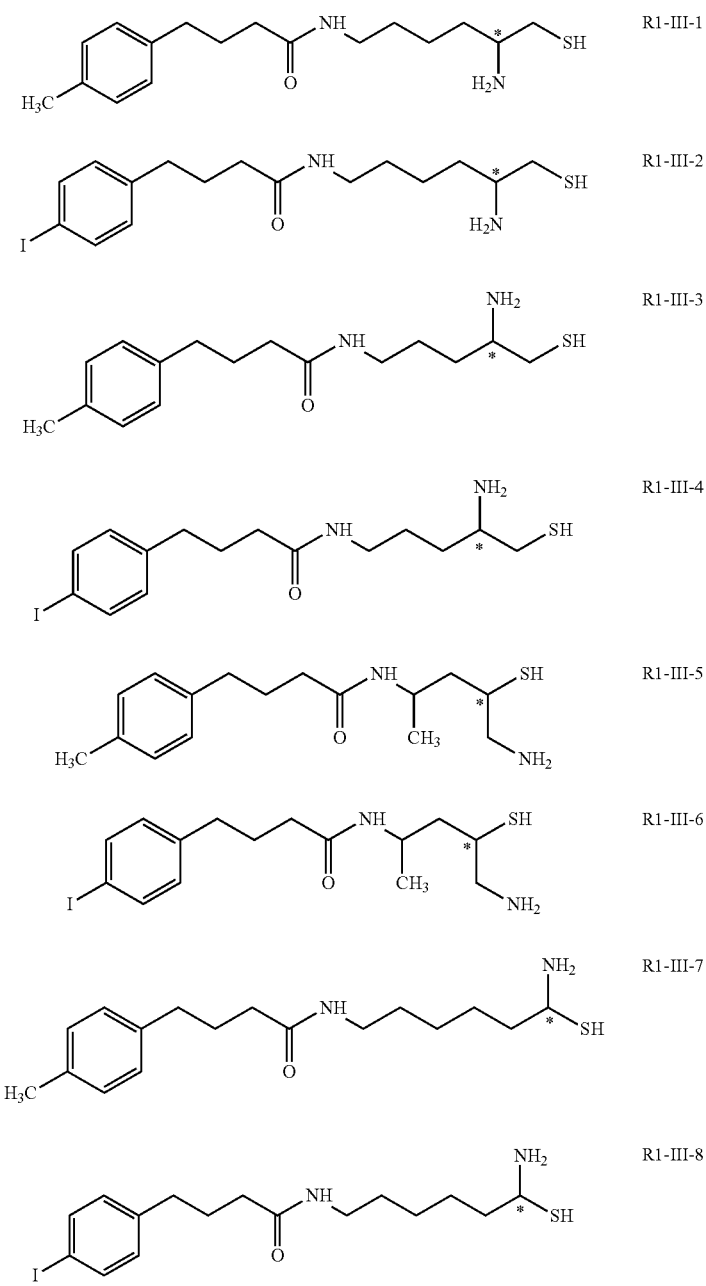

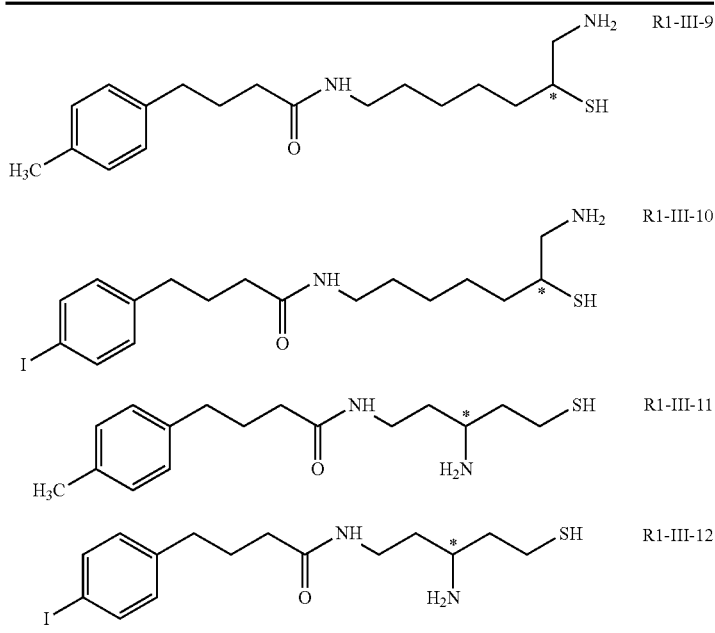

an amino group (—NH₂) of any structure in the set of R1-III is formed an amide bond with the D structure.

Or wherein R2 is selected from the set of R2-IV, R1 is selected from the set of R1-IV, wherein the set of R2-IV includes R2-IV-1, R2-IV-2, R2-IV-3, R2-IV-4, R2-IV-5, R2-IV-6, R2-IV-7, R2-IV-8, R2-IV-9, R2-IV-10, R2-IV-11, R2-IV-12, wherein the set of R1-IV includes R1-IV-1, R1-IV-2; each of q, j, and k in the set of R2-IV refers to an integer represented by the number of units of —CH₂—; a semicarbazide group (—C(O)NHNH₂)) in any structure of R2-IV-1, R2-IV-2, R2-IV-3, R2-IV-4, R2-IV-5, R2-IV-6, R2-IV-7 or R2-IV-8 is connected to an aldehyde group (—C(O)H) of any structure selected from the set of R1-IV to form an semicarbazone (—C(O)NHN=CH—) bond structure; the q in the structures of R2-IV-1, R2-IV-2, R2-IV-3 or R2-IV-4 is an integer of 2, 3, 4, 5, 6, or 7; the j in the structures of R2-IV-5, R2-IV-6, R2-IV-7 or R2-IV-8 is an integer of 1, 2, or 4; a hydrazino group (—NHNH₂) of any structure in R2-IV-9, R2-IV-10, R2-IV-11 or R2-IV-12 is connected to the aldehyde group (—C(O)H) of any structure in the set of R1-IV to form a hydrazone (—NHN=CH—); the k in the structures of R2-IV-9, R2-IV-10, R2-IV-11 or R2-IV-12 is an integer of 1, 2, or 3;

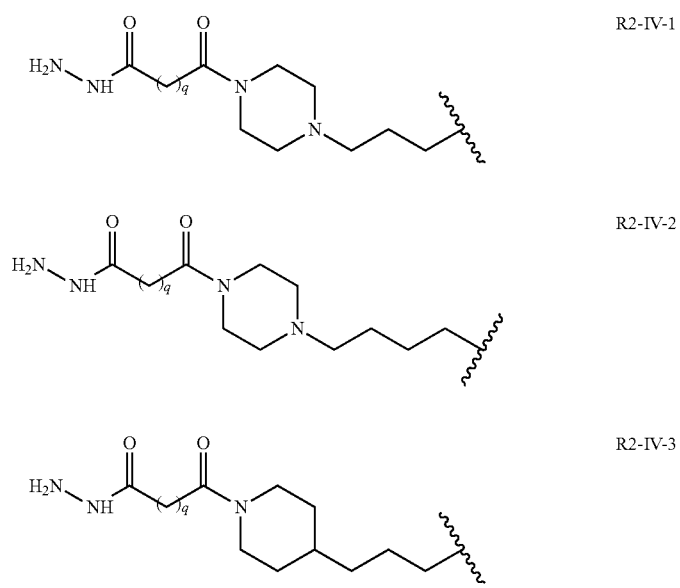

-continued
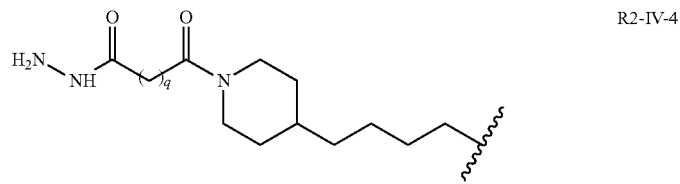
R2-IV-4
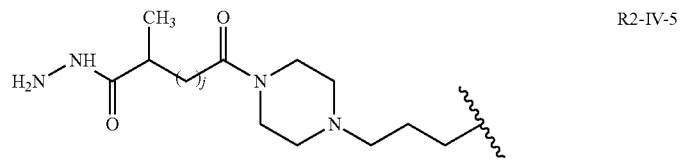
R2-IV-5
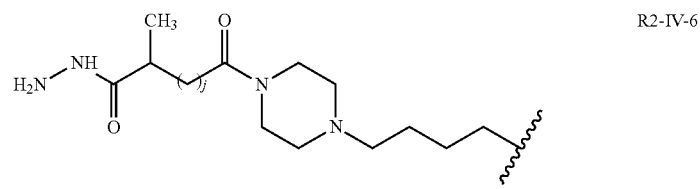
R2-IV-6
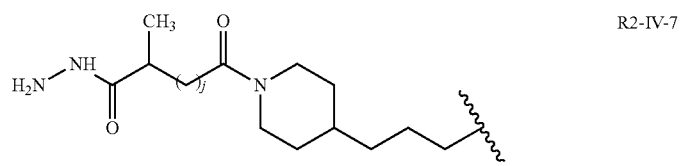
R2-IV-7
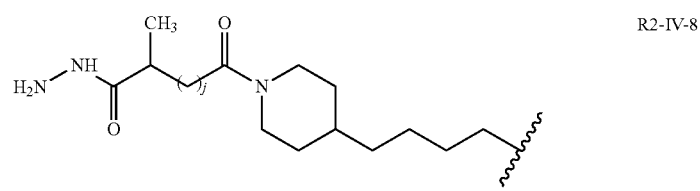
R2-IV-8
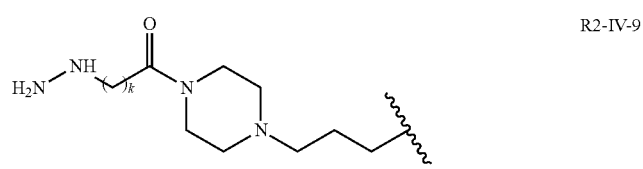
R2-IV-9
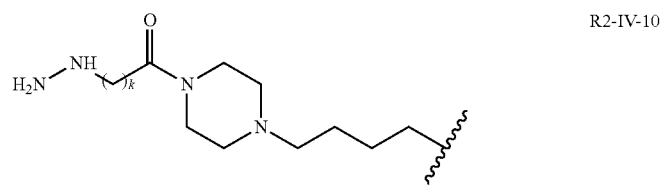
R2-IV-10

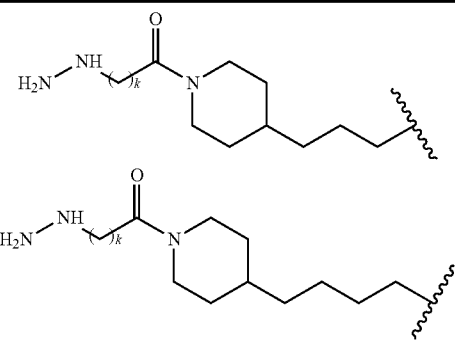

a symbol "*" in any structure of the set of R1-IV indicates a position of an optically active carbon having an R or S configuration of an optical structural isomer; the aldehyde group (—C(O)H) of any structure in the set of R1-IV is connected to a semicarbazide group (—C(O)NHNH₂) of any structure of R2-IV-1, R2-IV-2, R2-IV-3, R2-IV-4, R2-IV-5, R2-IV-6, R2-IV-7 or R2-IV-8 selected from the set of R2-IV group to form a semicarbazone (—C(O)NHN=CH—) bond structure, or connected to a hydrazino group (—NHNH₂) of any structure of R2-IV-9, R2-IV-10, R2-IV-11 or R2-IV-12 in the set of R2-IV to form a hydrazone (—NHN=CH—);

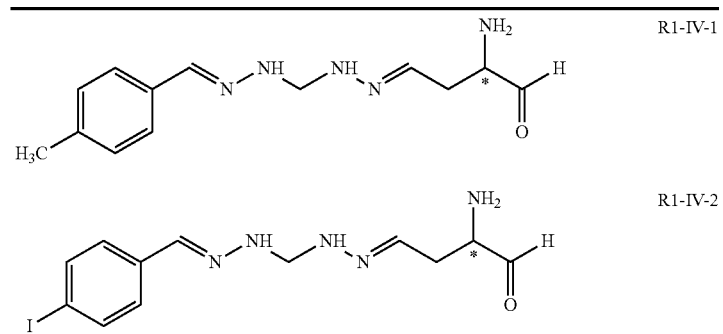

an amino group (—NH₂) of any structure in the set of R1-IV is connected to the D structure to form an amide bond.

Or wherein R2 is selected from the set of R2-V, R1 is selected from the set of R1-V, wherein the set of R2-V includes R2-V-1, R2-V-2, R2-V-3, R2-V-4, wherein the set of R1-V includes R1-IV-1, R1-IV-2; n in the set of R2-V refers to an integer represented by the number of units of —CH₂—; an aldehyde group (—C(O)H) of any structure in R2-V-1, R2-V-2, R2-V-3 or R2-V-4 is connected to a hydrazino group (—NHNH₂) of any structure in the set of R1-V to form a hydrazone (—NHN=CH—); the n is an integer of 2, 3, 4, 5, 6 or 7 in the structures of R2-V-1, R2-V-2, R2-V-3 or R2-V-4;

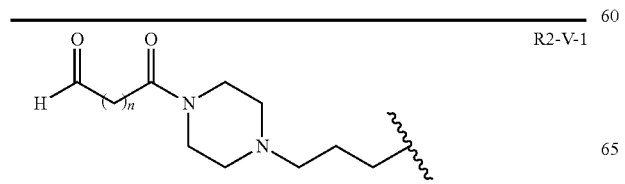

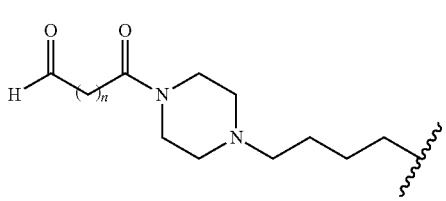

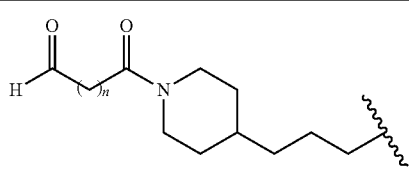

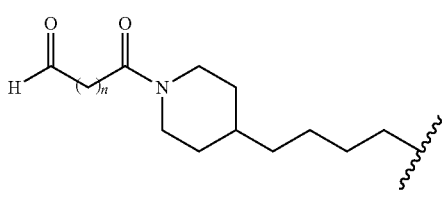

a symbol "*" in any structure of the set of R1-IV indicates a position of an optically active carbon having an R or S configuration of an optical structural isomer; the hydrazino group (—NHNH$_2$) of any structure in the set of R1-V is connected to the aldehyde group (—C(O)H) of any structure in the set of R2-V to form a hydrazone (—NHN═CH—);

a carboxyl group (—COOH) of R2-I reacts with an amide-terminal amino group (—C(O)—NH$_2$) of R1-I to form an amide bond, and then another amino group (—NH$_2$) of R1-I reacts with 1,4,7,10-tetraazacyclododecane-1,4,7,10-tetraacetic acid, 1-(2,5-dioxo-1-pyrrolidinyl) ester (DOTA-NHS ester) to produce the D-R1-R2-A-R' compound or its salt thereof.

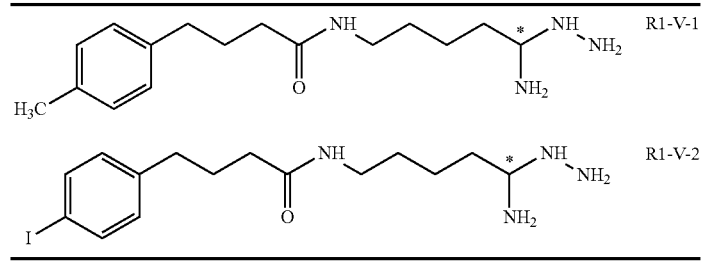

an amino group (—NH$_2$) of any structure in the set of R1-V is connected to the D structure to form an amide bond.

In one aspect, a method for preparing a compound represented by formula (I) D-R1-R2-A-R' or its salt thereof is provided, wherein R' is a cyano group, R2 is any structure selected from the set of R2-I, and the R1 structure is any structure selected from the set of R1-I, and the method includes a reaction scheme of synthesis shown below:

In one aspect, a method for preparing a compound represented by formula (I) D-R1-R2-A-R' or its salt thereof is provided, wherein R' is a cyano group, R2 is any structure selected from the set of R2-II, and the R1 structure is any structure selected from the set of R1-II, and the method includes a reaction scheme of synthesis shown below:

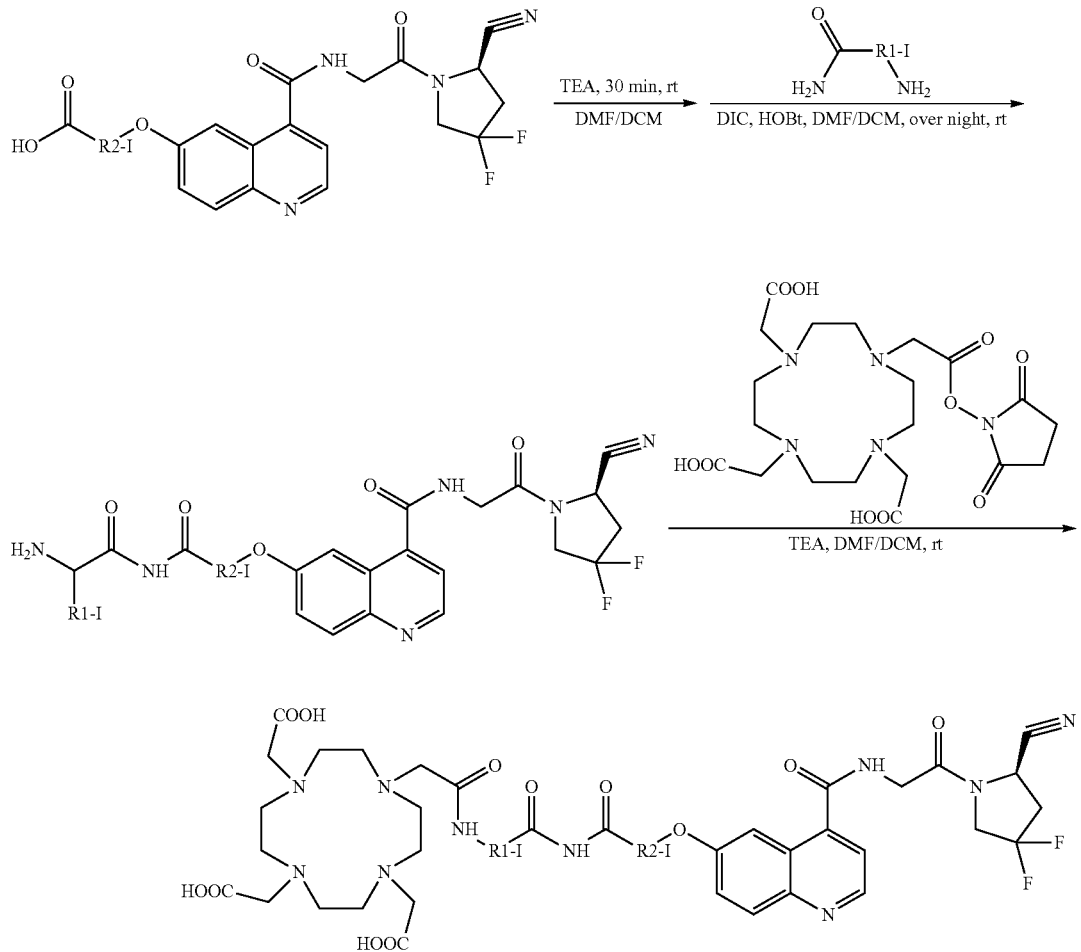

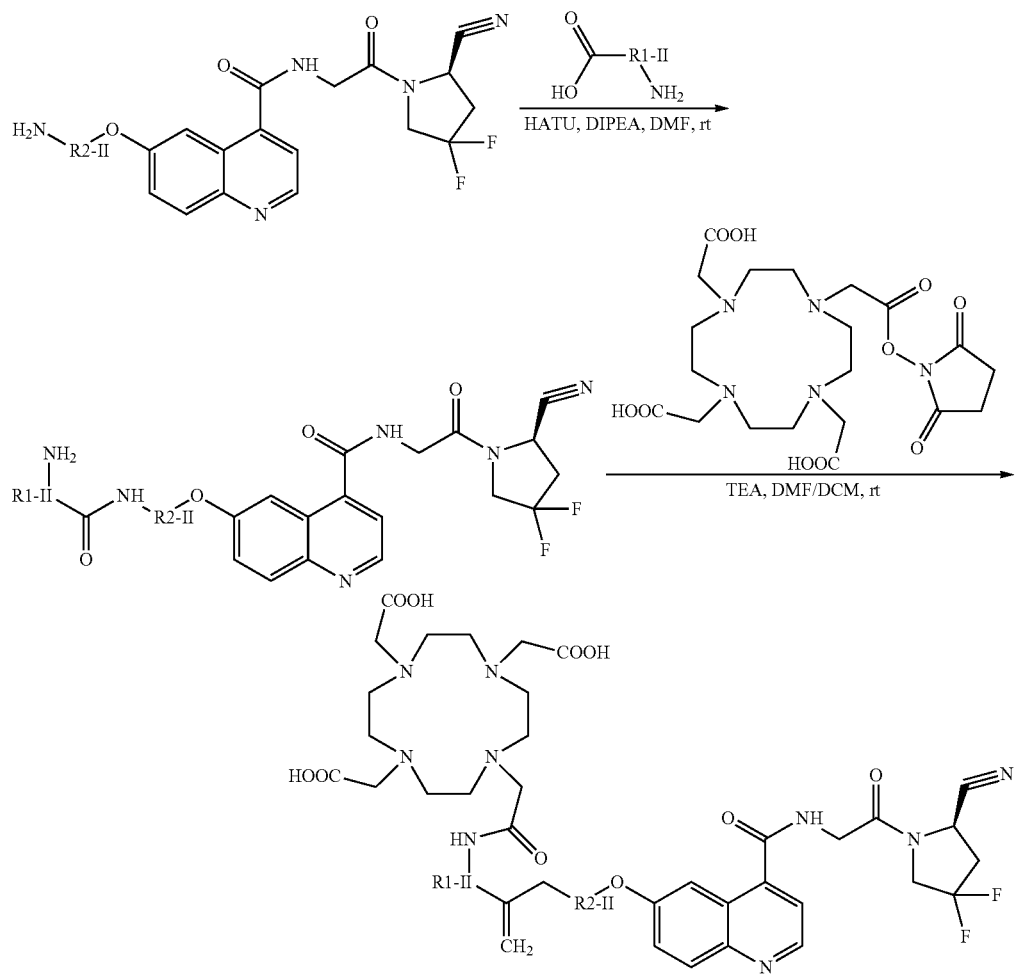

an amino group of R2-II reacts with a carboxyl group (—COOH) of R1-II to form an amide bond, and then an amino group of R1-II reacts with DOTA-NHS ester to produce the D-R1-R2-A-R' compound or its salt thereof.

In one aspect, a method for preparing a compound represented by formula (I) D-R1-R2-A-R' or its salt thereof is provided, wherein R' is a cyano group, R2 is any structure selected from the set of R2-III, and the R1 structure is any structure selected from the set of R1-III, and the method includes a reaction scheme of synthesis shown below:

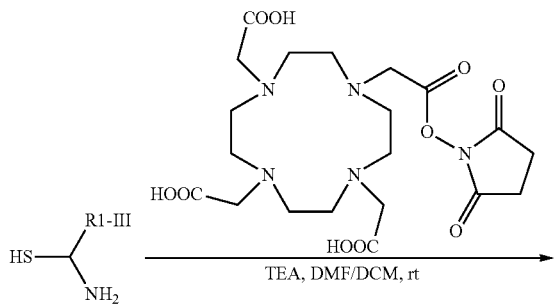

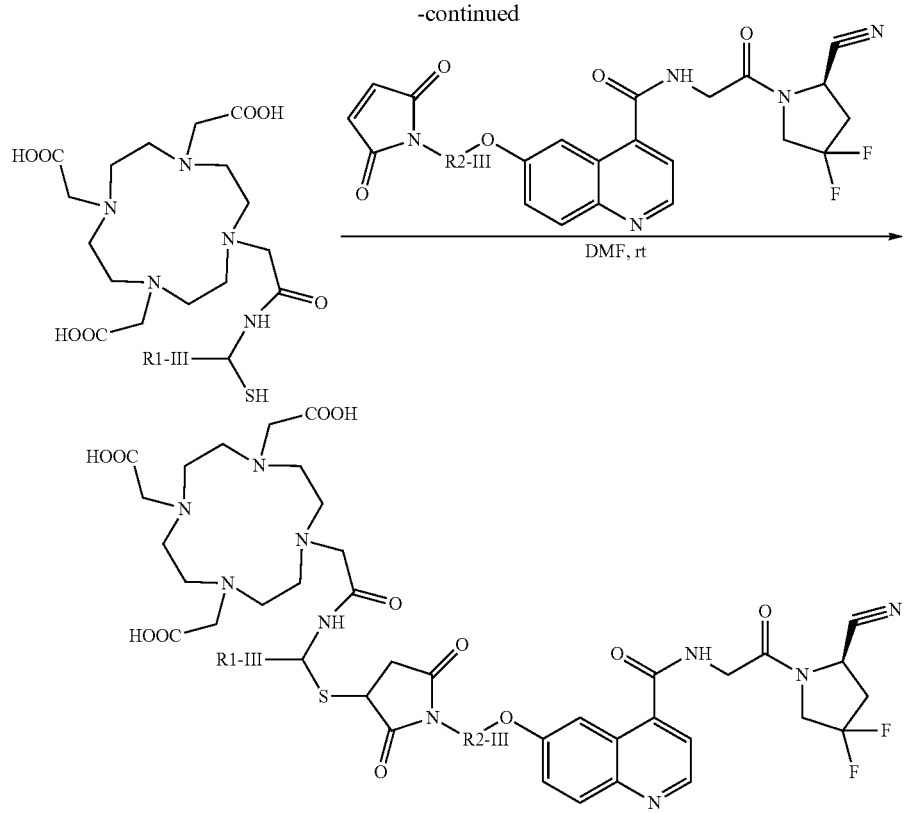

an amino group of R1-III reacts with DOTA-NHS ester to form an amide bond, and then a thiol group (—SH) of R1-III reacts with the maleimide group of R2-III to produce the D-R1-R2-A-R' compound or its salt thereof.

In one aspect, a method for preparing a compound represented by formula (I) D-R1-R2-A-R' or its salt thereof is provided, wherein R' is a cyano group, R2 is any structure selected from the set of R2-IV, and the R1 structure is any structure selected from the set of R1-IV, and the method includes a reaction scheme of synthesis shown below:

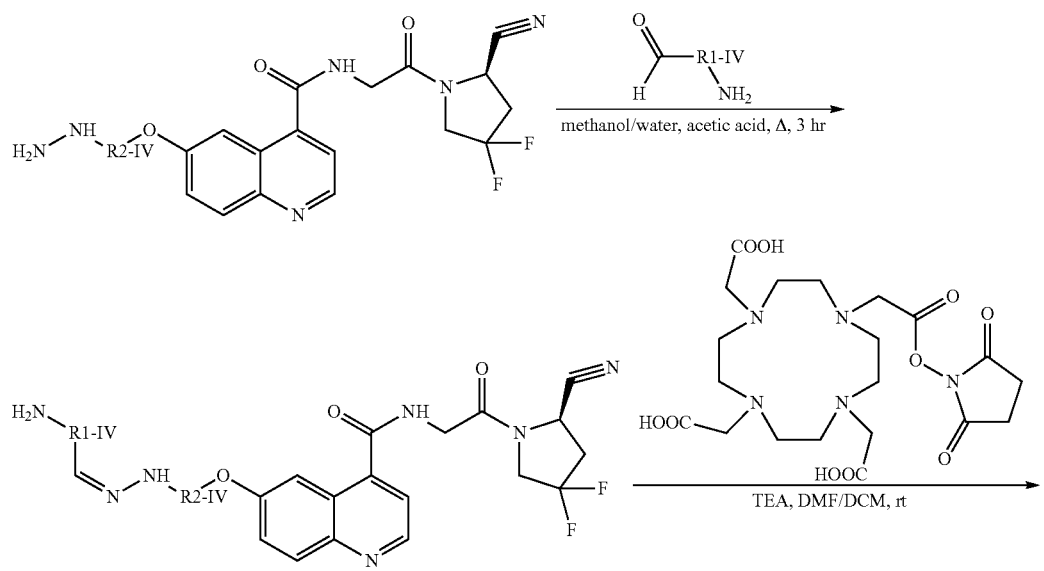

41

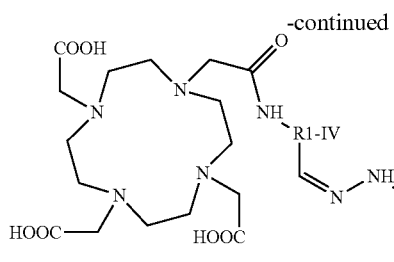

42

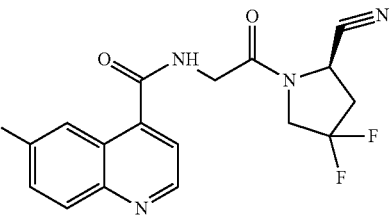

a semicarbazide group (—C(O)NHNH₂) of R2-IV reacts with an aldehyde group (—C(O)H) of R1-IV to form a semicarbazone bond, and then an amino group (—NH₂) of R1-IV reacts with DOTA-NHS ester to produce the D-R1-R2-A-R' compound or its salt thereof.

In one aspect, a method for preparing a compound represented by formula (I) D-R1-R2-A-R' or its salt thereof is provided, wherein R' is a cyano group, R2 is any structure selected from the set of R2-V, and the R1 structure is any structure selected from the set of R1-V, and the method includes a reaction scheme of synthesis shown below:

a semicarbazide group (—C(O)NHNH₂) of R2-V reacts with an aldehyde group (—C(O)H) of R1-V to form a semicarbazone bond, and then an amino group (—NH₂) of R1-V reacts with DOTA-NHS ester to produce the D-R1-R2-A-R' compound or its salt thereof.

In one aspect, a compound represented by formula (I) D-R1-R2-A-R' or its salt thereof is provided, wherein the D structure is

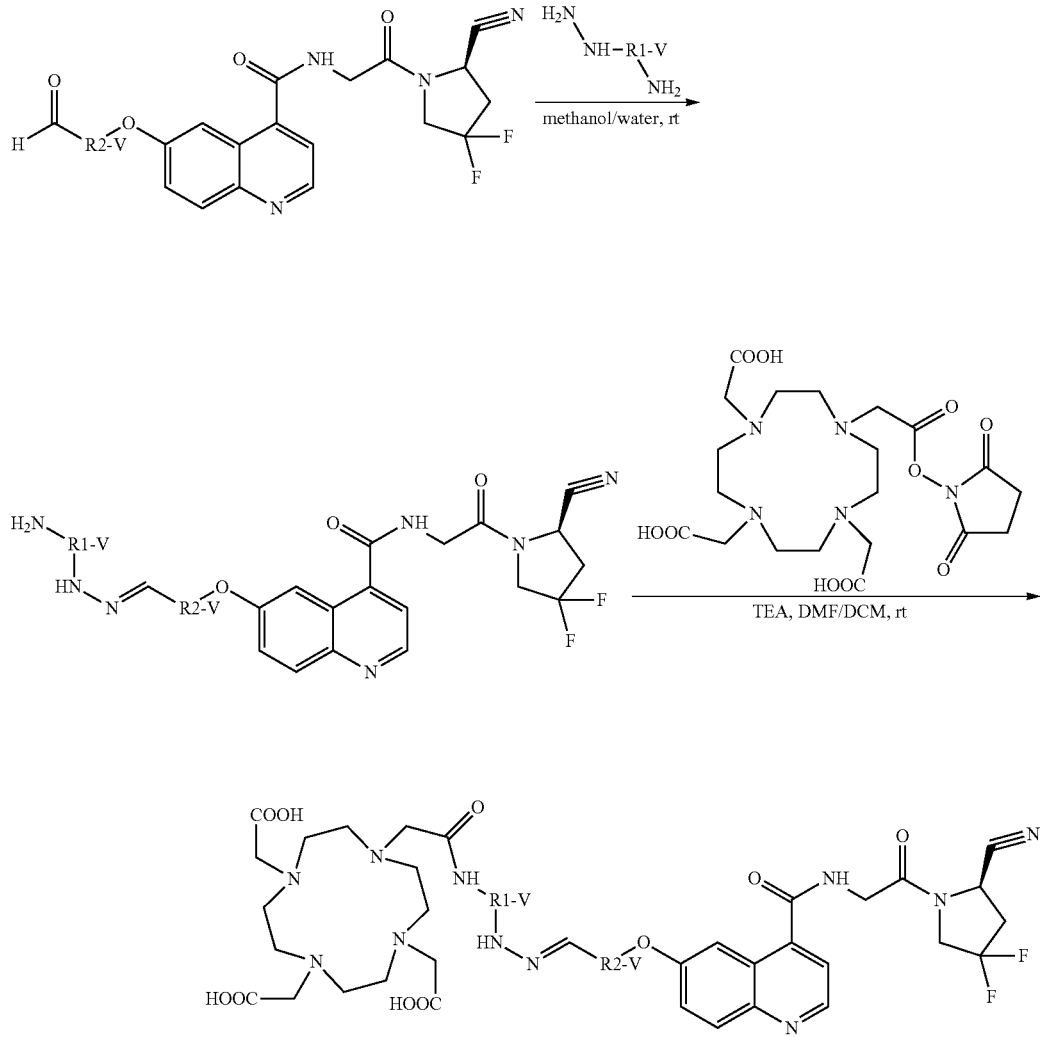

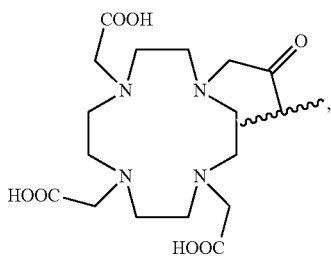 [SMILES: *C(=O)CN1CCN(CC(=O)O)CCN(CC(=O)O)CCN(CC(=O)O)CC1]

and is bonded to a positively charged trivalent metal ion M, wherein M is a positive trivalent metal ion selected from the group consisting of $^{111}$In, $^{68}$Ga, $^{67}$Ga, $^{90}$Y or $^{177}$Lu.

In one aspect, a compound represented by formula (I) D-R1-R2-A-R' or its salt thereof that bonded to M is provided, which is used for radiographic imaging or radioactive cytotoxicity of the long-circulating fibroblast activation protein for long cycle to kill tumor cells, wherein M is a positive trivalent metal ion selected from the group consisting of $^{111}$In. $^{68}$Ga, $^{67}$Ga, $^{90}$Y or $^{177}$Lu.

DETAILED DESCRIPTIONS OF EMBODIMENTS

Figure 1:
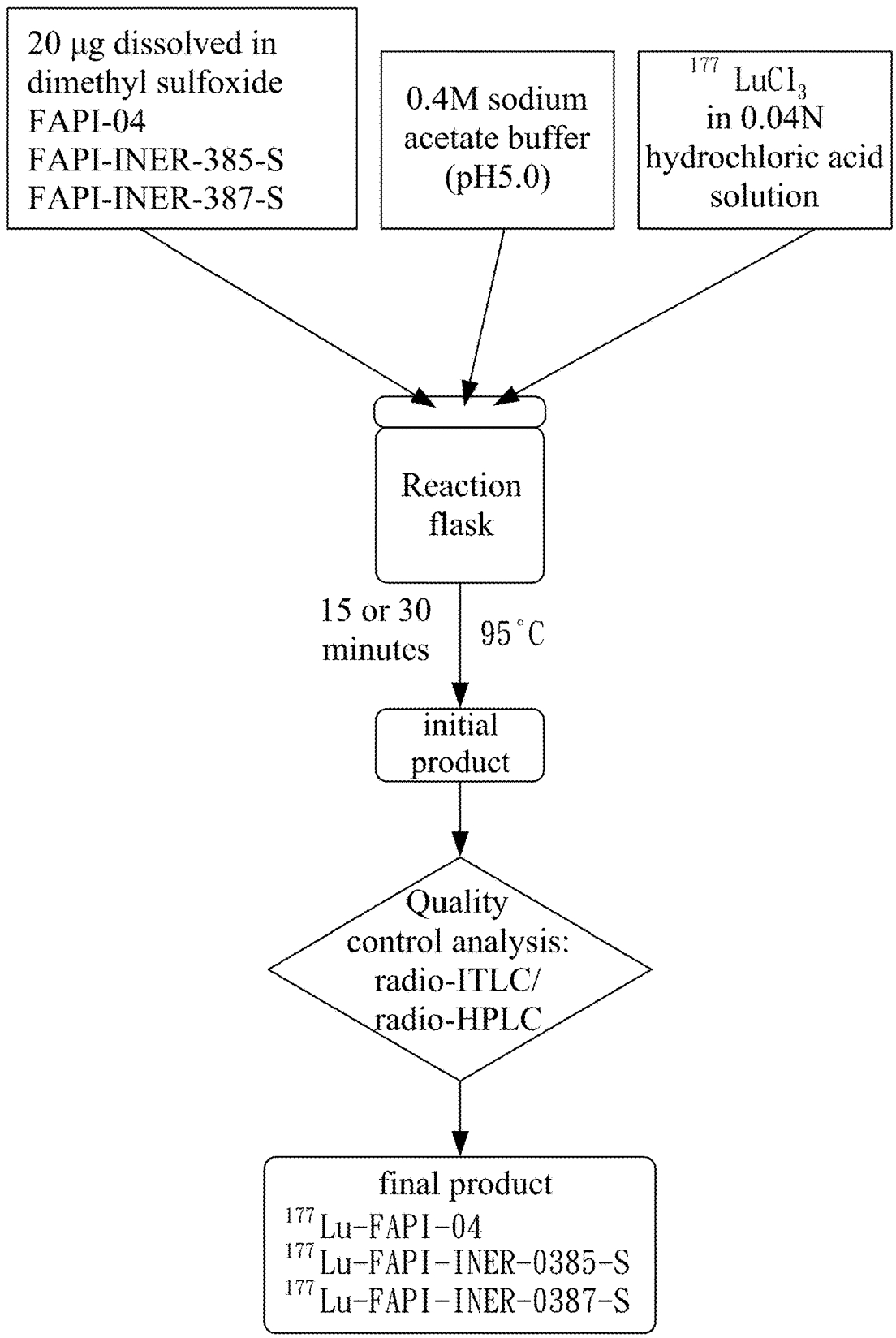
FIG. 1 is a schematic diagram of the preparation process of the radiolabel of a compound represented by formula (I) D-R1-R2-A-R' or its salt thereof.

In one embodiment according of the present disclosure, a compound represented by formula (I) D-R1-R2-A-R' or its salt thereof targeting fibroblast activation protein, wherein A is a group represented by

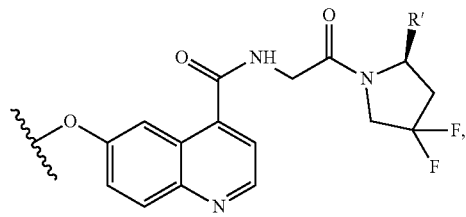

A is connected to R2 by forming an ether bond (—O—) therebetween, A is connected to R', R2 is connected to R1, R1 is connected to D; R' is a group represented by any structure selected from the group consisting of a cyano group (—CN), a methyl group (—CH$_3$) and an alkynyl group (—CCH); R2 is a group represented by any structure selected from a set of R2-I, a set of R2-II, a set of R2-III, a set of R2-IV or a set of R2-V; R1 is a group represented by any structure selected from a set of R1-I, a set of R1-II, a set of R1-III, a set of R1-IV or a set of R1-V; D is a group represented by a polycarboxylic macrocyclic ring structure selected from the group consisting of (DOTA)

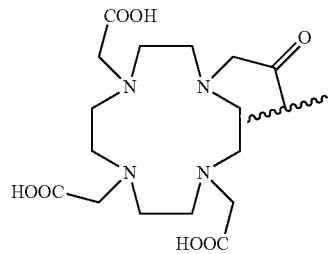 [SMILES: *C(=O)CN1CCN(CC(=O)O)CCN(CC(=O)O)CCN(CC(=O)O)CC1]

or

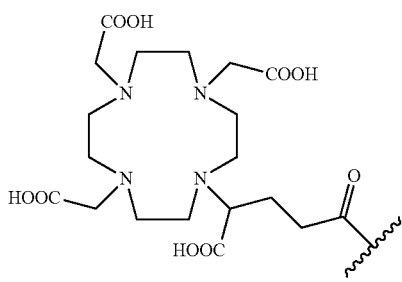 [SMILES: *C(=O)CCC(C(=O)O)N1CCN(CC(=O)O)CCN(CC(=O)O)CCN(CC(=O)O)CC1]

(DOTAGA) and is connected to any structure selected from the set of R1-I, the set of R1-II, the set of R1-III, the set of R1-IV or the set of R1-V to form an amide bond, and is bonded to a positively charged trivalent metal ion M, wherein M is a positive trivalent metal ion selected from the group consisting of $^{111}$In, $^{68}$Ga, $^{67}$Ga, $^{90}$Y or $^{177}$Lu.

In some embodiments, in the compound represented by formula (I) D-R1-R2-A-R' or its salt thereof, R' is a cyano group, R1 is selected from the set of R1-I, and R2 is selected from the set of R2-I, wherein the set of R1-I includes R1-I-1, R1-I-2, R1-I-3, R1-I-4, R1-I-5, R1-I-6, R1-I-7, R1-I-8, R1-I-9, R1-I-10, R1-I-11 R1-I-12, R1-I-13, R1-I-14, R1-I-15, R1-I-16, wherein the set of R2-I includes R2-I-1, R2-I-2, R2-I-3, R2-I-4;

wherein the structures of the set of R1-I are shown as below:

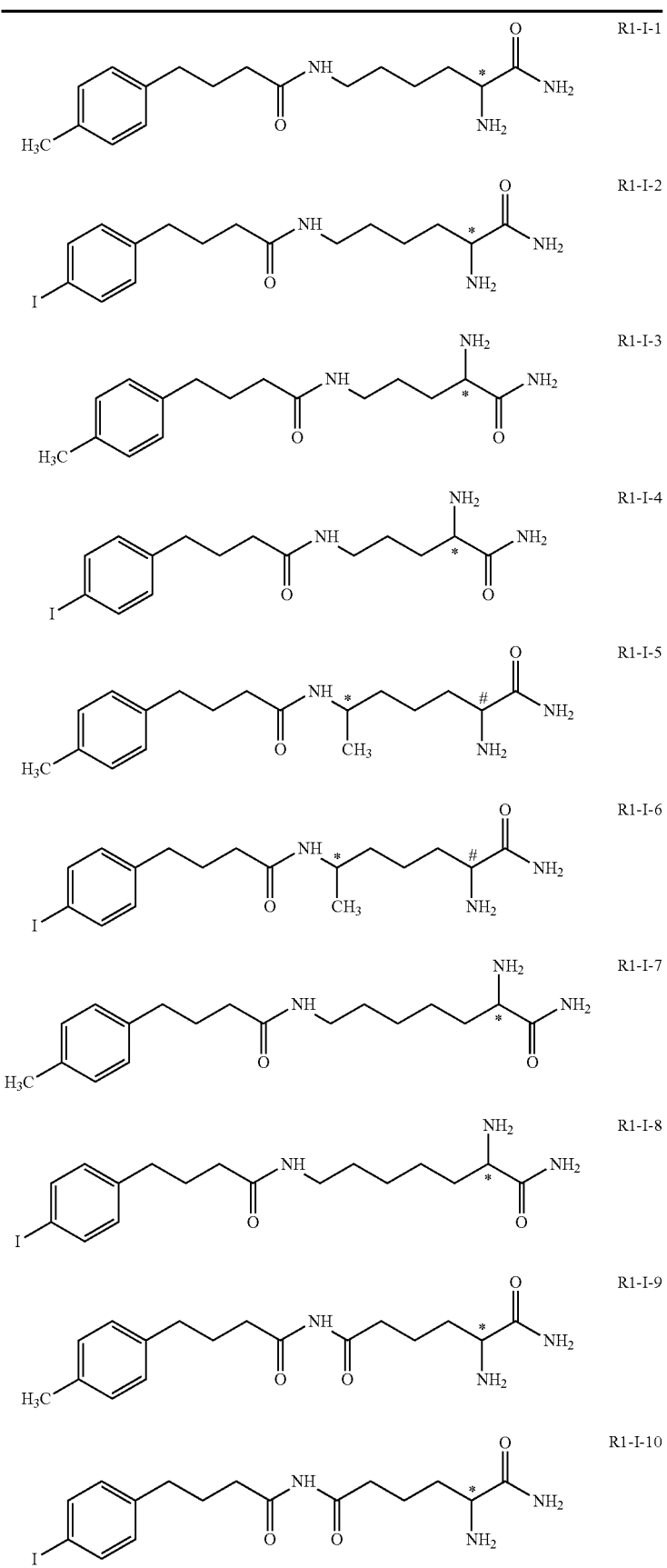

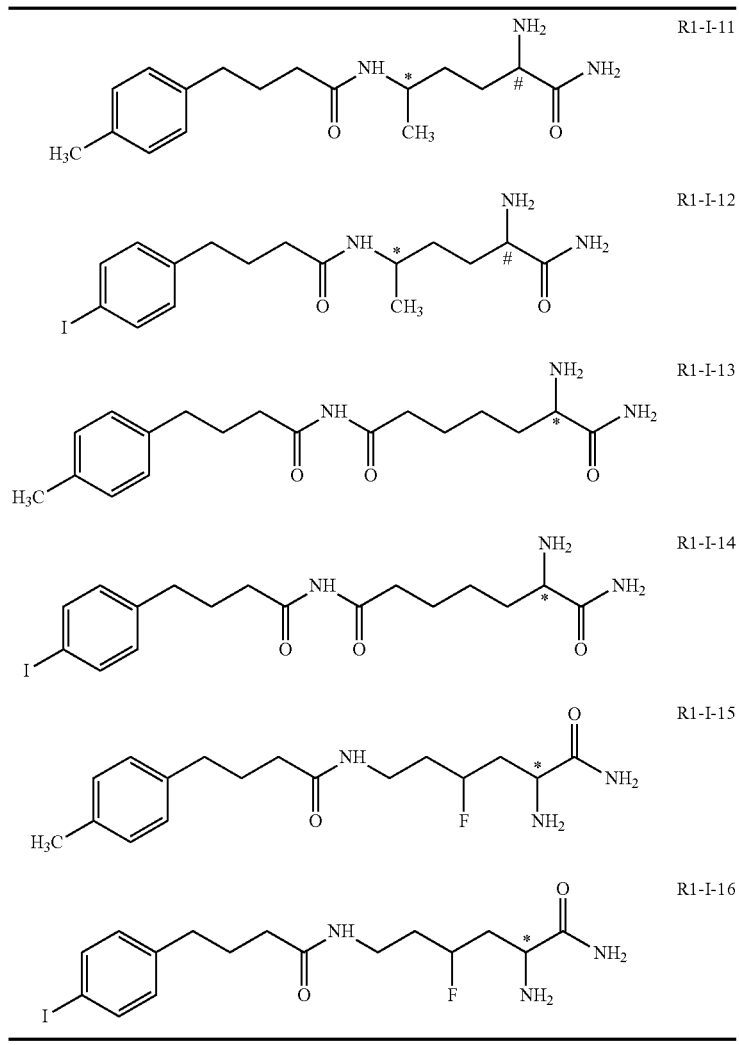

a symbol "*" or "#" in any structure of the set of R1-I indicates a position of an optically active carbon having a configuration selected from R or S;

wherein the structures of the set of R2-I are shown as below:

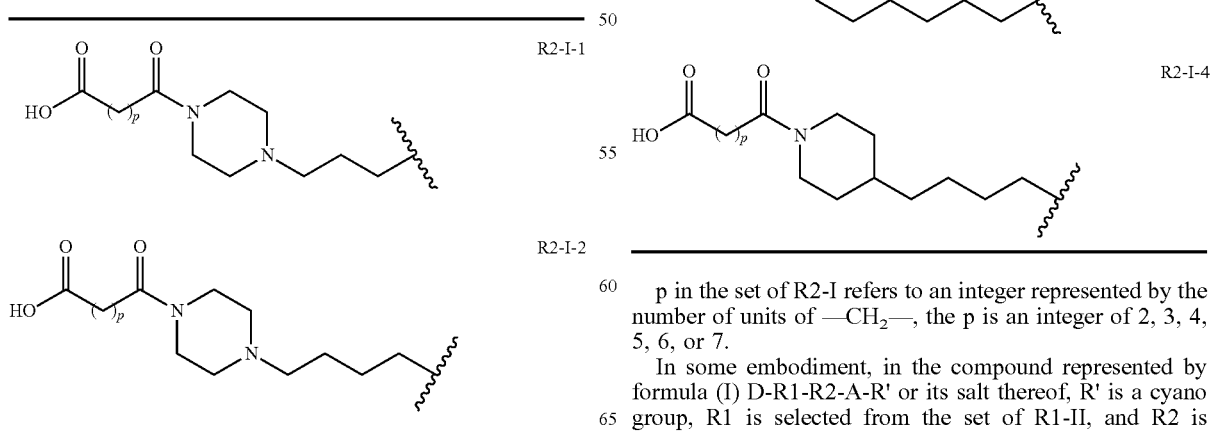

p in the set of R2-I refers to an integer represented by the number of units of —$CH_2$—, the p is an integer of 2, 3, 4, 5, 6, or 7.

In some embodiment, in the compound represented by formula (I) D-R1-R2-A-R' or its salt thereof, R' is a cyano group, R1 is selected from the set of R1-II, and R2 is selected from the set of R2-II, wherein the set of R1-II includes R1-II-1, R1-II-2, R1-II-3, R1-II-4, R1-II-5, R1-II- 6, R1-II-7, R1-II-8, R1-II-9, R1-II-10, R1-II-11, R1-II-12, R1-II-13, R1-II-14, R1-II-15, R1-II-16, R1-II-17, R1-II-18, R1-II-19, R1-II-20, R1-II-21, R1-II-22, R1-II-23, R1-II-24, R1-II-25, R1-II-26, R1-II-27, R1-II-28, wherein the set of R2-II includes R2-II-1, R2-II-2, R2-II-3, R2-II-4, R2-II-5, R2-II-6, R2-II-7, R2-II-8, R2-II-9, R2-II-10, R2-II-11, R2-II-12, R2-II-13, R2-II-14, R2-II-15, R2-II-16, R2-II-17, R2-II-18, R2-II-19, R2-II-20, R2-II-21, R2-II-22, R2-II-23, R2-II-24;
wherein the structures of the set of R1-II are shown as below:
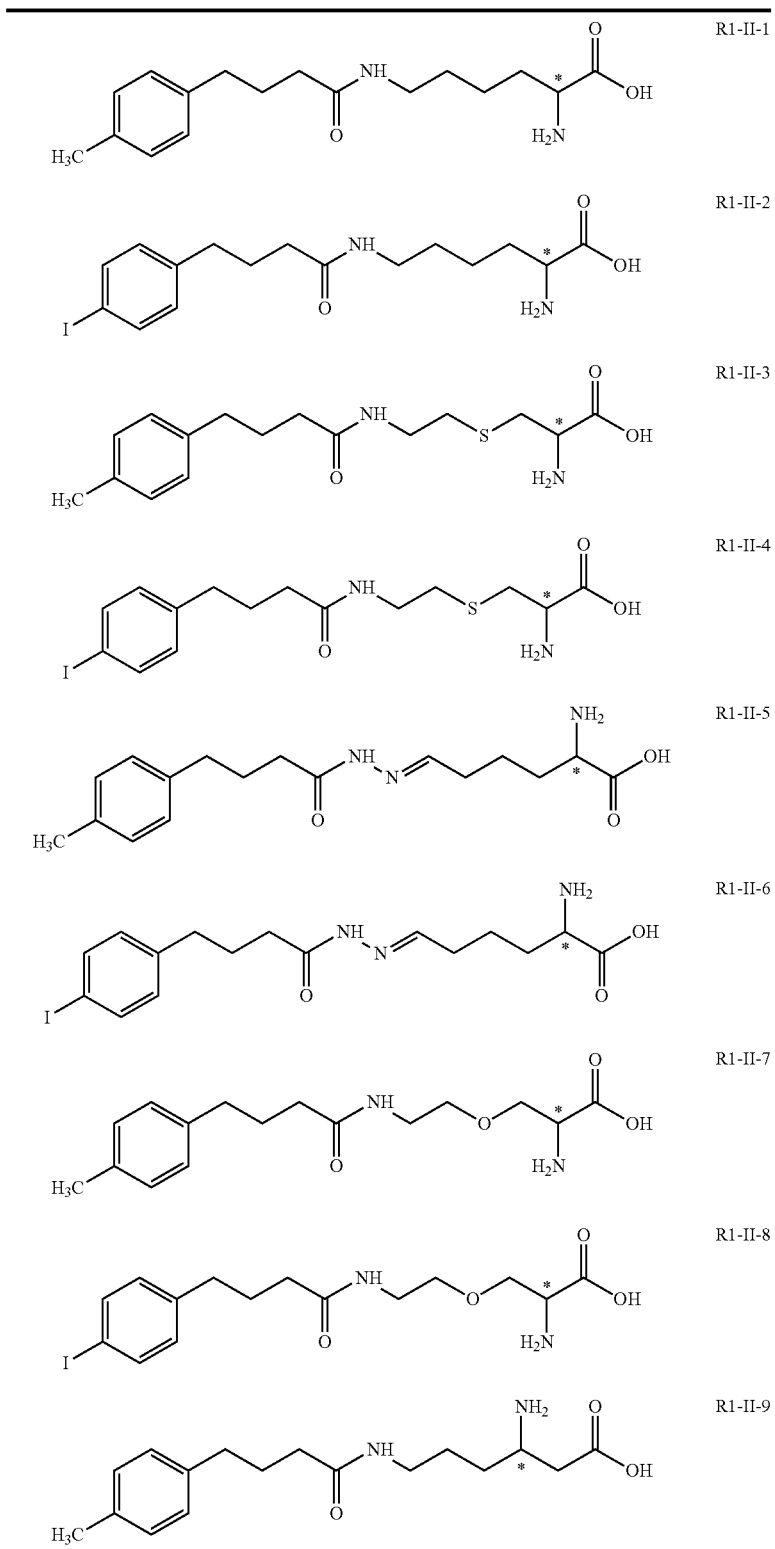

-continued
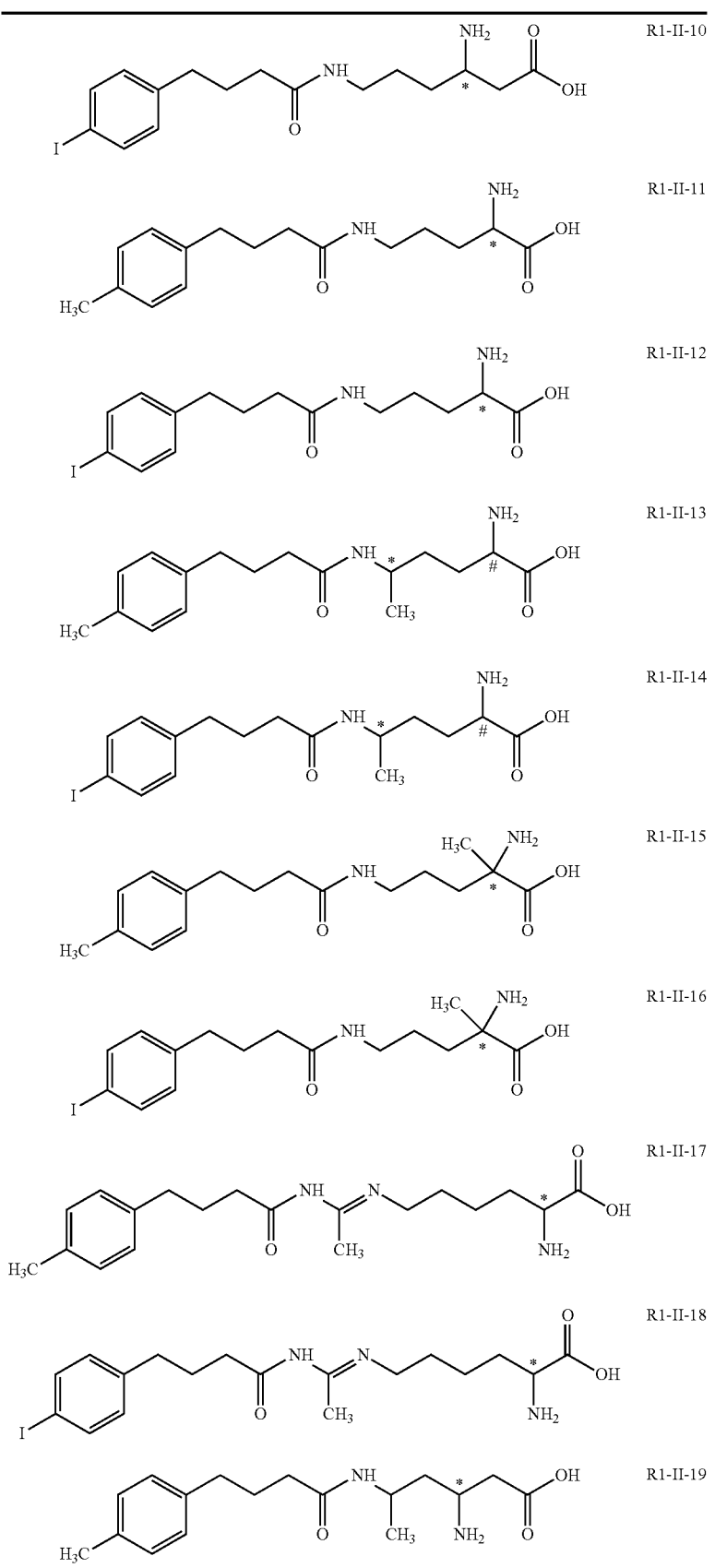

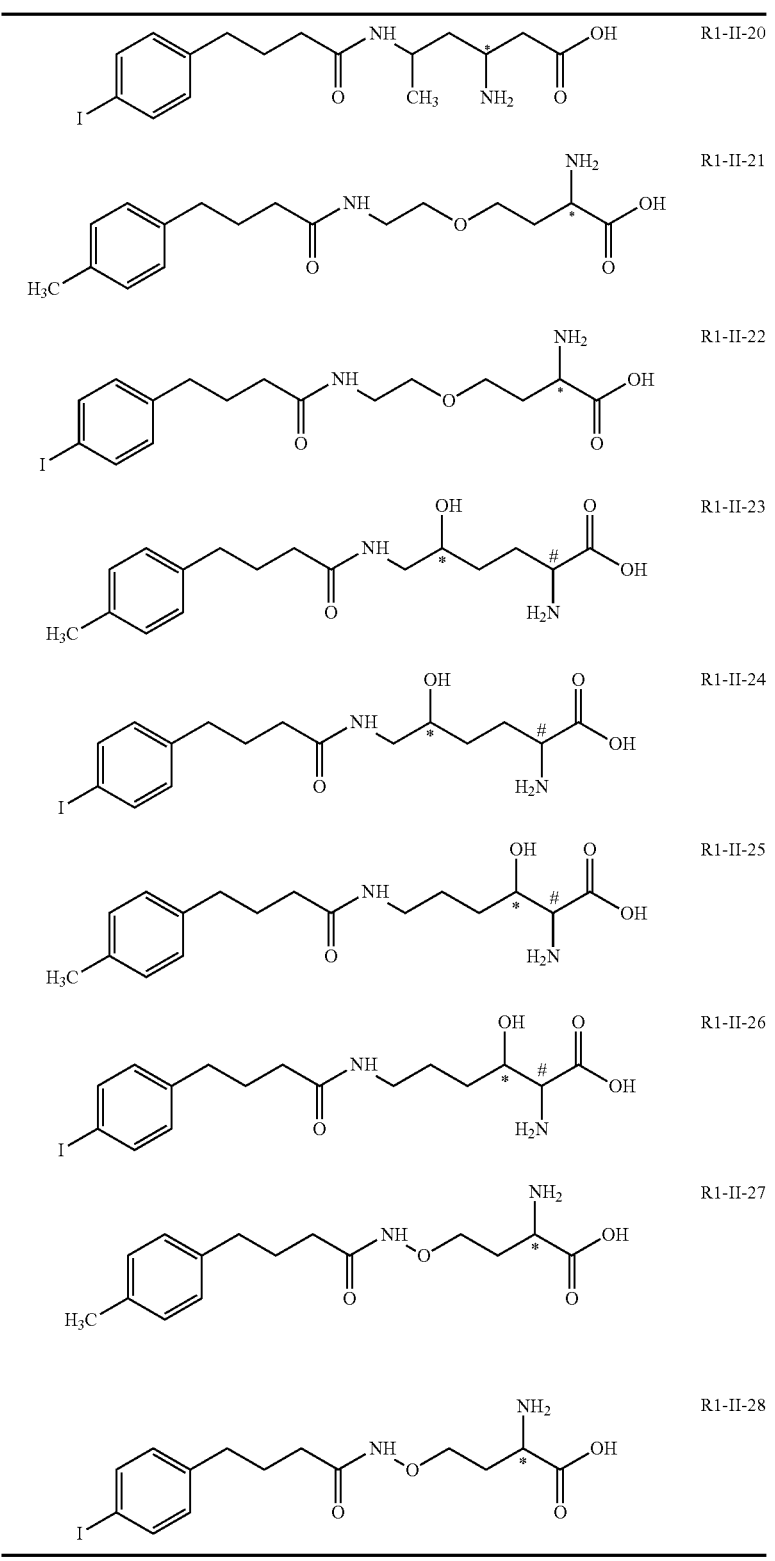
a symbol "*" or "#" in any structure of the set of R1-II indicates a position of an optically active carbon having a configuration selected from R or S;
wherein the structures of the set of R2-II are shown as below:

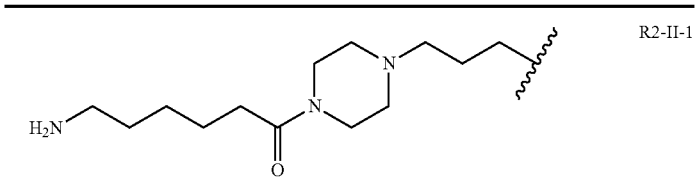
R2-II-1
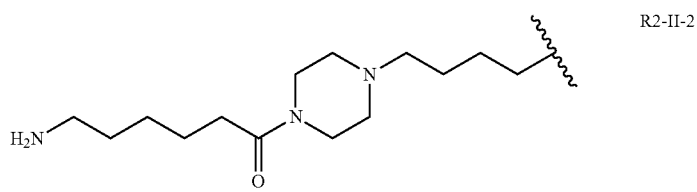
R2-II-2
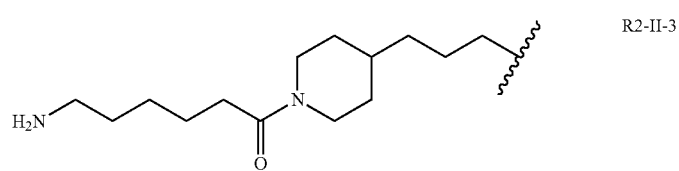
R2-II-3
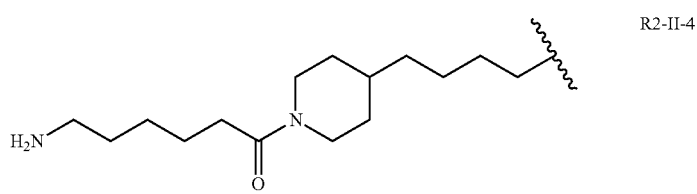
R2-II-4
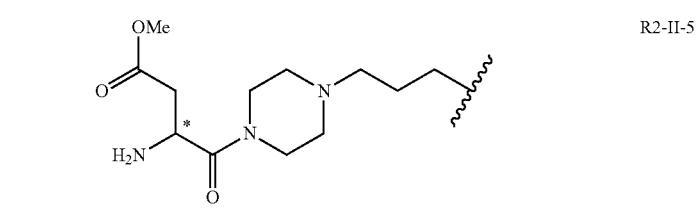
R2-II-5
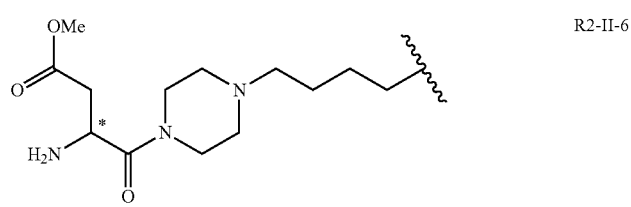
R2-II-6
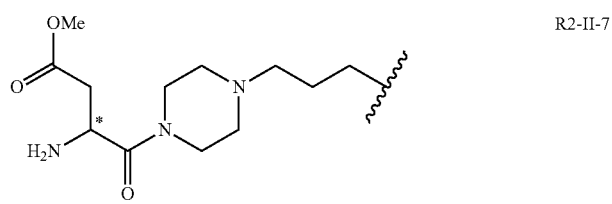
R2-II-7
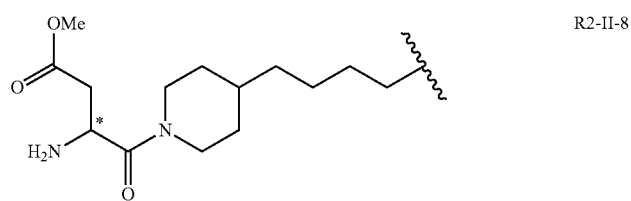
R2-II-8

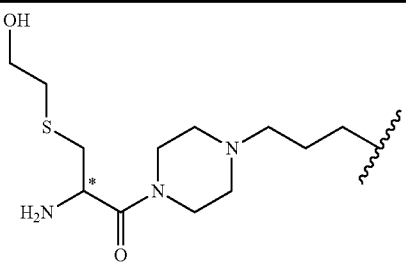 R2-II-9
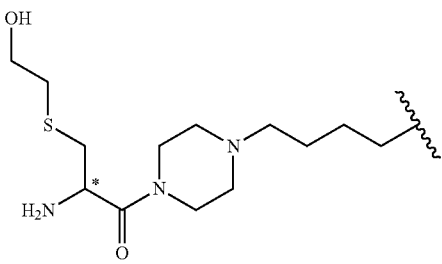 R2-II-10
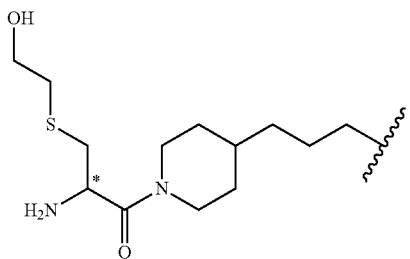 [SMILES: *CCCC1CCN(C(=O)C(N)CSCCO)CC1] R2-II-11
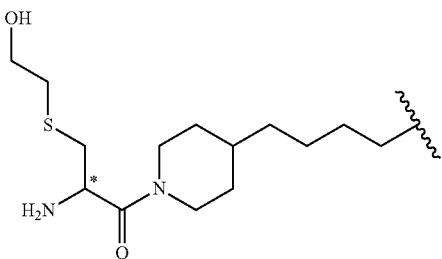 [SMILES: *CCCCC1CCN(C(=O)C(N)CSCCO)CC1] R2-II-12
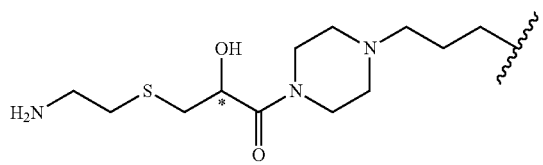 R2-II-13
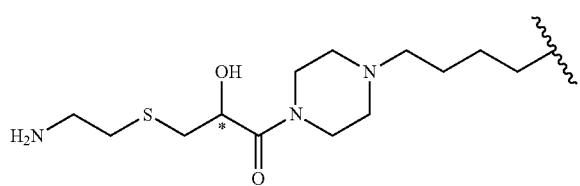 [SMILES: *CCCCN1CCN(C(=O)C(O)CSCCN)CC1] R2-II-14
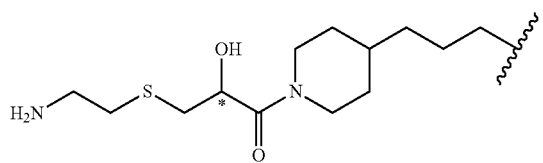 [SMILES: *CCCC1CCN(C(=O)C(O)CSCCN)CC1] R2-II-15

-continued
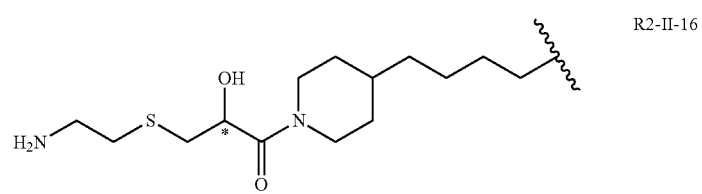
R2-II-16
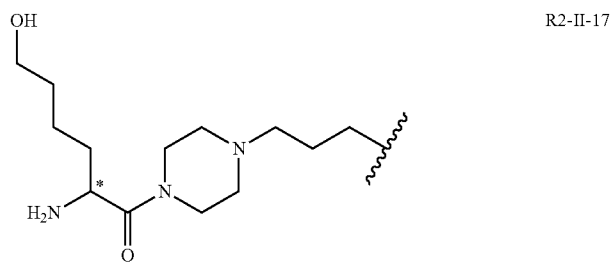
R2-II-17
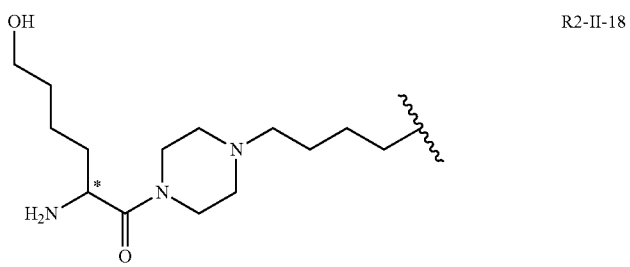
R2-II-18
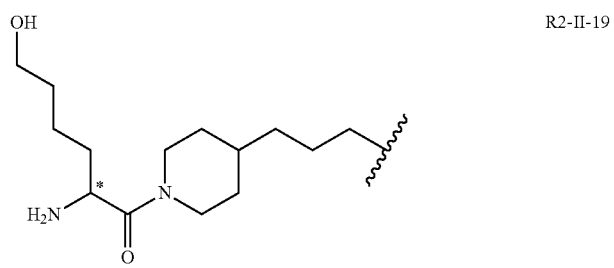
R2-II-19
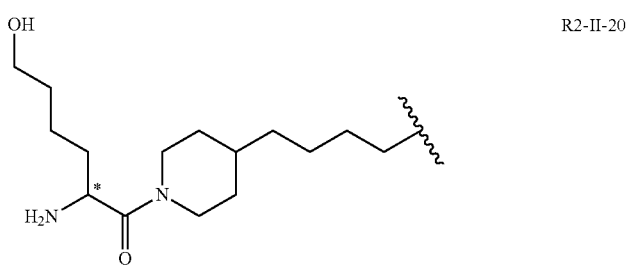
R2-II-20
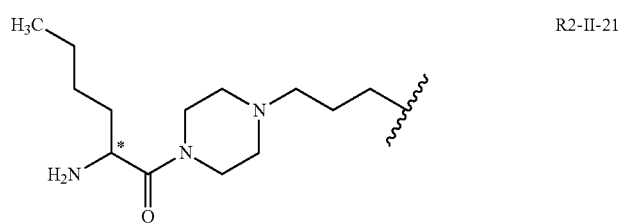
R2-II-21

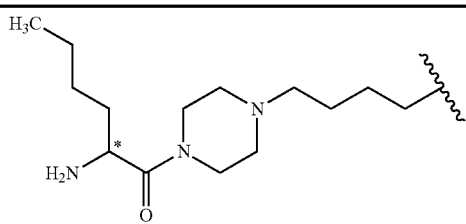

R2-II-22

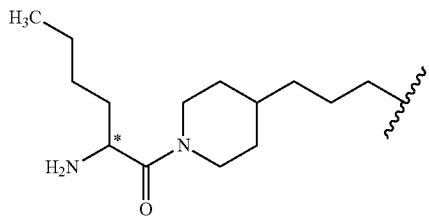

R2-II-23

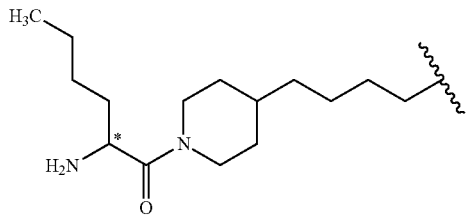 [SMILES: *CCCCC1CCN(C(=O)C(N)CCCC)CC1]

R2-II-24 a symbol "*" or "#" in any structure of the set of R2-II indicates a position of an optically active carbon having a configuration selected from R or S.

In some embodiments, in the compound represented by formula (I) D-R1-R2-A-R' or its salt thereof, R' is a cyano group, R1 is selected from the set of R1-III, and R2 is selected from the set of R2-III, wherein the set of R1-III includes R1-III-1, R1-III-2, R1-III-3, R1-III-4, R1-III-5, R1-III-6, R1-III-7, R1-III-8, R1-III-9, R1-III-10, R1-III-11, R1-III-12, wherein the set of R2-III includes R2-III-1, R2-III-2, R2-III-3, R2-III-4, R2-III-5, R2-III-6, R2-III-7, R2-III-8, R2-III-9, R2-III-10, R2-III-11, R2-III-12, R2-III-13, R2-III-14, R2-III-15, R2-III-16, R2-III-17, R2-III-18, R2-III-19, R2-III-20;

wherein the structures of the set of R1-III are shown as below:

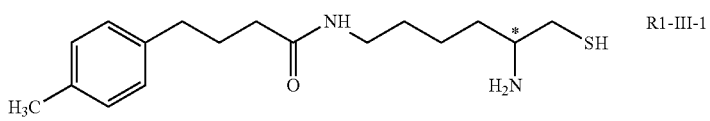

R1-III-1

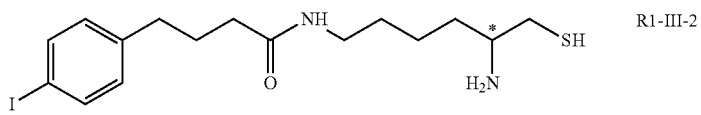

R1-III-2

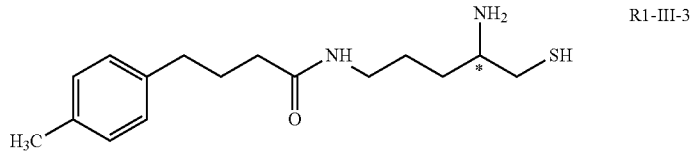

R1-III-3

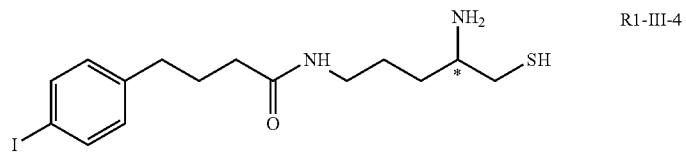

R1-III-4

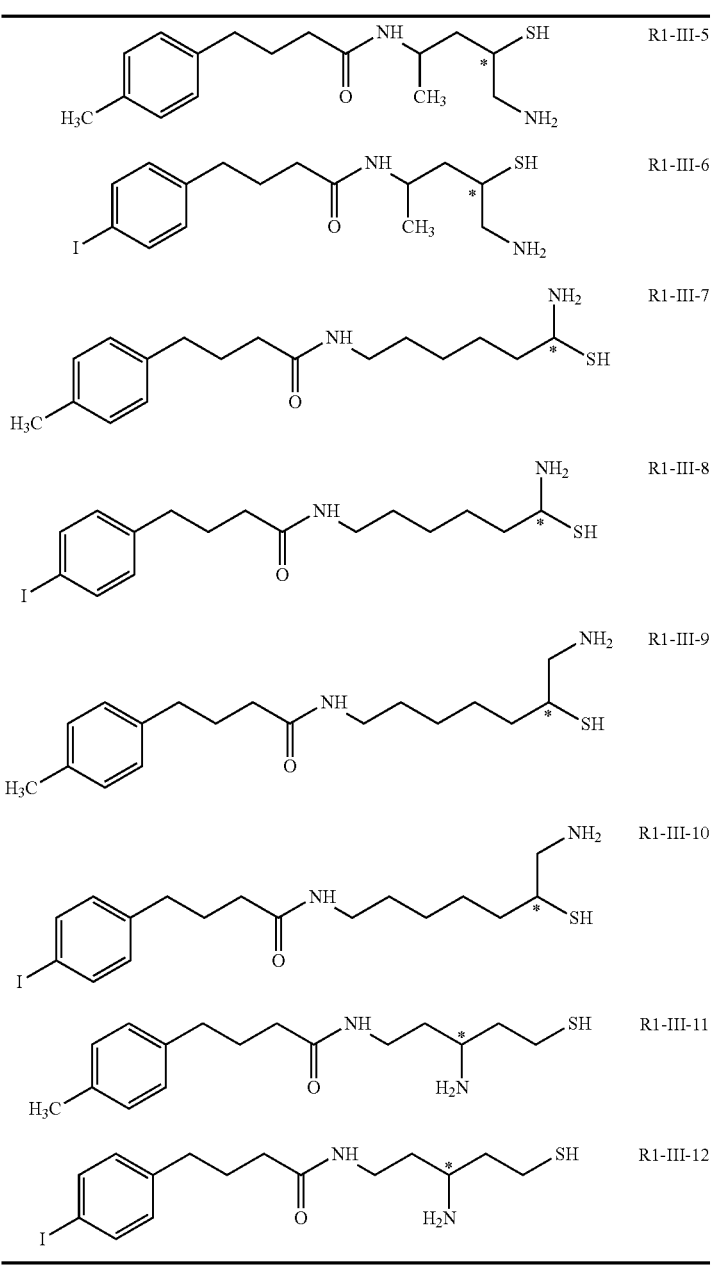
a symbol "*" in any structure of the set of R1-III indicates a position of an optically active carbon having a configuration selected from R or S;
wherein the structures of the set of R2-III are shown as below:
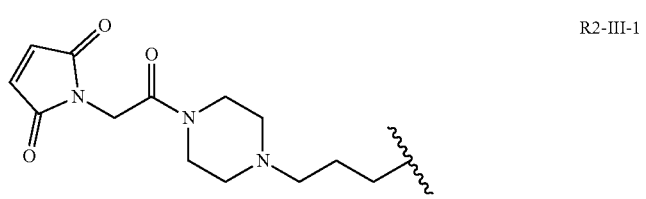

-continued
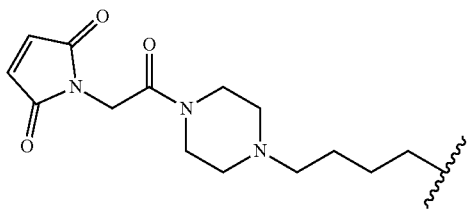 [SMILES: *CCCCN1CCN(C(=O)CN2C(=O)C=CC2=O)CC1]
R2-III-2
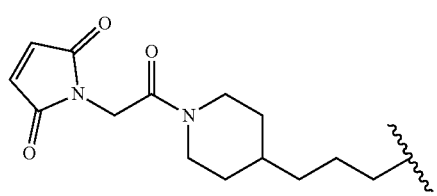 [SMILES: *CCCC1CCN(C(=O)CN2C(=O)C=CC2=O)CC1]
R2-III-3
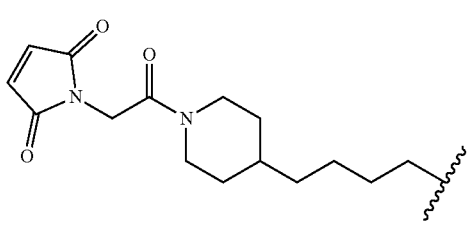 [SMILES: *CCCCC1CCN(C(=O)CN2C(=O)C=CC2=O)CC1]
R2-III-4
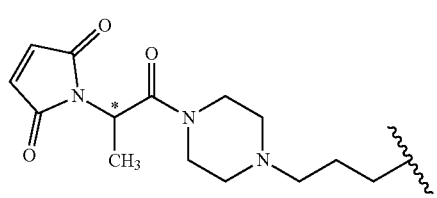 [SMILES: *CCCN1CCN(C(=O)C(C)N2C(=O)C=CC2=O)CC1]
R2-III-5
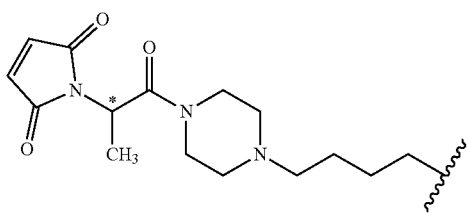 [SMILES: *CCCCN1CCN(C(=O)C(C)N2C(=O)C=CC2=O)CC1]
R2-III-6
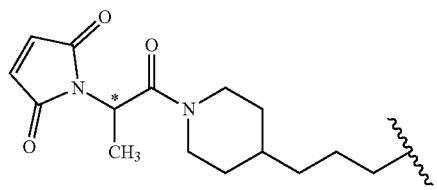 [SMILES: *CCCC1CCN(C(=O)C(C)N2C(=O)C=CC2=O)CC1]
R2-III-7
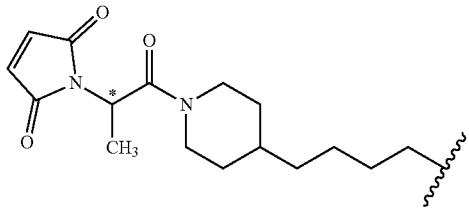 [SMILES: *CCCCC1CCN(C(=O)C(C)N2C(=O)C=CC2=O)CC1]
R2-III-8
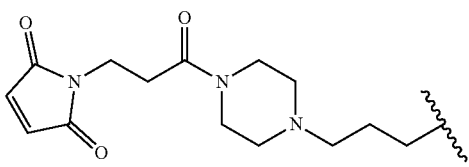 [SMILES: *CCCN1CCN(C(=O)CCN2C(=O)C=CC2=O)CC1]
R2-III-9

-continued
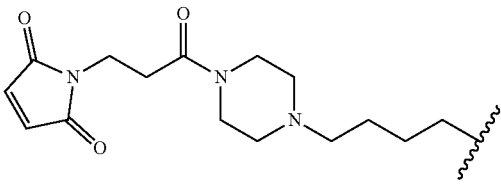 [SMILES: *CCCCN1CCN(C(=O)CCN2C(=O)C=CC2=O)CC1] R2-III-10
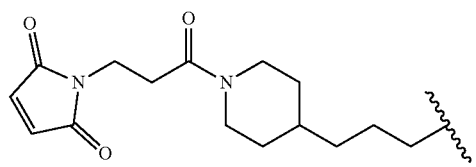 [SMILES: *CCCC1CCN(C(=O)CCN2C(=O)C=CC2=O)CC1] R2-III-11
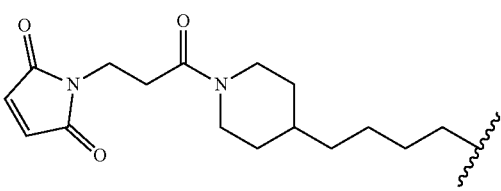 [SMILES: *CCCCC1CCN(C(=O)CCN2C(=O)C=CC2=O)CC1] R2-III-12
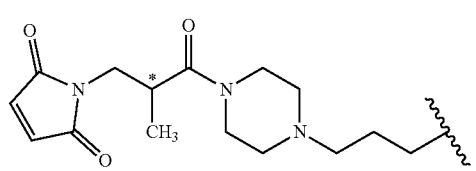 R2-III-13
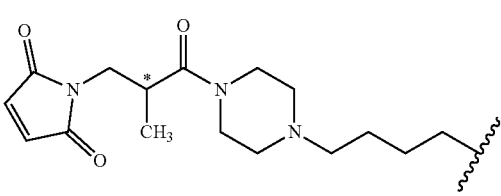 [SMILES: *CCCCN1CCN(C(=O)C(C)CN2C(=O)C=CC2=O)CC1] R2-III-14
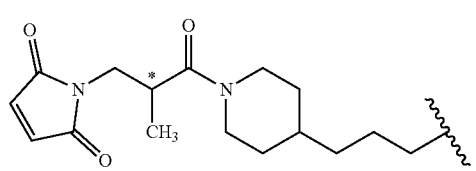 [SMILES: *CCCC1CCN(C(=O)C(C)CN2C(=O)C=CC2=O)CC1] R2-III-15
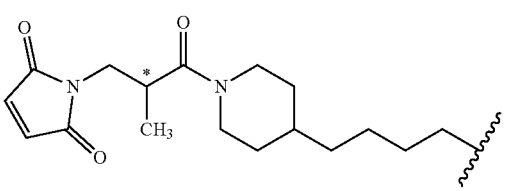 [SMILES: *CCCCC1CCN(C(=O)C(C)CN2C(=O)C=CC2=O)CC1] R2-III-16
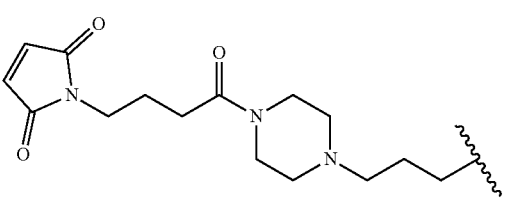 [SMILES: *CCCN1CCN(C(=O)CCCN2C(=O)C=CC2=O)CC1] R2-III-17

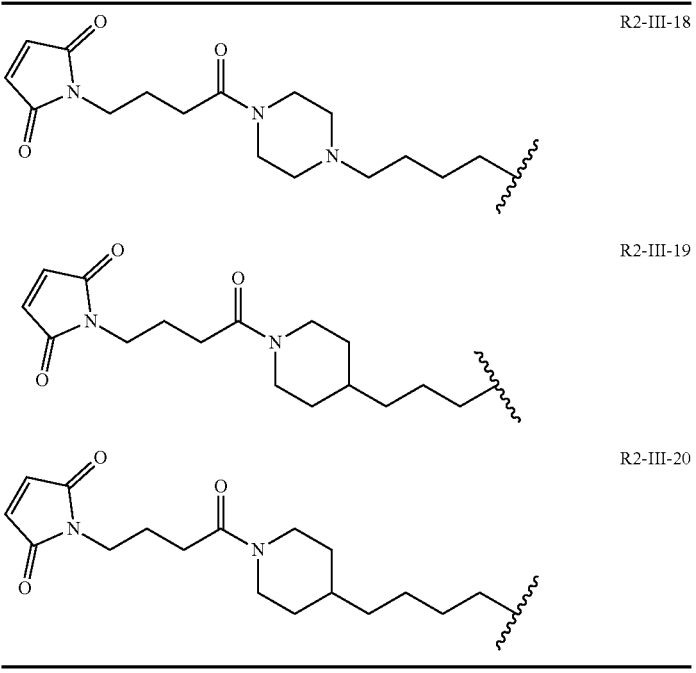

a symbol "*" in any structure of the set of R2-III indicates a position of an optically active carbon having a configuration selected from R or S.

In some embodiment, in the compound represented by formula (I) D-R1-R2-A-R' or its salt thereof, R' is a cyano group, R1 is selected from the set of R1-IV, and R2 is selected from the set of R2-IV, wherein the set of R1-IV includes R1-IV-1, R1-IV-2, wherein the set of R2-IV includes R2-IV-1, R2-IV-2, R2-IV-3, R2-IV-4, R2-IV-5, R2-IV-6, R2-IV-7, R2-IV-8, R2-IV-9, R2-IV-10, R2-IV-11, R2-IV-12;

wherein the structures of the set of R1-IV are shown as below:

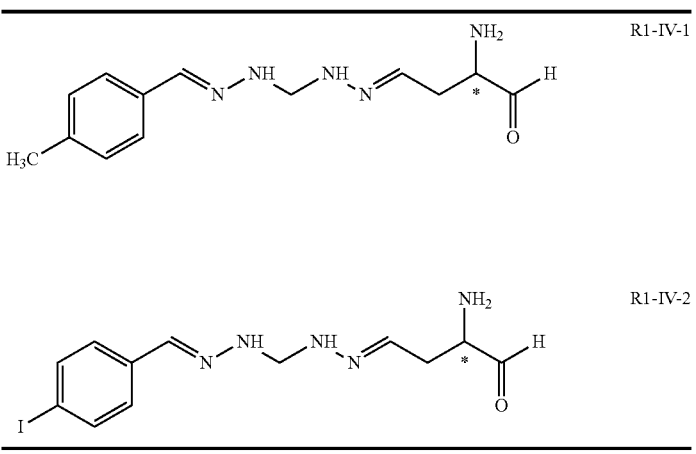

a symbol "*" in any structure of the set of R1-IV indicates a position of an optically active carbon having a configuration selected from R or S;

wherein the structures of the set of R2-IV are shown as below:

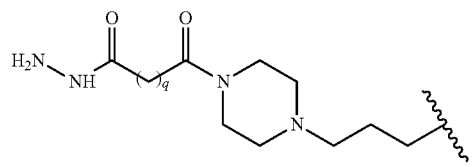 R2-IV-1
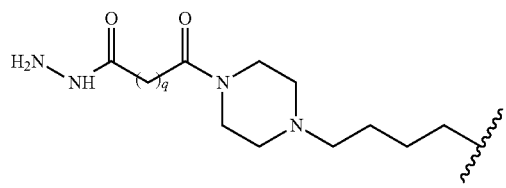 R2-IV-2
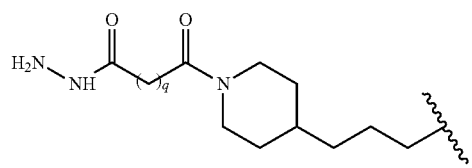 R2-IV-3
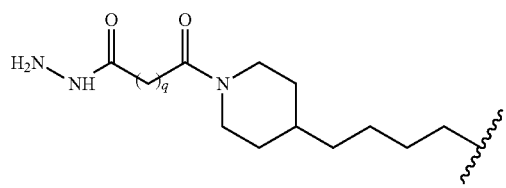 R2-IV-4
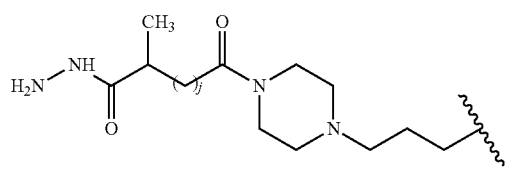 R2-IV-5
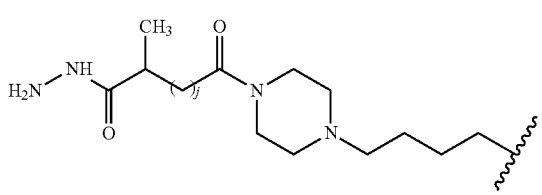 R2-IV-6
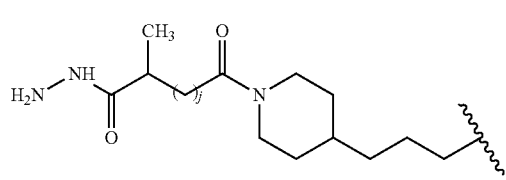 R2-IV-7
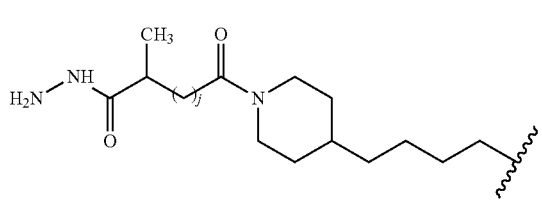 R2-IV-8
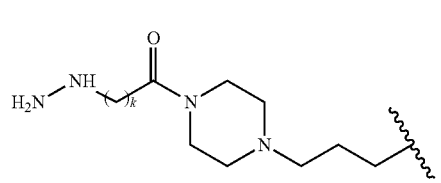 R2-IV-9

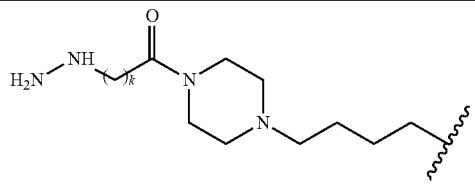

R2-IV-10

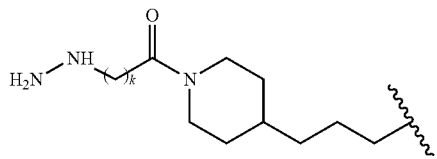

R2-IV-11

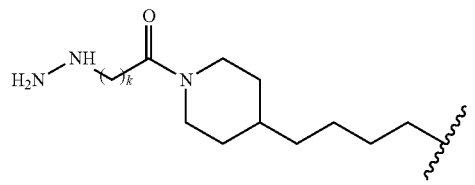

R2-IV-12 each of q, j and k in the set of R2-IV refers to an integer represented by the number of units of —$CH_2$—, wherein the q is an integer of 2, 3, 4, 5, 6 or 7, the j is an integer of 1, 2 or 4, the k is an integer of 1, 2 or 3.

In some embodiment, in the compound represented by formula (I) D-R1-R2-A-R' or its salt thereof, R' is a cyano group, R1 is selected from the set of R1-V, and R2 is selected from the set of R2-V, wherein the set of R1-V includes R1-IV-1, R1-IV-2, wherein the set of R2-V includes R2-V-1, R2-V-2, R2-V-3, R2-V-4;

wherein the structures of the set of R1-V are shown as below:

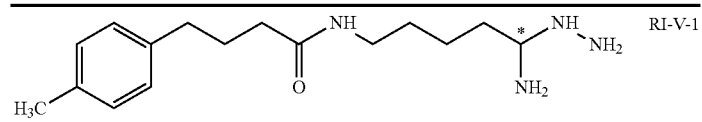

RI-V-1

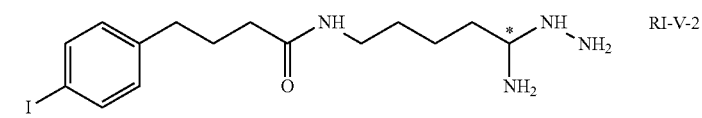

RI-V-2 a symbol "*" in any structure of the set of R1-V indicates a position of an optically active carbon having a configuration selected from R or S;

wherein the structures of the set of R2-V are shown as below:

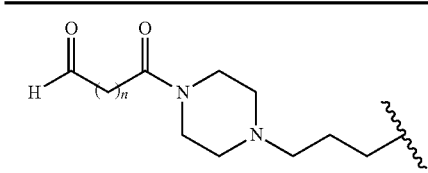

R2-V-1

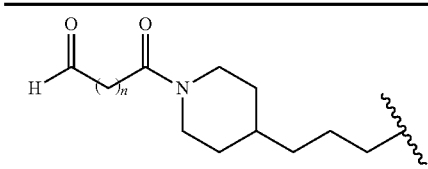

R2-V-2

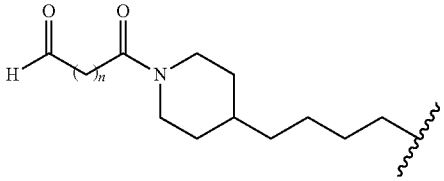

R2-V-3

R2-V-4 n in the set of R2-V refers to an integer represented by the number of units of —$CH_2$—, the n is an integer of 2, 3, 4, 5, 6 or 7.

Example 1: R' is a cyano group, R1 is selected from the set of R1-I, and R2 is selected from the set of R2-I according to a compound represented by formula (I) D-R1-R2-A-R' or its salt thereof:

| Code | R1 | R2 | [M + H]$^+$ |
|---|---|---|---|
| FAPI-INER-01-R | R1-I-1(R) | R2-I-1(5) | 1302.6 |
| FAPI-INER-01-S | R1-I-1(S) | R2-I-1(5) | 1302.6 |
| FAPI-INER-02-R | R1-I-1(R) | R2-I-2(5) | 1316.6 |
| FAPI-INER-02-S | R1-I-1(S) | R2-I-2(5) | 1316.6 |

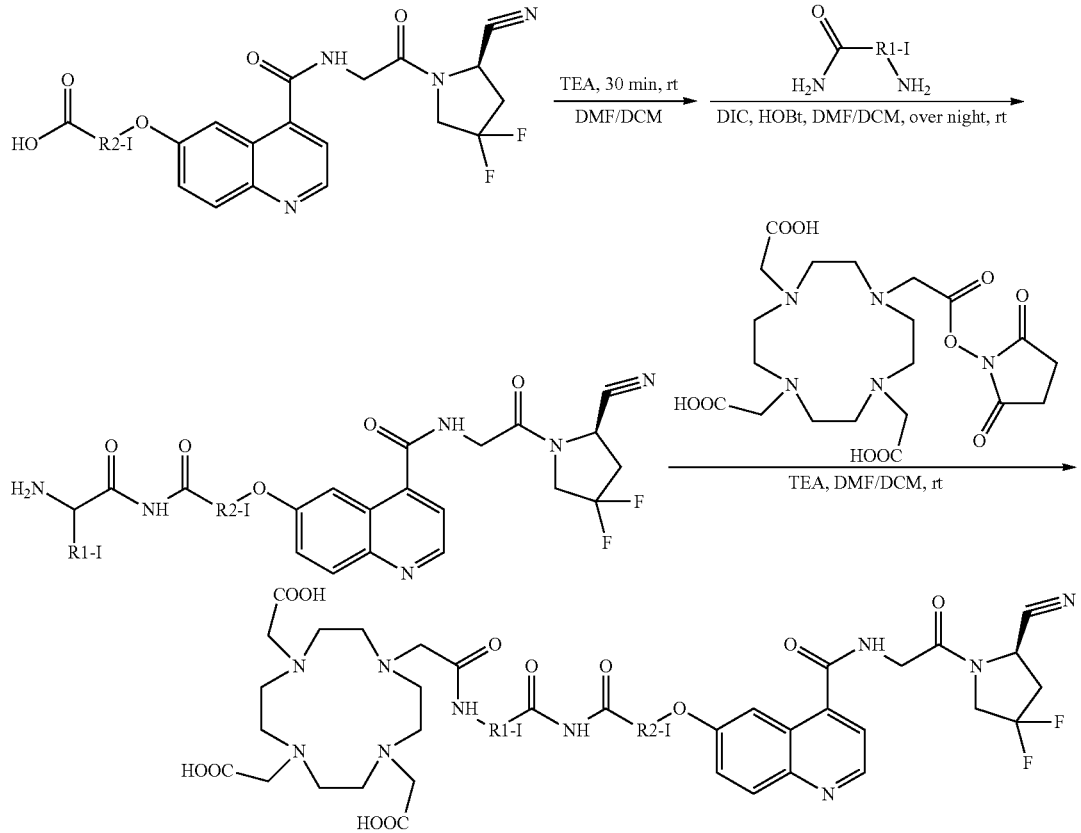

DMF/DCM mixed solution was composed of dimethylformamide (DMF) and dichloromethane (DCM) (DMF volume:DCM volume=1:1). 1 equivalent of R2-I connected to A was dissolved in DMF/DCM mixed solution, and 1.2 to 1.5 equivalents of triethylamine (TEA) was added to react at room temperature for 30 minutes. Next, DMF/DCM mixed solution containing equivalent of R1-I, 1 equivalent of N,N'-diisopropylcarbodiimide (DIC) and 1 equivalent of hydroxybenzotriazole (HOBt) was added to react overnight at room temperature, and 1 equivalent of purified product was dissolved in DMF/DCM mixed solution, and then the DMF/DCM mixed solution containing 1 equivalent of 1,4,7,10-tetraacetic acid 1-(2,5-dioxo-1-pyrrolidinyl) ester (also known as DOTA-NHS ester) and 1.2 to 1.5 equivalents of TEA was added to react at room temperature for 3 hours.

After performing preparative medium pressure liquid chromatography (MPLC) with purification by acetonitrile (ACN)/water gradient elution and analyzing [M+H]$^+$ by mass spectrometry to determine the molecular weight, the charge-to-mass ratio (m/z) of the compound as formula (I) D-R1-R2-A-R' or its salt thereof was obtained:

-continued

| Code | R1 | R2 | [M + H]$^+$ |
|---|---|---|---|
| FAPI-INER-03-R | R1-I-1(R) | R2-I-3(5) | 1301.6 |
| FAPI-INER-03-S | R1-I-1(S) | R2-I-3(5) | 1301.6 |
| FAPI-INER-04-R | R1-I-1(R) | R2-I-4(5) | 1315.6 |
| FAPI-INER-04-S | R1-I-1(S) | R2-I-4(5) | 1315.6 |
| FAPI-INER-05-R | R1-I-2(R) | R2-I-1(5) | 1414.5 |
| FAPI-INER-05-S | R1-I-2(S) | R2-I-1(5) | 1414.5 |
| FAPI-INER-06-R | R1-I-2(R) | R2-I-2(5) | 1428.5 |
| FAPI-INER-06-S | R1-I-2(S) | R2-I-2(5) | 1428.5 |
| FAPI-INER-07-R | R1-I-2(R) | R2-I-3(5) | 1413.5 |
| FAPI-INER-07-S | R1-I-2(S) | R2-I-3(5) | 1413.5 |
| FAPI-INER-08-R | R1-I-2(R) | R2-I-4(5) | 1397.5 |
| FAPI-INER-08-S | R1-I-2(S) | R2-I-4(5) | 1397.5 |
| FAPI-INER-09-R | R1-I-7(R) | R2-I-1(5) | 1316.6 |
| FAPI-INER-09-S | R1-I-7(S) | R2-I-1(5) | 1316.6 |
| FAPI-INER-10-R | R1-I-7(R) | R2-I-2(5) | 1330.7 |
| FAPI-INER-10-S | R1-I-7(S) | R2-I-2(5) | 1330.7 |
| FAPI-INER-11-R | R1-I-7(R) | R2-I-3(5) | 1315.6 |
| FAPI-INER-11-S | R1-I-7(S) | R2-I-3(5) | 1315.6 |
| FAPI-INER-12-R | R1-I-7(R) | R2-I-4(5) | 1329.7 |
| FAPI-INER-12-S | R1-I-7(S) | R2-I-4(5) | 1329.7 |
| FAPI-INER-13-R | R1-I-8(R) | R2-I-1(5) | 1428.5 |
| FAPI-INER-13-S | R1-I-8(S) | R2-I-1(5) | 1428.5 |
| FAPI-INER-14-R | R1-I-8(R) | R2-I-2(5) | 1442.5 |
| FAPI-INER-14-S | R1-I-8(S) | R2-I-2(5) | 1442.5 |
| FAPI-INER-15-R | R1-I-8(R) | R2-I-3(5) | 1427.5 |

| Code | R1 | R2 | [M + H]⁺ |
|---|---|---|---|
| FAPI-INER-15-S | R1-I-8(S) | R2-I-3(5) | 1427.5 |
| FAPI-INER-16-R | R1-I-8(R) | R2-I-4(5) | 1441.5 |
| FAPI-INER-16-S | R1-I-8(S) | R2-I-4(5) | 1441.5 |
| FAPI-INER-17-RR | R1-I-11(RR) | R2-I-1(5) | 1302.6 |
| FAPI-INER-17-RS | R1-I-11(RS) | R2-I-1(5) | 1302.6 |
| FAPI-INER-17-SR | R1-I-11(SR) | R2-I-1(5) | 1302.6 |
| FAPI-INER-17-SS | R1-I-11(SS) | R2-I-1(5) | 1302.6 |
| FAPI-INER-18-RR | R1-I-11(RR) | R2-I-2(5) | 1316.6 |
| FAPI-INER-18-RS | R1-I-11(RS) | R2-I-2(5) | 1316.6 |
| FAPI-INER-18-SR | R1-I-11(SR) | R2-I-2(5) | 1316.6 |
| FAPI-INER-18-SS | R1-I-11(SS) | R2-I-2(5) | 1316.6 |
| FAPI-INER-19-RR | R1-I-11(RR) | R2-I-3(5) | 1301.6 |
| FAPI-INER-19-RS | R1-I-11(RS) | R2-I-3(5) | 1301.6 |
| FAPI-INER-19-SR | R1-I-11(SR) | R2-I-3(5) | 1301.6 |
| FAPI-INER-19-SS | R1-I-11(SS) | R2-I-3(5) | 1301.6 |
| FAPI-INER-20-RR | R1-I-11(RR) | R2-I-4(5) | 1315.6 |
| FAPI-INER-20-RS | R1-I-11(RS) | R2-I-4(5) | 1315.6 |
| FAPI-INER-20-SR | R1-I-11(SR) | R2-I-4(5) | 1315.6 |
| FAPI-INER-20-SS | R1-I-11(SS) | R2-I-4(5) | 1315.6 |
| FAPI-INER-21-RR | R1-I-12(RR) | R2-I-1(5) | 1414.5 |
| FAPI-INER-21-RS | R1-I-12(RS) | R2-I-1(5) | 1414.5 |
| FAPI-INER-21-SR | R1-I-12(SR) | R2-I-1(5) | 1414.5 |
| FAPI-INER-21-SS | R1-I-12(SS) | R2-I-1(5) | 1414.5 |
| FAPI-INER-22-RR | R1-I-12(RR) | R2-I-2(5) | 1428.5 |
| FAPI-INER-22-RS | R1-I-12(RS) | R2-I-2(5) | 1428.5 |
| FAPI-INER-22-SR | R1-I-12(SR) | R2-I-2(5) | 1428.5 |
| FAPI-INER-22-SS | R1-I-12(SS) | R2-I-2(5) | 1428.5 |
| FAPI-INER-23-RR | R1-I-12(RR) | R2-I-3(5) | 1413.5 |
| FAPI-INER-23-RS | R1-I-12(RS) | R2-I-3(5) | 1413.5 |
| FAPI-INER-23-SR | R1-I-12(SR) | R2-I-3(5) | 1413.5 |
| FAPI-INER-23-SS | R1-I-12(SS) | R2-I-3(5) | 1413.5 |
| FAPI-INER-24-RR | R1-I-12(RR) | R2-I-4(5) | 1427.5 |
| FAPI-INER-24-RS | R1-I-12(RS) | R2-I-4(5) | 1427.5 |
| FAPI-INER-24-SR | R1-I-12(SR) | R2-I-4(5) | 1427.5 |
| FAPI-INER-24-SS | R1-I-12(SS) | R2-I-4(5) | 1427.5 |
| FAPI-INER-25-R | R1-I-15(R) | R2-I-1(5) | 1320.6 |
| FAPI-INER-25-S | R1-I-15(S) | R2-I-1(5) | 1320.6 |
| FAPI-INER-26-R | R1-I-15(R) | R2-I-2(5) | 1334.6 |
| FAPI-INER-26-S | R1-I-15(S) | R2-I-2(5) | 1334.6 |
| FAPI-INER-27-R | R1-I-15(R) | R2-I-3(5) | 1319.6 |
| FAPI-INER-27-S | R1-I-15(S) | R2-I-3(5) | 1319.6 |
| FAPI-INER-28-R | R1-I-15(R) | R2-I-4(5) | 1333.6 |
| FAPI-INER-28-S | R1-I-15(S) | R2-I-4(5) | 1333.6 |
| FAPI-INER-29-R | R1-I-16(R) | R2-I-1(5) | 1432.5 |
| FAPI-INER-29-S | R1-I-16(S) | R2-I-1(5) | 1432.5 |
| FAPI-INER-30-R | R1-I-16(R) | R2-I-2(5) | 1446.5 |
| FAPI-INER-30-S | R1-I-16(S) | R2-I-2(5) | 1446.5 |
| FAPI-INER-31-R | R1-I-16(R) | R2-I-3(5) | 1431.5 |
| FAPI-INER-31-S | R1-I-16(S) | R2-I-3(5) | 1431.5 |
| FAPI-INER-32-R | R1-I-16(R) | R2-I-4(5) | 1445.5 |
| FAPI-INER-32-S | R1-I-16(S) | R2-I-4(5) | 1445.5 |

The R or S in the brackets in the R1 column represents the configuration of the optically active carbon at "*" in the structures. As in the brackets in the R1 column are two codes, the left is the first code, the right is the second code, and the first code represents the configuration of the optically active carbon at "*", the second code represents the configuration of the optically active carbon at "#". The arabic numerals in the brackets in the R2 column are the integers represented by p; [M + H]⁺ represents the charge-to-mass ratio of the corresponding mass spectrum.

Example 2: R' is a cyano group, R1 is selected from the set of R1-II, and R2 is selected from the set of R2-II according to a compound represented by formula (I) D-R1-R2-A-R' or its salt thereof:

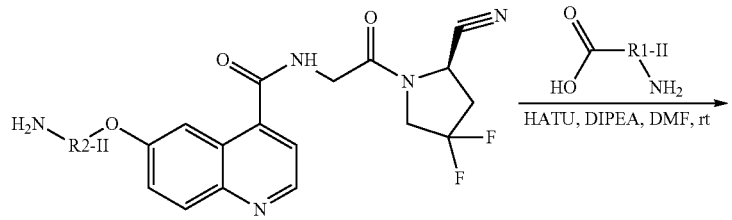

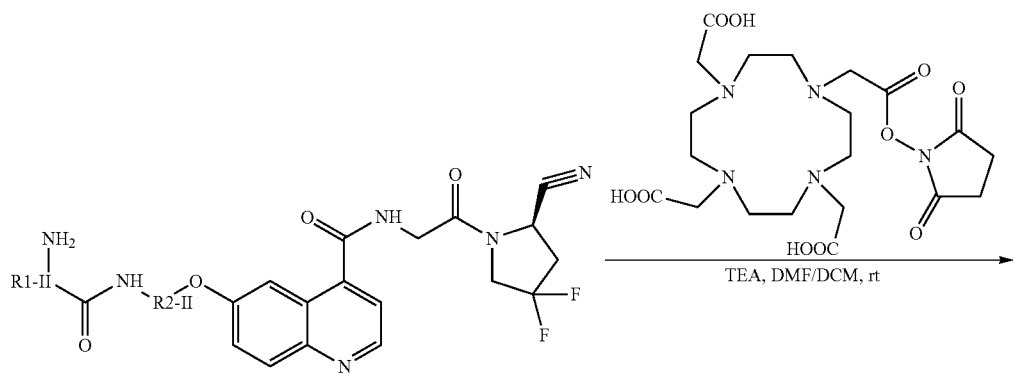

-continued

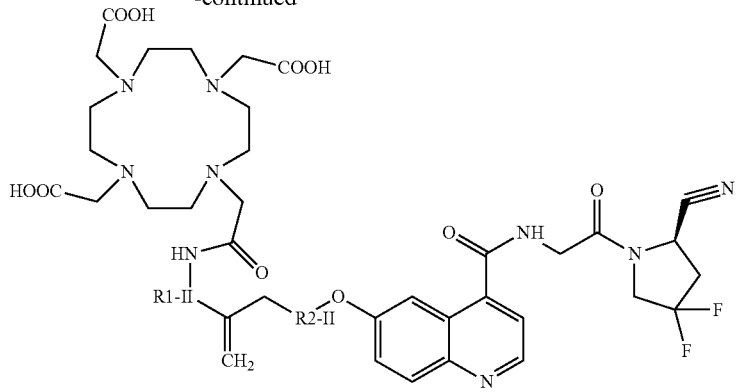

1 equivalent of R2-I connected to A was dissolved in DMF solvent, and DMT solvent containing 1.2 equivalents of 1-[Bis(dimethylamino)methylene]-1H-1,2,3-triazolo[4,5-b]pyridinium 3-oxide hexafluorophosphate (HATU), 1.2 equivalents of N,N-diisopropylethylamine (DIPEA) and 1 equivalent of R1-II was added to react at room temperature. Next, 1 equivalent of purified product was dissolved in DMF/DCM mixed solution (DMF volume:DCM volume=1:1), and then the DMF/DCM mixed solution containing 1 equivalent of DOTA-NHS ester and 1.2 to 1.5 equivalents of TEA was added to react at room temperature for 3 hours.

After performing preparative medium pressure liquid chromatography (MPLC) with purification by acetonitrile/water gradient elution and analyzing [M+H]$^+$ by mass spectrometry to determine the molecular weight, the compound as formula (I) D-R1-R2-A-R' or its salt thereof was obtained as the table below:

| Code | R1 | R2 | [M + H]$^+$ |
| --- | --- | --- | --- |
| FAPI-INER-385-R | R1-II-1(R) | R2-II-1 | 1274.6 |
| FAPI-INER-385-S | R1-II-1(S) | R2-II-1 | 1274.6 |
| FAPI-INER-386-R | R1-II-1(R) | R2-II-2 | 1288.6 |
| FAPI-INER-386-S | R1-II-1(S) | R2-II-2 | 1288.6 |
| FAPI-INER-387-R | R1-II-1(R) | R2-II-3 | 1273.6 |
| FAPI-INER-387-S | R1-II-1(S) | R2-II-3 | 1273.6 |
| FAPI-INER-388-R | R1-II-1(R) | R2-II-4 | 1287.6 |
| FAPI-INER-388-S | R1-II-1(S) | R2-II-4 | 1287.6 |
| FAPI-INER-389-R | R1-II-2(R) | R2-II-1 | 1386.5 |
| FAPI-INER-389-S | R1-II-2(S) | R2-II-1 | 1386.5 |
| FAPI-INER-390-R | R1-II-2(R) | R2-II-2 | 1400.3 |
| FAPI-INER-390-S | R1-II-2(S) | R2-II-2 | 1400.3 |
| FAPI-INER-391-R | R1-II-2(R) | R2-II-3 | 1385.5 |
| FAPI-INER-391-S | R1-II-2(S) | R2-II-3 | 1385.5 |
| FAPI-INER-392-R | R1-II-2(R) | R2-II-4 | 1399.5 |
| FAPI-INER-392-S | R1-II-2(S) | R2-II-4 | 1399.5 |
| FAPI-INER-393-R | R1-II-3(R) | R2-II-1 | 1292.6 |
| FAPI-INER-393-S | R1-II-3(S) | R2-II-1 | 1292.6 |
| FAPI-INER-394-R | R1-II-3(R) | R2-II-2 | 1306.6 |
| FAPI-INER-394-S | R1-II-3(S) | R2-II-2 | 1306.6 |
| FAPI-INER-395-R | R1-II-3(R) | R2-II-3 | 1291.6 |
| FAPI-INER-395-S | R1-II-3(S) | R2-II-3 | 1291.6 |
| FAPI-INER-396-R | R1-II-3(R) | R2-II-4 | 1305.6 |
| FAPI-INER-396-S | R1-II-3(S) | R2-II-4 | 1305.6 |
| FAPI-INER-397-R | R1-II-4(R) | R2-II-1 | 1404.5 |
| FAPI-INER-397-S | R1-II-4(S) | R2-II-1 | 1404.5 |
| FAPI-INER-398-R | R1-II-4(R) | R2-II-2 | 1418.5 |
| FAPI-INER-398-S | R1-II-4(S) | R2-II-2 | 1418.5 |
| FAPI-INER-399-R | R1-II-4(R) | R2-II-3 | 1403.5 |
| FAPI-INER-399-S | R1-II-4(S) | R2-II-3 | 1403.5 |
| FAPI-INER-400-R | R1-II-4(R) | R2-II-4 | 1417.5 |
| FAPI-INER-400-S | R1-II-4(S) | R2-II-4 | 1417.5 |
| FAPI-INER-401-R | R1-II-11(R) | R2-II-1 | 1260.6 |
| FAPI-INER-401-S | R1-II-11(S) | R2-II-1 | 1260.6 |
| FAPI-INER-402-R | R1-II-11(R) | R2-II-2 | 1274.6 |
| FAPI-INER-402-S | R1-II-11(S) | R2-II-2 | 1274.6 |
| FAPI-INER-403-R | R1-II-11(R) | R2-II-3 | 1259.6 |
| FAPI-INER-403-S | R1-II-11(S) | R2-II-3 | 1259.6 |
| FAPI-INER-404-R | R1-II-11(R) | R2-II-4 | 1273.6 |
| FAPI-INER-404-S | R1-II-11(S) | R2-II-4 | 1273.6 |
| FAPI-INER-405-R | R1-II-12(R) | R2-II-1 | 1372.5 |
| FAPI-INER-405-S | R1-II-12(S) | R2-II-1 | 1372.5 |
| FAPI-INER-406-R | R1-II-12(R) | R2-II-2 | 1386.5 |
| FAPI-INER-406-S | R1-II-12(S) | R2-II-2 | 1386.5 |
| FAPI-INER-407-R | R1-II-12(R) | R2-II-3 | 1371.5 |
| FAPI-INER-407-S | R1-II-12(S) | R2-II-3 | 1371.5 |
| FAPI-INER-408-R | R1-II-12(R) | R2-II-4 | 1385.5 |
| FAPI-INER-408-S | R1-II-12(S) | R2-II-4 | 1385.5 |
| FAPI-INER-409-R | R1-II-17(R) | R2-II-1 | 1315.7 |
| FAPI-INER-409-S | R1-II-17(S) | R2-II-1 | 1315.7 |
| FAPI-INER-410-R | R1-II-17(R) | R2-II-2 | 1329.7 |
| FAPI-INER-410-S | R1-II-17(S) | R2-II-2 | 1329.7 |
| FAPI-INER-411-R | R1-II-17(R) | R2-II-3 | 1314.7 |
| FAPI-INER-411-S | R1-II-17(S) | R2-II-3 | 1314.7 |
| FAPI-INER-412-R | R1-II-17(R) | R2-II-4 | 1328.7 |
| FAPI-INER-412-S | R1-II-17(S) | R2-II-4 | 1328.7 |
| FAPI-INER-413-R | R1-II-18(R) | R2-II-1 | 1427.5 |
| FAPI-INER-413-S | R1-II-18(S) | R2-II-1 | 1427.5 |
| FAPI-INER-414-R | R1-II-18(R) | R2-II-2 | 1441.5 |
| FAPI-INER-414-S | R1-II-18(S) | R2-II-2 | 1441.5 |
| FAPI-INER-415-R | R1-II-18(R) | R2-II-3 | 1426.5 |
| FAPI-INER-415-S | R1-II-18(S) | R2-II-3 | 1426.5 |
| FAPI-INER-416-R | R1-II-18(R) | R2-II-4 | 1440.6 |
| FAPI-INER-416-S | R1-II-18(S) | R2-II-4 | 1440.6 |
| FAPI-INER-417-R | R1-II-21(R) | R2-II-1 | 1290.6 |
| FAPI-INER-417-S | R1-II-21(S) | R2-II-1 | 1290.6 |
| FAPI-INER-418-R | R1-II-21(R) | R2-II-2 | 1304.6 |
| FAPI-INER-418-S | R1-II-21(S) | R2-II-2 | 1304.6 |
| FAPI-INER-419-R | R1-II-21(R) | R2-II-3 | 1289.6 |
| FAPI-INER-419-S | R1-II-21(S) | R2-II-3 | 1289.6 |
| FAPI-INER-420-R | R1-II-21(R) | R2-II-4 | 1303.6 |
| FAPI-INER-420-S | R1-II-21(S) | R2-II-4 | 1303.6 |
| FAPI-INER-421-R | R1-II-22(R) | R2-II-1 | 1402.5 |
| FAPI-INER-421-S | R1-II-22(S) | R2-II-1 | 1402.5 |
| FAPI-INER-422-R | R1-II-22(R) | R2-II-2 | 1416.5 |
| FAPI-INER-422-S | R1-II-22(S) | R2-II-2 | 1416.5 |
| FAPI-INER-423-R | R1-II-22(R) | R2-II-3 | 1401.5 |
| FAPI-INER-423-S | R1-II-22(S) | R2-II-3 | 1401.5 |
| FAPI-INER-424-R | R1-II-22(R) | R2-II-4 | 1415.5 |
| FAPI-INER-424-S | R1-II-22(S) | R2-II-4 | 1415.5 |
| FAPI-INER-425-RR | R1-II-1(R) | R2-II-5(R) | 1290.6 |
| FAPI-INER-425-RS | R1-II-1(R) | R2-II-5(S) | 1290.6 |
| FAPI-INER-425-SR | R1-II-1(S) | R2-II-5(R) | 1290.6 |
| FAPI-INER-425-SS | R1-II-1(S) | R2-II-5(S) | 1290.6 |
| FAPI-INER-426-RR | R1-II-1(R) | R2-II-6(R) | 1304.6 |
| FAPI-INER-426-RS | R1-II-1(R) | R2-II-6(S) | 1304.6 |
| FAPI-INER-426-SR | R1-II-1(S) | R2-II-6(R) | 1304.6 |
| FAPI-INER-426-SS | R1-II-1(S) | R2-II-6(S) | 1304.6 |
| FAPI-INER-427-RR | R1-II-1(R) | R2-II-7(R) | 1289.6 |

-continued

| Code | R1 | R2 | [M + H]+ |
|---|---|---|---|
| FAPI-INER-427-RS | R1-II-1(R) | R2-II-7(S) | 1289.6 |
| FAPI-INER-427-SR | R1-II-1(S) | R2-II-7(R) | 1289.6 |
| FAPI-INER-427-SS | R1-II-1(S) | R2-II-7(S) | 1289.6 |
| FAPI-INER-428-RR | R1-II-1(R) | R2-II-8(R) | 1303.6 |
| FAPI-INER-428-RS | R1-II-1(R) | R2-II-8(S) | 1303.6 |
| FAPI-INER-428-SR | R1-II-1(S) | R2-II-8(R) | 1303.6 |
| FAPI-INER-428-SS | R1-II-1(S) | R2-II-8(S) | 1303.6 |
| FAPI-INER-429-RR | R1-II-2(R) | R2-II-5(R) | 1402.5 |
| FAPI-INER-429-RS | R1-II-2(R) | R2-II-5(S) | 1402.5 |
| FAPI-INER-429-SR | R1-II-2(S) | R2-II-5(R) | 1402.5 |
| FAPI-INER-429-SS | R1-II-2(S) | R2-II-5(S) | 1402.5 |
| FAPI-INER-430-RR | R1-II-2(R) | R2-II-6(R) | 1416.5 |
| FAPI-INER-430-RS | R1-II-2(R) | R2-II-6(S) | 1416.5 |
| FAPI-INER-430-SR | R1-II-2(S) | R2-II-6(R) | 1416.5 |
| FAPI-INER-430-SS | R1-II-2(S) | R2-II-6(S) | 1416.5 |
| FAPI-INER-431-RR | R1-II-2(R) | R2-II-7(R) | 1401.5 |
| FAPI-INER-431-RS | R1-II-2(R) | R2-II-7(S) | 1401.5 |
| FAPI-INER-431-SR | R1-II-2(S) | R2-II-7(R) | 1401.5 |
| FAPI-INER-431-SS | R1-II-2(S) | R2-II-7(S) | 1401.5 |
| FAPI-INER-432-RR | R1-II-2(R) | R2-II-8(R) | 1415.5 |
| FAPI-INER-432-RS | R1-II-2(R) | R2-II-8(S) | 1415.5 |
| FAPI-INER-432-SR | R1-II-2(S) | R2-II-8(R) | 1415.5 |
| FAPI-INER-432-SS | R1-II-2(S) | R2-II-8(S) | 1415.5 |
| FAPI-INER-433-RR | R1-II-3(R) | R2-II-5(R) | 1308.5 |
| FAPI-INER-433-RS | R1-II-3(R) | R2-II-5(S) | 1308.5 |
| FAPI-INER-433-SR | R1-II-3(S) | R2-II-5(R) | 1308.5 |
| FAPI-INER-433-SS | R1-II-3(S) | R2-II-5(S) | 1308.5 |
| FAPI-INER-434-RR | R1-II-3(R) | R2-II-6(R) | 1322.6 |
| FAPI-INER-434-RS | R1-II-3(R) | R2-II-6(S) | 1322.6 |
| FAPI-INER-434-SR | R1-II-3(S) | R2-II-6(R) | 1322.6 |
| FAPI-INER-434-SS | R1-II-3(S) | R2-II-6(S) | 1322.6 |
| FAPI-INER-435-RR | R1-II-3(R) | R2-II-7(R) | 1307.5 |
| FAPI-INER-435-RS | R1-II-3(R) | R2-II-7(S) | 1307.5 |
| FAPI-INER-435-SR | R1-II-3(S) | R2-II-7(R) | 1307.5 |
| FAPI-INER-435-SS | R1-II-3(S) | R2-II-7(S) | 1307.5 |
| FAPI-INER-436-RR | R1-II-3(R) | R2-II-8(R) | 1321.6 |
| FAPI-INER-436-RS | R1-II-3(R) | R2-II-8(S) | 1321.6 |
| FAPI-INER-436-SR | R1-II-3(S) | R2-II-8(R) | 1321.6 |
| FAPI-INER-436-SS | R1-II-3(S) | R2-II-8(S) | 1321.6 |
| FAPI-INER-437-RR | R1-II-4(R) | R2-II-5(R) | 1420.4 |
| FAPI-INER-437-RS | R1-II-4(R) | R2-II-5(S) | 1420.4 |
| FAPI-INER-437-SR | R1-II-4(S) | R2-II-5(R) | 1420.4 |
| FAPI-INER-437-SS | R1-II-4(S) | R2-II-5(S) | 1420.4 |
| FAPI-INER-438-RR | R1-II-4(R) | R2-II-6(R) | 1434.4 |
| FAPI-INER-438-RS | R1-II-4(R) | R2-II-6(S) | 1434.4 |
| FAPI-INER-438-SR | R1-II-4(S) | R2-II-6(R) | 1434.4 |
| FAPI-INER-438-SS | R1-II-4(S) | R2-II-6(S) | 1434.4 |
| FAPI-INER-439-RR | R1-II-4(R) | R2-II-7(R) | 1419.4 |
| FAPI-INER-439-RS | R1-II-4(R) | R2-II-7(S) | 1419.4 |
| FAPI-INER-439-SR | R1-II-4(S) | R2-II-7(R) | 1419.4 |
| FAPI-INER-439-SS | R1-II-4(S) | R2-II-7(S) | 1419.4 |
| FAPI-INER-440-RR | R1-II-4(R) | R2-II-8(R) | 1433.4 |
| FAPI-INER-440-RS | R1-II-4(R) | R2-II-8(S) | 1433.4 |
| FAPI-INER-440-SR | R1-II-4(S) | R2-II-8(R) | 1433.4 |
| FAPI-INER-440-SS | R1-II-4(S) | R2-II-8(S) | 1433.4 |
| FAPI-INER-441-RR | R1-II-11(R) | R2-II-5(R) | 1276.6 |
| FAPI-INER-441-RS | R1-II-11(R) | R2-II-5(S) | 1276.6 |
| FAPI-INER-441-SR | R1-II-11(S) | R2-II-5(R) | 1276.6 |
| FAPI-INER-441-SS | R1-II-11(S) | R2-II-5(S) | 1276.6 |
| FAPI-INER-442-RR | R1-II-11(R) | R2-II-6(R) | 1290.6 |
| FAPI-INER-442-RS | R1-II-11(R) | R2-II-6(S) | 1290.6 |
| FAPI-INER-442-SR | R1-II-11(S) | R2-II-6(R) | 1290.6 |
| FAPI-INER-442-SS | R1-II-11(S) | R2-II-6(S) | 1290.6 |
| FAPI-INER-443-RR | R1-II-11(R) | R2-II-7(R) | 1275.6 |
| FAPI-INER-443-RS | R1-II-11(R) | R2-II-7(S) | 1275.6 |
| FAPI-INER-443-SR | R1-II-11(S) | R2-II-7(R) | 1275.6 |
| FAPI-INER-443-SS | R1-II-11(S) | R2-II-7(S) | 1275.6 |
| FAPI-INER-444-RR | R1-II-11(R) | R2-II-8(R) | 1289.6 |
| FAPI-INER-444-RS | R1-II-11(R) | R2-II-8(S) | 1289.6 |
| FAPI-INER-444-SR | R1-II-11(S) | R2-II-8(R) | 1289.6 |
| FAPI-INER-444-SS | R1-II-11(S) | R2-II-8(S) | 1289.6 |
| FAPI-INER-445-RR | R1-II-12(R) | R2-II-5(R) | 1388.4 |
| FAPI-INER-445-RS | R1-II-12(R) | R2-II-5(S) | 1388.4 |
| FAPI-INER-445-SR | R1-II-12(S) | R2-II-5(R) | 1388.4 |
| FAPI-INER-445-SS | R1-II-12(S) | R2-II-5(S) | 1388.4 |
| FAPI-INER-446-RR | R1-II-12(R) | R2-II-6(R) | 1402.5 |
| FAPI-INER-446-RS | R1-II-12(R) | R2-II-6(S) | 1402.5 |
| FAPI-INER-446-SR | R1-II-12(S) | R2-II-6(R) | 1402.5 |
| FAPI-INER-446-SS | R1-II-12(S) | R2-II-6(S) | 1402.5 |
| FAPI-INER-447-RR | R1-II-12(R) | R2-II-7(R) | 1387.5 |
| FAPI-INER-447-RS | R1-II-12(R) | R2-II-7(S) | 1387.5 |
| FAPI-INER-447-SR | R1-II-12(S) | R2-II-7(R) | 1387.5 |
| FAPI-INER-447-SS | R1-II-12(S) | R2-II-7(S) | 1387.5 |
| FAPI-INER-448-RR | R1-II-12(R) | R2-II-8(R) | 1401.5 |
| FAPI-INER-448-RS | R1-II-12(R) | R2-II-8(S) | 1401.5 |
| FAPI-INER-448-SR | R1-II-12(S) | R2-II-8(R) | 1401.5 |
| FAPI-INER-448-SS | R1-II-12(S) | R2-II-8(S) | 1401.5 |
| FAPI-INER-449-RR | R1-II-17(R) | R2-II-5(R) | 1331.6 |
| FAPI-INER-449-RS | R1-II-17(R) | R2-II-5(S) | 1331.6 |
| FAPI-INER-449-SR | R1-II-17(S) | R2-II-5(R) | 1331.6 |
| FAPI-INER-449-SS | R1-II-17(S) | R2-II-5(S) | 1331.6 |
| FAPI-INER-450-RR | R1-II-17(R) | R2-II-6(R) | 1345.6 |
| FAPI-INER-450-RS | R1-II-17(R) | R2-II-6(S) | 1345.6 |
| FAPI-INER-450-SR | R1-II-17(S) | R2-II-6(R) | 1345.6 |
| FAPI-INER-450-SS | R1-II-17(S) | R2-II-6(S) | 1345.6 |
| FAPI-INER-451-RR | R1-II-17(R) | R2-II-7(R) | 1330.4 |
| FAPI-INER-451-RS | R1-II-17(R) | R2-II-7(S) | 1330.4 |
| FAPI-INER-451-SR | R1-II-17(S) | R2-II-7(R) | 1330.4 |
| FAPI-INER-451-SS | R1-II-17(S) | R2-II-7(S) | 1330.4 |
| FAPI-INER-452-RR | R1-II-17(R) | R2-II-8(R) | 1344.6 |
| FAPI-INER-452-RS | R1-II-17(R) | R2-II-8(S) | 1344.6 |
| FAPI-INER-452-SR | R1-II-17(S) | R2-II-8(R) | 1344.6 |
| FAPI-INER-452-SS | R1-II-17(S) | R2-II-8(S) | 1344.6 |
| FAPI-INER-453-RR | R1-II-18(R) | R2-II-5(R) | 1443.5 |
| FAPI-INER-453-RS | R1-II-18(R) | R2-II-5(S) | 1443.5 |
| FAPI-INER-453-SR | R1-II-18(S) | R2-II-5(R) | 1443.5 |
| FAPI-INER-453-SS | R1-II-18(S) | R2-II-5(S) | 1443.5 |
| FAPI-INER-454-RR | R1-II-18(R) | R2-II-6(R) | 1457.5 |
| FAPI-INER-454-RS | R1-II-18(R) | R2-II-6(S) | 1457.5 |
| FAPI-INER-454-SR | R1-II-18(S) | R2-II-6(R) | 1457.5 |
| FAPI-INER-454-SS | R1-II-18(S) | R2-II-6(S) | 1457.5 |
| FAPI-INER-455-RR | R1-II-18(R) | R2-II-7(R) | 1442.5 |
| FAPI-INER-455-RS | R1-II-18(R) | R2-II-7(S) | 1442.5 |
| FAPI-INER-455-SR | R1-II-18(S) | R2-II-7(R) | 1442.5 |
| FAPI-INER-455-SS | R1-II-18(S) | R2-II-7(S) | 1442.5 |
| FAPI-INER-456-RR | R1-II-18(R) | R2-II-8(R) | 1456.5 |
| FAPI-INER-456-RS | R1-II-18(R) | R2-II-8(S) | 1456.5 |
| FAPI-INER-456-SR | R1-II-18(S) | R2-II-8(R) | 1456.5 |
| FAPI-INER-456-SS | R1-II-18(S) | R2-II-8(S) | 1456.5 |
| FAPI-INER-457-RR | R1-II-21(R) | R2-II-5(R) | 1306.6 |
| FAPI-INER-457-RS | R1-II-21(R) | R2-II-5(S) | 1306.6 |
| FAPI-INER-457-SR | R1-II-21(S) | R2-II-5(R) | 1306.6 |
| FAPI-INER-457-SS | R1-II-21(S) | R2-II-5(S) | 1306.6 |
| FAPI-INER-458-RR | R1-II-21(R) | R2-II-6(R) | 1320.6 |
| FAPI-INER-458-RS | R1-II-21(R) | R2-II-6(S) | 1320.6 |
| FAPI-INER-458-SR | R1-II-21(S) | R2-II-6(R) | 1320.6 |
| FAPI-INER-458-SS | R1-II-21(S) | R2-II-6(S) | 1320.6 |
| FAPI-INER-459-RR | R1-II-21(R) | R2-II-7(R) | 1305.6 |
| FAPI-INER-459-RS | R1-II-21(R) | R2-II-7(S) | 1305.6 |
| FAPI-INER-459-SR | R1-II-21(S) | R2-II-7(R) | 1305.6 |
| FAPI-INER-459-SS | R1-II-21(S) | R2-II-7(S) | 1305.6 |
| FAPI-INER-460-RR | R1-II-21(R) | R2-II-8(R) | 1319.6 |
| FAPI-INER-460-RS | R1-II-21(R) | R2-II-8(S) | 1319.6 |
| FAPI-INER-460-SR | R1-II-21(S) | R2-II-8(R) | 1319.6 |
| FAPI-INER-460-SS | R1-II-21(S) | R2-II-8(S) | 1319.6 |
| FAPI-INER-461-RR | R1-II-22(R) | R2-II-5(R) | 1418.5 |
| FAPI-INER-461-RS | R1-II-22(R) | R2-II-5(S) | 1418.5 |
| FAPI-INER-461-SR | R1-II-22(S) | R2-II-5(R) | 1418.5 |
| FAPI-INER-461-SS | R1-II-22(S) | R2-II-5(S) | 1418.5 |
| FAPI-INER-462-RR | R1-II-22(R) | R2-II-6(R) | 1432.5 |
| FAPI-INER-462-RS | R1-II-22(R) | R2-II-6(S) | 1432.5 |
| FAPI-INER-462-SR | R1-II-22(S) | R2-II-6(R) | 1432.5 |
| FAPI-INER-462-SS | R1-II-22(S) | R2-II-6(S) | 1432.5 |
| FAPI-INER-463-RR | R1-II-22(R) | R2-II-7(R) | 1417.5 |
| FAPI-INER-463-RS | R1-II-22(R) | R2-II-7(S) | 1417.5 |
| FAPI-INER-463-SR | R1-II-22(S) | R2-II-7(R) | 1417.5 |
| FAPI-INER-463-SS | R1-II-22(S) | R2-II-7(S) | 1417.5 |
| FAPI-INER-464-RR | R1-II-22(R) | R2-II-8(R) | 1431.5 |
| FAPI-INER-464-RS | R1-II-22(R) | R2-II-8(S) | 1431.5 |
| FAPI-INER-464-SR | R1-II-22(S) | R2-II-8(R) | 1431.5 |
| FAPI-INER-464-SS | R1-II-22(S) | R2-II-8(S) | 1431.5 |
| FAPI-INER-465-RR | R1-II-1(R) | R2-II-13(R) | 1308.6 |
| FAPI-INER-465-RS | R1-II-1(R) | R2-II-13(S) | 1308.6 |
| FAPI-INER-465-SR | R1-II-1(S) | R2-II-13(R) | 1308.6 |

| Code | R1 | R2 | [M + H]+ |
|---|---|---|---|
| FAPI-INER-465-SS | R1-II-1(S) | R2-II-13(S) | 1308.6 |
| FAPI-INER-466-RR | R1-II-1(R) | R2-II-14(R) | 1322.6 |
| FAPI-INER-466-RS | R1-II-1(R) | R2-II-14(S) | 1322.6 |
| FAPI-INER-466-SR | R1-II-1(S) | R2-II-14(R) | 1322.6 |
| FAPI-INER-466-SS | R1-II-1(S) | R2-II-14(S) | 1322.6 |
| FAPI-INER-467-RR | R1-II-1(R) | R2-II-15(R) | 1307.6 |
| FAPI-INER-467-RS | R1-II-1(R) | R2-II-15(S) | 1307.6 |
| FAPI-INER-467-SR | R1-II-1(S) | R2-II-15(R) | 1307.6 |
| FAPI-INER-467-SS | R1-II-1(S) | R2-II-15(S) | 1307.6 |
| FAPI-INER-468-RR | R1-II-1(R) | R2-II-16(R) | 1321.6 |
| FAPI-INER-468-RS | R1-II-1(R) | R2-II-16(S) | 1321.6 |
| FAPI-INER-468-SR | R1-II-1(S) | R2-II-16(R) | 1321.6 |
| FAPI-INER-468-SS | R1-II-1(S) | R2-II-16(S) | 1321.6 |
| FAPI-INER-469-RR | R1-II-2(R) | R2-II-13(R) | 1420.5 |
| FAPI-INER-469-RS | R1-II-2(R) | R2-II-13(S) | 1420.5 |
| FAPI-INER-469-SR | R1-II-2(S) | R2-II-13(R) | 1420.5 |
| FAPI-INER-469-SS | R1-II-2(S) | R2-II-13(S) | 1420.5 |
| FAPI-INER-470-RR | R1-II-2(R) | R2-II-14(R) | 1434.5 |
| FAPI-INER-470-RS | R1-II-2(R) | R2-II-14(S) | 1434.5 |
| FAPI-INER-470-SR | R1-II-2(S) | R2-II-14(R) | 1434.5 |
| FAPI-INER-470-SS | R1-II-2(S) | R2-II-14(S) | 1434.5 |
| FAPI-INER-471-RR | R1-II-2(R) | R2-II-15(R) | 1419.5 |
| FAPI-INER-471-RS | R1-II-2(R) | R2-II-15(S) | 1419.5 |
| FAPI-INER-471-SR | R1-II-2(S) | R2-II-15(R) | 1419.5 |
| FAPI-INER-471-SS | R1-II-2(S) | R2-II-15(S) | 1419.5 |
| FAPI-INER-472-RR | R1-II-2(R) | R2-II-16(R) | 1433.5 |
| FAPI-INER-472-RS | R1-II-2(R) | R2-II-16(S) | 1433.5 |
| FAPI-INER-472-SR | R1-II-2(S) | R2-II-16(R) | 1433.5 |
| FAPI-INER-472-SS | R1-II-2(S) | R2-II-16(S) | 1433.5 |
| FAPI-INER-473-RR | R1-II-3(R) | R2-II-13(R) | 1326.5 |
| FAPI-INER-473-RS | R1-II-3(R) | R2-II-13(S) | 1326.5 |
| FAPI-INER-473-SR | R1-II-3(S) | R2-II-13(R) | 1326.5 |
| FAPI-INER-473-SS | R1-II-3(S) | R2-II-13(S) | 1326.5 |
| FAPI-INER-474-RR | R1-II-3(R) | R2-II-14(R) | 1340.5 |
| FAPI-INER-474-RS | R1-II-3(R) | R2-II-14(S) | 1340.5 |
| FAPI-INER-474-SR | R1-II-3(S) | R2-II-14(R) | 1340.5 |
| FAPI-INER-474-SS | R1-II-3(S) | R2-II-14(S) | 1340.5 |
| FAPI-INER-475-RR | R1-II-3(R) | R2-II-15(R) | 1325.5 |
| FAPI-INER-475-RS | R1-II-3(R) | R2-II-15(S) | 1325.5 |
| FAPI-INER-475-SR | R1-II-3(S) | R2-II-15(R) | 1325.5 |
| FAPI-INER-475-SS | R1-II-3(S) | R2-II-15(S) | 1325.5 |
| FAPI-INER-476-RR | R1-II-3(R) | R2-II-16(R) | 1339.6 |
| FAPI-INER-476-RS | R1-II-3(R) | R2-II-16(S) | 1339.6 |
| FAPI-INER-476-SR | R1-II-3(S) | R2-II-16(R) | 1339.6 |
| FAPI-INER-476-SS | R1-II-3(S) | R2-II-16(S) | 1339.6 |
| FAPI-INER-477-RR | R1-II-4(R) | R2-II-13(R) | 1438.4 |
| FAPI-INER-477-RS | R1-II-4(R) | R2-II-13(S) | 1438.4 |
| FAPI-INER-477-SR | R1-II-4(S) | R2-II-13(R) | 1438.4 |
| FAPI-INER-477-SS | R1-II-4(S) | R2-II-13(S) | 1438.4 |
| FAPI-INER-478-RR | R1-II-4(R) | R2-II-14(R) | 1452.4 |
| FAPI-INER-478-RS | R1-II-4(R) | R2-II-14(S) | 1452.4 |
| FAPI-INER-478-SR | R1-II-4(S) | R2-II-14(R) | 1452.4 |
| FAPI-INER-478-SS | R1-II-4(S) | R2-II-14(S) | 1452.4 |
| FAPI-INER-479-RR | R1-II-4(R) | R2-II-15(R) | 1437.6 |
| FAPI-INER-479-RS | R1-II-4(R) | R2-II-15(S) | 1437.6 |
| FAPI-INER-479-SR | R1-II-4(S) | R2-II-15(R) | 1437.6 |
| FAPI-INER-479-SS | R1-II-4(S) | R2-II-15(S) | 1437.6 |
| FAPI-INER-480-RR | R1-II-4(R) | R2-II-16(R) | 1451.4 |
| FAPI-INER-480-RS | R1-II-4(R) | R2-II-16(S) | 1451.4 |
| FAPI-INER-480-SR | R1-II-4(S) | R2-II-16(R) | 1451.4 |
| FAPI-INER-480-SS | R1-II-4(S) | R2-II-16(S) | 1451.4 |
| FAPI-INER-481-RR | R1-II-11(R) | R2-II-13(R) | 1294.6 |
| FAPI-INER-481-RS | R1-II-11(R) | R2-II-13(S) | 1294.6 |
| FAPI-INER-481-SR | R1-II-11(S) | R2-II-13(R) | 1294.6 |
| FAPI-INER-481-SS | R1-II-11(S) | R2-II-13(S) | 1294.6 |
| FAPI-INER-482-RR | R1-II-11(R) | R2-II-14(R) | 1308.6 |
| FAPI-INER-482-RS | R1-II-11(R) | R2-II-14(S) | 1308.6 |
| FAPI-INER-482-SR | R1-II-11(S) | R2-II-14(R) | 1308.6 |
| FAPI-INER-482-SS | R1-II-11(S) | R2-II-14(S) | 1308.6 |
| FAPI-INER-483-RR | R1-II-11(R) | R2-II-15(R) | 1293.6 |
| FAPI-INER-483-RS | R1-II-11(R) | R2-II-15(S) | 1293.6 |
| FAPI-INER-483-SR | R1-II-11(S) | R2-II-15(R) | 1293.6 |
| FAPI-INER-483-SS | R1-II-11(S) | R2-II-15(S) | 1293.6 |
| FAPI-INER-484-RR | R1-II-11(R) | R2-II-16(R) | 1307.6 |
| FAPI-INER-484-RS | R1-II-11(R) | R2-II-16(S) | 1307.6 |
| FAPI-INER-484-SR | R1-II-11(S) | R2-II-16(R) | 1307.6 |
| FAPI-INER-484-SS | R1-II-11(S) | R2-II-16(S) | 1307.6 |
| FAPI-INER-485-RR | R1-II-12(R) | R2-II-13(R) | 1406.4 |
| FAPI-INER-485-RS | R1-II-12(R) | R2-II-13(S) | 1406.4 |
| FAPI-INER-485-SR | R1-II-12(S) | R2-II-13(R) | 1406.4 |
| FAPI-INER-485-SS | R1-II-12(S) | R2-II-13(S) | 1406.4 |
| FAPI-INER-486-RR | R1-II-12(R) | R2-II-14(R) | 1420.5 |
| FAPI-INER-486-RS | R1-II-12(R) | R2-II-14(S) | 1420.5 |
| FAPI-INER-486-SR | R1-II-12(S) | R2-II-14(R) | 1420.5 |
| FAPI-INER-486-SS | R1-II-12(S) | R2-II-14(S) | 1420.5 |
| FAPI-INER-487-RR | R1-II-12(R) | R2-II-15(R) | 1405.4 |
| FAPI-INER-487-RS | R1-II-12(R) | R2-II-15(S) | 1405.4 |
| FAPI-INER-487-SR | R1-II-12(S) | R2-II-15(R) | 1405.4 |
| FAPI-INER-487-SS | R1-II-12(S) | R2-II-15(S) | 1405.4 |
| FAPI-INER-488-RR | R1-II-12(R) | R2-II-16(R) | 1419.5 |
| FAPI-INER-488-RS | R1-II-12(R) | R2-II-16(S) | 1419.5 |
| FAPI-INER-488-SR | R1-II-12(S) | R2-II-16(R) | 1419.5 |
| FAPI-INER-488-SS | R1-II-12(S) | R2-II-16(S) | 1419.5 |
| FAPI-INER-489-RR | R1-II-17(R) | R2-II-13(R) | 1349.6 |
| FAPI-INER-489-RS | R1-II-17(R) | R2-II-13(S) | 1349.6 |
| FAPI-INER-489-SR | R1-II-17(S) | R2-II-13(R) | 1349.6 |
| FAPI-INER-489-SS | R1-II-17(S) | R2-II-13(S) | 1349.6 |
| FAPI-INER-490-RR | R1-II-17(R) | R2-II-14(R) | 1363.6 |
| FAPI-INER-490-RS | R1-II-17(R) | R2-II-14(S) | 1363.6 |
| FAPI-INER-490-SR | R1-II-17(S) | R2-II-14(R) | 1363.6 |
| FAPI-INER-490-SS | R1-II-17(S) | R2-II-14(S) | 1363.6 |
| FAPI-INER-491-RR | R1-II-17(R) | R2-II-15(R) | 1348.6 |
| FAPI-INER-491-RS | R1-II-17(R) | R2-II-15(S) | 1348.6 |
| FAPI-INER-491-SR | R1-II-17(S) | R2-II-15(R) | 1348.6 |
| FAPI-INER-491-SS | R1-II-17(S) | R2-II-15(S) | 1348.6 |
| FAPI-INER-492-RS | R1-II-17(R) | R2-II-16(S) | 1362.6 |
| FAPI-INER-492-SS | R1-II-17(S) | R2-II-16(S) | 1362.6 |
| FAPI-INER-493-RR | R1-II-18(R) | R2-II-13(R) | 1461.5 |
| FAPI-INER-493-RS | R1-II-18(R) | R2-II-13(S) | 1461.5 |
| FAPI-INER-493-SR | R1-II-18(S) | R2-II-13(R) | 1461.5 |
| FAPI-INER-493-SS | R1-II-18(S) | R2-II-13(S) | 1461.5 |
| FAPI-INER-494-RR | R1-II-18(R) | R2-II-14(R) | 1475.5 |
| FAPI-INER-494-RS | R1-II-18(R) | R2-II-14(S) | 1475.5 |
| FAPI-INER-494-SR | R1-II-18(S) | R2-II-14(R) | 1475.5 |
| FAPI-INER-494-SS | R1-II-18(S) | R2-II-14(S) | 1475.5 |
| FAPI-INER-495-RR | R1-II-18(R) | R2-II-15(R) | 1460.5 |
| FAPI-INER-495-RS | R1-II-18(R) | R2-II-15(S) | 1460.5 |
| FAPI-INER-495-SR | R1-II-18(S) | R2-II-15(R) | 1460.5 |
| FAPI-INER-495-SS | R1-II-18(S) | R2-II-15(S) | 1460.5 |
| FAPI-INER-496-RR | R1-II-18(R) | R2-II-16(R) | 1474.5 |
| FAPI-INER-496-RS | R1-II-18(R) | R2-II-16(S) | 1474.5 |
| FAPI-INER-496-SR | R1-II-18(S) | R2-II-16(R) | 1474.5 |
| FAPI-INER-496-SS | R1-II-18(S) | R2-II-16(S) | 1474.5 |
| FAPI-INER-497-RR | R1-II-21(R) | R2-II-13(R) | 1324.6 |
| FAPI-INER-497-RS | R1-II-21(R) | R2-II-13(S) | 1324.6 |
| FAPI-INER-497-SR | R1-II-21(S) | R2-II-13(R) | 1324.6 |
| FAPI-INER-497-SS | R1-II-21(S) | R2-II-13(S) | 1324.6 |
| FAPI-INER-498-RR | R1-II-21(R) | R2-II-14(R) | 1338.6 |
| FAPI-INER-498-RS | R1-II-21(R) | R2-II-14(S) | 1338.6 |
| FAPI-INER-498-SR | R1-II-21(S) | R2-II-14(R) | 1338.6 |
| FAPI-INER-498-SS | R1-II-21(S) | R2-II-14(S) | 1338.6 |
| FAPI-INER-499-RR | R1-II-21(R) | R2-II-15(R) | 1323.6 |
| FAPI-INER-499-RS | R1-II-21(R) | R2-II-15(S) | 1323.6 |
| FAPI-INER-499-SR | R1-II-21(S) | R2-II-15(R) | 1323.6 |
| FAPI-INER-499-SS | R1-II-21(S) | R2-II-15(S) | 1323.6 |
| FAPI-INER-500-RR | R1-II-21(R) | R2-II-16(R) | 1337.6 |
| FAPI-INER-500-RS | R1-II-21(R) | R2-II-16(S) | 1337.6 |
| FAPI-INER-500-SR | R1-II-21(S) | R2-II-16(R) | 1337.6 |
| FAPI-INER-500-SS | R1-II-21(S) | R2-II-16(S) | 1337.6 |
| FAPI-INER-501-RR | R1-II-22(R) | R2-II-13(R) | 1436.5 |
| FAPI-INER-501-RS | R1-II-22(R) | R2-II-13(S) | 1436.5 |
| FAPI-INER-501-SR | R1-II-22(S) | R2-II-13(R) | 1436.5 |
| FAPI-INER-501-SS | R1-II-22(S) | R2-II-13(S) | 1436.5 |
| FAPI-INER-502-RR | R1-II-22(R) | R2-II-14(R) | 1450.5 |
| FAPI-INER-502-RS | R1-II-22(R) | R2-II-14(S) | 1450.5 |
| FAPI-INER-502-SR | R1-II-22(S) | R2-II-14(R) | 1450.5 |
| FAPI-INER-502-SS | R1-II-22(S) | R2-II-14(S) | 1450.5 |
| FAPI-INER-503-RR | R1-II-22(R) | R2-II-15(R) | 1435.5 |
| FAPI-INER-503-RS | R1-II-22(R) | R2-II-15(S) | 1435.5 |
| FAPI-INER-503-SR | R1-II-22(S) | R2-II-15(R) | 1435.5 |
| FAPI-INER-503-SS | R1-II-22(S) | R2-II-15(S) | 1435.5 |
| FAPI-INER-504-RR | R1-II-22(R) | R2-II-16(R) | 1449.5 |

-continued

| Code | R1 | R2 | [M + H]⁺ |
| --- | --- | --- | --- |
| FAPI-INER-504-RS | R1-II-22(R) | R2-II-16(S) | 1449.5 |
| FAPI-INER-504-SR | R1-II-22(S) | R2-II-16(R) | 1449.5 |
| FAPI-INER-504-SS | R1-II-22(S) | R2-II-16(S) | 1449.5 |

The R or S in the brackets in the R1 column represents the configuration of the optically active carbon at "*" in the structures. The R or S in the brackets in the R2 column represents the configuration of the optically active carbon at "*" in the structures. [M + H]⁺ represents the charge-to-mass ratio of the corresponding mass spectrum.

Example 3: R' is a cyano group, R1 is selected from the set of R1-III, and R2 is selected from the set of R2-III according to a compound represented by formula (I) D-R1-R2-A-R' or its salt thereof:

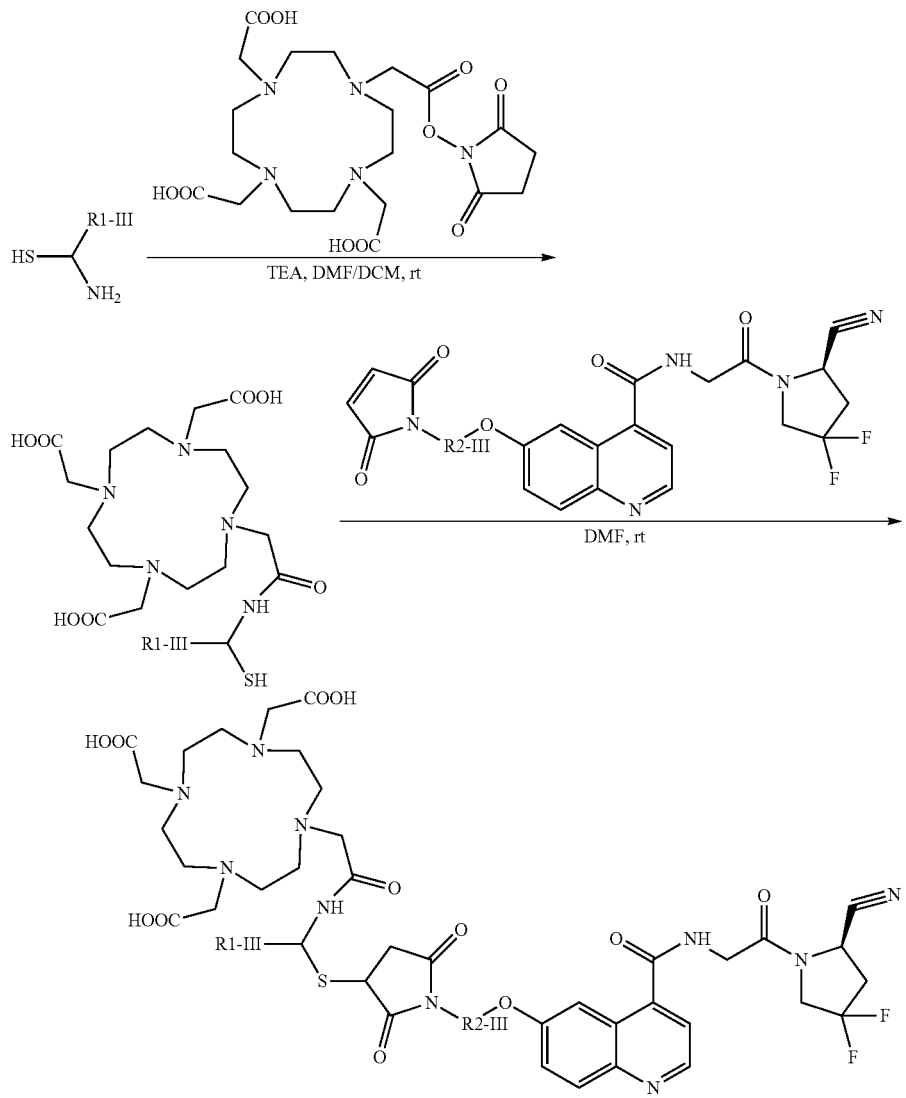

1 equivalent of R1-III was dissolved in DMF/DCM mixed solution (DMF volume:DCM volume=1:1). Next, DMF/DCM mixed solution containing equivalent of DOTA-NHS ester and 1.2 to 1.5 equivalents of TEA was added to react at room temperature, and then 1 equivalent of purified product was reconstituted in DMF/DCM mixed solution and 1 equivalent of R2-III connected to A was added to react at room temperature.

After performing preparative medium pressure liquid chromatography (MPLC) with purification by acetonitrile/water gradient elution and analyzing [M+H]⁺ by mass spectrometry to determine the molecular weight, the compound as formula (I) D-R1-R2-A-R' or its salt thereof was obtained as the table below:

| Code | R1 | R2 | [M + H]⁺ |
| --- | --- | --- | --- |
| FAPI-INER-1057-R | R1-III-1(R) | R2-III-1 | 1318.6 |
| FAPI-INER-1057-S | R1-III-1(S) | R2-III-1 | 1318.6 |
| FAPI-INER-1058-R | R1-III-1(R) | R2-III-2 | 1332.6 |
| FAPI-INER-1058-S | R1-III-1(S) | R2-III-2 | 1332.6 |

-continued

| Code | R1 | R2 | [M + H]⁺ |
| --- | --- | --- | --- |
| FAPI-INER-1059-R | R1-III-1(R) | R2-III-3 | 1317.6 |
| FAPI-INER-1059-S | R1-III-1(S) | R2-III-3 | 1317.6 |
| FAPI-INER-1060-R | R1-III-1(R) | R2-III-4 | 1331.6 |
| FAPI-INER-1060-S | R1-III-1(S) | R2-III-4 | 1331.6 |

| Code | R1 | R2 | [M + H]⁺ |
| --- | --- | --- | --- |
| FAPI-INER-1061-R | R1-III-2(R) | R2-III-1 | 1430.4 |
| FAPI-INER-1061-S | R1-III-2(S) | R2-III-1 | 1430.4 |
| FAPI-INER-1062-R | R1-III-2(R) | R2-III-2 | 1444.5 |
| FAPI-INER-1062-S | R1-III-2(S) | R2-III-2 | 1444.5 |
| FAPI-INER-1063-R | R1-III-2(R) | R2-III-3 | 1429.4 |
| FAPI-INER-1063-S | R1-III-2(S) | R2-III-3 | 1429.4 |
| FAPI-INER-1064-R | R1-III-2(R) | R2-III-4 | 1443.5 |
| FAPI-INER-1064-S | R1-III-2(S) | R2-III-4 | 1443.5 |
| FAPI-INER-1065-R | R1-III-9(R) | R2-III-1 | 1332.6 |
| FAPI-INER-1065-S | R1-III-9(S) | R2-III-1 | 1332.6 |
| FAPI-INER-1066-R | R1-III-9(R) | R2-III-2 | 1346.6 |
| FAPI-INER-1066-S | R1-III-9(S) | R2-III-2 | 1346.6 |
| FAPI-INER-1067-R | R1-III-9(R) | R2-III-3 | 1331.6 |
| FAPI-INER-1067-S | R1-III-9(S) | R2-III-3 | 1331.6 |
| FAPI-INER-1068-R | R1-III-9(R) | R2-III-4 | 1345.6 |
| FAPI-INER-1068-S | R1-III-9(S) | R2-III-4 | 1345.6 |
| FAPI-INER-1069-R | R1-III-10(R) | R2-III-1 | 1444.5 |
| FAPI-INER-1069-S | R1-III-10(S) | R2-III-1 | 1444.5 |
| FAPI-INER-1070-R | R1-III-10(R) | R2-III-2 | 1458.4 |
| FAPI-INER-1070-S | R1-III-10(S) | R2-III-2 | 1458.4 |
| FAPI-INER-1071-R | R1-III-10(R) | R2-III-3 | 1443.5 |
| FAPI-INER-1071-S | R1-III-10(S) | R2-III-3 | 1443.5 |
| FAPI-INER-1072-R | R1-III-10(R) | R2-III-4 | 1457.5 |
| FAPI-INER-1072-S | R1-III-10(S) | R2-III-4 | 1457.5 |
| FAPI-INER-1073-RR | R1-III-1(R) | R2-III-13(R) | 1346.6 |
| FAPI-INER-1073-RS | R1-III-1(S) | R2-III-13(S) | 1346.6 |
| FAPI-INER-1073-SR | R1-III-1(R) | R2-III-13(R) | 1346.6 |
| FAPI-INER-1073-SS | R1-III-1(S) | R2-III-13(S) | 1346.6 |
| FAPI-INER-1074-RR | R1-III-1(R) | R2-III-14(R) | 1360.6 |
| FAPI-INER-1074-RS | R1-III-1(S) | R2-III-14(S) | 1360.6 |
| FAPI-INER-1074-SR | R1-III-1(R) | R2-III-14(R) | 1360.6 |
| FAPI-INER-1074-SS | R1-III-1(S) | R2-III-14(S) | 1360.6 |
| FAPI-INER-1075-RR | R1-III-1(R) | R2-III-15(R) | 1345.6 |
| FAPI-INER-1075-RS | R1-III-1(S) | R2-III-15(S) | 1345.6 |
| FAPI-INER-1075-SR | R1-III-1(R) | R2-III-15(R) | 1345.6 |
| FAPI-INER-1075-SS | R1-III-1(S) | R2-III-15(S) | 1345.6 |
| FAPI-INER-1076-RR | R1-III-1(R) | R2-III-16(R) | 1359.6 |
| FAPI-INER-1076-RS | R1-III-1(S) | R2-III-16(S) | 1359.6 |
| FAPI-INER-1076-SR | R1-III-1(R) | R2-III-16(R) | 1359.6 |
| FAPI-INER-1076-SS | R1-III-1(S) | R2-III-16(S) | 1359.6 |
| FAPI-INER-1077-RR | R1-III-2(R) | R2-III-13(R) | 1458.5 |
| FAPI-INER-1077-RS | R1-III-2(S) | R2-III-13(S) | 1458.5 |
| FAPI-INER-1077-SR | R1-III-2(R) | R2-III-13(R) | 1458.5 |
| FAPI-INER-1077-SS | R1-III-2(S) | R2-III-13(S) | 1458.5 |
| FAPI-INER-1078-RR | R1-III-2(R) | R2-III-14(R) | 1472.5 |
| FAPI-INER-1078-RS | R1-III-2(S) | R2-III-14(S) | 1472.5 |
| FAPI-INER-1078-SR | R1-III-2(R) | R2-III-14(R) | 1472.5 |
| FAPI-INER-1078-SS | R1-III-2(S) | R2-III-14(S) | 1472.5 |
| FAPI-INER-1079-RR | R1-III-2(R) | R2-III-15(R) | 1457.5 |
| FAPI-INER-1079-RS | R1-III-2(S) | R2-III-15(S) | 1457.5 |
| FAPI-INER-1079-SR | R1-III-2(R) | R2-III-15(R) | 1457.5 |
| FAPI-INER-1079-SS | R1-III-2(S) | R2-III-15(S) | 1457.5 |
| FAPI-INER-1080-RR | R1-III-2(R) | R2-III-16(R) | 1471.5 |
| FAPI-INER-1080-RS | R1-III-2(S) | R2-III-16(S) | 1471.5 |
| FAPI-INER-1080-SR | R1-III-2(R) | R2-III-16(R) | 1471.5 |
| FAPI-INER-1080-SS | R1-III-2(S) | R2-III-16(S) | 1471.5 |
| FAPI-INER-1081-RR | R1-III-9(R) | R2-III-13(R) | 1360.6 |
| FAPI-INER-1081-RS | R1-III-9(S) | R2-III-13(S) | 1360.6 |
| FAPI-INER-1081-SR | R1-III-9(R) | R2-III-13(R) | 1360.6 |
| FAPI-INER-1081-SS | R1-III-9(S) | R2-III-13(S) | 1360.6 |
| FAPI-INER-1082-RR | R1-III-9(R) | R2-III-14(R) | 1374.6 |
| FAPI-INER-1082-RS | R1-III-9(S) | R2-III-14(S) | 1374.6 |
| FAPI-INER-1082-SR | R1-III-9(R) | R2-III-14(R) | 1374.6 |
| FAPI-INER-1082-SS | R1-III-9(S) | R2-III-14(S) | 1374.6 |
| FAPI-INER-1083-RR | R1-III-9(R) | R2-III-15(R) | 1359.6 |
| FAPI-INER-1083-RS | R1-III-9(S) | R2-III-15(S) | 1359.6 |
| FAPI-INER-1083-SR | R1-III-9(R) | R2-III-15(R) | 1359.6 |
| FAPI-INER-1083-SS | R1-III-9(S) | R2-III-15(S) | 1359.6 |
| FAPI-INER-1084-RR | R1-III-9(R) | R2-III-16(R) | 1373.6 |
| FAPI-INER-1084-RS | R1-III-9(S) | R2-III-16(S) | 1373.6 |
| FAPI-INER-1084-SR | R1-III-9(R) | R2-III-16(R) | 1373.6 |
| FAPI-INER-1084-SS | R1-III-9(S) | R2-III-16(S) | 1373.6 |
| FAPI-INER-1085-RR | R1-III-10(R) | R2-III-13(R) | 1472.5 |
| FAPI-INER-1085-RS | R1-III-10(S) | R2-III-13(S) | 1472.5 |
| FAPI-INER-1085-SR | R1-III-10(R) | R2-III-13(R) | 1472.5 |
| FAPI-INER-1085-SS | R1-III-10(S) | R2-III-13(S) | 1472.5 |
| FAPI-INER-1086-RR | R1-III-10(R) | R2-III-14(R) | 1486.5 |
| FAPI-INER-1086-RS | R1-III-10(S) | R2-III-14(S) | 1486.5 |
| FAPI-INER-1086-SR | R1-III-10(R) | R2-III-14(R) | 1486.5 |
| FAPI-INER-1086-SS | R1-III-10(S) | R2-III-14(S) | 1486.5 |
| FAPI-INER-1087-RR | R1-III-10(R) | R2-III-15(R) | 1471.5 |
| FAPI-INER-1087-RS | R1-III-10(S) | R2-III-15(S) | 1471.5 |
| FAPI-INER-1087-SR | R1-III-10(R) | R2-III-15(R) | 1471.5 |
| FAPI-INER-1087-SS | R1-III-10(S) | R2-III-15(S) | 1471.5 |
| FAPI-INER-1088-RR | R1-III-10(R) | R2-III-16(R) | 1485.5 |
| FAPI-INER-1088-RS | R1-III-10(S) | R2-III-16(S) | 1485.5 |
| FAPI-INER-1088-SR | R1-III-10(R) | R2-III-16(R) | 1485.5 |
| FAPI-INER-1088-SS | R1-III-10(S) | R2-III-16(S) | 1485.5 |
| FAPI-INER-1089-R | R1-III-1(R) | R2-III-17 | 1346.6 |
| FAPI-INER-1089-S | R1-III-1(S) | R2-III-17 | 1346.6 |
| FAPI-INER-1090-R | R1-III-1(R) | R2-III-18 | 1360.6 |
| FAPI-INER-1090-S | R1-III-1(S) | R2-III-18 | 1360.6 |
| FAPI-INER-1091-R | R1-III-1(R) | R2-III-19 | 1345.6 |
| FAPI-INER-1091-S | R1-III-1(S) | R2-III-19 | 1345.6 |
| FAPI-INER-1092-R | R1-III-1(R) | R2-III-20 | 1359.6 |
| FAPI-INER-1092-S | R1-III-1(S) | R2-III-20 | 1359.6 |
| FAPI-INER-1093-R | R1-III-2(R) | R2-III-17 | 1458.5 |
| FAPI-INER-1093-S | R1-III-2(S) | R2-III-17 | 1458.5 |
| FAPI-INER-1094-R | R1-III-2(R) | R2-III-18 | 1472.5 |
| FAPI-INER-1094-S | R1-III-2(S) | R2-III-18 | 1472.5 |
| FAPI-INER-1095-R | R1-III-2(R) | R2-III-19 | 1457.5 |
| FAPI-INER-1095-S | R1-III-2(S) | R2-III-19 | 1457.5 |
| FAPI-INER-1096-R | R1-III-2(R) | R2-III-20 | 1471.5 |
| FAPI-INER-1096-S | R1-III-2(S) | R2-III-20 | 1471.5 |
| FAPI-INER-1097-R | R1-III-9(R) | R2-III-17 | 1360.6 |
| FAPI-INER-1097-S | R1-III-9(S) | R2-III-17 | 1360.6 |
| FAPI-INER-1098-R | R1-III-9(R) | R2-III-18 | 1374.6 |
| FAPI-INER-1098-S | R1-III-9(S) | R2-III-18 | 1374.6 |
| FAPI-INER-1099-R | R1-III-9(R) | R2-III-19 | 1359.6 |
| FAPI-INER-1099-S | R1-III-9(S) | R2-III-19 | 1359.6 |
| FAPI-INER-1100-R | R1-III-9(R) | R2-III-20 | 1373.6 |
| FAPI-INER-1100-S | R1-III-9(S) | R2-III-20 | 1373.6 |
| FAPI-INER-1101-R | R1-III-10(R) | R2-III-17 | 1472.5 |
| FAPI-INER-1101-S | R1-III-10(S) | R2-III-17 | 1472.5 |
| FAPI-INER-1102-R | R1-III-10(R) | R2-III-18 | 1486.5 |
| FAPI-INER-1102-S | R1-III-10(S) | R2-III-18 | 1486.5 |
| FAPI-INER-1103-R | R1-III-10(R) | R2-III-19 | 1471.5 |
| FAPI-INER-1103-S | R1-III-10(S) | R2-III-19 | 1471.5 |
| FAPI-INER-1104-R | R1-III-10(R) | R2-III-20 | 1485.5 |
| FAPI-INER-1104-S | R1-III-10(S) | R2-III-20 | 1485.5 |

The R or S in the brackets in the R1 column represents the configuration of the optically active carbon at "*" in the structures. The R or S in the brackets in the R2 column represents the configuration of the optically active carbon at "*" in the structures. [M + H]⁺ represents the mass-to-charge ratio of the corresponding mass spectrum.

Example 4: R' is a cyano group, R1 is selected from the set of R1-IV, and R2 is selected from the set of R2-IV according to a compound represented by formula (I) D-R1-R2-A-R' or its salt thereof:

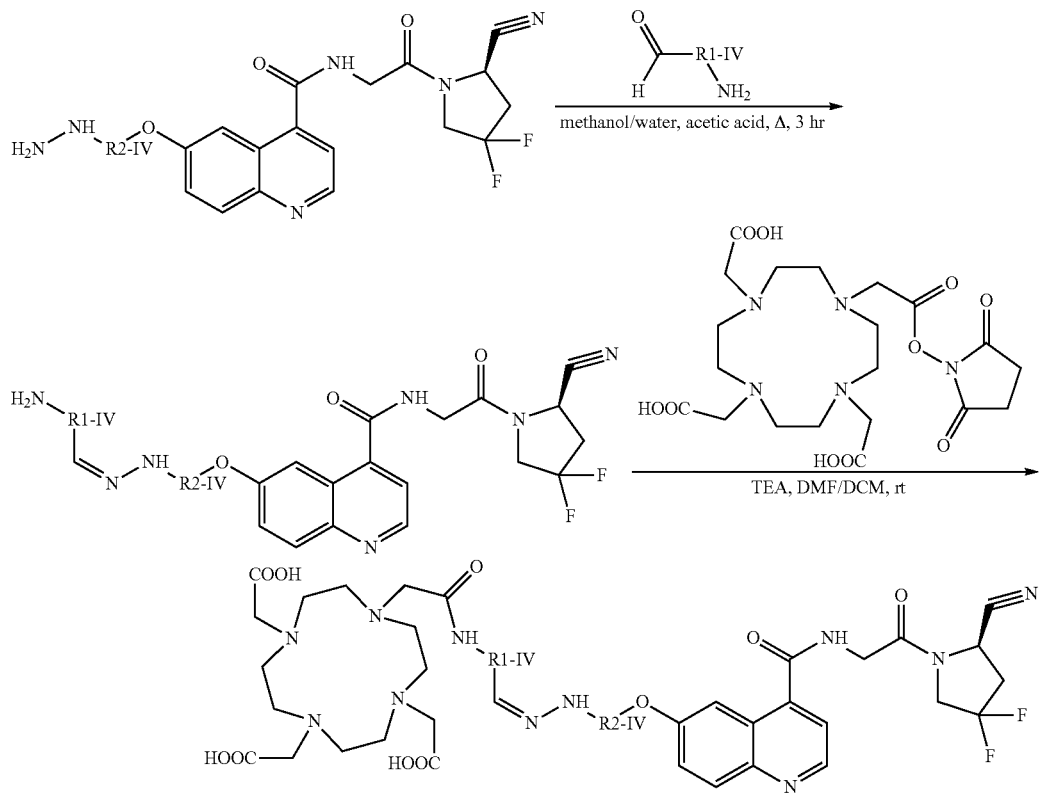

1 equivalent of R2-IV connected to A was added into a 67% methanol solution containing 1 equivalent of R1-IV and 1 equivalent of acetic acid and heated to react for 3 hours, then 1 equivalent of the purified product was dissolved in a DMF/DCM mixed solution (DMF volume:DCM volume=1: 1), DMF/DCM mixed solution containing 1 equivalent of DOTA-NHS ester and 1.2 to 1.5 equivalents of TEA was added to react at room temperature.

After performing preparative medium pressure liquid chromatography (MPLC) with purification by acetonitrile/water gradient elution and analyzing [M+I-I]$^+$ by mass spectrometry to determine the molecular weight, the compound as formula (I) D-R1-R2-A-R' or its salt thereof was obtained as the table below:

| Code | R1 | R2 | [M + H]$^+$ |
|---|---|---|---|
| FAPI-INER-1297-R | R1-IV-1(R) | R2-IV-1(5) | 1272.6 |
| FAPI-INER-1297-S | R1-IV-1(S) | R2-IV-1(5) | 1272.6 |
| FAPI-INER-1298-R | R1-IV-1(R) | R2-IV-2(5) | 1286.4 |
| FAPI-INER-1298-S | R1-IV-1(S) | R2-IV-2(5) | 1286.4 |
| FAPI-INER-1299-R | R1-IV-1(R) | R2-IV-3(5) | 1271.6 |
| FAPI-INER-1299-S | R1-IV-1(S) | R2-IV-3(5) | 1271.6 |
| FAPI-INER-1300-R | R1-IV-1(R) | R2-IV-4(5) | 1285.6 |
| FAPI-INER-1300-S | R1-IV-1(S) | R2-IV-4(5) | 1285.6 |
| FAPI-INER-1301-R | R1-IV-2(R) | R2-IV-1(5) | 1384.5 |
| FAPI-INER-1301-S | R1-IV-2(S) | R2-IV-1(5) | 1384.5 |
| FAPI-INER-1302-R | R1-IV-2(R) | R2-IV-2(5) | 1398.5 |
| FAPI-INER-1302-S | R1-IV-2(S) | R2-IV-2(5) | 1398.5 |
| FAPI-INER-1303-R | R1-IV-2(R) | R2-IV-3(5) | 1383.5 |
| FAPI-INER-1303-S | R1-IV-2(S) | R2-IV-3(5) | 1383.5 |
| FAPI-INER-1304-R | R1-IV-2(R) | R2-IV-4(5) | 1397.5 |

-continued

| Code | R1 | R2 | [M + H]$^+$ |
|---|---|---|---|
| FAPI-INER-1304-S | R1-IV-2(S) | R2-IV-4(5) | 1397.5 |
| FAPI-INER-1305-R | R1-IV-1(R) | R2-IV-9(2) | 1202.6 |
| FAPI-INER-1305-S | R1-IV-1(S) | R2-IV-9(2) | 1202.6 |
| FAPI-INER-1306-R | R1-IV-1(R) | R2-IV-10(2) | 1216.6 |
| FAPI-INER-1306-S | R1-IV-1(S) | R2-IV-10(2) | 1216.6 |
| FAPI-INER-1307-R | R1-IV-1(R) | R2-IV-11(2) | 1201.6 |
| FAPI-INER-1307-S | R1-IV-1(S) | R2-IV-11(2) | 1201.6 |
| FAPI-INER-1308-R | R1-IV-1(R) | R2-IV-12(2) | 1215.6 |
| FAPI-INER-1308-S | R1-IV-1(S) | R2-IV-12(2) | 1215.6 |
| FAPI-INER-1309-R | R1-IV-2(R) | R2-IV-9(2) | 1314.4 |
| FAPI-INER-1309-S | R1-IV-2(S) | R2-IV-9(2) | 1314.4 |
| FAPI-INER-1310-R | R1-IV-2(R) | R2-IV-10(2) | 1328.4 |
| FAPI-INER-1310-S | R1-IV-2(S) | R2-IV-10(2) | 1328.4 |
| FAPI-INER-1311-R | R1-IV-2(R) | R2-IV-11(2) | 1313.4 |
| FAPI-INER-1311-S | R1-IV-2(S) | R2-IV-11(2) | 1313.4 |
| FAPI-INER-1312-R | R1-IV-2(R) | R2-IV-12(2) | 1327.5 |
| FAPI-INER-1312-S | R1-IV-2(S) | R2-IV-12(2) | 1327.5 |

The R or S in the brackets in the R1 column represents the configuration of the optically active carbon at "*" in the structures. The arabic numerals in the brackets in the R2 column are the integers represented by q, j or k; [M + H]$^+$ represents the charge-to-mass ratio of the corresponding mass spectrum.

Example 5: R' is a cyano group, R1 is selected from the set of R1-V, and R2 is selected from the set of R2-V according to a compound represented by formula (I) D-R1-R2-A-R' or its salt thereof:

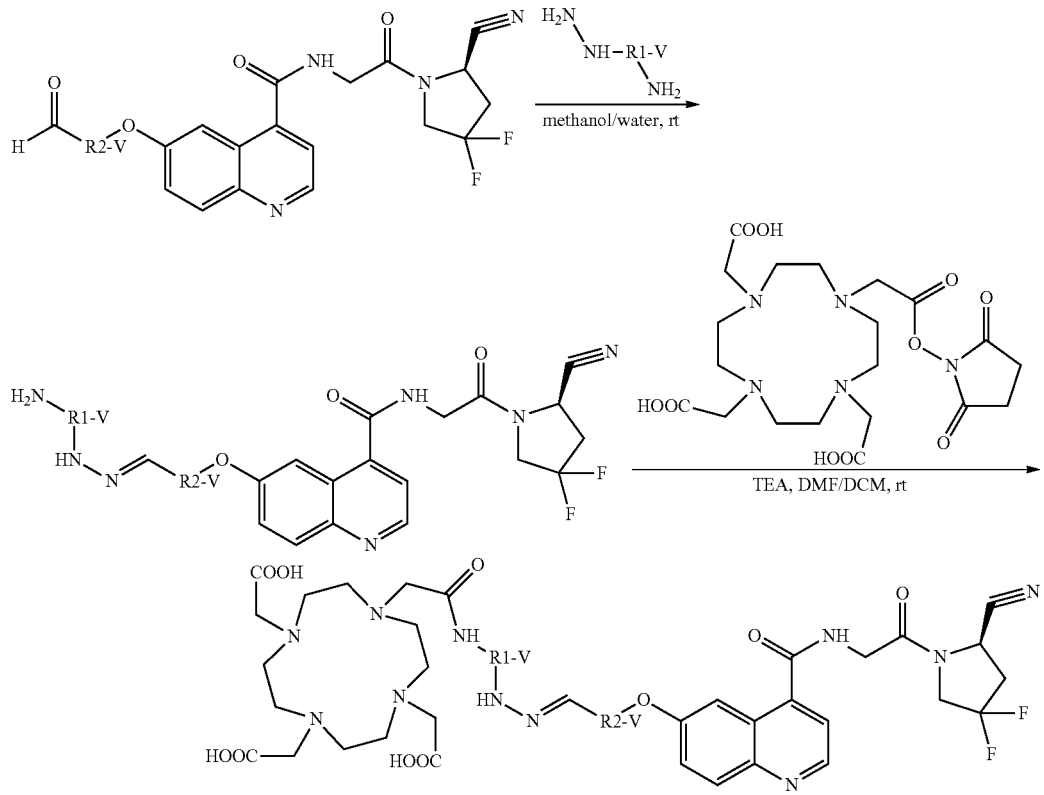

1 equivalent of R2-V connected to A was added to methanol/water solution containing 1 equivalent of R1-V to react at room temperature for 30 minutes, and then 1 equivalent of the purified product was dissolved in a DMF/DCM mixed solution (DMF volume:DCM volume=1:1), DMF/DCM mixed solution containing 1 equivalent of DOTA-NHS ester and 1.2 to 1.5 equivalents of TEA was added to react at room temperature.

After performing preparative medium pressure liquid chromatography (MPLC) with purification by acetonitrile/water gradient elution and analyzing $[M+H]^+$ by mass spectrometry to determine the molecular weight, the compound as formula (I) D-R1-R2-A-R' or its salt thereof was obtained as the table below:

| Code | R1 | R2 | $[M + H]^+$ |
|---|---|---|---|
| FAPI-INER-1393-R | R1-V-1(R) | R2-V-1(5) | 1273.6 |
| FAPI-INER-1393-S | R1-V-1(S) | R2-V-1(5) | 1273.6 |
| FAPI-INER-1394-R | R1-V-1(R) | R2-V-2(5) | 1287.7 |
| FAPI-INER-1394-S | R1-V-1(S) | R2-V-2(5) | 1287.7 |
| FAPI-INER-1395-R | R1-V-1(R) | R2-V-3(5) | 1272.6 |
| FAPI-INER-1395-S | R1-V-1(S) | R2-V-3(5) | 1272.6 |
| FAPI-INER-1396-R | R1-V-1(R) | R2-V-4(5) | 1286.7 |
| FAPI-INER-1396-S | R1-V-1(S) | R2-V-4(5) | 1286.7 |
| FAPI-INER-1397-R | R1-V-2(R) | R2-V-1(5) | 1385.5 |
| FAPI-INER-1397-S | R1-V-2(S) | R2-V-1(5) | 1385.5 |
| FAPI-INER-1398-R | R1-V-2(R) | R2-V-2(5) | 1399.5 |
| FAPI-INER-1398-S | R1-V-2(S) | R2-V-2(5) | 1399.5 |
| FAPI-INER-1399-R | R1-V-2(R) | R2-V-3(5) | 1384.5 |
| FAPI-INER-1399-S | R1-V-2(S) | R2-V-3(5) | 1384.5 |
| FAPI-INER-1400-R | R1-V-2(R) | R2-V-4(5) | 1398.5 |
| FAPI-INER-1400-S | R1-V-2(S) | R2-V-4(5) | 1398.5 |
| FAPI-INER-1401-R | R1-V-1(R) | R2-V-1(2) | 1231.6 |
| FAPI-INER-1401-S | R1-V-1(S) | R2-V-1(2) | 1231.6 |
| FAPI-INER-1402-R | R1-V-1(R) | R2-V-2(2) | 1245.6 |
| FAPI-INER-1402-S | R1-V-1(S) | R2-V-2(2) | 1245.6 |
| FAPI-INER-1403-R | R1-V-1(R) | R2-V-3(2) | 1230.6 |
| FAPI-INER-1403-S | R1-V-1(S) | R2-V-3(2) | 1230.6 |
| FAPI-INER-1404-R | R1-V-1(R) | R2-V-4(2) | 1244.6 |
| FAPI-INER-1404-S | R1-V-1(S) | R2-V-4(2) | 1244.6 |
| FAPI-INER-1405-R | R1-V-2(R) | R2-V-1(2) | 1343.5 |
| FAPI-INER-1405-S | R1-V-2(S) | R2-V-1(2) | 1343.5 |
| FAPI-INER-1406-R | R1-V-2(R) | R2-V-2(2) | 1357.5 |
| FAPI-INER-1406-S | R1-V-2(S) | R2-V-2(2) | 1357.5 |
| FAPI-INER-1407-R | R1-V-2(R) | R2-V-3(2) | 1342.5 |
| FAPI-INER-1407-S | R1-V-2(S) | R2-V-3(2) | 1342.5 |
| FAPI-INER-1408-R | R1-V-2(R) | R2-V-4(2) | 1356.5 |
| FAPI-INER-1408-S | R1-V-2(S) | R2-V-4(2) | 1356.5 |

The R or S in the brackets in the R1 column represents the configuration of the optically active carbon at "*" in the structures. The arabic numerals in the brackets in the R2 column are the integers represented by n; $[M + H]^+$ represents the charge-to-mass ratio of the corresponding mass spectrum.

Example 6: preparation and purity analysis of a radioactive marker of a compound of formula (I) D-R1-R2-A-R' or its salt thereof:

Step 1: Preparing the Sample

Figure 2:
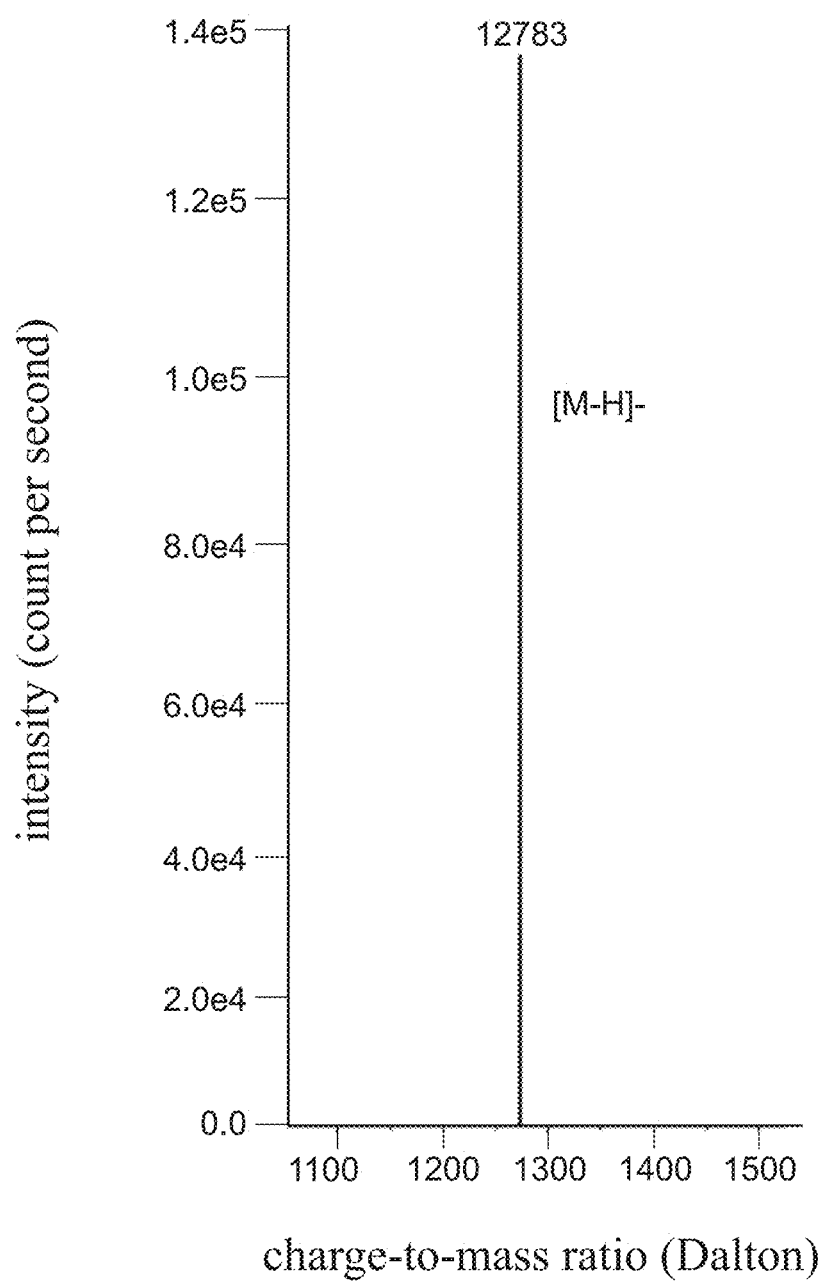
FIG. 2 is the mass spectrum of FAPI-INER-385-S.
Figure 3:
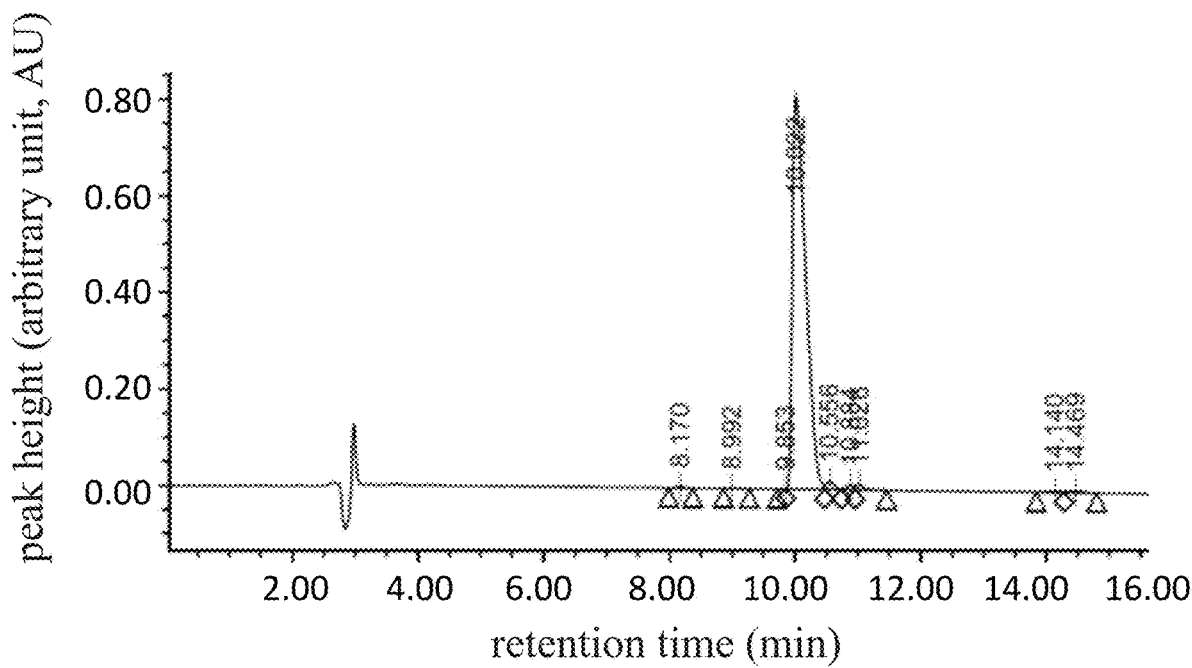
FIG. 3 is a chromatogram of high performance liquid chromatography of chemical purity of FAPI-INER-385-S.
Figure 4:
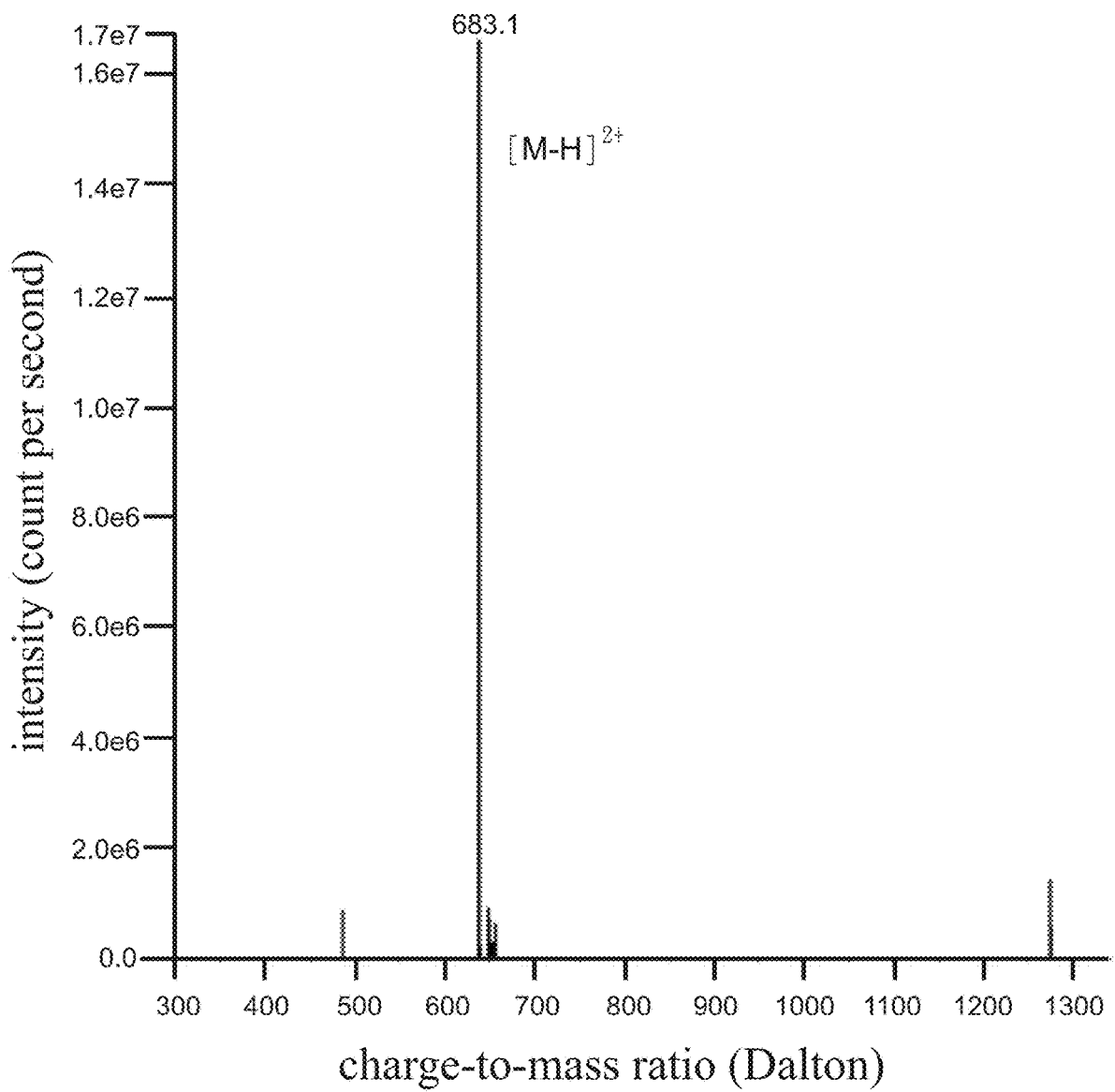
FIG. 4 is the mass spectrum of FAPI-INER-387-S.
Figure 5:
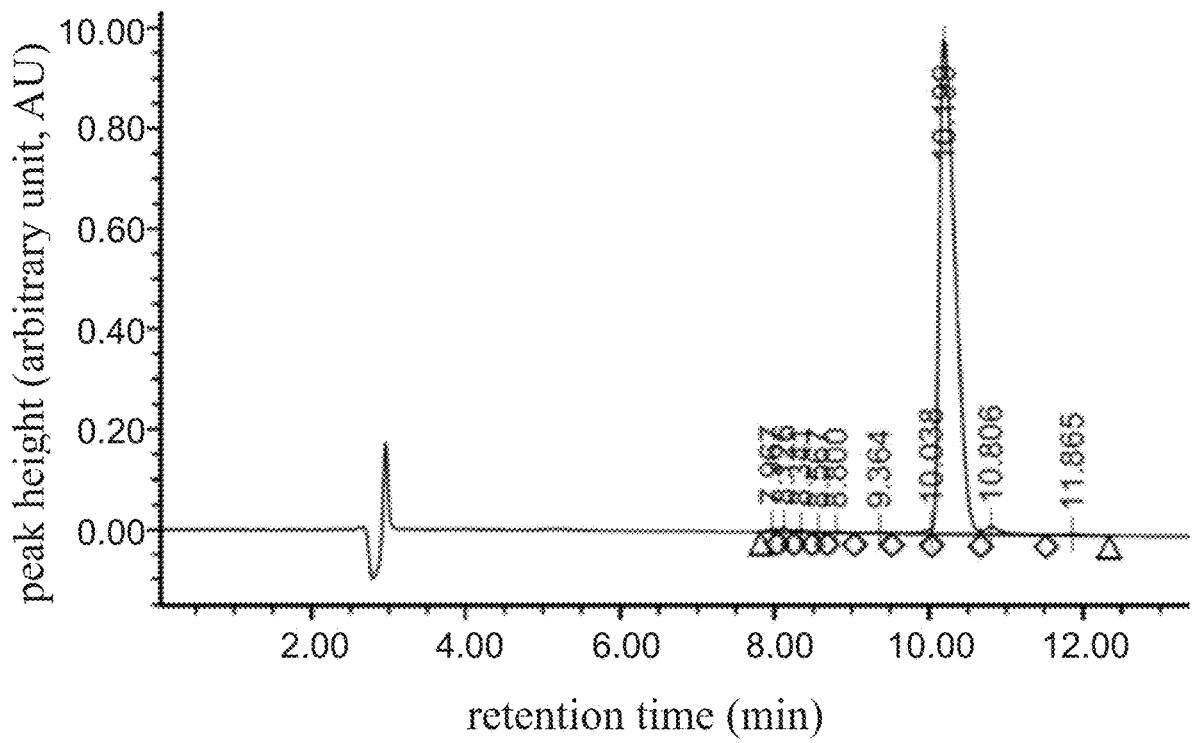
FIG. 5 is a chromatogram of high performance liquid chromatography of chemical purity of FAPI-INER-387-S.
Figure 6A:
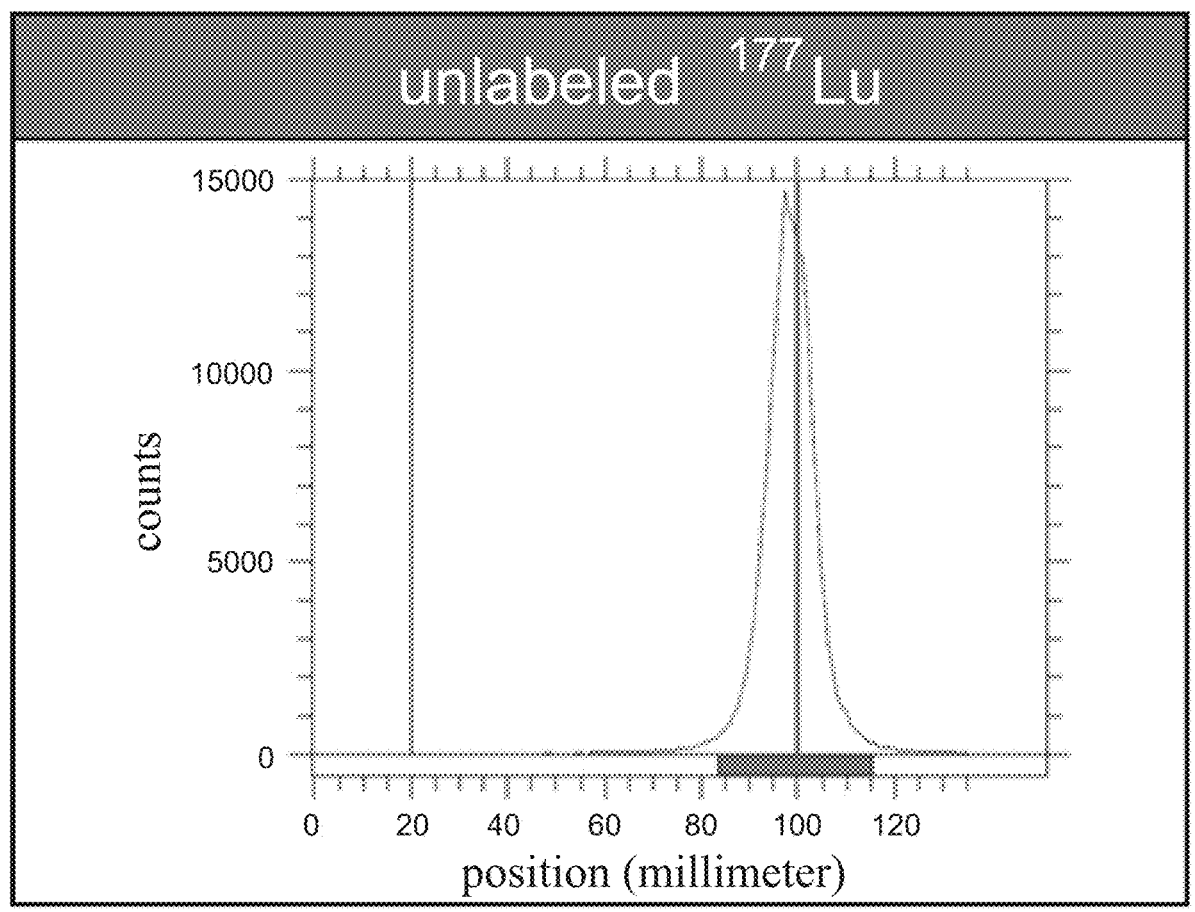
FIG. 6A is a chromatogram of radio-instant-thin-layer chromatography of $^{177}$LuCl$_3$ (unlabeled $^{177}$Lu).
Figure 6B:
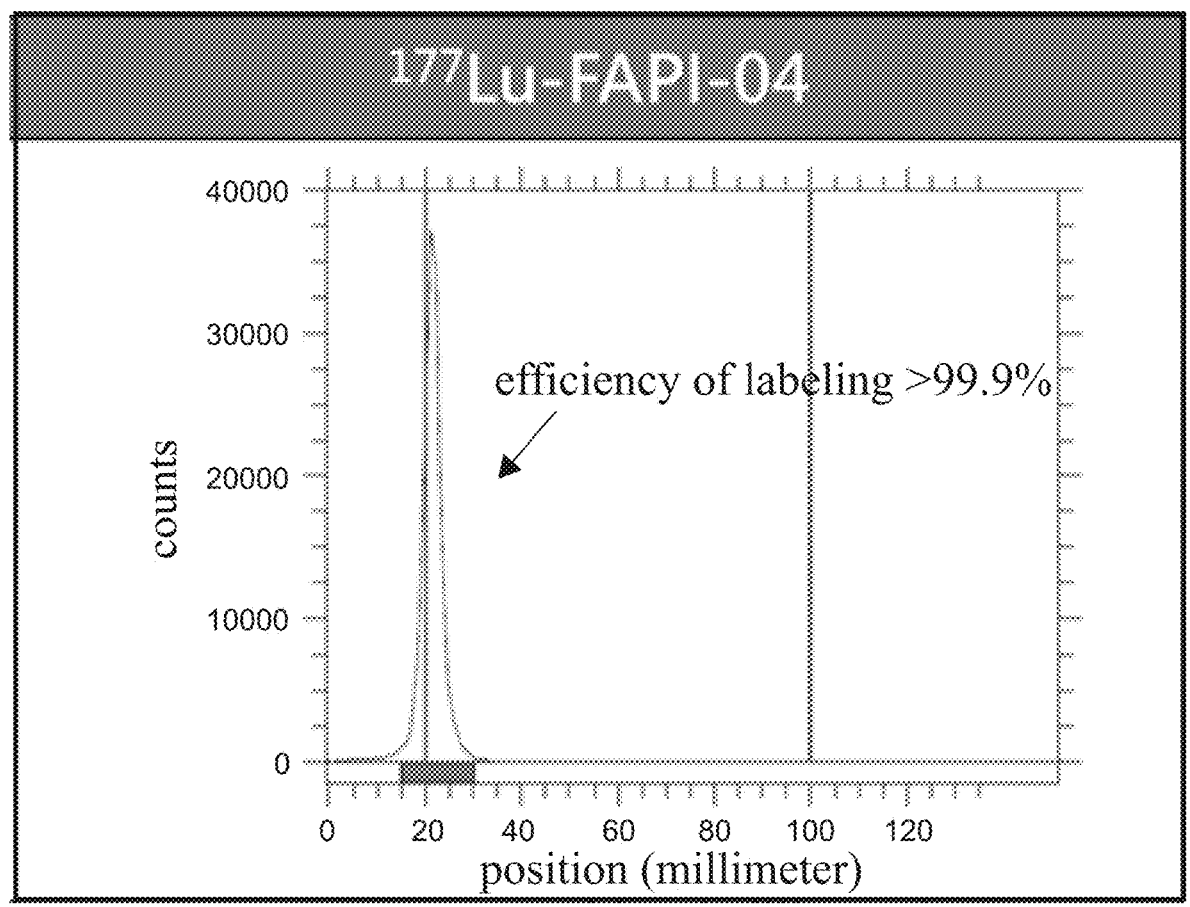
FIG. 6B is a chromatogram of radio-instant-thin-layer chromatography of $^{177}$Lu-FAPI-04.
Figure 6C:
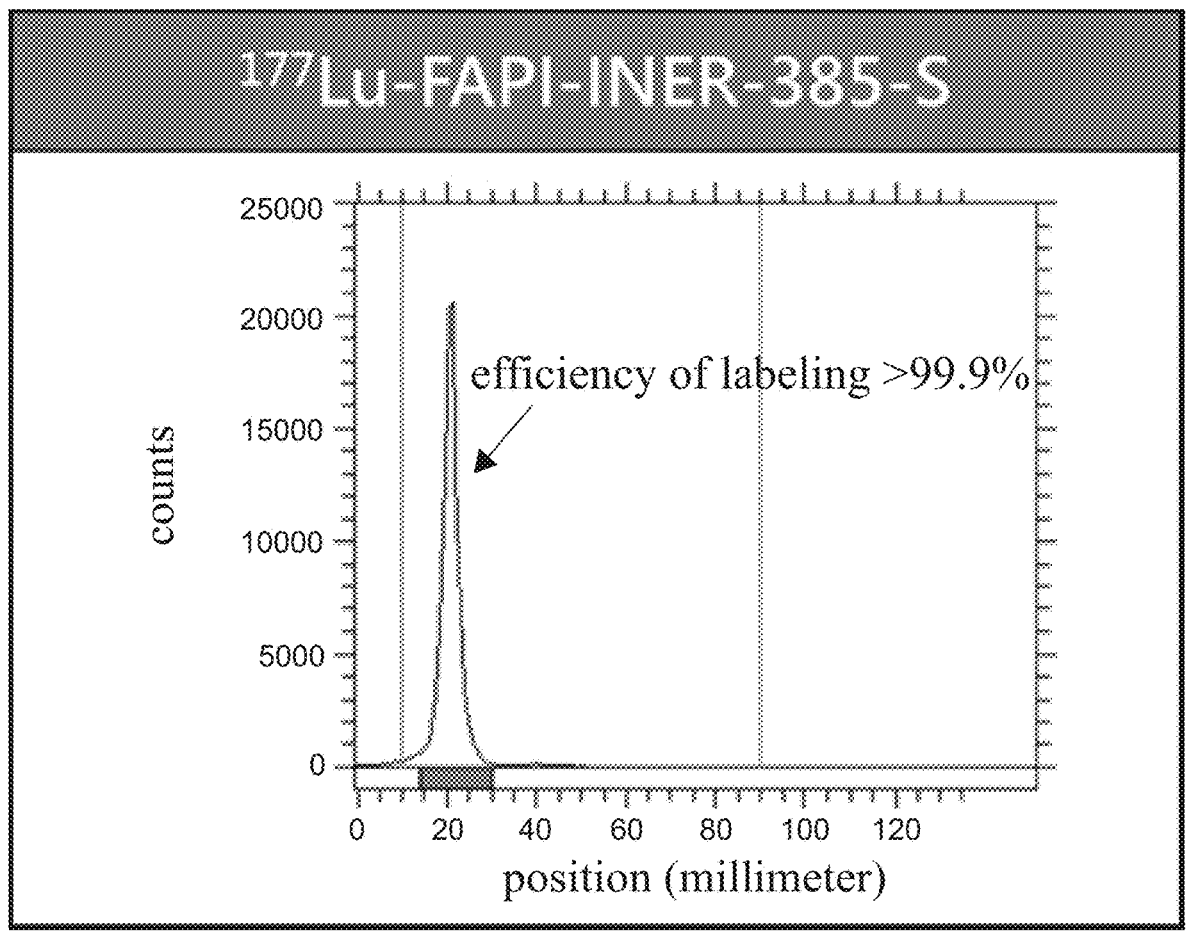
FIG. 6C is a chromatogram of radio-instant-thin-layer chromatography of $^{177}$Lu-FAPI-INER-385-S.
Figure 6D:
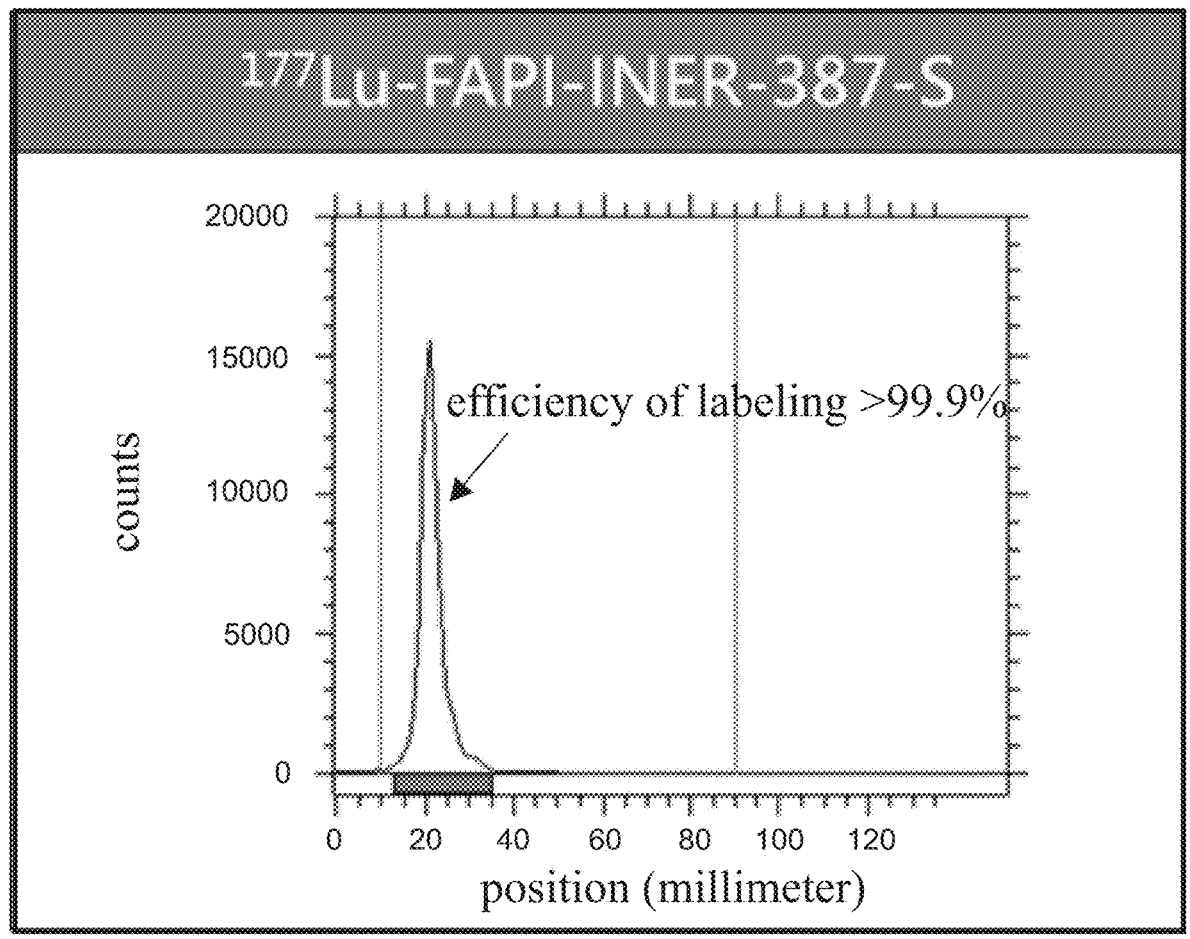
FIG. 6D is a chromatogram of radio-instant-thin-layer chromatography of $^{177}$Lu-FAPI-INER-387-S.

Referring to FIG. 1, FAPI-INER-385-S, FAPI-INER-387-S or FAPI-04 was formulated with dimethyl sulfoxide (DMSO) to prepare a 20 mg/mL sample, wherein FAPI-04 was used as the control group; wherein the theoretical molecular weight of FAPI-INER-385-S is 1274.4. Referring to FIG. 2, mass spectrometry identified $[M-H]^-$: 1273.8. Referring to FIG. 3, high performance liquid chromatography identified (at UV 220 nm) chemical purity 95.92%; where the theoretical molecular weight of FAPI-INER-387-S is 1273.4. Referring to FIG. 4, mass spectrometry identified [M+2H]$^{2+}$: 638.1. Referring to FIG. 5, high performance liquid chromatography identified (at UV 220 nm) chemical purity is 95.70%.

Step 2: Labeling $^{177}$Lu Radioactive Nuclide

Referring to FIG. 2, 20 μg sample of FAPI-INER-385-S, FAPI-INER-387-S or FAPI-04 was added to 0.4M sodium acetate buffer solution (NaOAc) with pH 5.0. Then, 0.04N hydrochloric acid solution containing $^{177}$Lu of phosphonium trichloride (LuCl$_3$) was added in the samples of FAPI-INER-385-S, FAPI-INER-387-S and FAPI-04 respectively for $^{177}$Lu radiolabeling in FAPI-INER-385-S, FAPI-INER-387-S or FAPI-04, wherein the sample of FAPI-04 was added in a 0.04N hydrochloric acid solution containing $^{177}$LuCl$_3$ with a radioactivity of 0.23 gigabacquerel (GBq), wherein the sample of FAPI-INER-385-S was added in a 0.04N hydrochloric acid solution of $^{177}$LuCl$_3$ with a radioactivity of 0.46 GBq, wherein the sample of FAPI-INER-387-S was added in a 0.04N hydrochloric acid solution of $^{177}$LuCl$_3$ with a radioactivity of 0.46 GBq, and mixed evenly then put the raw material in the constant temperature control device set at 95° C. to react for 15 minutes or 30 minutes to form a raw material. The oscillating speed was 500 revolutions per minute (500 rpm) during the heating, and the raw material was left to cool completely after the reaction was completed to obtain the initial product. The initial products are FAPI-04, FAPI-INER-385-S and FAPI-INER-387-S that that labelled by the $^{177}$Lu, wherein FAPI-04 labelled by the $^{177}$Lu was represented by $^{177}$Lu-FAPI-04, and the FAPI-INER-385-S labelled by the $^{177}$Lu was represented by $^{177}$Lu-FAPI-INER-385-S, and FAPI-INER-387-S labelled by the $^{177}$Lu was represented by $^{177}$Lu-FAPI-INER-387-S.

Step 3: Quality Control Analysis

Appropriate amounts of $^{177}$Lu-FAPI-04, $^{177}$Lu-FAPI-INER-385-S and $^{177}$Lu-FAPI-INER-3 87-5 and $^{177}$LuCl$_3$ were taken respectively, analyzed by radio-instant-thin-layer chromatography (radio-ITLC) to determine the efficiency of $^{177}$Lu radiolabeling, wherein $^{177}$LuCl$_3$ was used as the control group of radio-ITLC as the unlabeled $^{177}$Lu group. In addition, appropriate amounts of $^{177}$Lu-FAPI-04, $^{177}$Lu-FAPI-INER-385-S and $^{177}$Lu-FAPI-INER-387 were also taken and analyzed by radio-high-performance-liquid chromatography (radio-HPLC) to determine Referring to FIG. 6A, FIG. 6B, FIG. 6C and FIG. 6D, representing the chromatograms of radio-ITLC of $^{177}$LuCl$_3$ (unlabeled $^{177}$Lu), $^{177}$Lu-FAPI-04, $^{177}$Lu-FAPI-INER-385-S and $^{177}$Lu-FAPI-INER-387-S. The radio-ITLC method was to drop $^{177}$LuCl$_3$ and each initial product respectively at a distance of 20 mm from the bottom end of the thin layer chromatography sheet (TLC sheet), and the bottom end of the TLC was placed in analytical developing solution that can be moved from the bottom end to the top end of the TLC sheet. The top end of the TLC sheet is at 100 mm. The sample with successfully labeled $^{177}$Lu was not moved to the top end of the TLC sheet along with the analytical developing solution, while the sample with unsuccessfully labeled $^{177}$Lu was moved to the top end of the TLC sheet along with the analytical developing solution. The analytical developing solution was 0.1M citric acid solution.

FIG. 6A, FIG. 6B, FIG. 6C and FIG. 6D show that the $^{177}$Lu-unlabeled sample reached to 100 mm along with the analytical developing solution, and the samples of $^{177}$Lu-FAPI-04, $^{177}$Lu-FAPI-INER-385-S and $^{177}$Lu-FAPI-INER-387-S stayed at 20 mm, which means that the $^{177}$Lu labeling has been successfully carried out, and the efficiency of labeling was greater than 99.9%.

Radio HPLC was used with the analytical mobile phase which includes mobile phase A and mobile phase B, wherein A is acetonitrile containing 0.1% trifluoroacetic acid (TFA) and B is deionized water containing 0.1% trifluoroacetic acid, also with the static phase which includes a carbon-18 column (XSelect HSS T3 column, Waters, particle size: 5 microns, inner diameter: 4.6 mm, length: 250 mm). The flow rate was 0.8 ml/min, the analysis was proceeded for 20 minutes, and the elution gradient was shown as the following table:

| | Gradient | | | |
|---|---|---|---|---|
| | I | | II | |
| elution time (min) | mobile phase A | mobile phase B | mobile phase A | mobile phase B |
| 0 | 10% | 90% | 20% | 80% |
| 10 | 40% | 60% | 90% | 10% |
| 10.1 | 10% | 90% | 20% | 80% |
| 20.0 | 10% | 90% | 20% | 80% |

$^{177}$Lu-FAPI-04 was eluted using with Gradient I; $^{177}$Lu-FAPI-INER-385-S and $^{177}$Lu-FAPI-INER-387-S were eluted using with Gradient II.

Figure 7A:
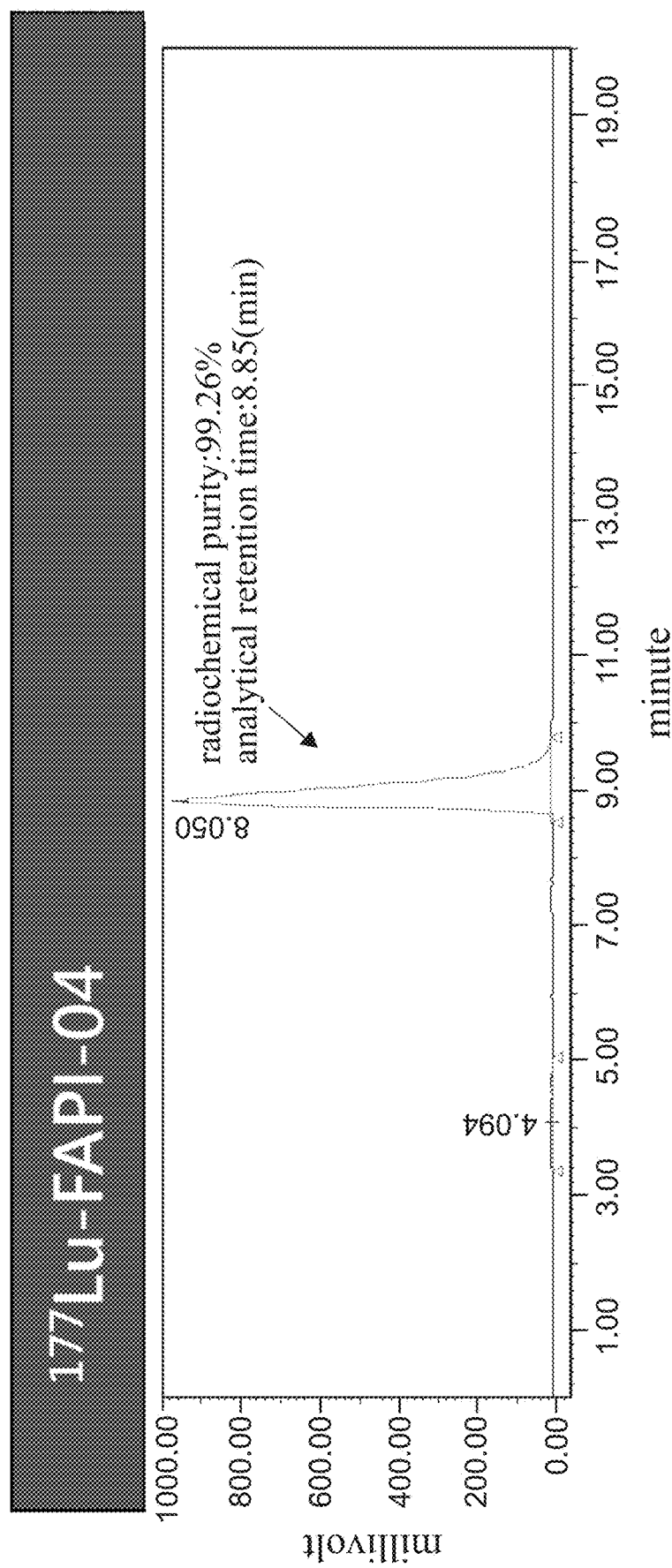
FIG. 7A is a chromatogram of radio-high-performance liquid chromatography of $^{177}$Lu-FAPI-04.
Figure 7B:
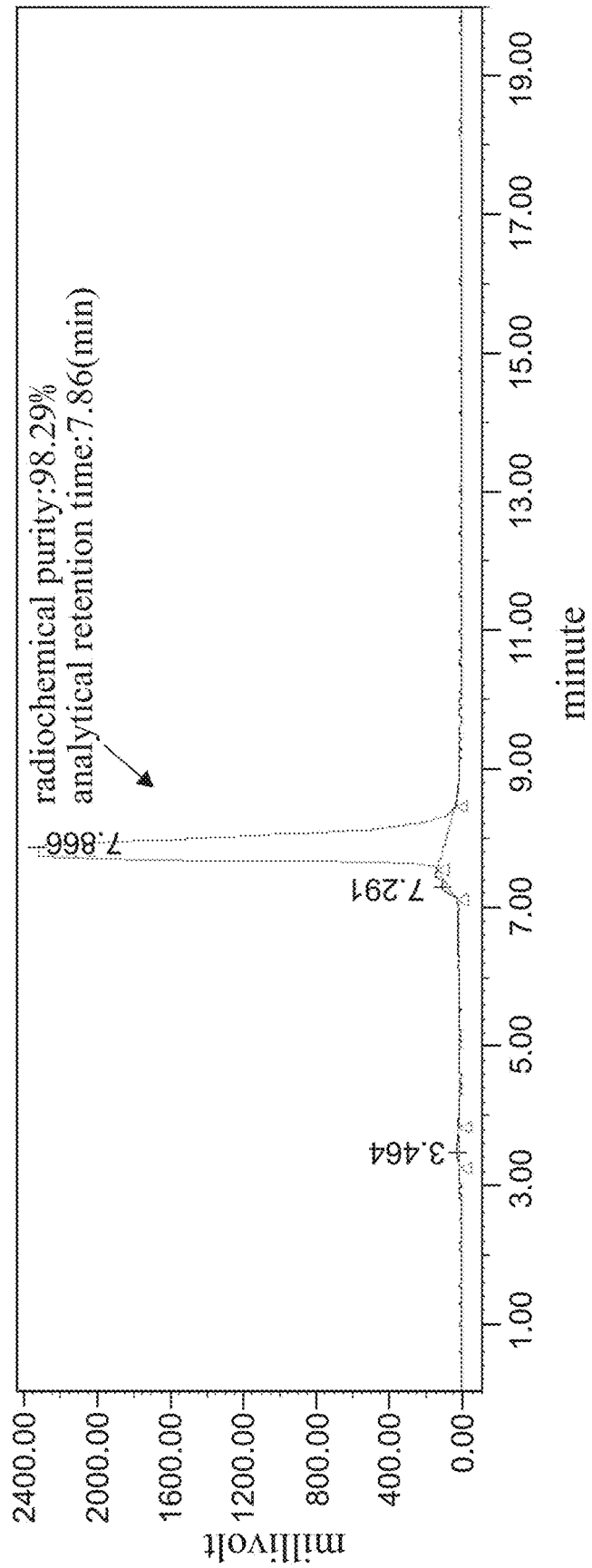
FIG. 7B is a chromatogram of radio-high-performance liquid chromatography of $^{177}$Lu-FAPI-INER-385-S.
Figure 7C:
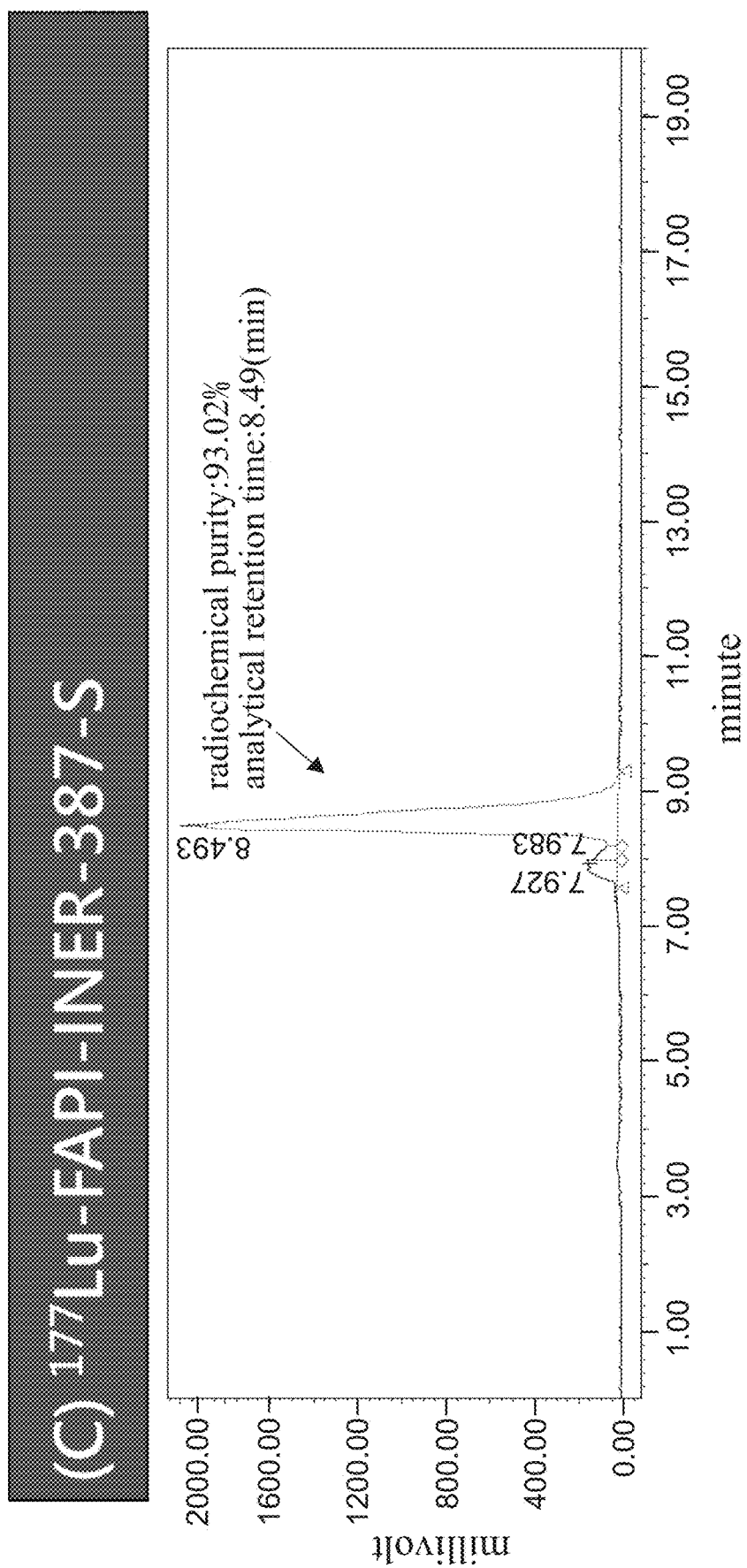
FIG. 7C is a chromatogram of radio-high-performance liquid chromatography of $^{177}$Lu-FAPI-INER-387-S.

Referring to FIG. 7A, FIG. 7B and FIG. 7C, representing the chromatograms of radio-high-performance liquid chromatography of $^{177}$Lu-FAPI-04, $^{177}$Lu-FAPI-INER-385-S and $^{177}$Lu-FAPI-INER-387-S by detecting with a radioactive detector. The radiochemical purity of $^{177}$Lu-FAPI-04 was 99.26%, and the analytical retention time was 8.85 minutes. The radiochemical purity of $^{177}$Lu-FAPI-INER-385-S was 98.29%, and the analytical retention time was 7.86 minutes. The radiochemical purity of $^{177}$Lu-FAPI-INER-387-S was 93.02%, and the analytical retention time was 8.49 minutes. The chemical purity of $^{177}$Lu-FAPI-04, $^{177}$Lu-FAPI-INER-385-S and $^{177}$Lu-FAPI-INER-387-S were all greater than 90.00%.

Figure 8:
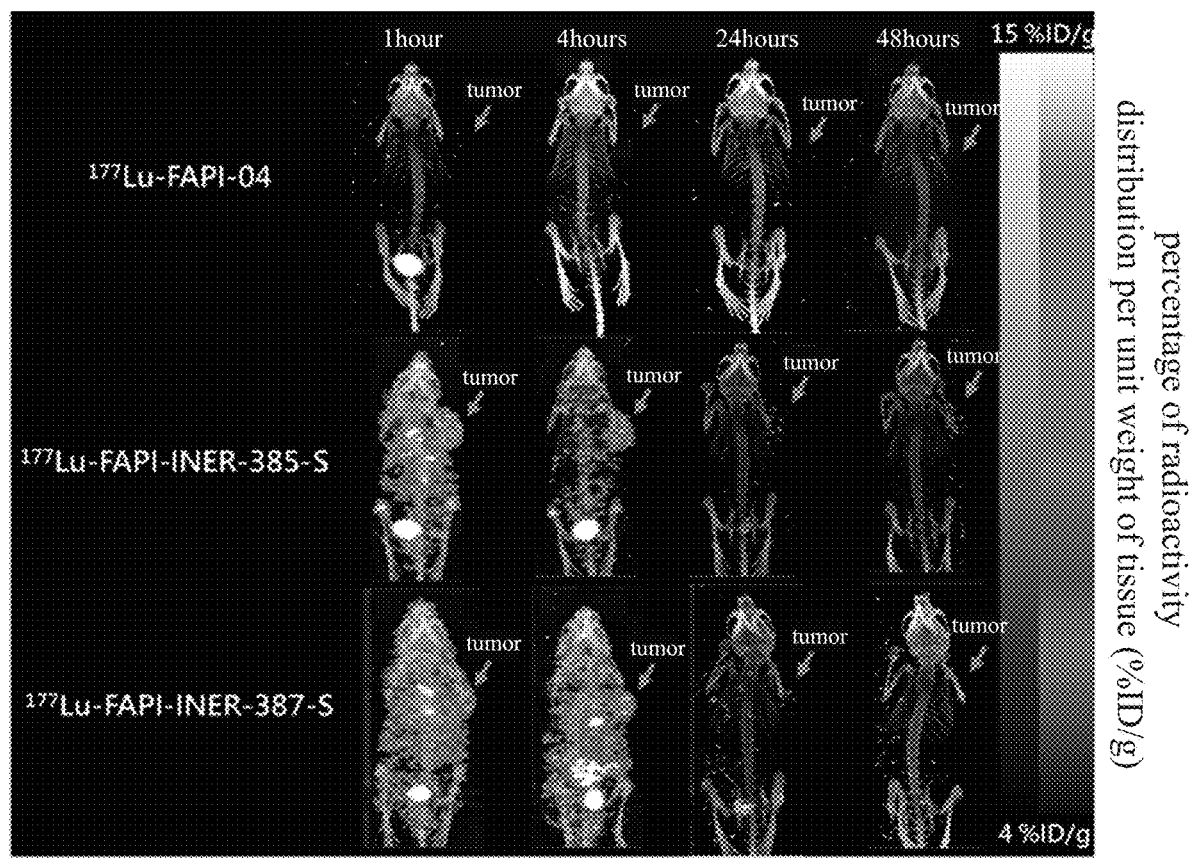
FIG. 8 is a graph showing that $^{177}$Lu-FAPI-04, $^{177}$Lu-FAPI-INER-385-S and $^{177}$Lu-FAPI-INER-387-S were injected into mice to perform in vivo imaging and recorded for 1 hour, 4 hours, 24 hours and 48 hours respectively.

Example 7: Use of radiolabeled compound of formula (I) D-R1-R2-A-R' or its salt thereof for in vivo imaging of animals Referring to FIG. 8, human prostate cancer cells (LNCaP cells) were inoculated into the forelimbs of mice with severe combined immunodeficiency disease (SCID), and the tumor size was 236 cubic millimeters (mm$^3$) to 410 cubic millimeters, $^{177}$Lu-FAPI-04, $^{177}$Lu-FAPI-INER-385-S or $^{177}$Lu-FAPI-INER-387-S were injected into the tail vein with a radioactivity of 13.7 megabacquerel (MBq) to 16.13 megabacquerel respectively. 1 hour, 4 hours, 24 hours and 48 hours after injection, a small animal single-photon computed tomography (nano SPECT/CT) was used for imaging. The radioactivity window in the image ranges from 4% ID/g to 15% ID/g, wherein "% ID/g" refers to the total radioactivity of the injection as 100%. The proportion of radioactivity distribution in the unit weight of the tissue was captured at each position on the image.

At 1 hour after the injection, the tumors of the mouse injected with $^{177}$Lu-FAPI-04 only had a slight accumulation of radioactivity, while in the mouse injected with $^{177}$Lu-FAPI-INER-385-S and the mouse injected with $^{177}$Lu-FAPI-INER-387-S, the radioactivity was distributed systemically and also accumulating in the tumor due to binding to albumin in the blood. At 4 hours after injection, the mouse injected with $^{177}$Lu-FAPI-04 have no radioactivity in the tumor, and the mouse injected with $^{177}$Lu-FAPI-INER-385-S and the mouse injected with $^{177}$Lu-FAPI-INER-387-S still had systemic distributions of radioactivity, and the tumor part still had high accumulations although the overall radioactivity were decreased. At 24 hours after injection, the mouse injected with $^{177}$Lu-FAPI-INER-385-S and the mouse injected with $^{177}$Lu-FAPI-INER-387-S still had small amounts of accumulation of radioactivity in their tumors. At 48 hours after injection, the mouse injected with $^{177}$Lu-FAPI-INER-385-S still had small amount of accumulation of radioactivity in the tumor. Therefore, from the distribution of animal images, it can be known that the modified radioactive marker such as the compound of formula (I) D-R1-R2-A-R' or its salt thereof had high accumulation in the tumors, and the distribution time is extended to 24 hours.

In summary, this present disclosure provides a compound represented by formula (I) D-R1-R2-A-R' or its salt thereof, as well as its preparation methods and uses, wherein the compound represented by formula (I) D-R1-R2-A-R' or its salt thereof can increase the circulation time of FAP inhibitors in the blood, and also increase the accumulation of the inhibitor in the tumor. The compound can be used for FAP imaging and for the preparation of drugs for radiotherapy.

What is claimed:

1. A compound represented by formula (I) D-R1-R2-A-R' or its salt thereof, wherein A is a group represented by

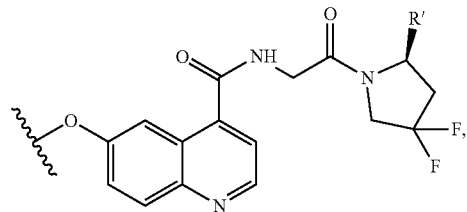

A is connected to R2 by forming an ether bond (—O—) therebetween, A is connected to R', R2 is connected to R1, R1 is connected to D;

R' is a group represented by selected from the group consisting of a cyano group (—CN), a methyl group (—CH$_3$) and an alkynyl group (—CCH);

R2 is a group represented by any structure selected from a set of R2-I, a set of R2-II, a set of R2-III, a set of R2-IV or a set of R2-V;

R1 is a group represented by any structure selected from a set of R1-I, a set of R1-II, a set of R1-III, a set of R1-IV or a set of R1-V;

D structure is a group represented by a polycarboxylic macrocyclic ring structure selected from the group consisting of

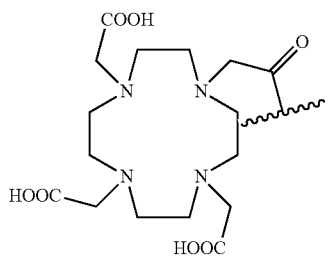

and

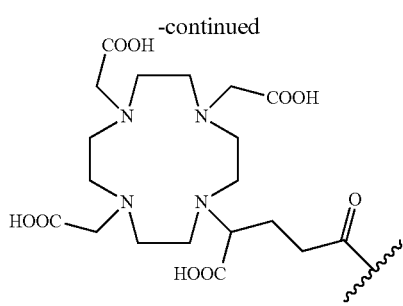

and is connected to any structure selected from the set of R1-I, the set of R1-II, the set of R1-III, the set of R1-IV or the set of R1-V to form an amide bond, and is bonded to a positively charged trivalent metal ion M, wherein M is a positive trivalent metal ion selected from the group consisting of $^{111}$In, $^{68}$Ga, $^{67}$Ga, $^{90}$Y or $^{177}$Lu; wherein R2 is selected from the set of R2-I, R1 is selected from the set of R1-I; wherein the set of R2-I includes R2-I-1, R2-I-2, R2-I-3, R2-I-4; wherein the set of R1-I includes R1-I-1, R1-I-2, R1-I-3, R1-I-4, R1-I-5, R1-I-6, R1-I-7, R1-I-8, R1-I-9, R1-I-10, R1-I-11 R1-I-12, R1-I-13, R1-I-14, R1-I-15, R1-I-16; p in the set of R2-I refers to an integer represented by the number of units of —CH$_2$—; a carboxyl group (—COOH) in any structure of R2-I-1, R2-I-2, R2-I-3 and R2-I-4 is connected to an amino group of an amide terminal (—C(O)NH$_2$) of any structure selected from the set of R1-I to form an amide bond, the p is an integer of 2, 3, 4, 5, 6, or 7 in the structures of R2-I-1, R2-I-2, R2-I-3 or R2-I-4,

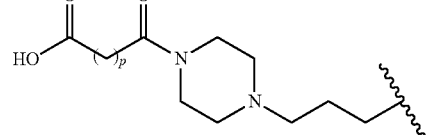

R2-I-1

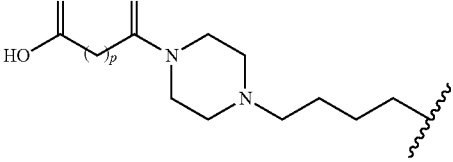

R2-I-2

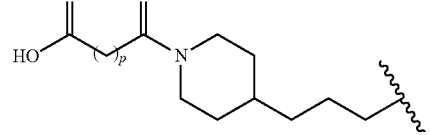

R2-I-3

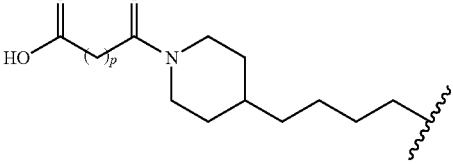

R2-I-4 a symbol "*" in any structure of the set of R1-I indicates a position of an optically active carbon having an R or S configuration of an optical structural isomer; an amide-terminated amino group (—C(O)NH$_2$) of any structure in the set of R1-I is connected to the carboxyl group (—COOH) of any molecule selected from the set of R2-I to form an amide bond;

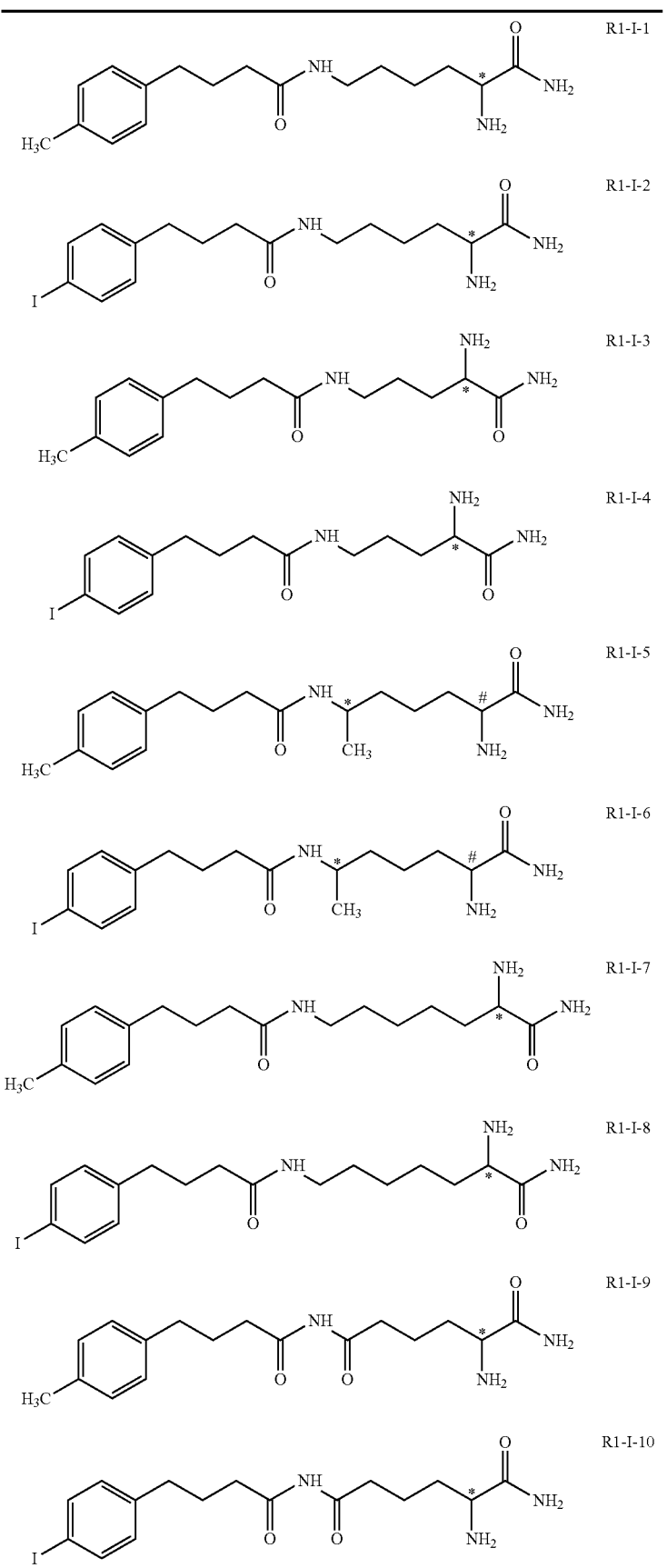

-continued

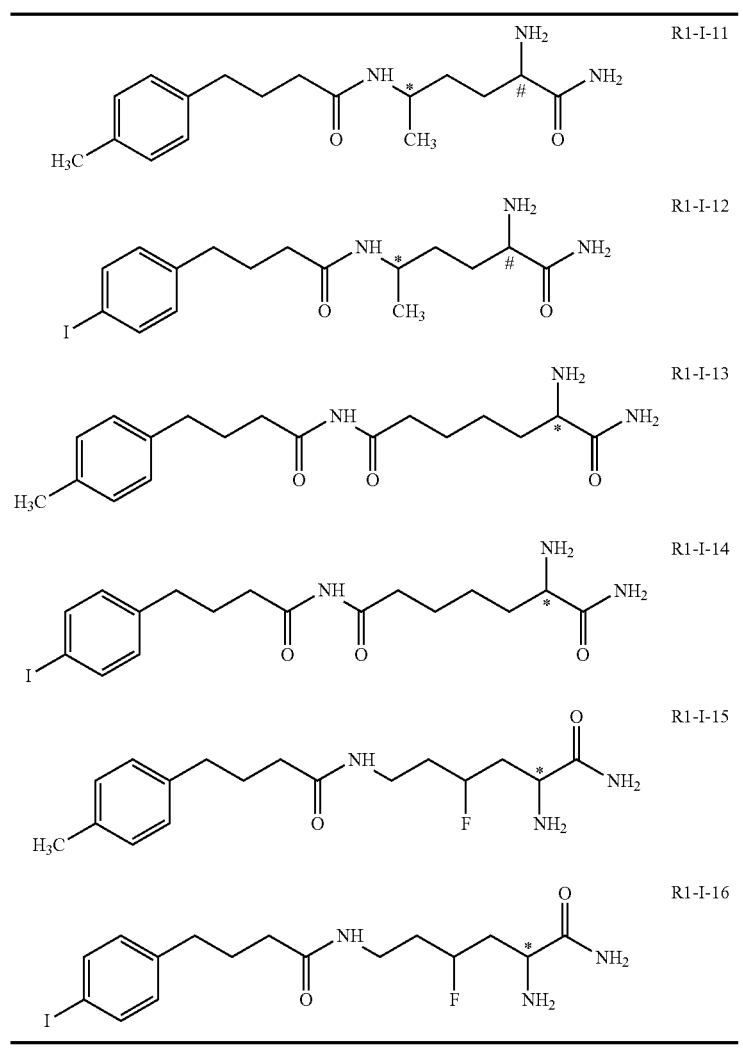

an amino group (—NH₂) that is connected to the optically active carbon of any structure in the set of R1-I is connected to the D structure to form an amide bond; or wherein R2 is selected from the set of R2-II, R1 is selected from the set of R1-II; wherein the set of R2-II includes R2-II-1, R2-II-2, R2-II-3, R2-II-4, R2-II-5, R2-II-6, R2-II-7, R2-II-8, R2-II-9, R2-II-10, R2-II-11, R2-II-12, R2-II-13, R2-II-14, R2-II-15, R2-II-16, R2-II-17, R2-II-18, R2-II-19, R2-II-20, R2-II-21, R2-II-22, R2-II-23, R2-II-24; wherein the set of R1-II includes R1-II-1, R1-II-2, R1-II-3, R1-II-4, R1-II-5, R1-II-6, R1-II-7, R1-II-8, R1-II-9, R1-II-10, R1-II-11, R1-II-12, R1-II-13, R1-II-14, R1-II-15, R1-II-16, R1-II-17, R1-II-18, R1-II-19, R1-II-20, R1-II-21, R1-II-22, R1-II-23, R1-II-24, R1-II-25, R1-II-26, R1-II-27, R1-II-28; a symbol "*" and "#" in any structure of the set of R2-II indicates a position of an optically active carbons having an R or S configuration of an optical structural isomer; an amino group (—NH₂) of any structure in the set of R1-II is connected to the carboxyl group (—COOH) of any structure in the set of R1-II to form an amide bond,

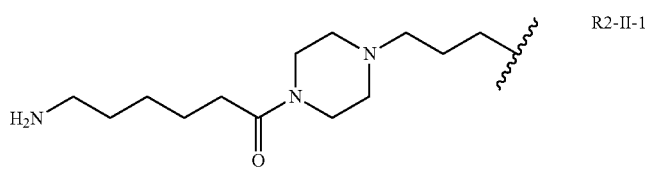

-continued
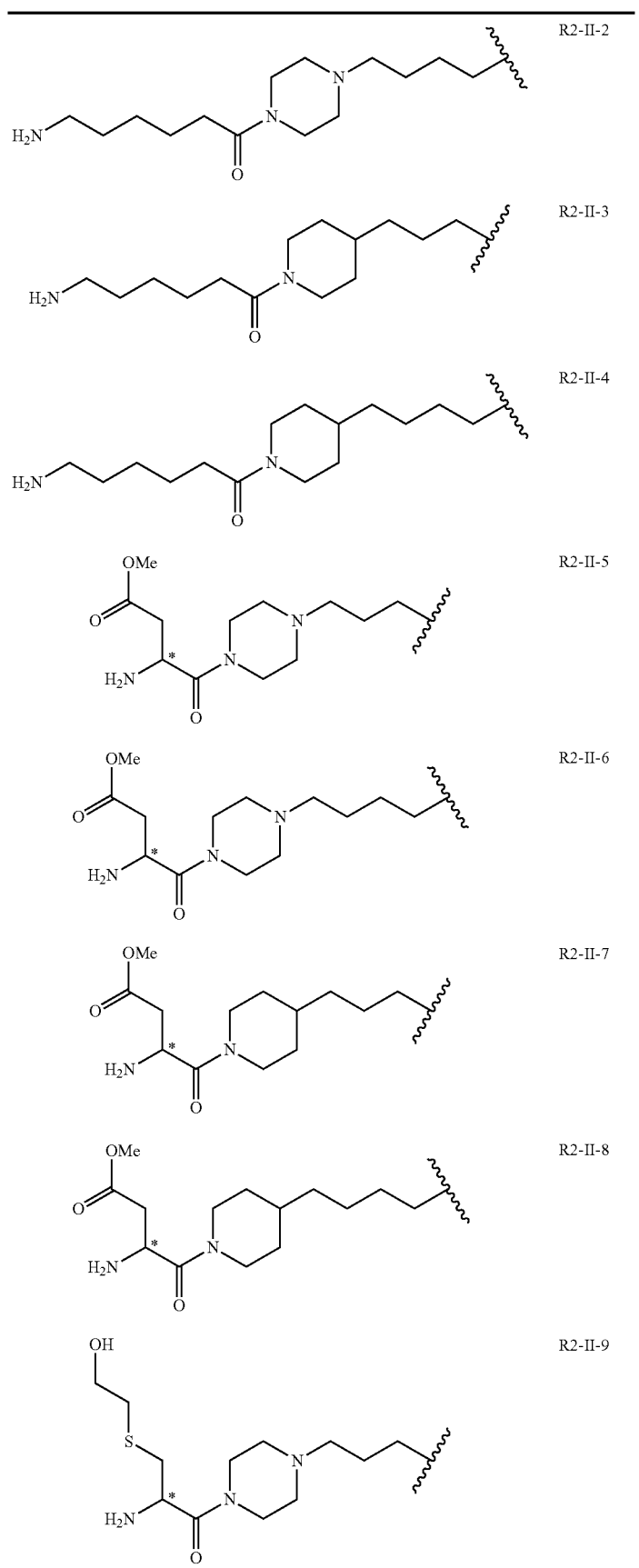

-continued
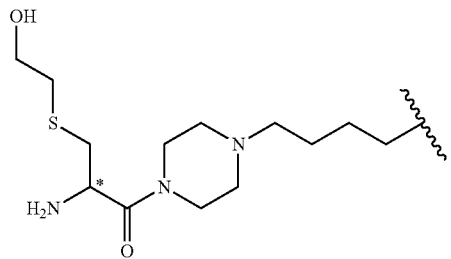 [SMILES: *CCCCN1CCN(C(=O)C(N)CSCCO)CC1]
R2-II-10
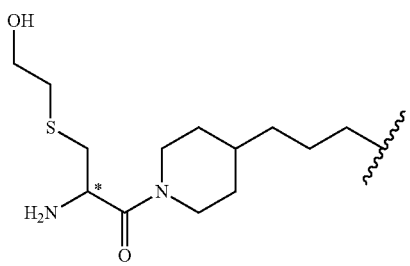
R2-II-11
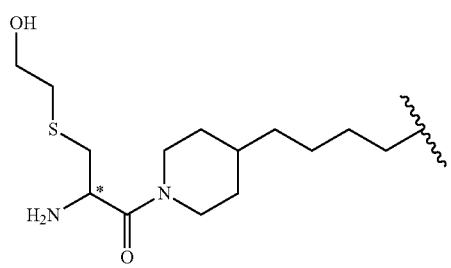 [SMILES: *CCCCC1CCN(C(=O)C(N)CSCCO)CC1]
R2-II-12
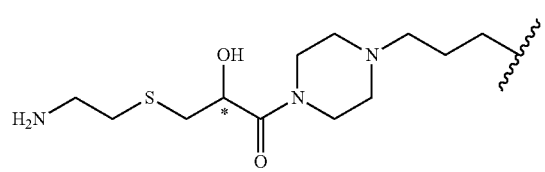 [SMILES: *CCCN1CCN(C(=O)C(O)CSCCN)CC1]
R2-II-13
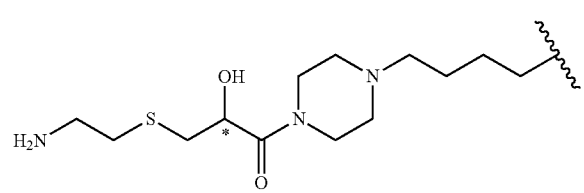 [SMILES: *CCCCN1CCN(C(=O)C(O)CSCCN)CC1]
R2-II-14
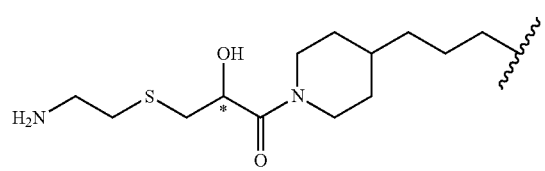
R2-II-15
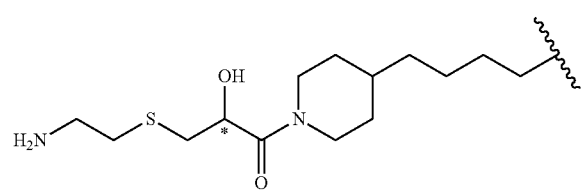 [SMILES: *CCCCC1CCN(C(=O)C(O)CSCCN)CC1]
R2-II-16

-continued
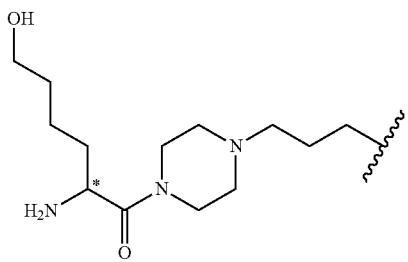
R2-II-17
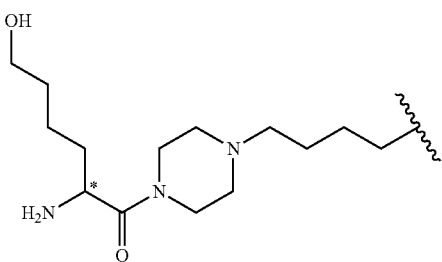 [SMILES: *CCCCN1CCN(C(=O)C(N)CCCCO)CC1]
R2-II-18
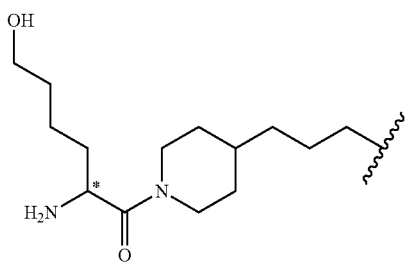
R2-II-19
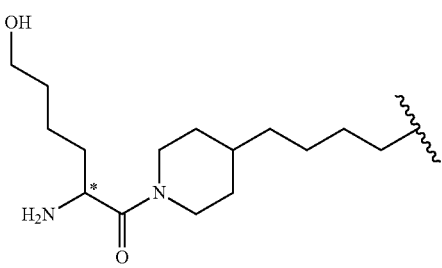
R2-II-20
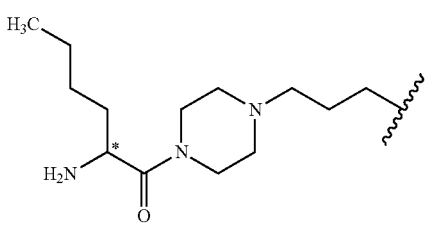 [SMILES: *CCCN1CCN(C(=O)C(N)CCCC)CC1]
R2-II-21
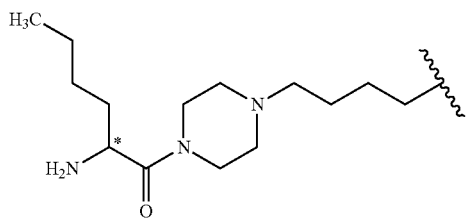
R2-II-22

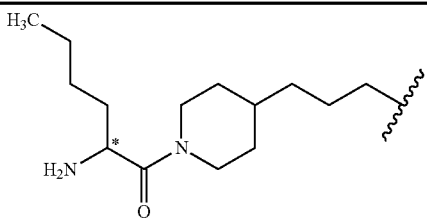
R2-II-23
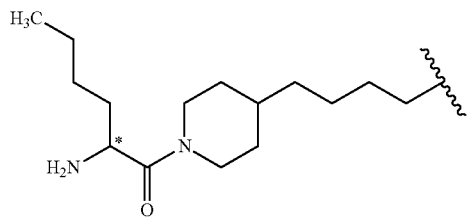
R2-II-24
a symbol "*" in any structure of the set of R1-II indicates a position of an optically active carbon having an R or S configuration of an optical structural isomer; the carboxyl group (—COOH) of any structure in the set of R1-II is connected to an amino group of any molecule selected from the set of R2-II to form an amide bond;
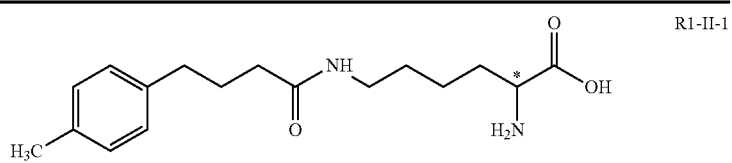
R1-II-1
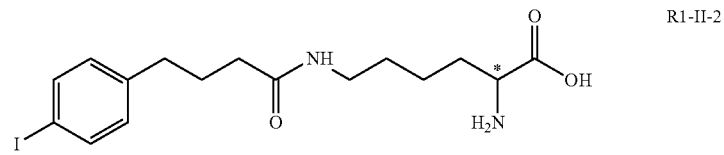
R1-II-2
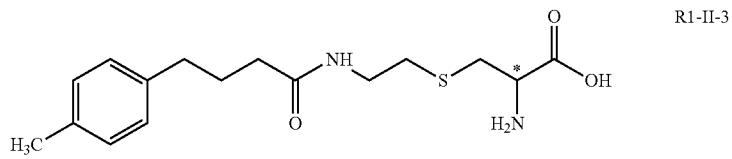
R1-II-3
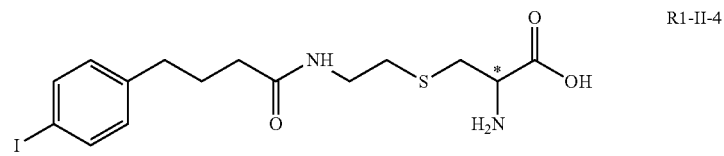
R1-II-4
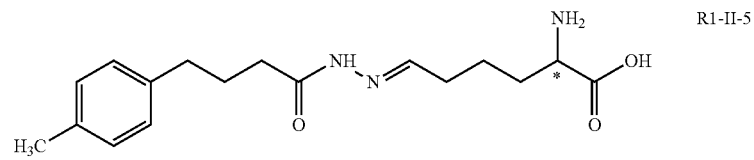
R1-II-5
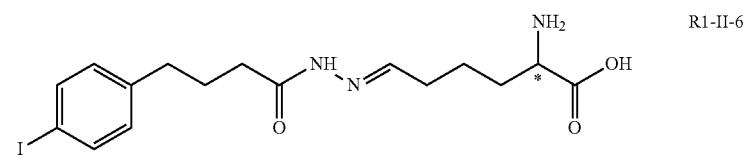
R1-II-6

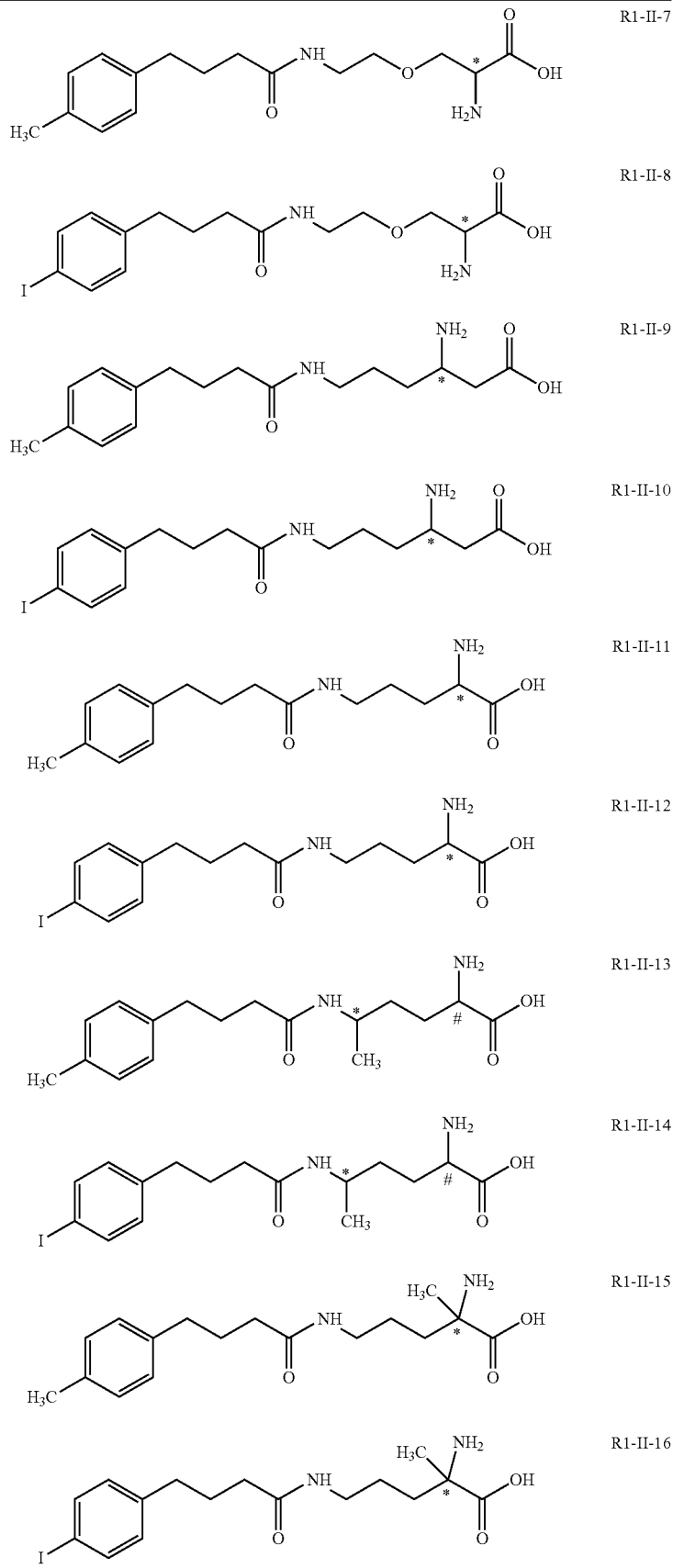

-continued
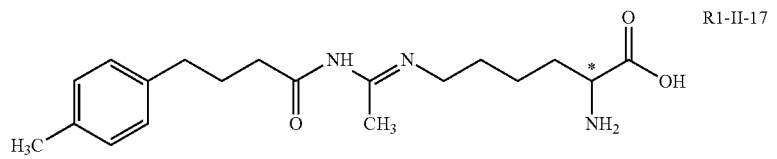
R1-II-17
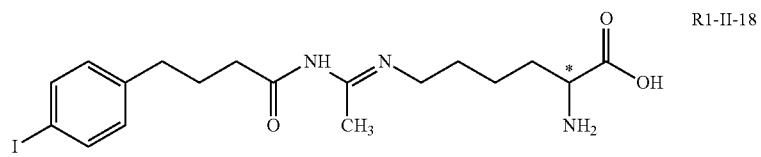
R1-II-18
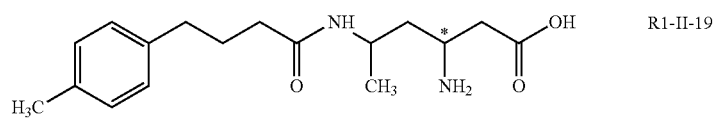
R1-II-19
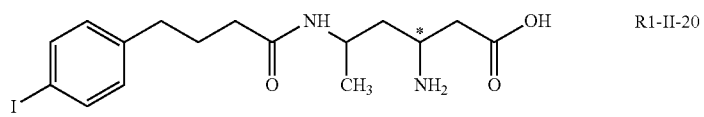
R1-II-20
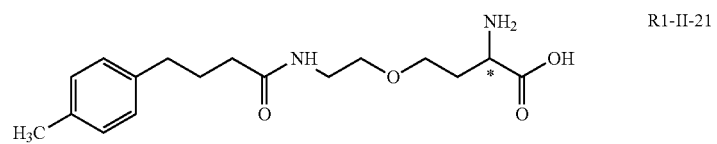
R1-II-21
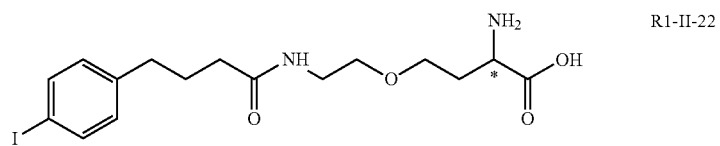
R1-II-22
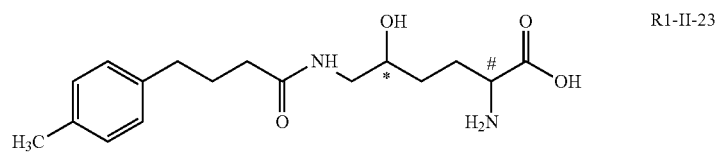
R1-II-23
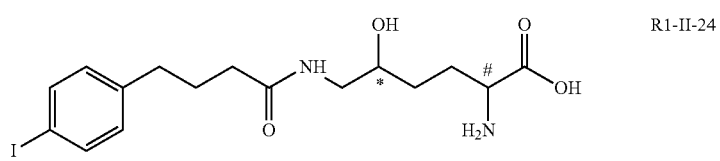
R1-II-24
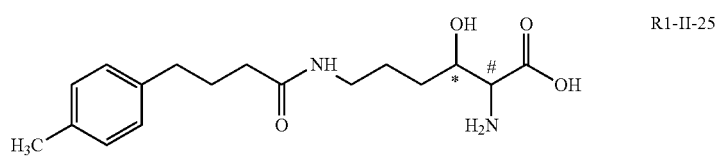
R1-II-25
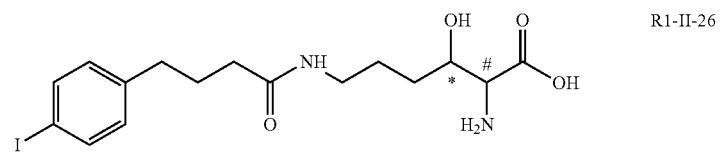
R1-II-26

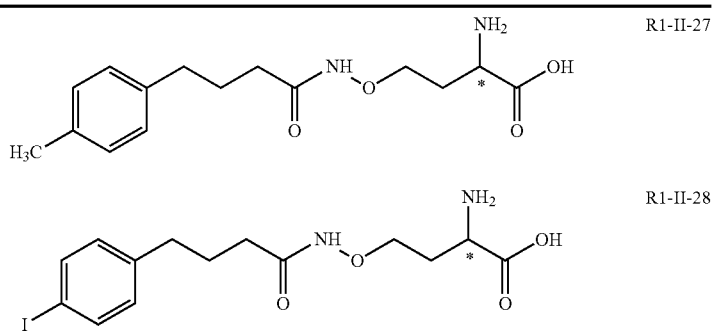

an amino group (—NH₂) of any structure in the set of R1-II is connected to the D structure to form an amide bond;

or wherein R2 is selected from the set of R2-III, R1 is selected from the set of R1-III;

wherein the set of R2-III includes R2-III-1, R2-III-2, R2-III-3, R2-III-4, R2-III-5, R2-III-6, R2-III-7, R2-III-8, R2-III-9, R2-III-10, R2-III-11, R2-III-12, R2-III-13, R2-III-14, R2-III-15, R2-III-16, R2-III-17, R2-III-18, R2-III-19, R2-III-20; wherein the set of R1-III includes R1-III-1, R1-III-2, R1-III-3, R1-III-4, R1-III-5, R1-III-6, R1-III-7, R1-III-8, R1-III-9, R1-III-10, R1-III-11, R1-III-12; a symbol "*" in any structure of the set of R2-III indicates a position of an optically active carbon having an R or S configuration of an optical structural isomer; a maleimide group of any structure in the set of R2-III is connected to a thiol group (—SH) of any structure in the set of R1-III to form a sulfide bond,

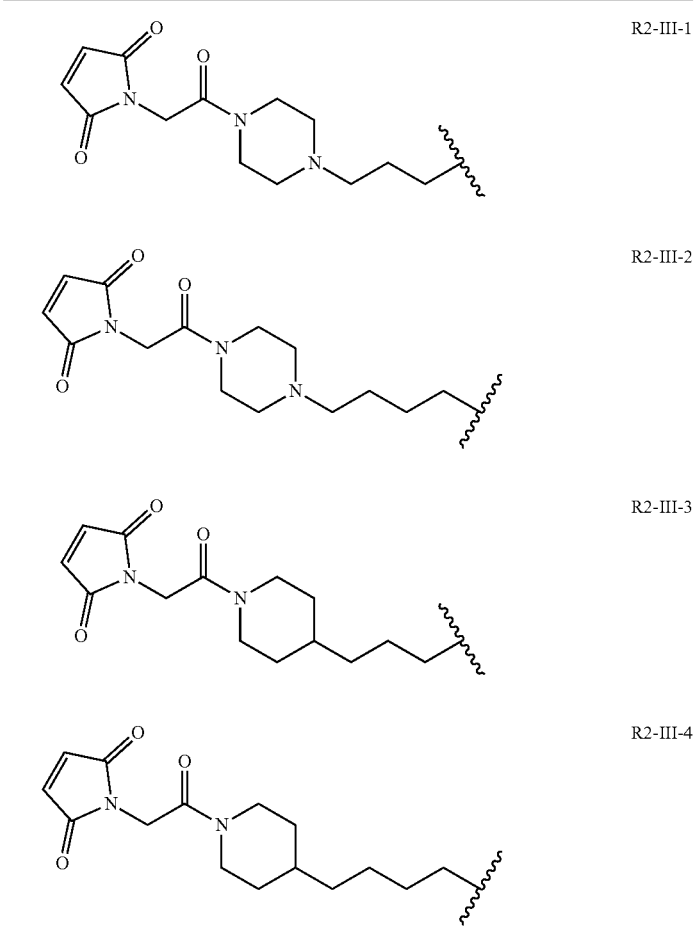

-continued
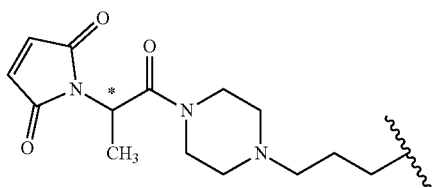
R2-III-5
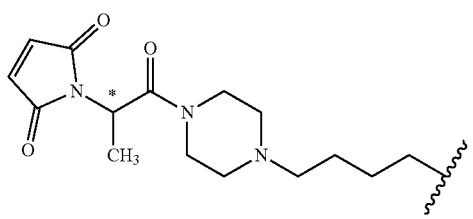 [SMILES: *CCCCN1CCN(C(=O)C(C)N2C(=O)C=CC2=O)CC1]
R2-III-6
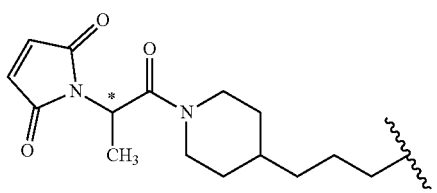 [SMILES: *CCCC1CCN(C(=O)C(C)N2C(=O)C=CC2=O)CC1]
R2-III-7
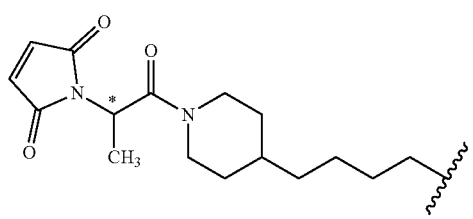 [SMILES: *CCCCC1CCN(C(=O)C(C)N2C(=O)C=CC2=O)CC1]
R2-III-8
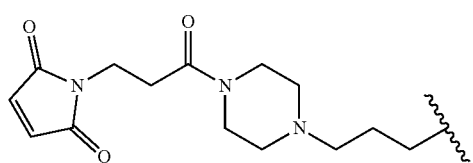 [SMILES: *CCCN1CCN(C(=O)CCN2C(=O)C=CC2=O)CC1]
R2-III-9
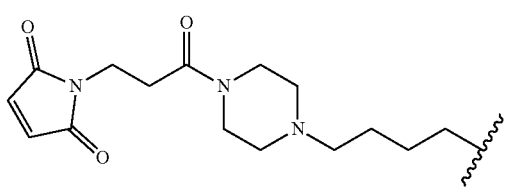
R2-III-10
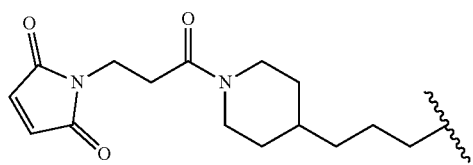
R2-III-11
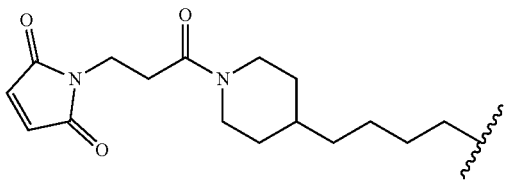 [SMILES: *CCCCN1CCN(C(=O)CCN2C(=O)C=CC2=O)CC1]
R2-III-12

-continued
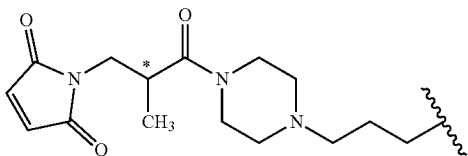 [SMILES: *CCCN1CCN(C(=O)C(C)CN2C(=O)C=CC2=O)CC1] R2-III-13
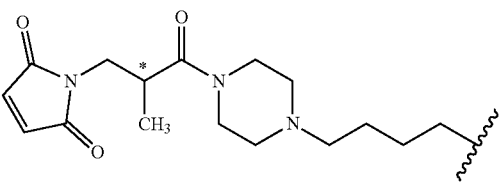 [SMILES: *CCCCN1CCN(C(=O)C(C)CN2C(=O)C=CC2=O)CC1] R2-III-14
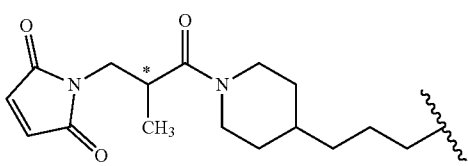 [SMILES: *CCCC1CCN(C(=O)C(C)CN2C(=O)C=CC2=O)CC1] R2-III-15
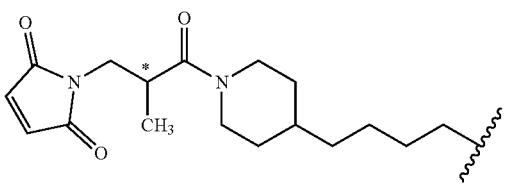 [SMILES: *CCCCC1CCN(C(=O)C(C)CN2C(=O)C=CC2=O)CC1] R2-III-16
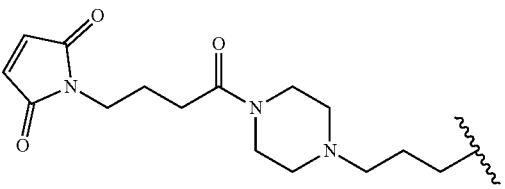 [SMILES: *CCCN1CCN(C(=O)CCCN2C(=O)C=CC2=O)CC1] R2-III-17
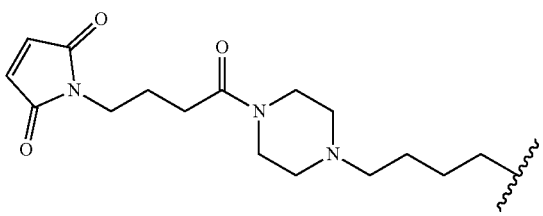 [SMILES: *CCCCN1CCN(C(=O)CCCN2C(=O)C=CC2=O)CC1] R2-III-18
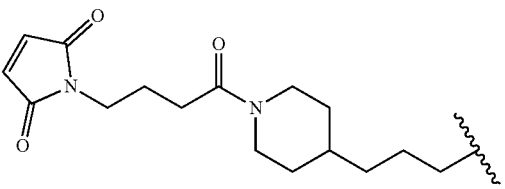 [SMILES: *CCCC1CCN(C(=O)CCCN2C(=O)C=CC2=O)CC1] R2-III-19
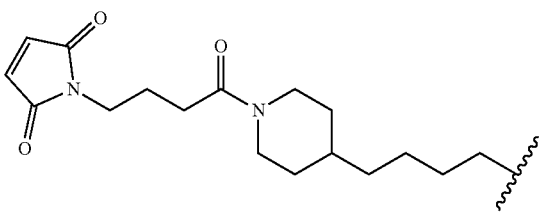 [SMILES: *CCCCC1CCN(C(=O)CCCN2C(=O)C=CC2=O)CC1] R2-III-20 a symbol "*" in any structure of the set of R1-III indicates a position of an optically active carbon having an R or S configuration of an optical structural isomer; a thiol group (—SH) of any structure in the set of R1-III is connected to the maleimide group of any structure selected from the set of R2-III to form an amide bond;
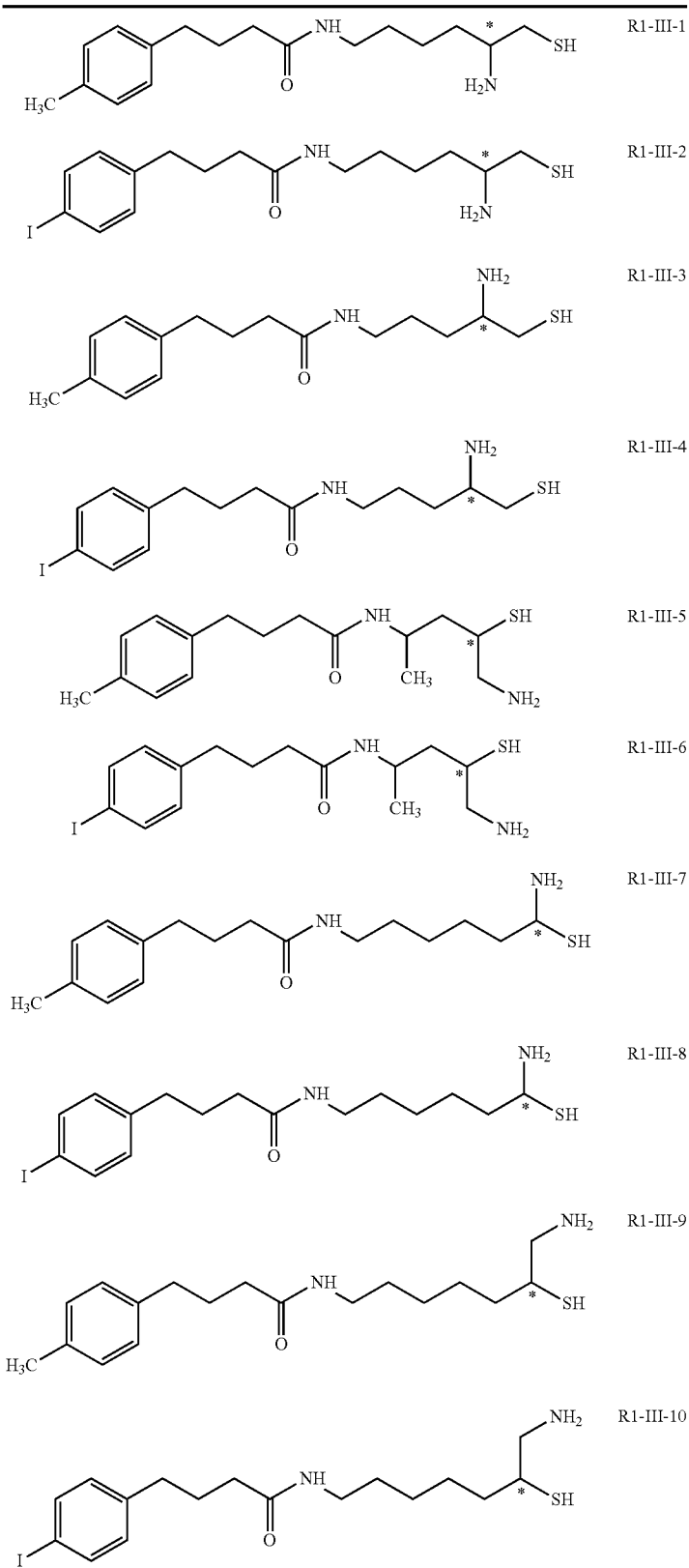

-continued

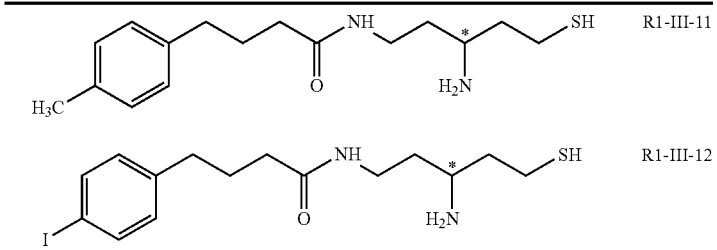

an amino group (—NH$_2$) of any structure in the set of R1-III is formed an amide bond with the D structure; or wherein R2 is selected from the set of R2-IV, R1 is selected from the set of R1-IV, wherein the set of R2-IV includes R2-IV-1, R2-IV-2, R2-IV-3, R2-IV-4, R2-IV-5, R2-IV-6, R2-IV-7, R2-IV-8, R2-IV-9, R2-IV-10, R2-IV-11, R2-IV-12; wherein the set of R1-IV includes R1-IV-1, R1-IV-2; each of q, j, and k in the set of R2-IV refers to an integer represented by the number of units of —CH$_2$—; a semicarbazide group (—C(O)NHNH$_2$)) in any structure of R2-IV-1, R2-IV-2, R2-IV-3, R2-IV-4, R2-IV-5, R2-IV-6, R2-IV-7 or R2-IV-8 is connected to an aldehyde group (—C(O)H) of any structure selected from the set of R1-IV to form an semicarbazone (—C(O)NHN=CH—) bond structure; the q in the structures of R2-IV-1, R2-IV-2, R2-IV-3 or R2-IV-4 is an integer of 2, 3, 4, 5, 6, or 7; the j in the structures of R2-IV-5, R2-IV-6, R2-IV-7 or R2-IV-8 is an integer of 1, 2, or 4; a hydrazino group (—NHNH$_2$) of any structure in R2-IV-9, R2-IV-10, R2-IV-11 or R2-IV-12 is connected to the aldehyde group (—C(O)H) of any structure in the set of R1-IV to form a hydrazone (—NHN=CH—); the k in the structures of R2-IV-9, R2-IV-10, R2-IV-11 or R2-IV-12 is an integer of 1, 2, or 3;

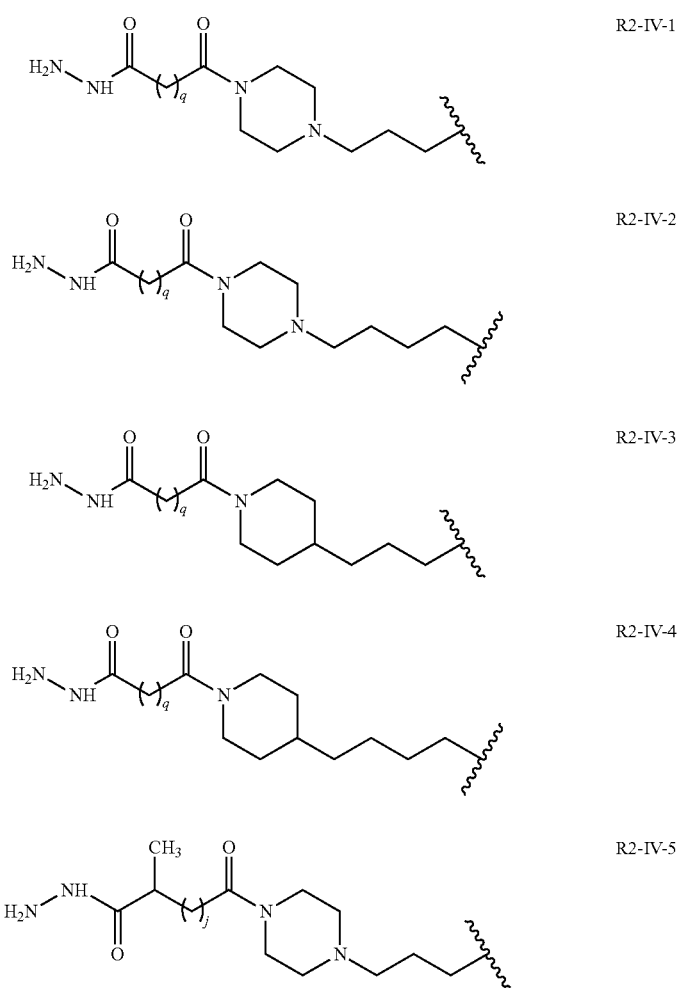

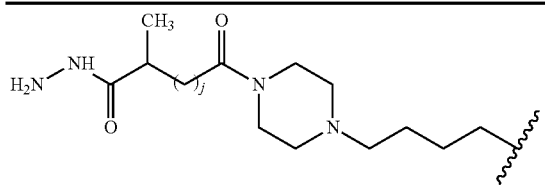

R2-IV-6

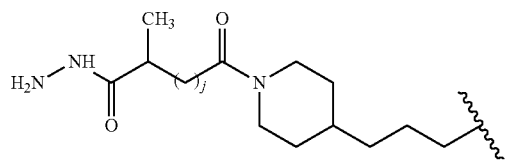

R2-IV-7

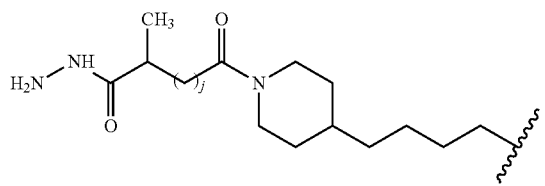

R2-IV-8

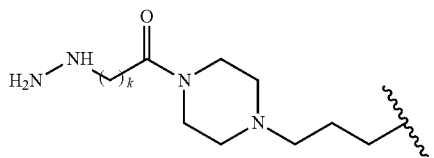

R2-IV-9

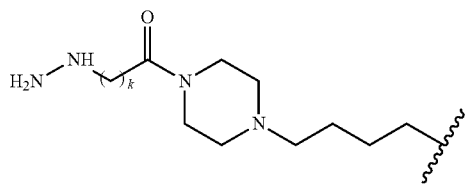

R2-IV-10

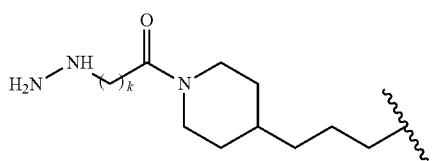

R2-IV-11

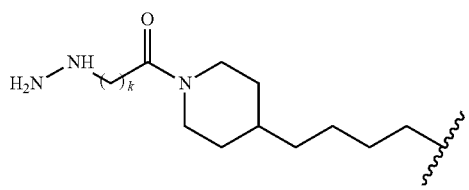

R2-IV-12 a symbol "*" in any structure of the set of R1-IV indicates a position of an optically active carbon having an R or S configuration of an optical structural isomer; the aldehyde group (—C(O)H) of any structure in the set of R1-IV is connected to a semicarbazide group (—C(O)NHNH$_2$) of any structure of R2-IV-1, R2-IV-2, R2-IV-3, R2-IV-4, R2-IV-5, R2-IV-6, R2-IV-7 or R2-IV-8 selected from the set of R2-IV group to form a semicarbazone (—C(O)NHN═CH—) bond structure, or connected to a hydrazino group (—NHNH$_2$) of any structure of R2-IV-9, R2-IV-10, R2-IV-11 or R2-IV-12 in the set of R2-IV to form a hydrazone (—NHN═CH—);

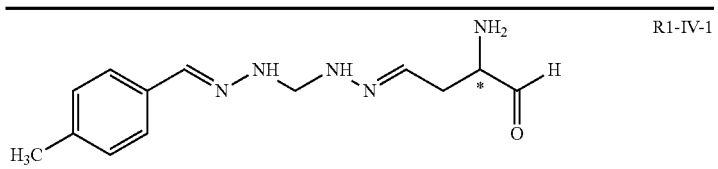
R1-IV-1

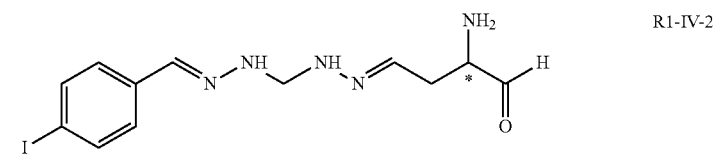
R1-IV-2 an amino group (—NH$_2$) of any structure in the set of R1-IV is connected to the D structure to form an amide bond;

or wherein R2 is selected from the set of R2-V, R1 is selected from the set of R1-V; wherein the set of R2-V includes R2-V-1, R2-V-2, R2-V-3, R2-V-4; wherein the set of R1-V includes R1-IV-1, R1-IV-2; n in the set of R2-V refers to an integer represented by the number of units of —CH$_2$—; an aldehyde group (—C(O)H) of any structure in R2-V-1, R2-V-2, R2-V-3, or R2-V-4 is connected to a hydrazino group (—NHNH$_2$) of any structure in the set of R1-V to form a hydrazone (—NHN=CH—); n is an integer of 2, 3, 4, 5, 6, or 7 in the structures of R2-V-1, R2-V-2, R2-V-3 or R2-V-4, -continued

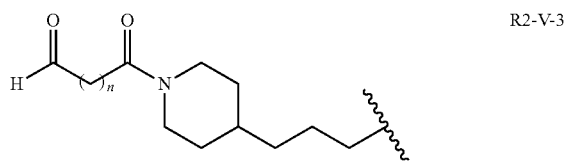
R2-V-3

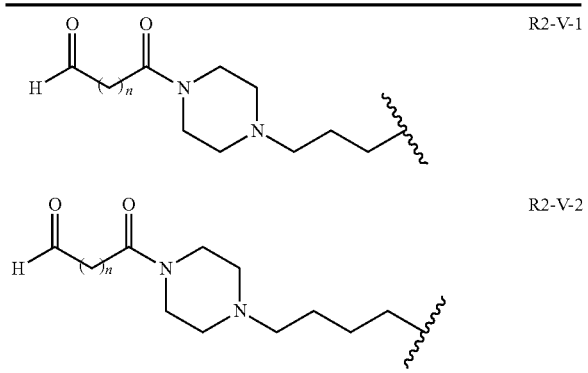
R2-V-1

R2-V-2

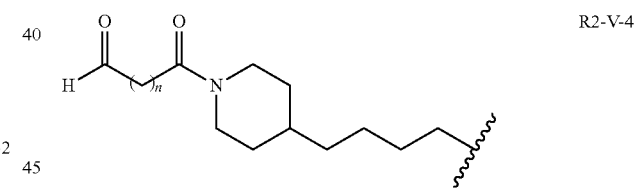
R2-V-4 the hydrazino group (—NHNH$_2$) of any structure in the set of R1-V is connected to the aldehyde group (—C(O)H) of any structure in the set of R2-V to form a hydrazone (—NHN=CH—);

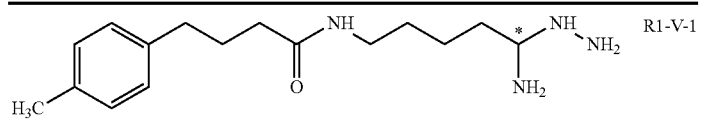
R1-V-1

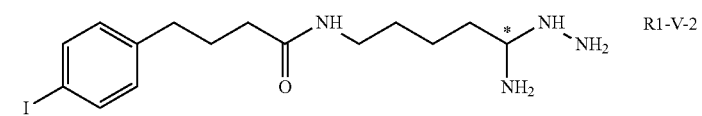
R1-V-2 an amino group (—NH$_2$) of any structure in the set of R1-V is connected to the D structure to form an amide bond.

2. The compound represented by formula (I) D-R1-R2-A-R' or its salt thereof according to claim 1, wherein R' is a cyano group (—CN).

3. The compound represented by formula (I) D-R1-R2-A-R' or its salt thereof according to claim 1, wherein R' is a methyl group (—CH$_3$).

4. The compound represented by formula (I) D-R1-R2-A-R' or its salt thereof according to claim 1, wherein R' is an alkynyl group (—CCH).

5. The compound represented by formula (I) D-R1-R2-A-R' or its salt thereof according to claim 1, wherein R' is a cyano group (—CN), R2 is selected from R2-I-1 of the set of R2-I and the p is and integer of 5, R1 is any structure selected from the set of R1-I, and the D structure is

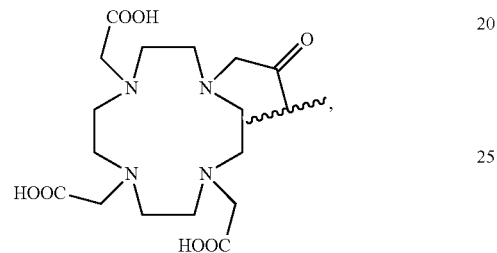

and thus the compound has a structure represented by formulas below:

Structure 1:

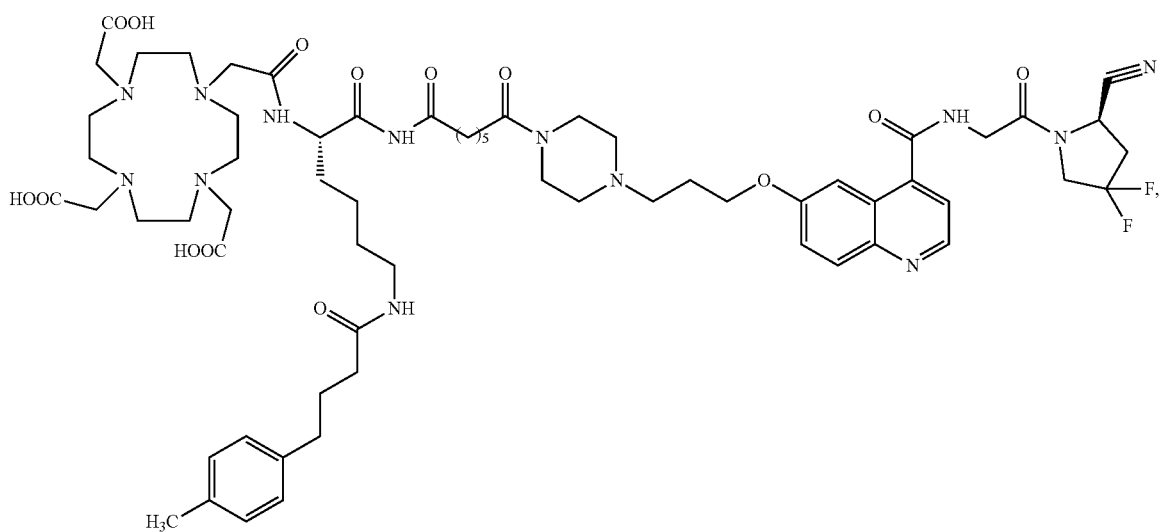

wherein

R1 is selected from R1-I-1, wherein the optical configuration of the optically active carbon is S configuration;

Code: FAPI-INER-01-S;

Molecular weight: 1302.4;

Molecular formula: $C_{64}H_{89}F_2N_{13}O_{14}$;

Structure 2;

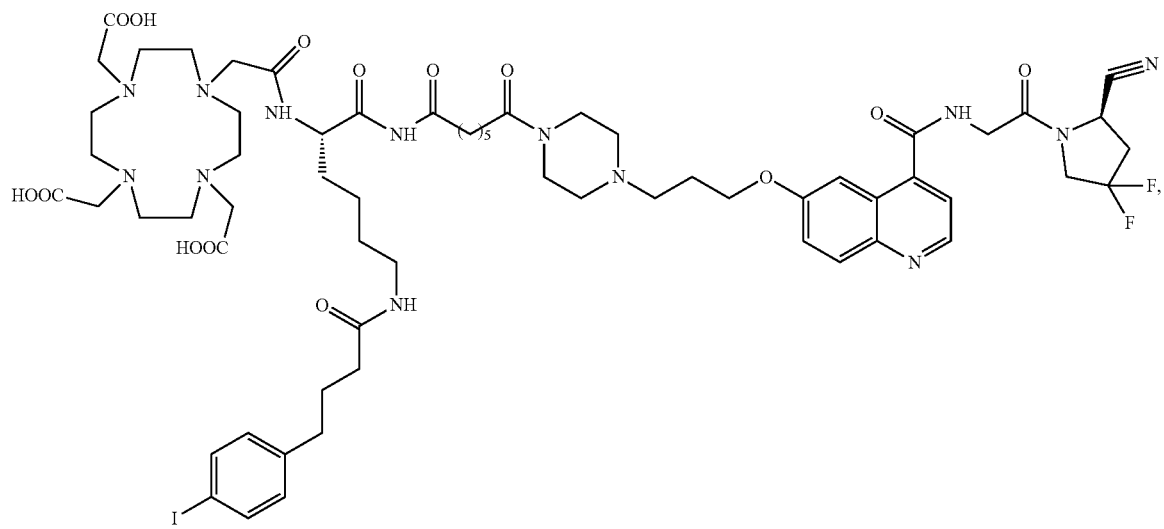

wherein
R1 is selected from R1-I-2, wherein the optical configuration of the optically active carbon is S configuration;
Code: FAPI-INER-05-S;
Molecular weight: 1414.3;
Molecular formula: $C_{63}H_{86}F_2IN_{13}O_{14}$;
Structure 3:

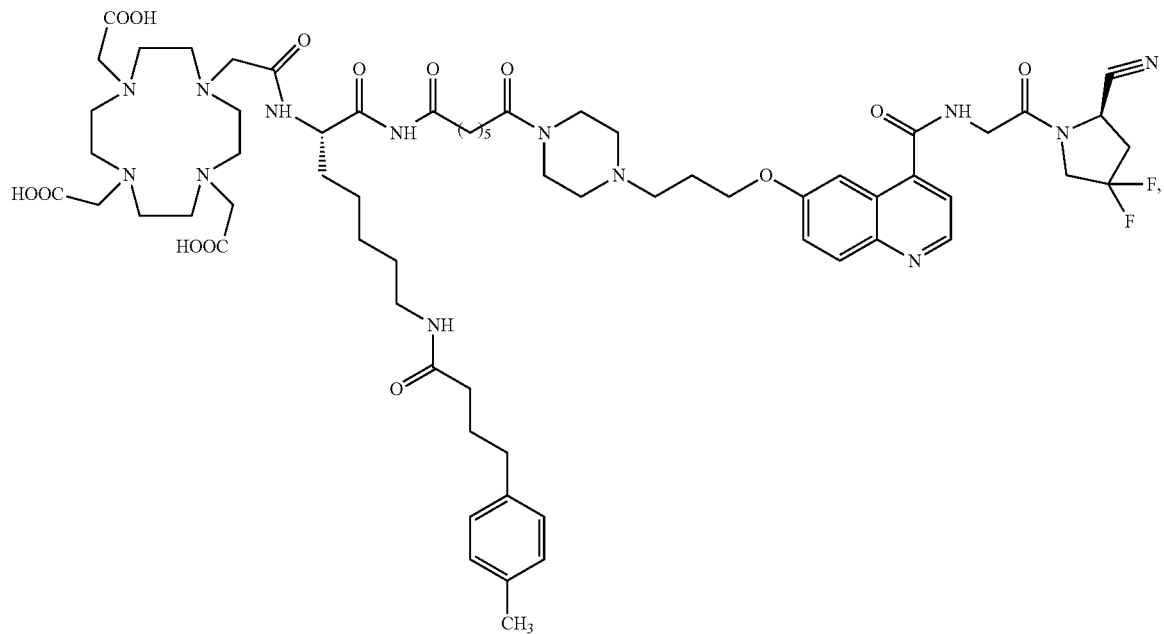

wherein
R1 is selected from R1-I-7, wherein the optical configuration of the optically active carbon is S configuration;
Code: FAPI-INER-09-S;
Molecular weight: 1316.4;
Molecular formula: $C_{65}H_{91}F_2N_{13}O_{14}$;

Structure 4:

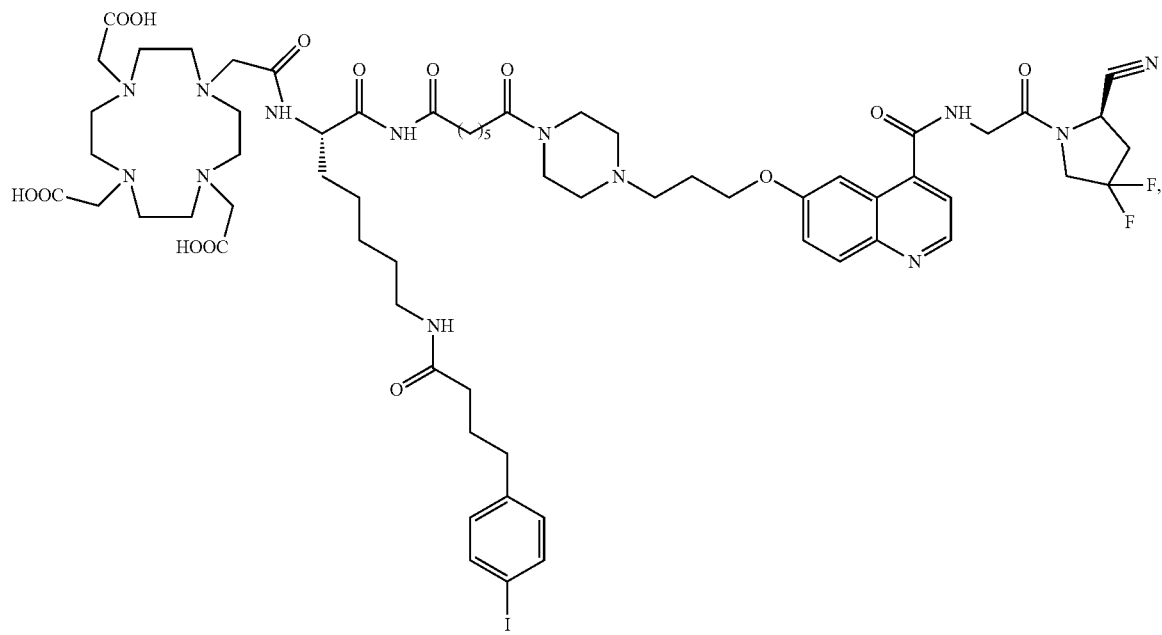

wherein
R1 is selected from R1-I-8, wherein the optical configuration of the optically active carbon is S configuration;
Code: FAPI-INER-13-S;
Molecular weight: 1428.3;
Molecular formula: $C_{64}H_{88}F_2IN_{13}O_{14}$;

Structure 5:

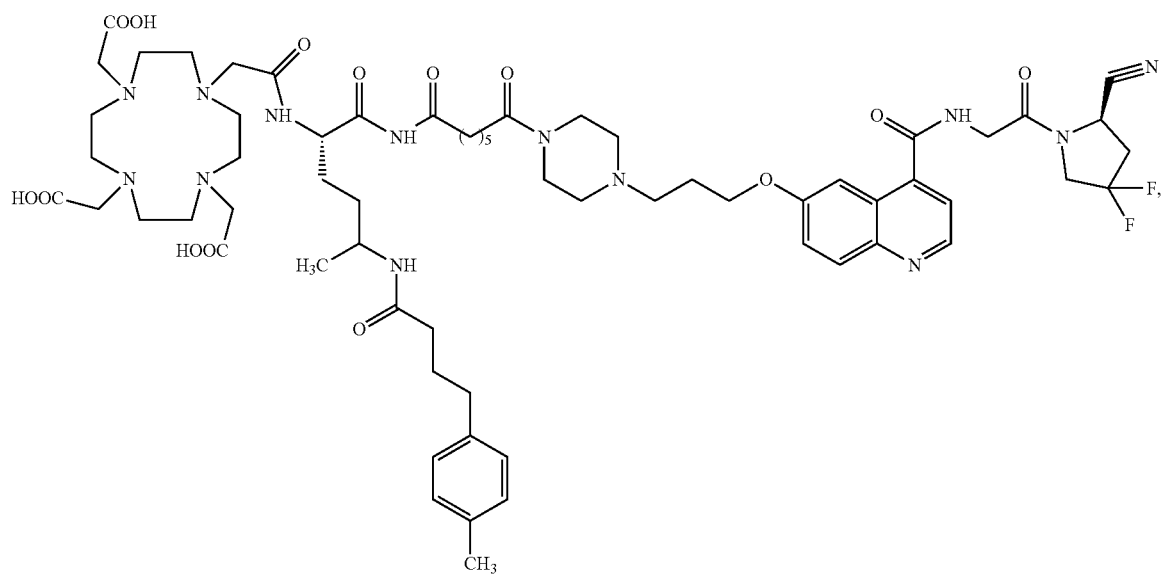

wherein
R1 is selected from R1-I-11, wherein the optical configurations of the two optically active carbons are S configurations respectively;
Code: FAPI-INER-17-SS;
Molecular weight: 1302.4;
Molecular formula: $C_{64}H_{89}F_2N_{13}O_{14}$;

Structure 6:

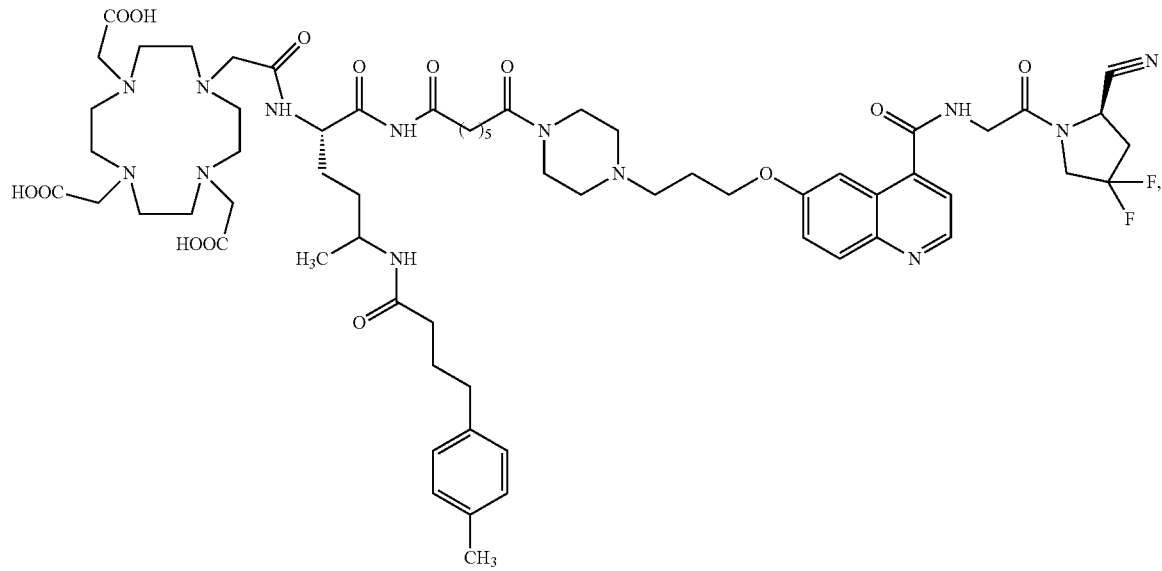

wherein
R1 is selected from R1-I-12, wherein the optical configurations of the two optically active carbons are S configurations respectively;
Code: FAPI-INER-21-SS;
Molecular weight: 1414.3;
Molecular formula: $C_{63}H_{86}F_2IN_{13}O_{14}$;

Structure 7:

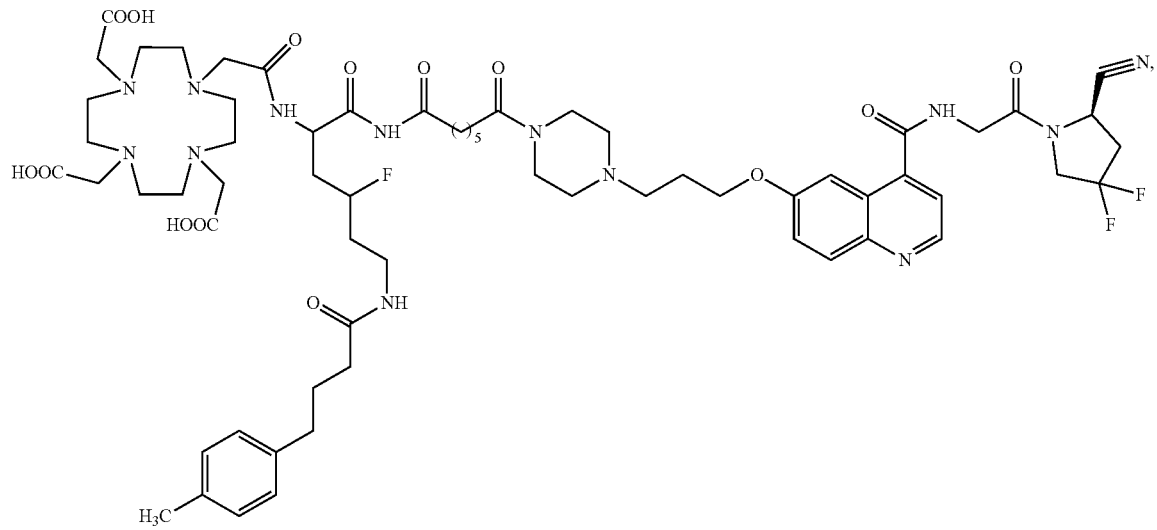

wherein
R1 is selected from R1-I-15, wherein the optical configuration of the optically active carbon is S configuration;
Code: FAPI-INER-25-S;
Molecular weight: 1320.4;
Molecular formula: $C_{64}H_{88}F_3N_{13}O_{14}$;

Structure 8:

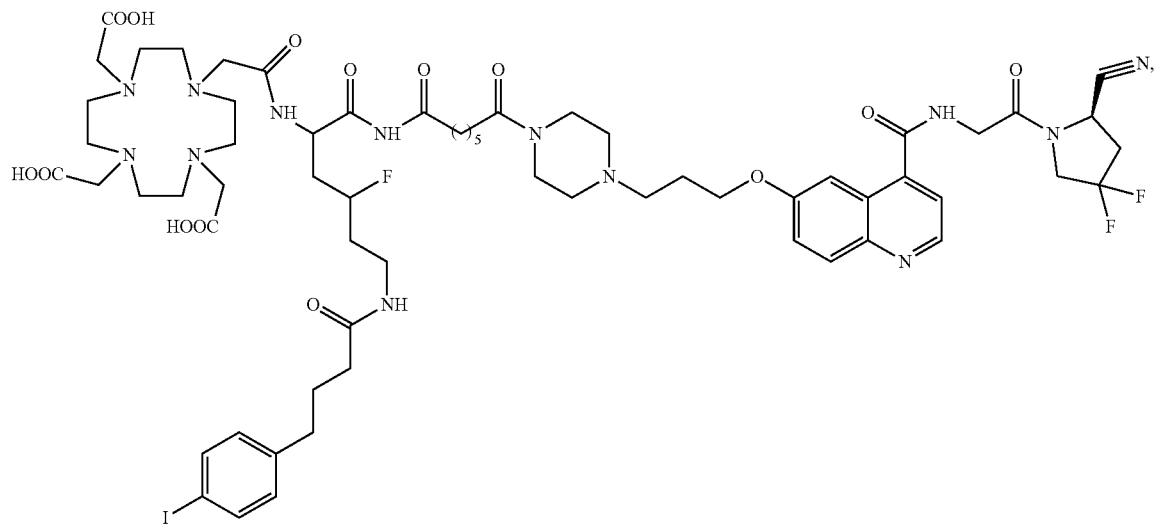

wherein
R1 is selected from R1-I-16, wherein the optical configuration of the optically active carbon is S configuration;
Code: FAPI-INER-29-S;
Molecular weight: 1432.3;
Molecular formula: $C_{63}H_{85}F_3IN_{13}O_{14}$;
or R2 is selected from R2-I-2 of the set of R2-I and the p is and integer of 5, R1 is any structure selected from the set of R1-I, and the D structure is

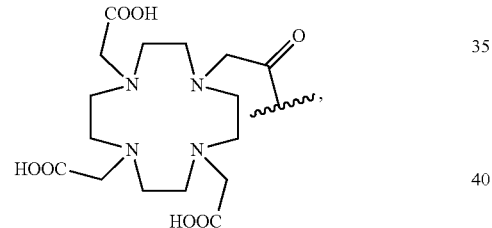

and thus the compound has a structure represented by formulas below:
Structure 9:

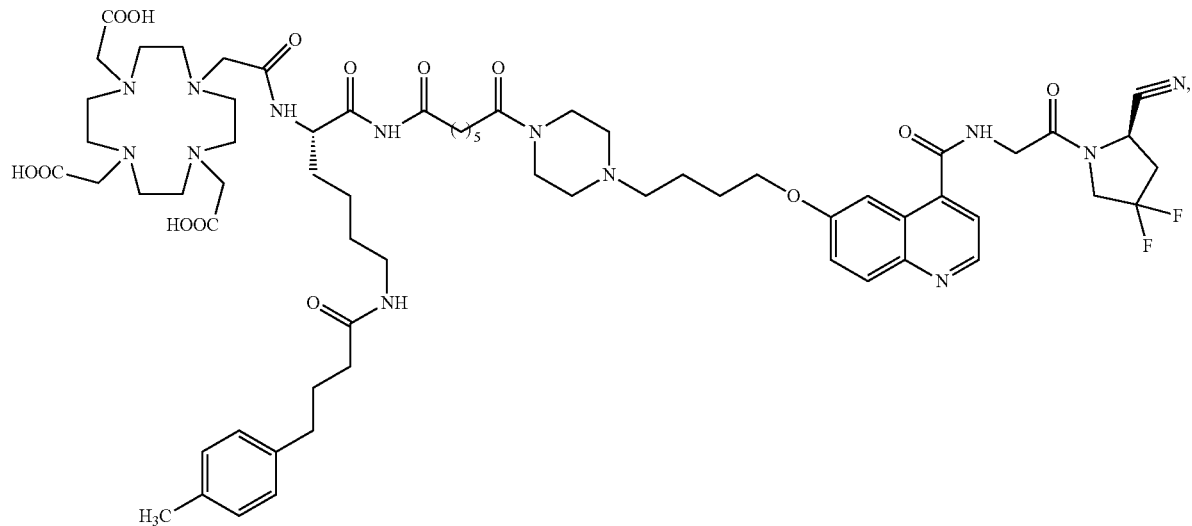

wherein
R1 is selected from R1-I-1, wherein the optical configuration of the optically active carbon is S configuration;
Code: FAPI-INER-02-S;
Molecular weight: 1316.4;
Molecular formula: $C_{65}H_{91}F_2N_{13}O_{14}$;
Structure 10:

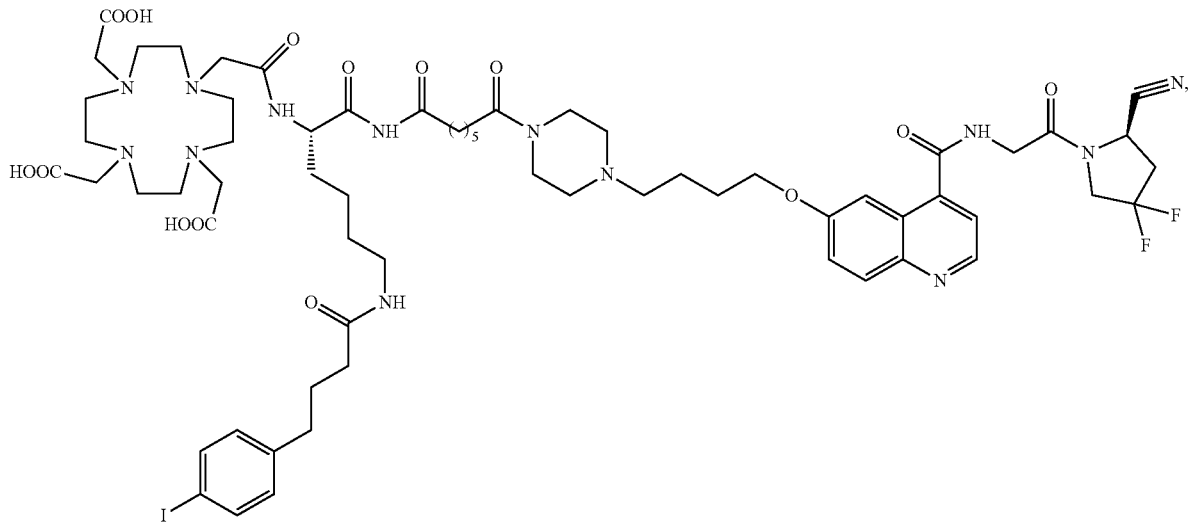

wherein
R1 is selected from R1-I-2, wherein the optical configuration of the optically active carbon is S configuration;
Code: FAPI-INER-06-S;
Molecular weight: 1428.3;
Molecular formula: $C_{64}H_{88}F_2IN_{13}O_{14}$;
Structure 11:

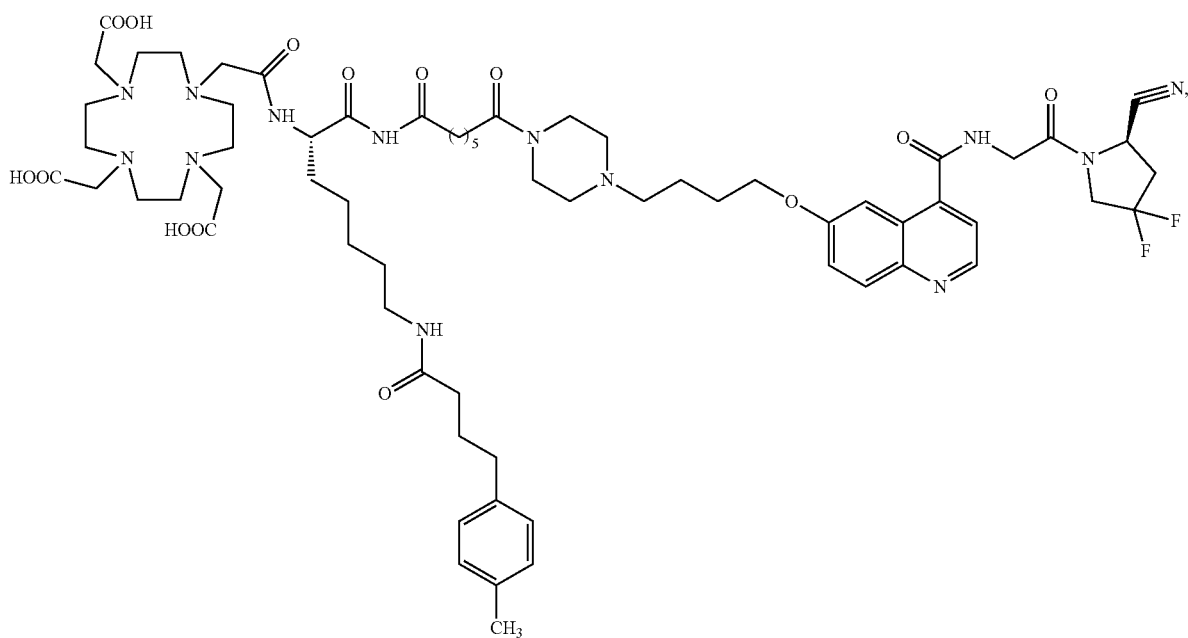

wherein
R1 is selected from R1-I-7, wherein the optical configuration of the optically active carbon is S configuration;
Code: FAPI-INER-10-S;
Molecular weight: 1330.5;
Molecular formula: $C_{66}H_{93}F_2N_{13}O_{14}$;
Structure 12:

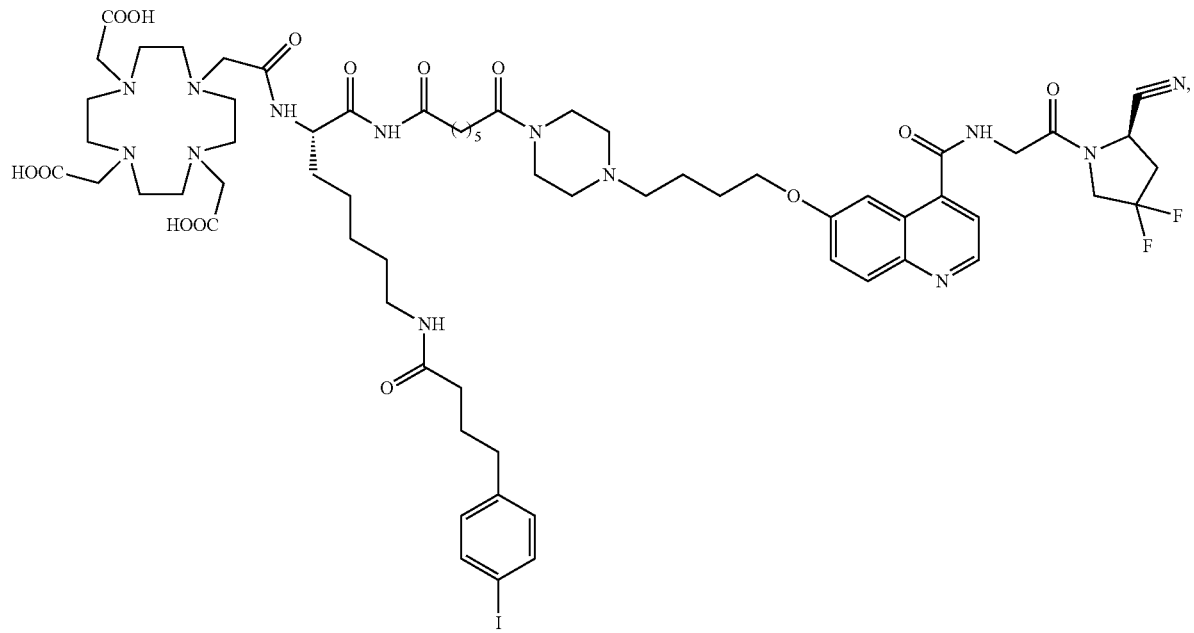

wherein
R1 is selected from R1-I-8, wherein the optical configuration of the optically active carbon is S configuration;
Code: FAPI-INER-14-S;
Molecular weight: 1442.3;
Molecular formula: $C_{65}H_{90}F_2IN_{13}O_{14}$;
Structure 13:

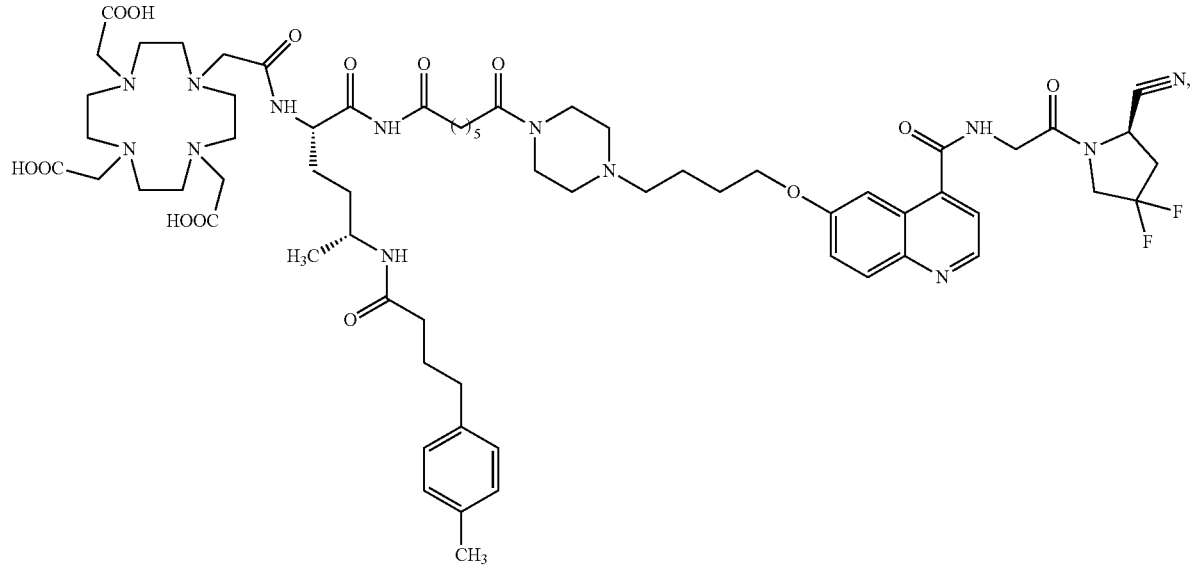

wherein
R1 is selected from R1-I-11, wherein the optical configurations of the two optically active carbons are S configurations respectively;
Code: FAPI-INER-18-SS;
Molecular weight: 1316.4;
Molecular formula: $C_{65}H_{91}F_2N_{13}O_{14}$;
Structure 14:

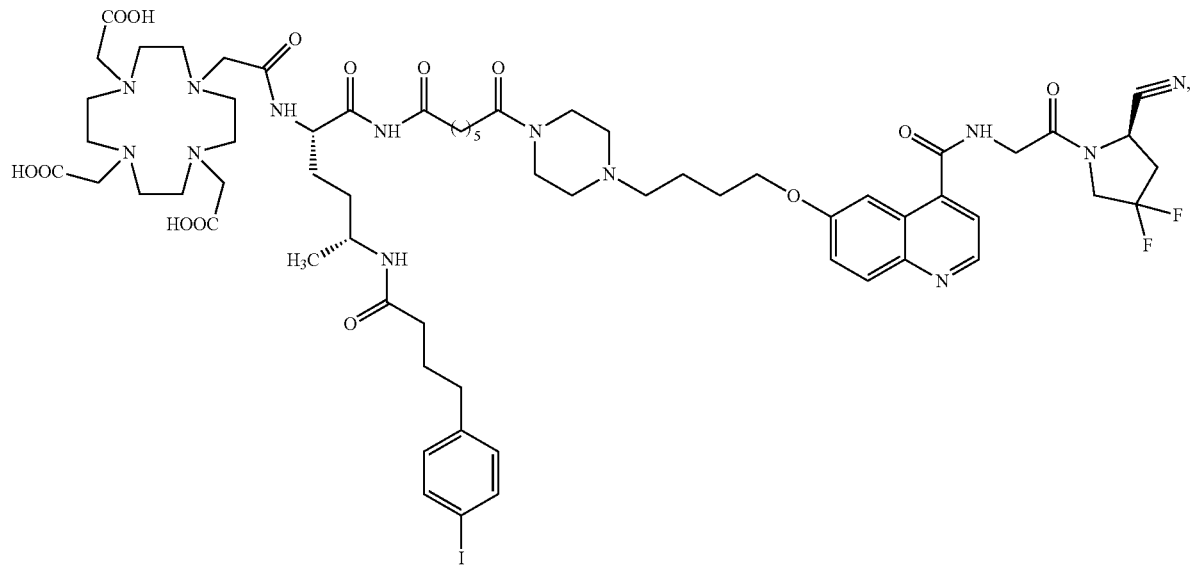

wherein
R1 is selected from R1-I-12, wherein the optical configurations of the two optically active carbons are S configurations respectively;
Code: FAPI-INER-22-SS;
Molecular weight: 1428.3;
Molecular formula: $C_{64}H_{88}F_2IN_{13}O_{14}$;
Structure 15:

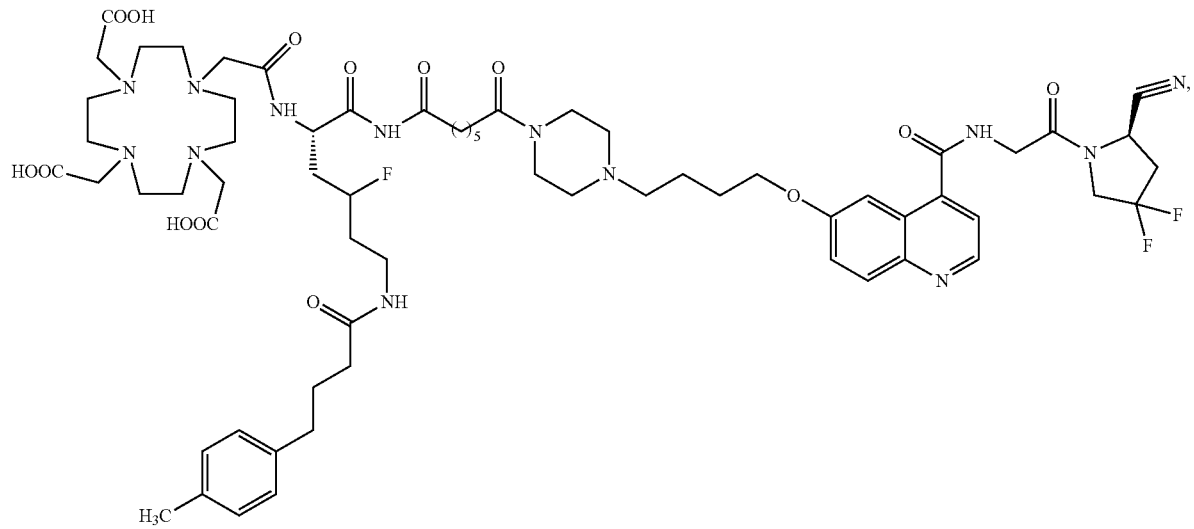

wherein
R1 is selected from R1-I-15, wherein the optical configuration of the optically active carbon is S configurations;
Code: FAPI-INER-26-S;
Molecular weight: 1334.4;
Molecular formula: $C_{65}H_{90}F_3N_{13}O_{14}$;
Structure 16:

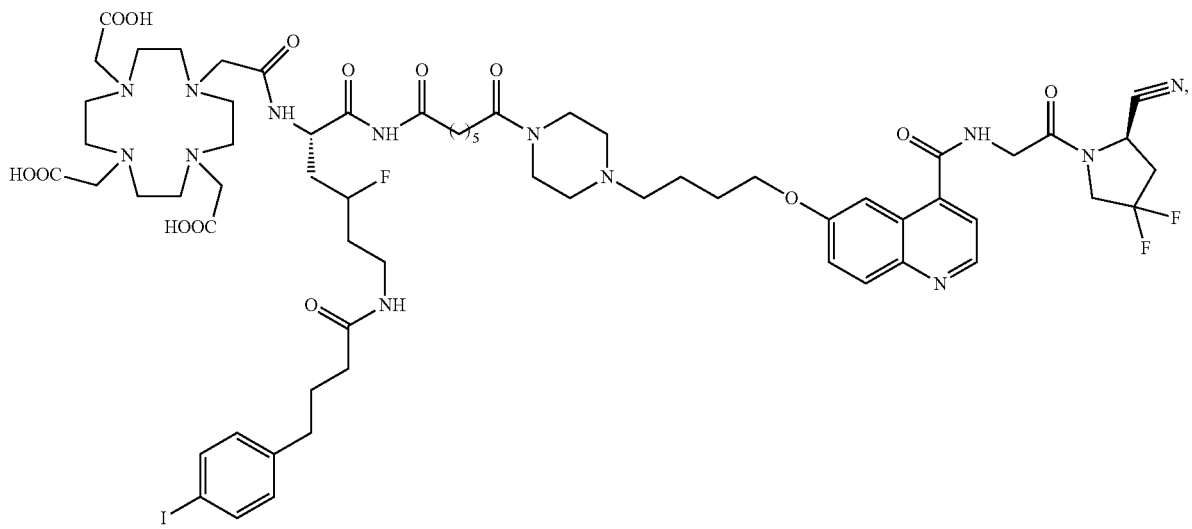

wherein
R1 is selected from R1-I-16, wherein the optical configuration of the optically active carbon is S configurations;
Code: FAPI-INER-30-S;
Molecular weight: 1446.3;
Molecular formula: $C_{64}H_{87}F_3IN_{13}O_{14}$;
or R2 is selected from R2-I-3 of the set of R2-I and the p is and integer of 5, R1 is any structure selected from the set of R1-I, and the D structure is

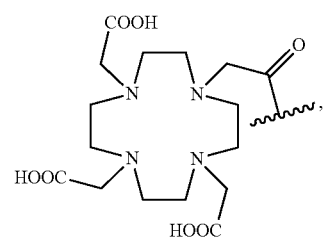

and thus the compound has a structure represented by formulas below:

Structure 17:

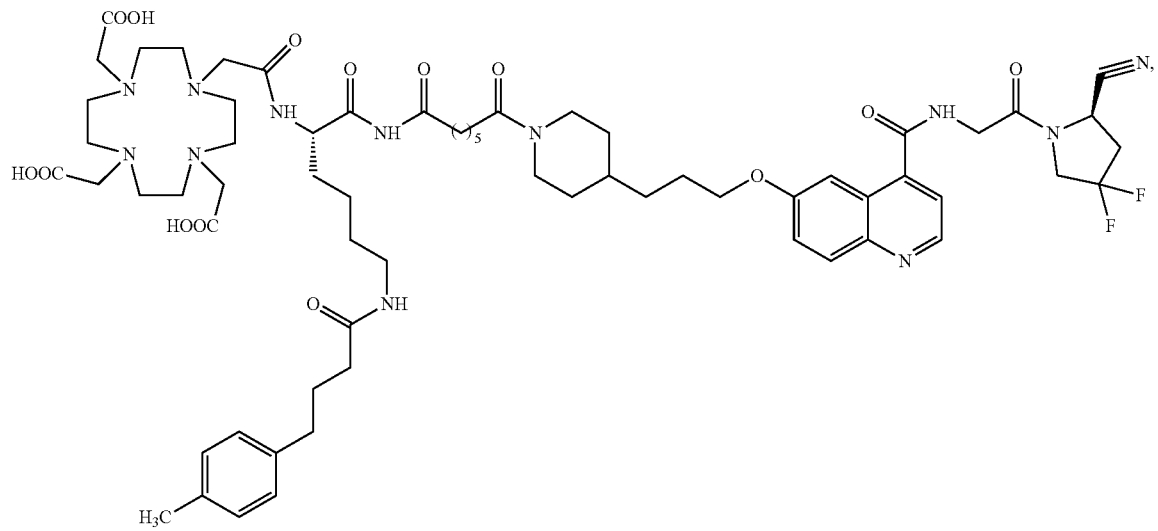

wherein
R1 is selected from R1-I-1, wherein the optical configuration of the optically active carbon is S configurations;
Code: FAPI-INER-03-S;
Molecular weight: 1301.4;
Molecular formula: $C_{65}H_{90}F_2N_{12}O_{14}$;

Structure 18:

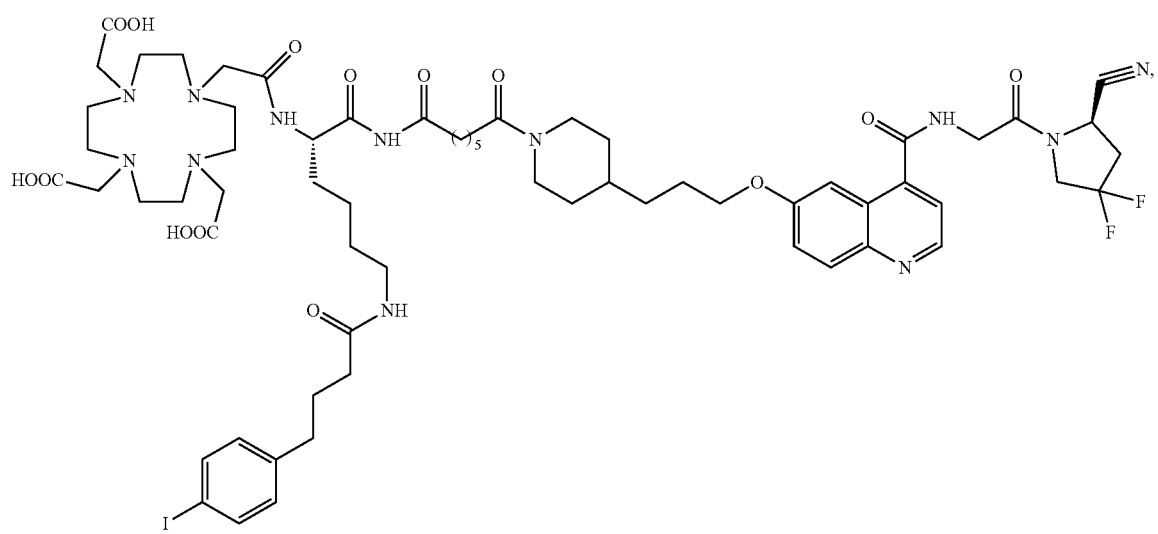

wherein
R1 is selected from R1-I-2, wherein the optical configuration of the optically active carbon is S configurations;
Code: FAPI-INER-07-S;
Molecular weight: 1413.3;
Molecular formula: $C_{64}H_{87}F_2IN_{12}O_{14}$;

Structure 19:

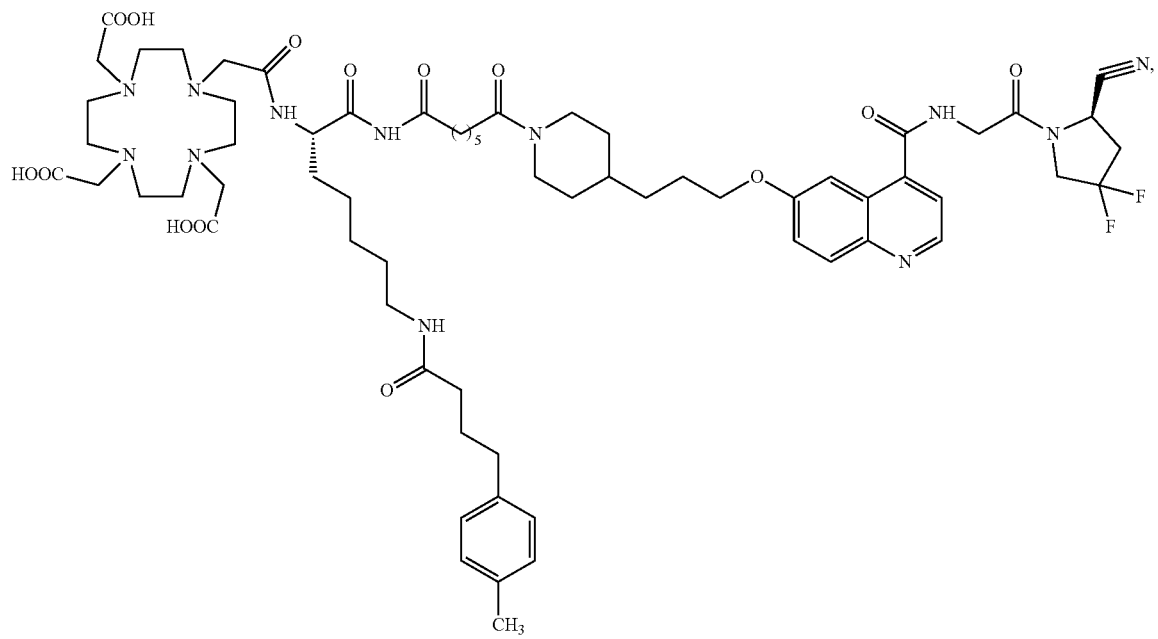

wherein
R1 is selected from R1-I-7, wherein the optical configuration of the optically active carbon is S configuration;
Code: FAPI-INER-11-S;
Molecular weight: 1315.5;
Molecular formula: $C_{66}H_{92}F_2N_{12}O_{14}$;

Structure 20:

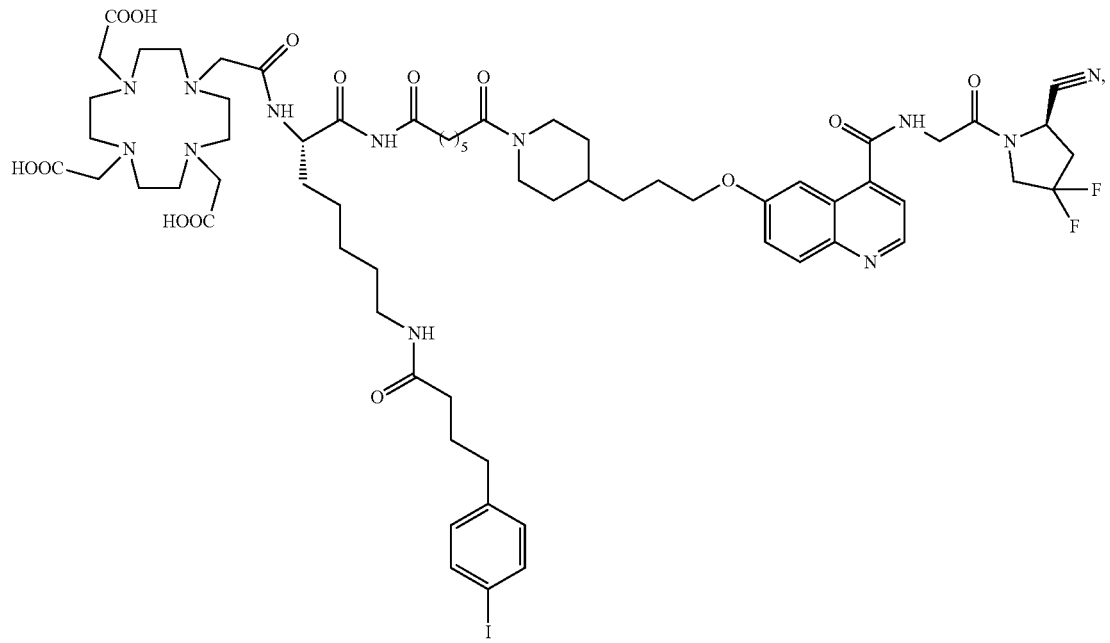

wherein
R1 is selected from R1-I-8, wherein the optical configuration of the optically active carbon is S configurations;
Code: FAPI-INER-15-S;
Molecular weight: 1427.3;
Molecular formula: $C_{65}H_{89}F_2IN_{12}O_{14}$;

Structure 21:

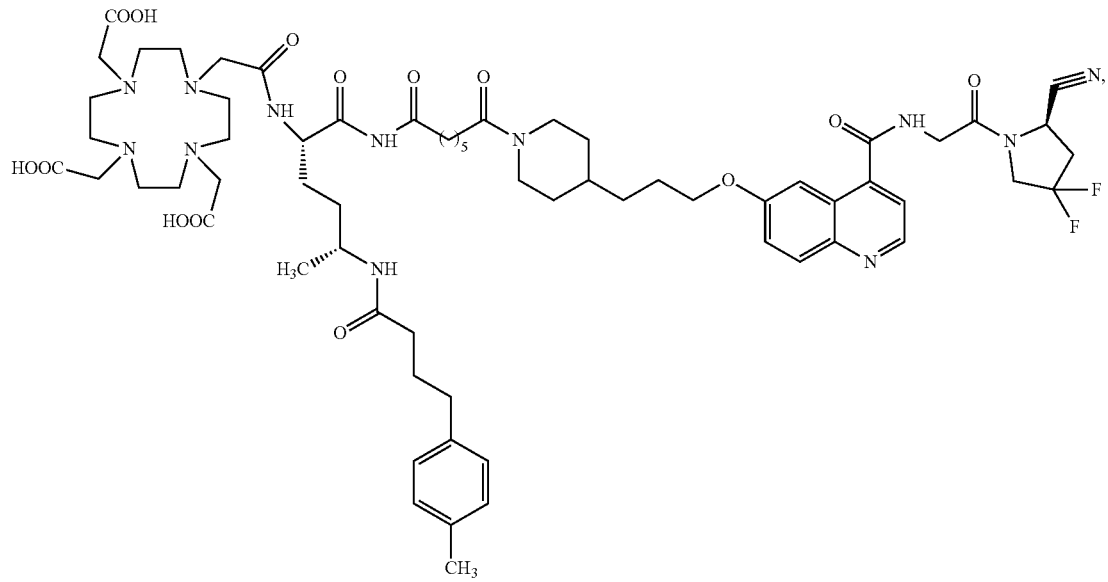

wherein
R1 is selected from R1-I-11, wherein the optical configurations of the two optically active carbons are S configurations respectively;
Code: FAPI-INER-19-SS;
Molecular weight: 1301.4;
Molecular formula: $C_{65}H_{90}F_2N_{12}O_{14}$;

Structure 22:

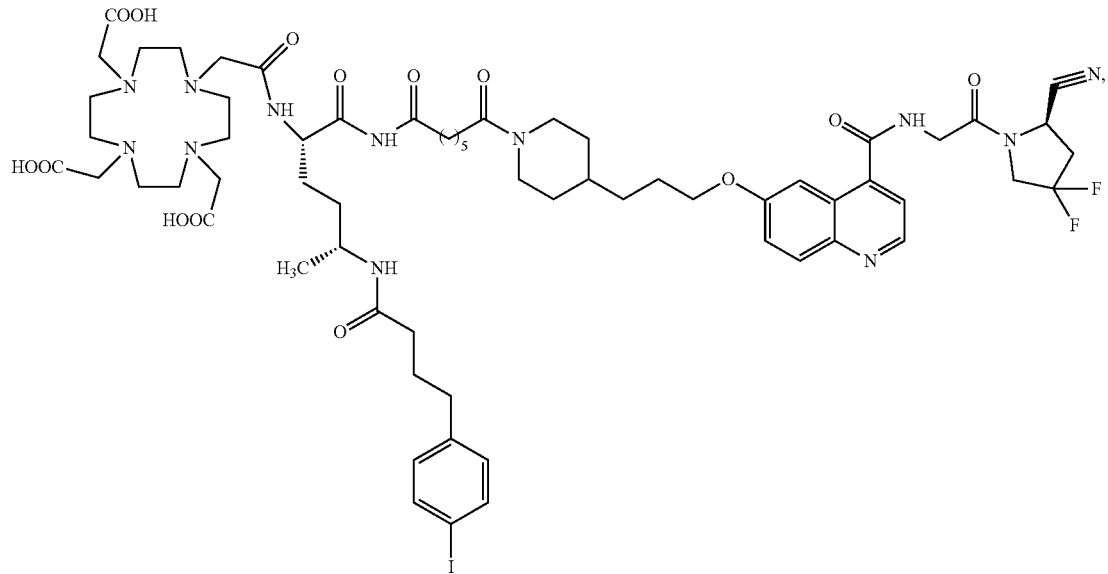

wherein
R1 is selected from R1-I-12, wherein the optical configurations of the two optically active carbons are S configurations respectively;
Code: FAPI-INER-23-SS;
Molecular weight: 1413.3;
Molecular formula: $C_{64}H_{87}F_2IN_{12}O_{14}$;

Structure 23:

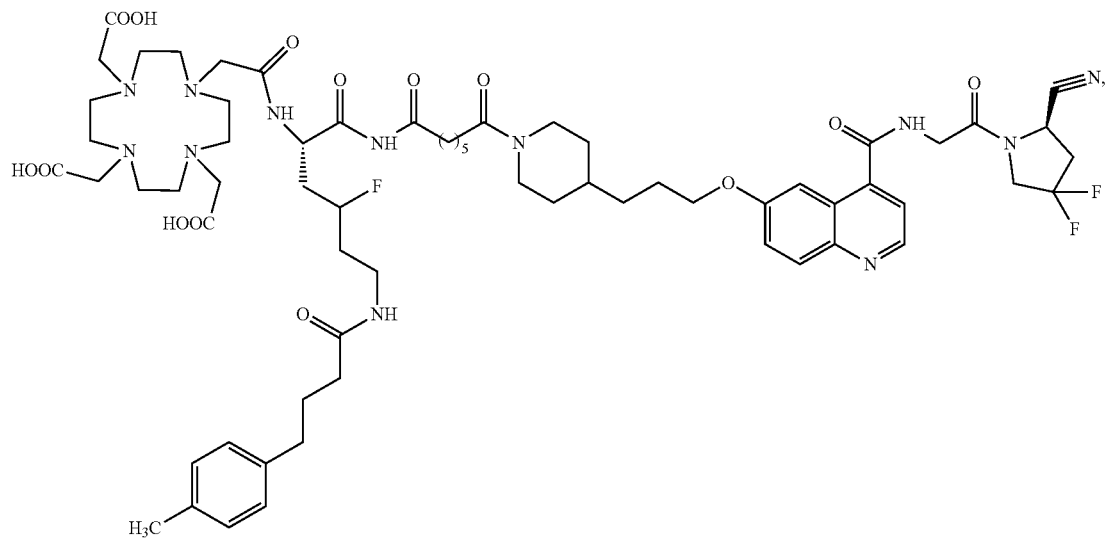

wherein
R1 is selected from R1-I-15, wherein the optical configuration of the optically active carbon is S configurations;
Code: FAPI-INER-27-S;
Molecular weight: 1319.4;
Molecular formula: $C_{65}H_{89}F_3N_{12}O_{14}$;

Structure 24:

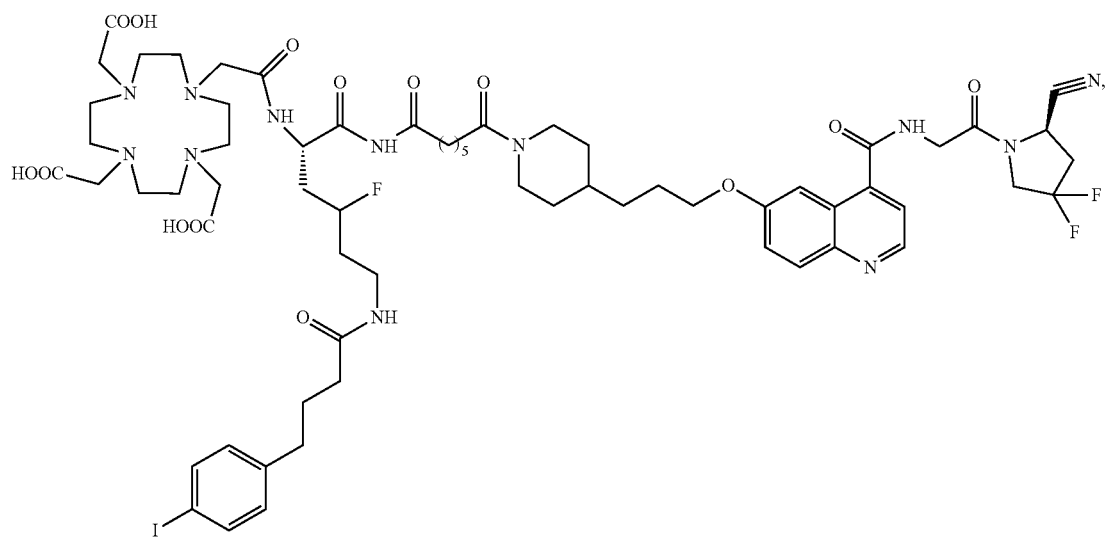

wherein
R1 is selected from R1-I-16, wherein the optical configuration of the optically active carbon is S configurations;
Code: FAPI-INER-31-S;
Molecular weight: 1431.3;
Molecular formula: $C_{64}H_{86}F_3IN_{12}O_{14}$;
or R2 is selected from R2-I-4 of the set of R2-I and the p is and integer of 5, R1 is any structure selected from the set of R1-I, and the D structure is

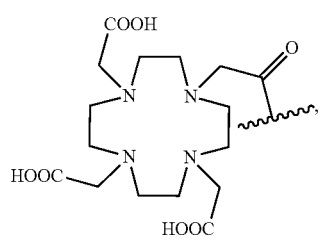 [SMILES: *C(=O)CN1CCN(CC(=O)O)CCN(CC(=O)O)CCN(CC(=O)O)CC1]

and thus the compound has a structure represented by formulas below:

Structure 25:

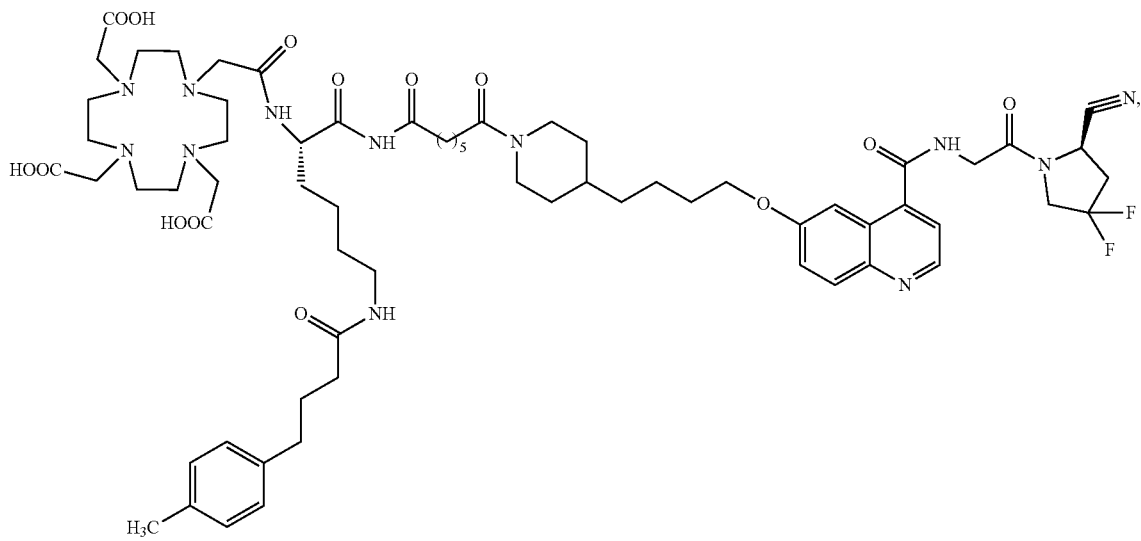

wherein
R1 is selected from R1-I-1, wherein the optical configuration of the optically active carbon is S configuration;
Code: FAPI-INER-04-S;
Molecular weight: 1315.5;
Molecular formula: $C_{66}H_{92}F_2N_{12}O_{14}$;

Structure 26:

wherein
R1 is selected from R1-I-2, wherein the optical configuration of the optically active carbon is S configuration;
Code: FAPI-INER-08-S;
Molecular weight: 1427.3;
Molecular formula: $C_{64}H_{89}F_2IN_{12}O_{14}$;

Structure 27:

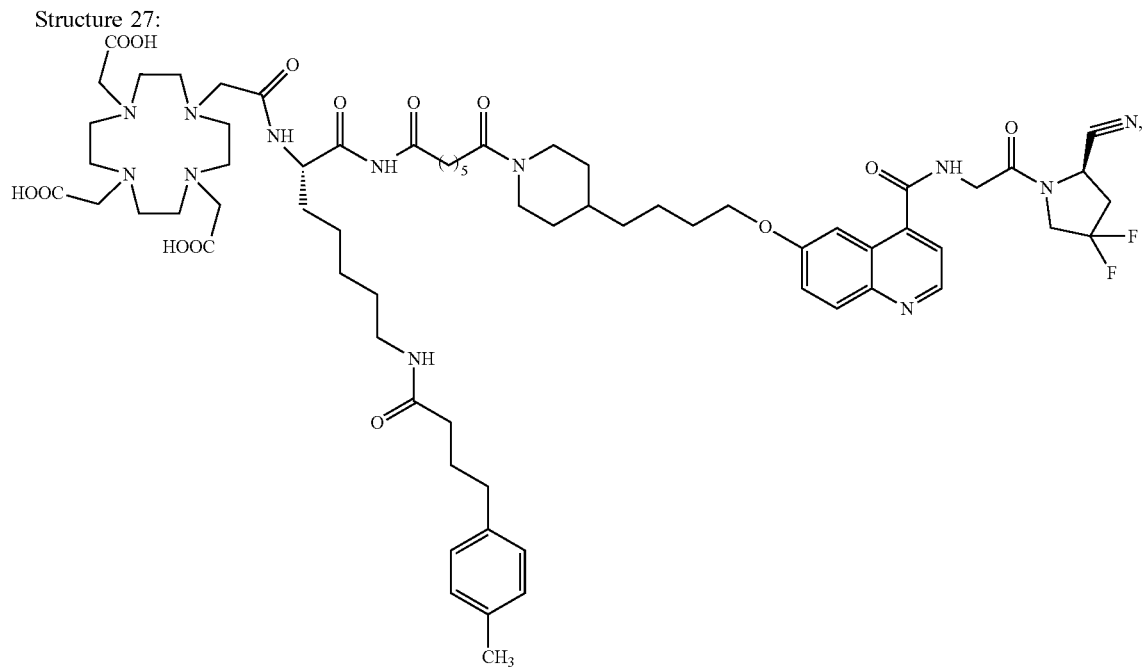

wherein
R1 is selected from R1-I-7, wherein the optical configuration of the optically active carbon is S configuration;
Code: FAPI-INER-12-S;
Molecular weight: 1329.5;
Molecular formula: $C_{67}H_{94}F_2N_{12}O_{14}$;

Structure 28:

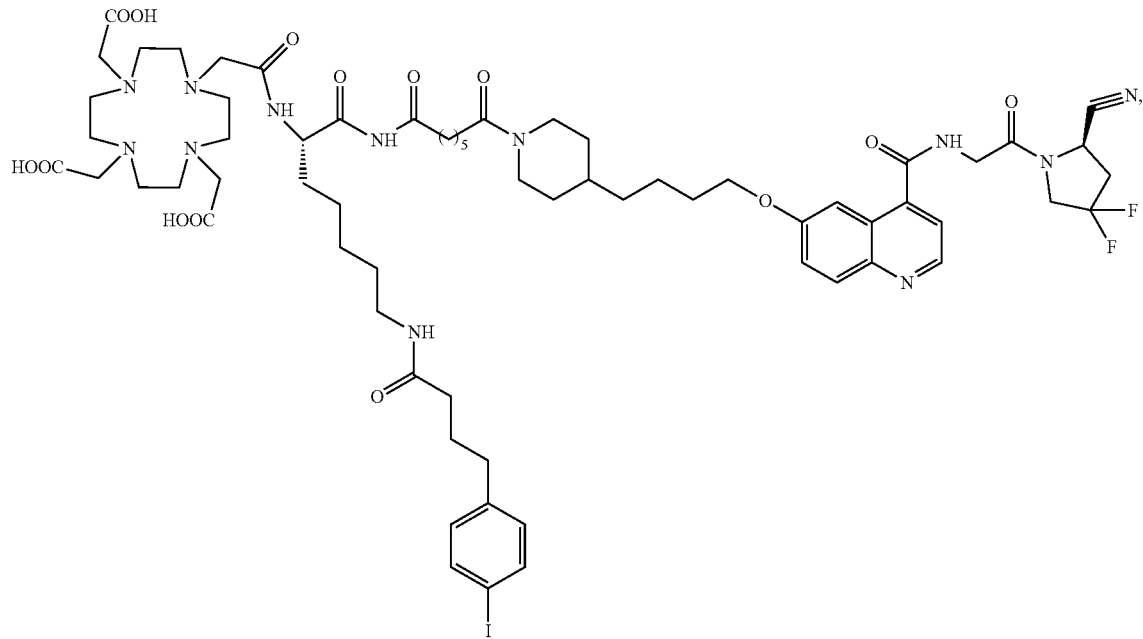

wherein
R1 is selected from R1-I-8, wherein the optical configuration of the optically active carbon is S configuration;
Code: FAPI-INER-16-S;
Molecular weight: 1441.4;
Molecular formula: $C_{66}H_{91}F_2IN_{12}O_{14}$;

Structure 29:

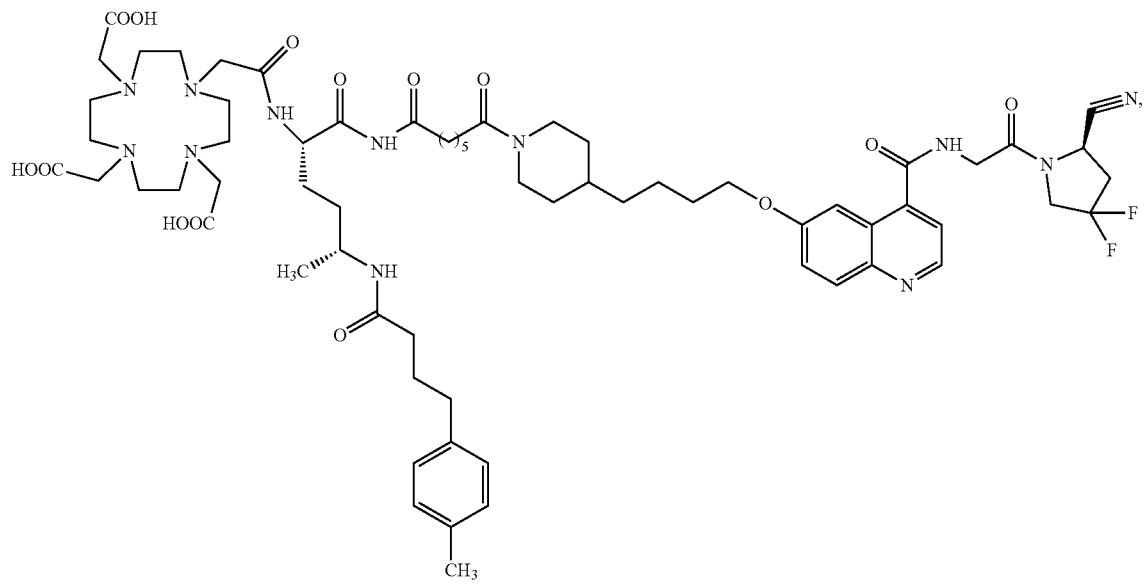

wherein
R1 is selected from R1-I-11, wherein the optical configurations of the two optically active carbons are S configurations respectively;
Code: FAPI-INER-20-SS;
Molecular weight: 1315.5;
Molecular formula: $C_{66}H_{92}F_2N_{12}O_{14}$;

Structure 30:

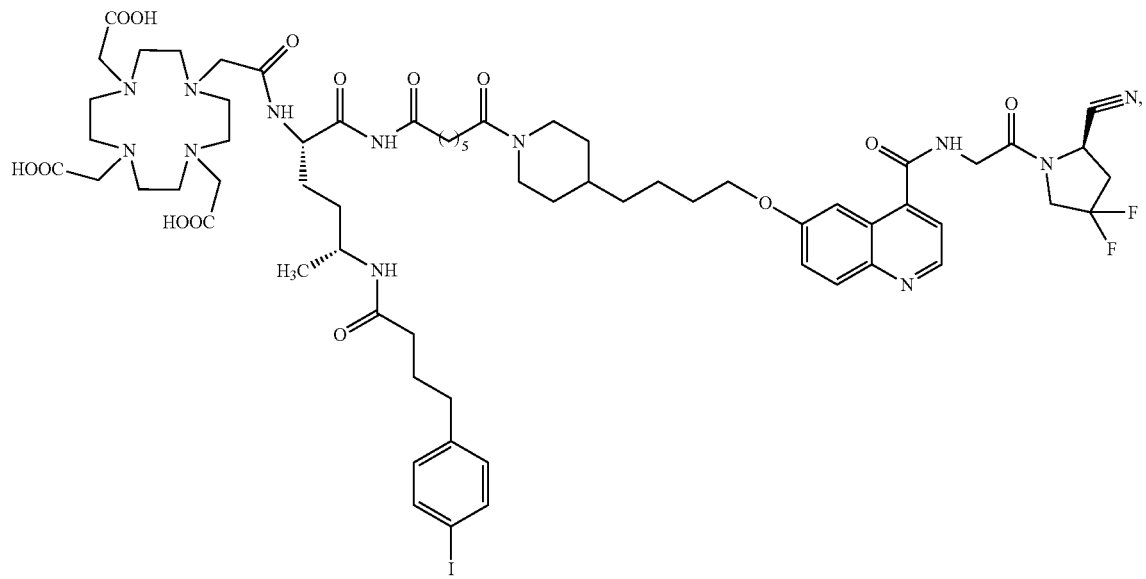

wherein
R1 is selected from R1-I-12, wherein the optical configurations of the two optically active carbons are S configurations respectively;
Code: FAPI-INER-24-SS;
Molecular weight: 1427.3;
Molecular formula: $C_{64}H_{89}F_2IN_{12}O_{14}$;

Structure 31:

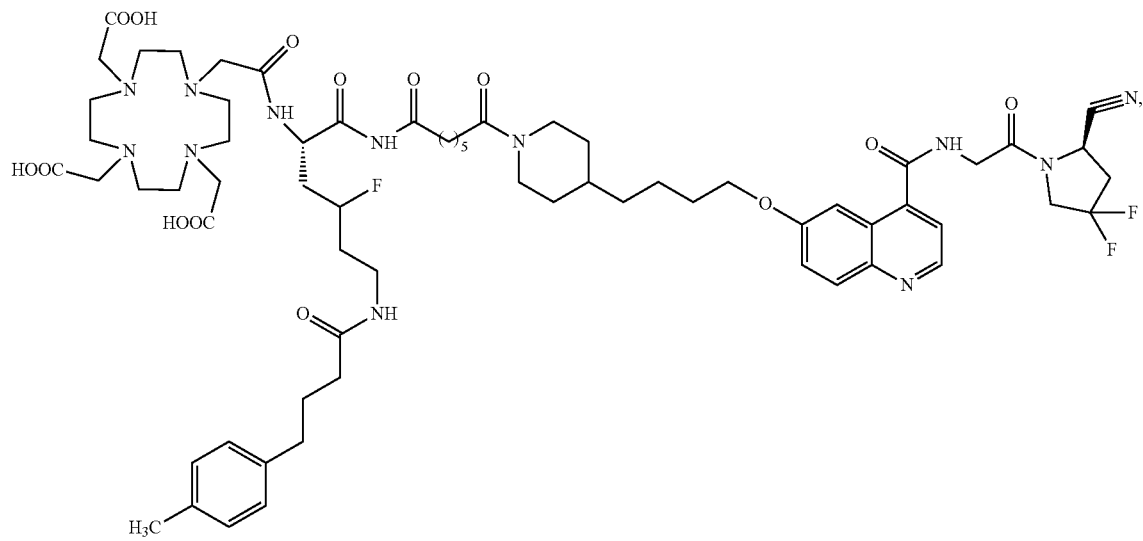

wherein
R1 is selected from R1-I-15, wherein the optical configuration of the optically active carbon is S configuration;
Code: FAPI-INER-28-S;
Molecular weight: 1333.4;
Molecular formula: $C_{66}H_{91}F_3N_{12}O_{14}$;

Structure 32:

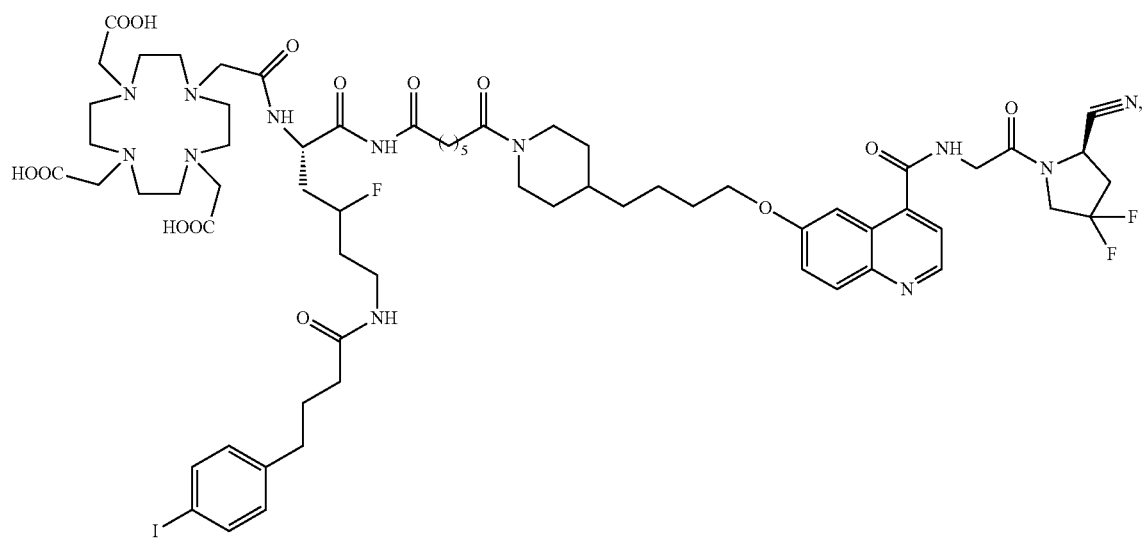

wherein
R1 is selected from R1-I-16, wherein the optical configuration of the optically active carbon is S configuration;
Code: FAPI-INER-32-S;
Molecular weight: 1445.3;
Molecular formula: $C_{64}H_{88}F_{31}N_{12}O_{14}$;
or R2 is selected from R2-II-1 of the set of R2-II, R1 is any structure selected from the set of R1-II, and the D structure is

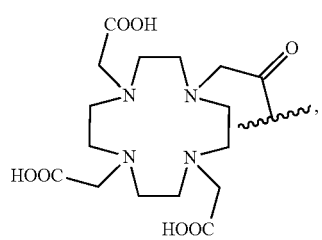 [SMILES: *C(=O)CN1CCN(CC(=O)O)CCN(CC(=O)O)CCN(CC(=O)O)CC1]

and thus the compound has a structure represented by formulas below,

Structure 33:

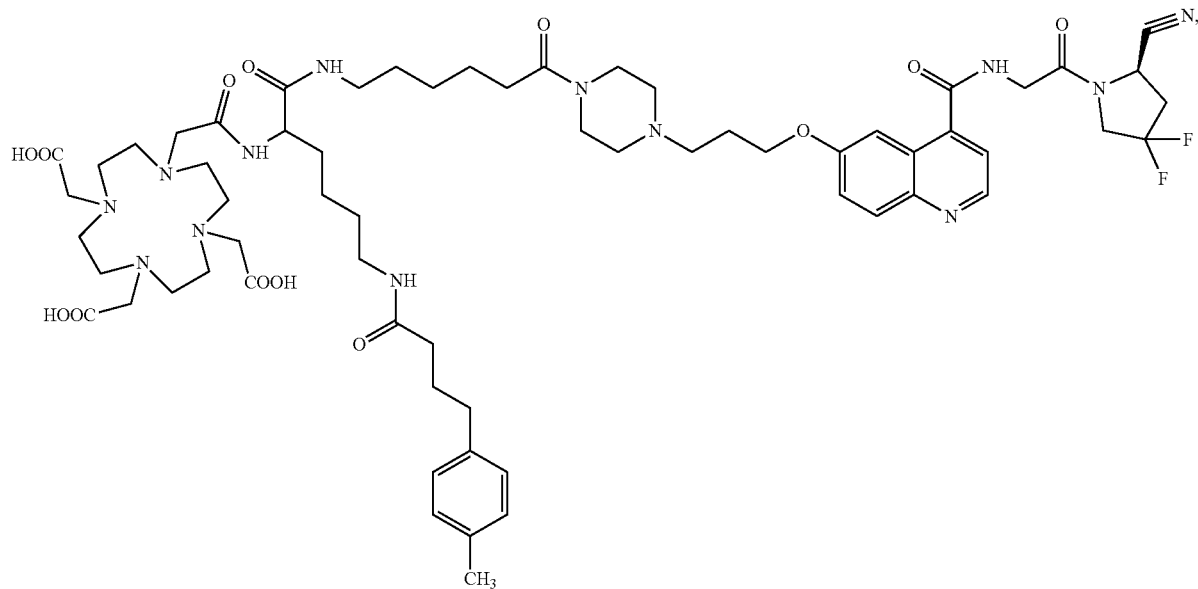

wherein
R1 is selected from R1-II-1, wherein the optical configuration of the optically active carbon is S configurations;
Code: FAPI-INER-385-S;
Molecular weight: 1274.4;
Molecular formula: $C_{63}H_{89}F_2N_{13}O_{13}$;

Structure 34:

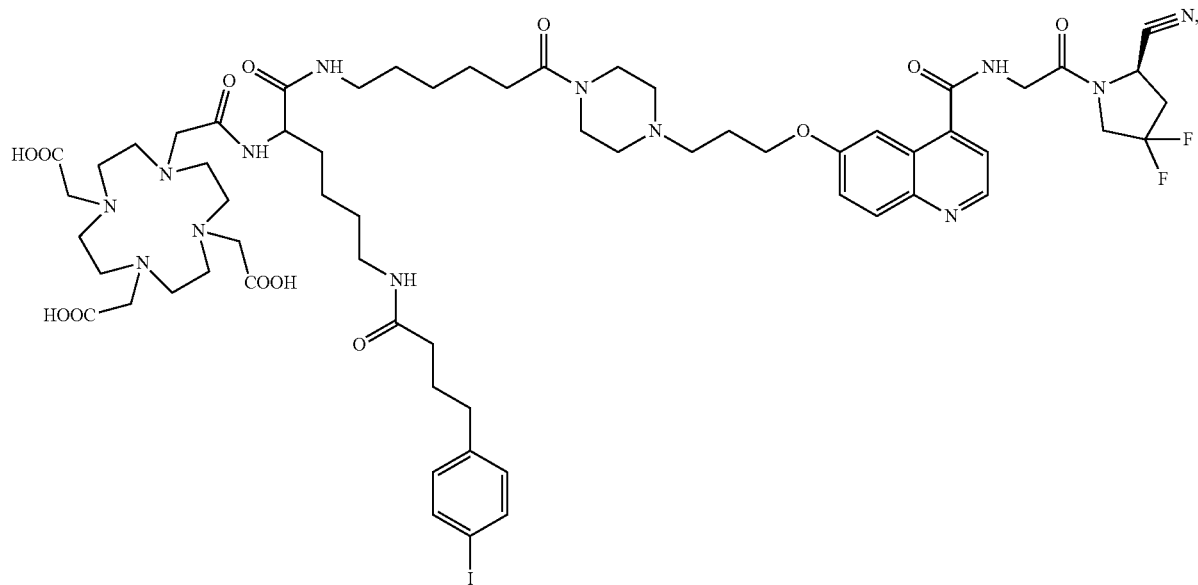

wherein
R1 is selected from R1-II-2, wherein the optical configuration of the optically active carbon is S configurations;
Code: FAPI-INER-389-S;
Molecular weight: 1386.3;
Molecular formula: $C_{62}H_{86}F_2IN_{13}O_{13}$;

Structure 35:

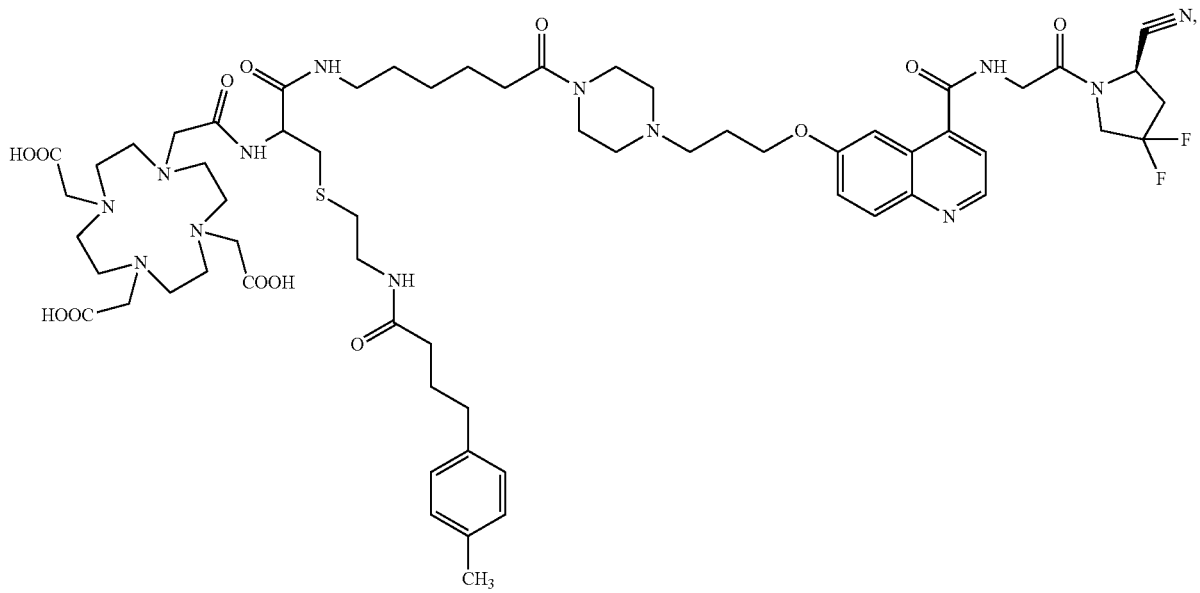

wherein
R1 is selected from R1-II-3, wherein the optical configuration of the optically active carbon is S configurations;
Code: FAPI-INER-393-S;
Molecular weight: 1292.4;
Molecular formula: $C_{62}H_{87}F_2N_{13}O_{13}S$;

Structure 36:

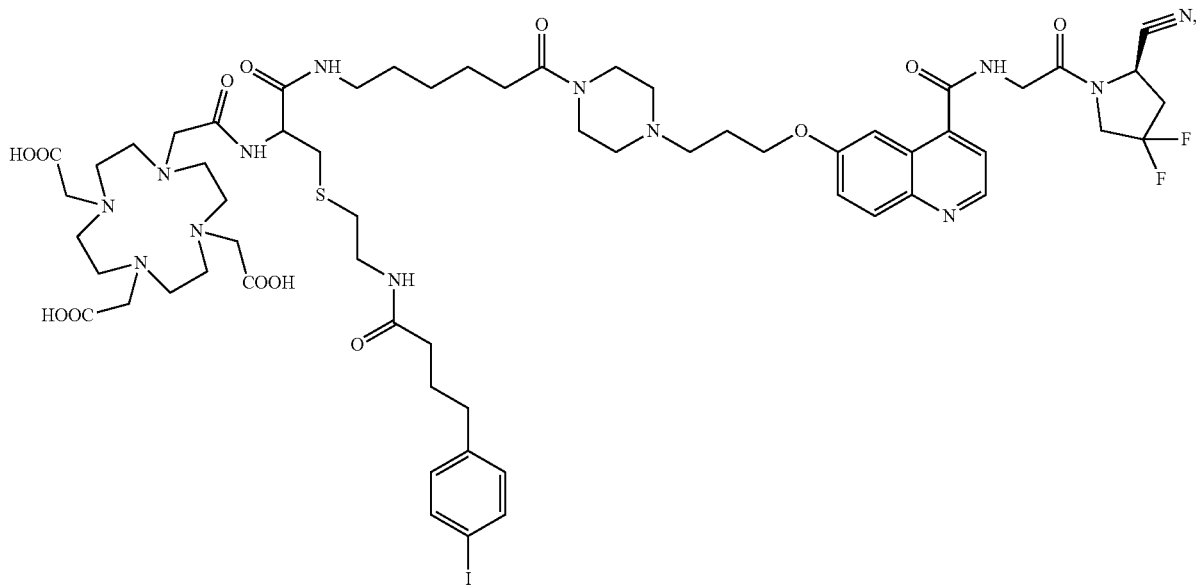

wherein
R1 is selected from R1-II-4, wherein the optical configuration of the optically active carbon is S configurations;
Code: FAPI-INER-397-S;
Molecular weight: 1404.3;
Molecular formula: $C_{61}H_{84}F_2IN_{13}O_{13}S$;

Structure 37:

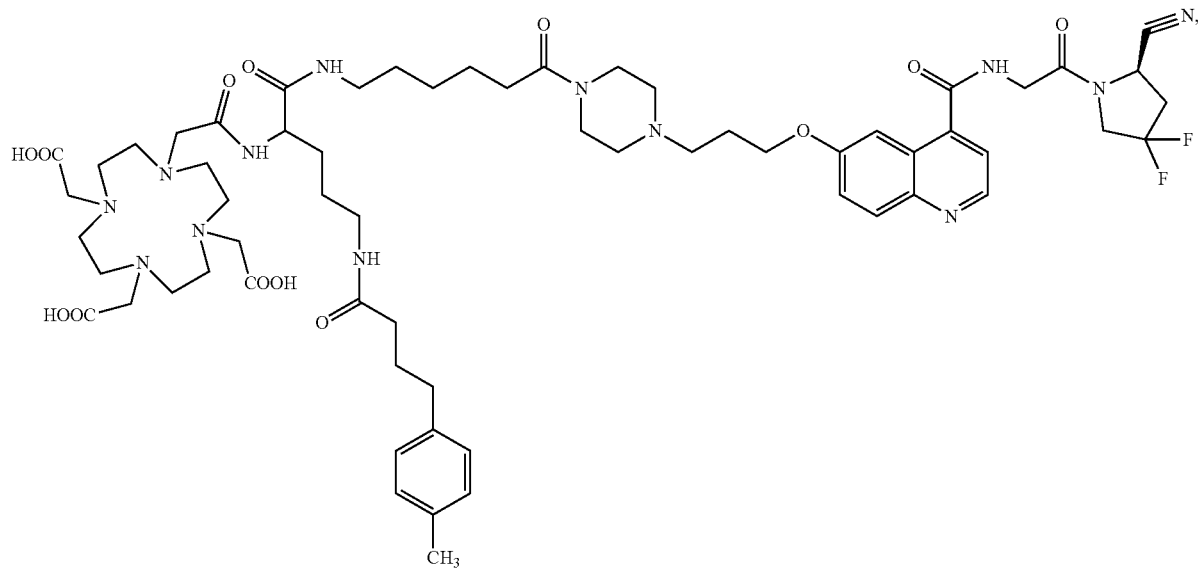

wherein
R1 is selected from R1-II-11, wherein the optical configuration of the optically active carbon is S configurations;
Code: FAPI-INER-401-S;
Molecular weight: 1260.4;
Molecular formula: $C_{62}H_{87}F_2N_{13}O_{13}$;

Structure 38:

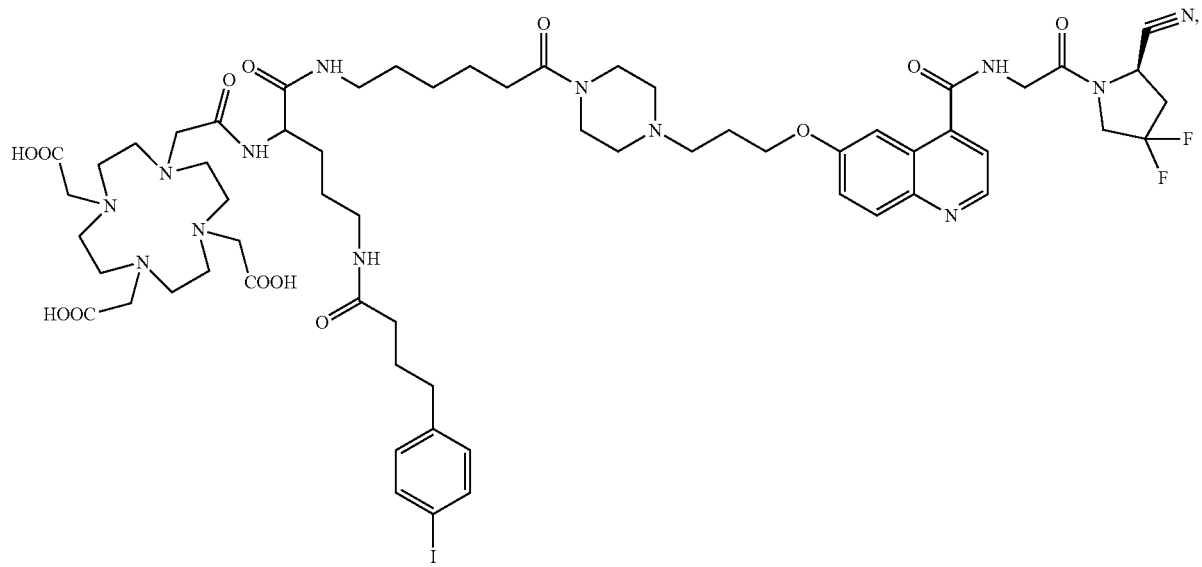

wherein
R1 is selected from R1-II-12, wherein the optical configuration of the optically active carbon is S configuration;
Code: FAPI-INER-405-S;
Molecular weight: 1372.3;
Molecular formula: $C_{61}H_{84}F_2IN_{13}O_{13}$;

Structure 39:

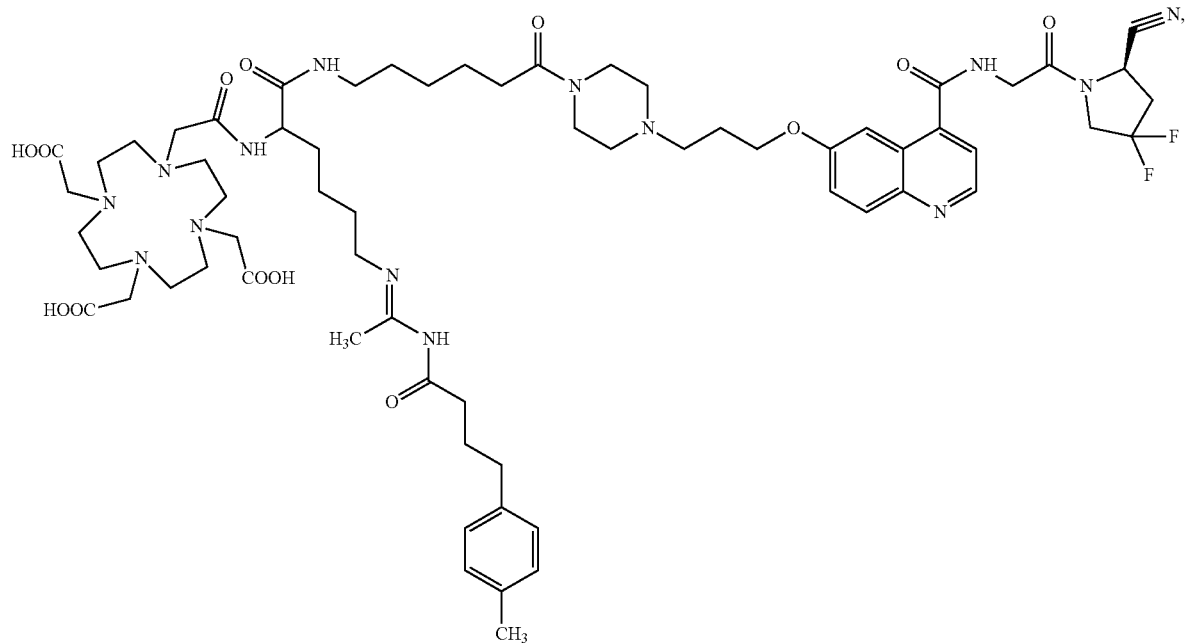

wherein
R1 is selected from R1-II-17, wherein the optical configuration of the optically active carbon is S configuration;
Code: FAPI-INER-409-S;
Molecular weight: 1315.5;
Molecular formula: $C_{65}H_{92}F_2N_{14}O_{13}$;

Structure 40:

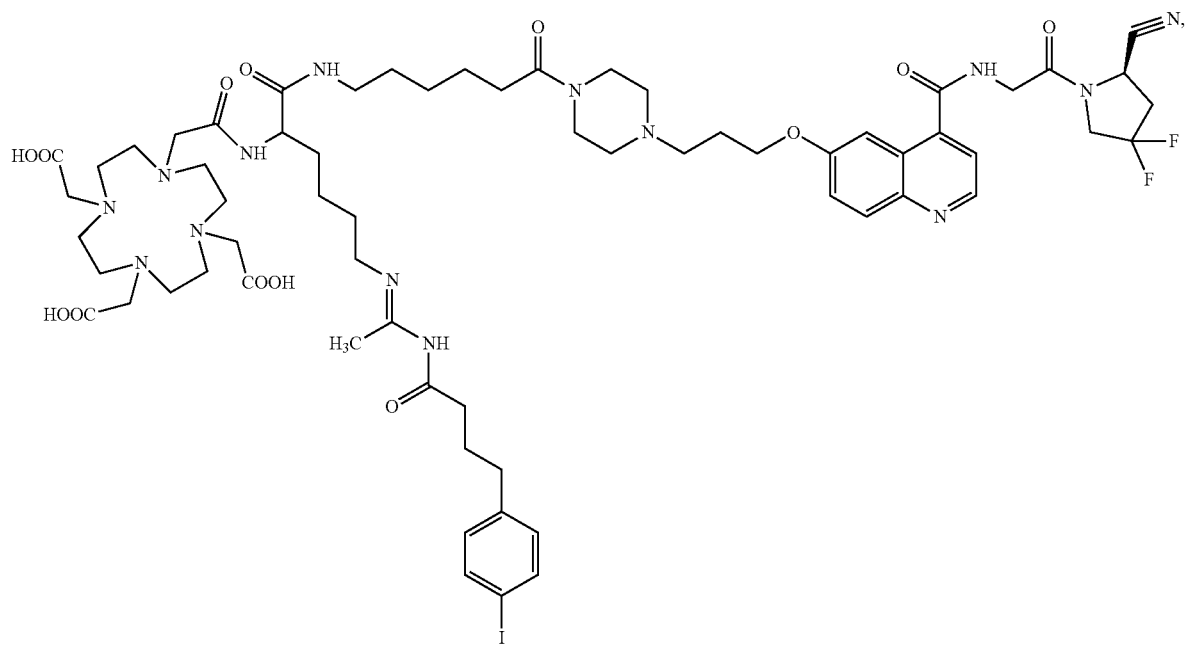

wherein
R1 is selected from R1-II-18, wherein the optical configuration of the optically active carbon is S configuration;
Code: FAPI-INER-413-S;
Molecular weight: 1427.3;
Molecular formula: $C_{64}H_{89}F_2IN_{14}O_{13}$;

Structure 41:

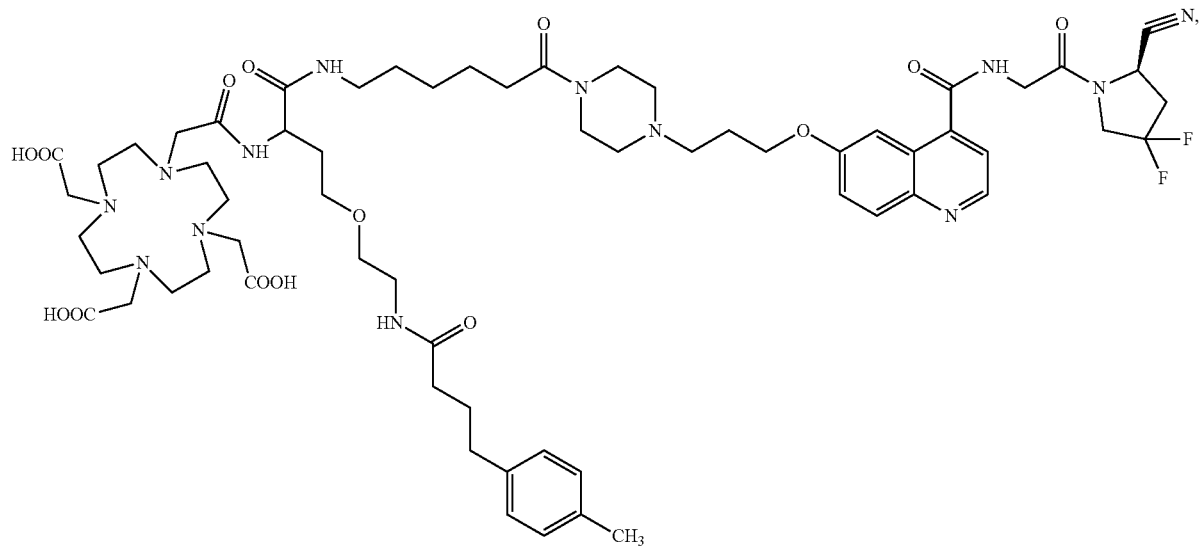

wherein
R1 is selected from R1-II-21, wherein the optical configuration of the optically active carbon is S configuration;
Code: FAPI-INER-417-S;
Molecular weight: 1290.4;
Molecular formula: $C_{63}H_{89}F_2N_{13}O_{14}$;

Structure 42:

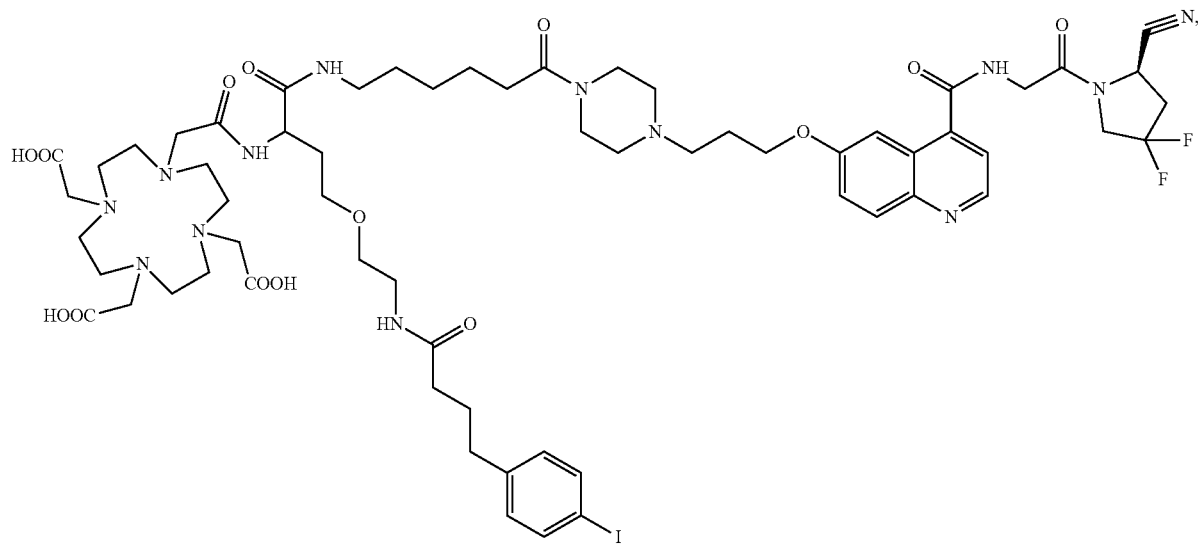

wherein
R1 is selected from R1-II-22, wherein the optical configuration of the optically active carbon is S configuration;
Code: FAPI-INER-421-S;
Molecular weight: 1402.3;
Molecular formula: $C_{62}H_{86}F_2IN_{13}O_{14}$;
or R2 is selected from R2-II-2 of the set of R2-II, R1 is any structure selected from the set of R1-II, and the D structure is

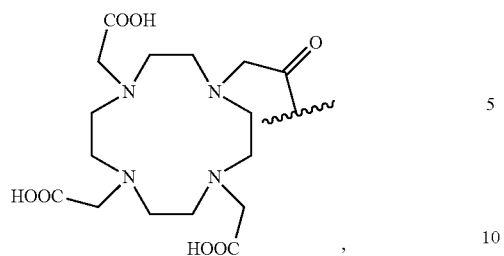
and thus the compound has a structure represented by formulas below:
Structure 43:
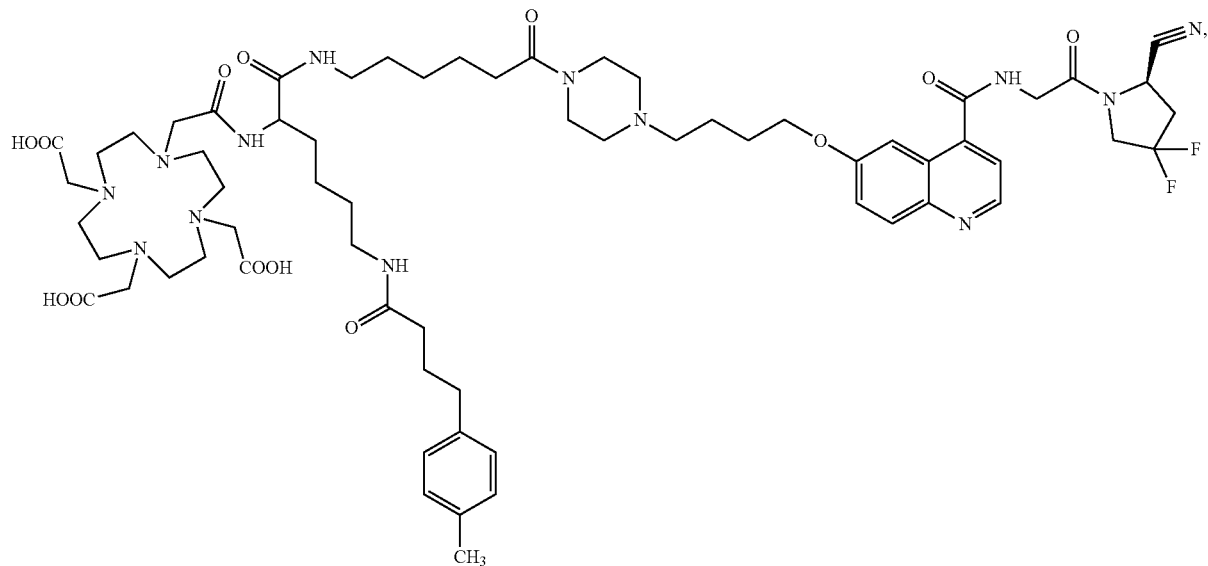
wherein
R1 is selected from R1-II-1, wherein the optical configuration of the optically active carbon is S configuration;
Code: FAPI-INER-386-S;
Molecular weight: 1288.4;
Molecular formula: $C_{64}H_{91}F_2N_{13}O_{13}$;

Structure 44:

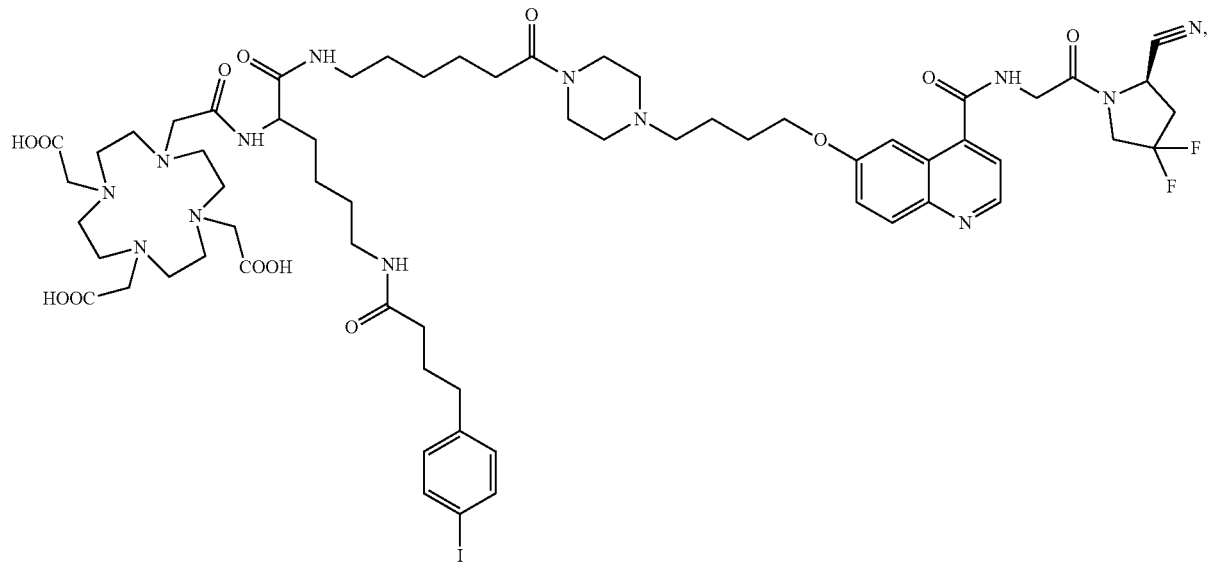

wherein
R1 is selected from R1-II-2, wherein the optical configuration of the optically active carbon is S configuration;
Code: FAPI-INER-390-S;
Molecular weight: 1400.3;
Molecular formula: $C_{63}H_{88}F_2IN_{13}O_{13}$;

Structure 45:

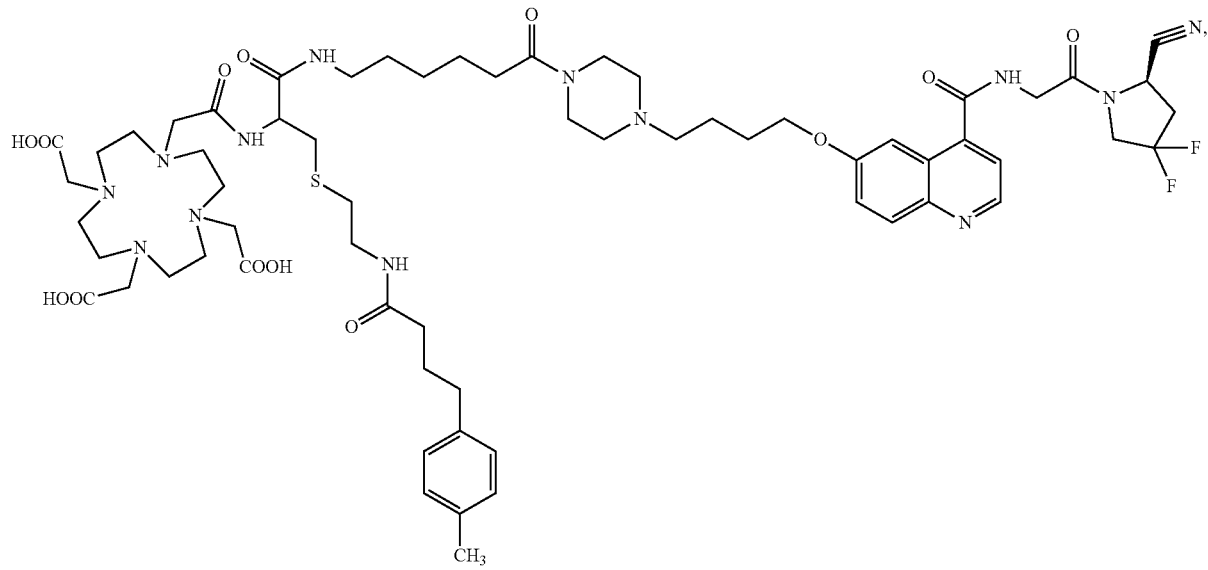

wherein
R1 is selected from R1-II-3, wherein the optical configuration of the optically active carbon is S configuration;
Code: FAPI-INER-394-S;
Molecular weight: 1306.5;
Molecular formula: $C_{63}H_{89}F_2N_{13}O_{13}S$;

Structure 46:

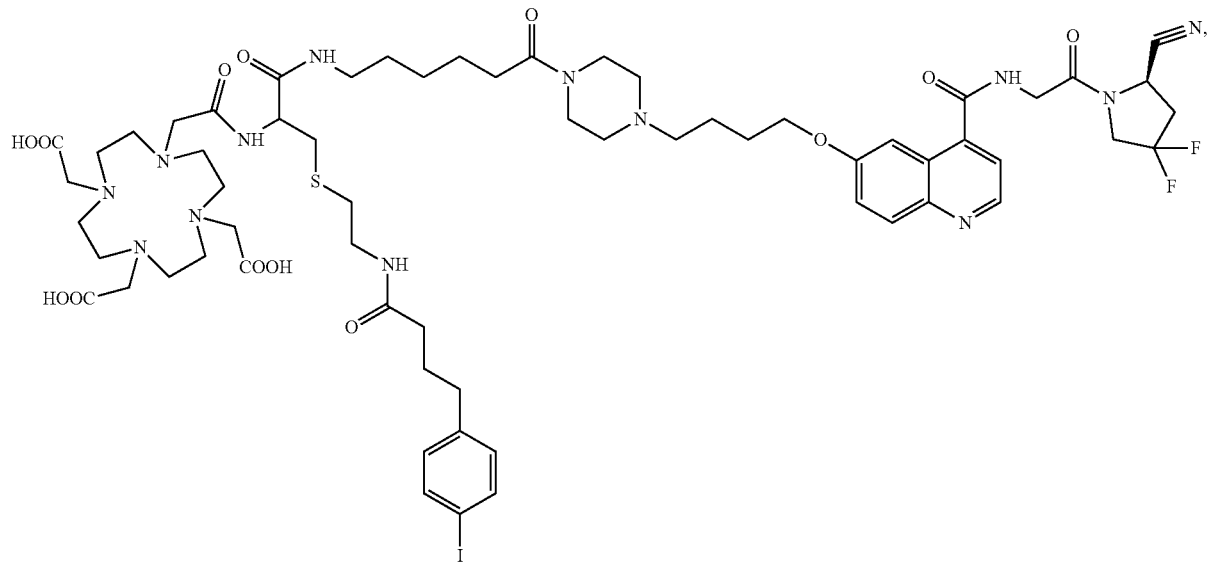

wherein
R1 is selected from R1-II-4, wherein the optical configuration of the optically active carbon is S configuration;
Code: FAPI-INER-398-S;
Molecular weight: 1418.3;
Molecular formula: $C_{62}H_{86}F_2IN_{13}O_{13}S$;

Structure 47:

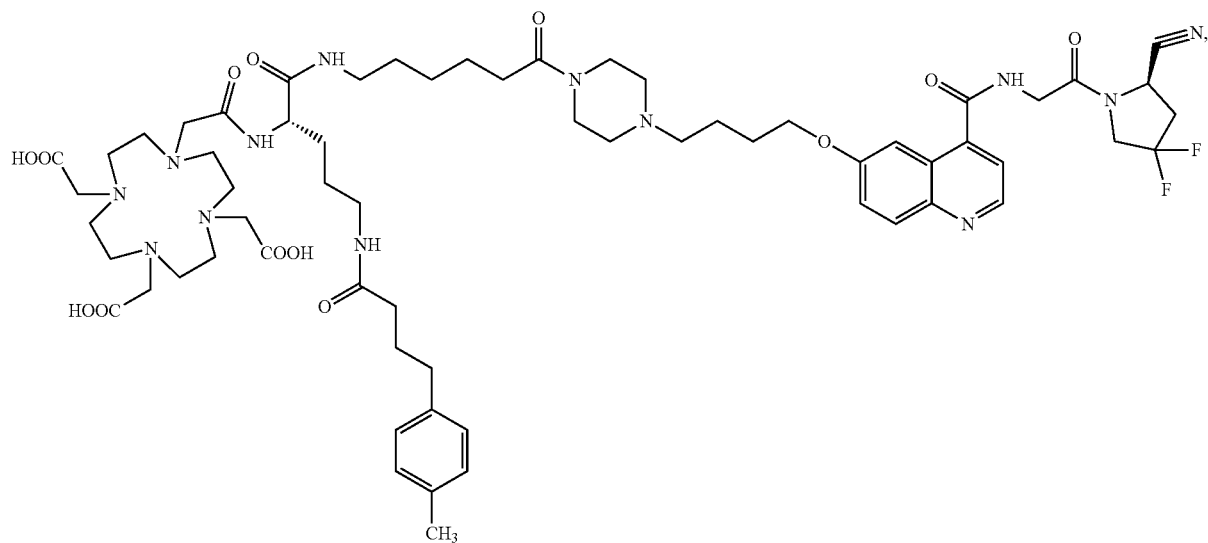

wherein
R1 is selected from R1-II-11, wherein the optical configuration of the optically active carbon is S configuration;
Code: FAPI-INER-402-S;
Molecular weight: 1274.4;
Molecular formula: $C_{63}H_{89}F_2N_{13}O_{13}$;

Structure 48:

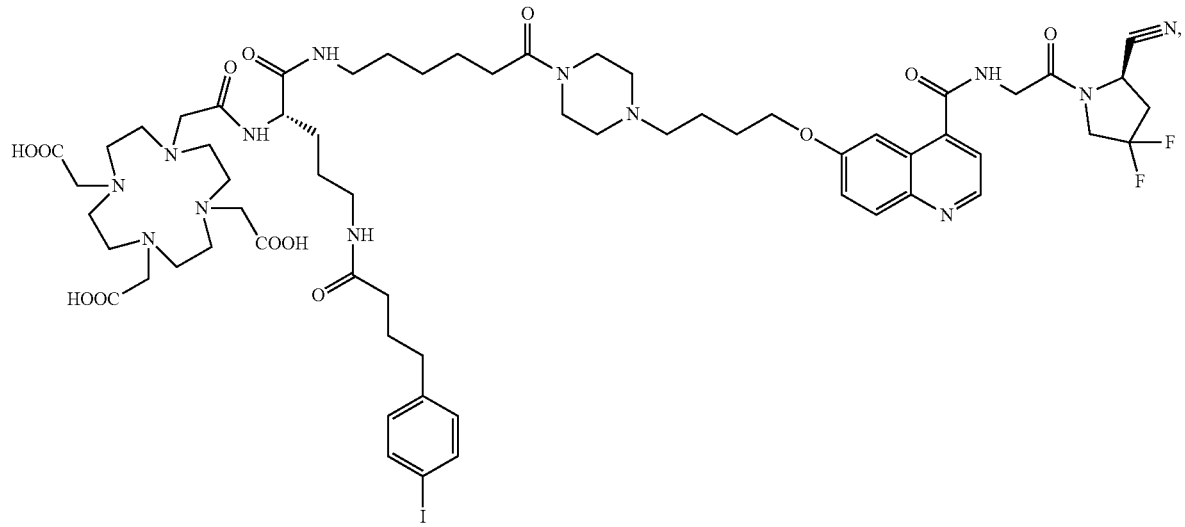

wherein
R1 is selected from R1-II-12, wherein the optical configuration of the optically active carbon is S configuration;
Code: FAPI-INER-406-S;
Molecular weight: 1386.3;
Molecular formula: $C_{62}H_{86}F_2IN_{13}O_{13}$;
Structure 49:

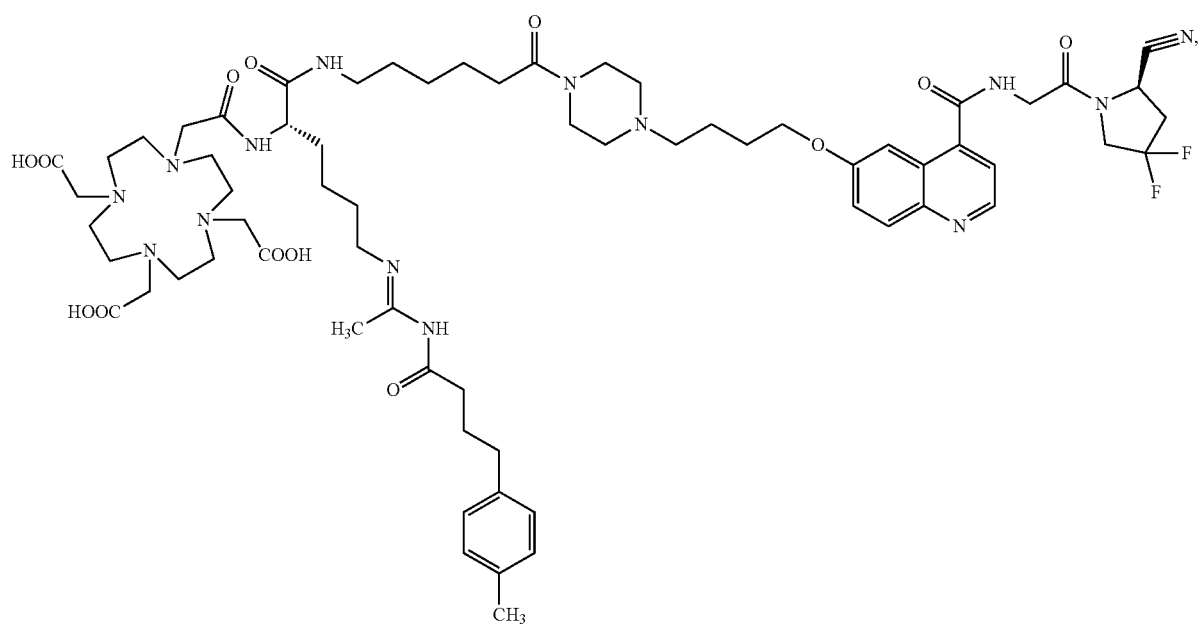

wherein
R1 is selected from R1-II-17, wherein the optical configuration of the optically active carbon is S configuration;
Code: FAPI-INER-410-S;
Molecular weight: 1329.5;
Molecular formula: $C_{66}H_{94}F_2N_{14}O_{13}$;

Structure 50:

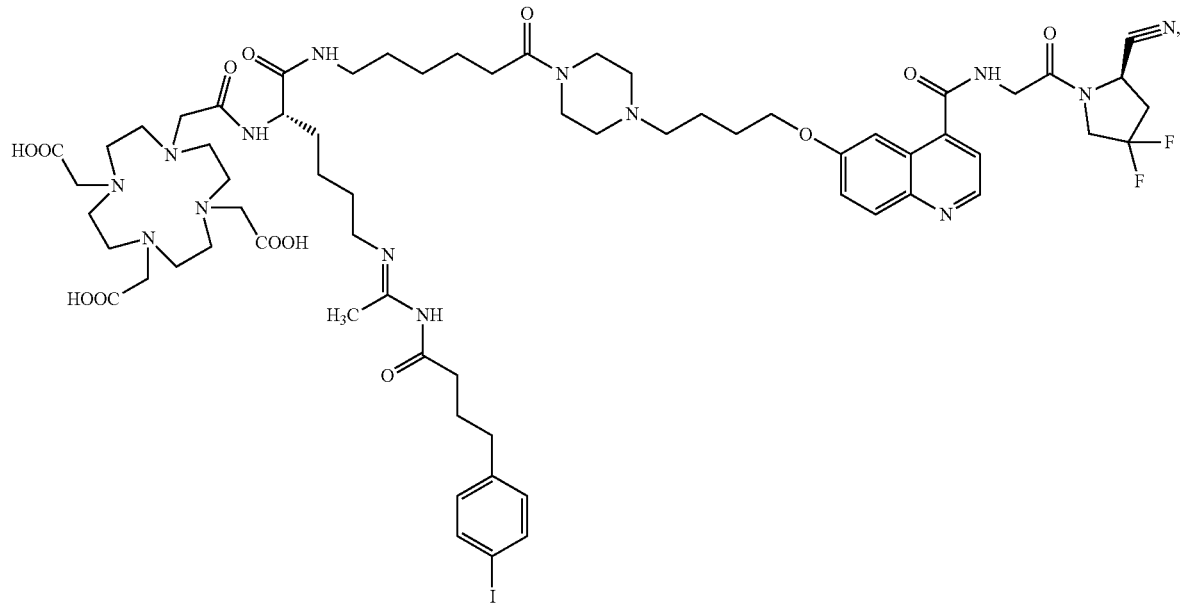

wherein
R1 is selected from R1-II-18, wherein the optical configuration of the optically active carbon is S configuration;
Code: FAPI-INER-414-S;
Molecular weight: 1441.4;
Molecular formula: $C_{65}H_{91}F_2IN_{14}O_{13}$;

Structure 51:

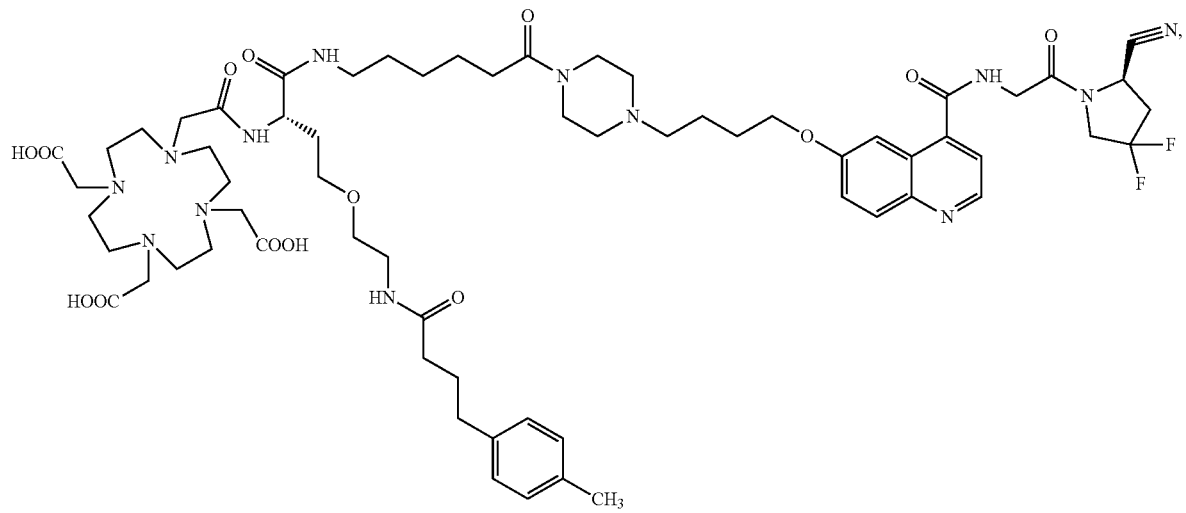

wherein
R1 is selected from R1-II-21, wherein the optical configuration of the optically active carbon is S configuration;
Code: FAPI-INER-418-S;
Molecular weight: 1304.4;
Molecular formula: $C_{64}H_{91}F_2N_{13}O_{14}$;

Structure 52:

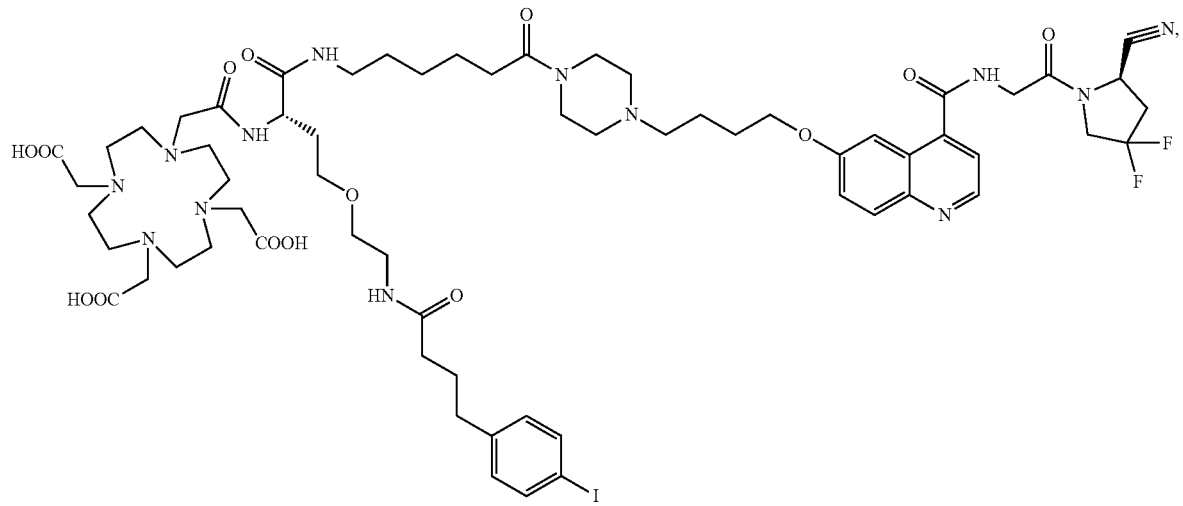

wherein

R1 is selected from R1-II-22, wherein the optical configuration of the optically active carbon is S configuration;

Code: FAPI-INER-422-S;

Molecular weight: 1416.3;

Molecular formula: $C_{63}H_{88}F_2IN_{13}O_{14}$;

or R2 is selected from R2-II-3 of the set of R2-II, R1 is any structure selected from the set of R1-II, and the D structure is

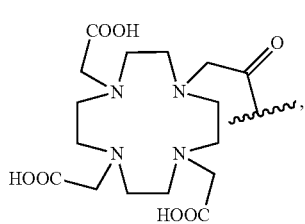 [SMILES: *C(=O)CN1CCN(CC(=O)O)CCN(CC(=O)O)CCN(CC(=O)O)CC1]

and thus the compound has a structure represented by formulas below:

Structure 53:

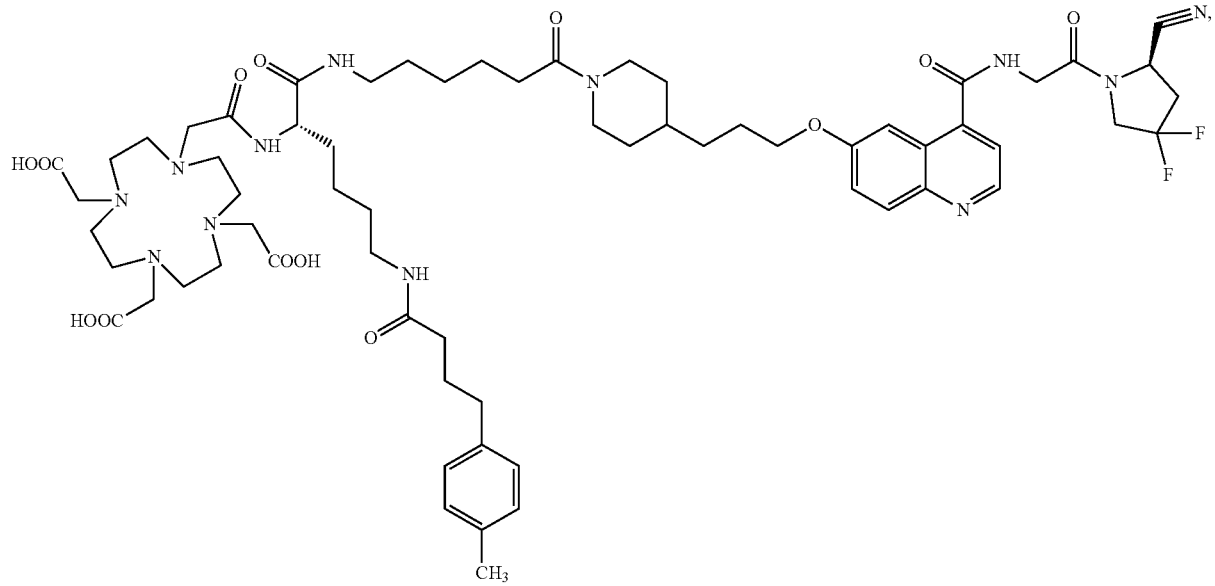

wherein
R1 is selected from R1-II-1, wherein the optical configuration of the optically active carbon is S configuration;
Code: FAPI-INER-387-S;
Molecular weight: 1273.4;
Molecular formula: $C_{64}H_{90}F_2N_{12}O_{13}$;

Structure 54:

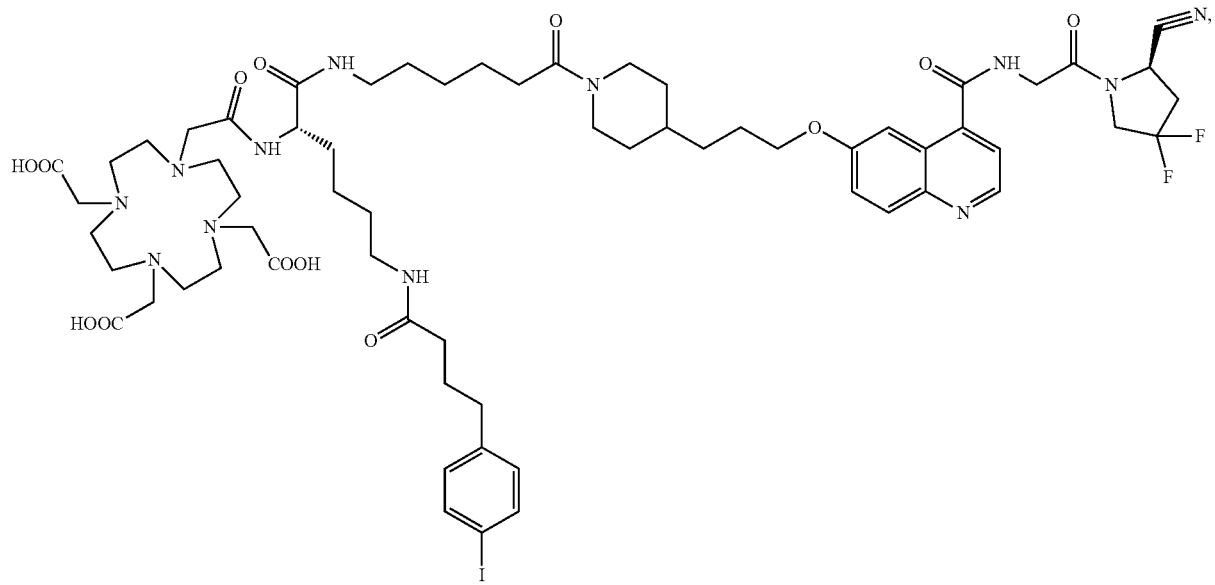

wherein
R1 is selected from R1-II-2, wherein the optical configuration of the optically active carbon is S configuration;
Code: FAPI-INER-391-S;
Molecular weight: 1385.3;
Molecular formula: $C_{63}H_{87}F_2IN_{12}O_{13}$;

Structure 55:

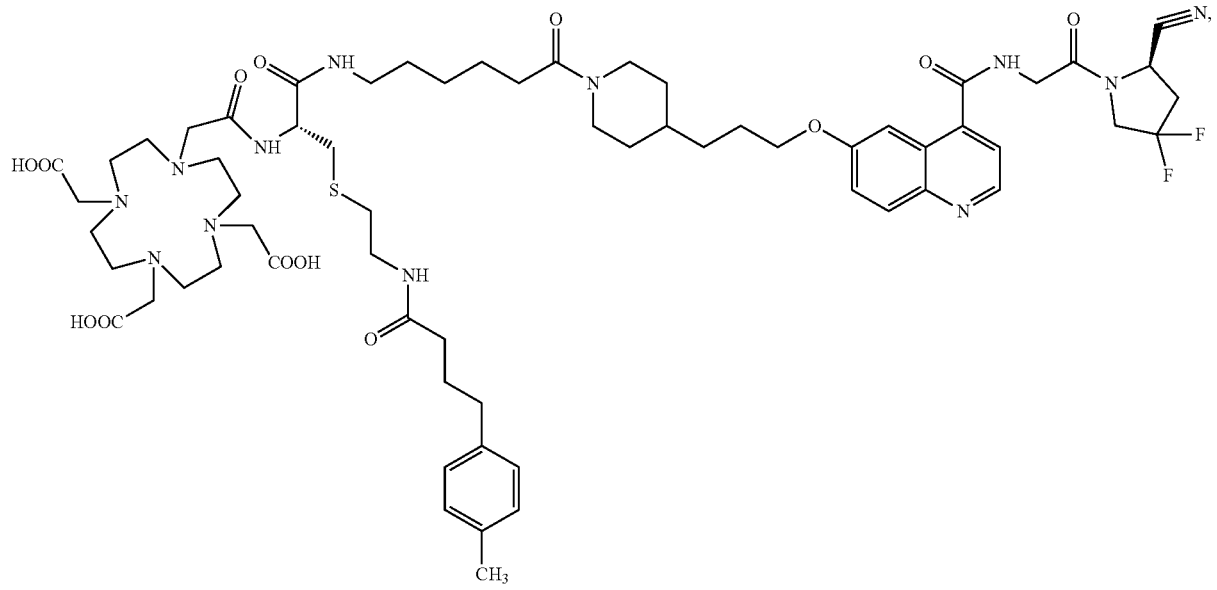

wherein
R1 is selected from R1-II-3, wherein the optical configuration of the optically active carbon is S configuration;
Code: FAPI-INER-395-S;
Molecular weight: 1291.5;
Molecular formula: $C_{63}H_{88}F_2N_{12}O_{13}S$;

Structure 56:

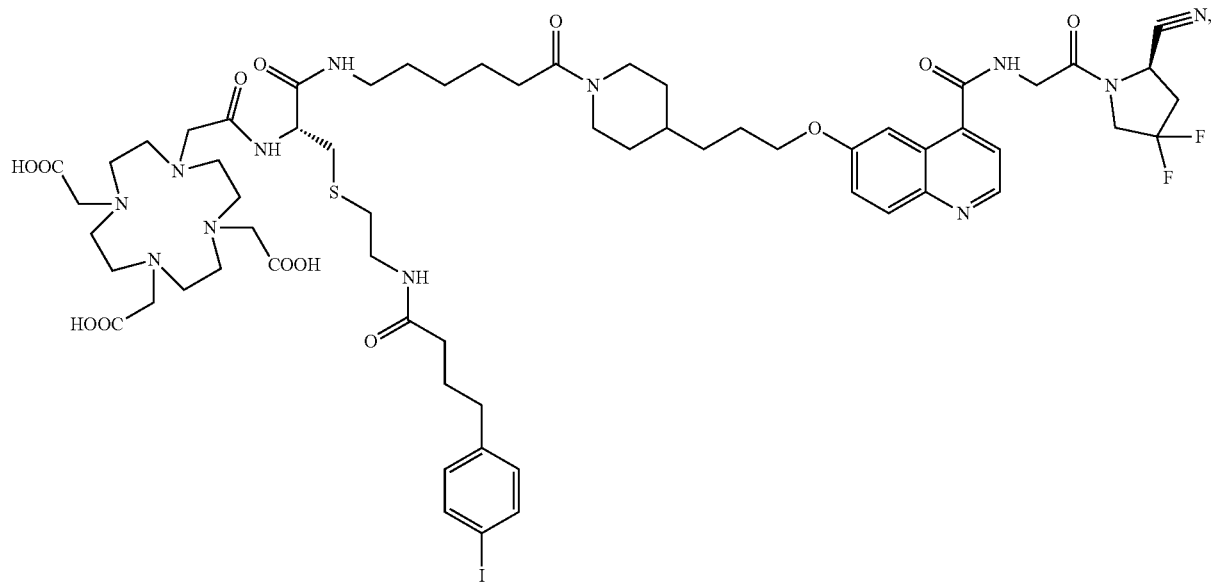

wherein
R1 is selected from R1-II-4, wherein the optical configuration of the optically active carbon is S configuration;
Code: FAPI-INER-399-S;
Molecular weight: 1403.3;
Molecular formula: $C_{62}H_{85}F_2IN_{12}O_{13}S$;

Structure 57:

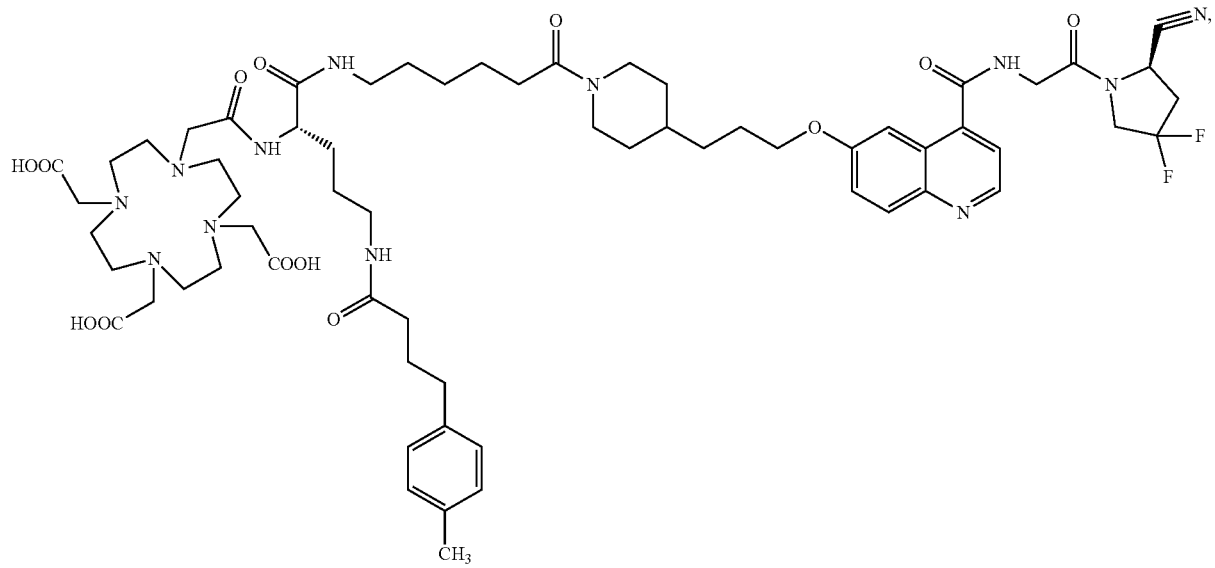

wherein
R1 is selected from R1-II-11, wherein the optical configuration of the optically active carbon is S configuration;
Code: FAPI-INER-403-S;
Molecular weight: 1259.4;
Molecular formula: $C_{63}H_{88}F_2N_{12}O_{13}$;

Structure 58:

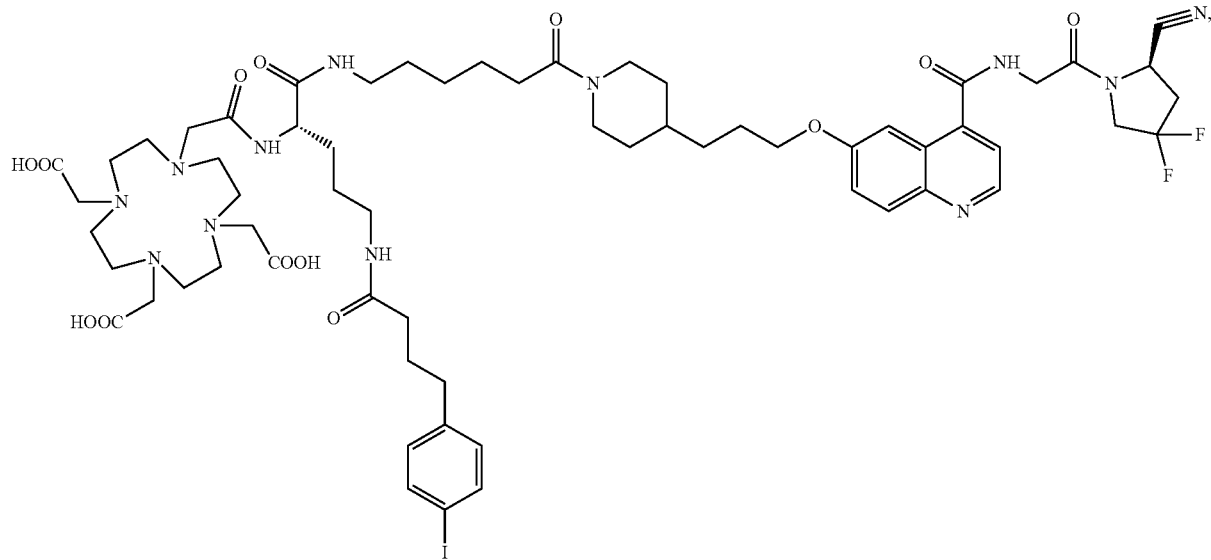

wherein
R1 is selected from R1-II-12, wherein the optical configuration of the optically active carbon is S configuration;
Code: FAPI-INER-407-S;
Molecular weight: 1371.3;
Molecular formula: $C_{62}H_{85}F_2IN_{12}O_{13}$;

Structure 59:

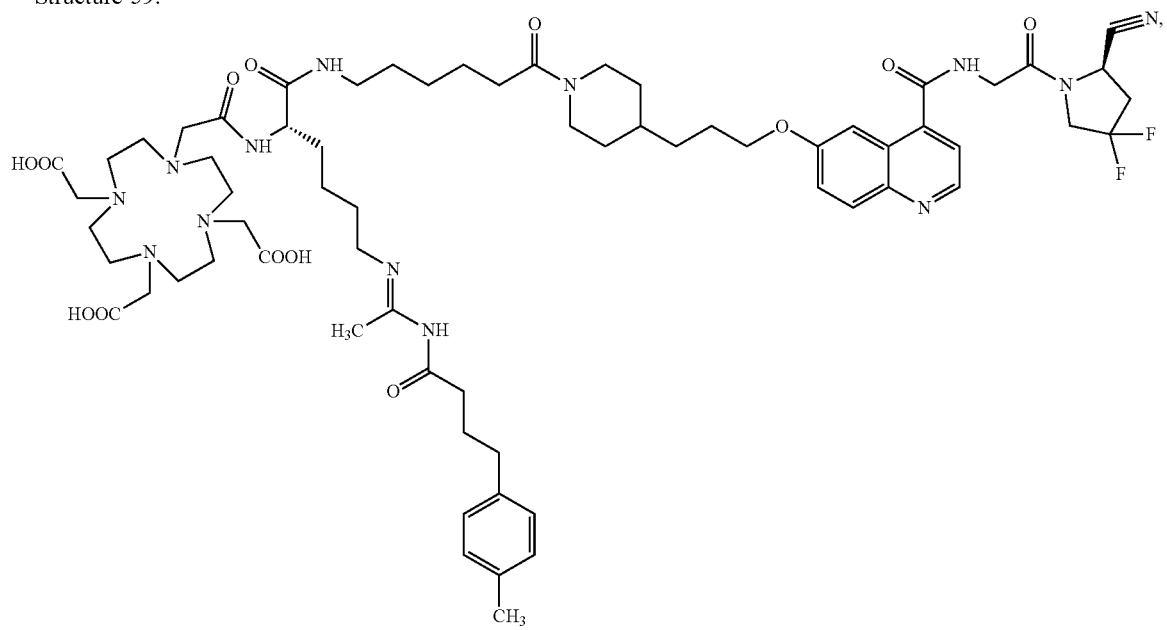

wherein
R1 is selected from R1-II-17, wherein the optical configuration of the optically active carbon is S configuration;
Code: FAPI-INER-411-S;
Molecular weight: 1314.5;
Molecular formula: $C_{66}H_{93}F_2N_{13}O_{13}$;

Structure 60:

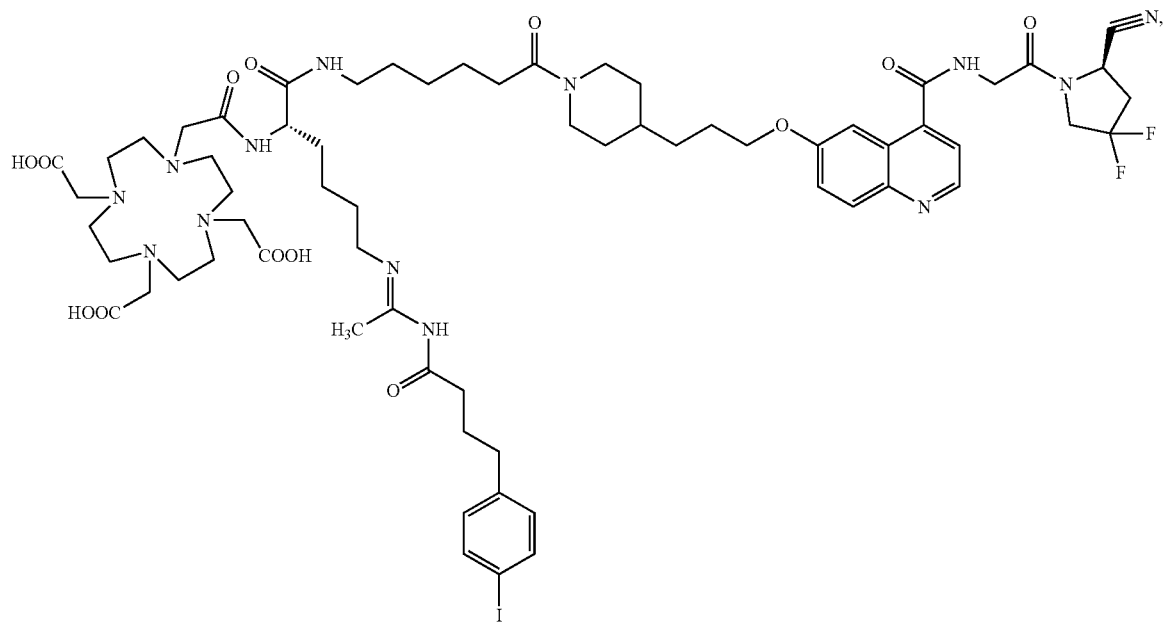

wherein
R1 is selected from R1-II-18, wherein the optical configuration of the optically active carbon is S configuration;
Code: FAPI-INER-415-S;
Molecular weight: 1426.3;
Molecular formula: $C_{65}H_{90}F_2IN_{13}O_{13}$;

Structure 61:

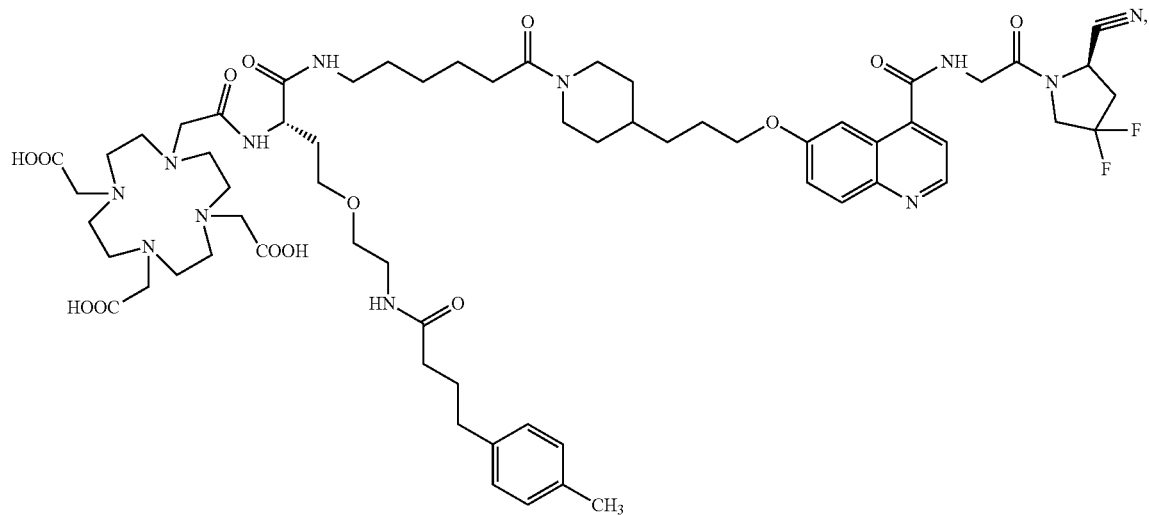

wherein
R1 is selected from R1-II-21, wherein the optical configuration of the optically active carbon is S configuration;
Code: FAPI-INER-419-S;
Molecular weight: 1289.4;
Molecular formula: $C_{64}H_{90}F_2N_{12}O_{14}$;

Structure 62:

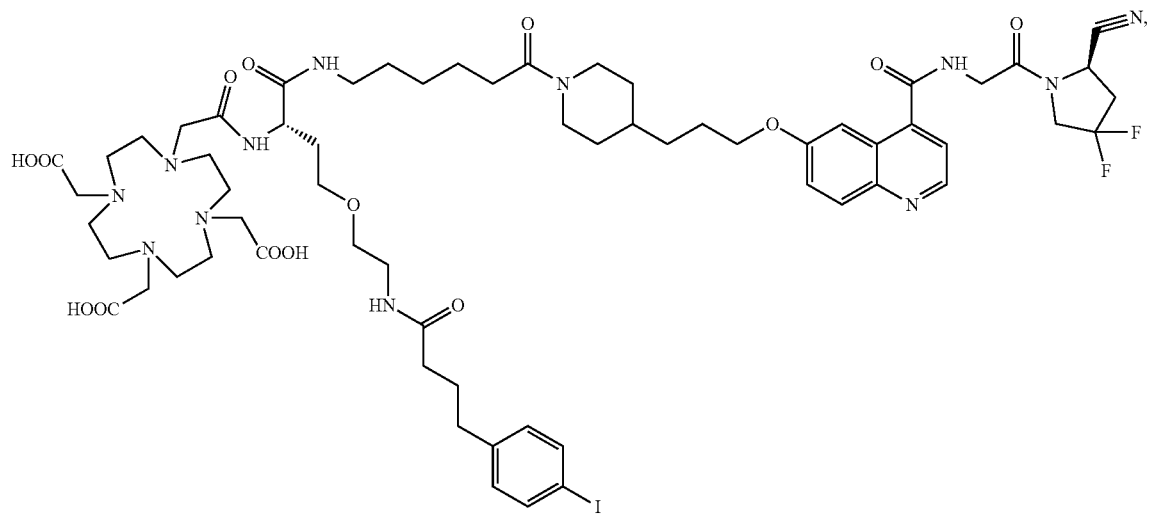

wherein
R1 is selected from R1-II-22, wherein the optical configuration of the optically active carbon is S configuration;
Code: FAPI-INER-423-S;
Molecular weight: 1401.3;
Molecular formula: $C_{63}H_{87}F_2IN_{12}O_{14}$;
or R2 is selected from R2-II-4 of the set of R2-II, R1 is any structure selected from the set of R1-II, and the D structure is

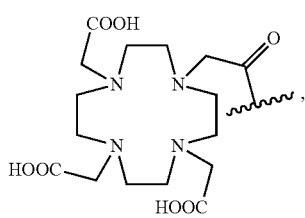 [SMILES: *C(=O)CN1CCN(CC(=O)O)CCN(CC(=O)O)CCN(CC(=O)O)CC1]

and thus the compound has a structure represented by formulas below:

Structure 63:

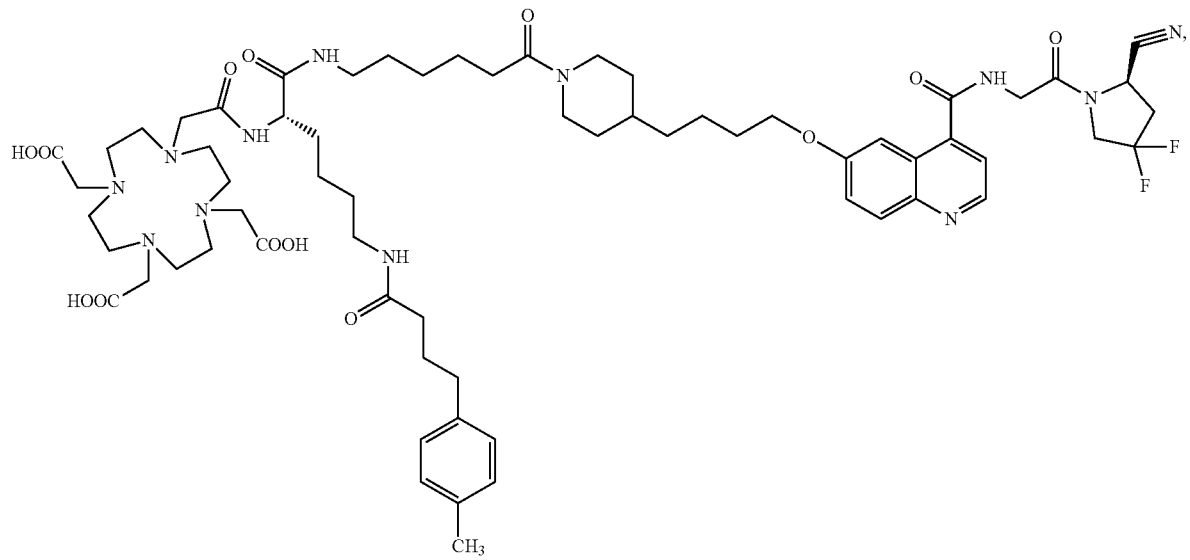

wherein
R1 is selected from R1-II-1, wherein the optical configuration of the optically active carbon is S configuration;
Code: FAPI-INER-388-S;
Molecular weight: 1287.4;
Molecular formula: $C_{65}H_{92}F_2N_{12}O_{13}$;
Structure 64:

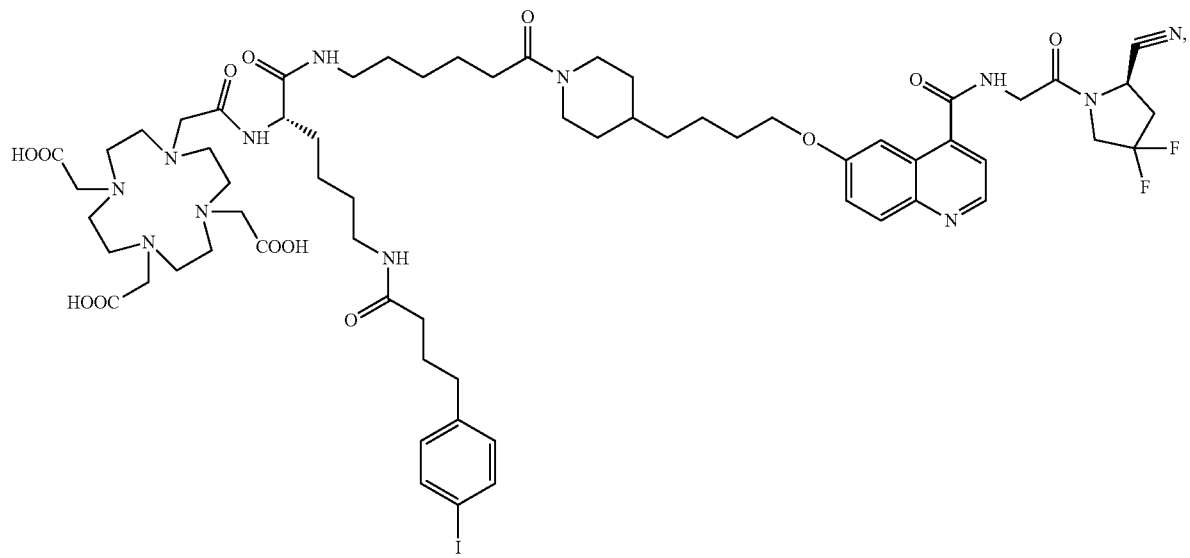

wherein
R1 is selected from R1-II-2, wherein the optical configuration of the optically active carbon is S configuration;
Code: FAPI-INER-392-S;
Molecular weight: 1399.3;
Molecular formula: $C_{64}H_{89}F_2IN_{12}O_{13}$;

Structure 65:

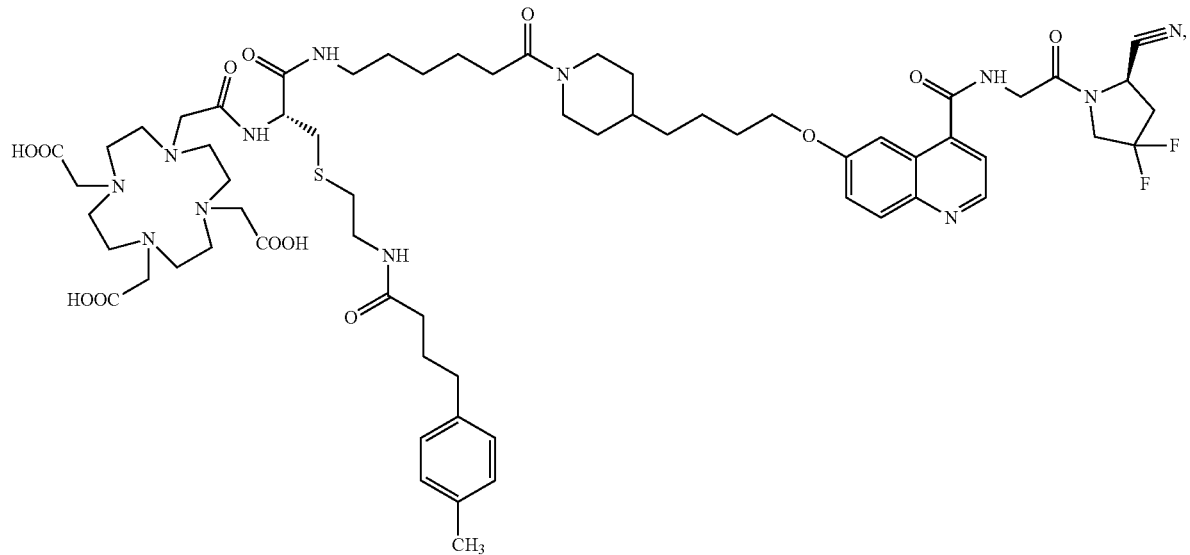

wherein
R1 is selected from R1-II-3, wherein the optical configuration of the optically active carbon is S configuration;
Code: FAPI-INER-396-S;
Molecular weight: 1305.5;
Molecular formula: $C_{64}H_{90}F_2N_{12}O_{13}S$;

Structure 66:

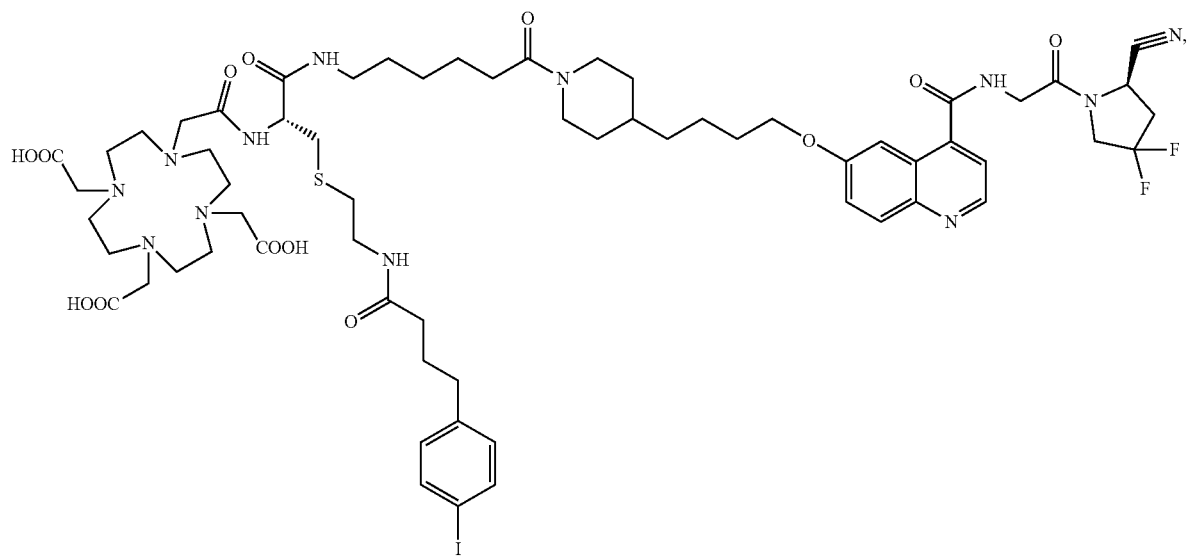

wherein
R1 is selected from R1-II-4, wherein the optical configuration of the optically active carbon is S configuration;
Code: FAPI-INER-400-S;
Molecular weight: 1417.4;
Molecular formula: $C_{63}H_{87}F_2IN_{12}O_{13}S$;

Structure 67:

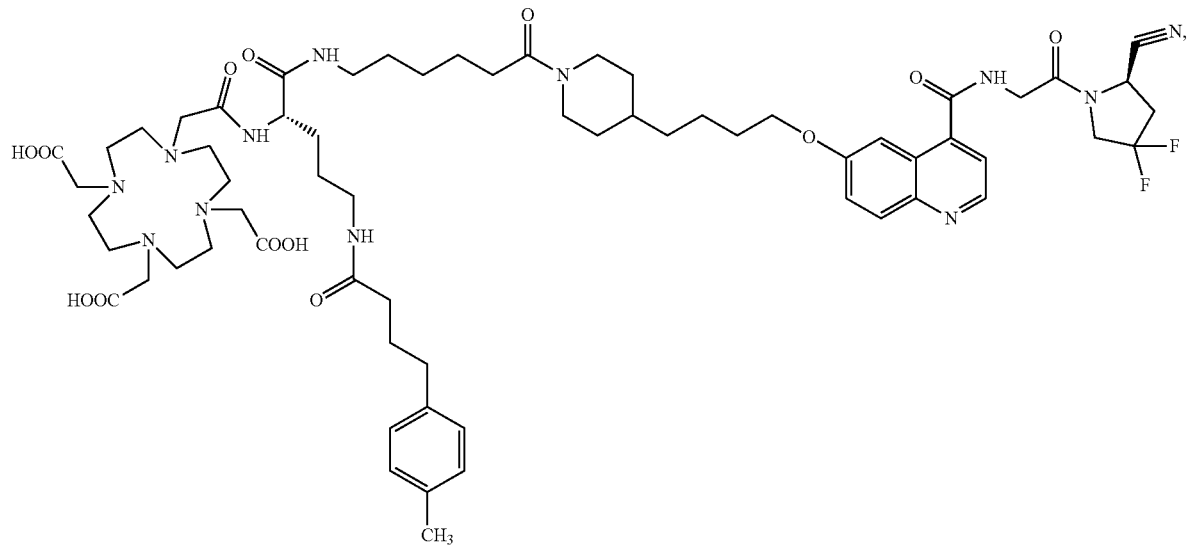

wherein
R1 is selected from R1-II-11, wherein the optical configuration of the optically active carbon is S configuration;
Code: FAPI-INER-404-S;
Molecular weight: 1273.4;
Molecular formula: $C_{64}H_{90}F_2N_{12}O_{13}$;

Structure 68:

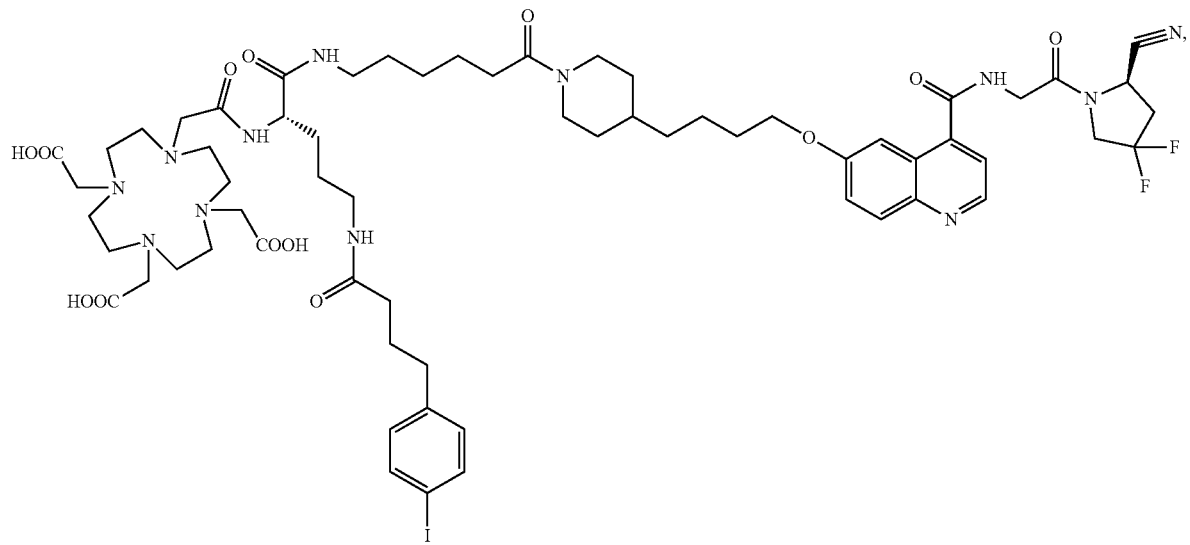

wherein
R1 is selected from R1-II-12, wherein the optical configuration of the optically active carbon is S configuration;
Code: FAPI-INER-408-S;
Molecular weight: 1385.3;
Molecular formula: $C_{63}H_{87}F_2IN_{12}O_{13}$;

Structure 69:

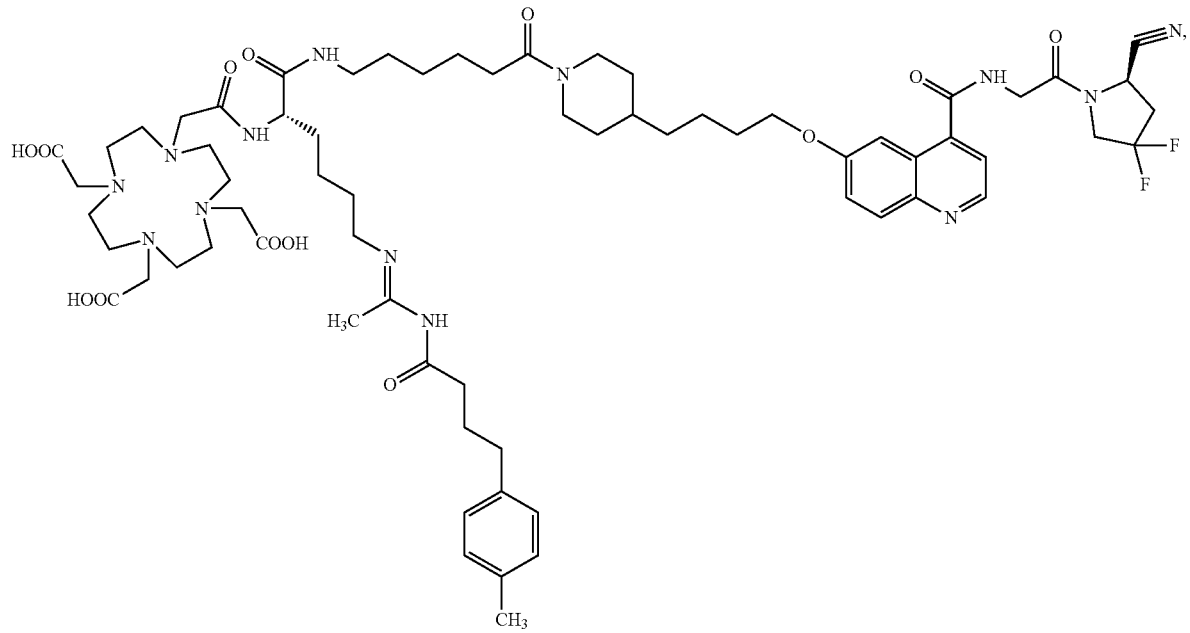

wherein
R1 is selected from R1-II-17, wherein the optical configuration of the optically active carbon is S configuration;
Code: FAPI-INER-412-S;
Molecular weight: 1328.5;
Molecular formula: $C_{67}H_{95}F_2N_{13}O_{13}$;

wherein
R1 is selected from R1-II-18, wherein the optical configuration of the optically active carbon is S configuration;
Code: FAPI-INER-416-S;
Molecular weight: 1440.4;
Molecular formula: $C_{66}H_{92}F_2IN_{13}O_{13}$;

Structure 70:

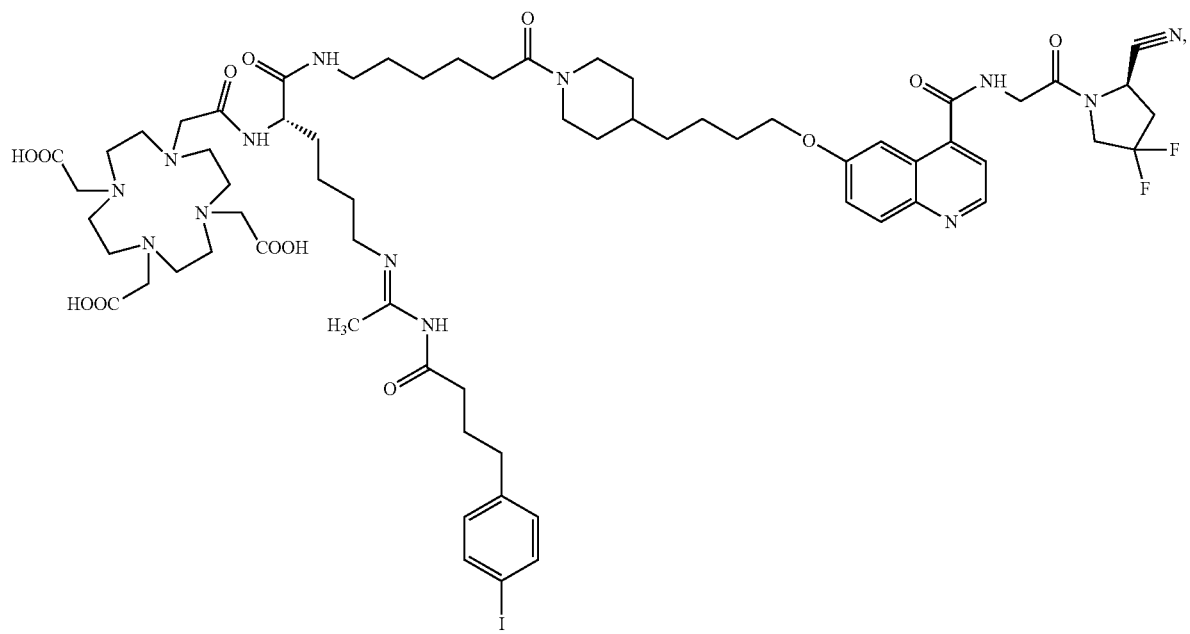 [SMILES: C/C(=N\CCCC[C@H](NC(=O)CN1CCN(CC(=O)O)CCN(CC(=O)O)CCN(CC(=O)O)CC1)C(=O)NCCCCCC(=O)N1CCC(CCCCOc2ccc3nccc(C(=O)NCC(=O)N4CC(F)(F)C[C@@H]4C#N)c3c2)CC1)NC(=O)CCCc1ccc(I)cc1]

Structure 71:

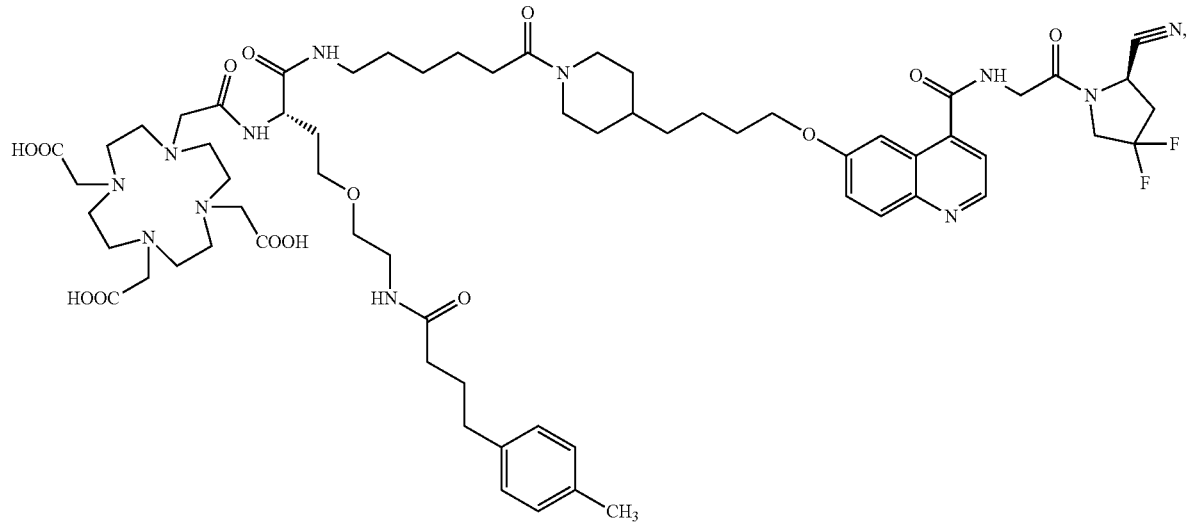

wherein
R1 is selected from R1-II-21, wherein the optical configuration of the optically active carbon is S configuration;
Code: FAPI-INER-420-S;
Molecular weight: 1303.4;
Molecular formula: $C_{65}H_{92}F_2N_{12}O_{14}$;

Structure 72:

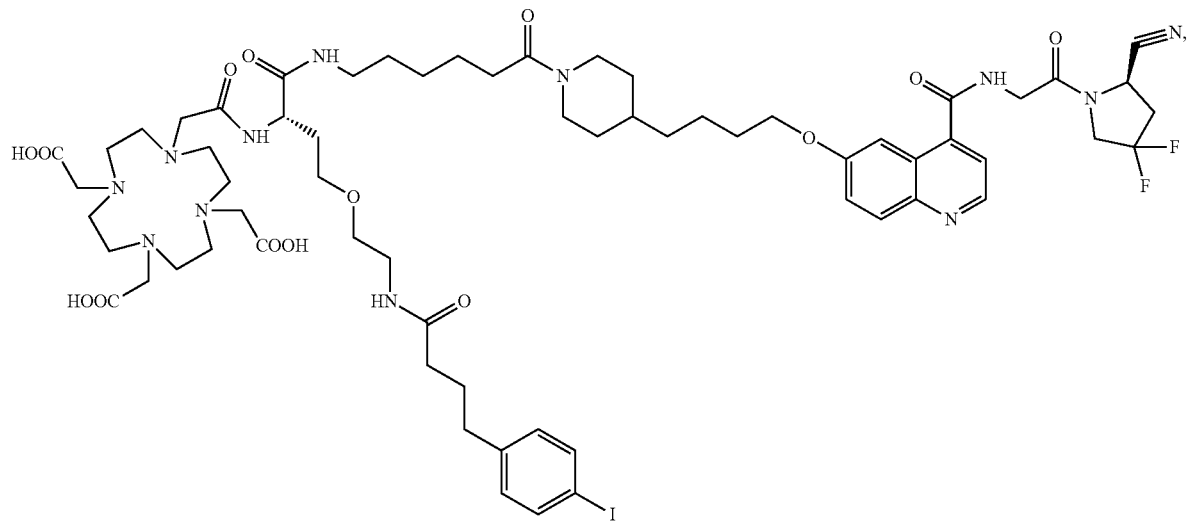

wherein
R1 is selected from R1-II-22, wherein the optical configuration of the optically active carbon is S configuration;
Code: FAPI-INER-424-S;
Molecular weight: 1415.3;
Molecular formula: $C_{64}H_{89}F_2IN_{12}O_{14}$;
or R2 is selected from R2-II-5 of the set of R2-II, R1 is any structure selected from the set of R1-II, and the D structure is

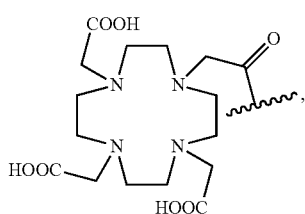 [SMILES: *C(=O)CN1CCN(CC(=O)O)CCN(CC(=O)O)CCN(CC(=O)O)CC1]

and thus the compound has a structure represented by formulas below:

Structure 73:

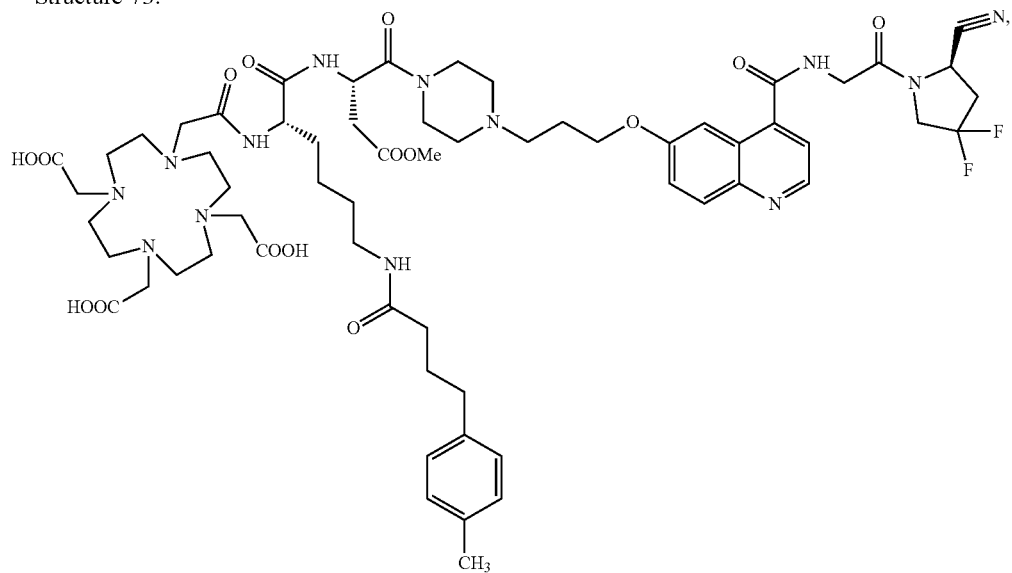

wherein
the optical configuration of the optically active carbon of R2-II-5 is S configuration; R1 is selected from R1-II-1, wherein the optical configuration of the optically active carbon is S configuration;
Code: FAPI-INER-425-SS;
Molecular weight: 1290.4;
Molecular formula: $C_{62}H_{85}F_2N_{13}O_{15}$;

Structure 74:

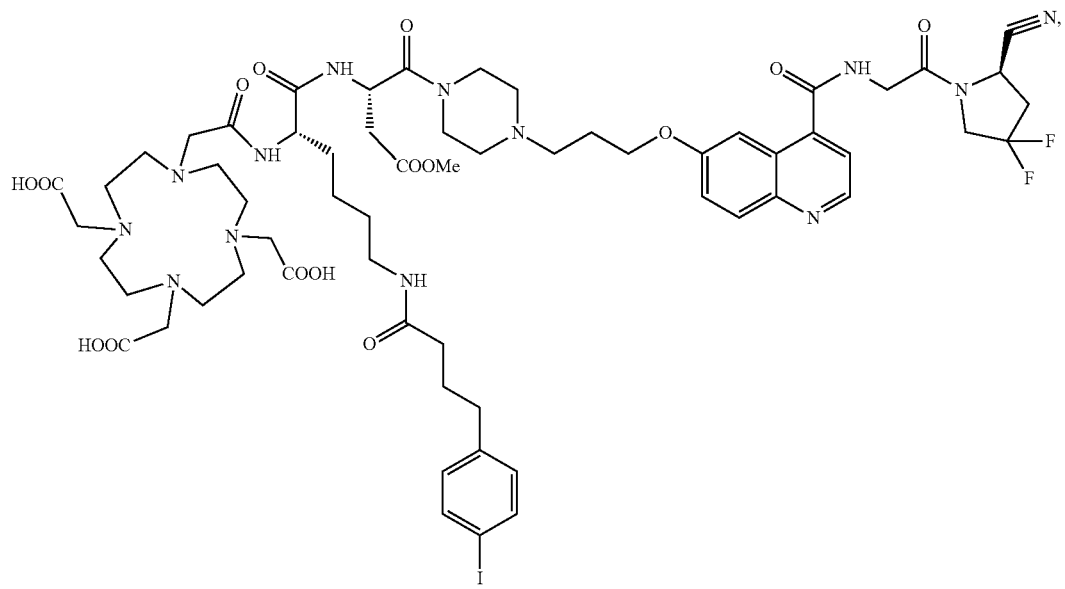 [SMILES: COC(=O)C[C@H](NC(=O)[C@H](CCCCNC(=O)CCCc1ccc(I)cc1)NC(=O)CN1CCN(CC(=O)O)CCN(CC(=O)O)CCN(CC(=O)O)CC1)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-II-5 is S configuration; R1 is selected from R1-II-2, wherein the optical configuration of the optically active carbon is S configuration;
Code: FAPI-INER-429-SS;
Molecular weight: 1402.2;
Molecular formula: $C_{61}H_{82}F_2IN_{13}O_{15}$;

Structure 75:

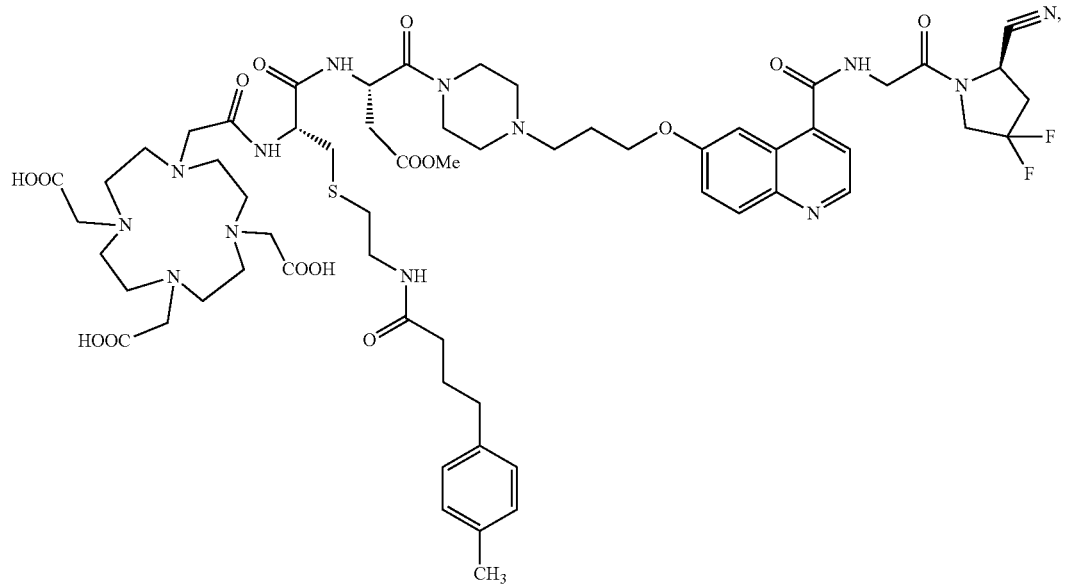 [SMILES: COC(=O)C[C@H](NC(=O)[C@H](CSCCNC(=O)CCCc1ccc(C)cc1)NC(=O)CN1CCN(CC(=O)O)CCN(CC(=O)O)CCN(CC(=O)O)CC1)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-II-5 is S configuration; R1 is selected from R1-II-3, wherein the optical configuration of the optically active carbon is S configuration;
Code: FAPI-INER-433-SS;
Molecular weight: 1308.4;
Molecular formula: $C_{61}H_{83}F_2N_{13}O_{15}S$;

Structure 76:

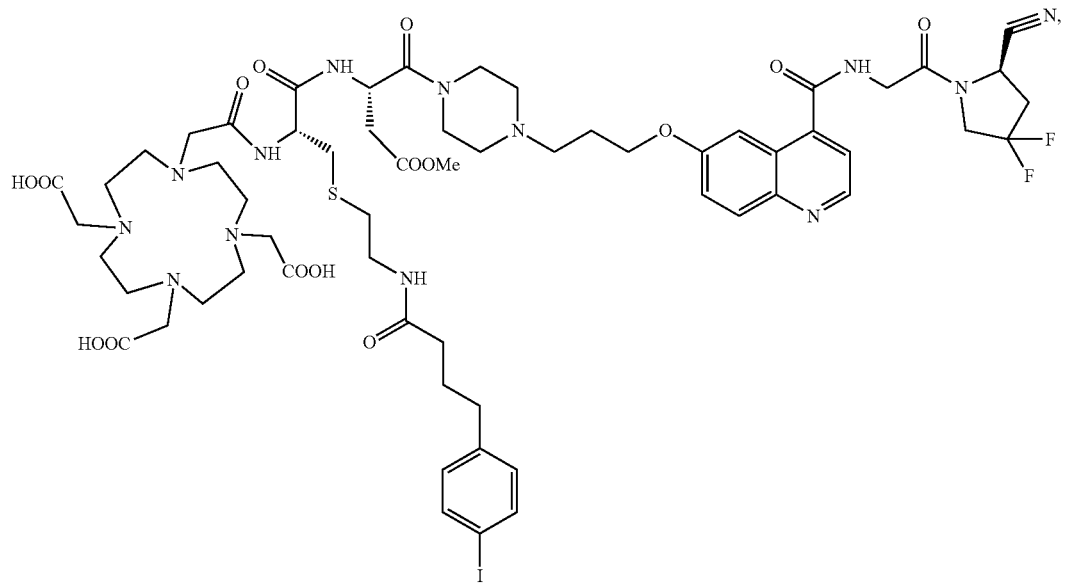 [SMILES: COC(=O)C[C@H](NC(=O)[C@H](CSCCNC(=O)CCCc1ccc(I)cc1)NC(=O)CN1CCN(CC(=O)O)CCN(CC(=O)O)CCN(CC(=O)O)CC1)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-II-5 is S configuration; R1 is selected from R1-II-4, wherein the optical configuration of the optically active carbon is S configuration;
Code: FAPI-INER-437-SS;
Molecular weight: 1420.3;
Molecular formula: $C_{60}H_{80}F_2IN_{13}O_{15}S$;

Structure 77:

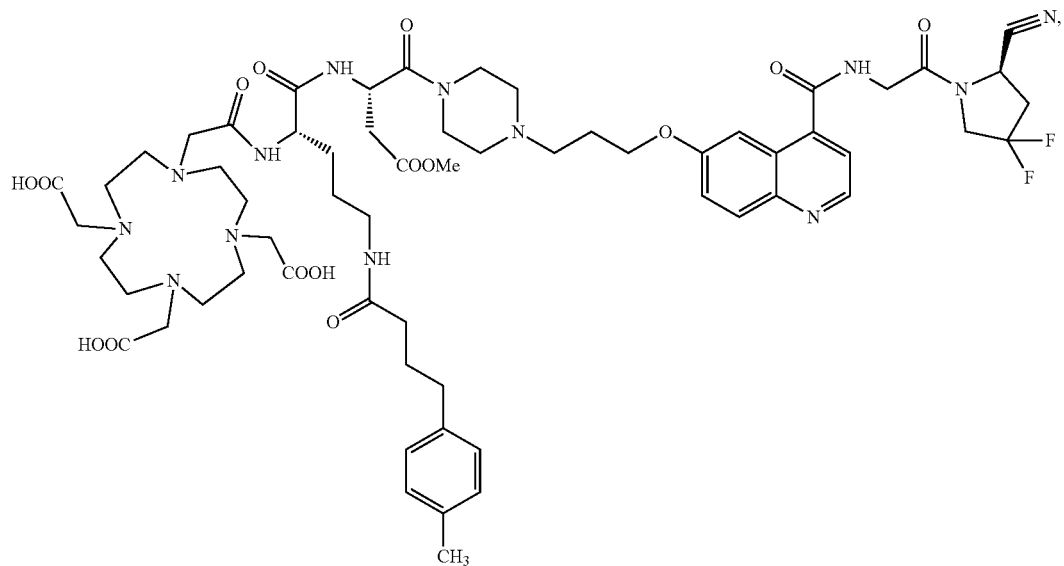 [SMILES: COC(=O)C[C@H](NC(=O)[C@H](CCCNC(=O)CCCc1ccc(C)cc1)NC(=O)CN1CCN(CC(=O)O)CCN(CC(=O)O)CCN(CC(=O)O)CC1)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-II-5 is S configuration; R1 is selected from R1-II-11, wherein the optical configuration of the optically active carbon is S configuration;
Code: FAPI-INER-441-SS;
Molecular weight: 1276.3;
Molecular formula: $C_{61}H_{83}F_2N_{13}O_{15}$;

Structure 78:

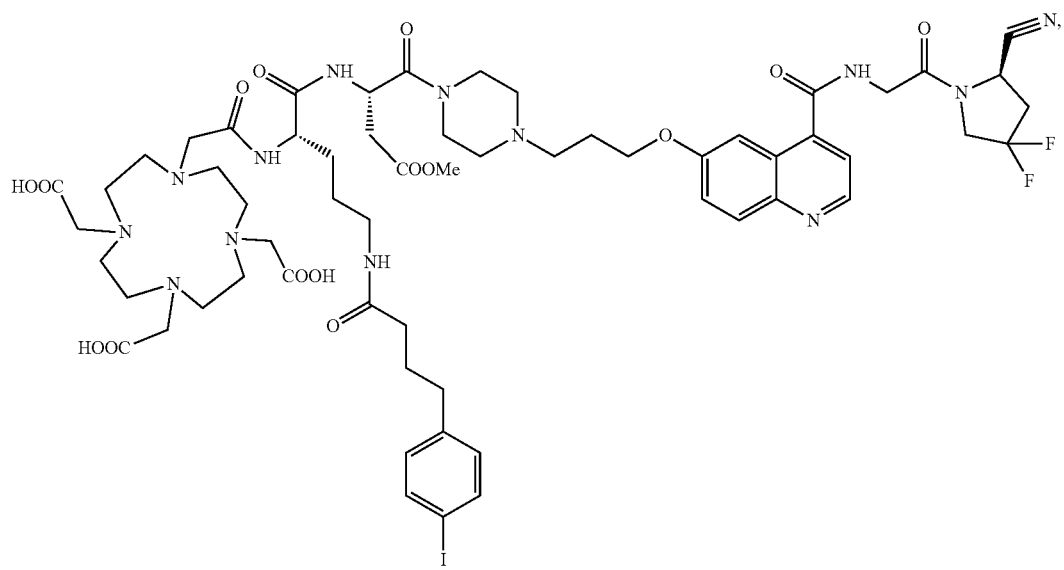 [SMILES: COC(=O)C[C@H](NC(=O)[C@H](CCCNC(=O)CCCc1ccc(I)cc1)NC(=O)CN1CCN(CC(=O)O)CCN(CC(=O)O)CCN(CC(=O)O)CC1)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-II-5 is S configuration; R1 is selected from R1-II-12, wherein the optical configuration of the optically active carbon is S configuration;
Code: FAPI-INER-445-SS;
Molecular weight: 1388.2;
Molecular formula: $C_{60}H_{80}F_2IN_{13}O_{15}$;

Structure 79:

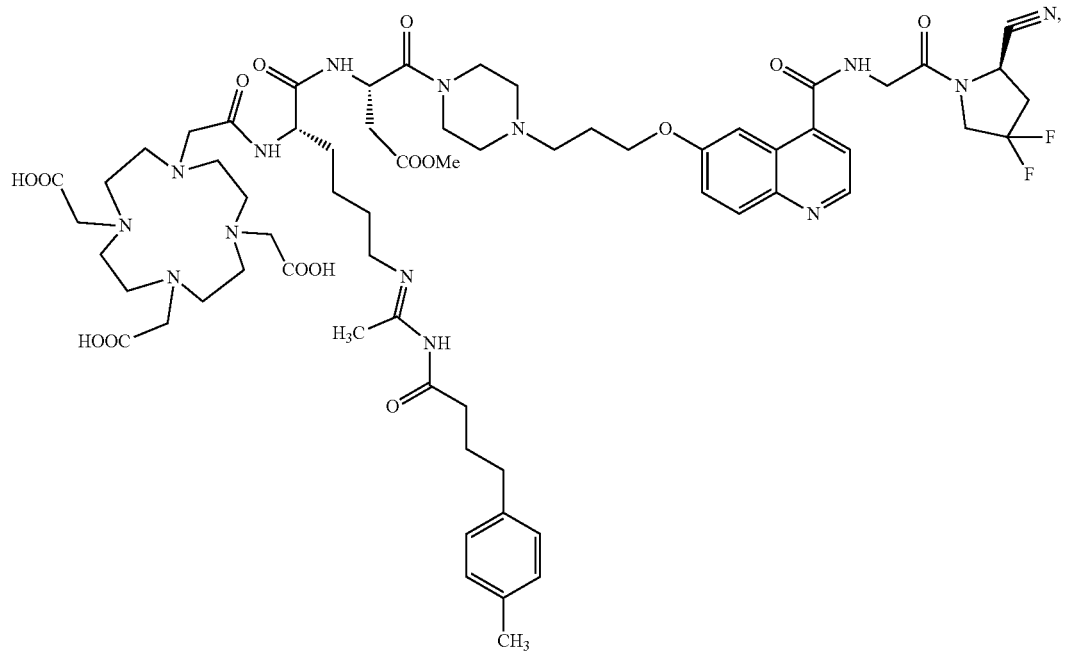 [SMILES: COC(=O)C[C@H](NC(=O)[C@H](CCCC/N=C(\C)NC(=O)CCCc1ccc(C)cc1)NC(=O)CN1CCN(CC(=O)O)CCN(CC(=O)O)CCN(CC(=O)O)CC1)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-II-5 is S configuration; R1 is selected from R1-II-17, wherein the optical configuration of the optically active carbon is S configuration;
Code: FAPI-INER-449-SS;
Molecular weight: 1331.4;
Molecular formula: $C_{64}H_{88}F_2N_{14}O_{15}$;
Structure 80:

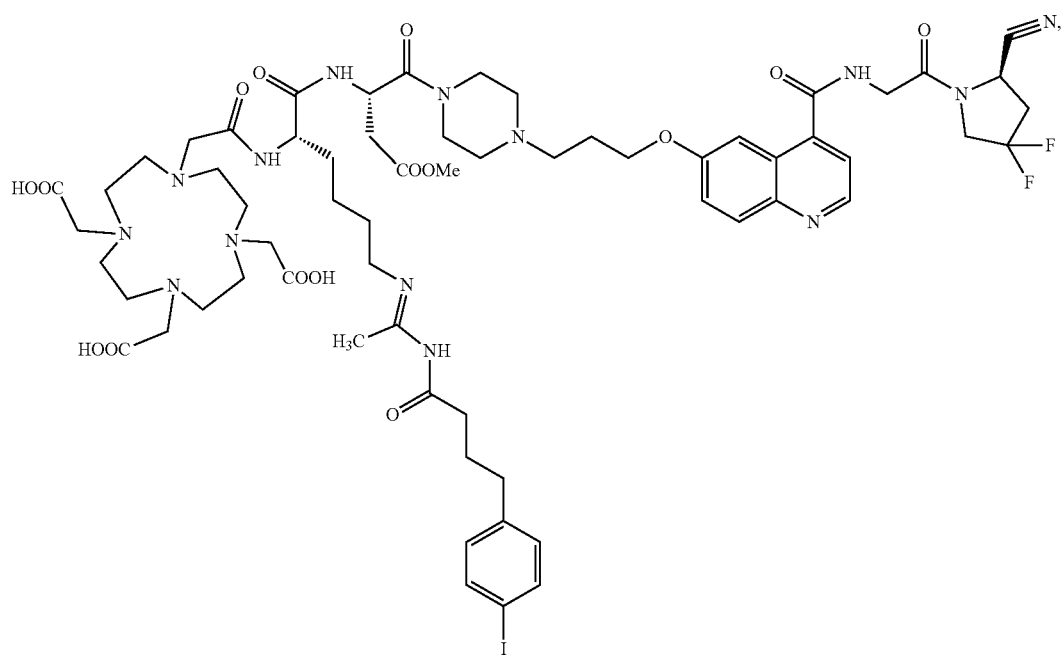 [SMILES: COC(=O)C[C@H](NC(=O)[C@H](CCCC/N=C(\C)NC(=O)CCCc1ccc(I)cc1)NC(=O)CN1CCN(CC(=O)O)CCN(CC(=O)O)CCN(CC(=O)O)CC1)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-II-5 is S configuration; R1 is selected from R1-II-18, wherein the optical configuration of the optically active carbon is S configuration;
Code: FAPI-INER-453-SS;
Molecular weight: 1443.3;
Molecular formula: $C_{63}H_{85}F_2IN_{14}O_{15}$;

Structure 81:

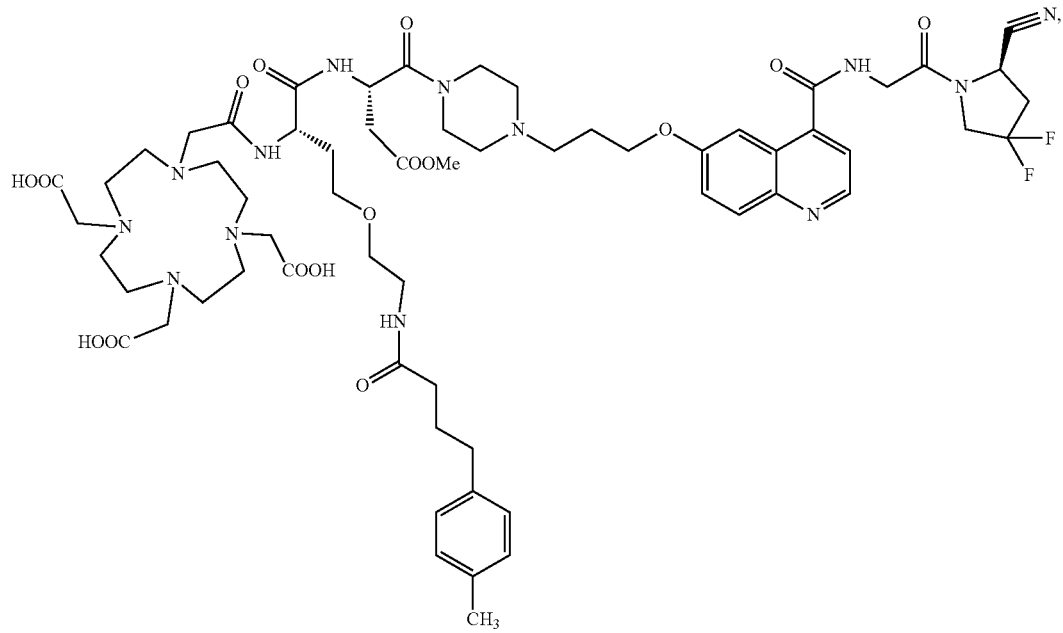 [SMILES: COC(=O)C[C@H](NC(=O)[C@H](CCOCCNC(=O)CCCc1ccc(C)cc1)NC(=O)CN1CCN(CC(=O)O)CCN(CC(=O)O)CCN(CC(=O)O)CC1)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-II-5 is S configuration; R1 is selected from R1-II-21, wherein the optical configuration of the optically active carbon is S configuration;
Code: FAPI-INER-457-SS;
Molecular weight: 1306.4;
Molecular formula: $C_{62}H_{85}F_2N_{13}O_{16}$;
Structure 82:

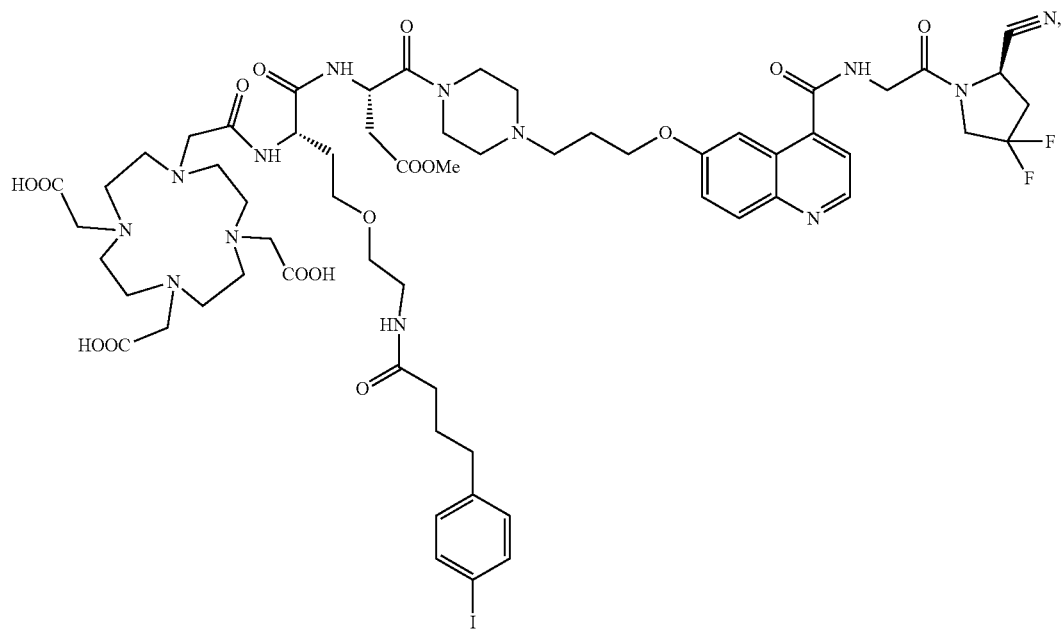 [SMILES: COC(=O)C[C@H](NC(=O)[C@H](CCOCCNC(=O)CCCc1ccc(I)cc1)NC(=O)CN1CCN(CC(=O)O)CCN(CC(=O)O)CCN(CC(=O)O)CC1)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-II-5 is S configuration; R1 is selected from R1-II-22, wherein the optical configuration of the optically active carbon is S configuration;
Code: FAPI-INER-461-SS;
Molecular weight: 1418.2;
Molecular formula: $C_{61}H_{82}F_2IN_{13}O_{16}$;

or R2 is selected from R2-II-6 of the set of R2-II, R1 is any structure selected from the set of R1-II, and the D structure is

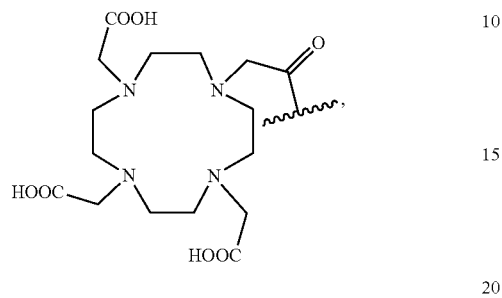

and thus the compound has a structure represented by formulas below:
Structure 83:

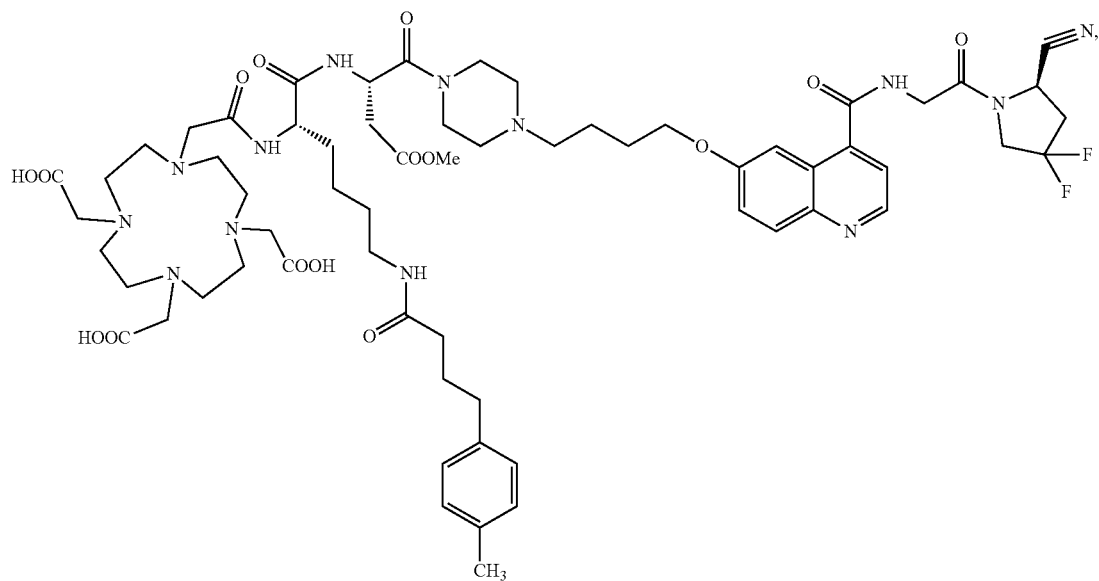

wherein
the optical configuration of the optically active carbon of R2-II-6 is S configuration; R1 is selected from R1-II-1, wherein the optical configuration of the optically active carbon is S configuration;

Code: FAPI-INER-426-SS;

Molecular weight: 1304.4;

Molecular formula: $C_{63}H_{87}F_2N_{13}O_{15}$;

Structure 84:

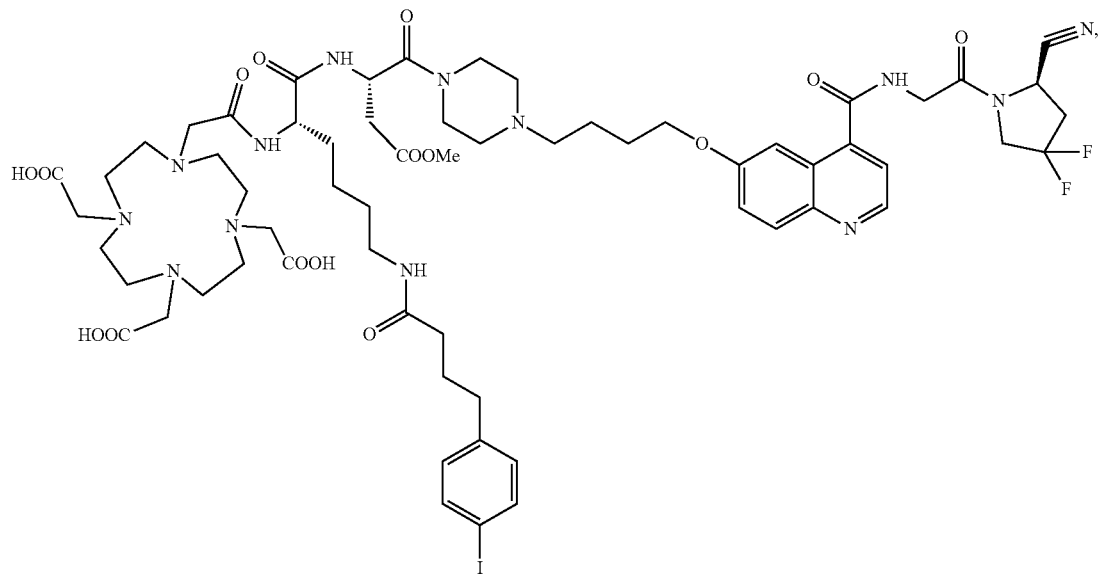

wherein
the optical configuration of the optically active carbon of R2-II-6 is S configuration; R1 is selected from R1-II-2, wherein the optical configuration of the optically active carbon is S configuration;
Code: FAPI-INER-430-SS;
Molecular weight: 1416.3;
Molecular formula: $C_{62}H_{84}F_2IN_{13}O_{15}$;

Structure 85:

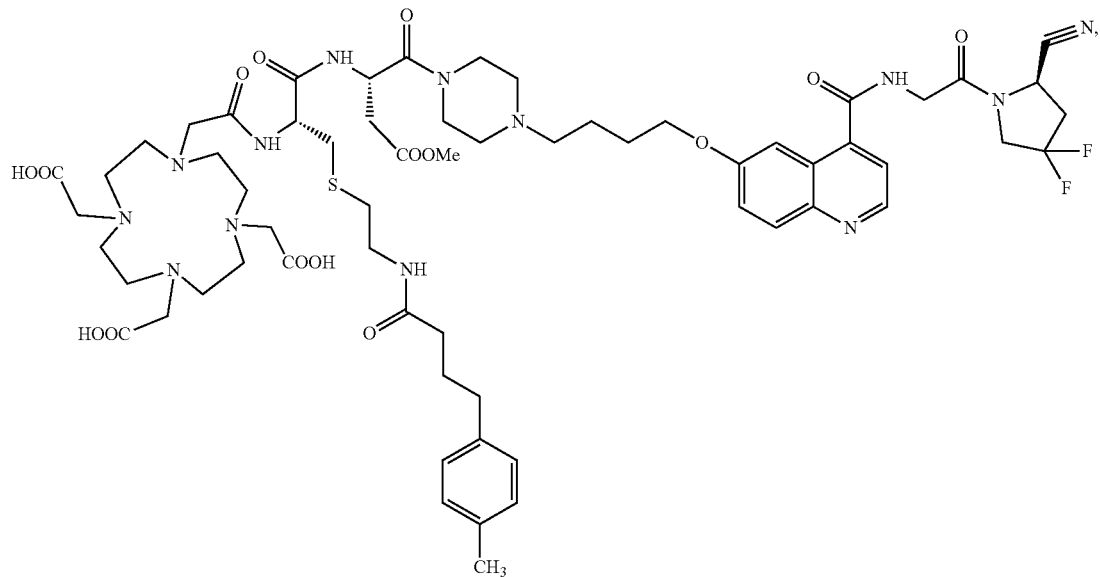 [SMILES: COC(=O)C[C@H](NC(=O)[C@H](CSCCNC(=O)CCCc1ccc(C)cc1)NC(=O)CN1CCN(CC(=O)O)CCN(CC(=O)O)CCN(CC(=O)O)CC1)C(=O)N1CCN(CCCCOc2ccc3nccc(C(=O)NCC(=O)N4CC(F)(F)C[C@@H]4C#N)c3c2)CC1]

wherein
the optical configuration of the optically active carbon of R2-II-6 is S configuration; R1 is selected from R1-II-3, wherein the optical configuration of the optically active carbon is S configuration;
Code: FAPI-INER-434-SS;
Molecular weight: 1322.4;
Molecular formula: $C_{62}H_{85}F_2N_{13}O_{15}S$;

Structure 86:

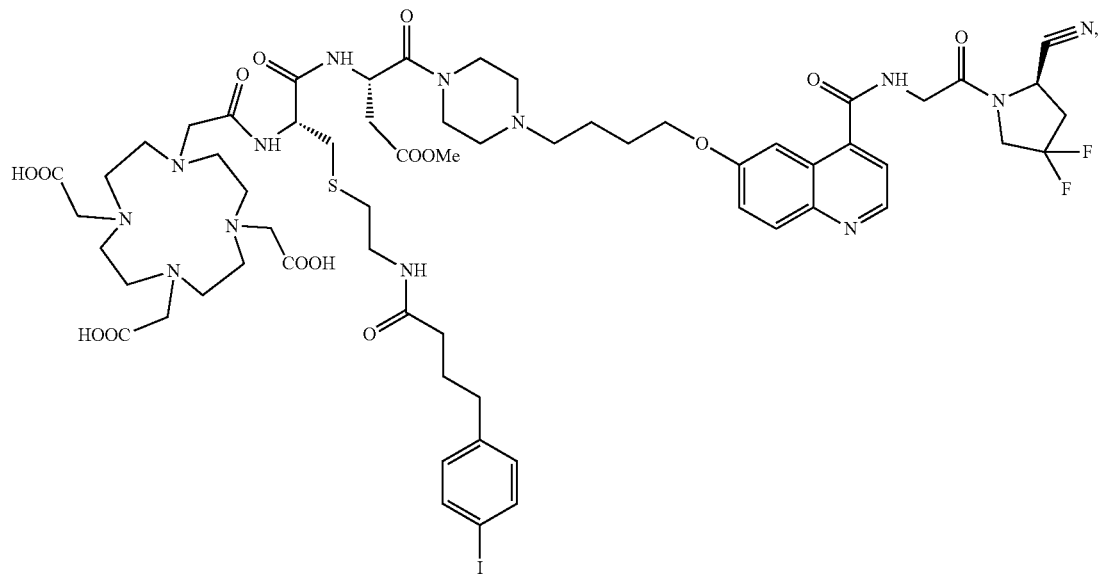 [SMILES: COC(=O)C[C@H](NC(=O)[C@H](CSCCNC(=O)CCCc1ccc(I)cc1)NC(=O)CN1CCN(CC(=O)O)CCN(CC(=O)O)CCN(CC(=O)O)CC1)C(=O)N1CCN(CCCCOc2ccc3nccc(C(=O)NCC(=O)N4CC(F)(F)C[C@@H]4C#N)c3c2)CC1]

wherein
the optical configuration of the optically active carbon of R2-II-6 is S configuration; R1 is selected from R1-II-4, wherein the optical configuration of the optically active carbon is S configuration;
Code: FAPI-INER-438-SS;
Molecular weight: 1434.3;
Molecular formula: $C_{61}H_{82}F_2IN_{13}O_{15}S$;

Structure 87:

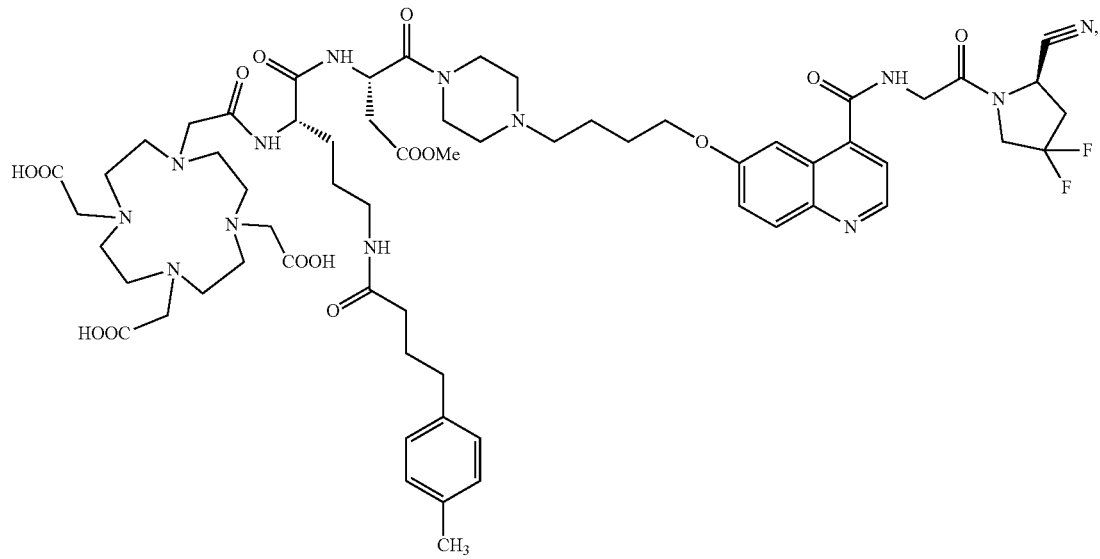 [SMILES: COC(=O)C[C@H](NC(=O)[C@H](CCCNC(=O)CCCc1ccc(C)cc1)NC(=O)CN1CCN(CC(=O)O)CCN(CC(=O)O)CCN(CC(=O)O)CC1)C(=O)N1CCN(CCCCOc2ccc3nccc(C(=O)NCC(=O)N4CC(F)(F)C[C@@H]4C#N)c3c2)CC1]

wherein
the optical configuration of the optically active carbon of R2-II-6 is S configuration; R1 is selected from R1-II-11, wherein the optical configuration of the optically active carbon is S configuration;
Code: FAPI-INER-442-SS;
Molecular weight: 1290.4;
Molecular formula: $C_{62}H_{85}F_2N_{13}O_{15}$;

Structure 88:

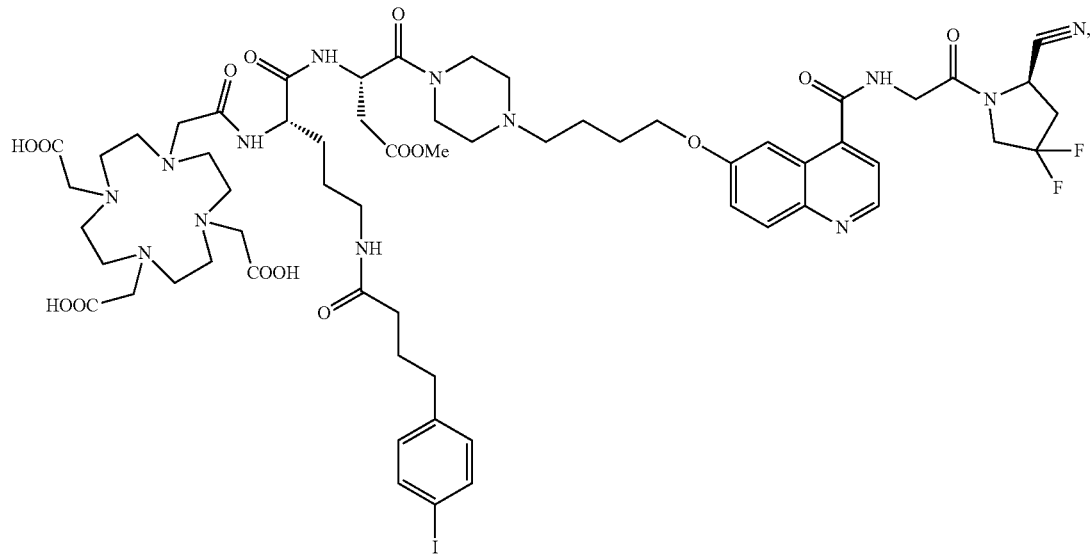 [SMILES: COC(=O)C[C@H](NC(=O)[C@H](CCCNC(=O)CCCc1ccc(I)cc1)NC(=O)CN1CCN(CC(=O)O)CCN(CC(=O)O)CCN(CC(=O)O)CC1)C(=O)N1CCN(CCCCOc2ccc3nccc(C(=O)NCC(=O)N4CC(F)(F)C[C@@H]4C#N)c3c2)CC1]

wherein
the optical configuration of the optically active carbon of R2-II-6 is S configuration; R1 is selected from R1-II-11, wherein the optical configuration of the optically active carbon is S configuration;
Code: FAPI-INER-446-SS;
Molecular weight: 1402.2;
Molecular formula: $C_{61}H_{82}F_2IN_{13}O_{15}$;

Structure 89:

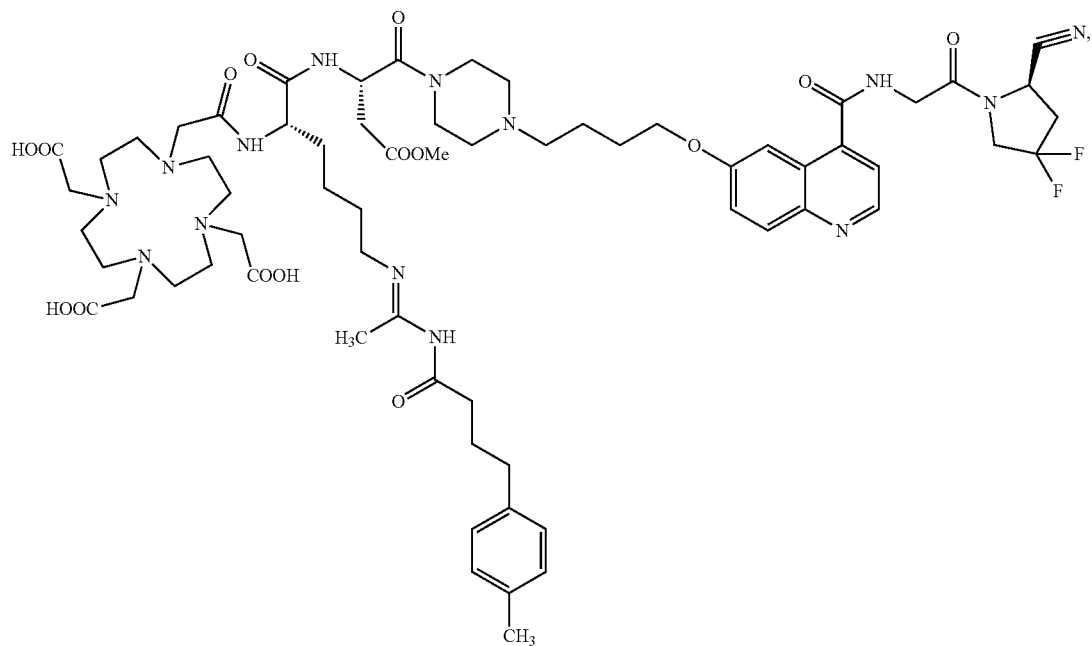

wherein
the optical configuration of the optically active carbon of R2-II-6 is S configuration; R1 is selected from R1-II-17, wherein the optical configuration of the optically active carbon is S configuration;
Code: FAPI-INER-450-SS;
Molecular weight: 1345.4;
Molecular formula: $C_{65}H_{90}F_2N_{14}O_{15}$;

Structure 90:

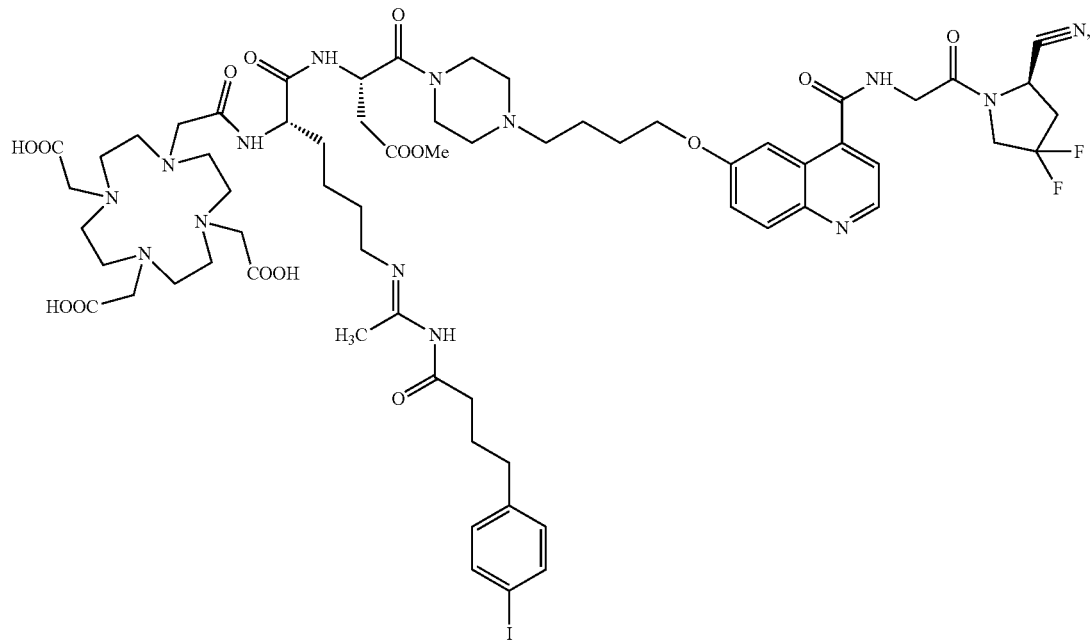 [SMILES: COC(=O)C[C@H](NC(=O)[C@H](CCCC/N=C(\C)NC(=O)CCCc1ccc(I)cc1)NC(=O)CN1CCN(CC(=O)O)CCN(CC(=O)O)CCN(CC(=O)O)CC1)C(=O)N1CCN(CCCCOc2ccc3nccc(C(=O)NCC(=O)N4CC(F)(F)C[C@@H]4C#N)c3c2)CC1]

wherein
the optical configuration of the optically active carbon of R2-II-6 is S configuration; R1 is selected from R1-II-18, wherein the optical configuration of the optically active carbon is S configuration;
Code: FAPI-INER-454-SS;
Molecular weight: 1457.3;
Molecular formula $C_{64}H_{87}F_2IN_{14}O_{15}$;
Structure 91:

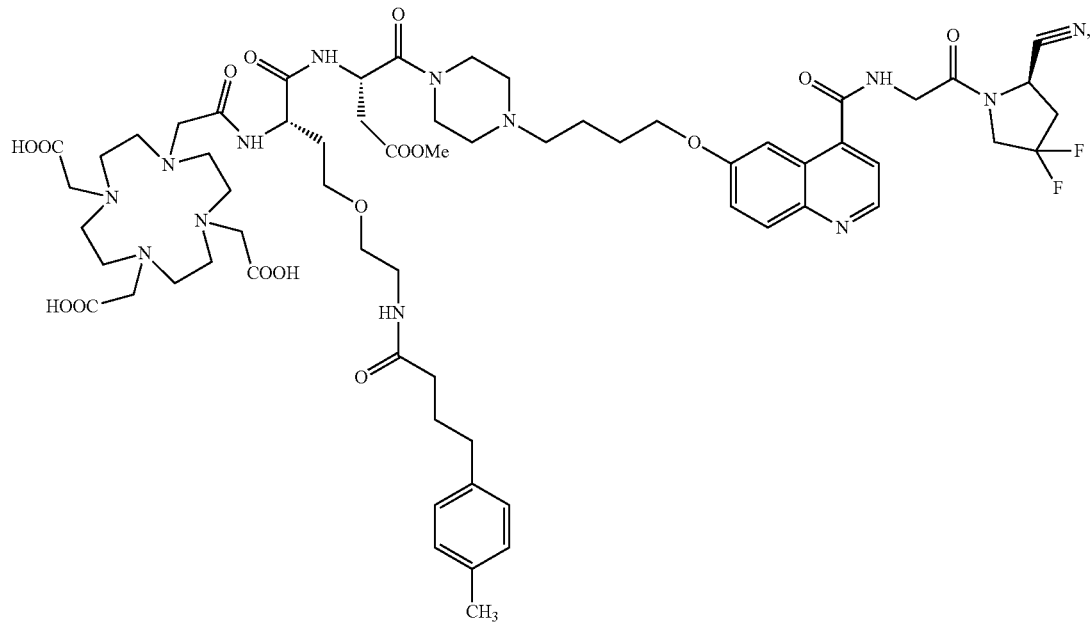

wherein
the optical configuration of the optically active carbon of R2-II-6 is S configuration; R1 is selected from R1-II-21, wherein the optical configuration of the optically active carbon is S configuration;
Code: FAPI-INER-458-SS;
Molecular weight: 1320.4;
Molecular formula: $C_{63}H_{87}F_2N_{13}O_{16}$;

Structure 92:

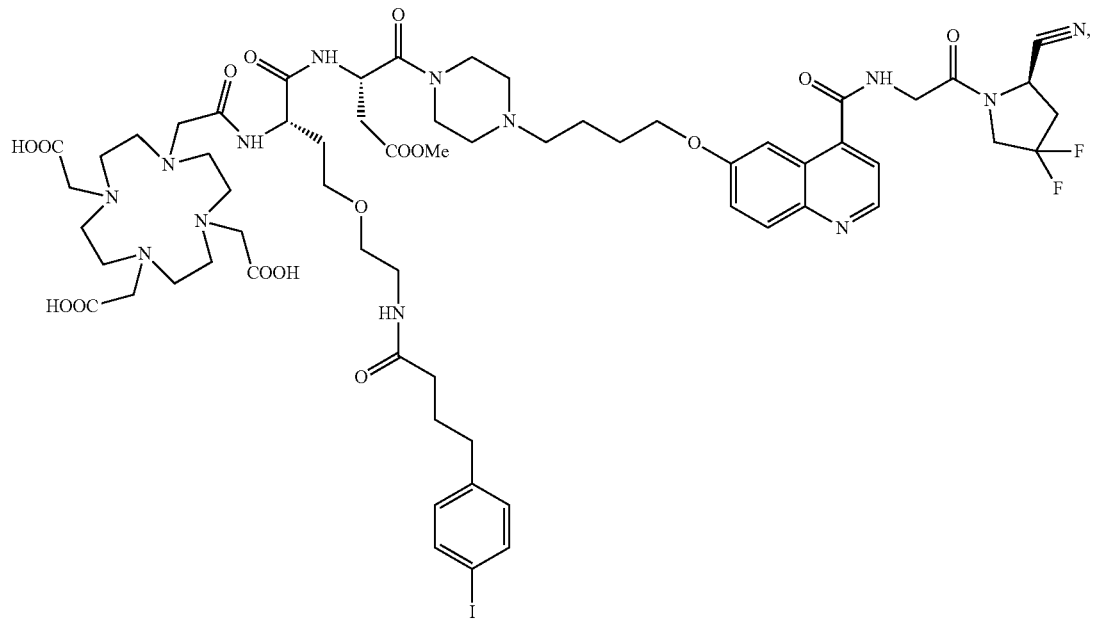 [SMILES: COC(=O)C[C@H](NC(=O)[C@H](CCOCCNC(=O)CCCc1ccc(I)cc1)NC(=O)CN1CCN(CC(=O)O)CCN(CC(=O)O)CCN(CC(=O)O)CC1)C(=O)N1CCN(CCCCOc2ccc3nccc(C(=O)NCC(=O)N4CC(F)(F)C[C@@H]4C#N)c3c2)CC1]

wherein
the optical configuration of the optically active carbon of R2-II-6 is S configuration; R1 is selected from R1-II-22, wherein the optical configuration of the optically active carbon is S configuration;

Code: FAPI-INER-462-SS;

Molecular weight: 1432.3;

Molecular formula: $C_{62}H_{84}F_2IN_{13}O_{16}$;

or R2 is selected from R2-II-7 of the set of R2-II, R1 is any structure selected from the set of R1-II, and the D structure is

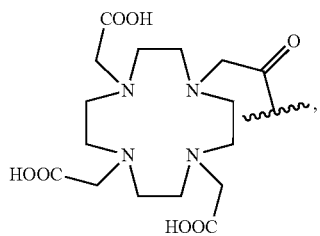 [SMILES: *C(=O)CN1CCN(CC(=O)O)CCN(CC(=O)O)CCN(CC(=O)O)CC1]

and thus the compound has a structure represented by formulas below:

Structure 93:

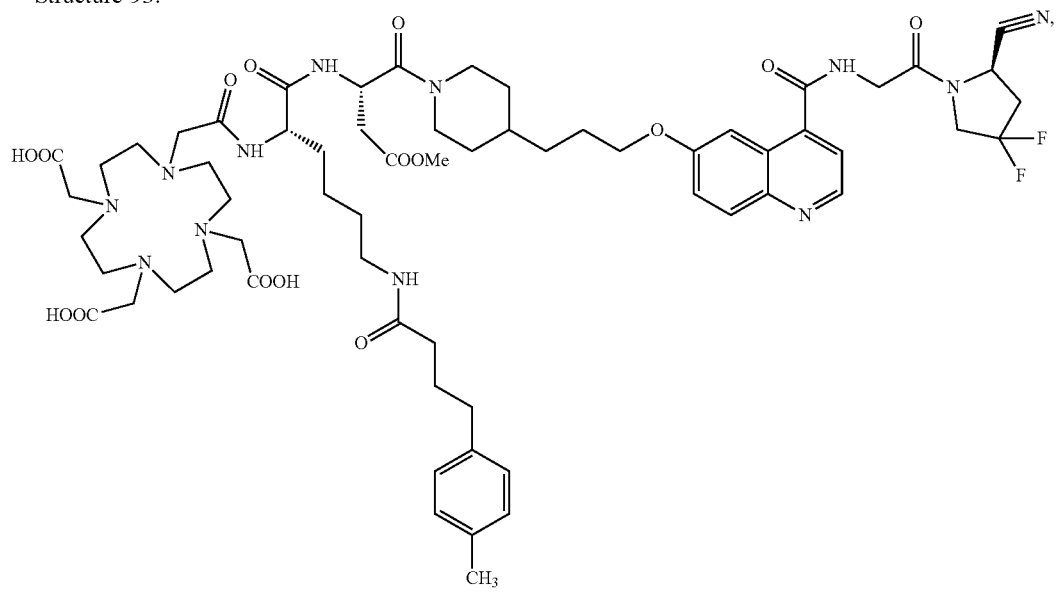

wherein
the optical configuration of the optically active carbon of R2-II-7 is S configuration; R1 is selected from R1-II-1, wherein the optical configuration of the optically active carbon is S configuration;
Code: FAPI-INER-427-SS;
Molecular weight: 1289.4;
Molecular formula: $C_{63}H_{86}F_2N_{12}O_{15}$;

Structure 94:

wherein
the optical configuration of the optically active carbon of R2-II-7 is S configuration; R1 is selected from R1-II-2, wherein the optical configuration of the optically active carbon is S configuration;
Code: FAPI-INER-431-SS;
Molecular weight: 1401.2;
Molecular formula: $C_{62}H_{83}F_2IN_{12}O_{15}$;

Structure 95:

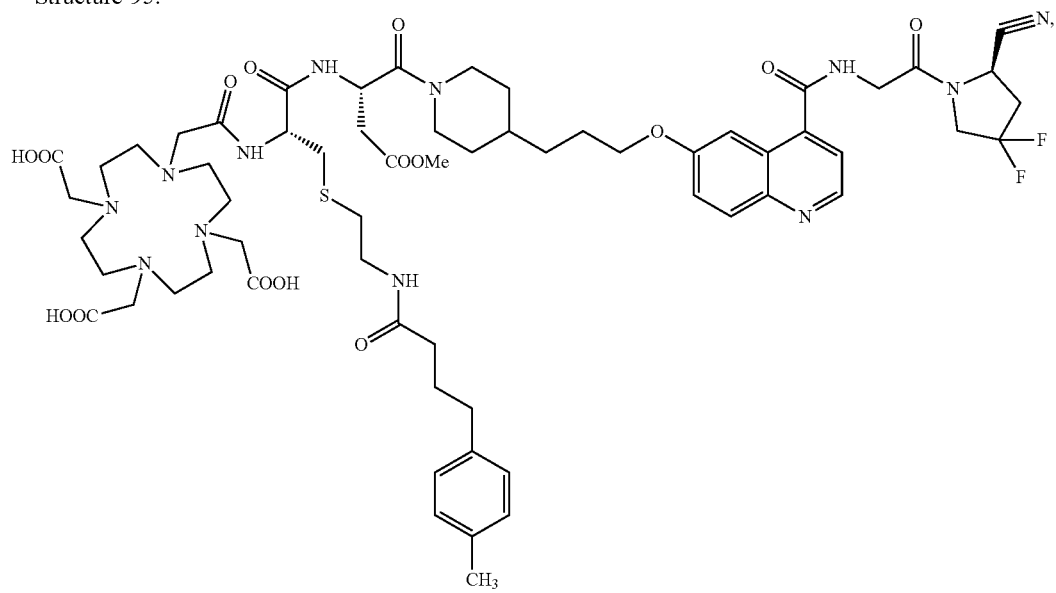

wherein
the optical configuration of the optically active carbon of R2-II-7 is S configuration; R1 is selected from R1-II-3, wherein the optical configuration of the optically active carbon is S configuration;
Code: FAPI-INER-435-SS;
Molecular weight: 1307.4;
Molecular formula: $C_{62}H_{84}F_2N_{12}O_{15}S$;

Structure 96:

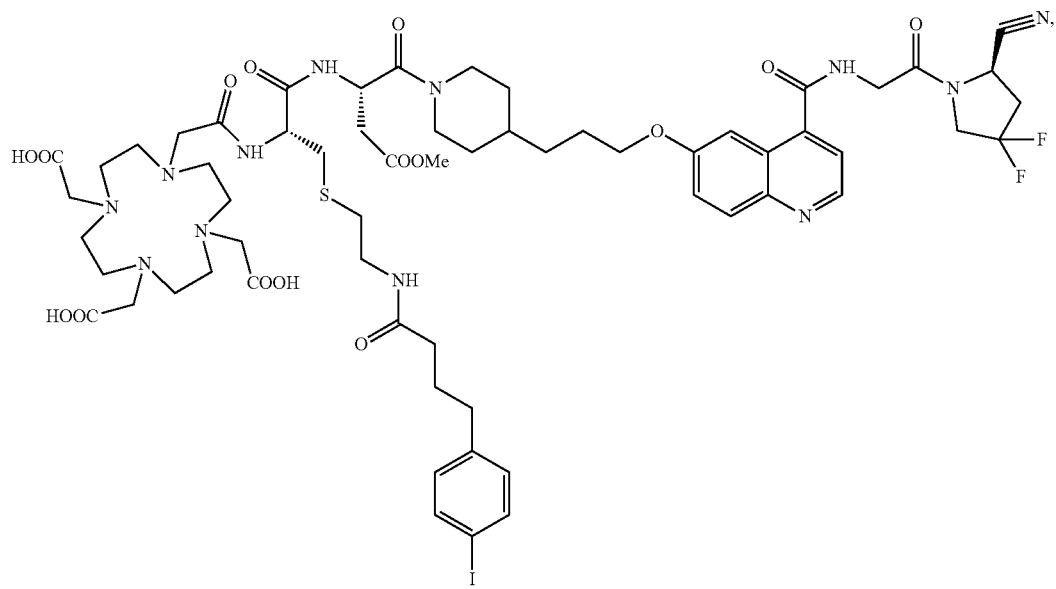 [SMILES: COC(=O)C[C@H](NC(=O)[C@H](CSCCNC(=O)CCCc1ccc(I)cc1)NC(=O)CN1CCN(CC(=O)O)CCN(CC(=O)O)CCN(CC(=O)O)CC1)C(=O)N1CCC(CCCOc2ccc3nccc(C(=O)NCC(=O)N4CC(F)(F)C[C@@H]4C#N)c3c2)CC1]

wherein
the optical configuration of the optically active carbon of R2-II-7 is S configuration; R1 is selected from R1-II-4, wherein the optical configuration of the optically active carbon is S configuration;
Code: FAPI-INER-439-SS;
Molecular weight: 1419.3;
Molecular formula: $C_{61}H_{81}F_2IN_{12}O_{15}S$;

Structure 97:

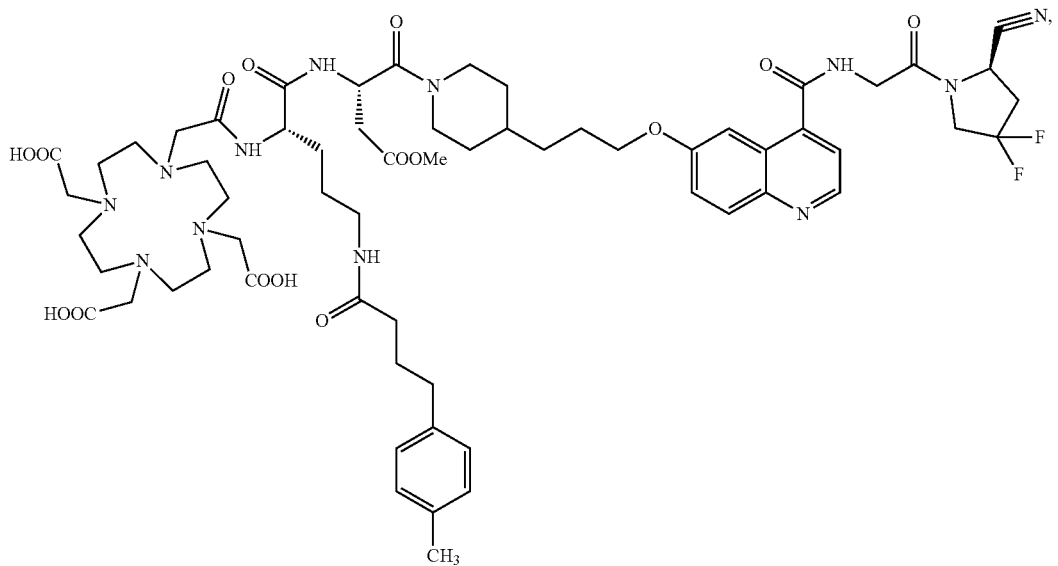 [SMILES: COC(=O)C[C@H](NC(=O)[C@H](CCCNC(=O)CCCc1ccc(C)cc1)NC(=O)CN1CCN(CC(=O)O)CCN(CC(=O)O)CCN(CC(=O)O)CC1)C(=O)N1CCC(CCCOc2ccc3nccc(C(=O)NCC(=O)N4CC(F)(F)C[C@@H]4C#N)c3c2)CC1]

wherein
the optical configuration of the optically active carbon of R2-II-7 is S configuration; R1 is selected from R1-II-11, wherein the optical configuration of the optically active carbon is S configuration;
Code: FAPI-INER-443-SS;
Molecular weight: 1275.3;
Molecular formula: $C_{62}H_{84}F_2N_{12}O_{15}$;

Structure 98:

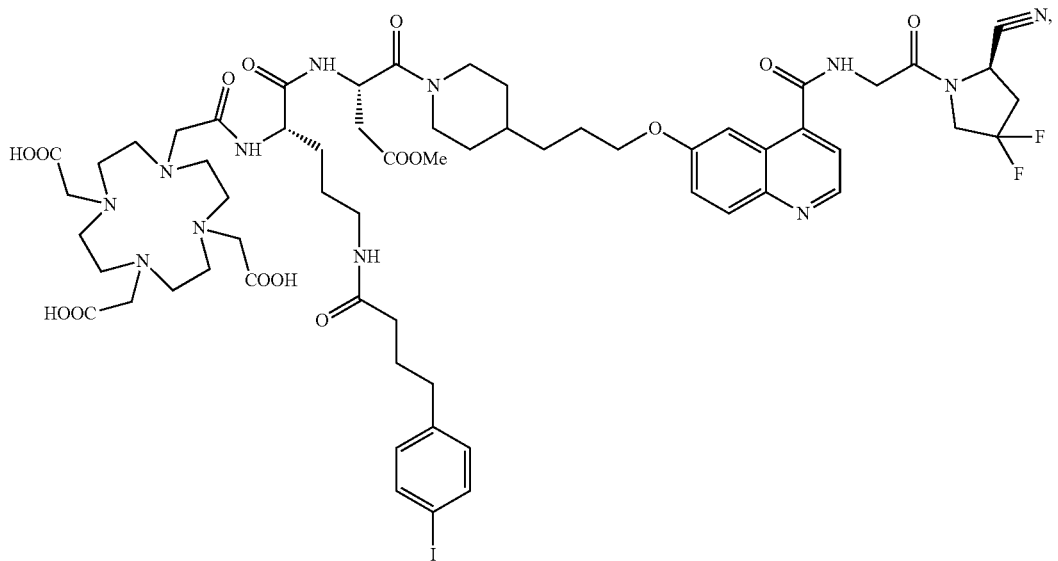 [SMILES: COC(=O)C[C@H](NC(=O)[C@H](CCCNC(=O)CCCc1ccc(I)cc1)NC(=O)CN1CCN(CC(=O)O)CCN(CC(=O)O)CCN(CC(=O)O)CC1)C(=O)N1CCC(CCCOc2ccc3nccc(C(=O)NCC(=O)N4CC(F)(F)C[C@@H]4C#N)c3c2)CC1]

wherein
the optical configuration of the optically active carbon of R2-II-7 is S configuration; R1 is selected from R1-II-12, wherein the optical configuration of the optically active carbon is S configuration;
Code: FAPI-INER-447-SS;
Molecular weight: 1387.2;
Molecular formula: $C_{61}H_{81}F_2IN_{12}O_{15}$;

Structure 99:

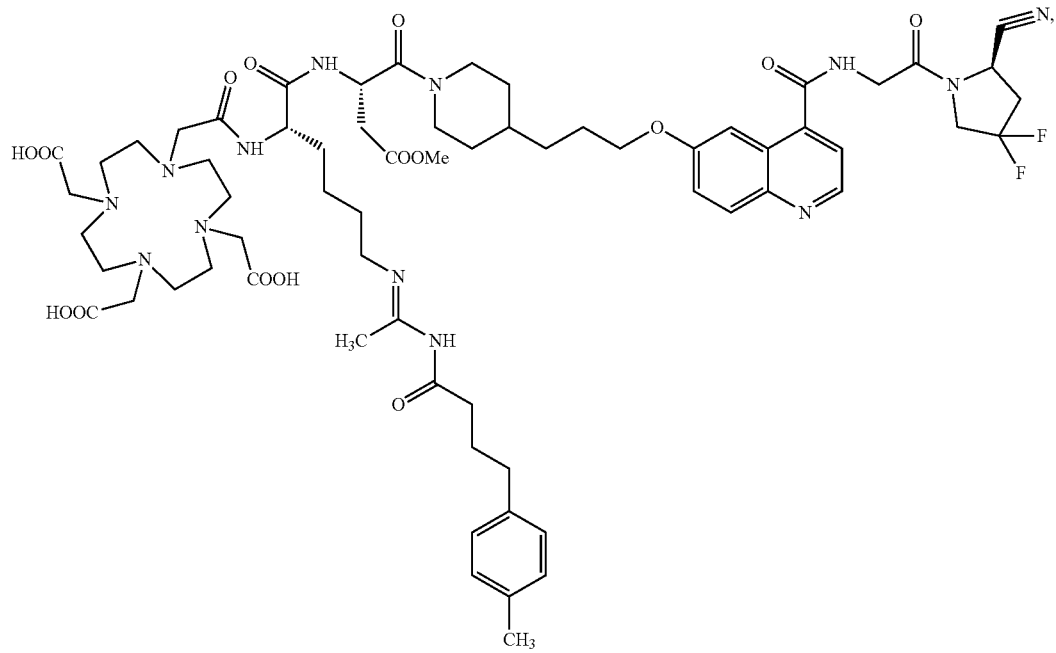

wherein
the optical configuration of the optically active carbon of R2-II-7 is S configuration; R1 is selected from R1-II-17, wherein the optical configuration of the optically active carbon is S configuration;
Code: FAPI-INER-451-SS;
Molecular weight: 1330.4;
Molecular formula: $C_{65}H_{89}F_2N_{13}O_{15}$;
Structure 100:

wherein
the optical configuration of the optically active carbon of R2-II-7 is S configuration; R1 is selected from R1-II-18, wherein the optical configuration of the optically active carbon is S configuration;
Code: FAPI-INER-455-SS;
Molecular weight: 1442.3;
Molecular formula: $C_{64}H_{86}F_2IN_{13}O_{15}$;

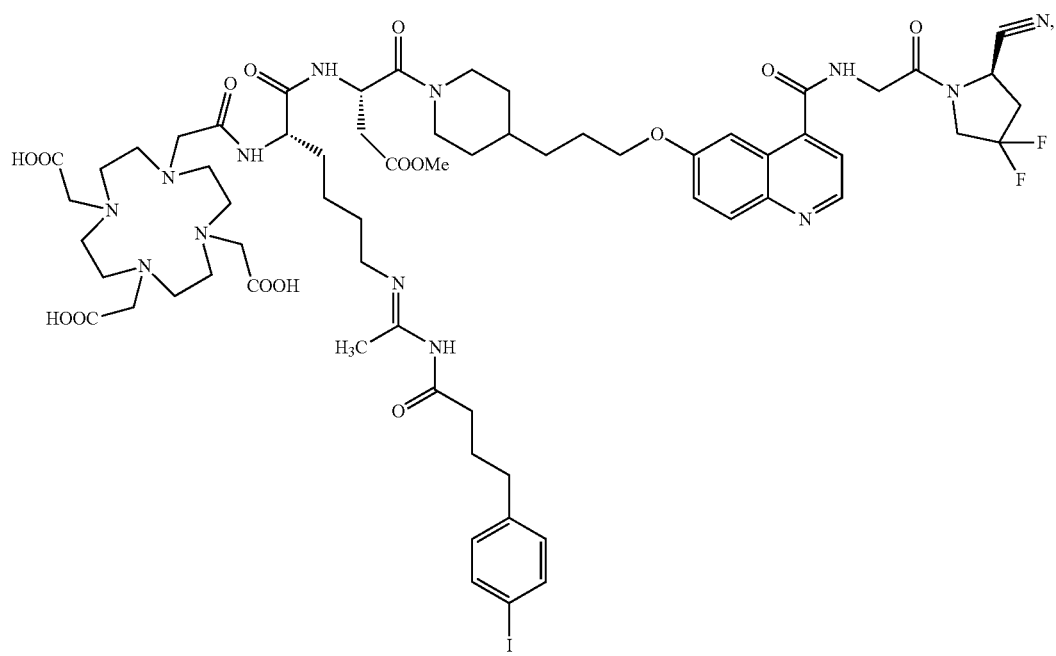 [SMILES: COC(=O)C[C@H](NC(=O)[C@H](CCCC/N=C(\C)NC(=O)CCCc1ccc(I)cc1)NC(=O)CN1CCN(CC(=O)O)CCN(CC(=O)O)CCN(CC(=O)O)CC1)C(=O)N1CCC(CCCOc2ccc3nccc(C(=O)NCC(=O)N4CC(F)(F)C[C@@H]4C#N)c3c2)CC1]

Structure 101:

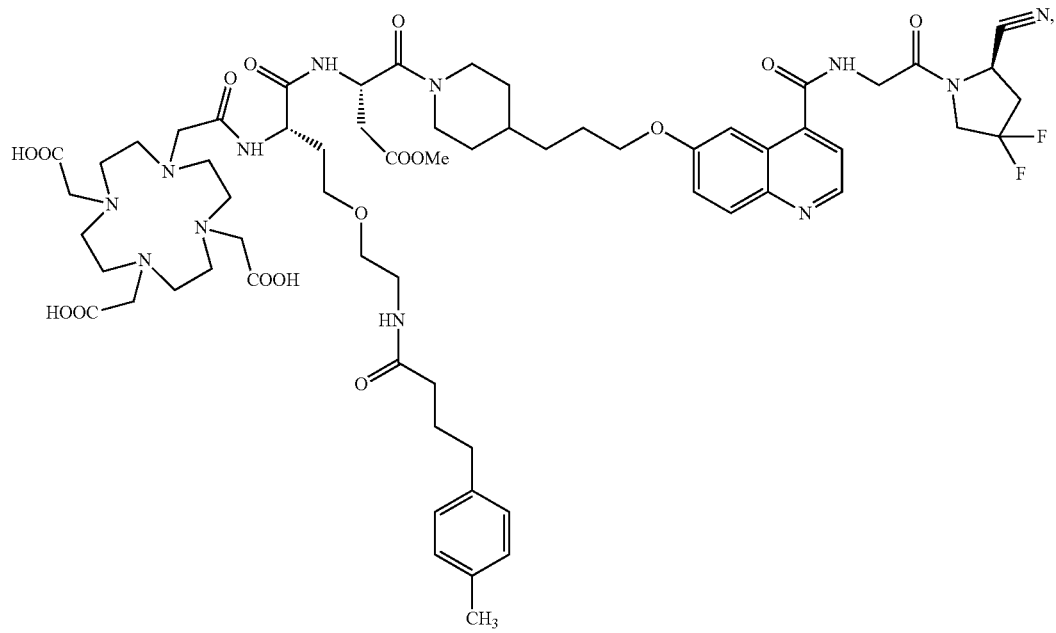 [SMILES: COC(=O)C[C@H](NC(=O)[C@H](CCOCCNC(=O)CCCc1ccc(C)cc1)NC(=O)CN1CCN(CC(=O)O)CCN(CC(=O)O)CCN(CC(=O)O)CC1)C(=O)N1CCC(CCCOc2ccc3nccc(C(=O)NCC(=O)N4CC(F)(F)C[C@@H]4C#N)c3c2)CC1]

wherein
the optical configuration of the optically active carbon of R2-II-7 is S configuration; R1 is selected from R1-II-21, wherein the optical configuration of the optically active carbon is S configuration;
Code: FAPI-INER-459-SS;
Molecular weight: 1305.4;
Molecular formula: $C_{63}H_{86}F_2N_{12}O_{16}$;

Structure 102:

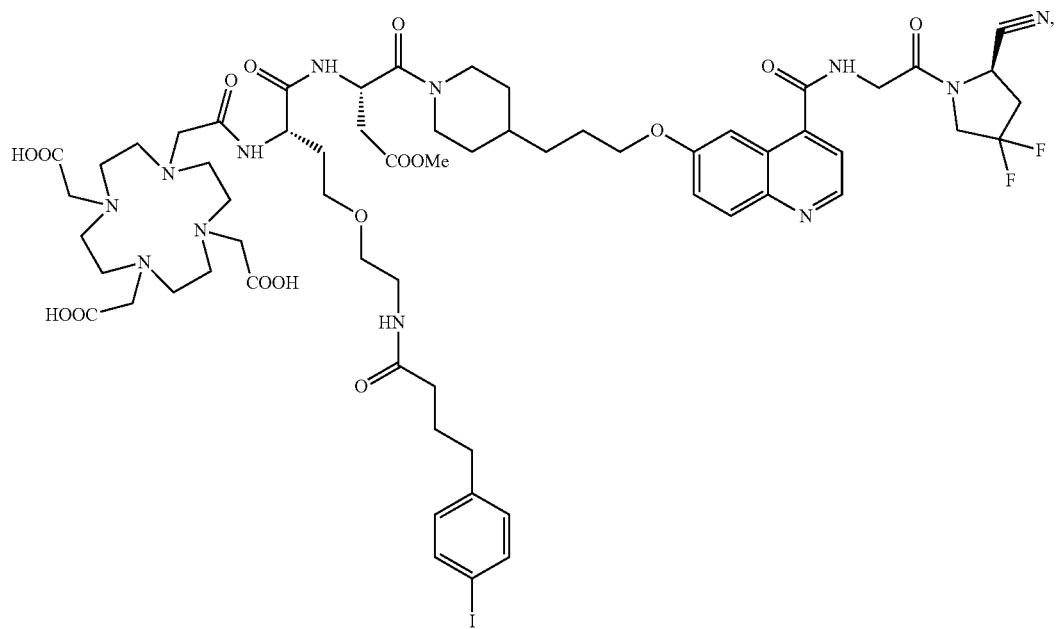 [SMILES: COC(=O)C[C@H](NC(=O)[C@H](CCOCCNC(=O)CCCc1ccc(I)cc1)NC(=O)CN1CCN(CC(=O)O)CCN(CC(=O)O)CCN(CC(=O)O)CC1)C(=O)N1CCC(CCCOc2ccc3nccc(C(=O)NCC(=O)N4CC(F)(F)C[C@@H]4C#N)c3c2)CC1]

wherein
the optical configuration of the optically active carbon of R2-II-7 is S configuration; R1 is selected from R1-II-22, wherein the optical configuration of the optically active carbon is S configuration;
Code: FAPI-INER-463-SS;
Molecular weight: 1417.2;
Molecular formula: $C_{62}H_{83}F_2IN_{13}O_{16}$;

or R2 is selected from R2-II-8 of the set of R2-II, R1 is any structure selected from the set of R1-II, and the D structure is

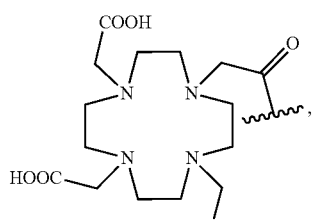

and thus the compound has a structure represented by formulas below:
Structure 103:

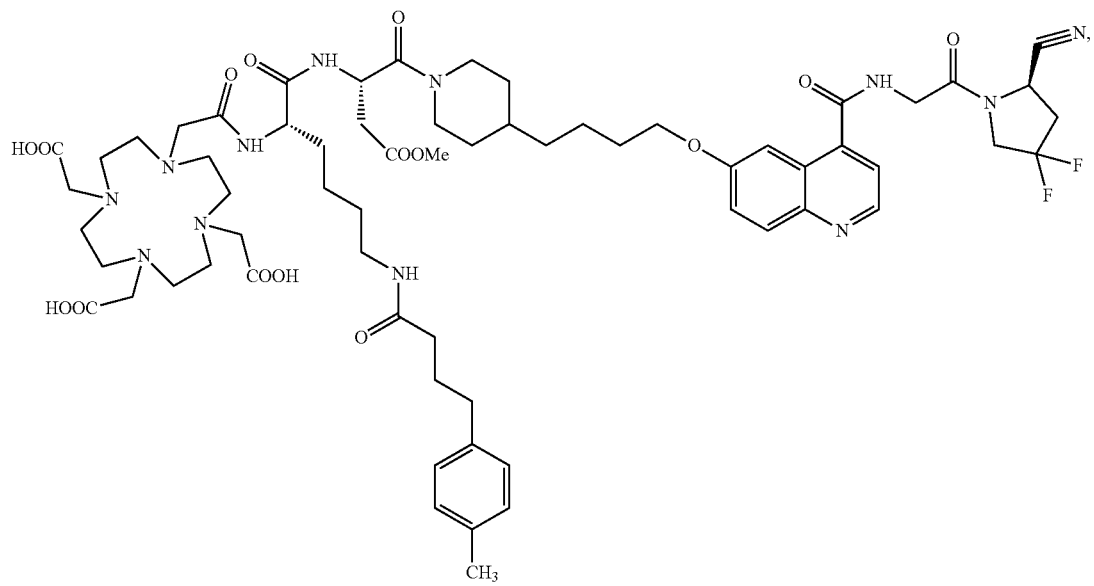 [SMILES: COC(=O)C[C@H](NC(=O)[C@H](CCCCNC(=O)CCCc1ccc(C)cc1)NC(=O)CN1CCN(CC(=O)O)CCN(CC(=O)O)CCN(CC(=O)O)CC1)C(=O)N1CCC(CCCCOc2ccc3nccc(C(=O)NCC(=O)N4CC(F)(F)C[C@@H]4C#N)c3c2)CC1]

wherein
the optical configuration of the optically active carbon of R2-II-8 is S configuration; R1 is selected from R1-II-1, wherein the optical configuration of the optically active carbon is S configuration;

Code: FAPI-INER-428-SS;

Molecular weight: 1303.4;

Molecular formula: $C_{64}H_{88}F_2N_{12}O_{15}$;

Structure 104:

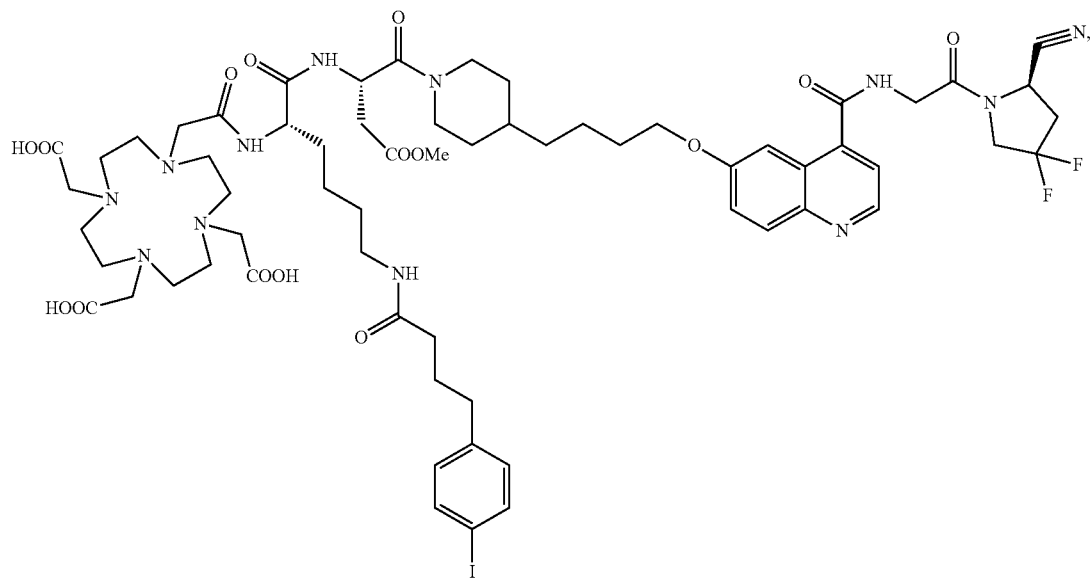 [SMILES: COC(=O)C[C@H](NC(=O)[C@H](CCCCNC(=O)CCCc1ccc(I)cc1)NC(=O)CN1CCN(CC(=O)O)CCN(CC(=O)O)CCN(CC(=O)O)CC1)C(=O)N1CCC(CCCCOc2ccc3nccc(C(=O)NCC(=O)N4CC(F)(F)C[C@@H]4C#N)c3c2)CC1]

wherein
the optical configuration of the optically active carbon of R2-II-8 is S configuration; R1 is selected from R1-II-2, wherein the optical configuration of the optically active carbon is S configuration;
Code: FAPI-INER-432-SS;
Molecular weight: 1415.3;
Molecular formula: $C_{63}H_{85}F_2IN_{12}O_{15}$;

Structure 105:

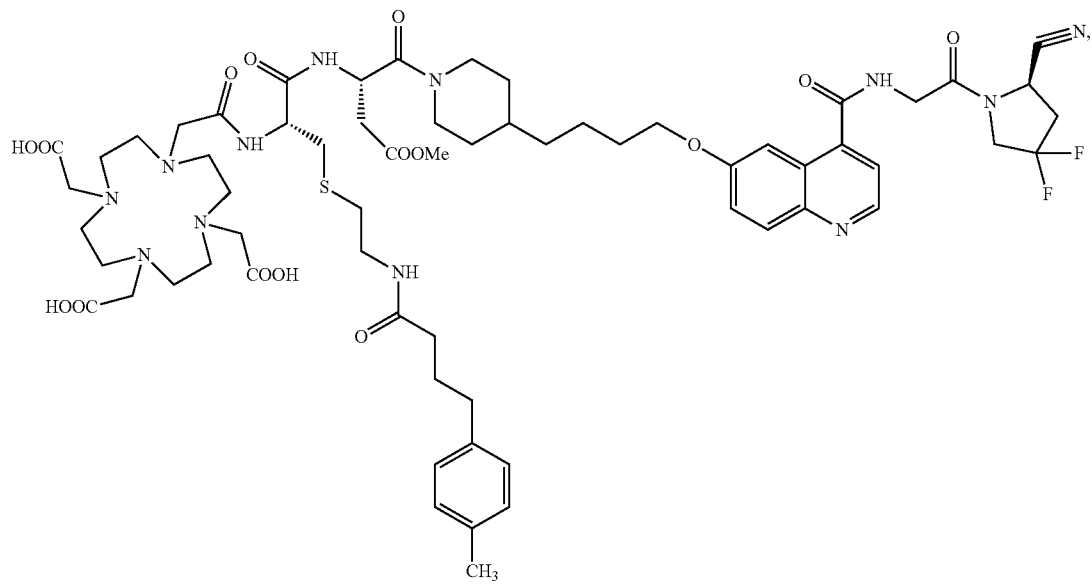 [SMILES: COC(=O)C[C@H](NC(=O)[C@H](CSCCNC(=O)CCCc1ccc(C)cc1)NC(=O)CN1CCN(CC(=O)O)CCN(CC(=O)O)CCN(CC(=O)O)CC1)C(=O)N1CCC(CCCCOc2ccc3nccc(C(=O)NCC(=O)N4CC(F)(F)C[C@@H]4C#N)c3c2)CC1]

wherein
the optical configuration of the optically active carbon of R2-II-8 is S configuration; R1 is selected from R1-II-3, wherein the optical configuration of the optically active carbon is S configuration;
Code: FAPI-INER-436-SS;
Molecular weight: 1321.4;
Molecular formula: $C_{63}H_{86}F_2N_{12}O_{15}S$;

Structure 106:

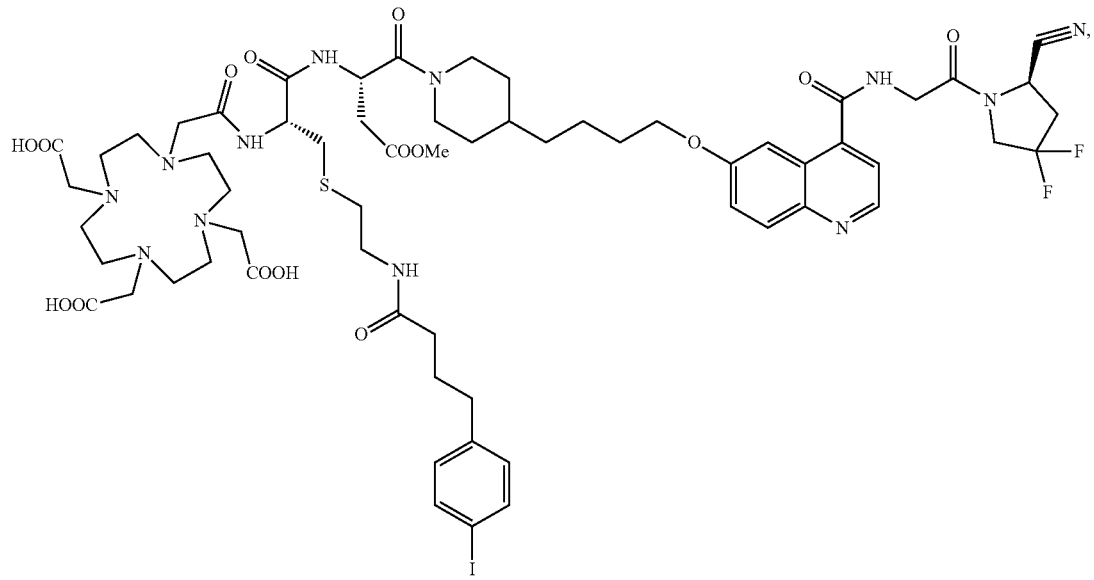 [SMILES: COC(=O)C[C@H](NC(=O)[C@H](CSCCNC(=O)CCCc1ccc(I)cc1)NC(=O)CN1CCN(CC(=O)O)CCN(CC(=O)O)CCN(CC(=O)O)CC1)C(=O)N1CCC(CCCCOc2ccc3nccc(C(=O)NCC(=O)N4CC(F)(F)C[C@@H]4C#N)c3c2)CC1]

wherein
the optical configuration of the optically active carbon of R2-II-8 is S configuration; R1 is selected from R1-II-4, wherein the optical configuration of the optically active carbon is S configuration;
Code: FAPI-INER-440-SS;
Molecular weight: 1433.3;
Molecular formula: $C_{62}H_{83}F_2IN_{12}O_{15}S$;

Structure 107:

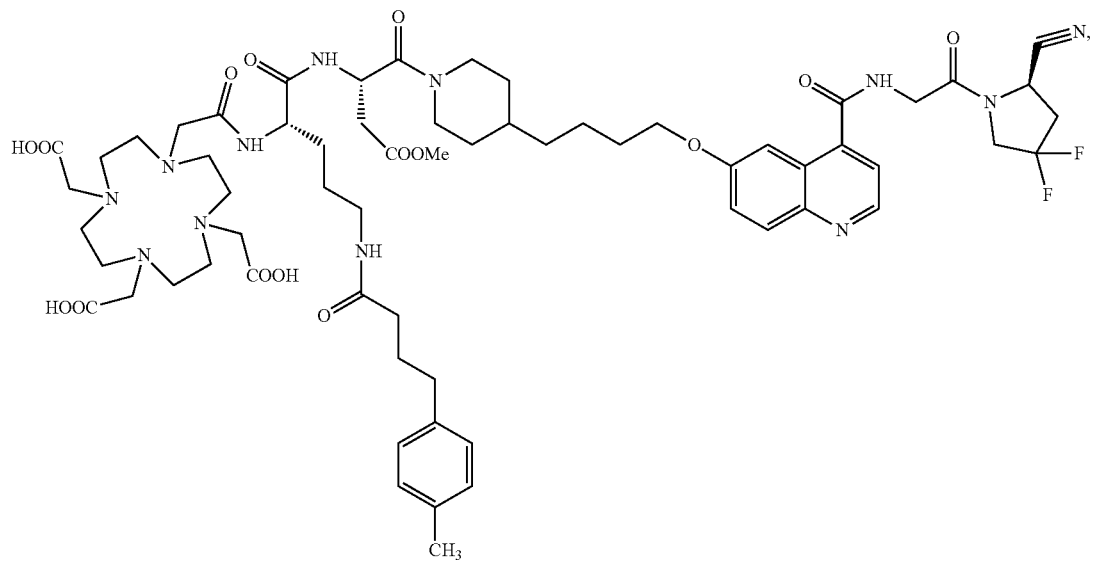 [SMILES: COC(=O)C[C@H](NC(=O)[C@H](CCCNC(=O)CCCc1ccc(C)cc1)NC(=O)CN1CCN(CC(=O)O)CCN(CC(=O)O)CCN(CC(=O)O)CC1)C(=O)N1CCC(CCCCOc2ccc3nccc(C(=O)NCC(=O)N4CC(F)(F)C[C@@H]4C#N)c3c2)CC1]

wherein
the optical configuration of the optically active carbon of R2-II-8 is S configuration; R1 is selected from R1-II-11, wherein the optical configuration of the optically active carbon is S configuration;
Code: FAPI-INER-444-SS;
Molecular weight: 1289.4;
Molecular formula: $C_{63}H_{86}F_2N_{12}O_{15}$;

Structure 108:

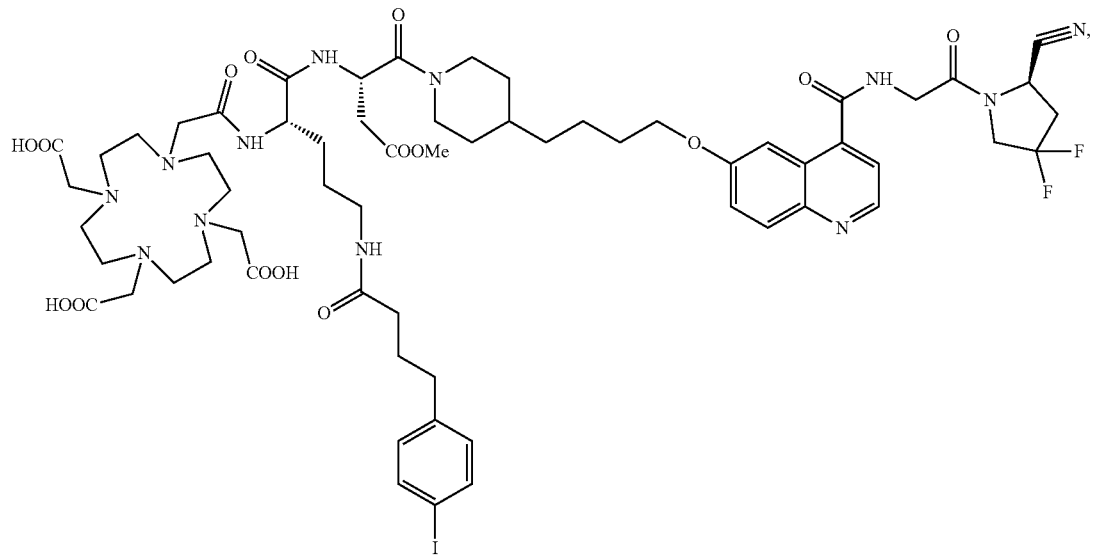 [SMILES: COC(=O)C[C@H](NC(=O)[C@H](CCCNC(=O)CCCc1ccc(I)cc1)NC(=O)CN1CCN(CC(=O)O)CCN(CC(=O)O)CCN(CC(=O)O)CC1)C(=O)N1CCC(CCCCOc2ccc3nccc(C(=O)NCC(=O)N4CC(F)(F)C[C@@H]4C#N)c3c2)CC1]

wherein
  the optical configuration of the optically active carbon of R2-II-8 is S configuration; R1 is selected from R1-II-12, wherein the optical configuration of the optically active carbon is S configuration;
Code: FAPI-INER-448-SS;
Molecular weight: 1401.2;
Molecular formula: $C_{62}H_{83}F_2IN_{12}O_{15}$;
Structure 109:

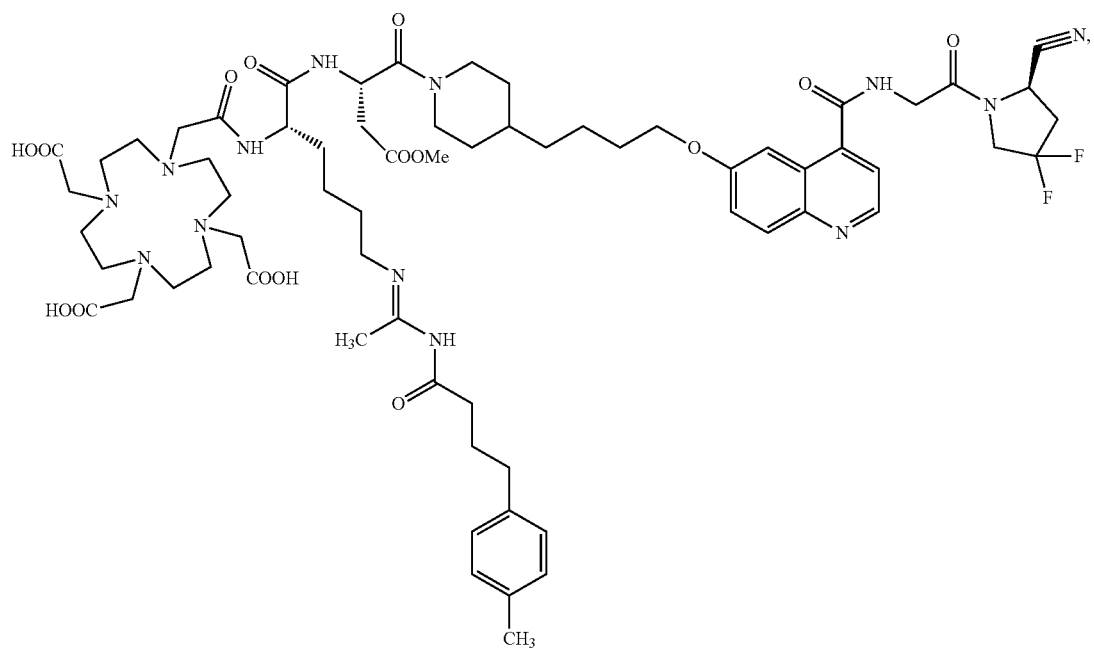 [SMILES: COC(=O)C[C@H](NC(=O)[C@H](CCCC/N=C(\C)NC(=O)CCCc1ccc(C)cc1)NC(=O)CN1CCN(CC(=O)O)CCN(CC(=O)O)CCN(CC(=O)O)CC1)C(=O)N1CCC(CCCCOc2ccc3nccc(C(=O)NCC(=O)N4CC(F)(F)C[C@@H]4C#N)c3c2)CC1]

wherein
  the optical configuration of the optically active carbon of R2-II-8 is S configuration; R1 is selected from R1-II-17, wherein the optical configuration of the optically active carbon is S configuration;
Code: FAPI-INER-452-SS;
Molecular weight: 1344.5;
Molecular formula: $C_{66}H_{91}F_2N_{13}O_{15}$;

Structure 110:

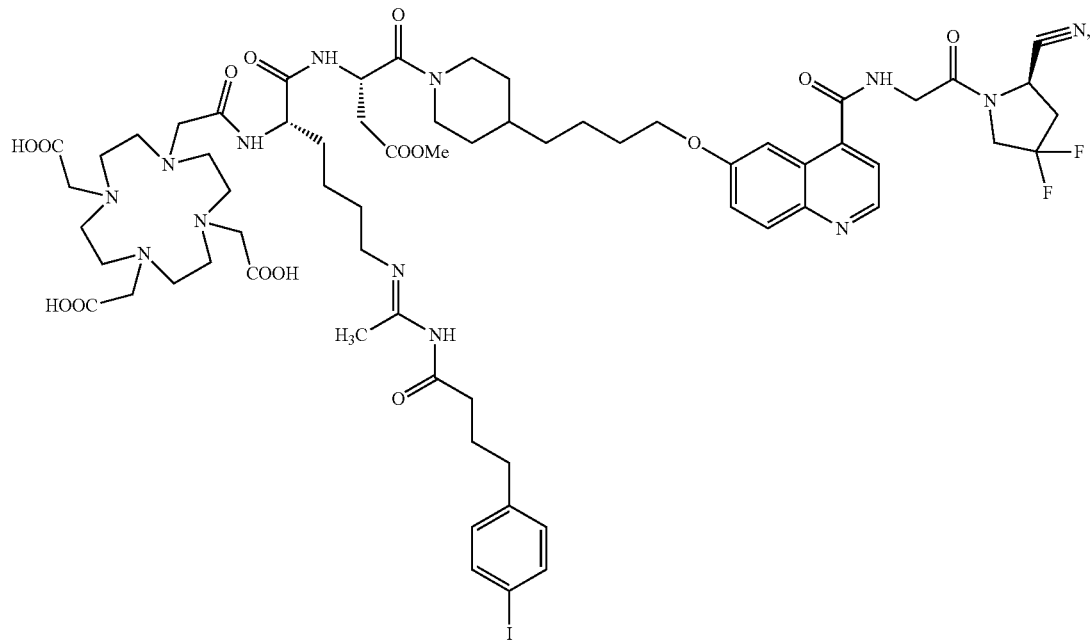 [SMILES: COC(=O)C[C@H](NC(=O)[C@H](CCCC/N=C(\C)NC(=O)CCCc1ccc(I)cc1)NC(=O)CN1CCN(CC(=O)O)CCN(CC(=O)O)CCN(CC(=O)O)CC1)C(=O)N1CCC(CCCCOc2ccc3nccc(C(=O)NCC(=O)N4CC(F)(F)C[C@@H]4C#N)c3c2)CC1]

wherein
the optical configuration of the optically active carbon of R2-II-8 is S configuration; R1 is selected from R1-II-18, wherein the optical configuration of the optically active carbon is S configuration;
Code: FAPI-INER-456-SS;
Molecular weight: 1456.3;
Molecular formula: $C_{64}H_{88}F_2IN_{13}O_{15}$;
Structure 111:

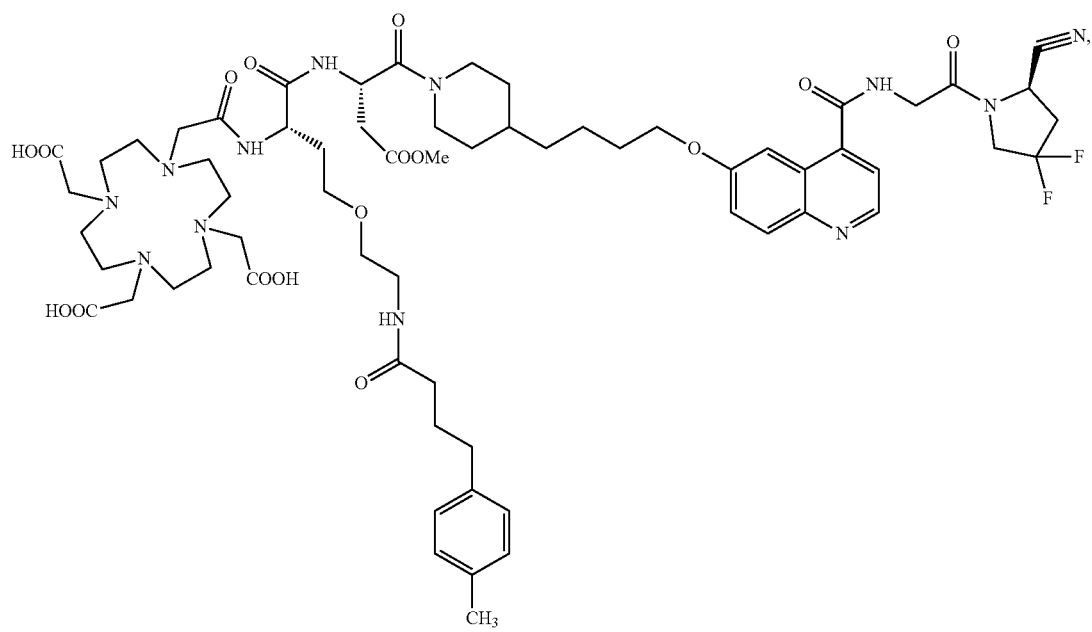 [SMILES: COC(=O)C[C@H](NC(=O)[C@H](CCOCCNC(=O)CCCc1ccc(C)cc1)NC(=O)CN1CCN(CC(=O)O)CCN(CC(=O)O)CCN(CC(=O)O)CC1)C(=O)N1CCC(CCCCOc2ccc3nccc(C(=O)NCC(=O)N4CC(F)(F)C[C@@H]4C#N)c3c2)CC1]

wherein
the optical configuration of the optically active carbon of R2-II-8 is S configuration; R1 is selected from R1-II-21, wherein the optical configuration of the optically active carbon is S configuration;
Code: FAPI-INER-460-SS;
Molecular weight: 1319.4;
Molecular formula: $C_{64}H_{88}F_2N_{12}O_{16}$;

Structure 112:

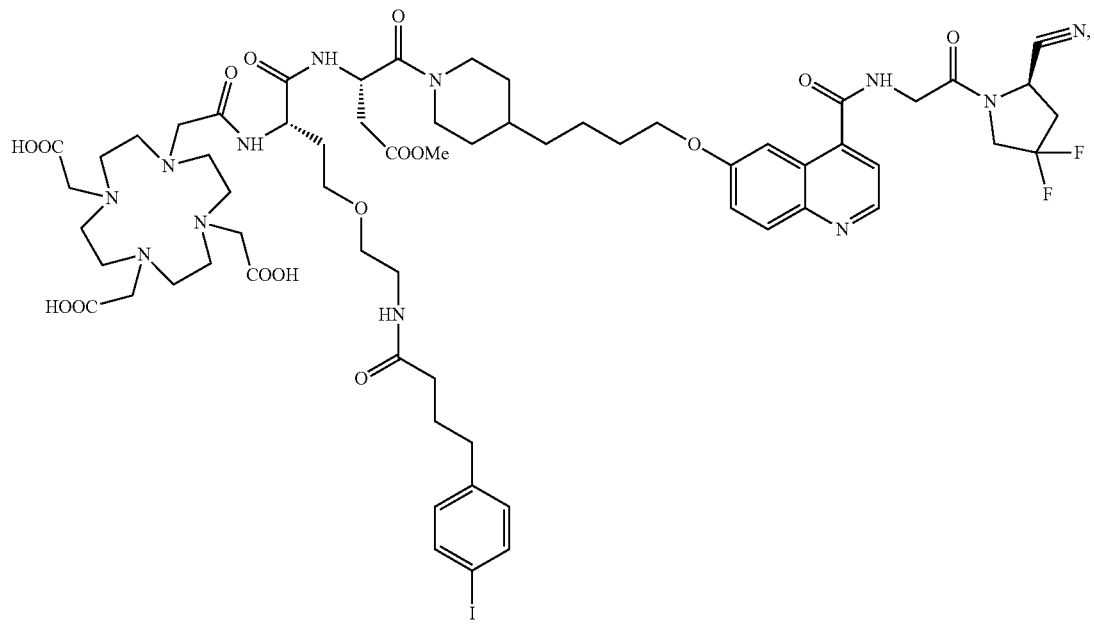 [SMILES: COC(=O)C[C@H](NC(=O)[C@H](CCOCCNC(=O)CCCc1ccc(I)cc1)NC(=O)CN1CCN(CC(=O)O)CCN(CC(=O)O)CCN(CC(=O)O)CC1)C(=O)N1CCC(CCCCOc2ccc3nccc(C(=O)NCC(=O)N4CC(F)(F)C[C@@H]4C#N)c3c2)CC1]

wherein
the optical configuration of the optically active carbon of R2-II-8 is S configuration; R1 is selected from R1-II-22, wherein the optical configuration of the optically active carbon is S configuration;

Code: FAPI-INER-464-SS;

Molecular weight: 1431.3;

Molecular formula: $C_{63}H_{85}F_2IN_{12}O_{16}$;

or R2 is selected from R2-II-13 of the set of R2-II, R1 is any structure selected from the set of R1-II, and the D structure is

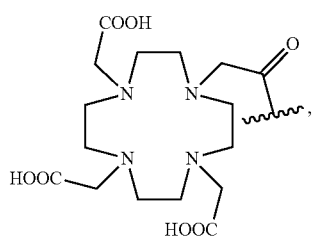

and thus the compound has a structure represented by formulas below:

Structure 113:

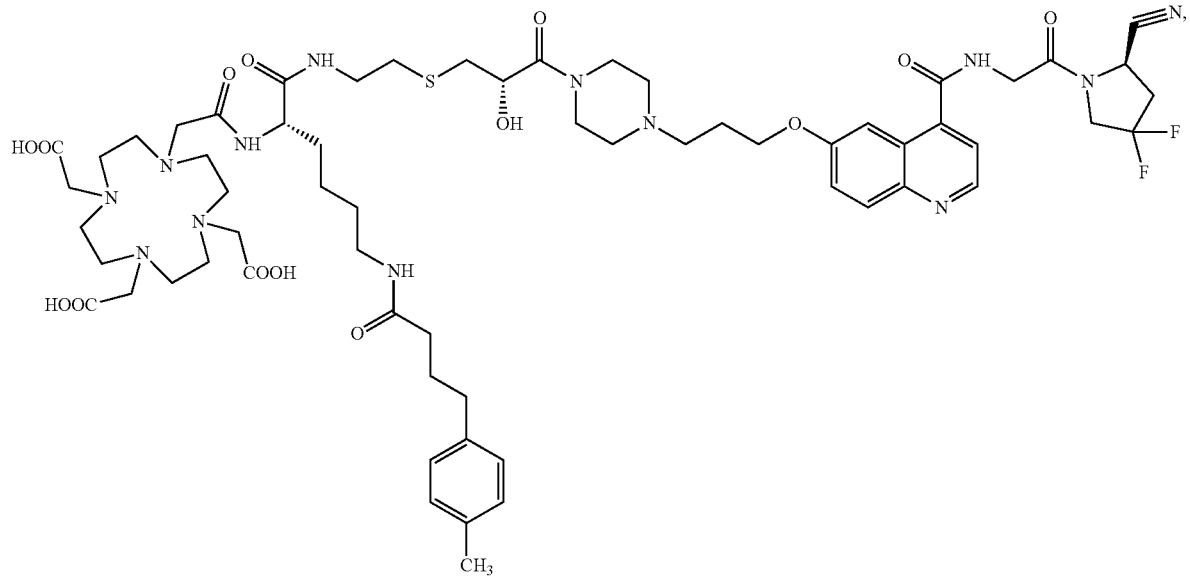 [SMILES: Cc1ccc(CCCC(=O)NCCCC[C@H](NC(=O)CN2CCN(CC(=O)O)CCN(CC(=O)O)CCN(CC(=O)O)CC2)C(=O)NCCSC[C@@H](O)C(=O)N2CCN(CCCOc3ccc4nccc(C(=O)NCC(=O)N5CC(F)(F)C[C@@H]5C#N)c4c3)CC2)cc1]

wherein
the optical configuration of the optically active carbon of R2-II-13 is S configuration; R1 is selected from R1-II-1, wherein the optical configuration of the optically active carbon is S configuration;
Code: FAPI-INER-465-SS;
Molecular weight: 1308.4;
Molecular formula: $C_{62}H_{87}F_2N_{13}O_{14}S$;

Structure 114:

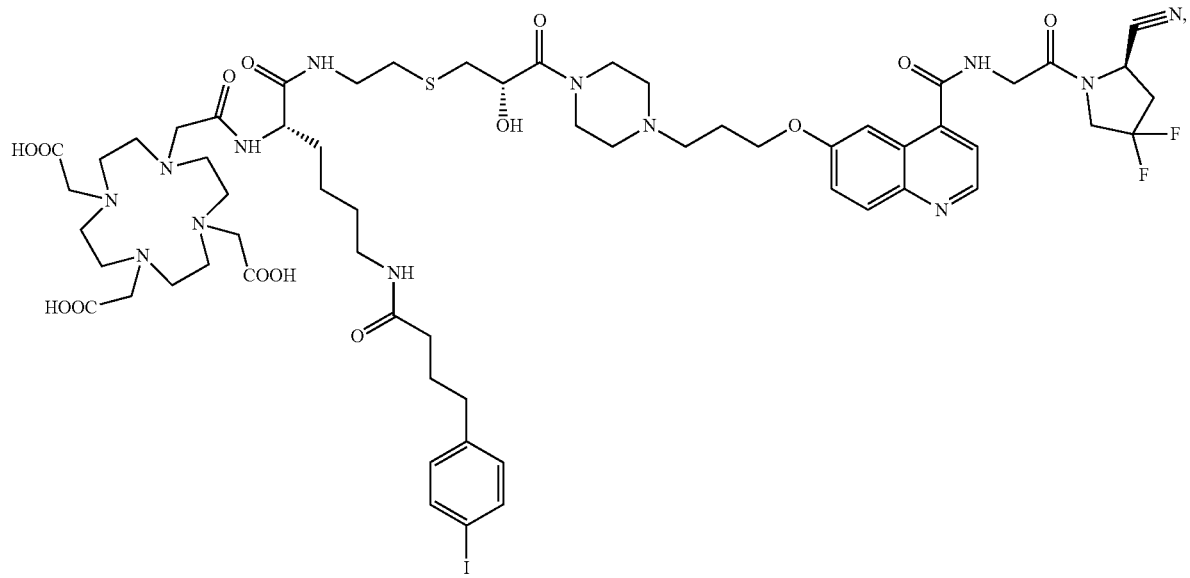 [SMILES: N#C[C@H]1CC(F)(F)CN1C(=O)CNC(=O)c1ccnc2ccc(OCCCN3CCN(C(=O)[C@H](O)CSCCNC(=O)[C@H](CCCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-13 is S configuration; R1 is selected from R1-II-2, wherein the optical configuration of the optically active carbon is S configuration;
Code: FAPI-INER-469-SS;
Molecular weight: 1420.3;
Molecular formula: $C_{61}H_{84}F_2IN_{13}O_{14}S$;

Structure 115:

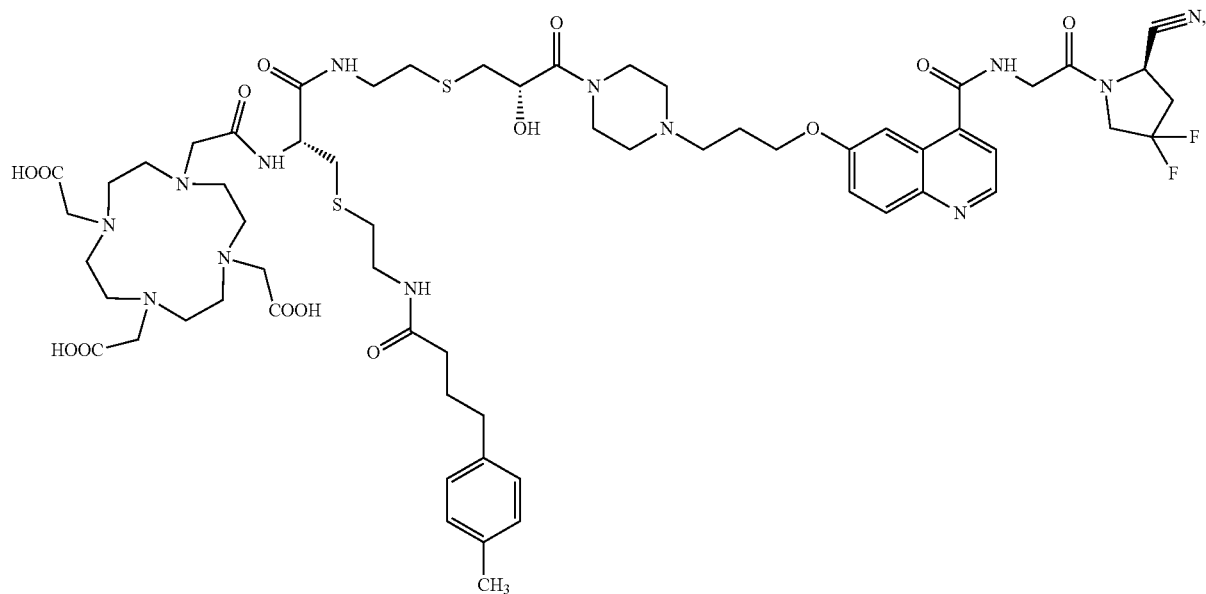 [SMILES: Cc1ccc(CCCC(=O)NCCSC[C@H](NC(=O)CN2CCN(CC(=O)O)CCN(CC(=O)O)CCN(CC(=O)O)CC2)C(=O)NCCSC[C@@H](O)C(=O)N2CCN(CCCOc3ccc4nccc(C(=O)NCC(=O)N5CC(F)(F)C[C@@H]5C#N)c4c3)CC2)cc1]

wherein
the optical configuration of the optically active carbon of R2-II-13 is S configuration; R1 is selected from R1-II-3, wherein the optical configuration of the optically active carbon is S configuration;
Code: FAPI-INER-473-SS;
Molecular weight: 1326.5;
Molecular formula: $C_{61}H_{85}F_2N_{13}O_{14}S_2$;
Structure 116:

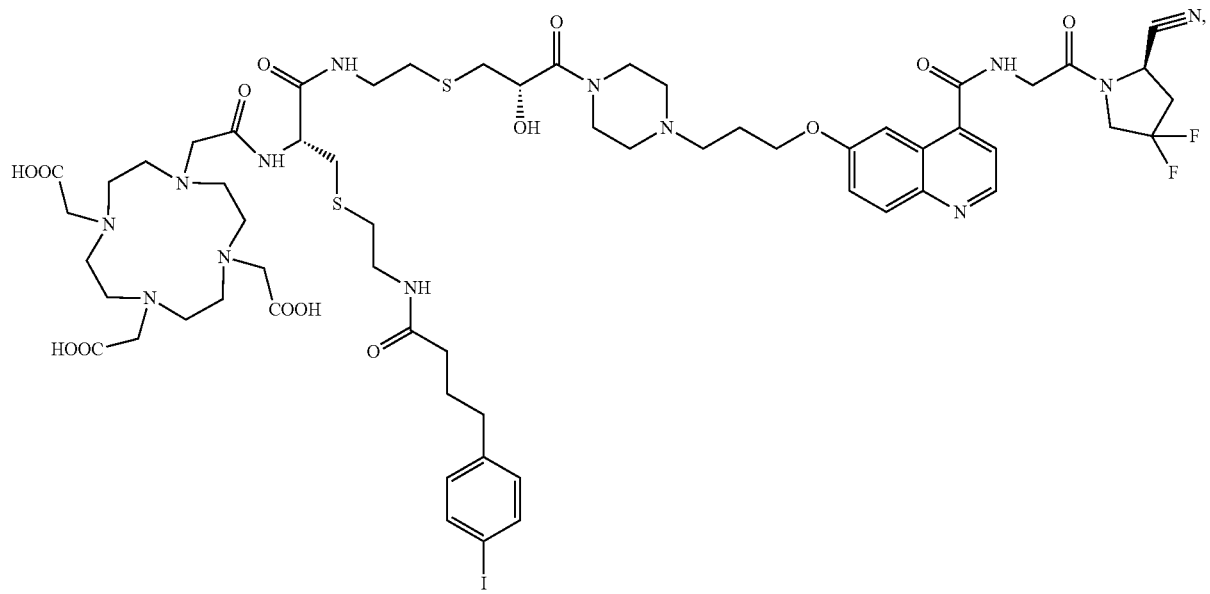 [SMILES: N#C[C@H]1CC(F)(F)CN1C(=O)CNC(=O)c1ccnc2ccc(OCCCN3CCN(C(=O)[C@H](O)CSCCNC(=O)[C@H](CSCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-13 is S configuration; R1 is selected from R1-II-4, wherein the optical configuration of the optically active carbon is S configuration;
Code: FAPI-INER-477-SS;
Molecular weight: 1438.4;
Molecular formula: $C_{60}H_{82}F_2IN_{13}O_{14}S_2$;

Structure 117:

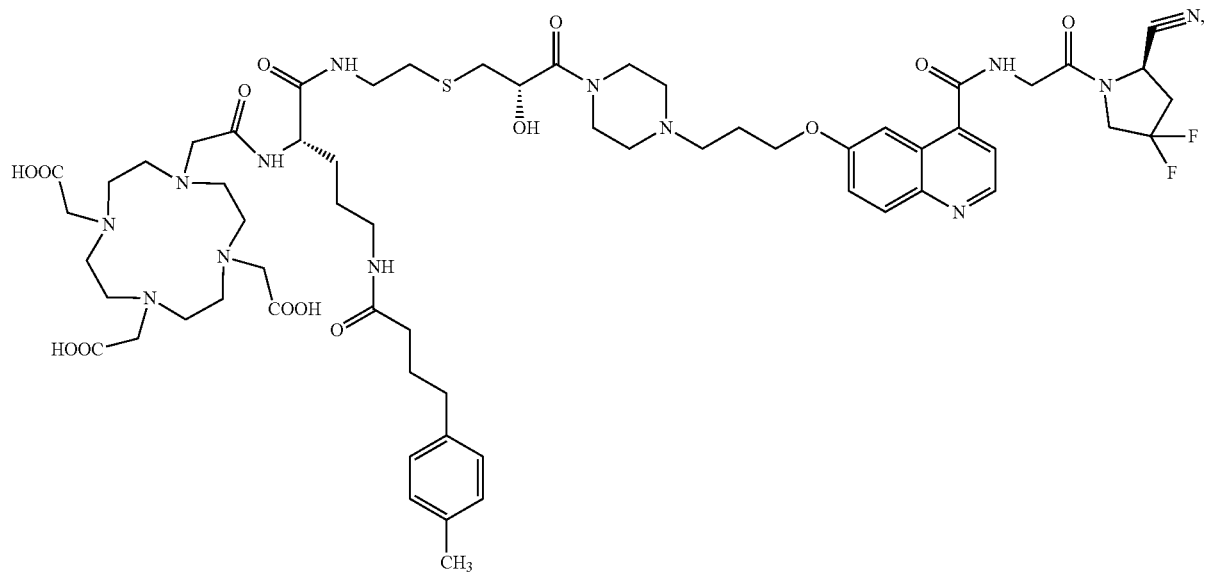 [SMILES: Cc1ccc(CCCC(=O)NCCC[C@H](NC(=O)CN2CCN(CC(=O)O)CCN(CC(=O)O)CCN(CC(=O)O)CC2)C(=O)NCCSC[C@@H](O)C(=O)N2CCN(CCCOc3ccc4nccc(C(=O)NCC(=O)N5CC(F)(F)C[C@@H]5C#N)c4c3)CC2)cc1]

wherein
the optical configuration of the optically active carbon of R2-II-13 is S configuration; R1 is selected from R1-II-11, wherein the optical configuration of the optically active carbon is S configuration;
Code: FAPI-INER-481-SS;
Molecular weight: 1294.4;
Molecular formula: $C_{61}H_{85}F_2N_{13}O_{14}S$;
Structure 118:

wherein
the optical configuration of the optically active carbon of R2-II-13 is S configuration; R1 is selected from R1-II-12, wherein the optical configuration of the optically active carbon is S configuration;
Code: FAPI-INER-485-SS;
Molecular weight: 1406.3;
Molecular formula: $C_{60}H_{82}F_2IN_{13}O_{14}S$;

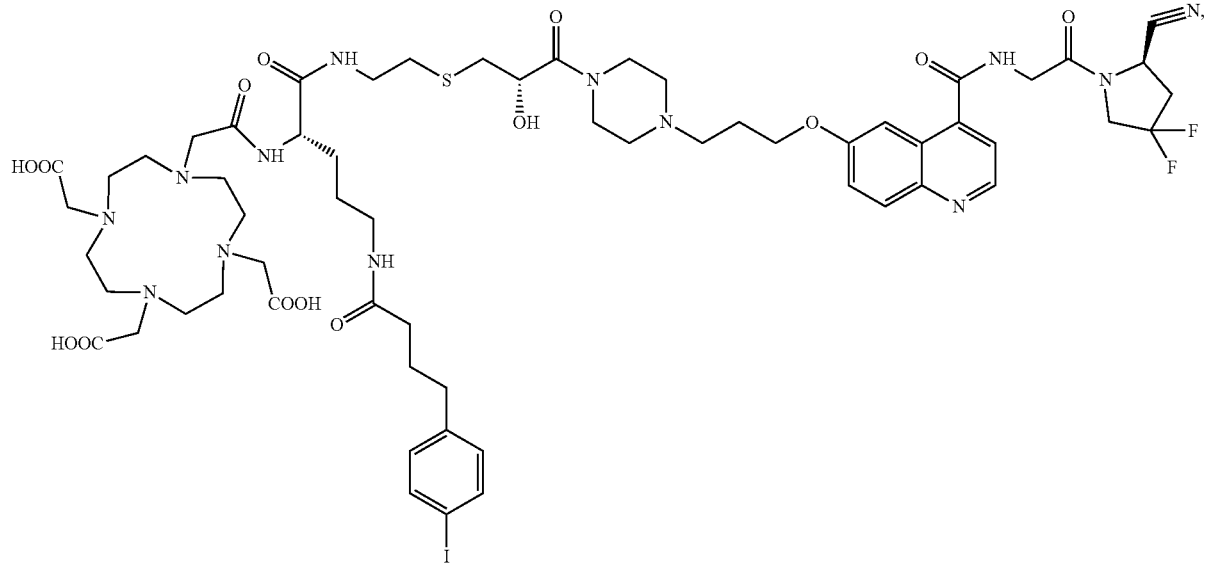 [SMILES: N#C[C@H]1CC(F)(F)CN1C(=O)CNC(=O)c1ccnc2ccc(OCCCN3CCN(C(=O)[C@H](O)CSCCNC(=O)[C@H](CCCNC(=O)CCCc4ccc(I)cc4)NC(=O)CN4CCN(CC(=O)O)CCN(CC(=O)O)CCN(CC(=O)O)CC4)CC3)cc12]

Structure 119:

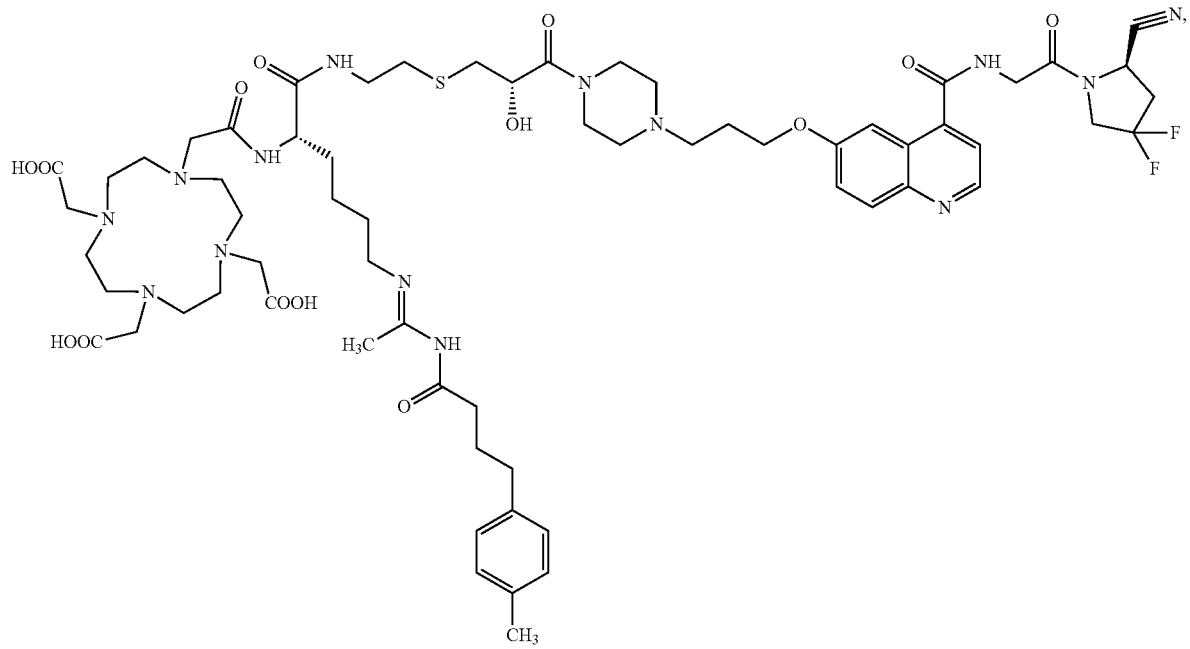 [SMILES: C/C(=N\CCCC[C@H](NC(=O)CN1CCN(CC(=O)O)CCN(CC(=O)O)CCN(CC(=O)O)CC1)C(=O)NCCSC[C@@H](O)C(=O)N1CCN(CCCOc2ccc3nccc(C(=O)NCC(=O)N4CC(F)(F)C[C@@H]4C#N)c3c2)CC1)NC(=O)CCCc1ccc(I)cc1]

wherein
the optical configuration of the optically active carbon of R2-II-13 is S configuration; R1 is selected from R1-II-17, wherein the optical configuration of the optically active carbon is S configuration;
Code: FAPI-INER-489-SS;
Molecular weight: 1349.5;
Molecular formula: $C_{64}H_{90}F_2N_{14}O_{14}S$;
Structure 120:

wherein
the optical configuration of the optically active carbon of R2-II-13 is S configuration; R1 is selected from R1-II-18, wherein the optical configuration of the optically active carbon is S configuration;
Code: FAPI-INER-493-SS;
Molecular weight: 1461.4;
Molecular formula: $C_{63}H_{87}F_2IN_{14}O_{14}S$;

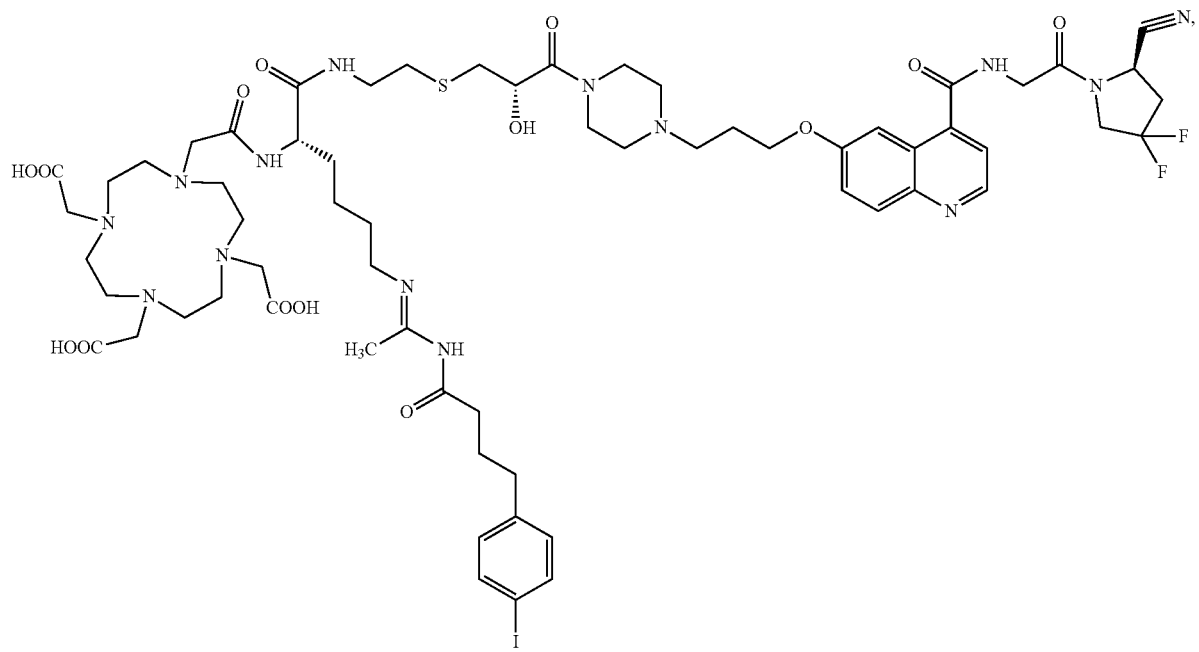

Structure 121:

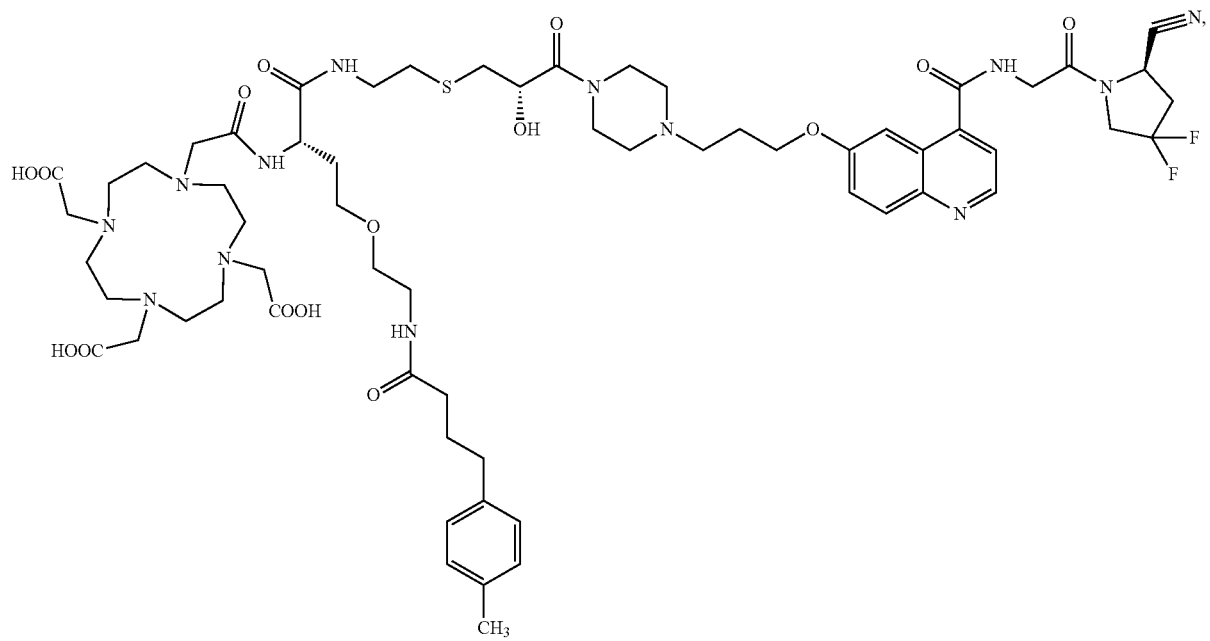

wherein
the optical configuration of the optically active carbon of R2-II-13 is S configuration; R1 is selected from R1-II-21, wherein the optical configuration of the optically active carbon is S configuration;
Code: FAPI-INER-497-SS;
Molecular weight: 1305.4;
Molecular formula: $C_{63}H_{86}F_2N_{12}O_{16}$;
Structure 122:

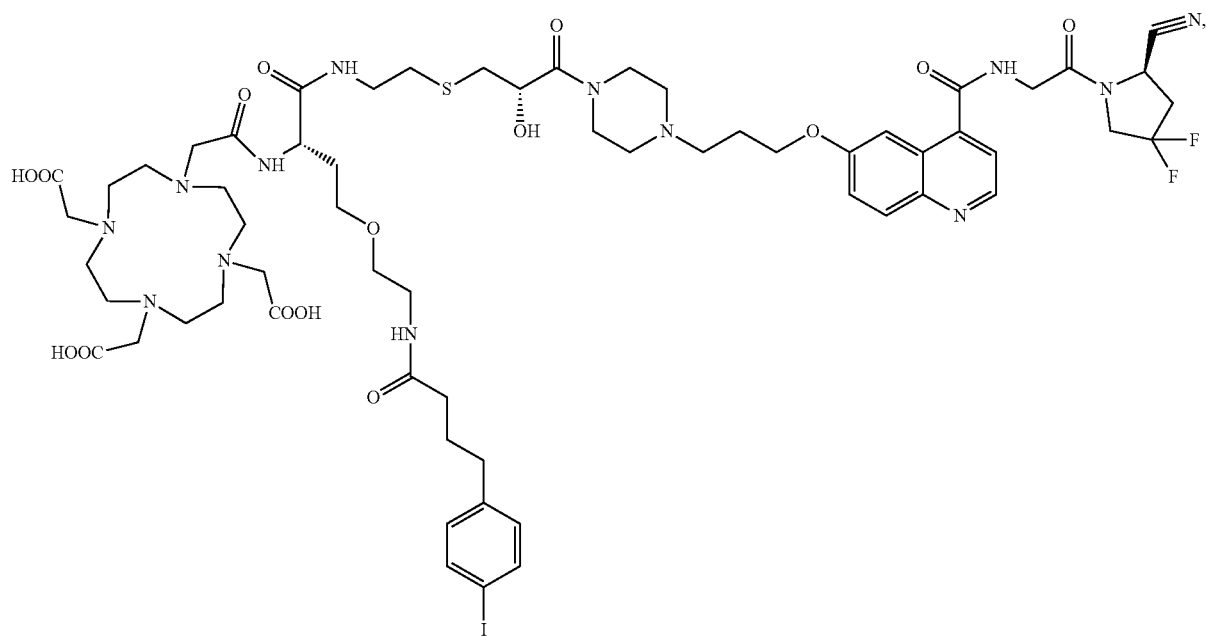 [SMILES: N#C[C@H]1CC(F)(F)CN1C(=O)CNC(=O)c1ccnc2ccc(OCCCN3CCN(C(=O)[C@H](O)CSCCNC(=O)[C@H](CCOCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-13 is S configuration; R1 is selected from R1-II-22, wherein the optical configuration of the optically active carbon is S configuration;
Code: FAPI-INER-501-SS;
Molecular weight: 1436.3;
Molecular formula: $C_{61}H_{84}F_2IN_{13}O_{15}S$;

or R2 is selected from R2-II-14 of the set of R2-II, R1 is any structure selected from the set of R1-II, and the D structure is

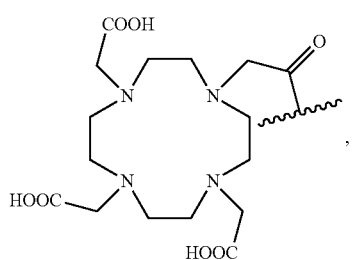 [SMILES: *C(=O)CN1CCN(CC(=O)O)CCN(CC(=O)O)CCN(CC(=O)O)CC1]

and thus the compound has a structure represented by formulas below:

Structure 123:

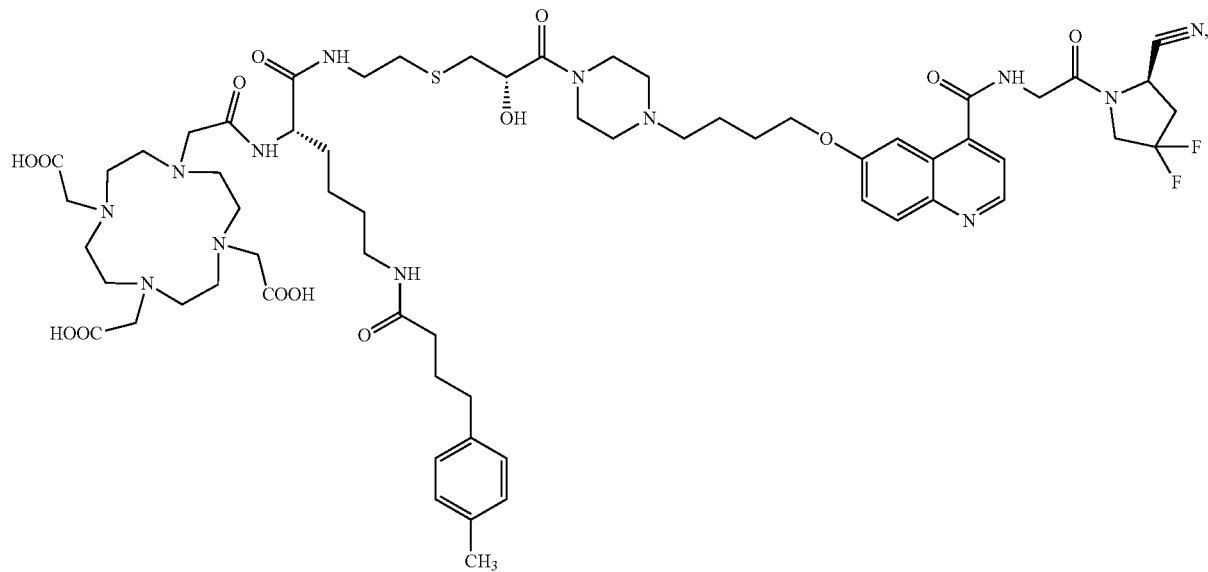

wherein
the optical configuration of the optically active carbon of R2-II-14 is S configuration; R1 is selected from R1-II-1, wherein the optical configuration of the optically active carbon is S configuration;

Code: FAPI-INER-466-SS;

Molecular weight: 1322.5;

Molecular formula: $C_{63}H_{89}F_2N_{13}O_{14}S$;

Structure 124:

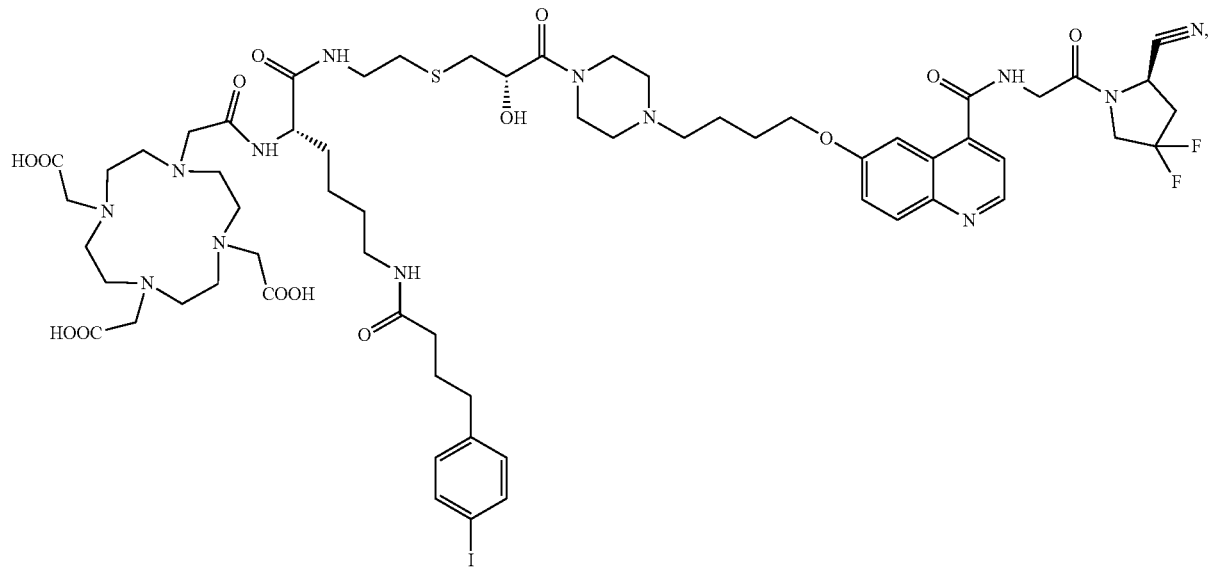 [SMILES: N#C[C@H]1CC(F)(F)CN1C(=O)CNC(=O)c1ccnc2ccc(OCCCCN3CCN(C(=O)[C@H](O)CSCCNC(=O)[C@H](CCCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-14 is S configuration; R1 is selected from R1-II-2, wherein the optical configuration of the optically active carbon is S configuration;
Code: FAPI-INER-470-SS;
Molecular weight: 1434.3;
Molecular formula: $C_{62}H_{86}F_2IN_{13}O_{14}S$;

Structure 125:

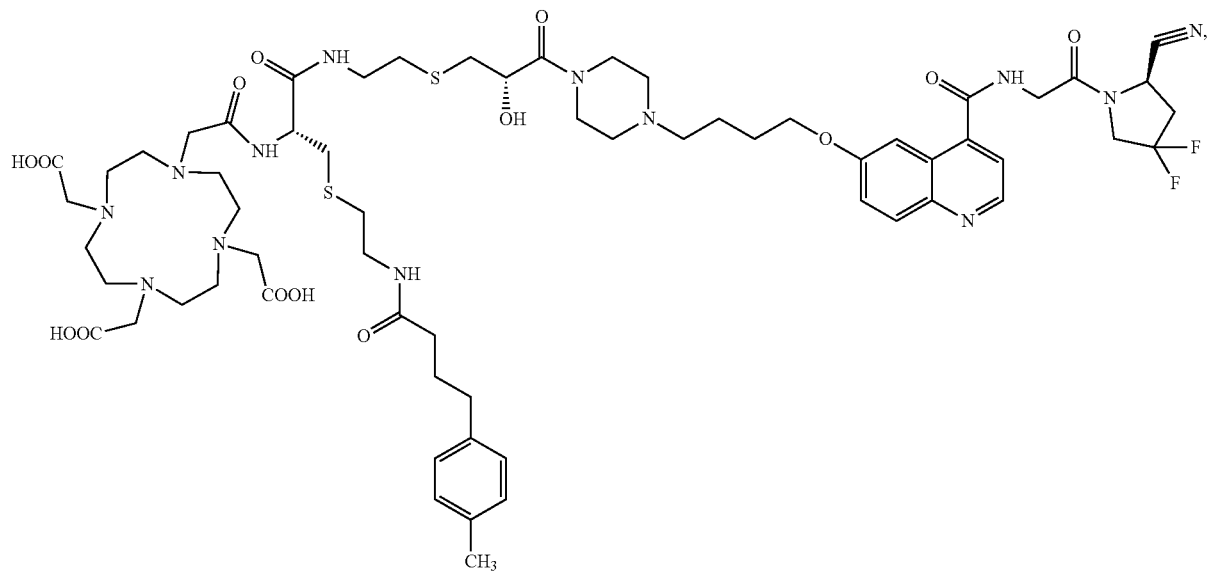 [SMILES: Cc1ccc(CCCC(=O)NCCSC[C@H](NC(=O)CN2CCN(CC(=O)O)CCN(CC(=O)O)CCN(CC(=O)O)CC2)C(=O)NCCSC[C@@H](O)C(=O)N2CCN(CCCCOc3ccc4nccc(C(=O)NCC(=O)N5CC(F)(F)C[C@@H]5C#N)c4c3)CC2)cc1]

wherein
the optical configuration of the optically active carbon of R2-II-14 is S configuration; R1 is selected from R1-II-3, wherein the optical configuration of the optically active carbon is S configuration;
Code: FAPI-INER-474-SS;
Molecular weight: 1340.5;
Molecular formula: $C_{62}H_{87}F_2N_{13}O_{14}S_2$;

Structure 126:

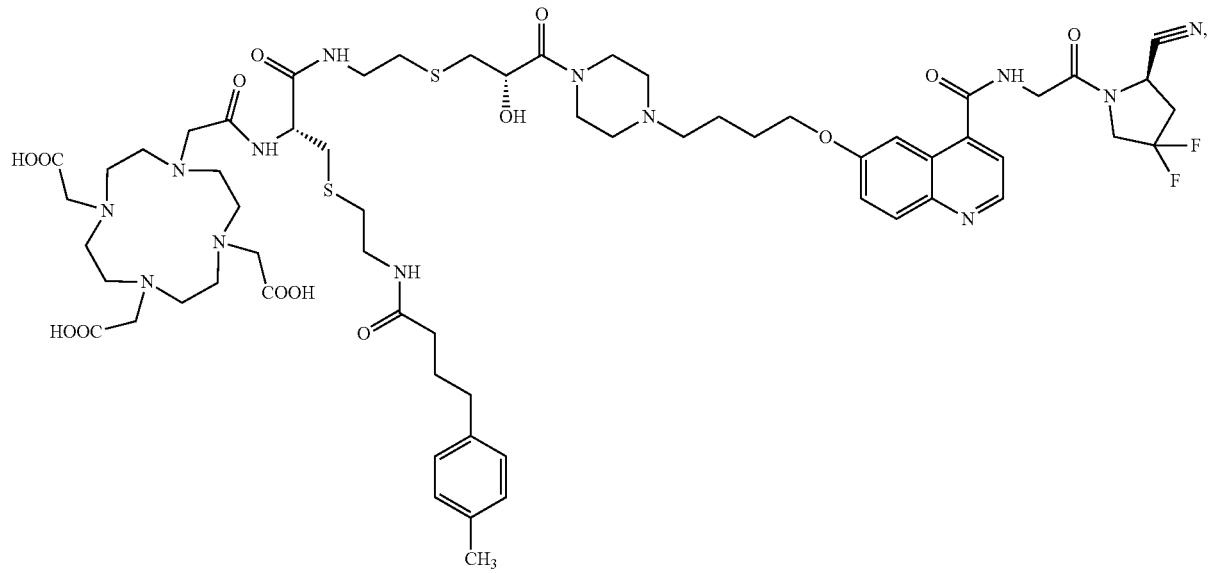 [SMILES: Cc1ccc(CCCC(=O)NCCSC[C@H](NC(=O)CN2CCN(CC(=O)O)CCN(CC(=O)O)CCN(CC(=O)O)CC2)C(=O)NCCSC[C@@H](O)C(=O)N2CCN(CCCCOc3ccc4nccc(C(=O)NCC(=O)N5CC(F)(F)C[C@@H]5C#N)c4c3)CC2)cc1]

wherein
the optical configuration of the optically active carbon of R2-II-14 is S configuration; R1 is selected from R1-II-4, wherein the optical configuration of the optically active carbon is S configuration;
Code: FAPI-INER-478-SS;
Molecular weight: 1452.4;
Molecular formula: $C_{61}H_{84}F_2IN_{13}O_{14}S_2$;

Structure 127:

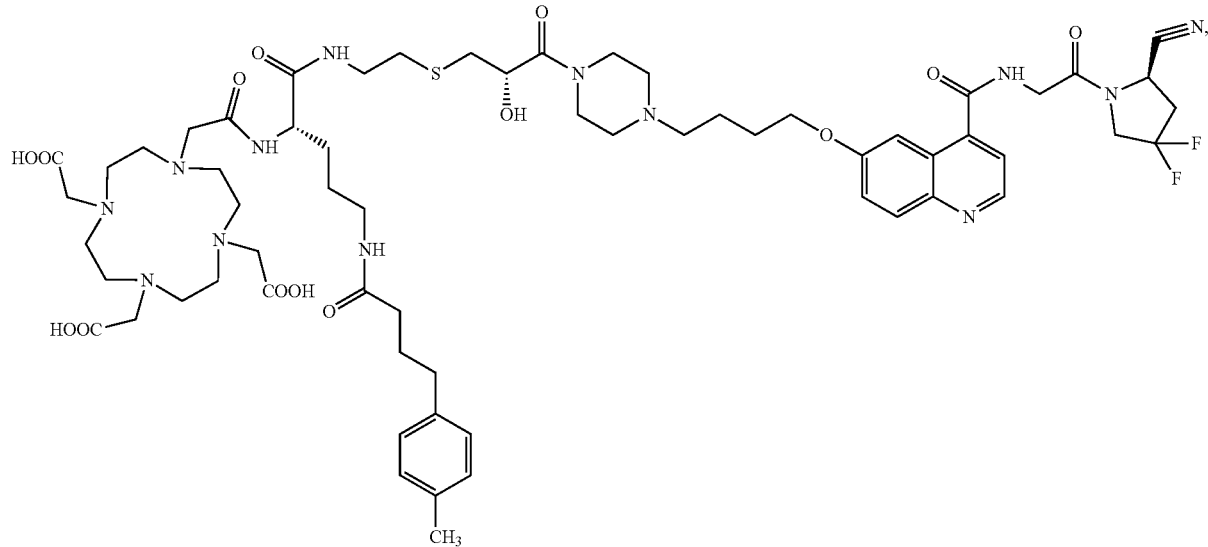 [SMILES: Cc1ccc(CCCC(=O)NCCC[C@H](NC(=O)CN2CCN(CC(=O)O)CCN(CC(=O)O)CCN(CC(=O)O)CC2)C(=O)NCCSC[C@@H](O)C(=O)N2CCN(CCCCOc3ccc4nccc(C(=O)NCC(=O)N5CC(F)(F)C[C@@H]5C#N)c4c3)CC2)cc1]

wherein
the optical configuration of the optically active carbon of R2-II-14 is S configuration; R1 is selected from R1-II-11, wherein the optical configuration of the optically active carbon is S configuration;
Code: FAPI-INER-482-SS;
Molecular weight: 1308.4;
Molecular formula: $C_{62}H_{87}F_2N_{13}O_{14}S$;

Structure 128:

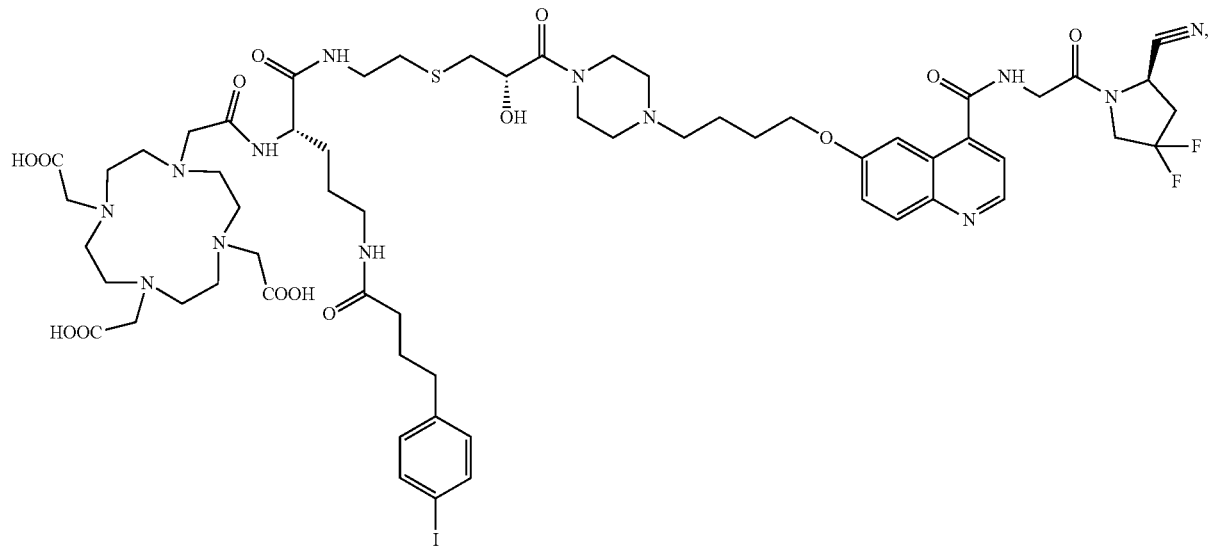 [SMILES: N#C[C@H]1CC(F)(F)CN1C(=O)CNC(=O)c1ccnc2ccc(OCCCCN3CCN(C(=O)[C@H](O)CSCCNC(=O)[C@H](CCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-14 is S configuration; R1 is selected from R1-II-12, wherein the optical configuration of the optically active carbon is S configuration;
Code: FAPI-INER-486-SS;
Molecular weight: 1420.3;
Molecular formula: $C_{61}H_{84}F_2IN_{13}O_{14}S$;

Structure 129:

wherein
the optical configuration of the optically active carbon of R2-II-14 is S configuration; R1 is selected from R1-II-17, wherein the optical configuration of the optically active carbon is S configuration;
Code: FAPI-INER-490-SS;
Molecular weight: 1363.5;
Molecular formula: $C_{65}H_{92}F_2N_{14}O_{14}S$;

Structure 130:

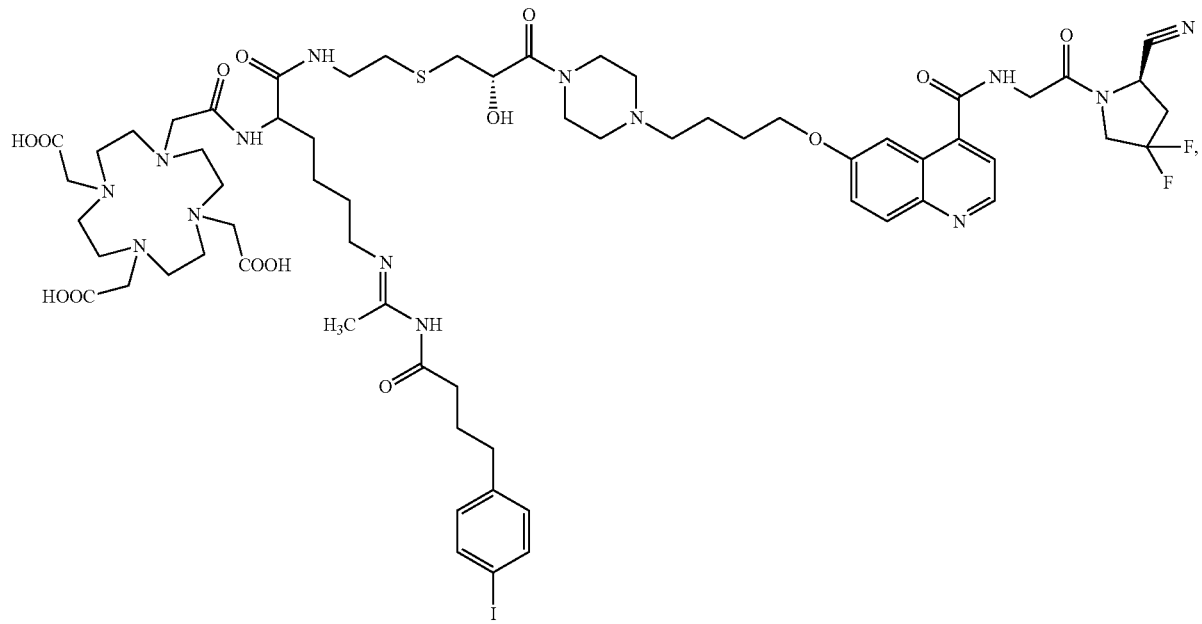 [SMILES: C/C(=N\CCCCC(NC(=O)CN1CCN(CC(=O)O)CCN(CC(=O)O)CCN(CC(=O)O)CC1)C(=O)NCCSC[C@@H](O)C(=O)N1CCN(CCCCOc2ccc3nccc(C(=O)NCC(=O)N4CC(F)(F)C[C@@H]4C#N)c3c2)CC1)NC(=O)CCCc1ccc(I)cc1]

wherein
the optical configuration of the optically active carbon of R2-II-14 is S configuration; R1 is selected from R1-II-18, wherein the optical configuration of the optically active carbon is S configuration;
Code: FAPI-INER-494-SS;
Molecular weight: 1475.4;
Molecular formula: $C_{64}H_{89}F_2IN_{14}O_{14}S$;

Structure 131:

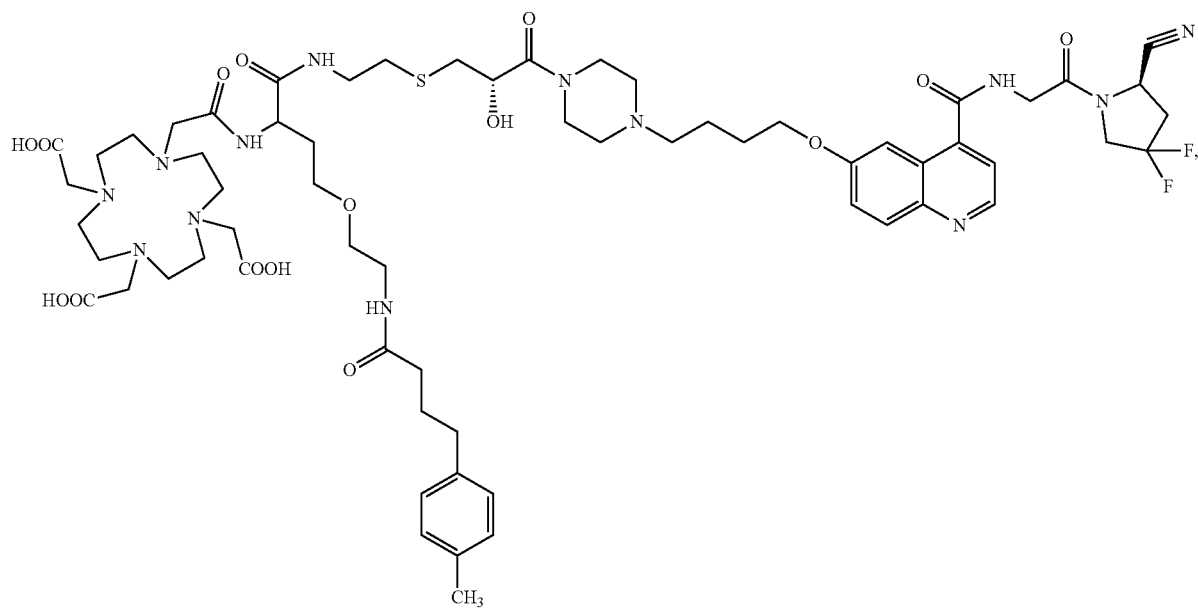 [SMILES: Cc1ccc(CCCC(=O)NCCOCCC(NC(=O)CN2CCN(CC(=O)O)CCN(CC(=O)O)CCN(CC(=O)O)CC2)C(=O)NCCSC[C@@H](O)C(=O)N2CCN(CCCCOc3ccc4nccc(C(=O)NCC(=O)N5CC(F)(F)C[C@@H]5C#N)c4c3)CC2)cc1]

wherein
the optical configuration of the optically active carbon of R2-II-14 is S configuration; R1 is selected from R1-II-21, wherein the optical configuration of the optically active carbon is S configuration;
Code: FAPI-INER-498-SS;
Molecular weight: 1338.5;
Molecular formula: $C_{63}H_{89}F_2N_{13}O_{15}S$;

Structure 132:

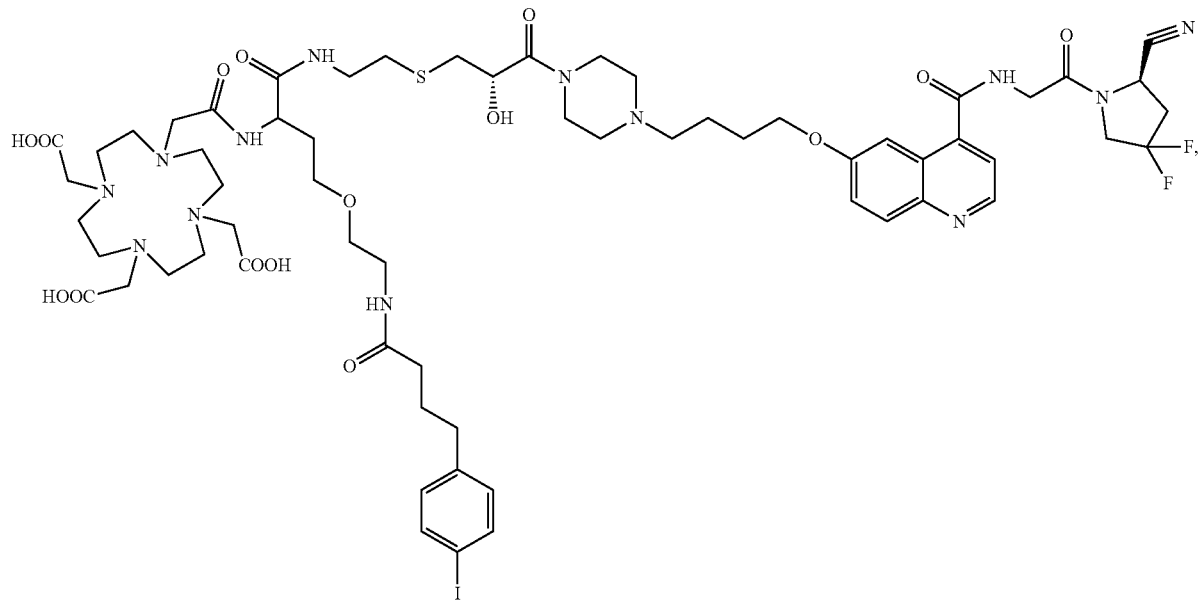 [SMILES: N#C[C@H]1CC(F)(F)CN1C(=O)CNC(=O)c1ccnc2ccc(OCCCCN3CCN(C(=O)[C@H](O)CSCCNC(=O)C(CCOCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-14 is S configuration; R1 is selected from R1-II-22, wherein the optical configuration of the optically active carbon is S configuration;

Code: FAPI-INER-502-SS;
Molecular weight: 1450.3;
Molecular formula: $C_{62}H_{86}F_2IN_{13}O_{15}S$;
or R2 is selected from R2-II-15 of the set of R2-II, R1 is any structure selected from the set of R1-II, and the D structure is and thus the compound has a structure represented by formulas below:
Structure 133:

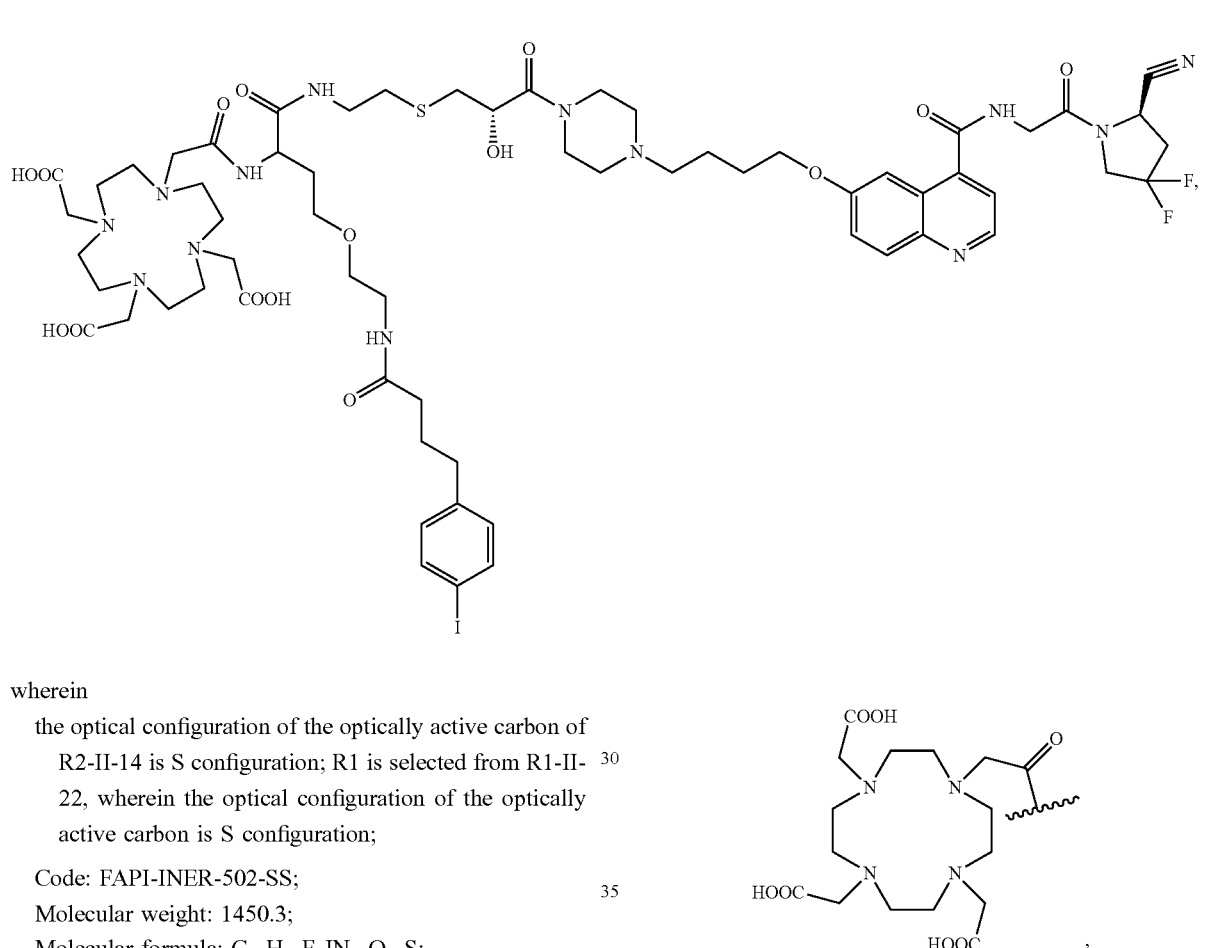

wherein
the optical configuration of the optically active carbon of R2-II-15 is S configuration; R1 is selected from R1-II-1, wherein the optical configuration of the optically active carbon is S configuration;
Code: FAPI-INER-467-SS;
Molecular weight: 1307.5;
Molecular formula: $C_{63}H_{88}F_2N_{12}O_{14}S$;
Structure 134:

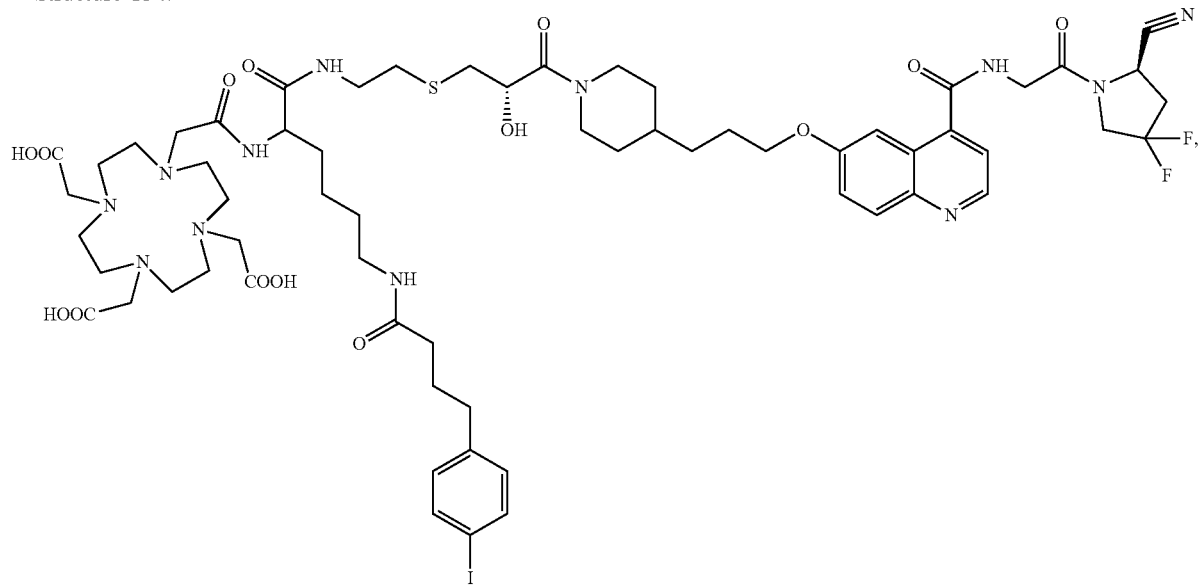

wherein
the optical configuration of the optically active carbon of R2-II-15 is S configuration; R1 is selected from R1-II-2, wherein the optical configuration of the optically active carbon is S configuration;
Code: FAPI-INER-471-SS;
Molecular weight: 1419.3;
Molecular formula: $C_{62}H_{85}F_2IN_{12}O_{14}S$;
Structure 135:

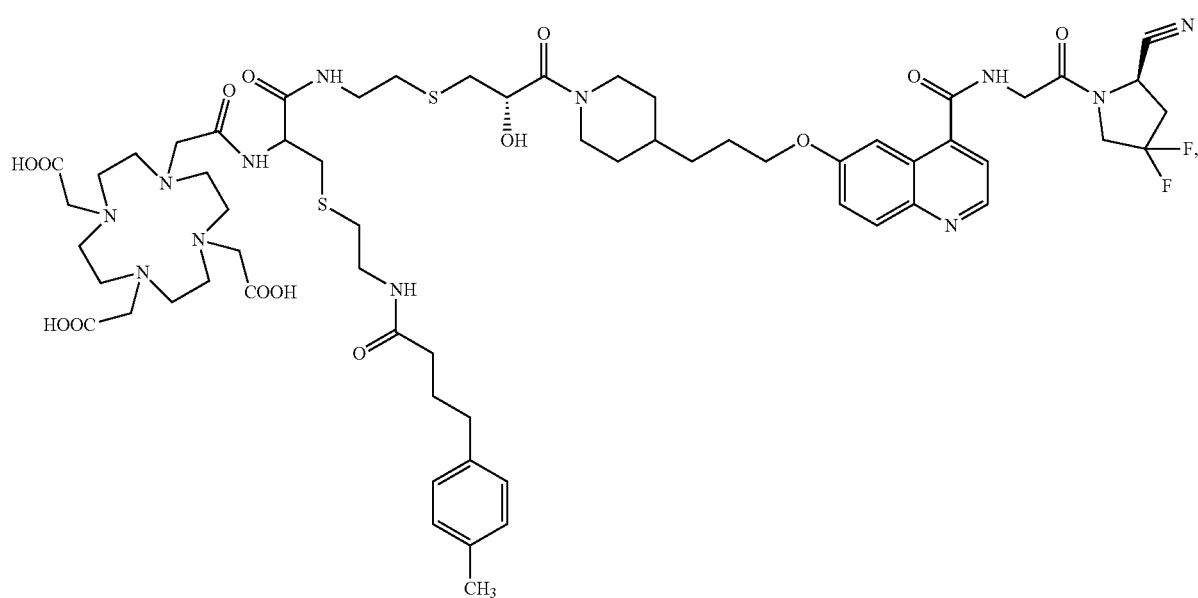 [SMILES: Cc1ccc(CCCC(=O)NCCSCC(NC(=O)CN2CCN(CC(=O)O)CCN(CC(=O)O)CCN(CC(=O)O)CC2)C(=O)NCCSC[C@@H](O)C(=O)N2CCC(CCCOc3ccc4nccc(C(=O)NCC(=O)N5CC(F)(F)C[C@@H]5C#N)c4c3)CC2)cc1]

wherein
the optical configuration of the optically active carbon of R2-II-15 is S configuration; R1 is selected from R1-II-3, wherein the optical configuration of the optically active carbon is S configuration;
Code: FAPI-INER-475-SS;
Molecular weight: 1325.5;
Molecular formula: $C_{62}H_{86}F_2N_{12}O_{14}S_2$;
Structure 136:

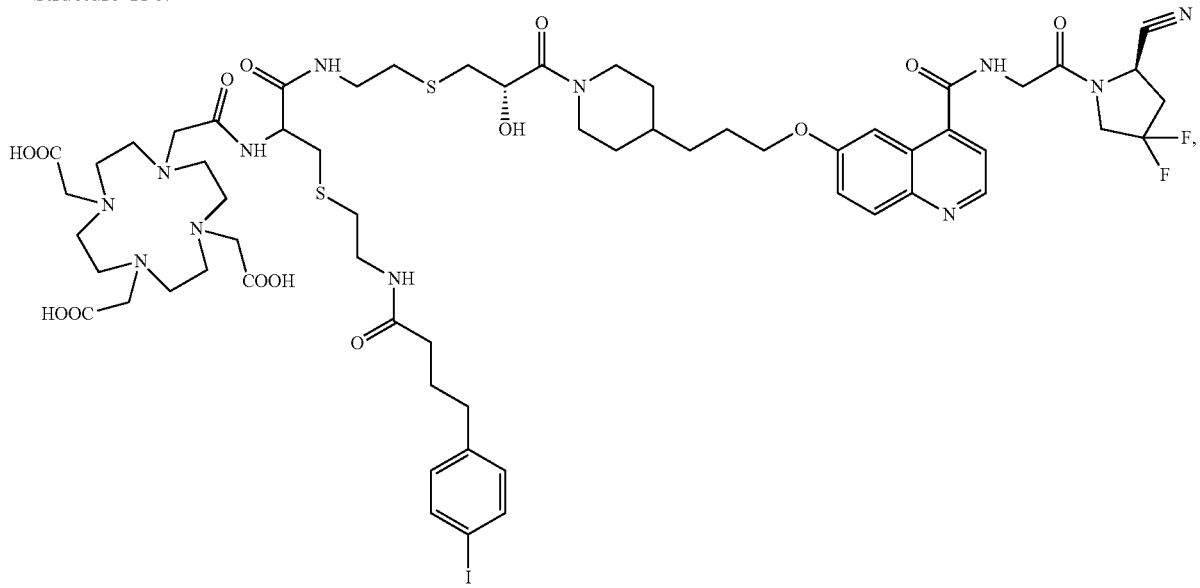 [SMILES: N#C[C@H]1CC(F)(F)CN1C(=O)CNC(=O)c1ccnc2ccc(OCCCC3CCN(C(=O)[C@H](O)CSCCNC(=O)C(CSCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-15 is S configuration; R1 is selected from R1-II-4, wherein the optical configuration of the optically active carbon is S configuration;
Code: FAPI-INER-479-SS;
Molecular weight: 1437.4;
Molecular formula: $C_{61}H_{83}F_2IN_{12}O_{14}S_2$;
Structure 137:

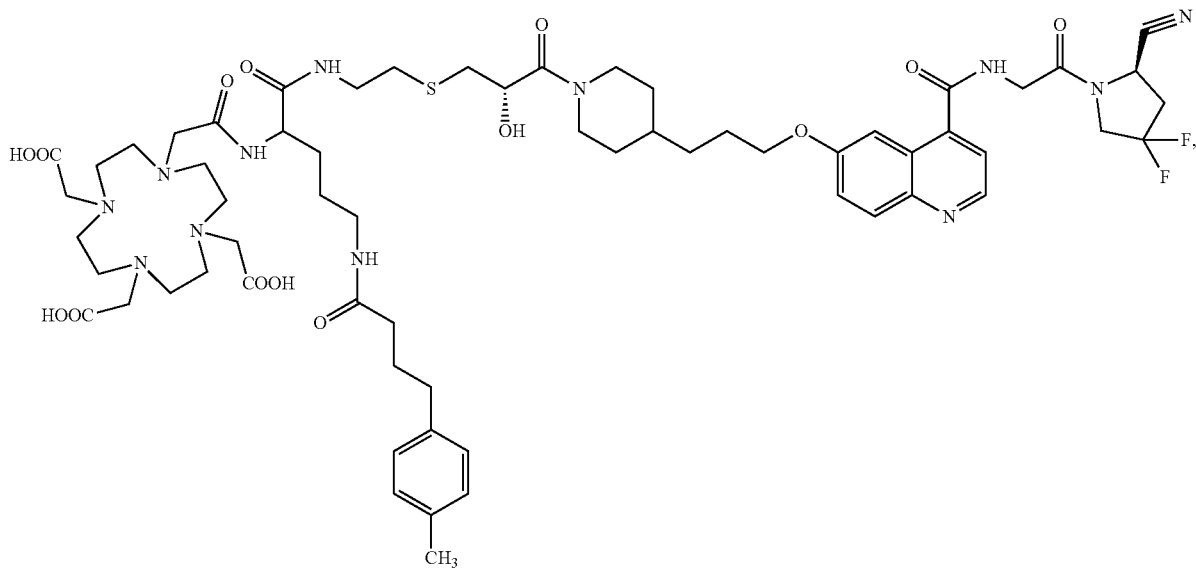 [SMILES: Cc1ccc(CCCC(=O)NCCCC(NC(=O)CN2CCN(CC(=O)O)CCN(CC(=O)O)CCN(CC(=O)O)CC2)C(=O)NCCSC[C@@H](O)C(=O)N2CCC(CCCOc3ccc4nccc(C(=O)NCC(=O)N5CC(F)(F)C[C@@H]5C#N)c4c3)CC2)cc1]

wherein
the optical configuration of the optically active carbon of R2-II-15 is S configuration; R1 is selected from R1-II-11, wherein the optical configuration of the optically active carbon is S configuration;
Code: FAPI-INER-483-SS;
Molecular weight: 1293.4;
Molecular formula: $C_{62}H_{86}F_2N_{12}O_{14}S$;
Structure 138:

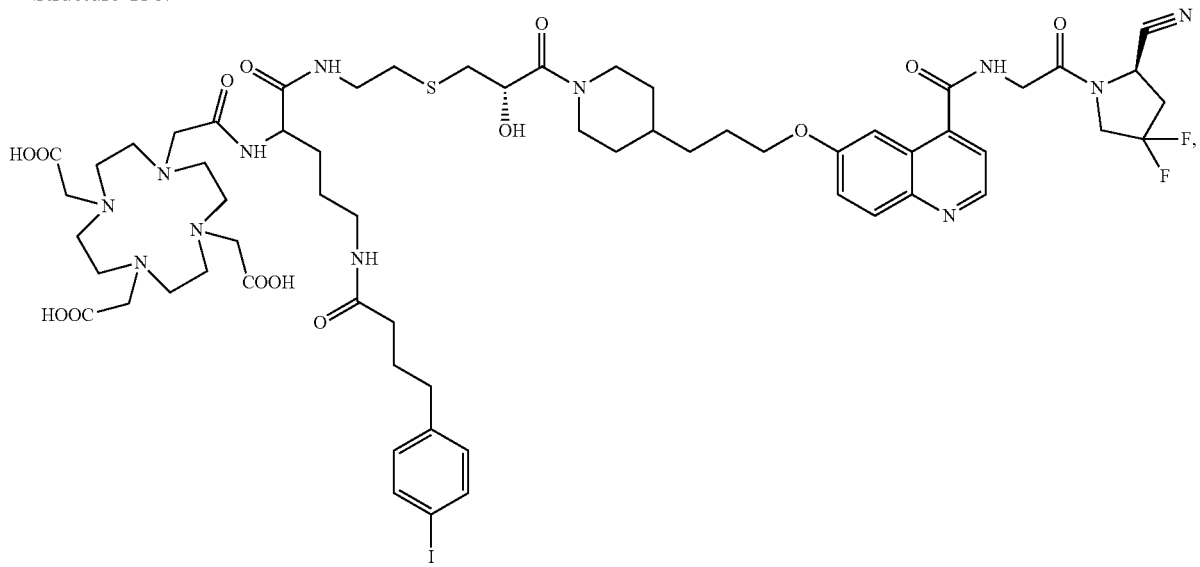 [SMILES: N#C[C@H]1CC(F)(F)CN1C(=O)CNC(=O)c1ccnc2ccc(OCCCC3CCN(C(=O)[C@H](O)CSCCNC(=O)C(CCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-15 is S configuration; R1 is selected from R1-II-12, wherein the optical configuration of the optically active carbon is S configuration;
Code: FAPI-INER-487-SS;
Molecular weight: 1405.3;
Molecular formula: $C_{61}H_{83}F_2IN_{12}O_{14}S$;
Structure 139:

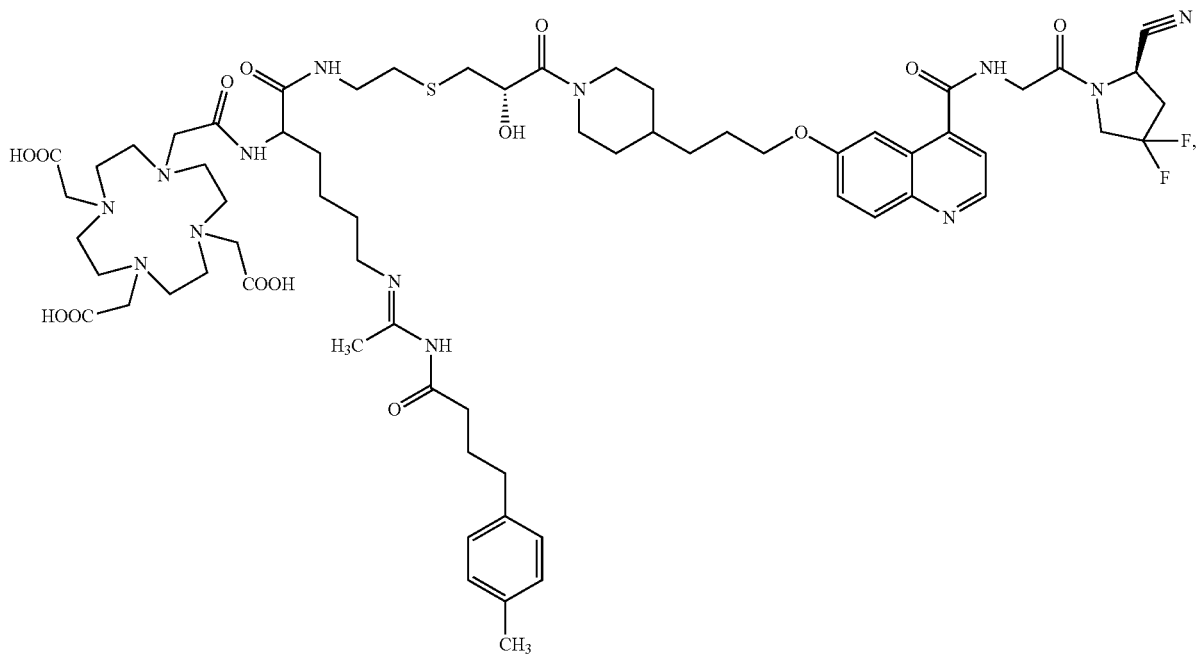 [SMILES: C/C(=N\CCCCC(NC(=O)CN1CCN(CC(=O)O)CCN(CC(=O)O)CCN(CC(=O)O)CC1)C(=O)NCCSC[C@@H](O)C(=O)N1CCC(CCCOc2ccc3nccc(C(=O)NCC(=O)N4CC(F)(F)C[C@@H]4C#N)c3c2)CC1)NC(=O)CCCc1ccc(C)cc1]

wherein
the optical configuration of the optically active carbon of R2-II-15 is S configuration; R1 is selected from R1-II-17, wherein the optical configuration of the optically active carbon is S configuration;

Code: FAPI-INER-491-SS;
Molecular weight: 1348.5;
Molecular formula: $C_{65}H_{91}F_2N_{13}O_{14}S$;
Structure 140:

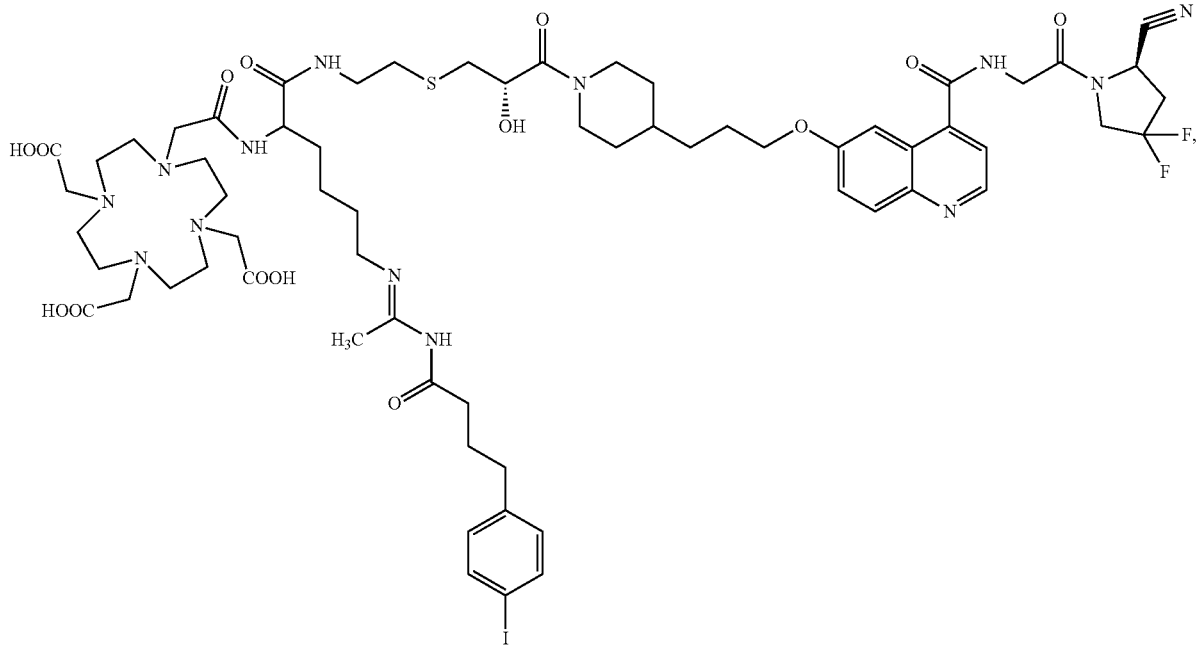 [SMILES: C/C(=N\CCCCC(NC(=O)CN1CCN(CC(=O)O)CCN(CC(=O)O)CCN(CC(=O)O)CC1)C(=O)NCCSC[C@@H](O)C(=O)N1CCC(CCCOc2ccc3nccc(C(=O)NCC(=O)N4CC(F)(F)C[C@@H]4C#N)c3c2)CC1)NC(=O)CCCc1ccc(I)cc1]

wherein
the optical configuration of the optically active carbon of R2-II-15 is S configuration; R1 is selected from R1-II-18, wherein the optical configuration of the optically active carbon is S configuration;
Code: FAPI-INER-495-SS;
Molecular weight: 1460.4;
Molecular formula: $C_{64}H_{88}F_2IN_{13}O_{14}S$;
Structure 141:

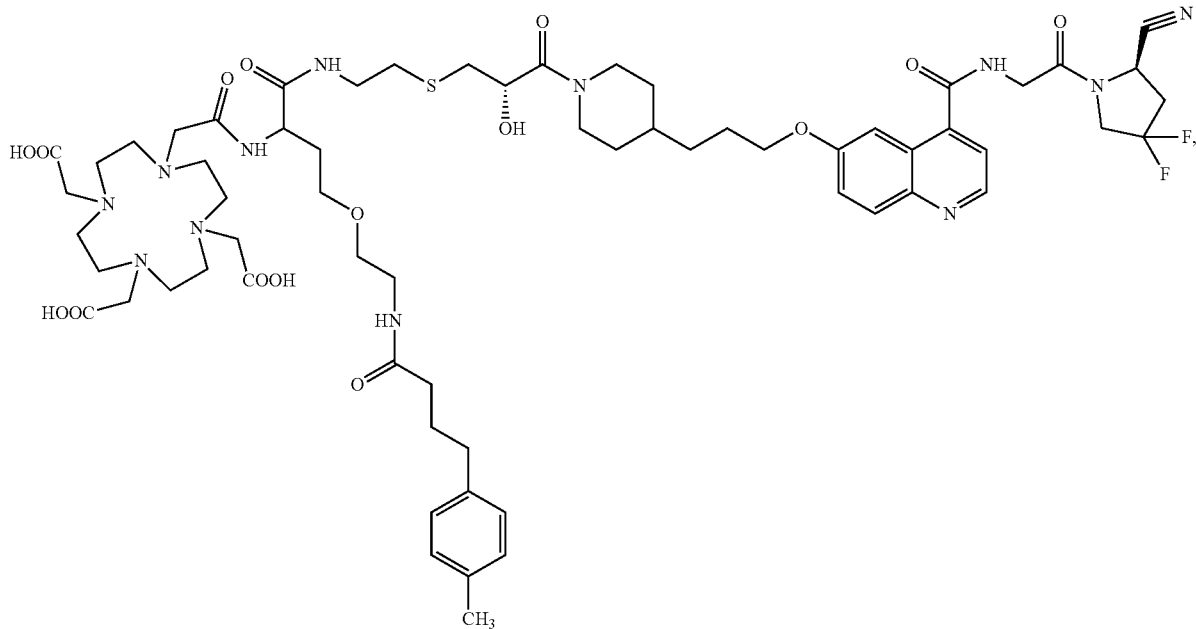 [SMILES: Cc1ccc(CCCC(=O)NCCOCCC(NC(=O)CN2CCN(CC(=O)O)CCN(CC(=O)O)CCN(CC(=O)O)CC2)C(=O)NCCSC[C@@H](O)C(=O)N2CCC(CCCOc3ccc4nccc(C(=O)NCC(=O)N5CC(F)(F)C[C@@H]5C#N)c4c3)CC2)cc1]

wherein
the optical configuration of the optically active carbon of R2-II-15 is S configuration; R1 is selected from R1-II-21, wherein the optical configuration of the optically active carbon is S configuration;

Code: FAPI-INER-499-SS;
Molecular weight: 1323.5;
Molecular formula: $C_{63}H_{88}F_2N_{12}O_{15}S$;
Structure 142:

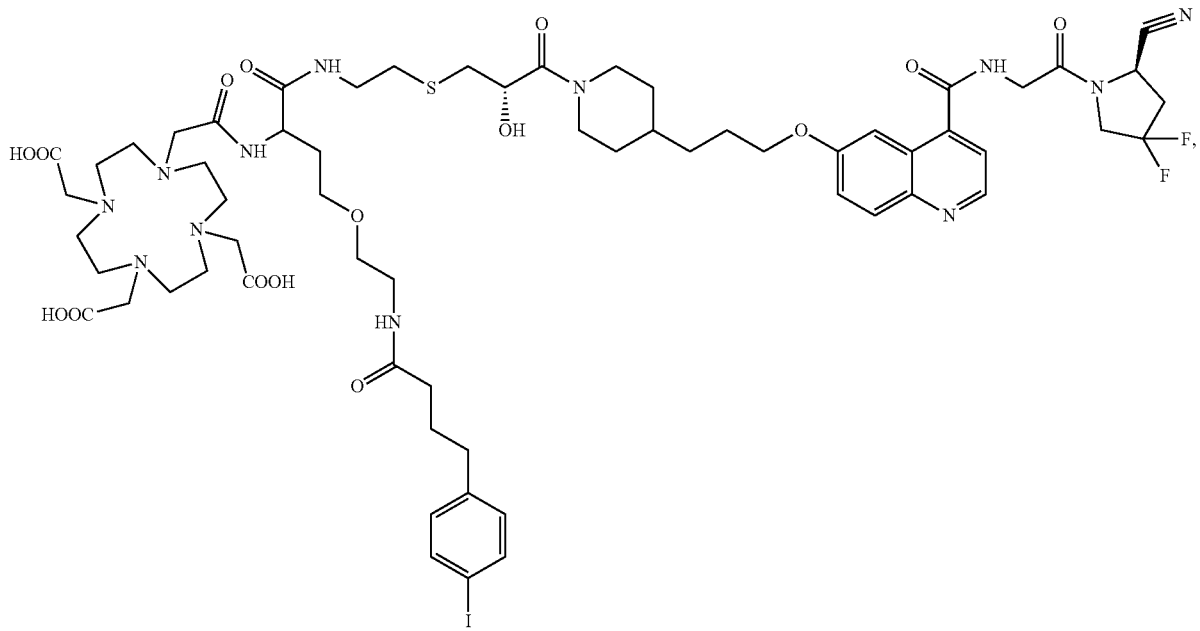 [SMILES: N#C[C@H]1CC(F)(F)CN1C(=O)CNC(=O)c1ccnc2ccc(OCCCC3CCN(C(=O)[C@H](O)CSCCNC(=O)C(CCOCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-15 is S configuration; R1 is selected from R1-II-22, wherein the optical configuration of the optically active carbon is S configuration;

Code: FAPI-INER-503-SS;
Molecular weight: 1435.3;
Molecular formula: $C_{62}H_{85}F_2IN_{12}O_{15}S$;

or R2 is selected from R2-II-16 of the set of R2-II, R1 is any structure selected from the set of R1-II, and the D structure is

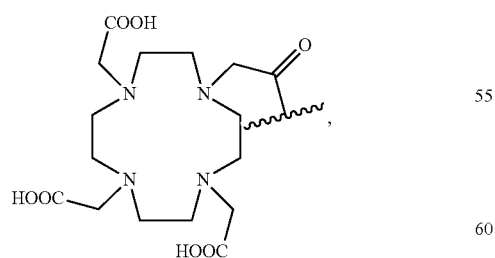

and thus the compound has a structure represented by formulas below:

Structure 143:

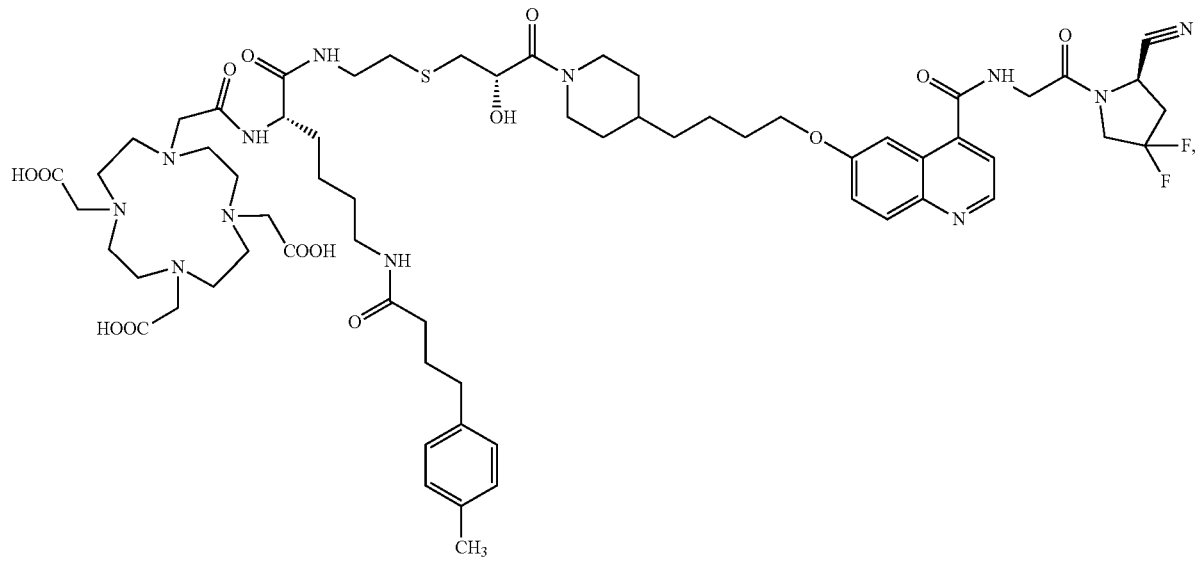 [SMILES: Cc1ccc(CCCC(=O)NCCSC[C@H](NC(=O)CN2CCN(CC(=O)O)CCN(CC(=O)O)CCN(CC(=O)O)CC2)C(=O)NCCSC[C@@H](O)C(=O)N2CCC(CCCCOc3ccc4nccc(C(=O)NCC(=O)N5CC(F)(F)C[C@@H]5C#N)c4c3)CC2)cc1]

wherein
the optical configuration of the optically active carbon of R2-II-16 is S configuration; R1 is selected from R1-II-1, wherein the optical configuration of the optically active carbon is S configuration;
Code: FAPI-INER-468-SS;
Molecular weight: 1321.5;
Molecular formula: $C_{64}H_{90}F_2N_{12}O_{14}S$;

Structure 144:

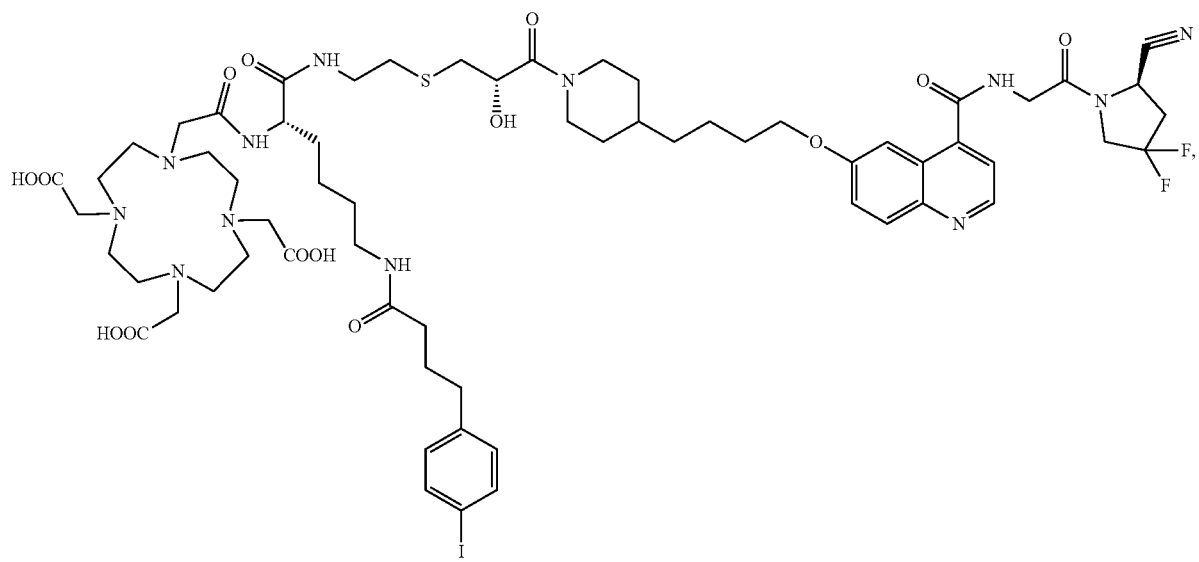

wherein
the optical configuration of the optically active carbon of R2-II-16 is S configuration; R1 is selected from R1-II-2, wherein the optical configuration of the optically active carbon is S configuration;
Code: FAPI-INER-472-SS;
Molecular weight: 1433.4;
Molecular formula: $C_{63}H_{87}F_2IN_{12}O_{14}S$;

Structure 145:

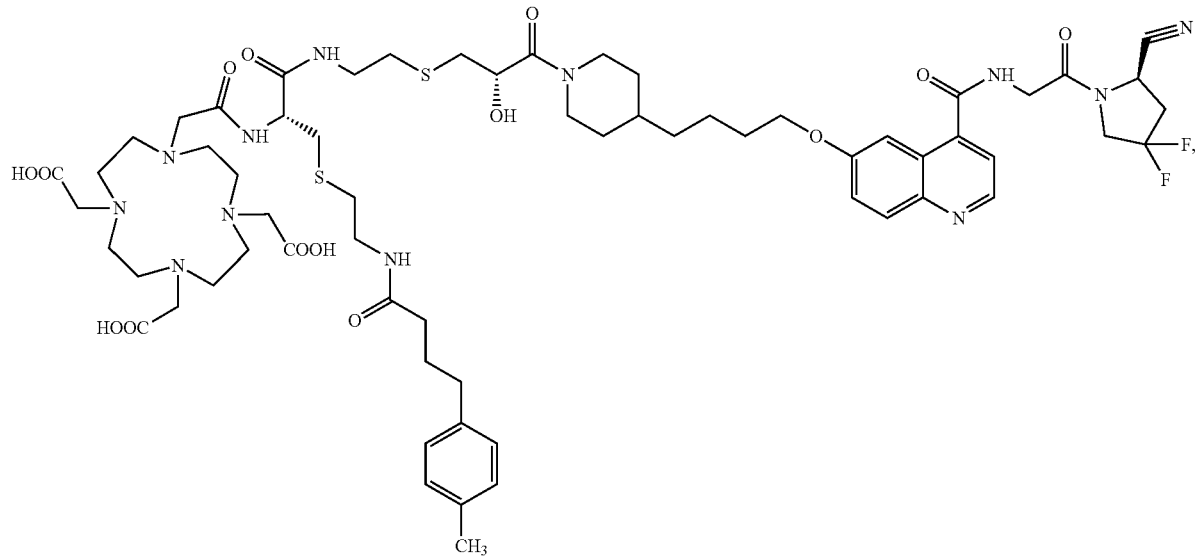

wherein
the optical configuration of the optically active carbon of R2-II-16 is S configuration; R1 is selected from R1-II-3, wherein the optical configuration of the optically active carbon is S configuration;
Code: FAPI-INER-476-SS;
Molecular weight: 1339.5;
Molecular formula: $C_{63}H_{88}F_2N_{12}O_{14}S_2$;

Structure 146:

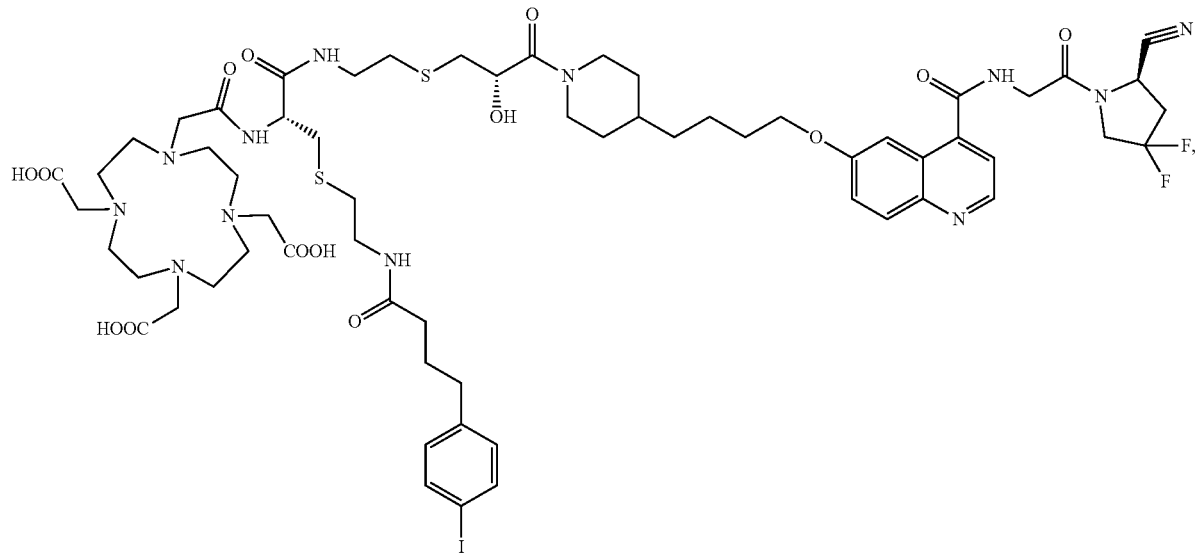 [SMILES: N#C[C@H]1CC(F)(F)CN1C(=O)CNC(=O)c1ccnc2ccc(OCCCCC3CCN(C(=O)[C@H](O)CSCCNC(=O)[C@H](CSCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-16 is S configuration; R1 is selected from R1-II-4, wherein the optical configuration of the optically active carbon is S configuration;
Code: FAPI-INER-480-SS;
Molecular weight: 1451.4;
Molecular formula: $C_{62}H_{85}F_2IN_{12}O_{14}S_2$;

Structure 147:

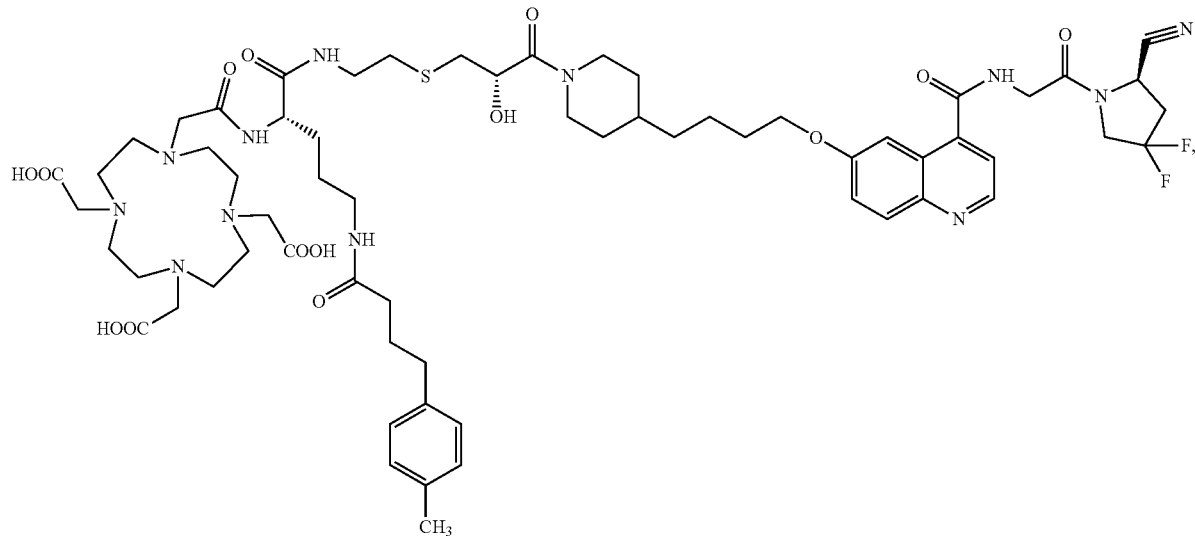 [SMILES: Cc1ccc(CCCC(=O)NCCC[C@H](NC(=O)CN2CCN(CC(=O)O)CCN(CC(=O)O)CCN(CC(=O)O)CC2)C(=O)NCCSC[C@@H](O)C(=O)N2CCC(CCCCOc3ccc4nccc(C(=O)NCC(=O)N5CC(F)(F)C[C@@H]5C#N)c4c3)CC2)cc1]

wherein
the optical configuration of the optically active carbon of R2-II-16 is S configuration; R1 is selected from R1-II-11, wherein the optical configuration of the optically active carbon is S configuration;
Code: FAPI-INER-484-SS;
Molecular weight: 1307.5;
Molecular formula: $C_{63}H_{88}F_2N_{12}O_{14}S$;

Structure 148:

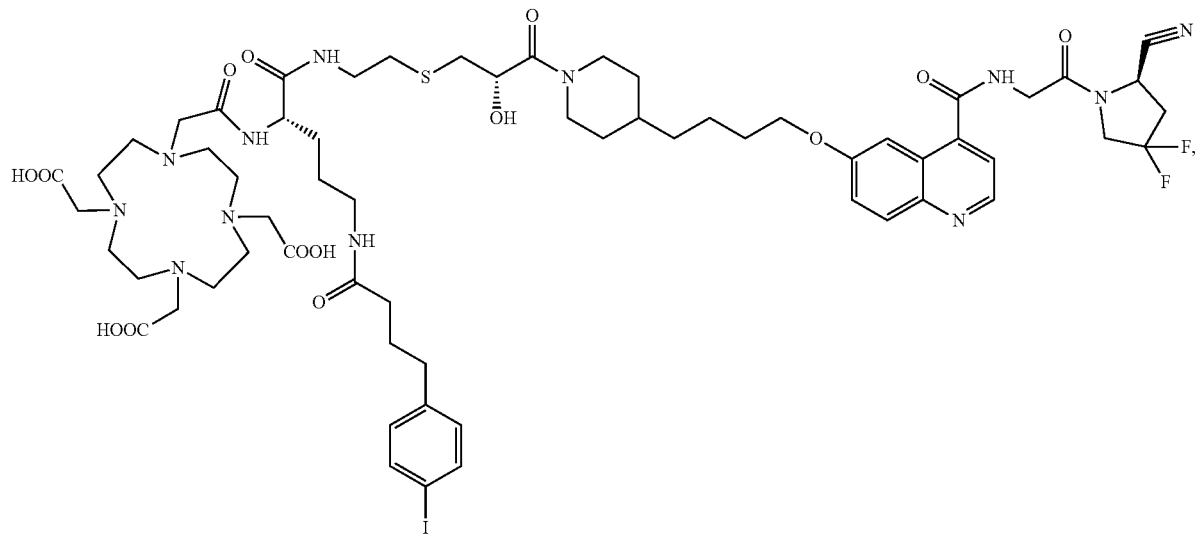 [SMILES: N#C[C@H]1CC(F)(F)CN1C(=O)CNC(=O)c1ccnc2ccc(OCCCCC3CCN(C(=O)[C@H](O)CSCCNC(=O)[C@H](CCCNC(=O)CCCc4ccc(I)cc4)NC(=O)CN4CCN(CC(=O)O)CCN(CC(=O)O)CCN(CC(=O)O)CC4)CC3)cc12]

wherein
the optical configuration of the optically active carbon of R2-II-16 is S configuration; R1 is selected from R1-II-12, wherein the optical configuration of the optically active carbon is S configuration;
Code: FAPI-INER-488-SS;
Molecular weight: 1419.3;
Molecular formula: $C_{62}H_{85}F_2IN_{12}O_{14}S$;

Structure 149:

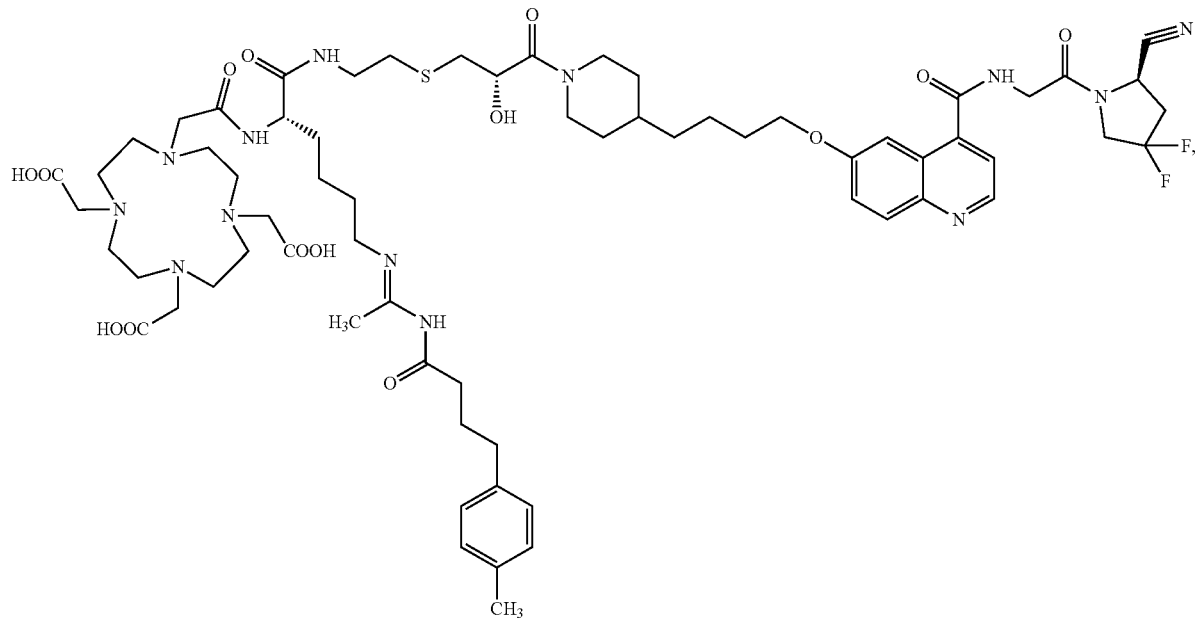 [SMILES: C/C(=N\CCCC[C@H](NC(=O)CN1CCN(CC(=O)O)CCN(CC(=O)O)CCN(CC(=O)O)CC1)C(=O)NCCSC[C@@H](O)C(=O)N1CCC(CCCCOc2ccc3nccc(C(=O)NCC(=O)N4CC(F)(F)C[C@@H]4C#N)c3c2)CC1)NC(=O)CCCc1ccc(C)cc1]

wherein
the optical configuration of the optically active carbon of R2-II-16 is S configuration; R1 is selected from R1-II-17, wherein the optical configuration of the optically active carbon is S configuration;
Code: FAPI-INER-492-SS;
Molecular weight: 1362.5;
Molecular formula: $C_{66}H_{93}F_2N_{13}O_{14}S$;
Structure 150:

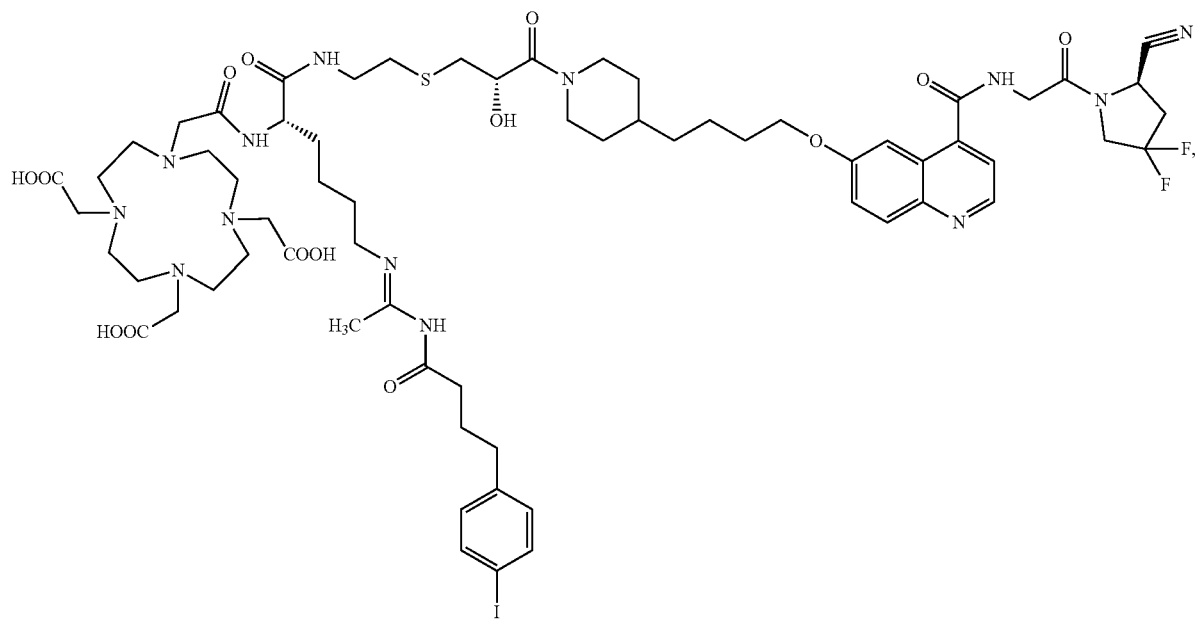 [SMILES: C/C(=N\CCCC[C@H](NC(=O)CN1CCN(CC(=O)O)CCN(CC(=O)O)CCN(CC(=O)O)CC1)C(=O)NCCSC[C@@H](O)C(=O)N1CCC(CCCCOc2ccc3nccc(C(=O)NCC(=O)N4CC(F)(F)C[C@@H]4C#N)c3c2)CC1)NC(=O)CCCc1ccc(I)cc1]

wherein
the optical configuration of the optically active carbon of R2-II-16 is S configuration; R1 is selected from R1-II-18, wherein the optical configuration of the optically active carbon is S configuration;
Code: FAPI-INER-496-SS;
Molecular weight: 1474.4;
Molecular formula: $C_{65}H_{90}F_2IN_{13}O_{14}S$;

Structure 151:

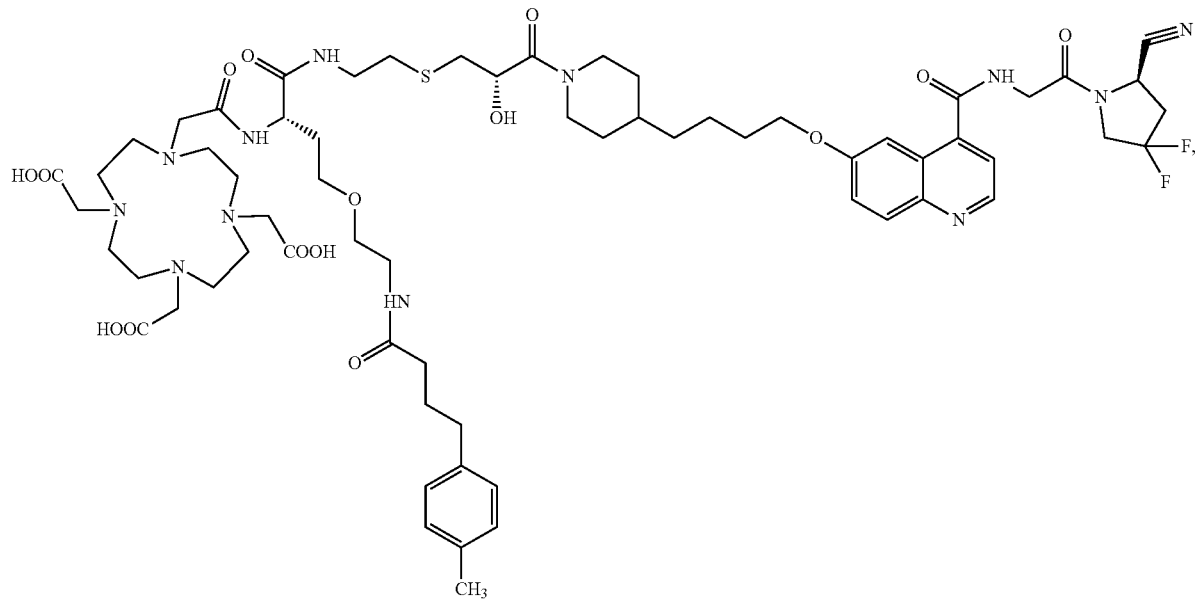

wherein
the optical configuration of the optically active carbon of R2-II-16 is S configuration; R1 is selected from R1-II-21, wherein the optical configuration of the optically active carbon is S configuration;
Code: FAPI-INER-500-SS;
Molecular weight: 1337.5;
Molecular formula: $C_{64}H_{90}F_2N_{12}O_{15}S$;
Structure 152:

wherein
the optical configuration of the optically active carbon of R2-II-16 is S configuration; R1 is selected from R1-II-22, wherein the optical configuration of the optically active carbon is S configuration;
Code: FAPI-INER-504-SS;
Molecular weight: 1449.4;
Molecular formula: $C_{63}H_{87}F_2IN_{12}O_{15}S$;

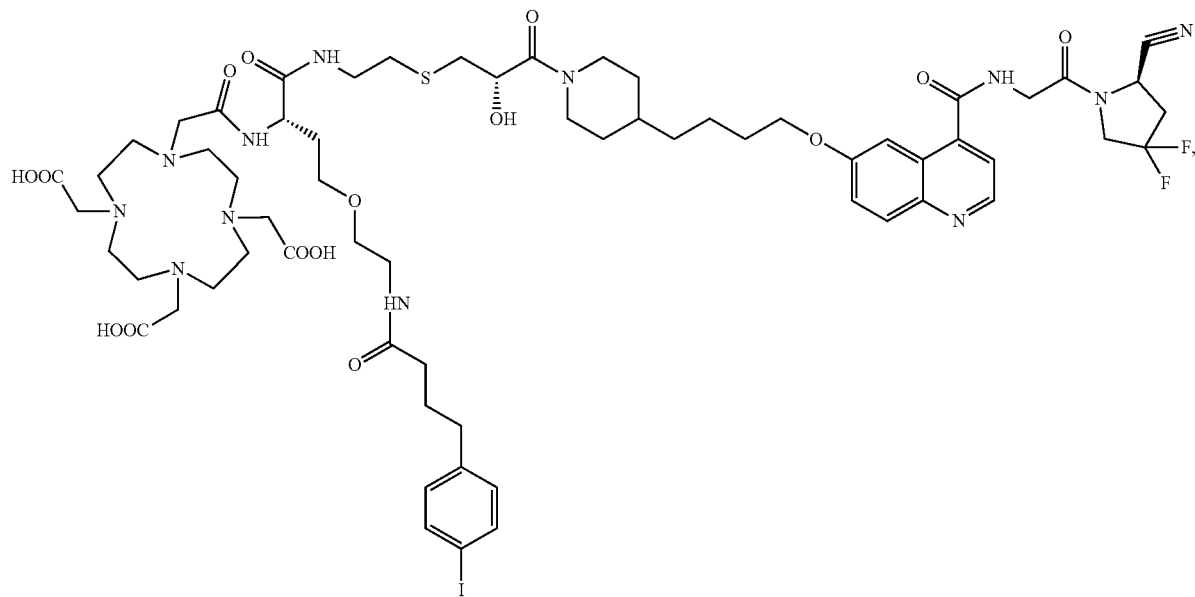 [SMILES: N#C[C@H]1CC(F)(F)CN1C(=O)CNC(=O)c1ccnc2ccc(OCCCCC3CCN(C(=O)[C@H](O)CSCCNC(=O)[C@H](CCOCCNC(=O)CCCc4ccc(I)cc4)NC(=O)CN4CCN(CC(=O)O)CCN(CC(=O)O)CCN(CC(=O)O)CC4)CC3)cc12]

or R2 is selected from R2-III-1 of the set of R2-III, R1 is any structure selected from the set of R1-III, and the D structure is

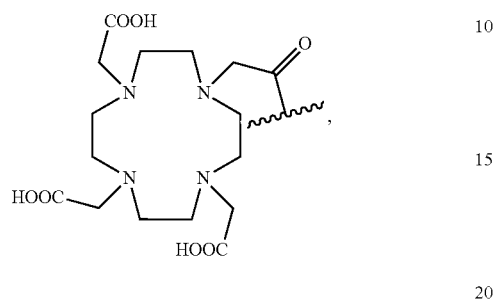

and thus the compound has a structure represented by formulas below:
Structure 153:

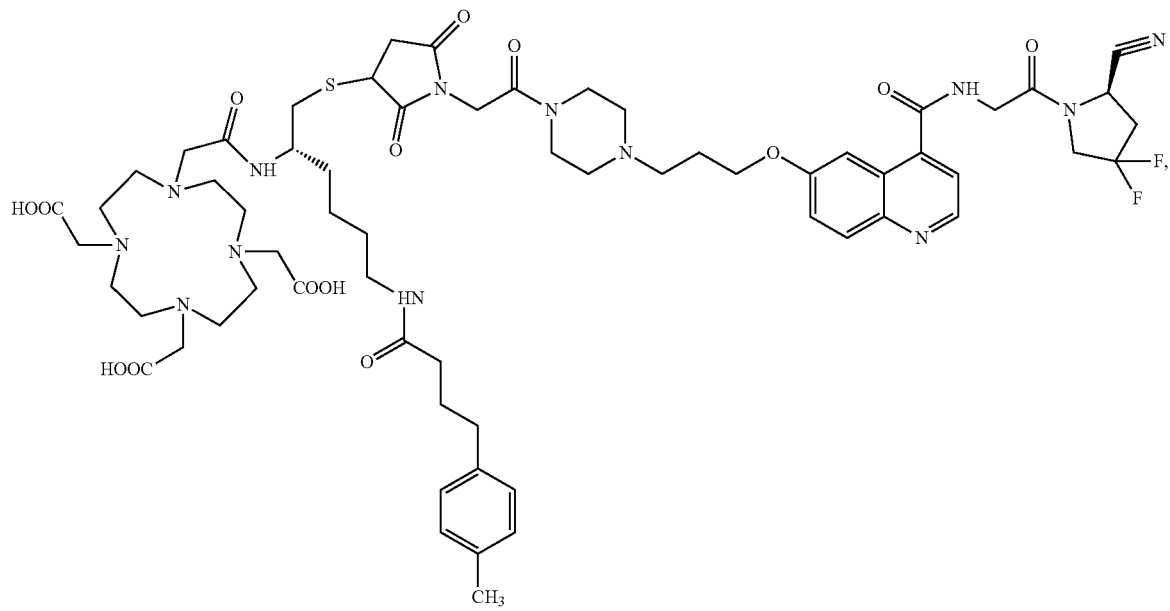

wherein
R1 is selected from R1-III-1, wherein the optical configuration of the optically active carbon is S configuration;
Code: FAPI-INER-1057-S;
Molecular weight: 1318.4;
Molecular formula: $C_{63}H_{85}F_2N_{13}O_{14}S$;

Structure 154:

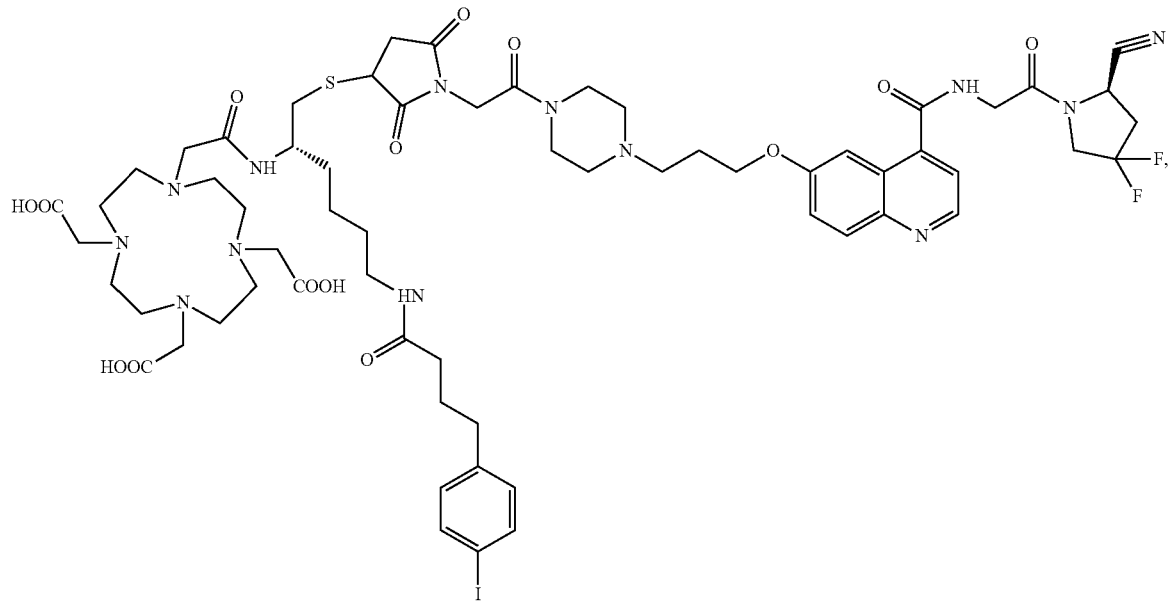

wherein
R1 is selected from R1-III-2, wherein the optical configuration of the optically active carbon is S configuration;
Code: FAPI-INER-1061-S;
Molecular weight: 1430.3;
Molecular formula: $C_{62}H_{82}F_2IN_{13}O_{14}S$;

Structure 155:

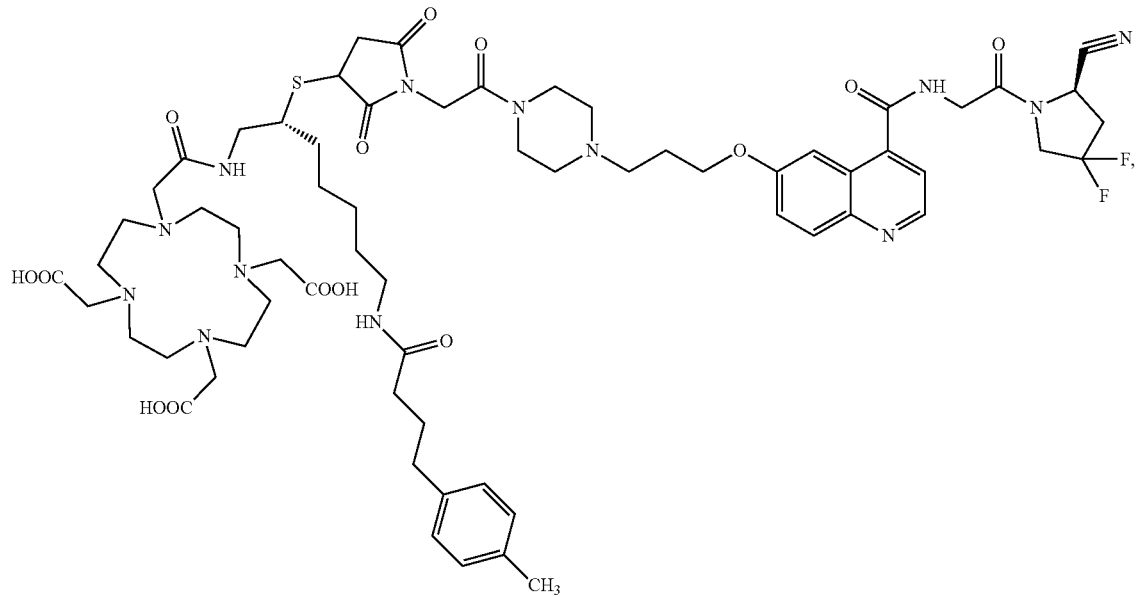

wherein
R1 is selected from R1-III-9, wherein the optical configuration of the optically active carbon is S configuration;
Code: FAPI-INER-1065-S;
Molecular weight: 1332.5;
Molecular formula: $C_{64}H_{87}F_2N_{13}O_{14}S$;

Structure 156:

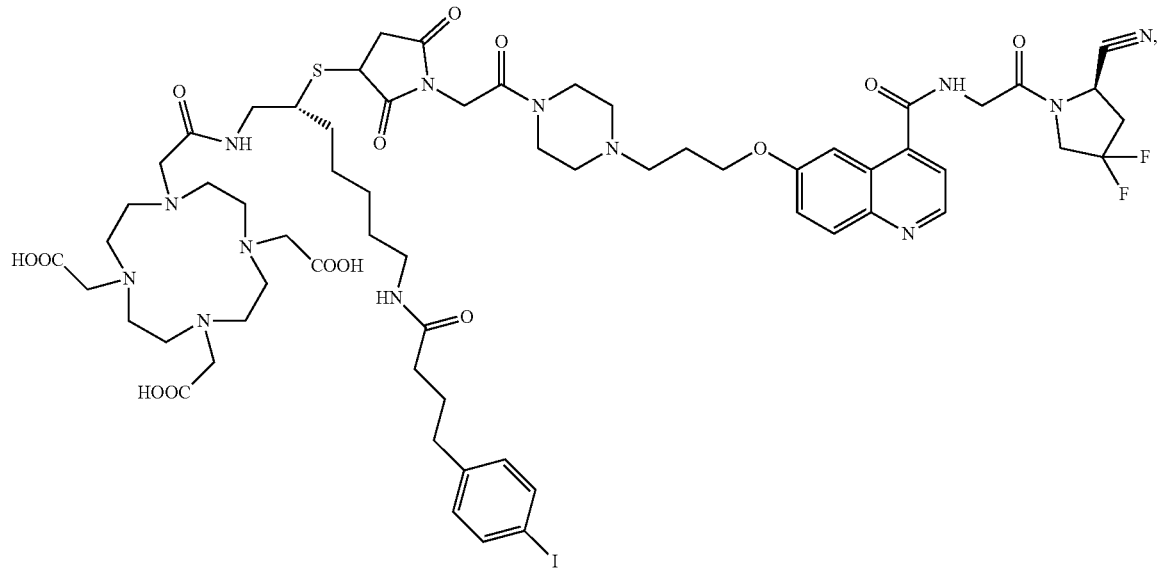

wherein
R1 is selected from R1-III-10, wherein the optical configuration of the optically active carbon is S configuration;

Code: FAPI-INER-1069-S;

Molecular weight: 1444.3;

Molecular formula: $C_{63}H_{84}F_2IN_{13}O_{14}S$;

or R2 is selected from R2-III-2 of the set of R2-III, R1 is any structure selected from the set of R1-III, and the D structure is

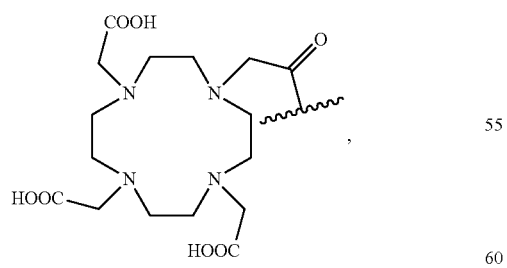

and thus the compound has a structure represented by formulas below:

Structure 157:

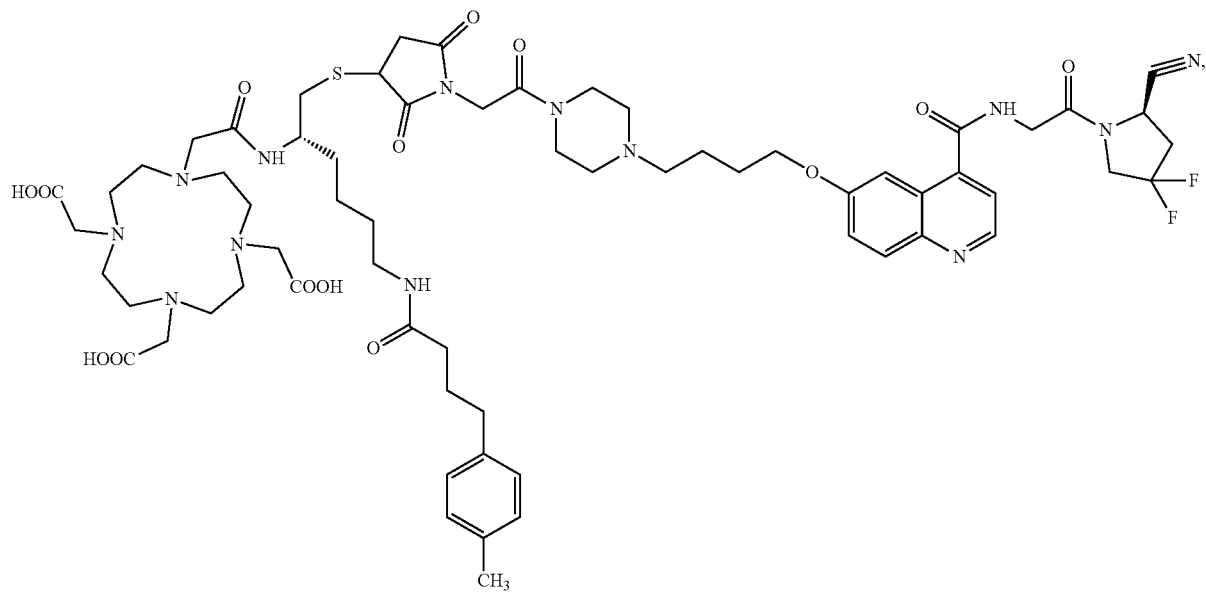

wherein
R1 is selected from R1-III-1, wherein the optical configuration of the optically active carbon is S configuration;
Code: FAPI-INER-1058-S;
Molecular weight: 1332.5;
Molecular formula: $C_{64}H_{87}F_2N_{13}O_{14}S$;

Structure 158:

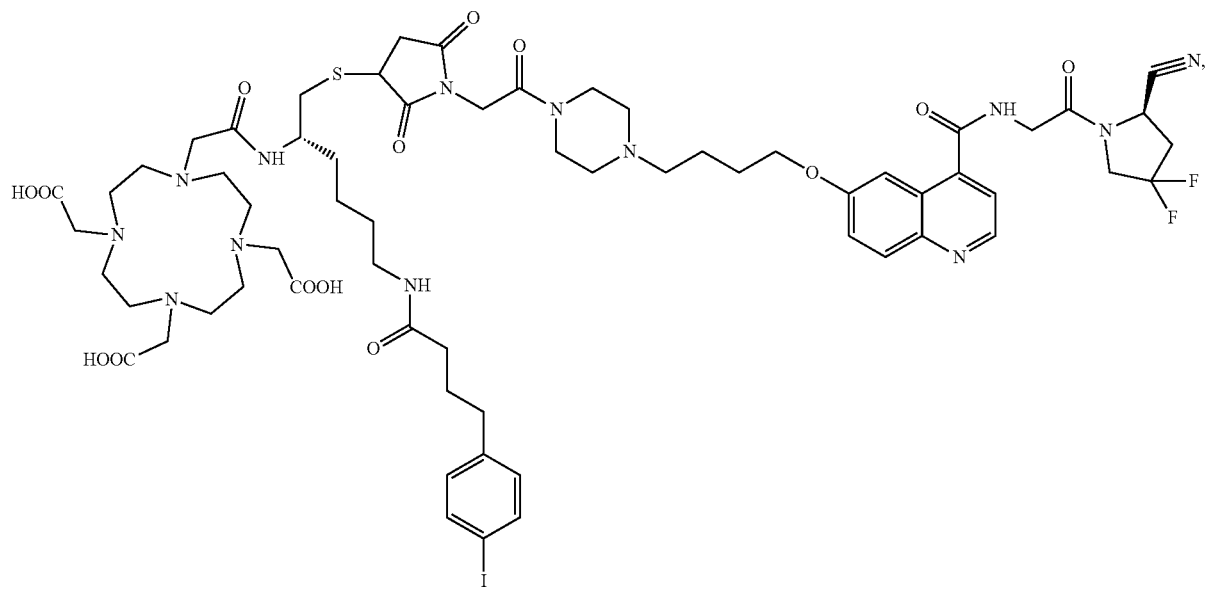

wherein
R1 is selected from R1-III-2, wherein the optical configuration of the optically active carbon is S configuration;
Code: FAPI-INER-1062-S;
Molecular weight: 1444.3;
Molecular formula: $C_{63}H_{84}F_2IN_{13}O_{14}S$;

Structure 159:

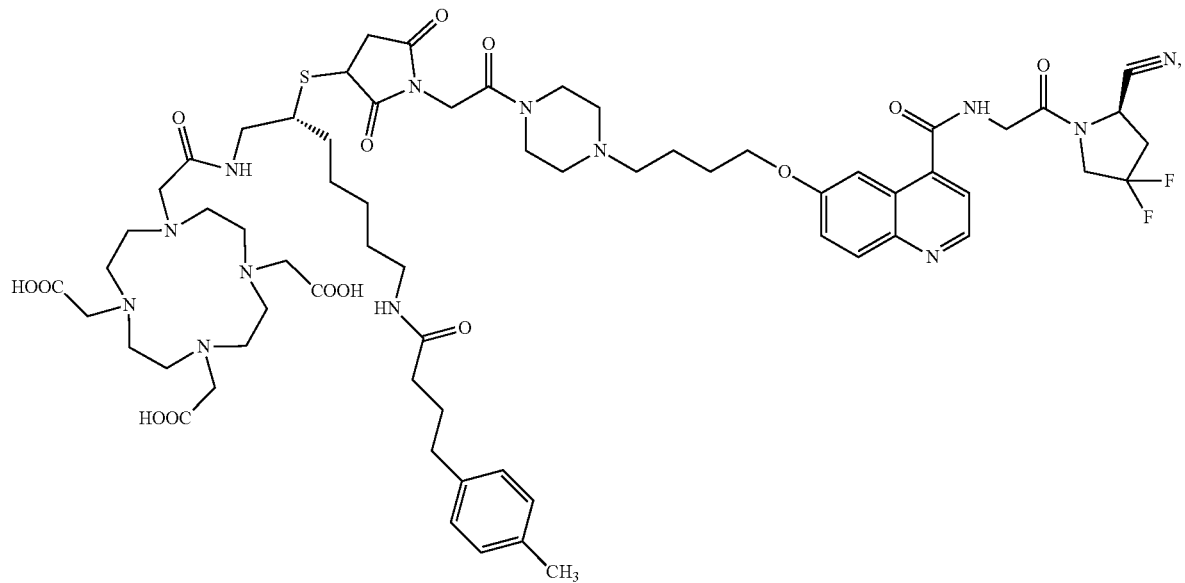

wherein
R1 is selected from R1-III-9, wherein the optical configuration of the optically active carbon is S configuration;
Code: FAPI-INER-1066-S;
Molecular weight: 1346.5;
Molecular formula: $C_{65}H_{89}F_2N_{13}O_{14}S$;

Structure 160:

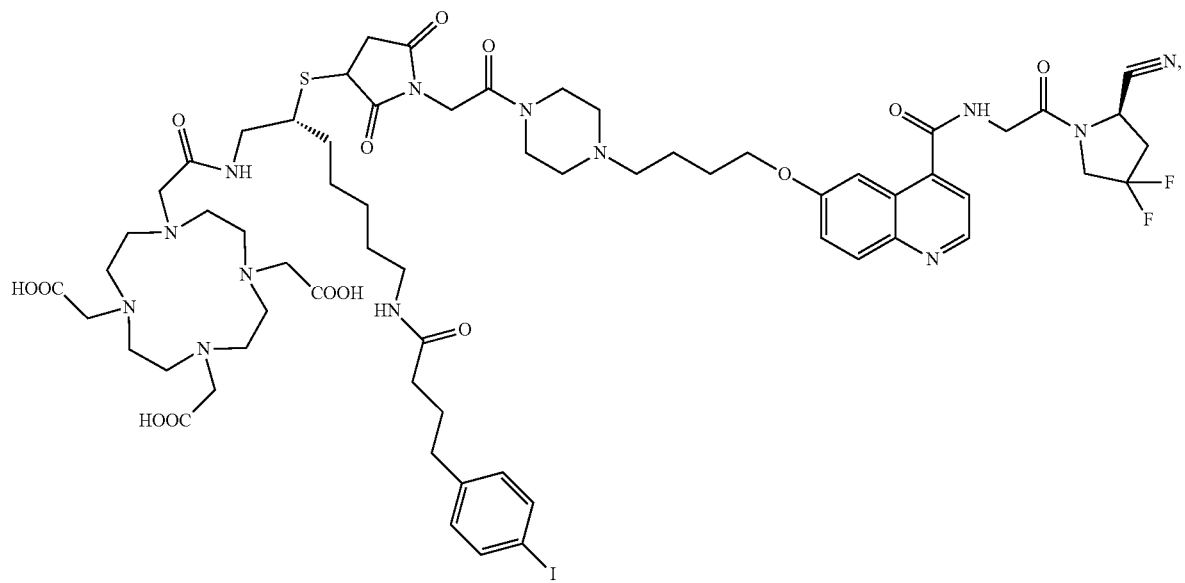

wherein
R1 is selected from R1-III-10, wherein the optical configuration of the optically active carbon is S configuration;
Code: FAPI-INER-1070-S;
Molecular weight: 1458.4;
Molecular formula: $C_{64}H_{86}F_2IN_{13}O_{14}S$;
or R2 is selected from R2-III-3 of the set of R2-III, R1 is any structure selected from the set of R1-III, and the D structure is

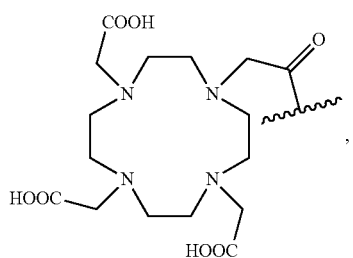 [SMILES: *C(=O)CN1CCN(CC(=O)O)CCN(CC(=O)O)CCN(CC(=O)O)CC1]
and thus the compound has a structure represented by formulas below:
Structure 161:
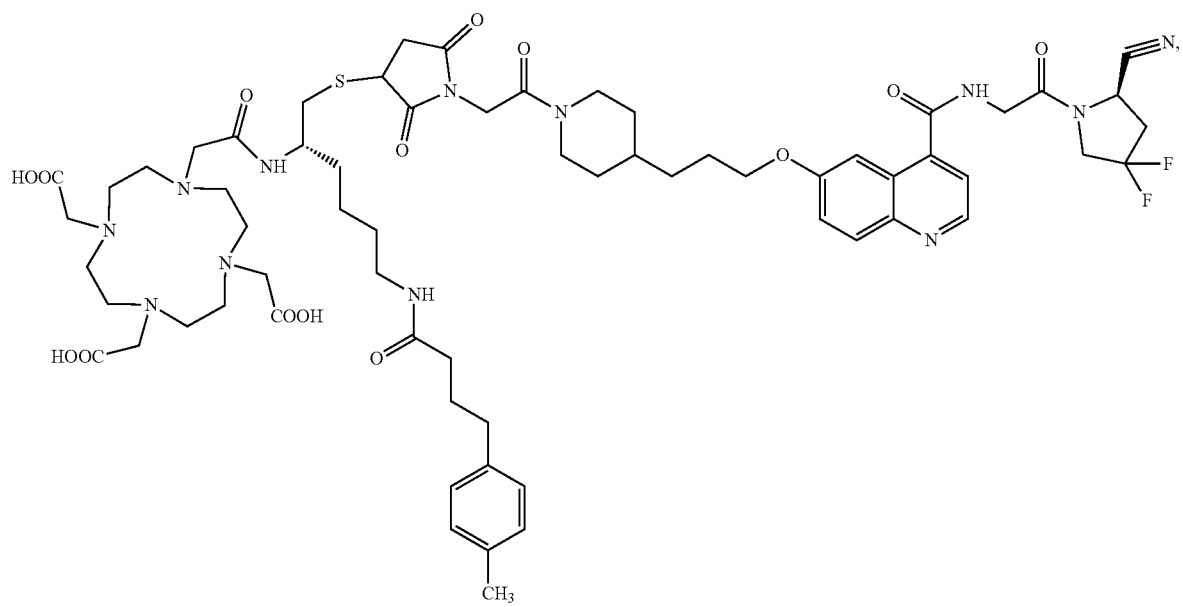
wherein
R1 is selected from R1-III-1, wherein the optical configuration of the optically active carbon is S configuration;
Code: FAPI-INER-1059-S;
Molecular weight: 1317.5;
Molecular formula: $C_{64}H_{86}F_2N_{12}O_{14}S$;

Structure 162:

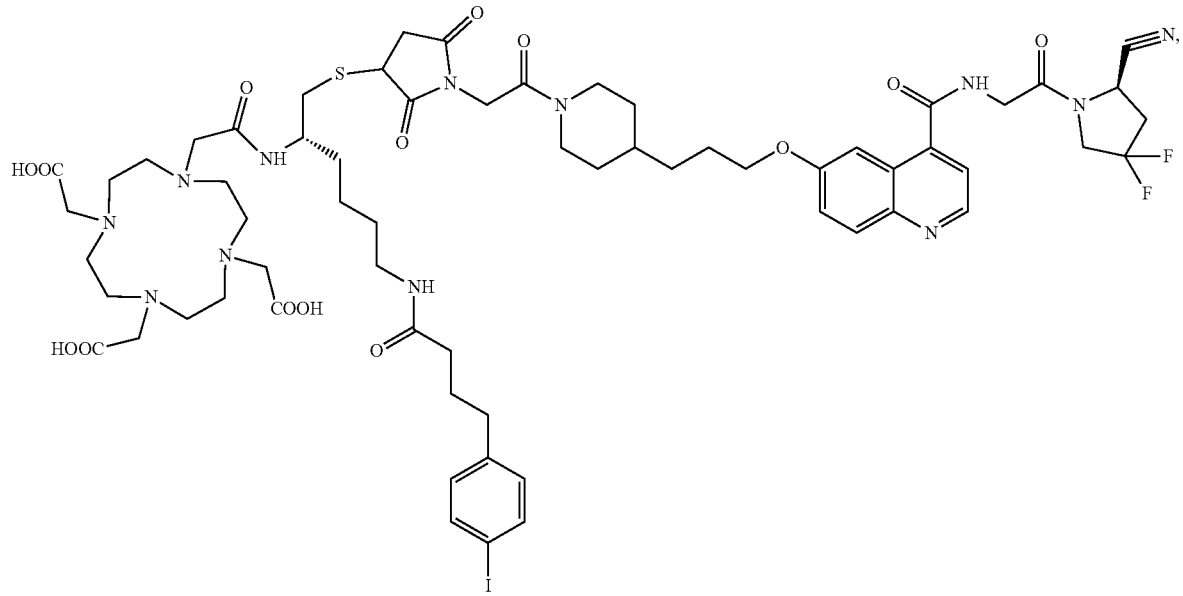

wherein
R1 is selected from R1-III-2, wherein the optical configuration of the optically active carbon is S configuration;
Code: FAPI-INER-1063-S;
Molecular weight: 1429.3;
Molecular formula: $C_{63}H_{83}F_2IN_{12}O_{14}S$;

Structure 163:

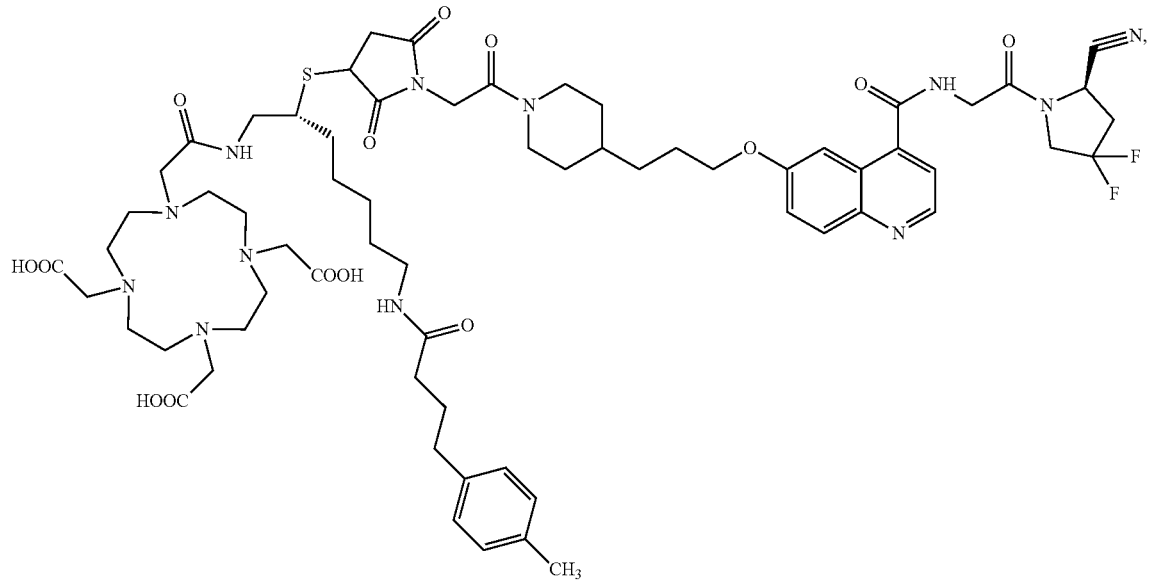

wherein
R1 is selected from R1-III-9, wherein the optical configuration of the optically active carbon is S configuration;
Code: FAPI-INER-1067-S;
Molecular weight: 1331.5;
Molecular formula: $C_{65}H_{88}F_2N_{12}O_{14}S$;

Structure 164:

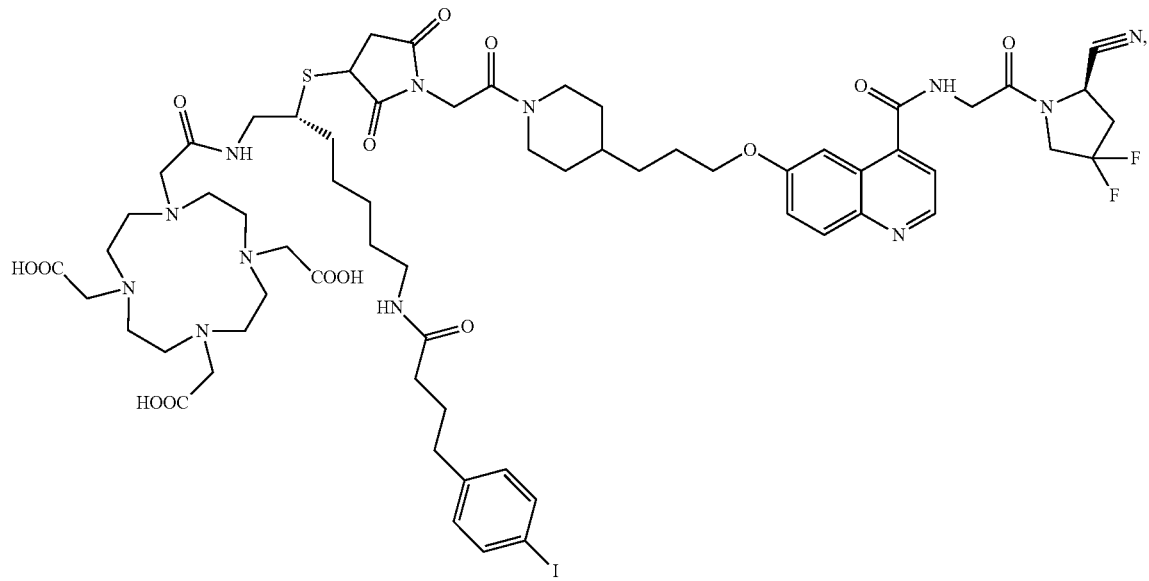

wherein
R1 is selected from R1-III-10, wherein the optical configuration of the optically active carbon is S configuration;

Code: FAPI-INER-1071-S;
Molecular weight: 1458.4;
Molecular formula: $C_{64}H_{86}F_2IN_{13}O_{14}S$;
or R2 is selected from R2-III-4 of the set of R2-III, R1 is any structure selected from the set of R1-III, and the D structure is

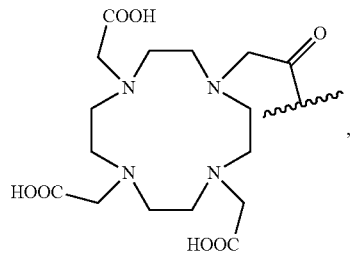 [SMILES: *C(=O)CN1CCN(CC(=O)O)CCN(CC(=O)O)CCN(CC(=O)O)CC1]

and thus the compound has a structure represented by formulas below:
Structure 165:

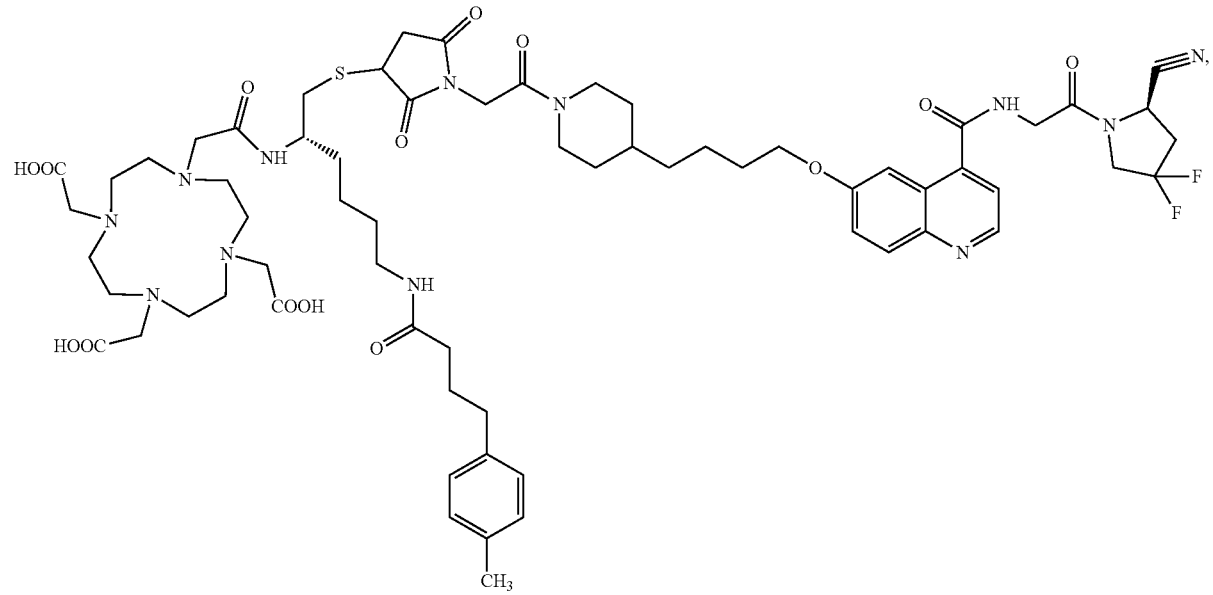

wherein
R1 is selected from R1-III-1, wherein the optical configuration of the optically active carbon is S configuration;
Code: FAPI-INER-1060-S;
Molecular weight: 1331.5;
Molecular formula: $C_{65}H_{88}F_2N_{12}O_{14}S$;
Structure 166:

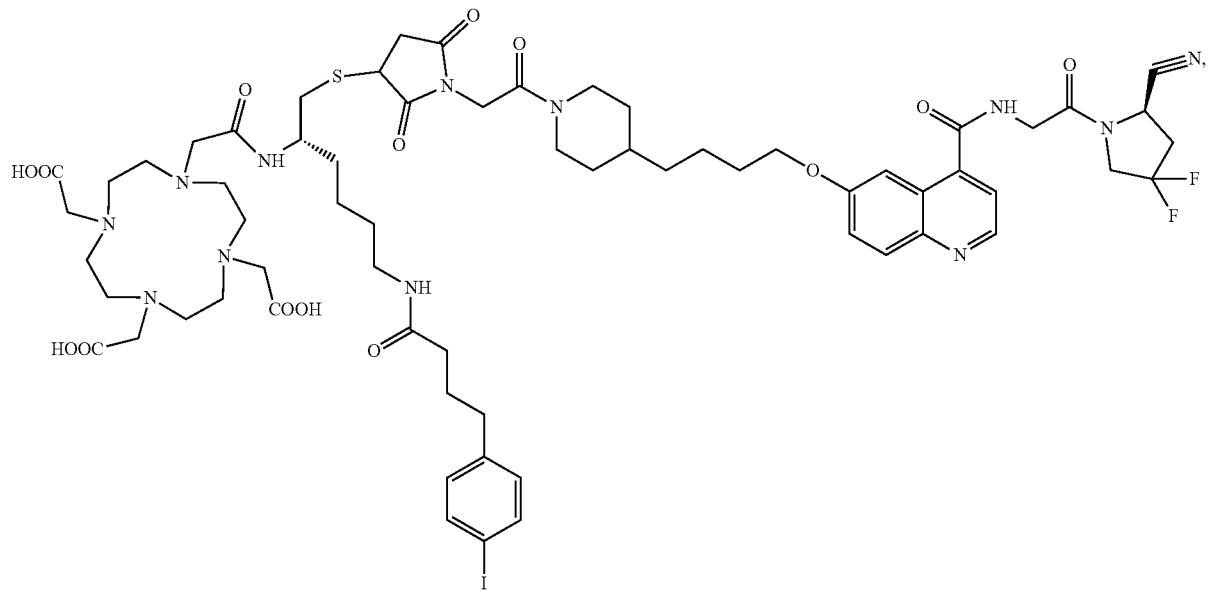

wherein
R1 is selected from R1-III-2, wherein the optical configuration of the optically active carbon is S configuration;
Code: FAPI-INER-1064-S;
Molecular weight: 1443.3;
Molecular formula: $C_{64}H_{85}F_2IN_{12}O_{14}S$;
Structure 167:

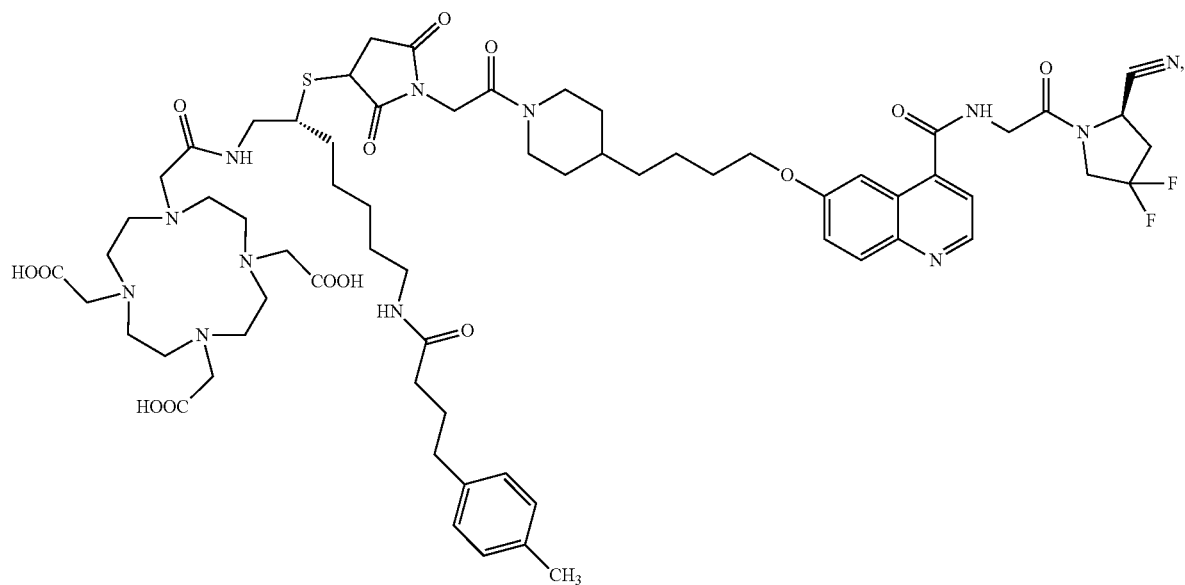

wherein
R1 is selected from R1-III-9, wherein the optical configuration of the optically active carbon is S configuration;
Code: FAPI-INER-1068-S;
Molecular weight: 1345.5;
Molecular formula: $C_{66}H_{90}F_2N_{12}O_{14}S$;
Structure 168:

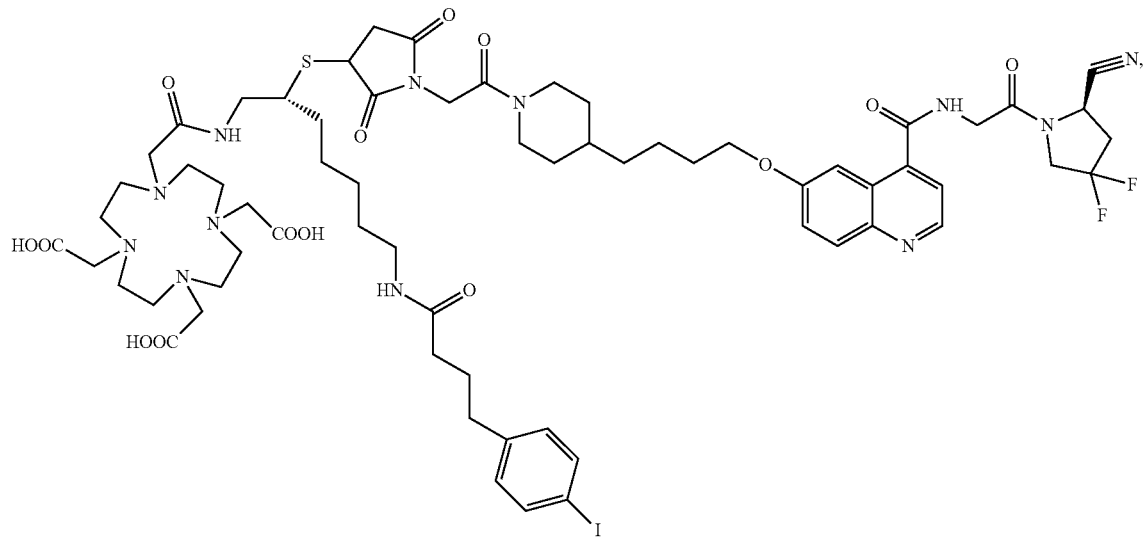

wherein
R1 is selected from R1-III-10, wherein the optical configuration of the optically active carbon is S configuration;
Code: FAPI-INER-1072-S;
Molecular weight: 1457.4;
Molecular formula: $C_{65}H_{87}F_2IN_{12}O_{14}S$;
or R2 is selected from R2-III-13 of the set of R2-III, R1 is any structure selected from the set of R1-III, and the D structure is

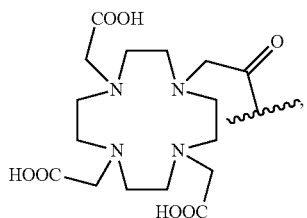

and thus the compound has a structure represented by formulas below:

Structure 169:
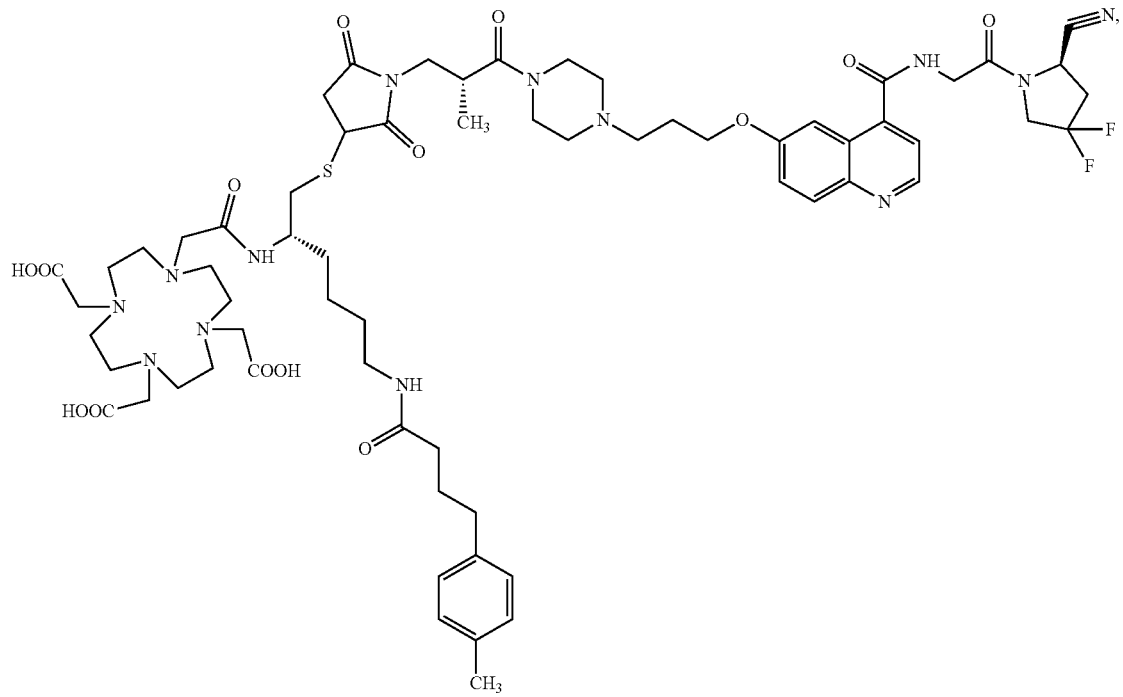
wherein
the optical configuration of the optically active carbon of R2-III-13 is S configuration; R1 is selected from R1-III-1, wherein the optical configuration of the optically active carbon is S configuration;
Code: FAPI-INER-1073-SS;
Molecular weight: 1346.5;
Molecular formula: $C_{65}H_{89}F_2N_{13}O_{14}S$;
Structure 170:
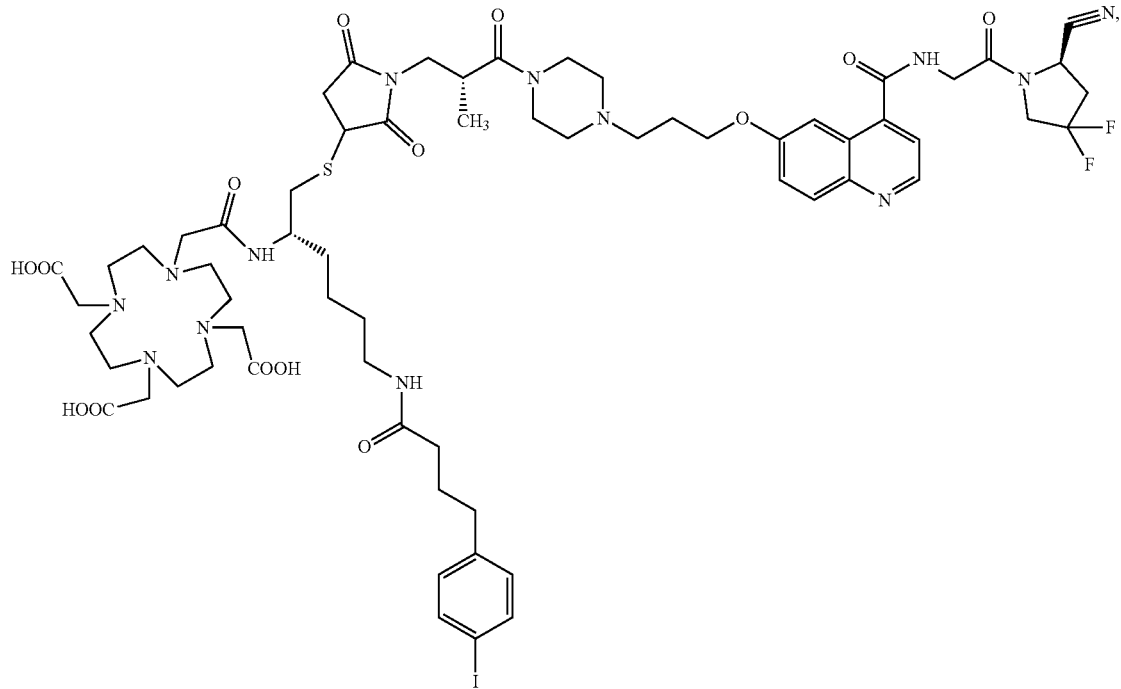 [SMILES: C[C@H](CN1C(=O)CC(SC[C@H](CCCCNC(=O)CCCc2ccc(I)cc2)NC(=O)CN2CCN(CC(=O)O)CCN(CC(=O)O)CCN(CC(=O)O)CC2)C1=O)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-III-13 is S configuration; R1 is selected from R1-III-2, wherein the optical configuration of the optically active carbon is S configuration;

Code: FAPI-INER-1077-SS;
Molecular weight: 1458.4;
Molecular formula: $C_{64}H_{86}F_2IN_{13}O_{14}S$;
Structure 171:

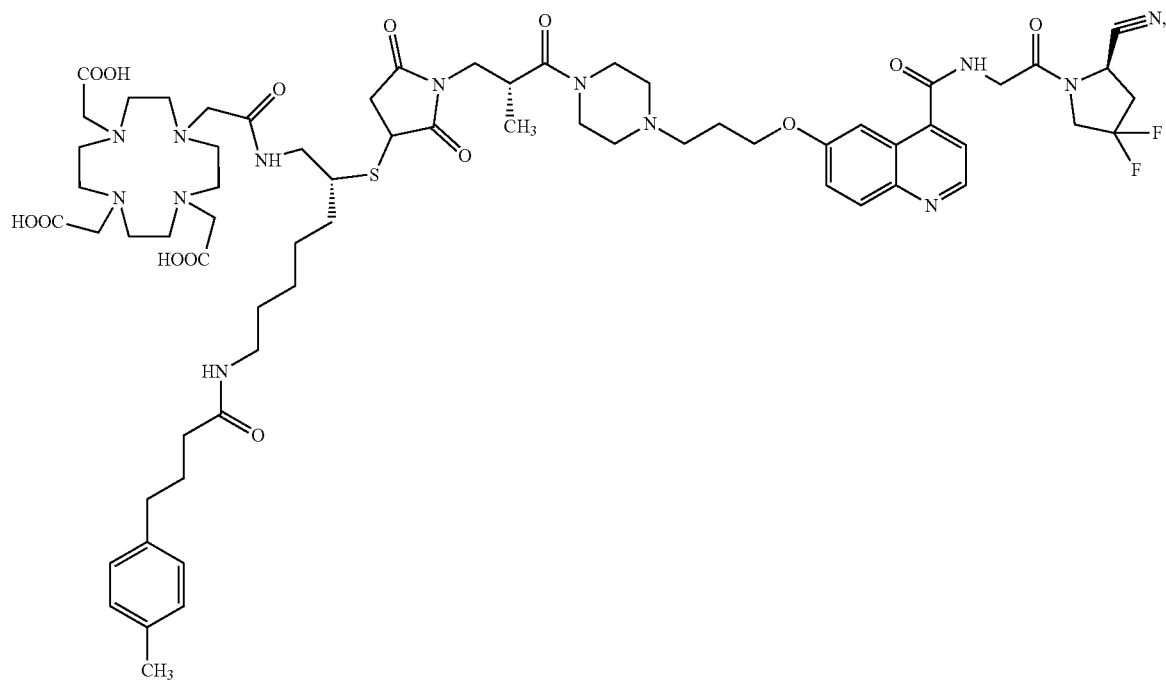 [SMILES: Cc1ccc(CCCC(=O)NCCCCC[C@H](CNC(=O)CN2CCN(CC(=O)O)CCN(CC(=O)O)CCN(CC(=O)O)CC2)SC2CC(=O)N(C[C@@H](C)C(=O)N3CCN(CCCOc4ccc5nccc(C(=O)NCC(=O)N6CC(F)(F)C[C@@H]6C#N)c5c4)CC3)C2=O)cc1]

wherein
the optical configuration of the optically active carbon of R2-III-13 is S configuration; R1 is selected from R1-III-9, wherein the optical configuration of the optically active carbon is S configuration;

Code: FAPI-INER-1081-SS;
Molecular weight: 1360.5;
Molecular formula: $C_{66}H_{91}F_2N_{13}O_{14}S$;

Structure 172:

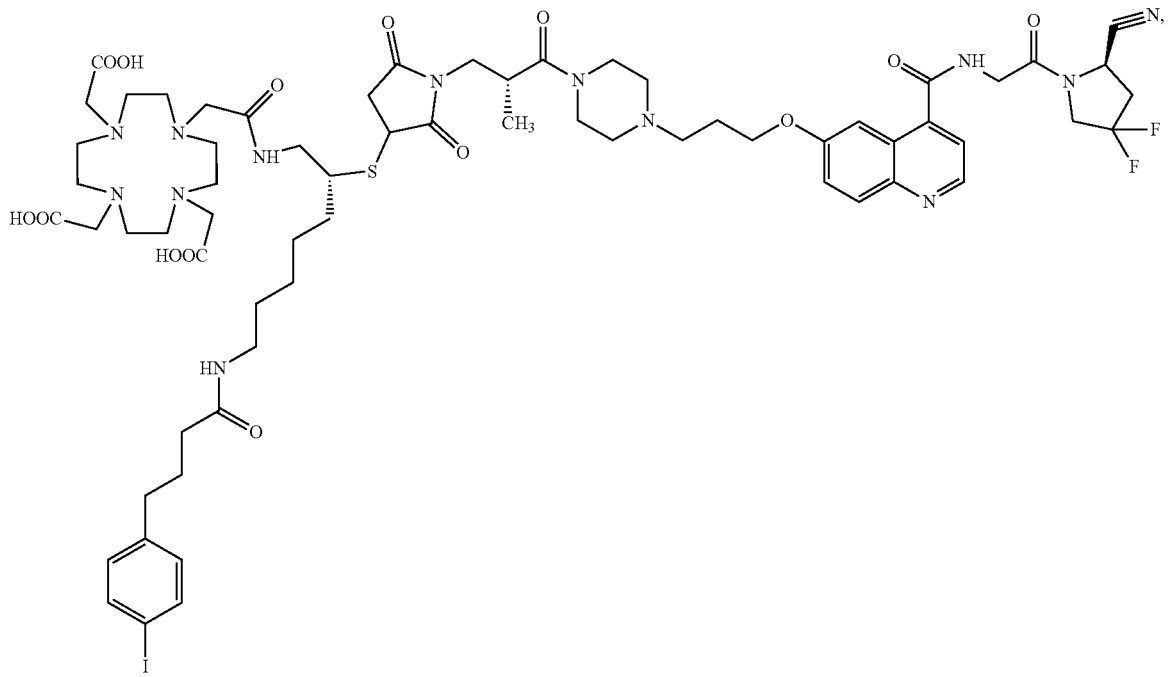 [SMILES: C[C@H](CN1C(=O)CC(S[C@H](CCCCCNC(=O)CCCc2ccc(I)cc2)CNC(=O)CN2CCN(CC(=O)O)CCN(CC(=O)O)CCN(CC(=O)O)CC2)C1=O)C(=O)N1CCN(CCCOc2ccc3nccc(C(=O)NCC(=O)N4CC(F)(F)C[C@@H]4C#N)c3c2)CC1]

wherein
the optical configuration of the optically active carbon of R2-III-13 is S configuration; R1 is selected from R1-III-10, wherein the optical configuration of the optically active carbon is S configuration;

Code: FAPI-INER-1085-SS;

Molecular weight: 1472.4;

Molecular formula: $C_{65}H_{88}F_2IN_{13}O_{14}S$ or R2 is selected from R2-III-14 of the set of R2-III, R1 is any structure selected from the set of R1-III, and the D structure is

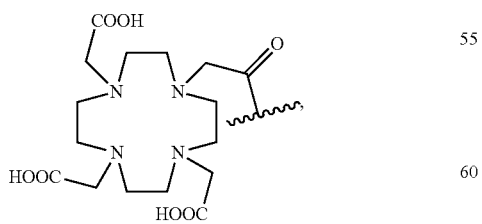

and thus the compound has a structure represented by formulas below:

Structure 173:
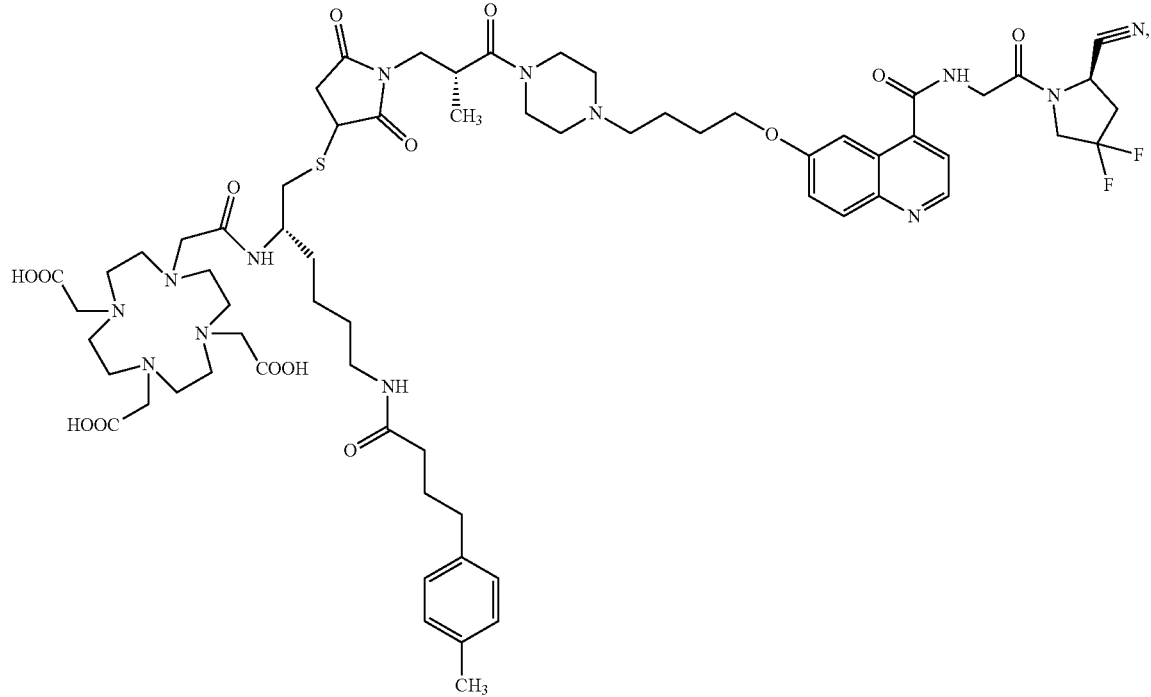 [SMILES: Cc1ccc(CCCC(=O)NCCCC[C@@H](CSC2CC(=O)N(C[C@@H](C)C(=O)N3CCN(CCCCOc4ccc5nccc(C(=O)NCC(=O)N6CC(F)(F)C[C@@H]6C#N)c5c4)CC3)C2=O)NC(=O)CN2CCN(CC(=O)O)CCN(CC(=O)O)CCN(CC(=O)O)CC2)cc1]
wherein
the optical configuration of the optically active carbon of R2-III-14 is S configuration; R1 is selected from R1-III-1, wherein the optical configuration of the optically active carbon is S configuration;
Code: FAPI-INER-1074-SS;
Molecular weight: 1360.5;
Molecular formula: $C_{66}H_{91}F_2N_{13}O_{14}S$;
Structure 174:
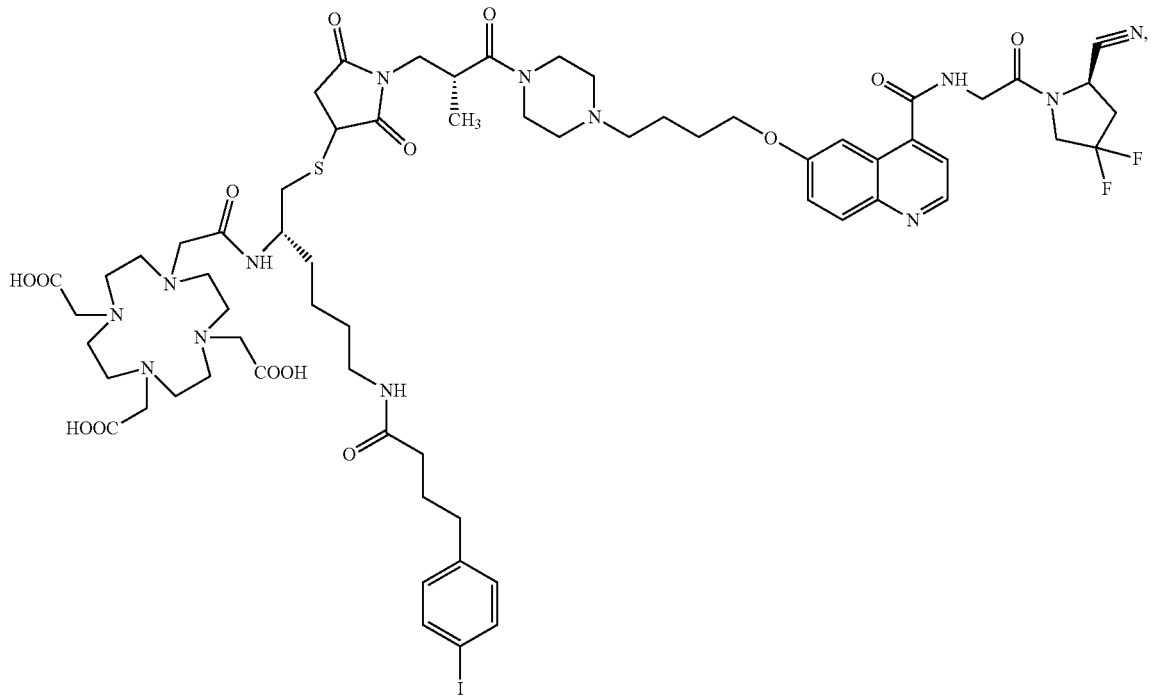 [SMILES: C[C@H](CN1C(=O)CC(SC[C@H](CCCCNC(=O)CCCc2ccc(I)cc2)NC(=O)CN2CCN(CC(=O)O)CCN(CC(=O)O)CCN(CC(=O)O)CC2)C1=O)C(=O)N1CCN(CCCCOc2ccc3nccc(C(=O)NCC(=O)N4CC(F)(F)C[C@@H]4C#N)c3c2)CC1]

wherein
the optical configuration of the optically active carbon of R2-III-14 is S configuration; R1 is selected from R1-III-2, wherein the optical configuration of the optically active carbon is S configuration;
Code: FAPI-INER-1078-SS;
Molecular weight: 1472.4;
Molecular formula: $C_{65}H_{88}F_2IN_{13}O_{14}S$;
Structure 175:

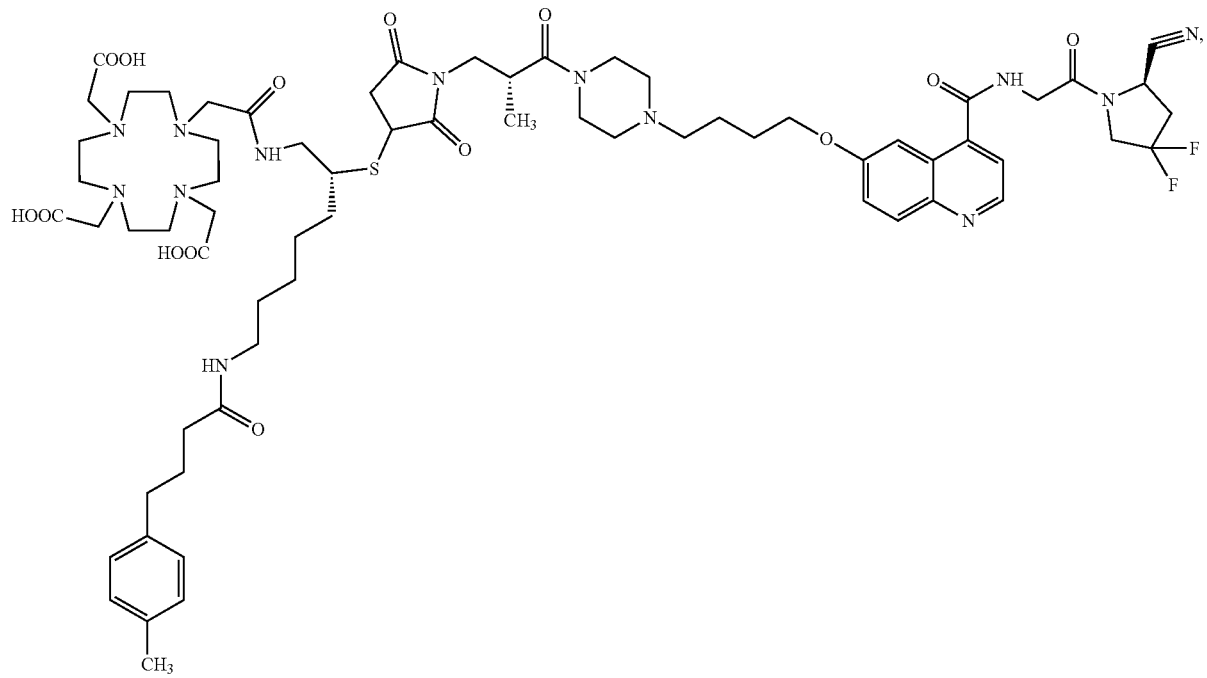 [SMILES: Cc1ccc(CCCC(=O)NCCCCC[C@H](CNC(=O)CN2CCN(CC(=O)O)CCN(CC(=O)O)CCN(CC(=O)O)CC2)SC2CC(=O)N(C[C@@H](C)C(=O)N3CCN(CCCCOc4ccc5nccc(C(=O)NCC(=O)N6CC(F)(F)C[C@@H]6C#N)c5c4)CC3)C2=O)cc1]

wherein
the optical configuration of the optically active carbon of R2-III-14 is S configuration; R1 is selected from R1-III-9, wherein the optical configuration of the optically active carbon is S configuration;
Code: FAPI-INER-1082-SS;
Molecular weight: 1374.5;
Molecular formula: $C_{67}H_{93}F_2N_{13}O_{14}S$;

Structure 176:

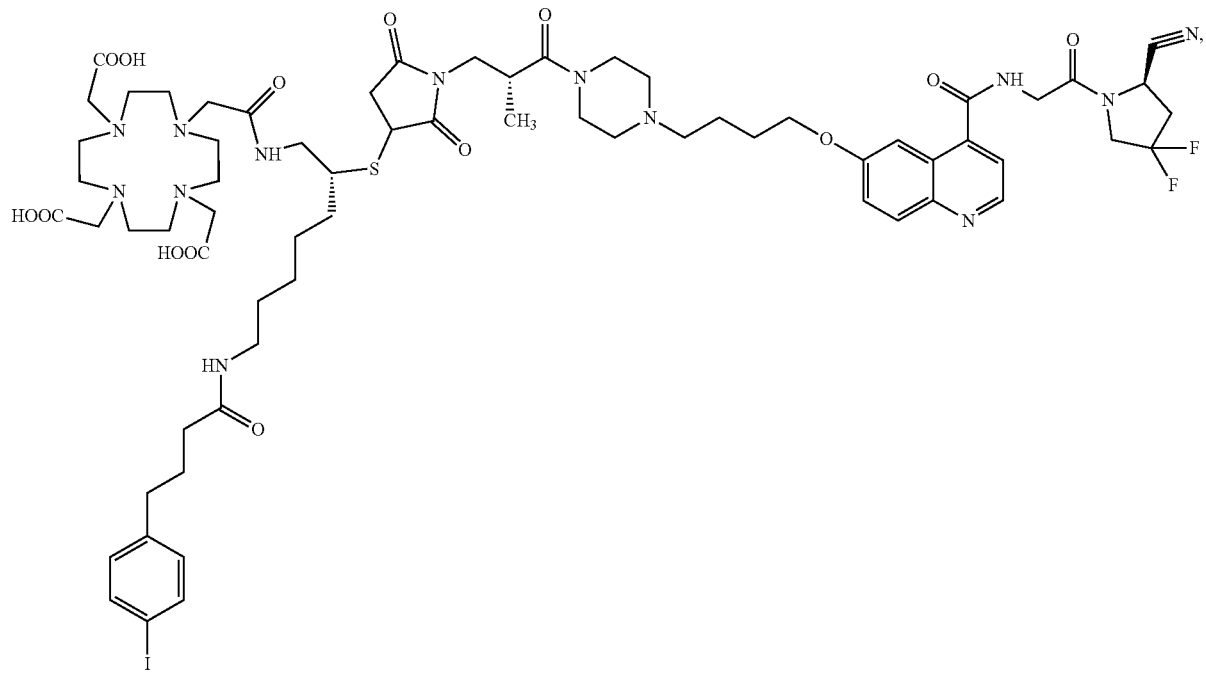 [SMILES: C[C@H](CN1C(=O)CC(S[C@H](CCCCCNC(=O)CCCc2ccc(I)cc2)CNC(=O)CN2CCN(CC(=O)O)CCN(CC(=O)O)CCN(CC(=O)O)CC2)C1=O)C(=O)N1CCN(CCCCOc2ccc3nccc(C(=O)NCC(=O)N4CC(F)(F)C[C@@H]4C#N)c3c2)CC1]

wherein the optical configuration of the optically active carbon of R2-III-14 is S configuration; R1 is selected from R1-III-10, wherein the optical configuration of the optically active carbon is S configuration;

Code: FAPI-INER-1086-SS;

Molecular weight: 1486.4;

Molecular formula: $C_{66}H_{90}F_2IN_{13}O_{14}S$;

or R2 is selected from R2-III-15 of the set of R2-III, R1 is any structure selected from the set of R1-III, and the D structure is

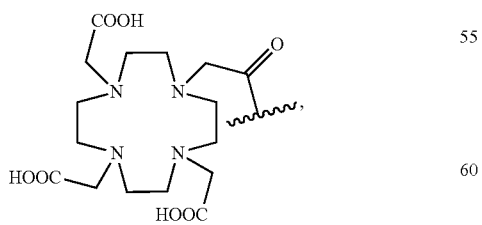

and thus the compound has a structure represented by formulas below:

Structure 177:
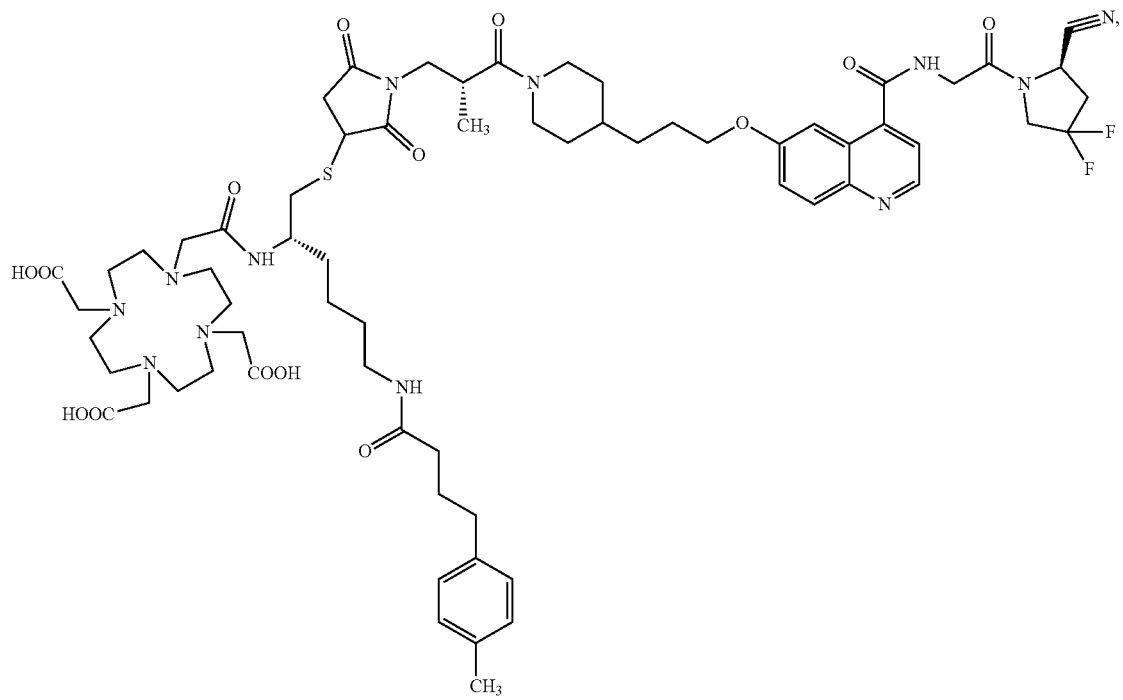 [SMILES: C[C@H](CN1C(=O)CC(SC[C@H](CCCCNC(=O)CCCc2ccc(I)cc2)NC(=O)CN2CCN(CC(=O)O)CCN(CC(=O)O)CCN(CC(=O)O)CC2)C1=O)C(=O)N1CCC(CCCOc2ccc3nccc(C(=O)NCC(=O)N4CC(F)(F)C[C@@H]4C#N)c3c2)CC1]
wherein
the optical configuration of the optically active carbon of R2-III-15 is S configuration; R1 is selected from R1-III-1, wherein the optical configuration of the optically active carbon is S configuration;
Code: FAPI-INER-1075-SS;
Molecular weight: 1345.5;
Molecular formula: $C_{66}H_{90}F_2N_{12}O_{14}S$;
Structure 178:
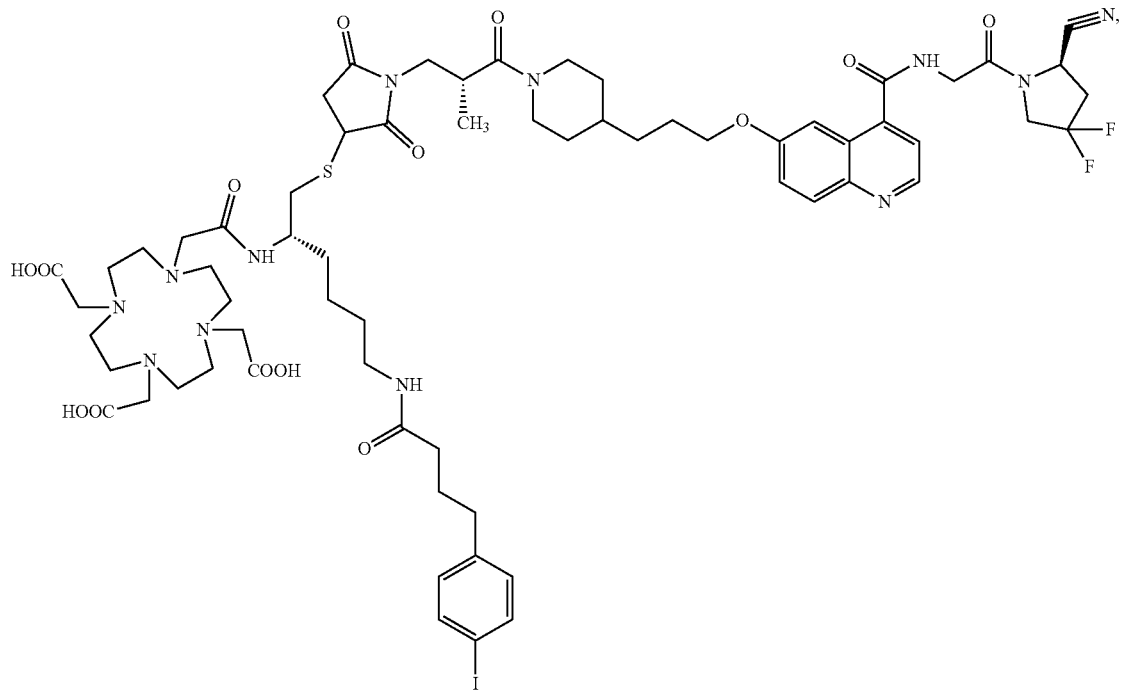

wherein
the optical configuration of the optically active carbon of R2-III-15 is S configuration; R1 is selected from R1-III-2, wherein the optical configuration of the optically active carbon is S configuration;

Code: FAPI-INER-1079-SS;
Molecular weight: 1457.4;
Molecular formula: $C_{65}H_{87}F_2IN_{12}O_{14}S$;
Structure 179:

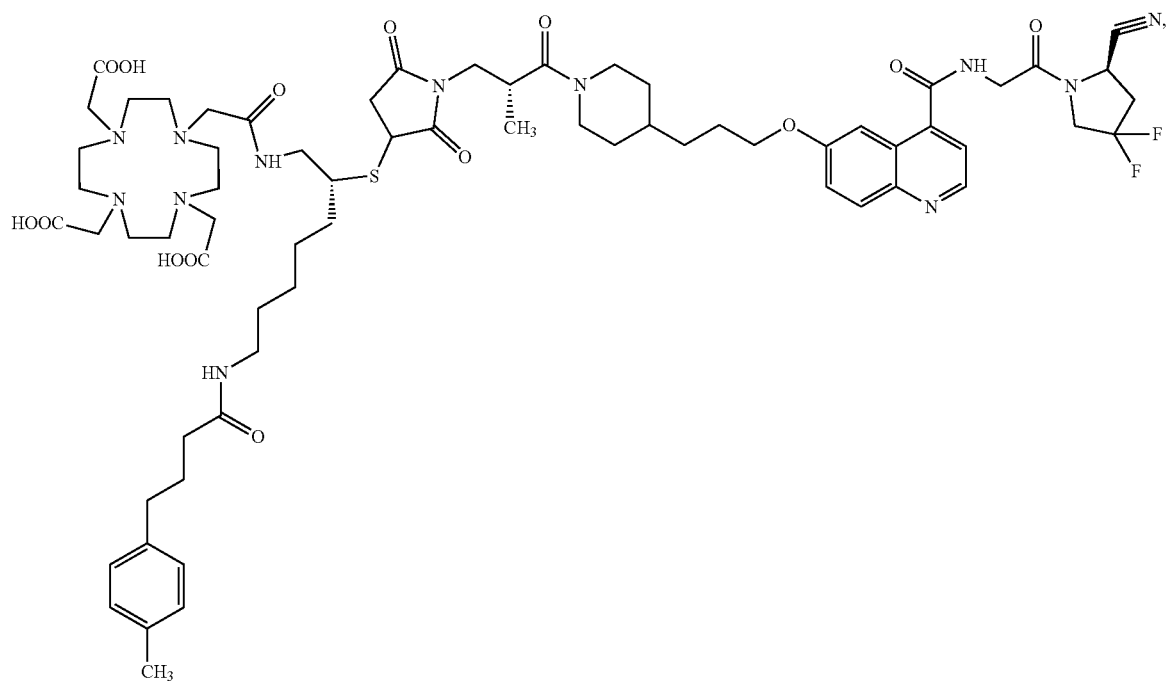 [SMILES: Cc1ccc(CCCC(=O)NCCCCC[C@H](CNC(=O)CN2CCN(CC(=O)O)CCN(CC(=O)O)CCN(CC(=O)O)CC2)SC2CC(=O)N(C[C@@H](C)C(=O)N3CCC(CCCOc4ccc5nccc(C(=O)NCC(=O)N6CC(F)(F)C[C@@H]6C#N)c5c4)CC3)C2=O)cc1]

wherein
the optical configuration of the optically active carbon of R2-III-15 is S configuration; R1 is selected from R1-III-9, wherein the optical configuration of the optically active carbon is S configuration;

Code: FAPI-INER-1083-SS;
Molecular weight: 1359.5;
Molecular formula: $C_{67}H_{92}F_2N_{12}O_{14}S$;

Structure 180:

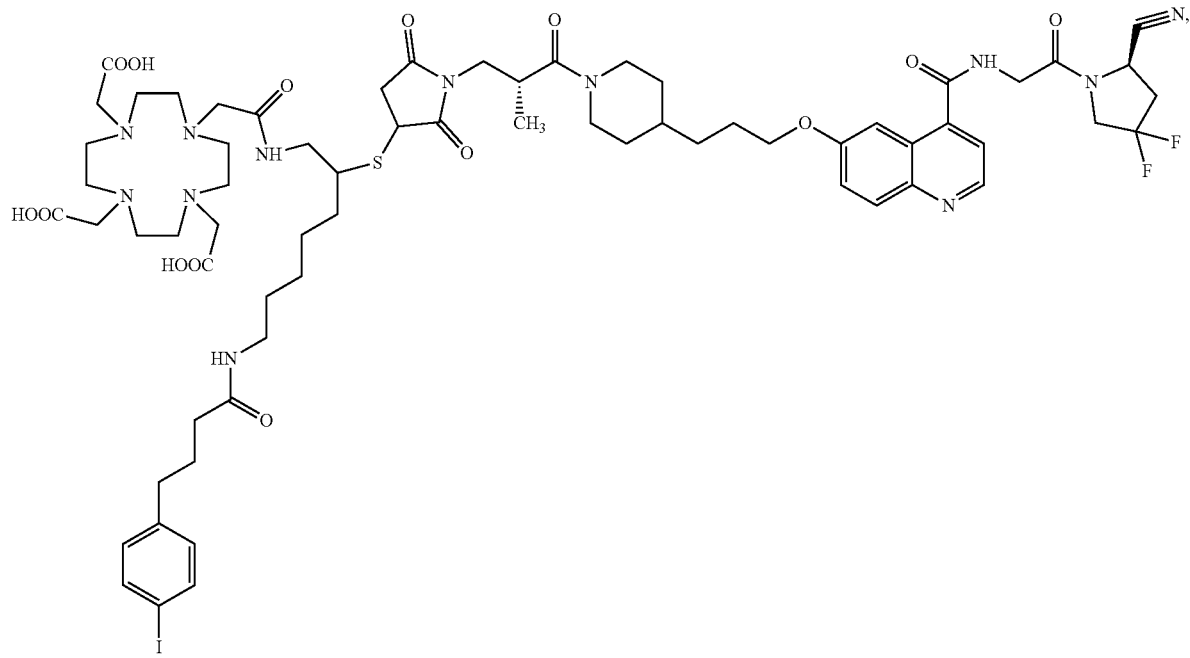 [SMILES: C[C@H](CN1C(=O)CC(SC(CCCCCNC(=O)CCCc2ccc(I)cc2)CNC(=O)CN2CCN(CC(=O)O)CCN(CC(=O)O)CCN(CC(=O)O)CC2)C1=O)C(=O)N1CCC(CCCOc2ccc3nccc(C(=O)NCC(=O)N4CC(F)(F)C[C@@H]4C#N)c3c2)CC1]

wherein
the optical configuration of the optically active carbon of R2-III-15 is S configuration; R1 is selected from R1-III-10, wherein the optical configuration of the optically active carbon is S configuration;

Code: FAPI-INER-1087-SS;

Molecular weight: 1471.4;

Molecular formula: $C_{66}H_{89}F_2IN_{12}O_{14}S$;

or R2 is selected from R2-III-16 of the set of R2-III, R1 is any structure selected from the set of R1-III, and the D structure is

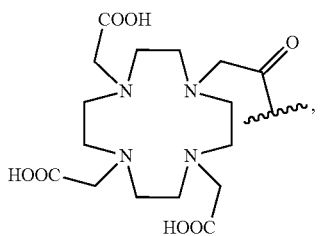

and thus the compound has a structure represented by formulas below:

Structure 181:

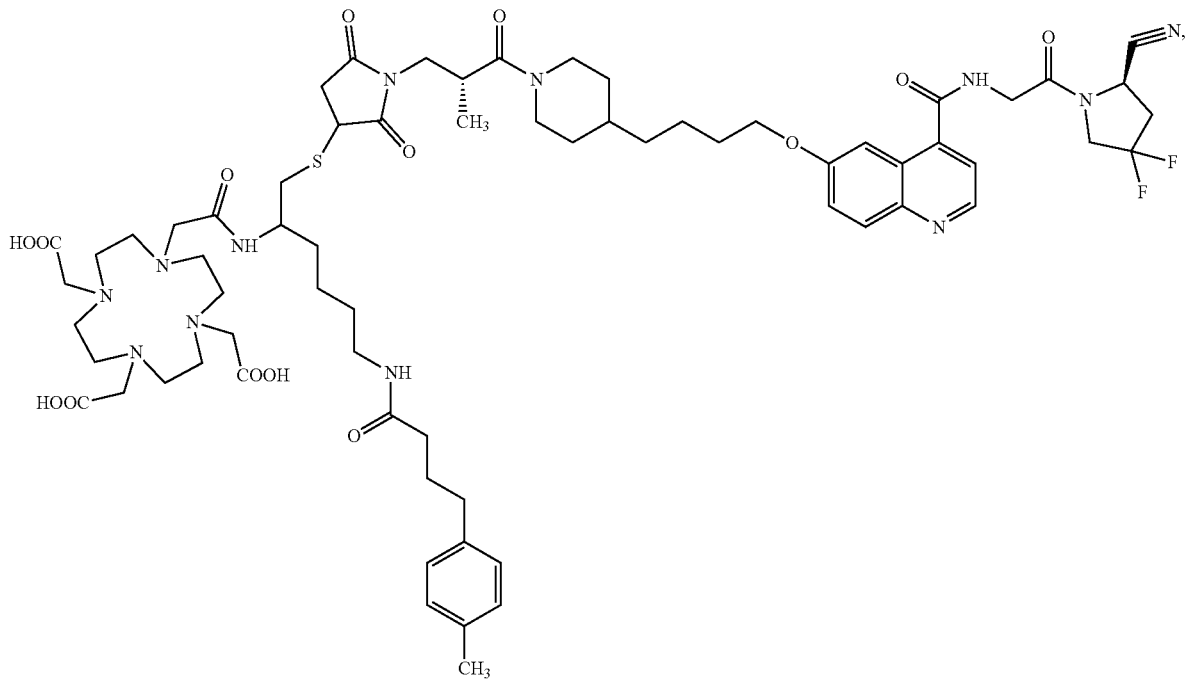 [SMILES: Cc1ccc(CCCC(=O)NCCCCC(CSC2CC(=O)N(C[C@@H](C)C(=O)N3CCC(CCCCOc4ccc5nccc(C(=O)NCC(=O)N6CC(F)(F)C[C@@H]6C#N)c5c4)CC3)C2=O)NC(=O)CN2CCN(CC(=O)O)CCN(CC(=O)O)CCN(CC(=O)O)CC2)cc1]

wherein
the optical configuration of the optically active carbon of R2-III-16 is S configuration; R1 is selected from R1-III-1, wherein the optical configuration of the optically active carbon is S configuration;
Code: FAPI-INER-1076-SS;
Molecular weight: 1359.5;
Molecular formula: $C_{67}H_{92}F_2N_{12}O_{14}S$;

Structure 182:

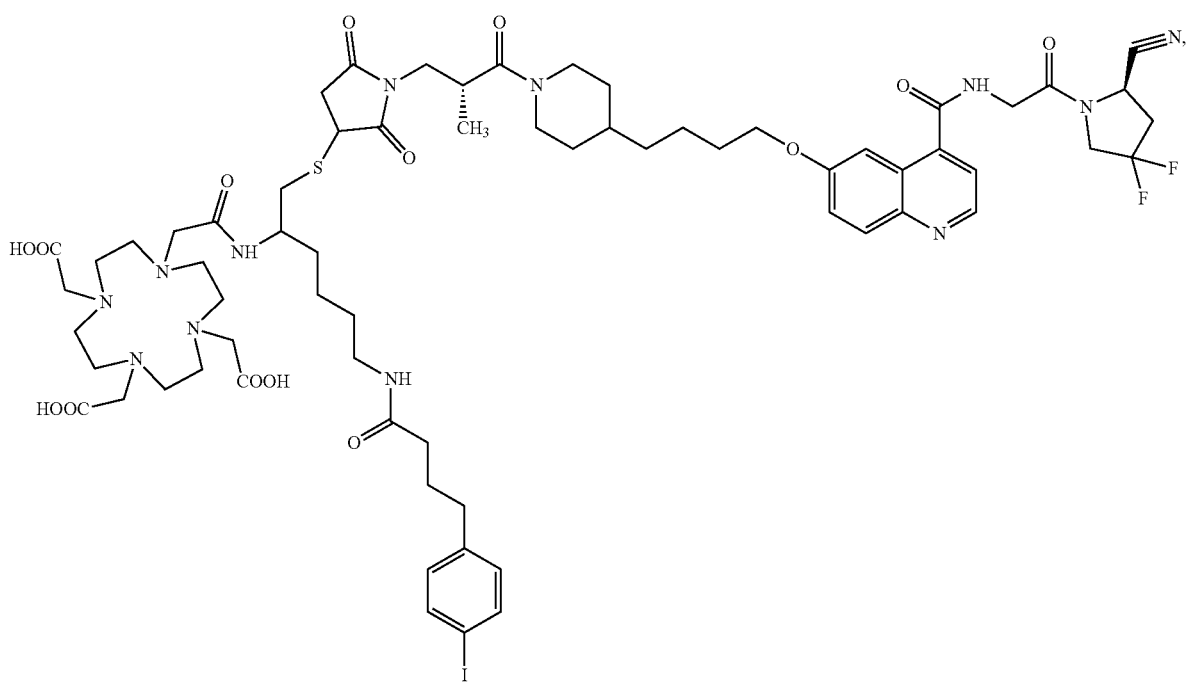 [SMILES: C[C@H](CN1C(=O)CC(SCC(CCCCNC(=O)CCCc2ccc(I)cc2)NC(=O)CN2CCN(CC(=O)O)CCN(CC(=O)O)CCN(CC(=O)O)CC2)C1=O)C(=O)N1CCC(CCCCOc2ccc3nccc(C(=O)NCC(=O)N4CC(F)(F)C[C@@H]4C#N)c3c2)CC1]

wherein
the optical configuration of the optically active carbon of R2-III-16 is S configuration; R1 is selected from R1-III-2, wherein the optical configuration of the optically active carbon is S configuration;
Code: FAPI-INER-1080-SS;
Molecular weight: 1471.4;
Molecular formula: $C_{66}H_{89}F_2IN_{12}O_{14}S$;

Structure 183:

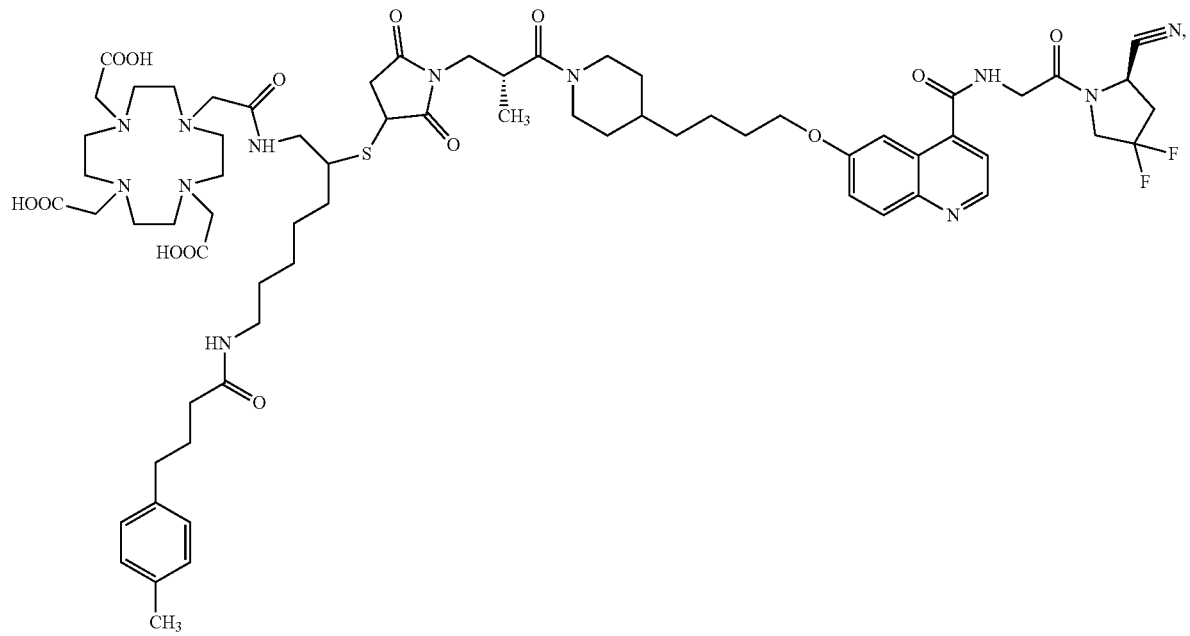 [SMILES: Cc1ccc(CCCC(=O)NCCCCCC(CNC(=O)CN2CCN(CC(=O)O)CCN(CC(=O)O)CCN(CC(=O)O)CC2)SC2CC(=O)N(C[C@@H](C)C(=O)N3CCC(CCCCOc4ccc5nccc(C(=O)NCC(=O)N6CC(F)(F)C[C@@H]6C#N)c5c4)CC3)C2=O)cc1]

wherein
the optical configuration of the optically active carbon of R2-III-16 is S configuration; R1 is selected from R1-III-9, wherein the optical configuration of the optically active carbon is S configuration;
Code: FAPI-INER-1084-SS;
Molecular weight: 1373.6;
Molecular formula: $C_{68}H_{94}F_2N_{12}O_{14}S$;

Structure 184:

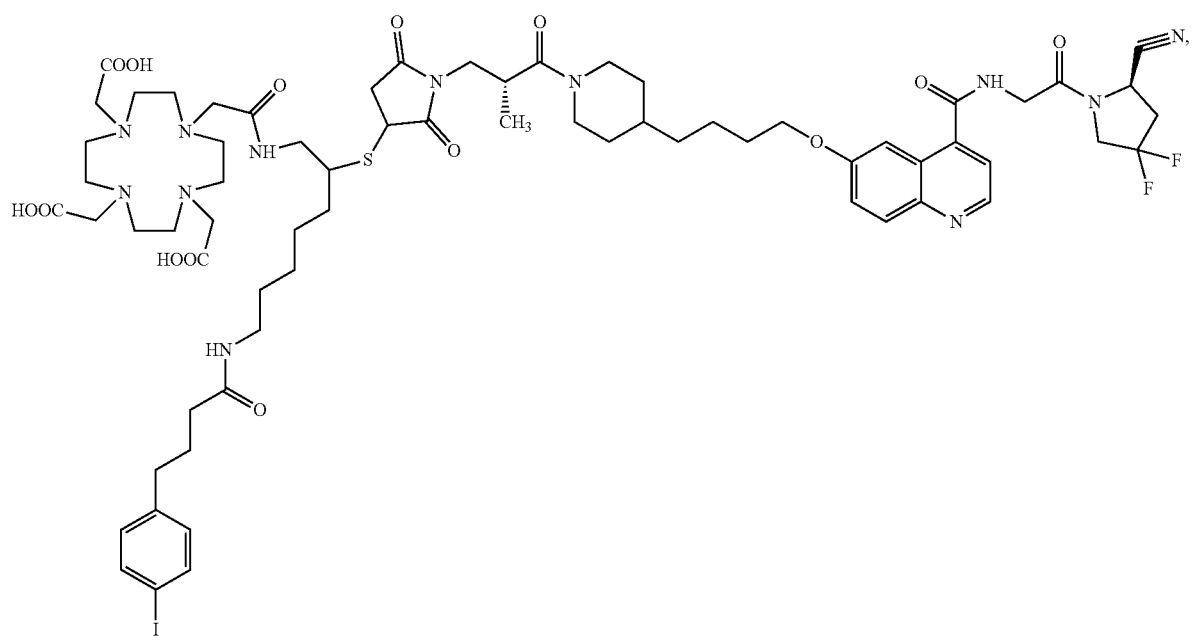 [SMILES: C[C@H](CN1C(=O)CC(SC(CCCCCNC(=O)CCCc2ccc(I)cc2)CNC(=O)CN2CCN(CC(=O)O)CCN(CC(=O)O)CCN(CC(=O)O)CC2)C1=O)C(=O)N1CCC(CCCCOc2ccc3nccc(C(=O)NCC(=O)N4CC(F)(F)C[C@@H]4C#N)c3c2)CC1]

wherein
the optical configuration of the optically active carbon of R2-III-16 is S configuration; R1 is selected from R1-III-10, wherein the optical configuration of the optically active carbon is S configuration;
Code: FAPI-INER-1088-SS;
Molecular weight: 1485.4;
Molecular formula: $C_{67}H_{91}F_2IN_{12}O_{14}S$;

or R2 is selected from R2-III-17 of the set of R2-III, R1 is any structure selected from the set of R1-III, and the D structure is

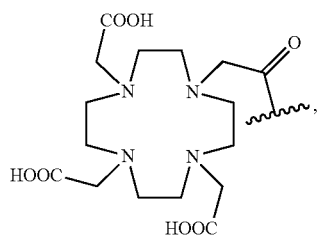

and thus the compound has a structure represented by formulas below:
Structure 185:

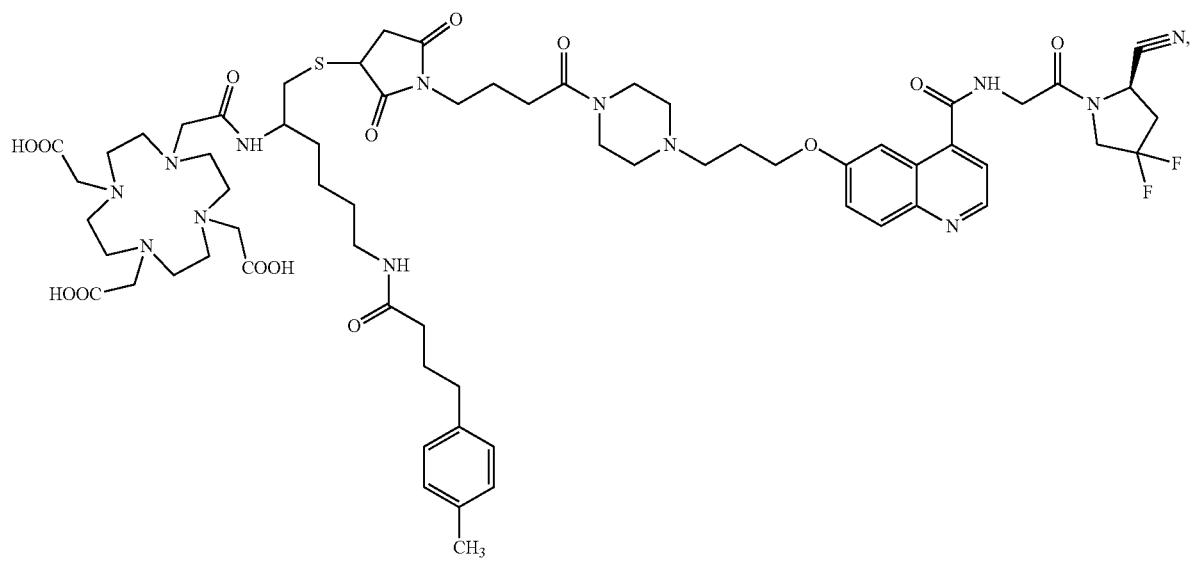

wherein
R1 is selected from R1-III-1, wherein the optical configuration of the optically active carbon is S configuration;
Code: FAPI-INER-1089-S;
Molecular weight: 1346.5;
Molecular formula: $C_{65}H_{89}F_2N_{13}O_{14}S$;

Structure 186:

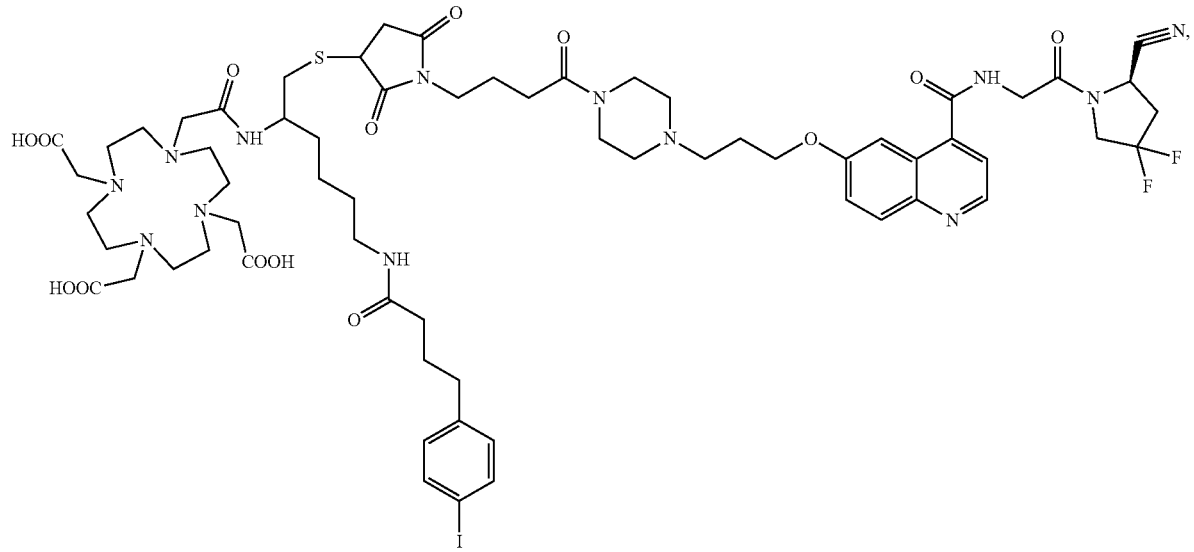

wherein
R1 is selected from R1-III-2, wherein the optical configuration of the optically active carbon is S configuration;
Code: FAPI-INER-1093-S;
Molecular weight: 1458.4;
Molecular formula: $C_{64}H_{86}F_2IN_{13}O_{14}S$;

Structure 187:

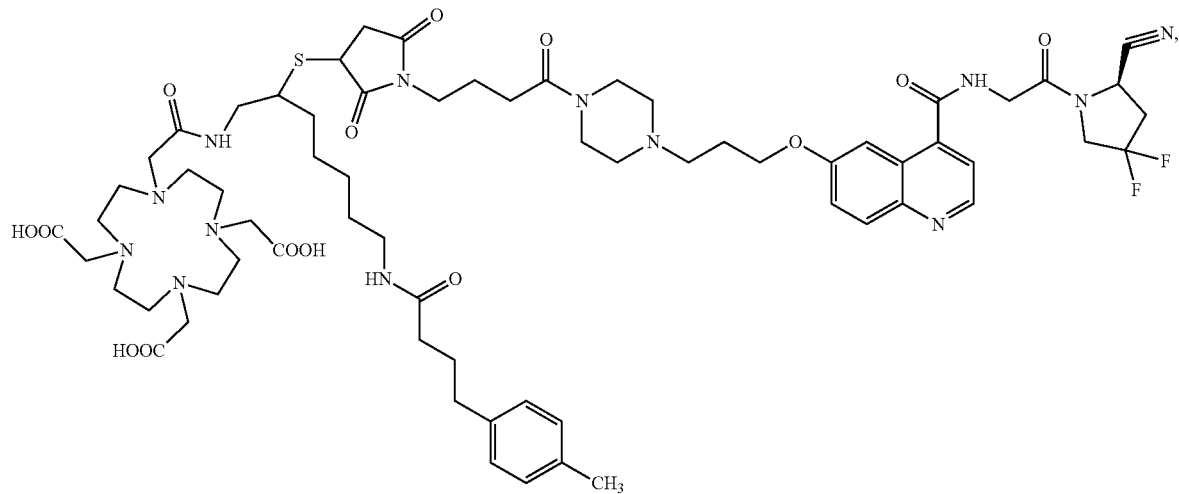

wherein
R1 is selected from R1-III-9, wherein the optical configuration of the optically active carbon is S configuration;
Code: FAPI-INER-1097-S;
Molecular weight: 1360.5;
Molecular formula: $C_{66}H_{91}F_2N_{13}O_{14}S$;

Structure 188:

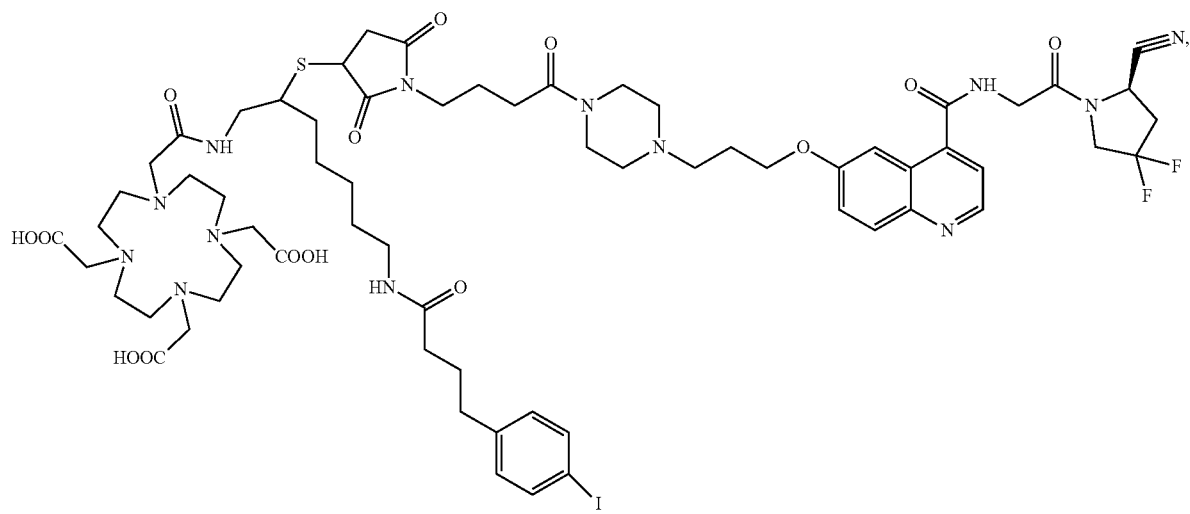

wherein
R1 is selected from R1-III-10, wherein the optical configuration of the optically active carbon is S configuration;

Code: FAPI-INER-1101-S;

Molecular weight: 1472.4;

Molecular formula: $C_{65}H_{88}F_2IN_{13}O_{14}S$;

or R2 is selected from R2-III-18 of the set of R2-III, R1 is any structure selected from the set of R1-III, and the D structure is

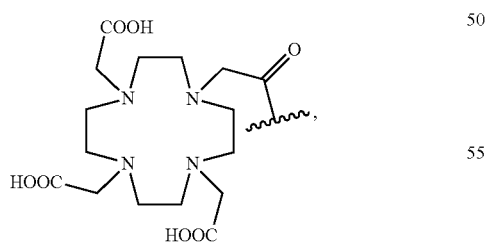

and thus the compound has a structure represented by formulas below:

Structure 189:

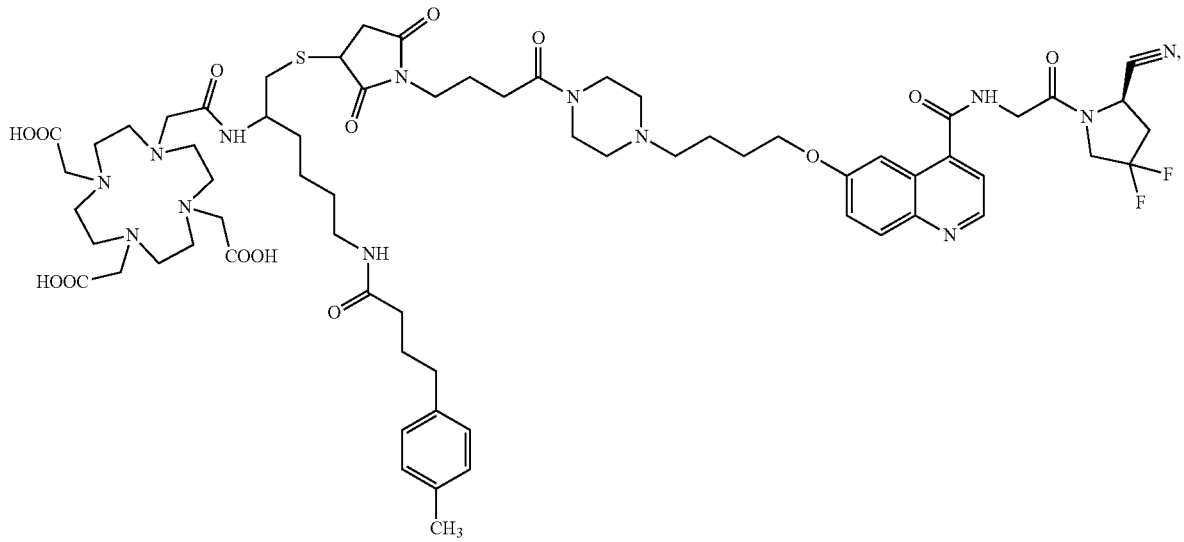

wherein
R1 is selected from R1-III-1, wherein the optical configuration of the optically active carbon is S configuration;
Code: FAPI-INER-1090-S;
Molecular weight: 1360.5;
Molecular formula: $C_{66}H_{91}F_2N_{13}O_{14}S$;

Structure 190:

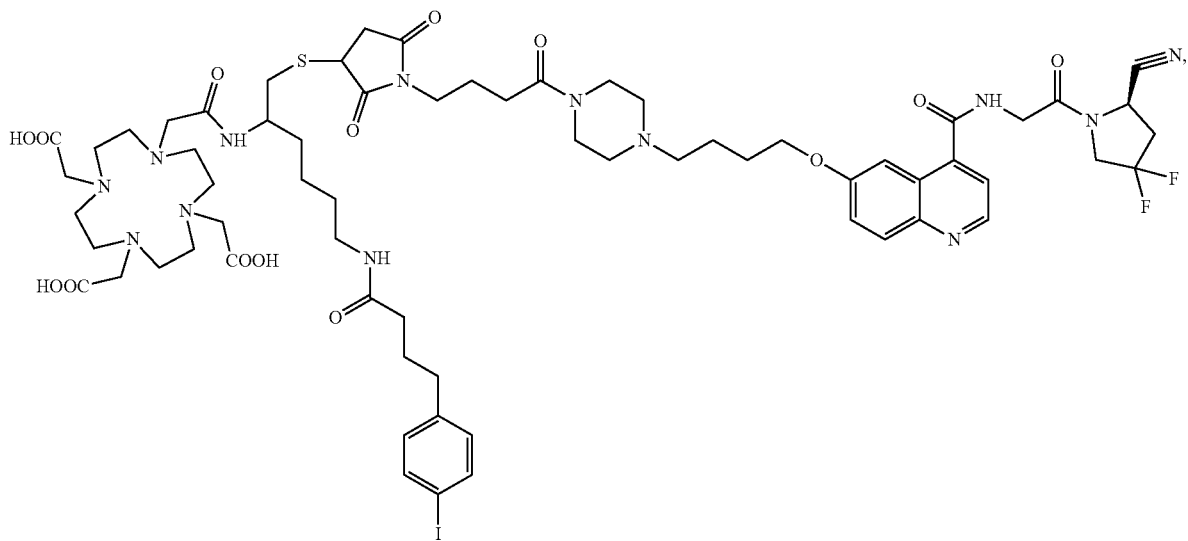

wherein
R1 is selected from R1-III-2, wherein the optical configuration of the optically active carbon is S configuration;
Code: FAPI-INER-1094-S;
Molecular weight: 1472.4;
Molecular formula: $C_{65}H_{88}F_2IN_{13}O_{14}S$;

Structure 191:

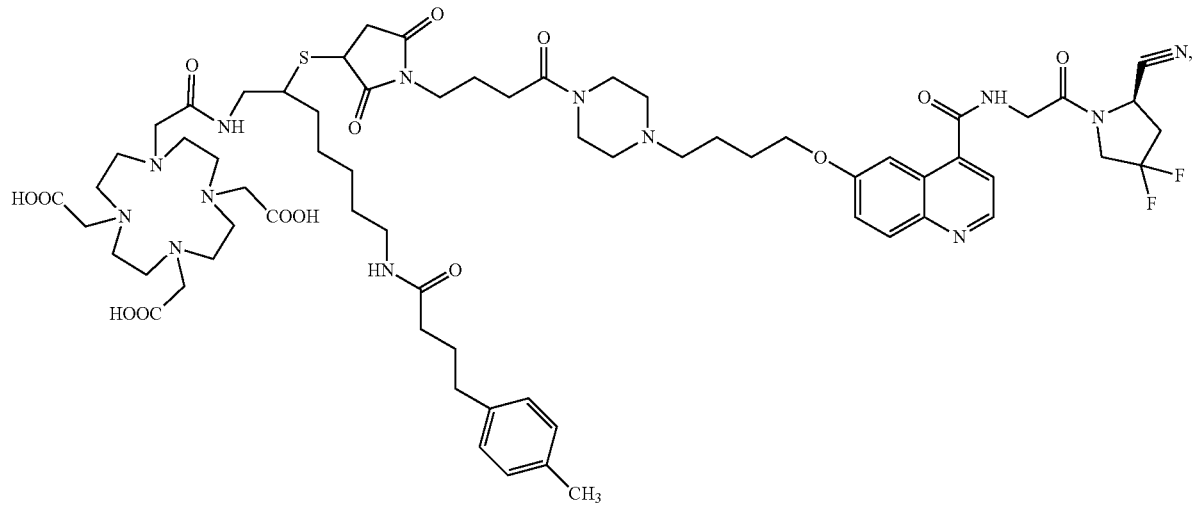

wherein
R1 is selected from R1-III-9, wherein the optical configuration of the optically active carbon is S configuration;
Code: FAPI-INER-1098-S;
Molecular weight: 1374.5;
Molecular formula: $C_{67}H_{93}F_2N_{13}O_{14}S$;

Structure 192:

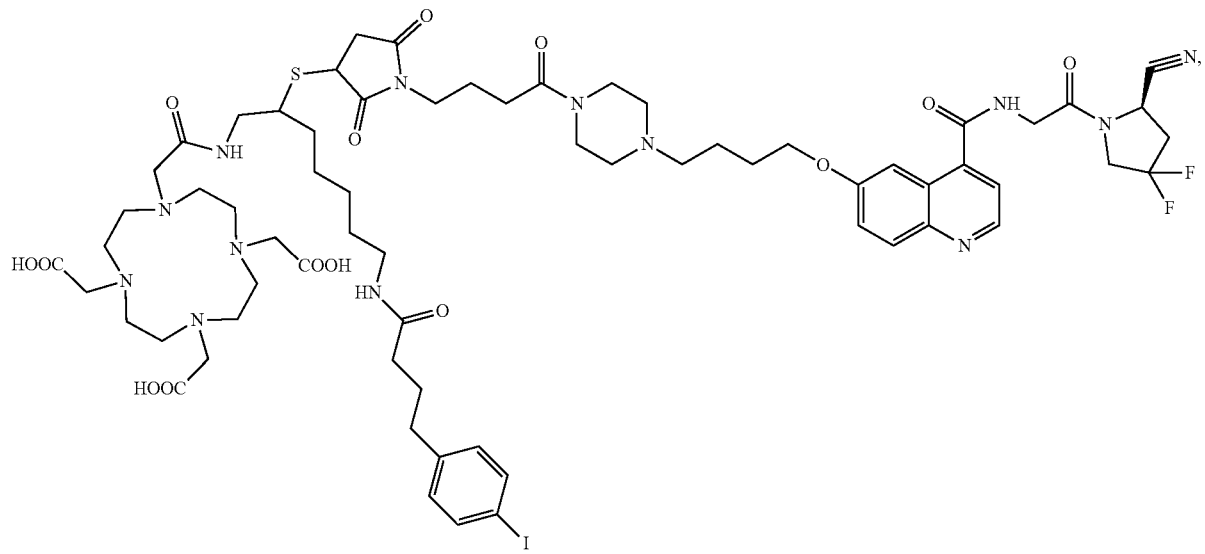

wherein
R1 is selected from R1-III-10, wherein the optical configuration of the optically active carbon is S configuration;
Code: FAPI-INER-1102-S;
Molecular weight: 1457.4;
Molecular formula: $C_{65}H_{87}F_2IN_{12}O_{14}S$;
or R2 is selected from R2-III-19 of the set of R2-III, R1 is any structure selected from the set of R1-III, and the D structure is

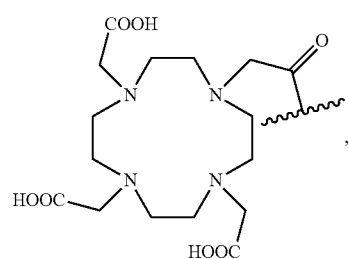 [SMILES: *C(=O)CN1CCN(CC(=O)O)CCN(CC(=O)O)CCN(CC(=O)O)CC1]

and thus the compound has a structure represented by formulas below:

Structure 193:

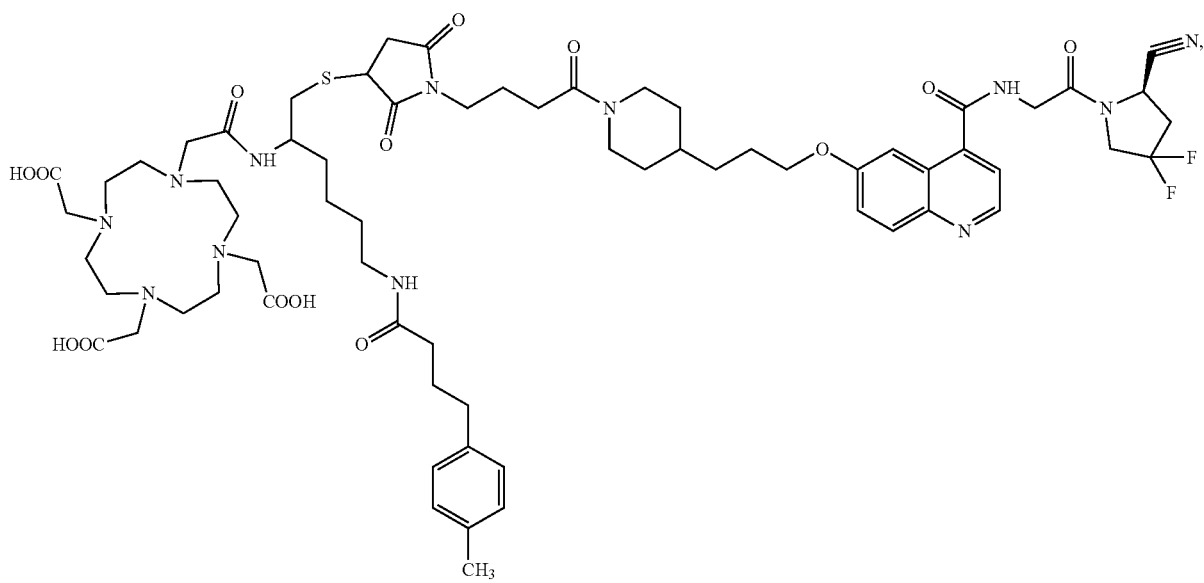

wherein
R1 is selected from R1-III-1, wherein the optical configuration of the optically active carbon is S configuration;
Code: FAPI-INER-1091-S;
Molecular weight: 1345.5;
Molecular formula: $C_{66}H_{90}F_2N_{12}O_{14}S$;

Structure 194:

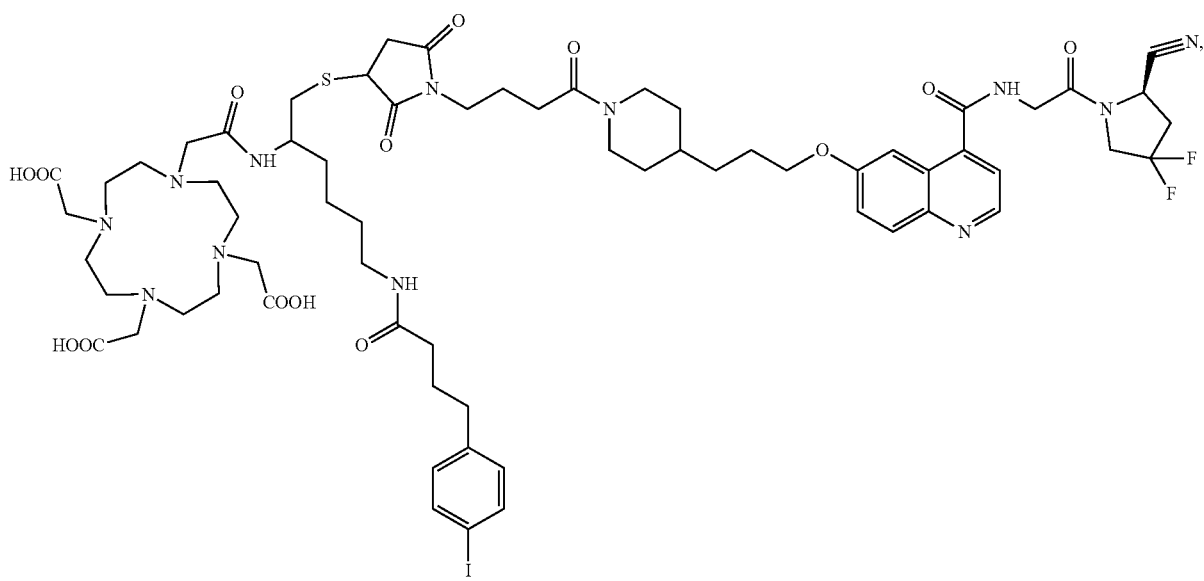

wherein
R1 is selected from R1-III-2, wherein the optical configuration of the optically active carbon is S configuration;
Code: FAPI-INER-1095-S;
Molecular weight: 1457.4;
Molecular formula: $C_{65}H_{87}F_2IN_{12}O_{14}S$;

Structure 195:

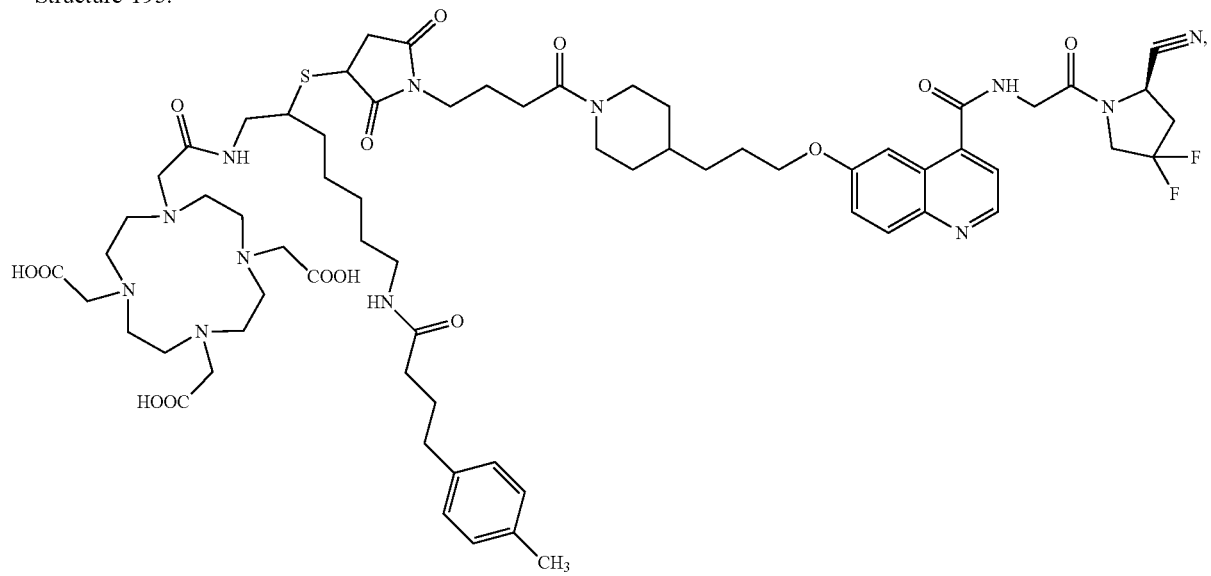

wherein
R1 is selected from R1-III-9, wherein the optical configuration of the optically active carbon is S configuration;
Code: FAPI-INER-1099-S;
Molecular weight: 1359.5;
Molecular formula: $C_{67}H_{92}F_2N_{12}O_{14}S$;

Structure 196:

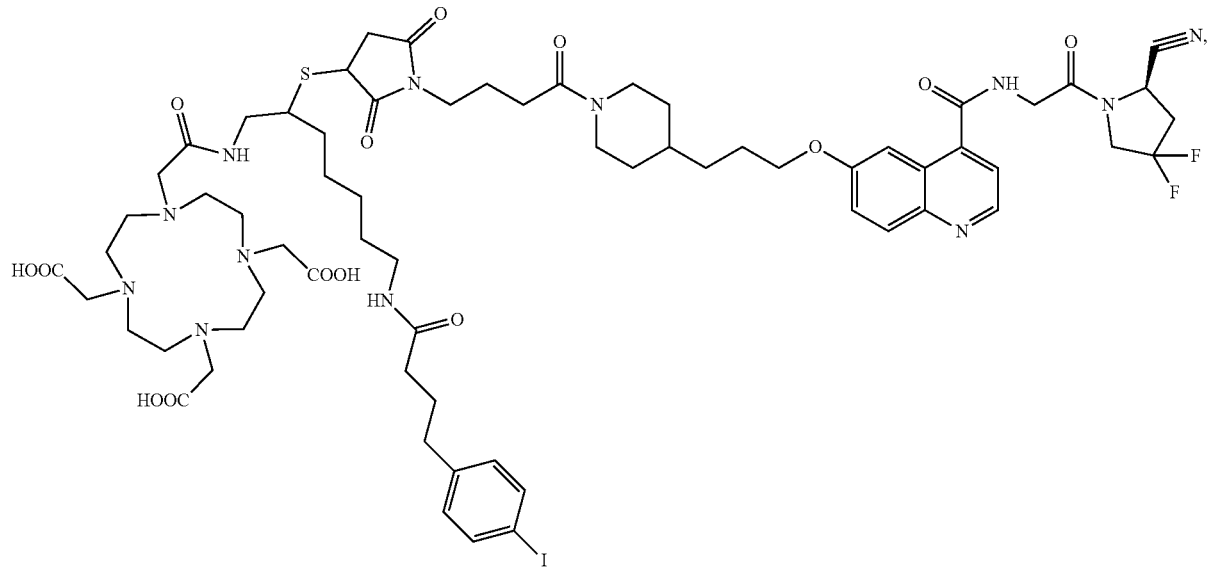

wherein
R1 is selected from R1-III-10, wherein the optical configuration of the optically active carbon is S configuration;
Code: FAPI-INER-1103-S;
Molecular weight: 1471.4;
Molecular formula: $C_{66}H_{89}F_2IN_{12}O_{14}S$;
or R2 is selected from R2-III-20 of the set of R2-III, R1 is any structure selected from the set of R1-III, and the D structure is

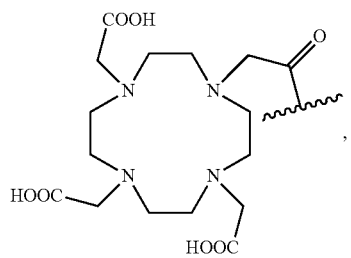 [SMILES: *C(=O)CN1CCN(CC(=O)O)CCN(CC(=O)O)CCN(CC(=O)O)CC1]
and thus the compound has a structure represented by formulas below:
Structure 197:
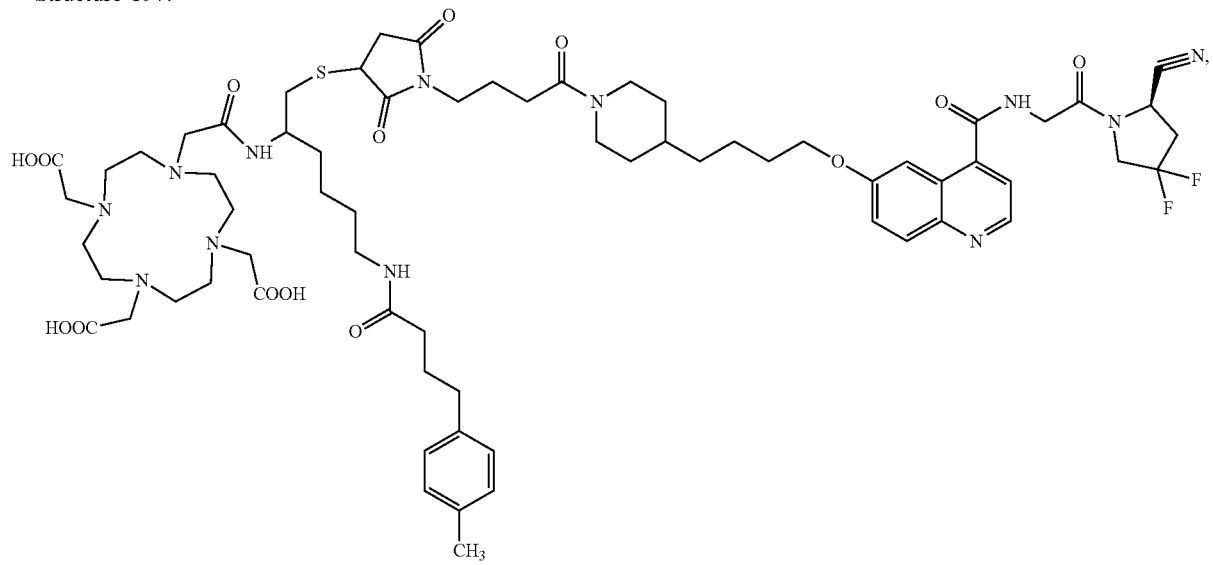
wherein
R1 is selected from R1-III-1, wherein the optical configuration of the optically active carbon is S configuration;
Code: FAPI-INER-1092-S;
Molecular weight: 1359.5;
Molecular formula: $C_{67}H_{92}F_2N_{12}O_{14}S$;
Structure 198:
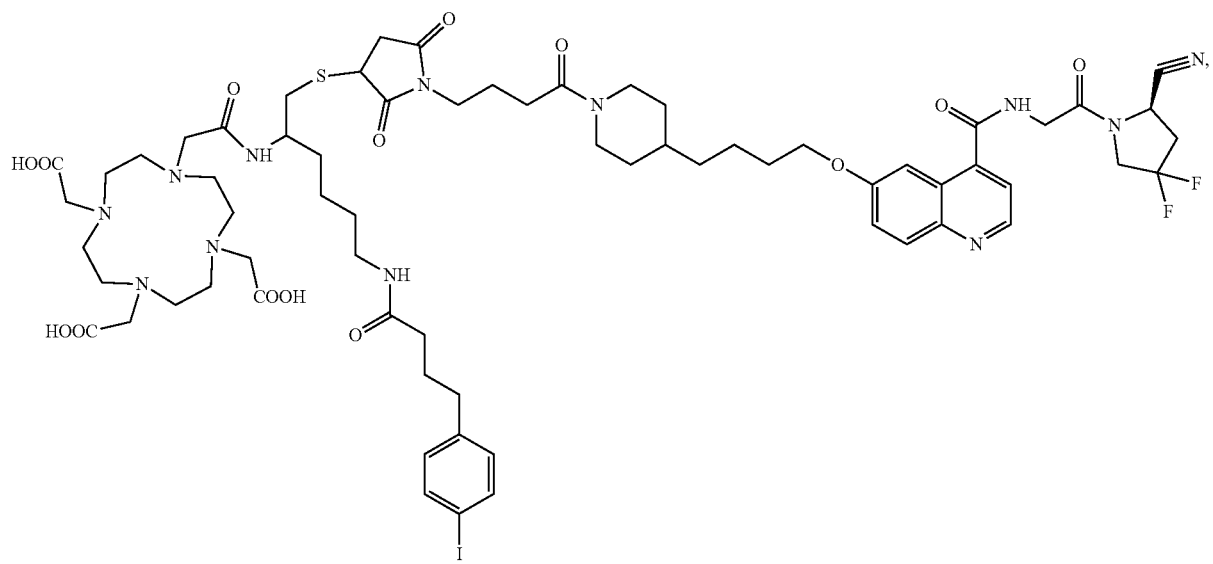

wherein
R1 is selected from R1-III-2, wherein the optical configuration of the optically active carbon is S configuration;
Code: FAPI-INER-1096-S;
Molecular weight: 1471.4;
Molecular formula: $C_{66}H_{89}F_2IN_{12}O_{14}S$;
Structure 199:

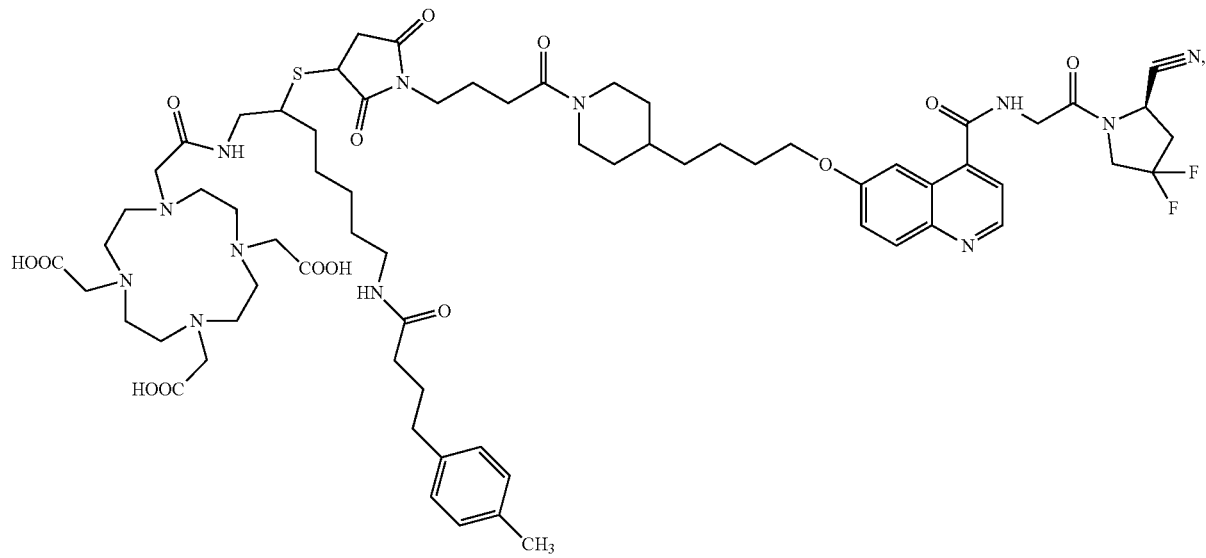

wherein
R1 is selected from R1-III-9, wherein the optical configuration of the optically active carbon is S configuration;
Code: FAPI-INER-1100-S;
Molecular weight: 1373.6;
Molecular formula: $C_{68}H_{94}F_2N_{12}O_{14}S$;
Structure 200:

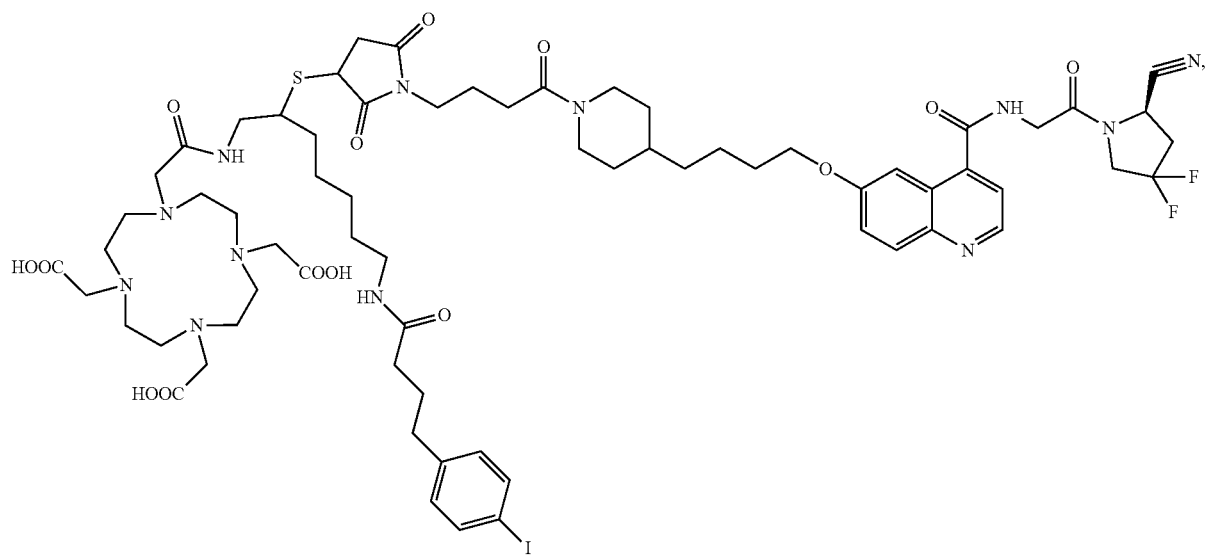

wherein
R1 is selected from R1-III-10, wherein the optical configuration of the optically active carbon is S configuration;
Code: FAPI-INER-1104-S;
Molecular weight: 1485.4;
Molecular formula: $C_{67}H_{91}F_2IN_{12}O_{14}S$;
or R2 is selected from R2-IV-1 of the set of R2-IV and the q is an integer of 5, R1 is any structure selected from the set of R1-IV, and the D structure is

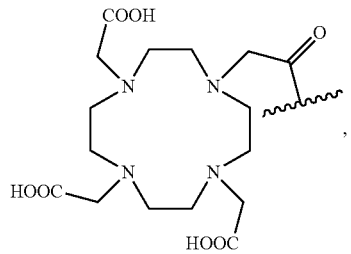 [SMILES: *C(=O)CN1CCN(CC(=O)O)CCN(CC(=O)O)CCN(CC(=O)O)CC1]

and thus the compound has a structure represented by formulas below:

Structure 201:

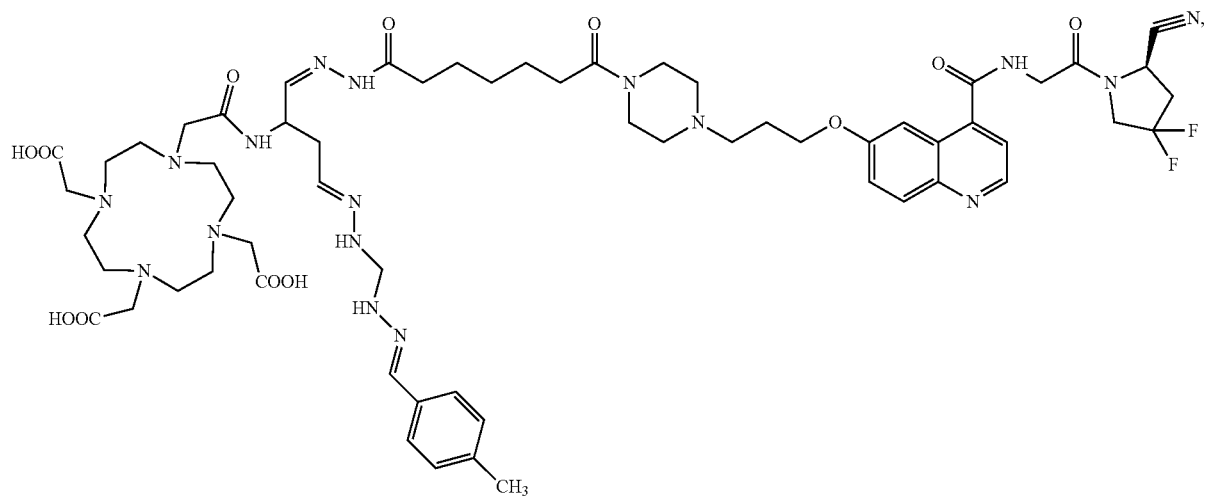

wherein
R1 is selected from R1-IV-1, wherein the optical configuration of the optically active carbon is S configuration;
Code: FAPI-INER-1297-S;
Molecular weight: 1272.4;
Molecular formula: $C_{60}H_{83}F_2N_{17}O_{12}$;

Structure 202:

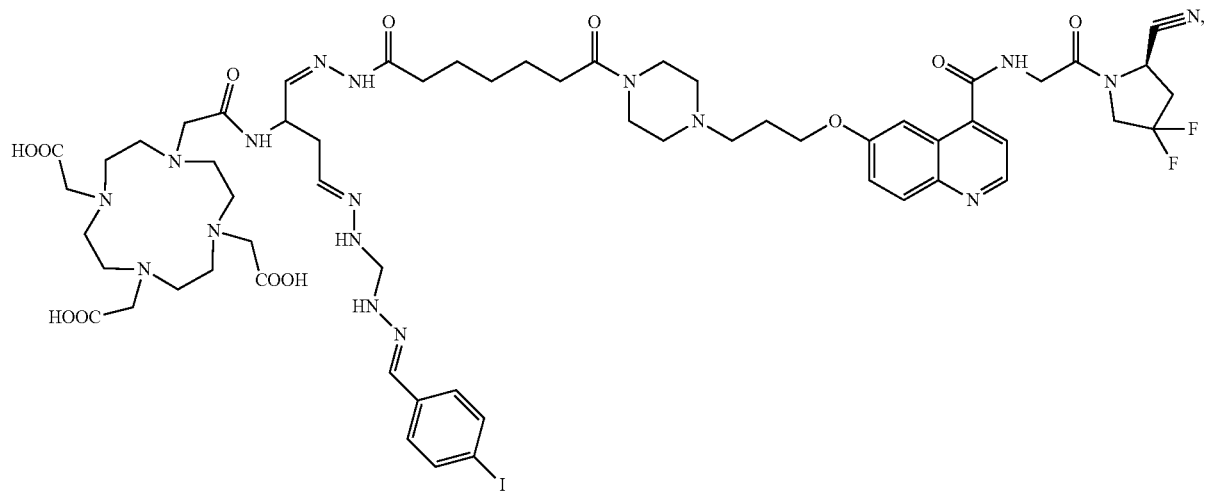

wherein
R1 is selected from R1-IV-2, wherein the optical configuration of the optically active carbon is S configuration;
Code: FAPI-INER-1301-S;
Molecular weight: 1384.2;
Molecular formula: $C_{59}H_{80}F_2IN_{17}O_{12}$;
or R2 is selected from R2-IV-2 of the set of R2-IV and the q is an integer of 5, R1 is any structure selected from the set of R1-IV, and the D structure is

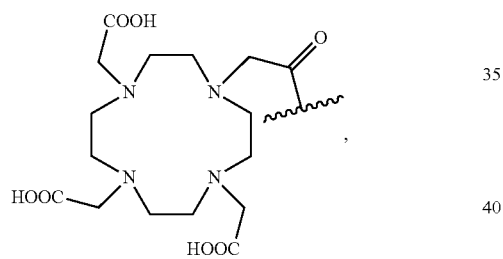

and thus the compound has a structure represented by formulas below:

Structure 203:

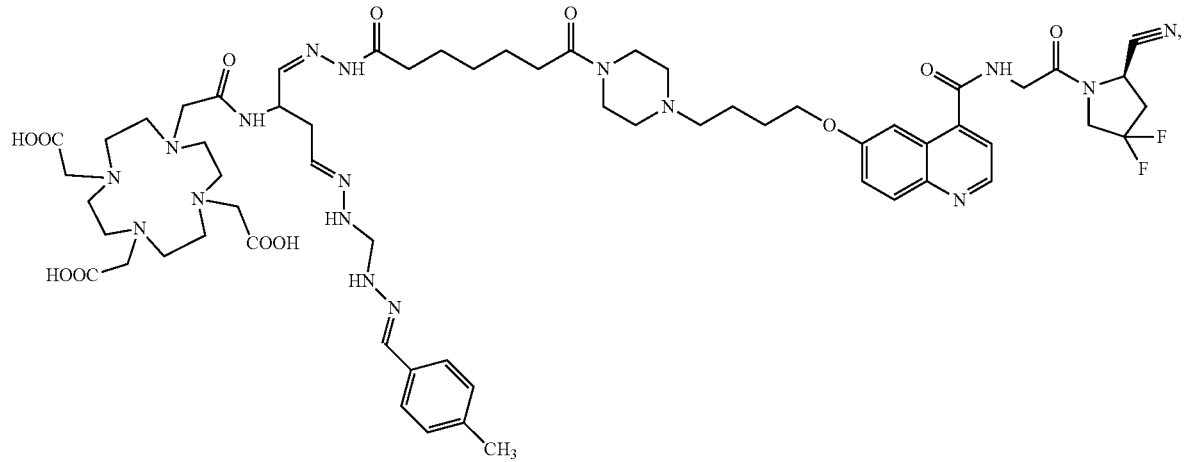

wherein
R1 is selected from R1-IV-1, wherein the optical configuration of the optically active carbon is S configuration;
Code: FAPI-INER-1298-S;
Molecular weight: 1286.4;
Molecular formula: $C_{61}H_{85}F_2N_{17}O_{12}$;
Structure 204:

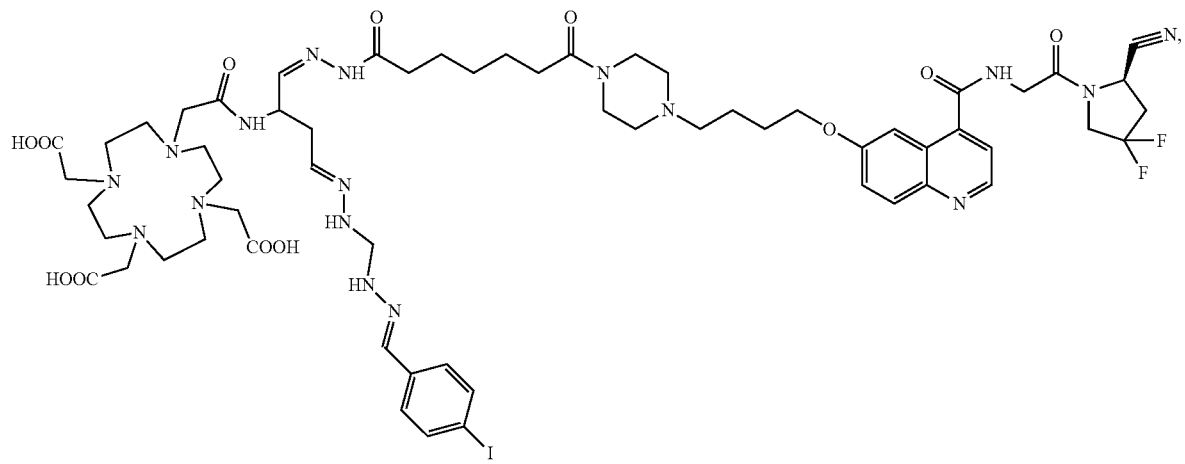

wherein
R1 is selected from R1-IV-2, wherein the optical configuration of the optically active carbon is S configuration;
Code: FAPI-INER-1302-S;
Molecular weight: 1398.3;
Molecular formula: $C_{64}H_{82}F_2IN_{17}O_{12}$;
or R2 is selected from R2-IV-3 of the set of R2-IV and the q is an integer of 5, R1 is any structure selected from the set of R1-IV, and the D structure is

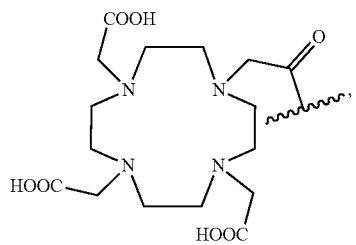 [SMILES: *C(=O)CN1CCN(CC(=O)O)CCN(CC(=O)O)CCN(CC(=O)O)CC1]

and thus the compound has a structure represented by formulas below:

Structure 205:

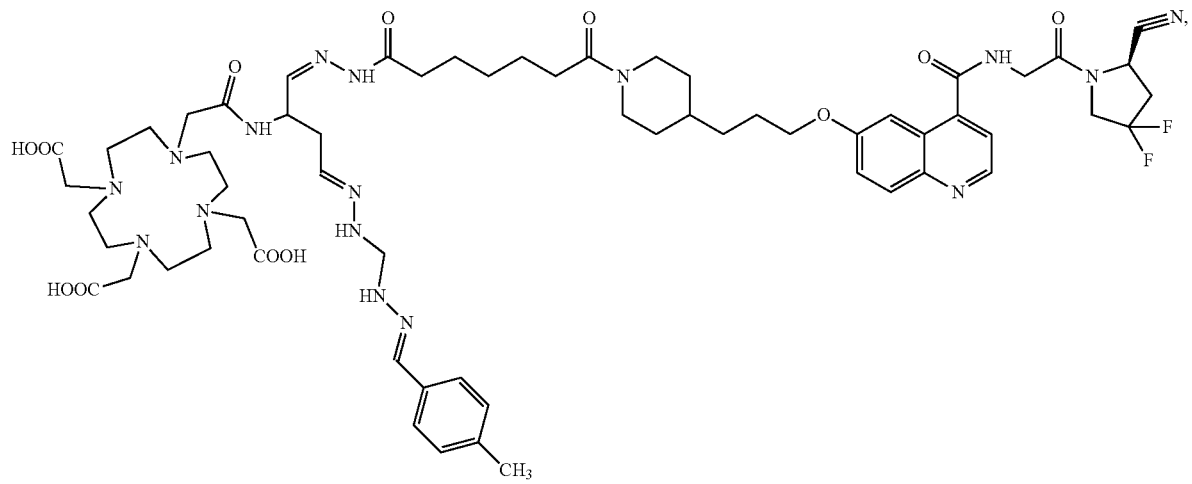

wherein
R1 is selected from R1-IV-1, wherein the optical configuration of the optically active carbon is S configuration;
Code: FAPI-INER-1299-S;
Molecular weight: 1271.4;
Molecular formula: $C_{61}H_{84}F_2N_{16}O_{12}$;

Structure 206:

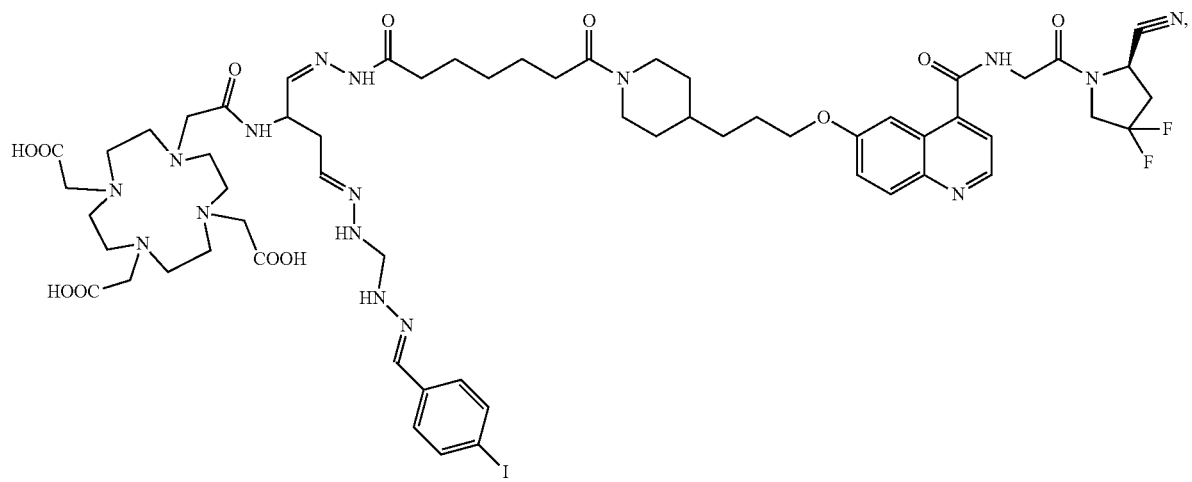

wherein
R1 is selected from R1-IV-2, wherein the optical configuration of the optically active carbon is S configuration;
Code: FAPI-INER-1303-S;
Molecular weight: 1383.2;
Molecular formula: $C_{60}H_{81}F_2IN_{16}O_{12}$;

or R2 is selected from R2-IV-4 of the set of R2-IV and the q is an integer of 5, R1 is any structure selected from the set of R1-IV, and the D structure is

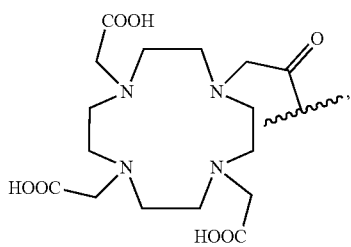 [SMILES: *C(=O)CN1CCN(CC(=O)O)CCN(CC(=O)O)CCN(CC(=O)O)CC1]

and thus the compound has a structure represented by formulas below:

Structure 207:

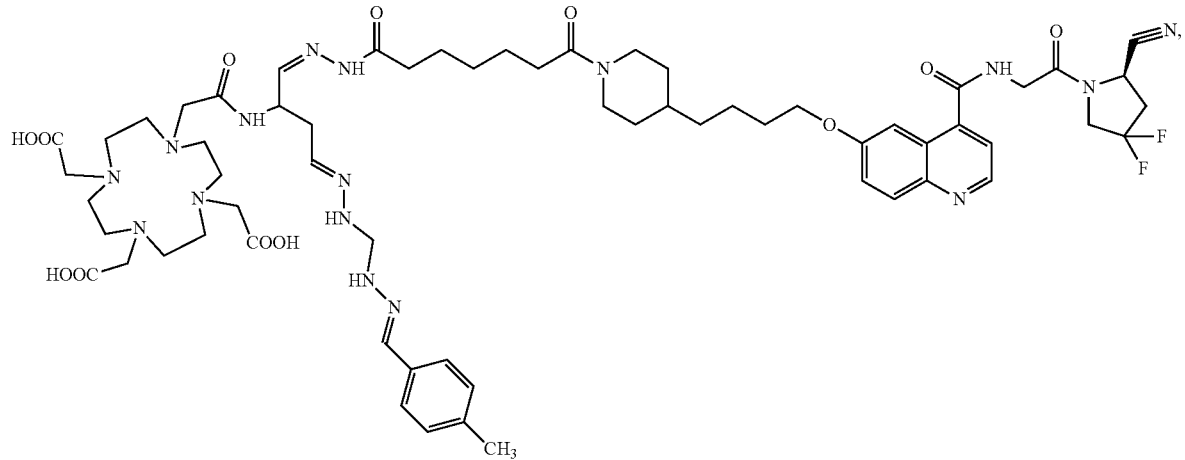

wherein
R1 is selected from R1-IV-1, wherein the optical configuration of the optically active carbon is S configuration;
Code: FAPI-INER-1300-S;
Molecular weight: 1285.4;
Molecular formula: $C_{62}H_{86}F_2N_{16}O_{12}$;

Structure 208:

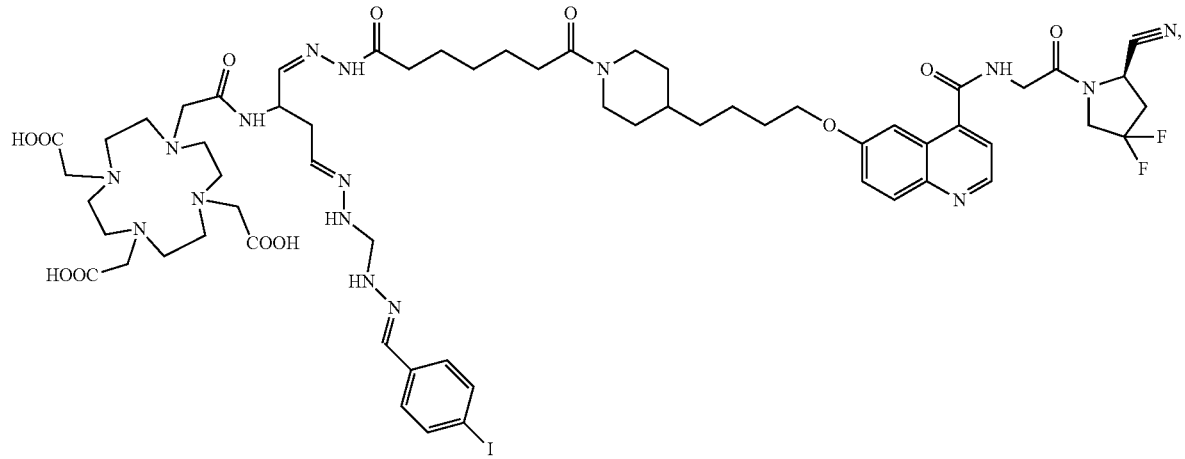

wherein
R1 is selected from R1-IV-2, wherein the optical configuration of the optically active carbon is S configuration;
Code: FAPI-INER-1304-S;
Molecular weight: 1397.3;
Molecular formula: $C_{61}H_{83}F_2IN_{16}O_{12}$;
or R2 is selected from R2-IV-9 of the set of R2-IV and the k is an integer of 2, R1 is any structure selected from the set of R1-IV, and the D structure is

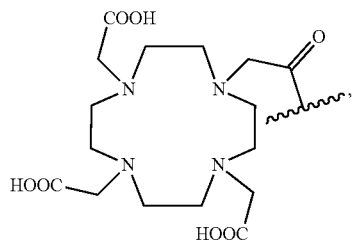 [SMILES: *C(=O)CN1CCN(CC(=O)O)CCN(CC(=O)O)CCN(CC(=O)O)CC1]
and thus the compound has a structure represented by formulas below:
Structure 209:
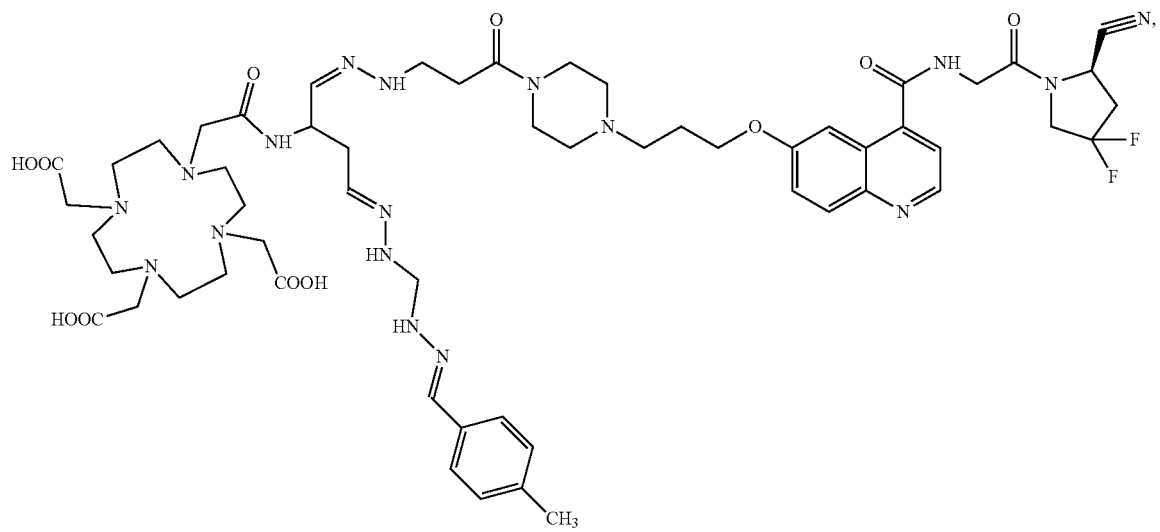
wherein
R1 is selected from R1-IV-1, wherein the optical configuration of the optically active carbon is S configuration;
Code: FAPI-INER-1305-S;
Molecular weight: 1285.4;
Molecular formula: $C_{56}H_{77}F_2N_{17}O_{11}$;
Structure 210:
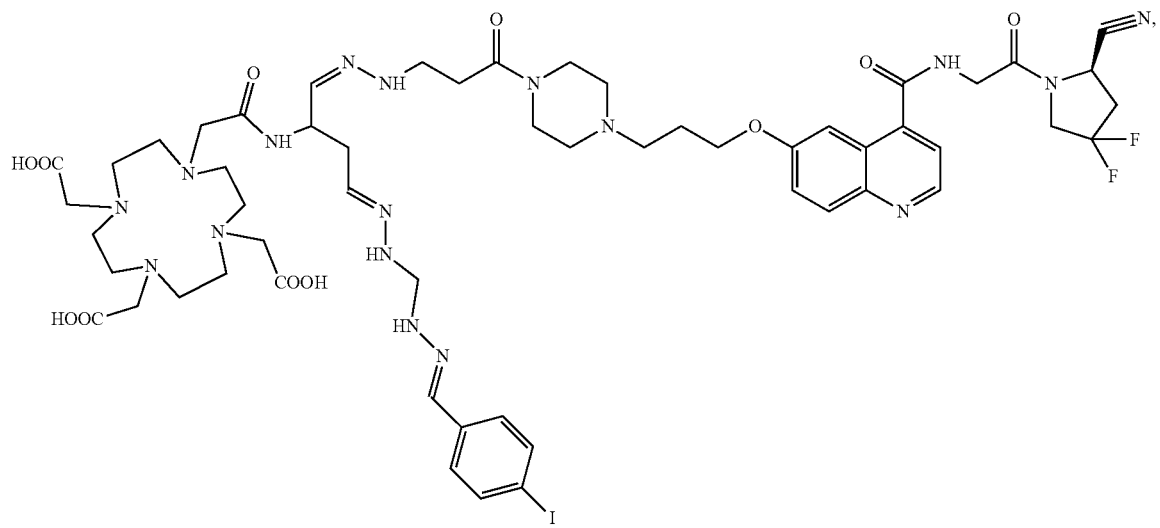

wherein
R1 is selected from R1-IV-2, wherein the optical configuration of the optically active carbon is S configuration;
Code: FAPI-INER-1309-S;
Molecular weight: 1314.1;
Molecular formula: $C_{55}H_{74}F_2IN_{17}O_{11}$;
or R2 is selected from R2-IV-10 of the set of R2-IV and the k is an integer of 2, R1 is any structure selected from the set of R1-IV, and the D structure is

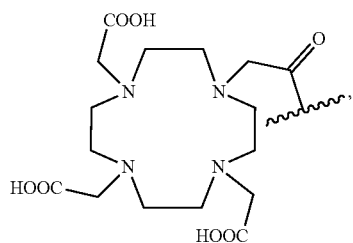 [SMILES: *C(=O)CN1CCN(CC(=O)O)CCN(CC(=O)O)CCN(CC(=O)O)CC1]

and thus the compound has a structure represented by formulas below:
Structure 211:

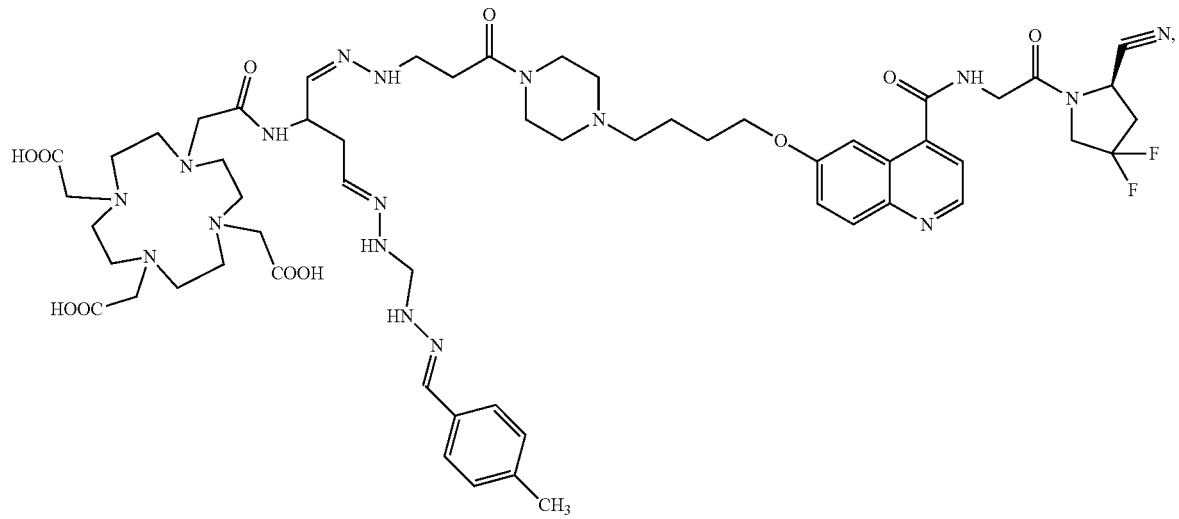

wherein
R1 is selected from R1-IV-1, wherein the optical configuration of the optically active carbon is S configuration;
Code: FAPI-INER-1306-S;
Molecular weight: 1216.3;
Molecular formula: $C_{57}H_{79}F_2N_{17}O_{11}$;

Structure 212:

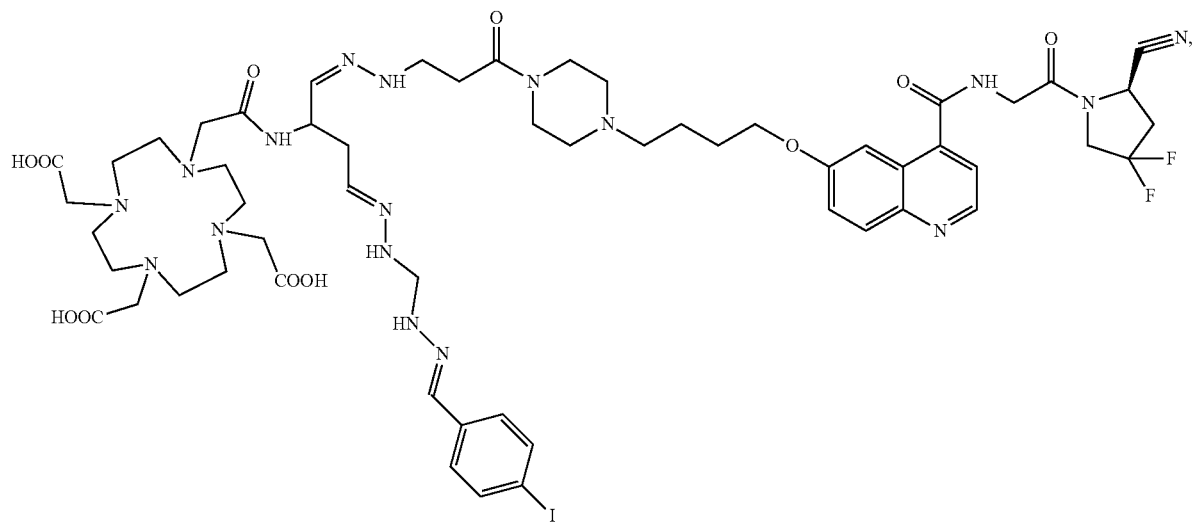

wherein
R1 is selected from R1-IV-2, wherein the optical configuration of the optically active carbon is S configuration;
Code: FAPI-INER-1310-S;
Molecular weight: 1328.2;
Molecular formula: $C_{56}H_{76}F_2IN_{17}O_{11}$;
or R2 is selected from R2-IV-11 of the set of R2-IV and the k is an integer of 2, R1 is any structure selected from the set of R1-IV, and the D structure is

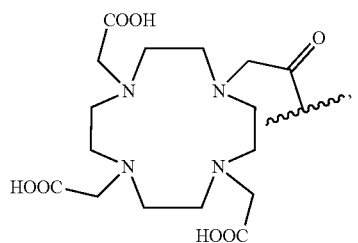 [SMILES: *C(=O)CN1CCN(CC(=O)O)CCN(CC(=O)O)CCN(CC(=O)O)CC1]

and thus the compound has a structure represented by formulas below:

Structure 213:

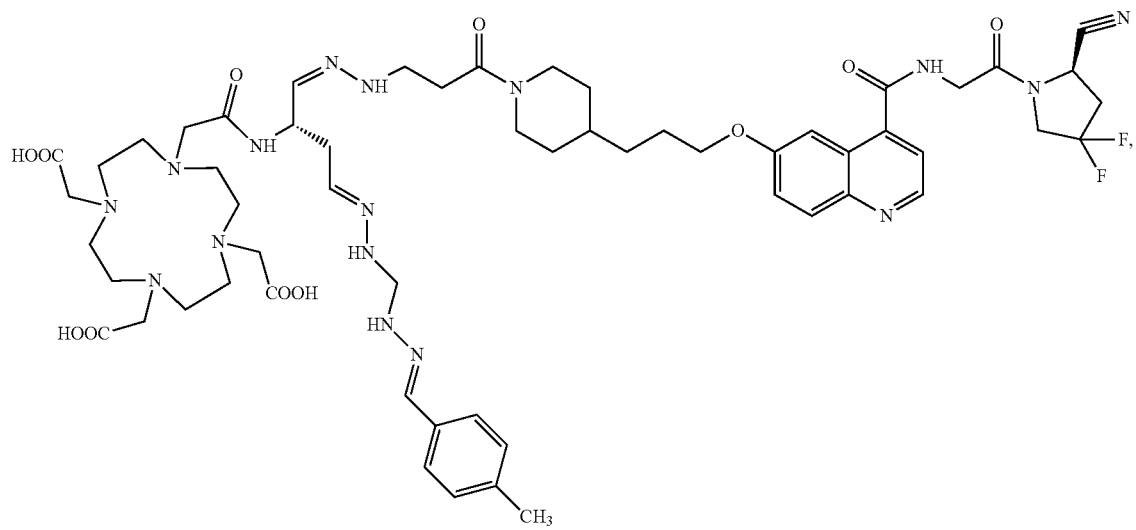

wherein
R1 is selected from R1-IV-1, wherein the optical configuration of the optically active carbon is S configuration;
Code: FAPI-INER-1307-S;
Molecular weight: 1201.3;
Molecular formula: $C_{57}H_{78}F_2N_{16}O_{11}$;

Structure 214:

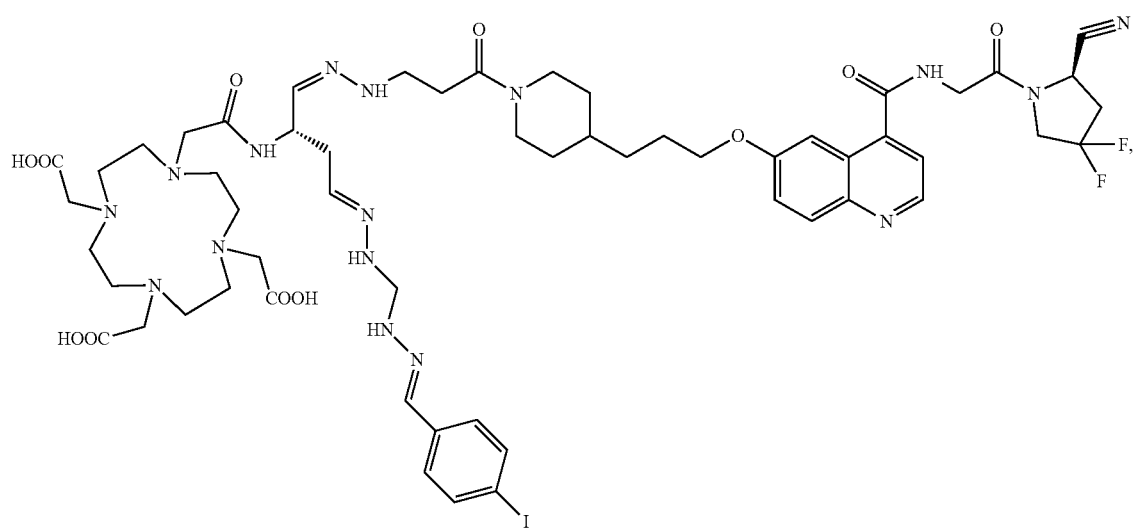

wherein
R1 is selected from R1-IV-2, wherein the optical configuration of the optically active carbon is S configuration;
Code: FAPI-INER-1311-S;
Molecular weight: 1313.1;
Molecular formula: $C_{56}H_{75}F_2IN_{16}O_{11}$;
or R2 is selected from R2-IV-12 of the set of R2-IV and the k is an integer of 2, R1 is any structure selected from the set of R1-IV, and the D structure is

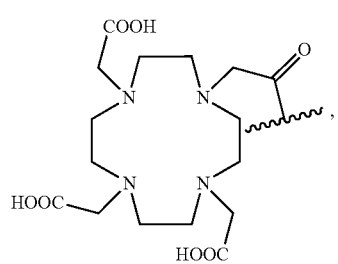

and thus the compound has a structure represented by formulas below:

Structure 215:

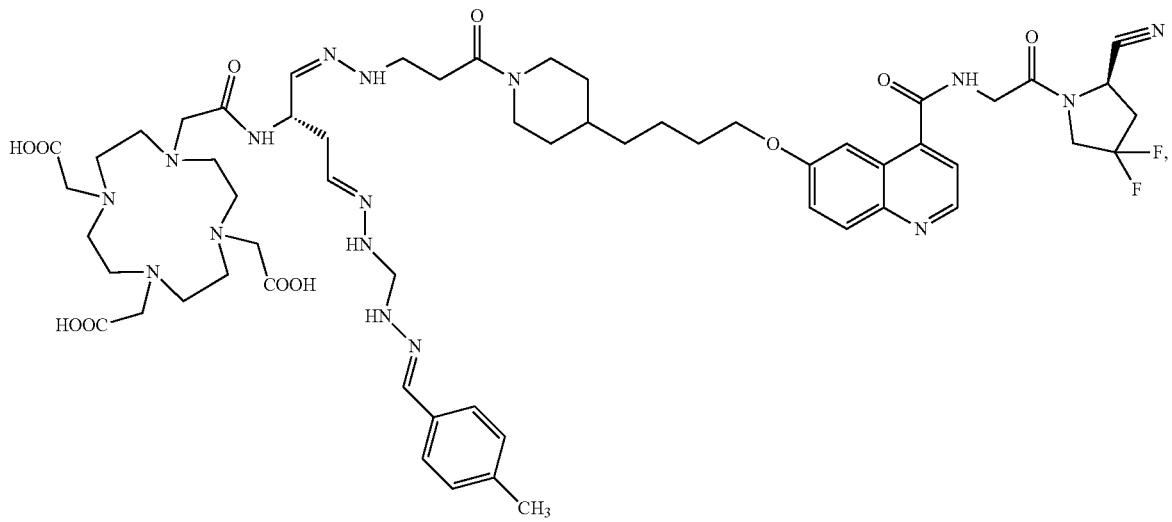

wherein
R1 is selected from R1-IV-1, wherein the optical configuration of the optically active carbon is S configuration;
Code: FAPI-INER-1308-S;
Molecular weight: 1215.3;
Molecular formula: $C_{58}H_{80}F_2N_{16}O_{11}$;

Structure 216:

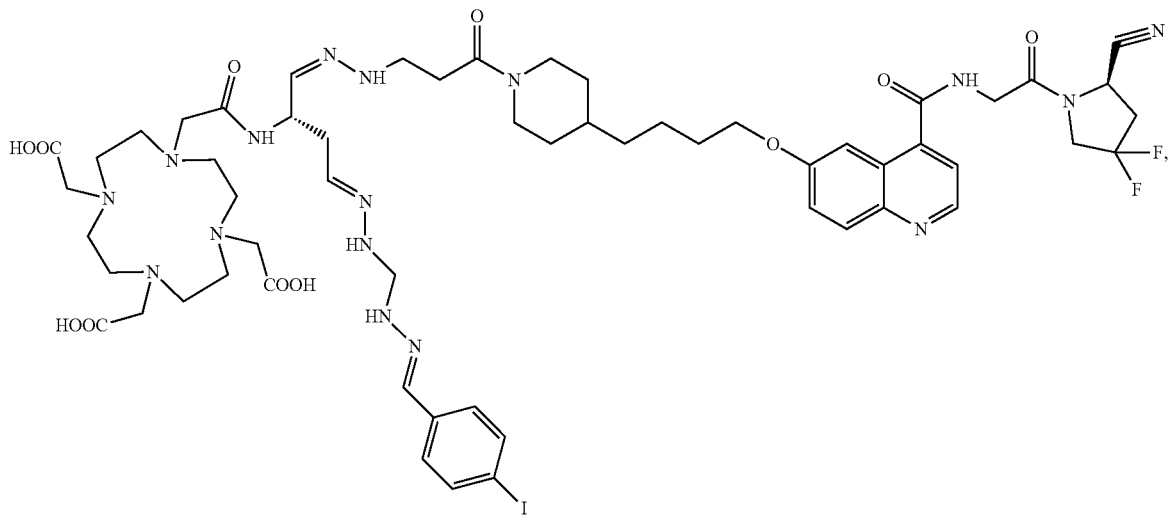

wherein
R1 is selected from R1-IV-2, wherein the optical configuration of the optically active carbon is S configuration;
Code: FAPI-INER-1312-S;
Molecular weight: 1327.2;
Molecular formula: $C_{57}H_{77}F_2IN_{16}O_{11}$;
or R2 is selected from R2-V-1 of the set of R2-V and then is an integer of 5, R1 is any structure selected from the set of R1-IV, and the D structure is

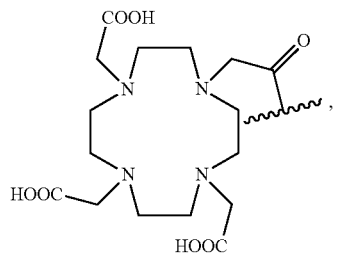
and thus the compound has a structure represented by formulas below:
Structure 217:
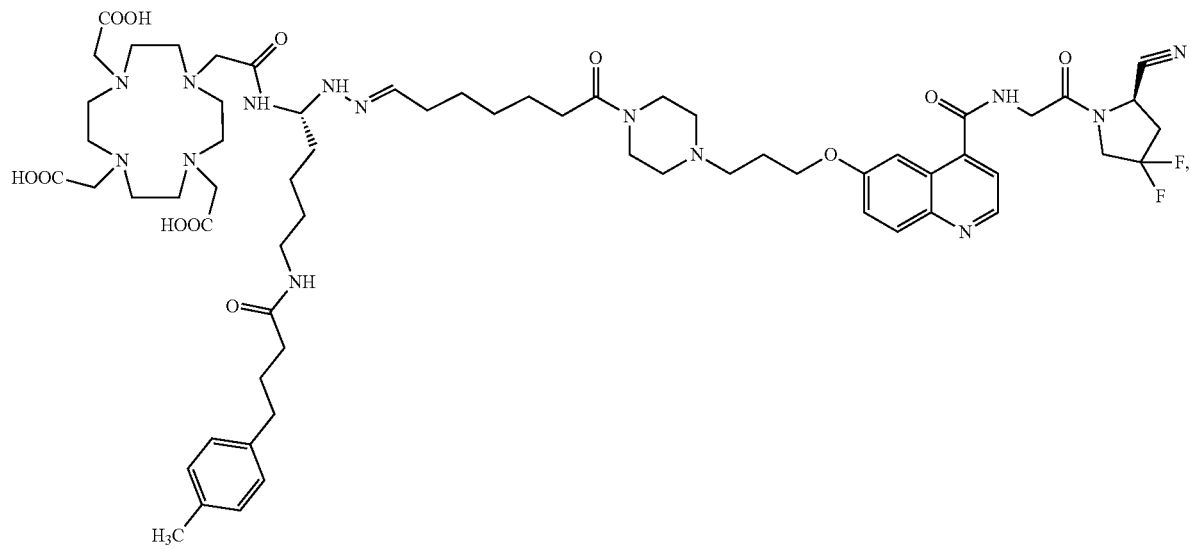
wherein
R1 is selected from R1-V-1, wherein the optical configuration of the optically active carbon is S configuration;
Code: FAPI-INER-1393-S;
Molecular weight: 1273.4;
Molecular formula: $C_{63}H_{90}F_2N_{14}O_{12}$;
Structure 218:
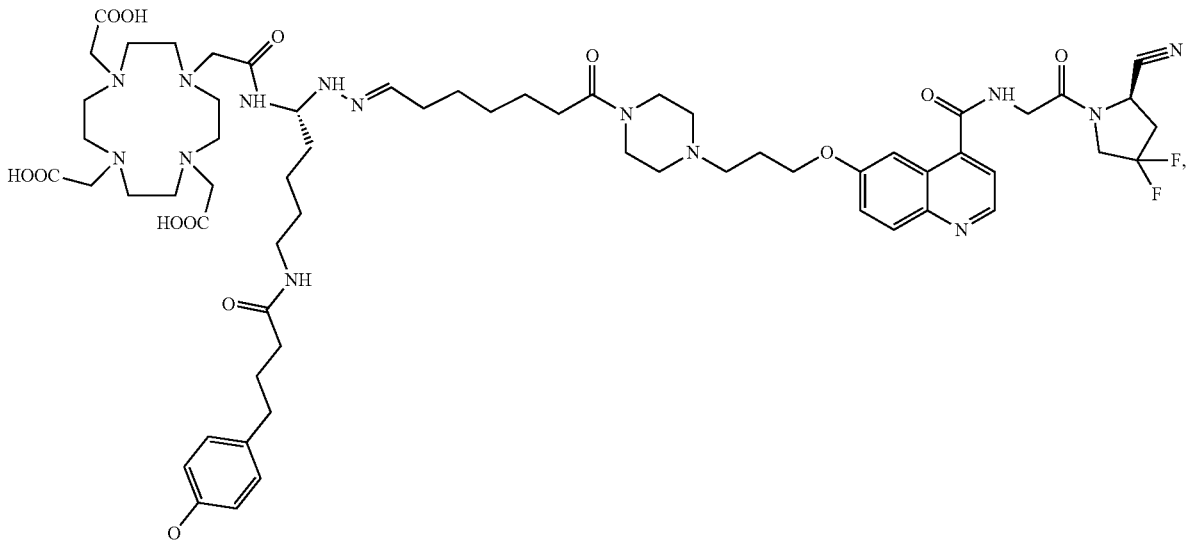

wherein
R1 is selected from R1-V-2, wherein the optical configuration of the optically active carbon is S configuration;
Code: FAPI-INER-1397-S;
Molecular weight: 1385.3;
Molecular formula: $C_{62}H_{87}F_2IN_{14}O_{12}$;
or R2 is selected from R2-V-1 of the set of R2-V and then is an integer of 2, R1 is any structure selected from the set of R1-V, and the D structure is

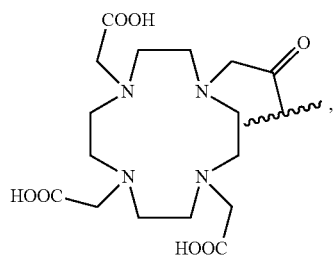

and thus the compound has a structure represented by formulas below:

Structure 219:

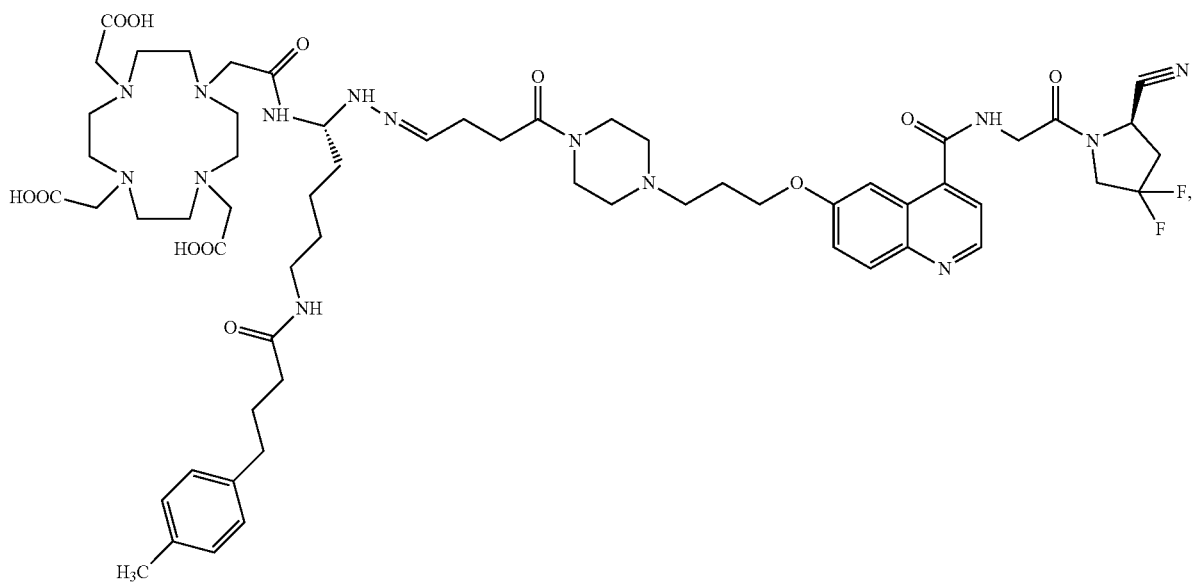

wherein
R1 is selected from R1-V-1, wherein the optical configuration of the optically active carbon is S configuration;
Code: FAPI-INER-1401-S;
Molecular weight: 1231.3;
Molecular formula: $C_{64}H_{84}F_2N_{14}O_{12}$;

Structure 220:

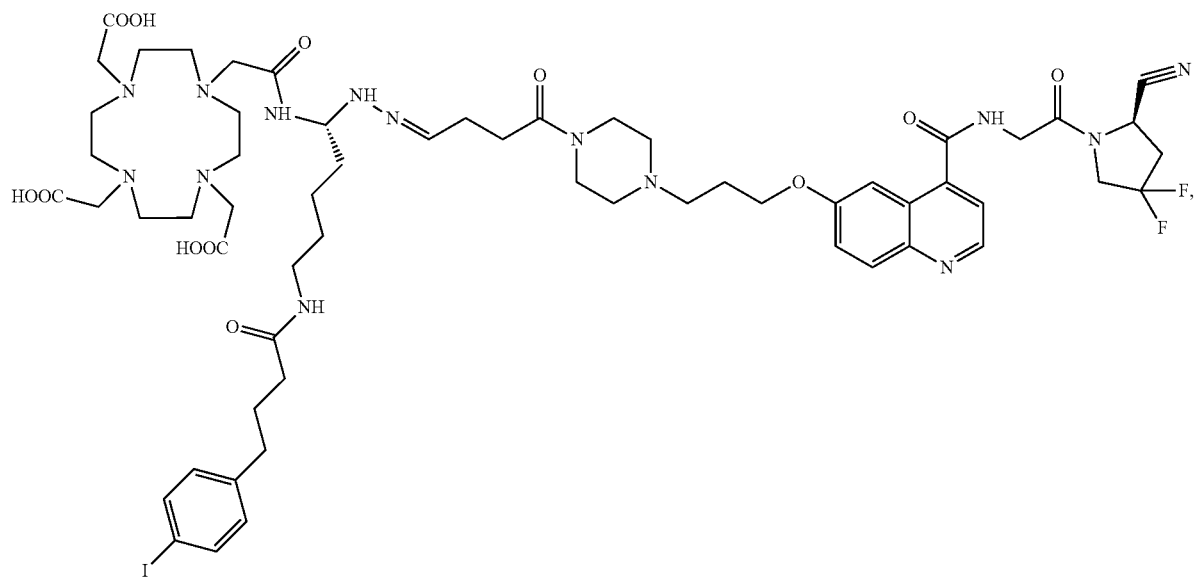

wherein

R1 is selected from R1-V-2, wherein the optical configuration of the optically active carbon is S configuration;

Code: FAPI-INER-1405-S;

Molecular weight: 1343.2;

Molecular formula: $C_{59}H_{81}F_2IN_{14}O_{12}$;

or R2 is selected from R2-V-2 of the set of R2-V and the n is an integer of 5, R1 is any structure selected from the set of R1-V, and the D structure is

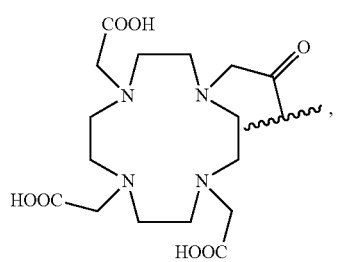

and thus the compound has a structure represented by formulas below:

Structure 221:

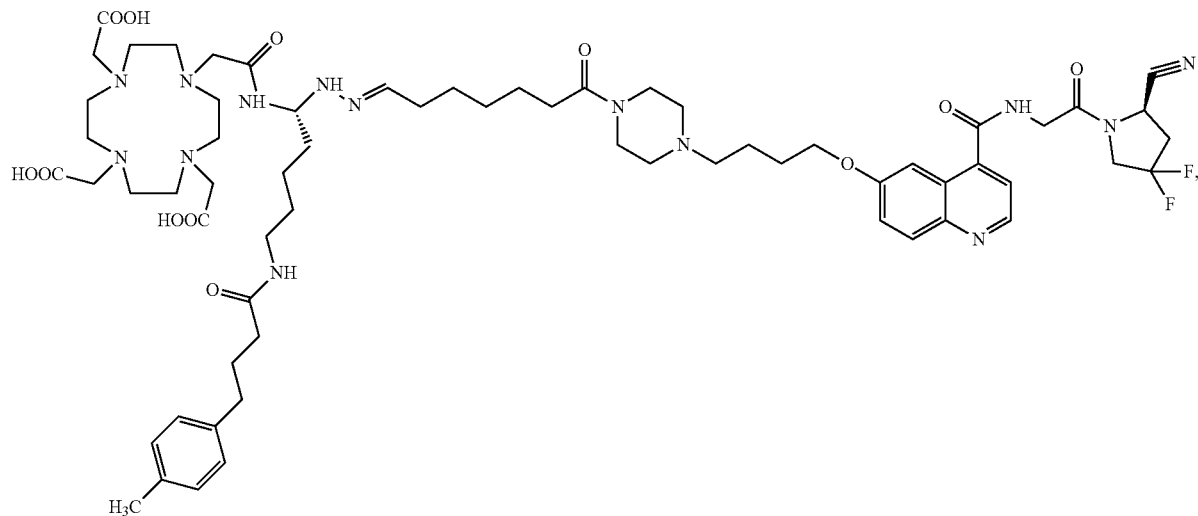

wherein
R1 is selected from R1-V-1, wherein the optical configuration of the optically active carbon is S configuration;
Code: FAPI-INER-1394-S;
Molecular weight: 1287.4;
Molecular formula: $C_{64}H_{92}F_2N_{14}O_{12}$;

Structure 222:

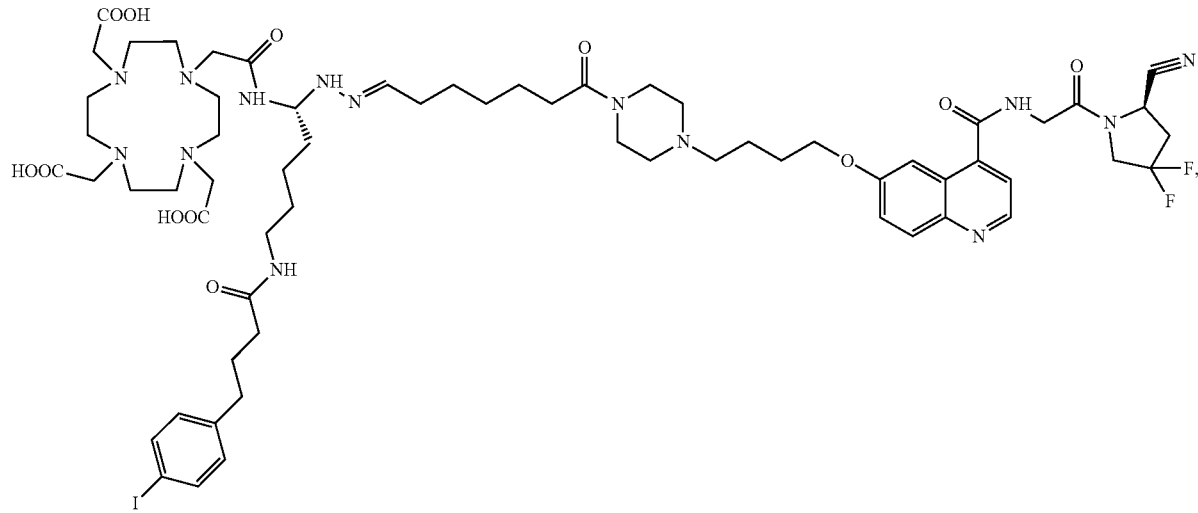

wherein
R1 is selected from R1-V-2, wherein the optical configuration of the optically active carbon is S configuration;
Code: FAPI-INER-1398-S;
Molecular weight: 1399.3;
Molecular formula: $C_{63}H_{89}F_2IN_{14}O_{12}$;
or R2 is selected from R2-V-2 of the set of R2-V and then is an integer of 2, R1 is any structure selected from the set of R1-V, and the D structure is

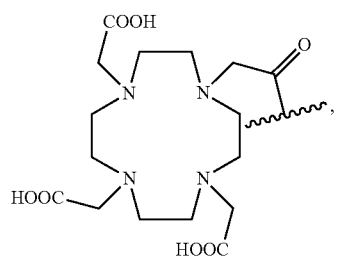

the compound has a structure represented by formulas below:
Structure 223:

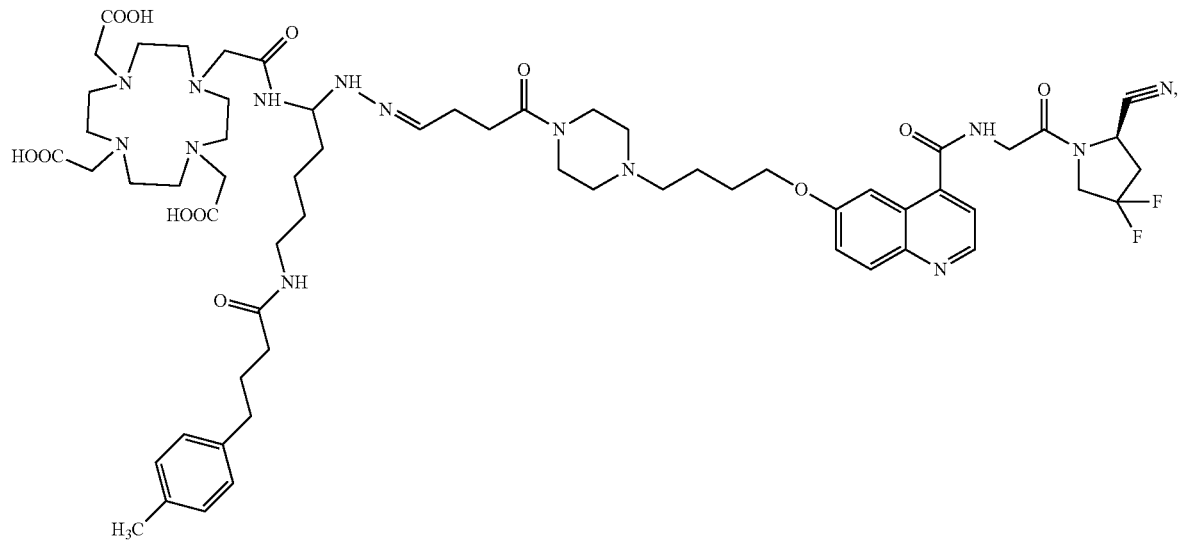

wherein
R1 is selected from R1-V-1, wherein the optical configuration of the optically active carbon is S configuration;
Code: FAPI-INER-1402-S;
Molecular weight: 1245.4;
Molecular formula: $C_{61}H_{86}F_2N_{14}O_{12}$;
Structure 224:

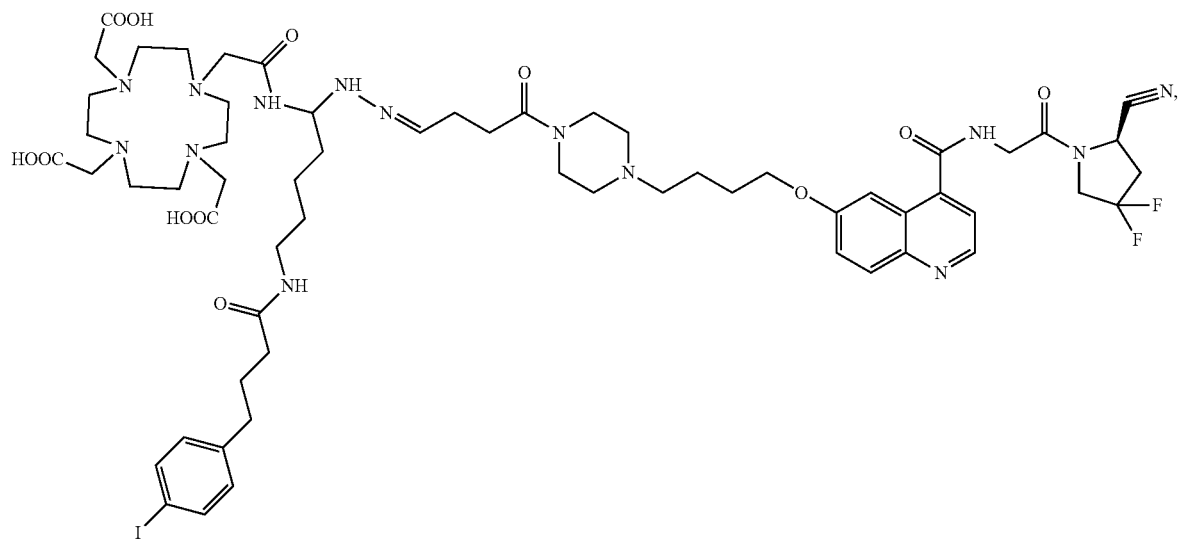

wherein
R1 is selected from R1-V-2, wherein the optical configuration of the optically active carbon is S configuration;
Code: FAPI-INER-1406-S;
Molecular weight: 1357.2;
Molecular formula: $C_{60}H_{83}F_2IN_{14}O_{12}$;
or R2 is selected from R2-V-3 of the set of R2-V and the n is an integer of 5, R1 is any structure selected from the set of R1-V, and the D structure is

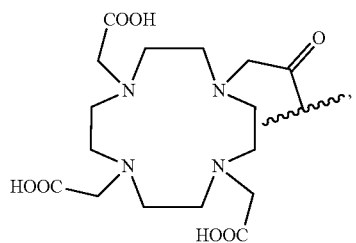 [SMILES: *C(=O)CN1CCN(CC(=O)O)CCN(CC(=O)O)CCN(CC(=O)O)CC1]
the compound has a structure represented by formulas below:
Structure 225:
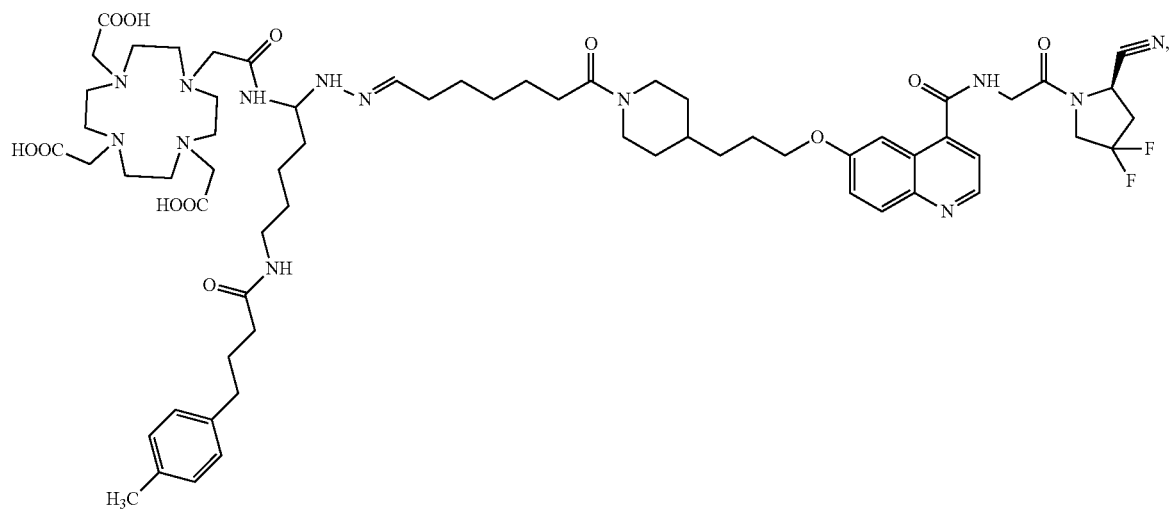
wherein
R1 is selected from R1-V-1, wherein the optical configuration of the optically active carbon is S configuration;
Code: FAPI-INER-1395-S;
Molecular weight: 1272.4;
Molecular formula: $C_{64}H_{91}F_2N_{13}O_{12}$;
Structure 226:
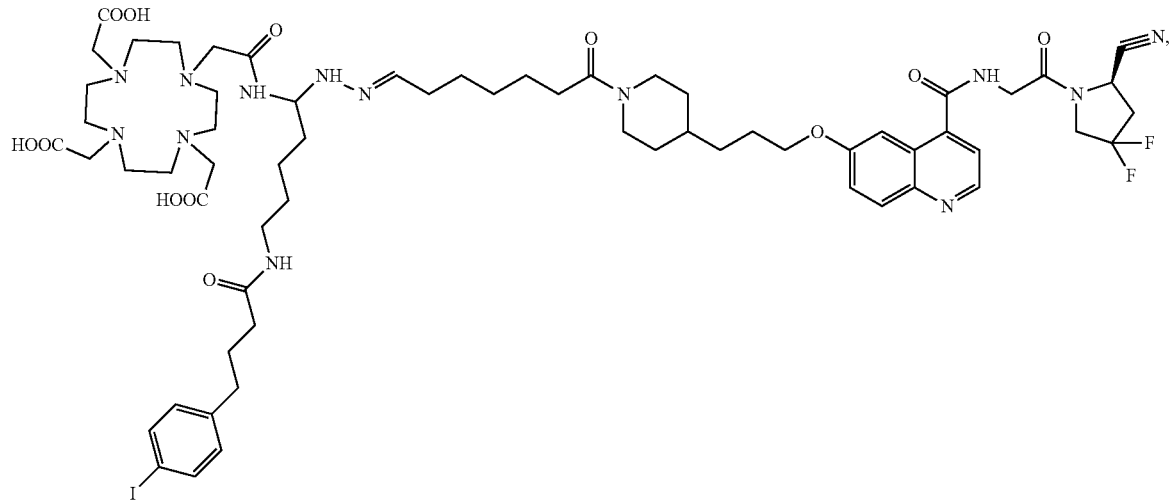

wherein
R1 is selected from R1-V-2, wherein the optical configuration of the optically active carbon is S configuration;
Code: FAPI-INER-1399-S;
Molecular weight: 1384.3;
Molecular formula: $C_{63}H_{88}F_2IN_{13}O_{12}$;
or R2 is selected from R2-V-3 of the set of R2-V and then is an integer of 2, R1 is any structure selected from the set of R1-V, and the D structure is

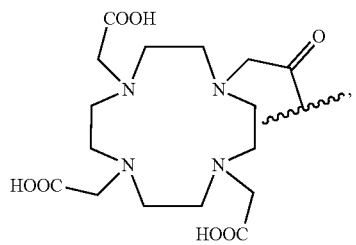 [SMILES: *C(=O)CN1CCN(CC(=O)O)CCN(CC(=O)O)CCN(CC(=O)O)CC1]

and thus the compound has a structure represented by formulas below:

Structure 227:

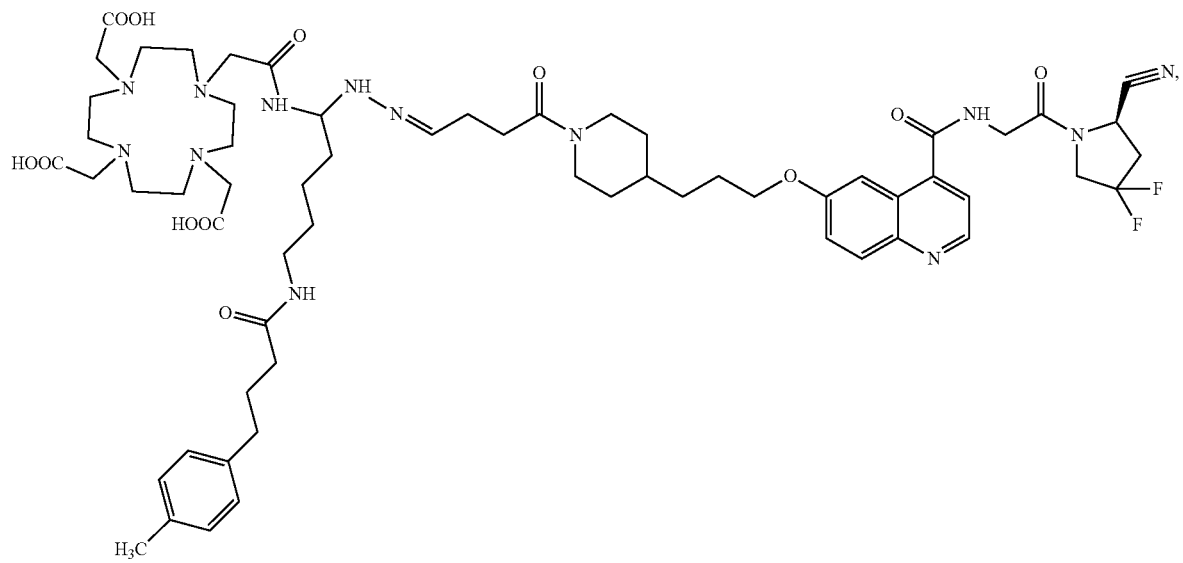

wherein
R1 is selected from R1-V-1, wherein the optical configuration of the optically active carbon is S configuration;
Code: FAPI-INER-1403-S;
Molecular weight: 1230.4;
Molecular formula: $C_{61}H_{85}F_2N_{13}O_{12}$;

Structure 228:

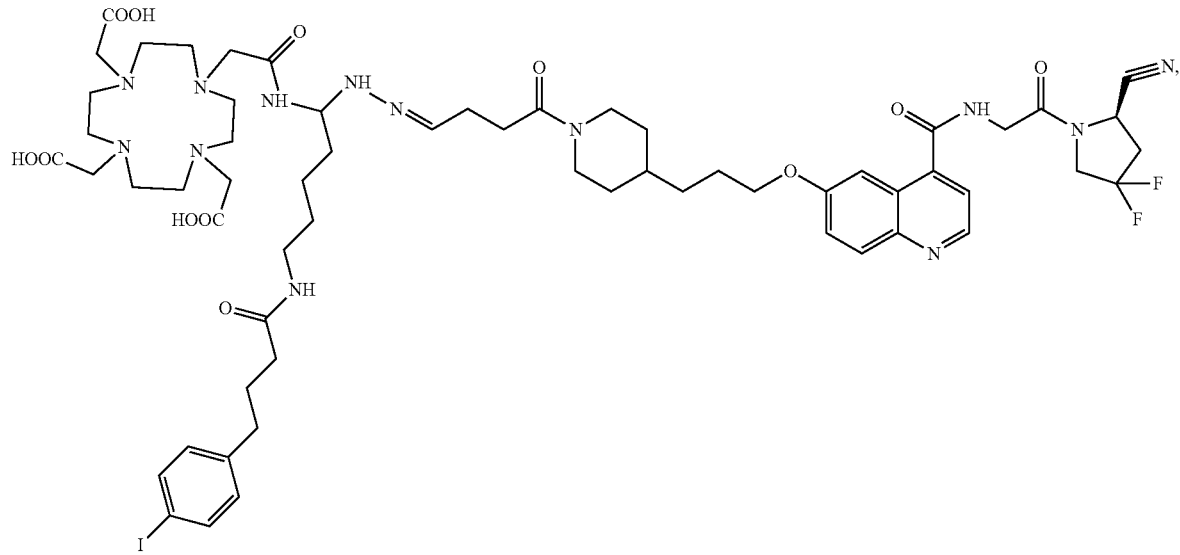

wherein
R1 is selected from R1-V-2, wherein the optical configuration of the optically active carbon is S configuration;
Code: FAPI-INER-1407-S;
Molecular weight: 1342.2;
Molecular formula: $C_{601}H_{82}F_2IN_{13}O_{12}$;
or R2 is selected from R2-V-4 of the set of R2-V and the n is an integer of 5, R1 is any structure selected from the set of R1-V, and the D structure is

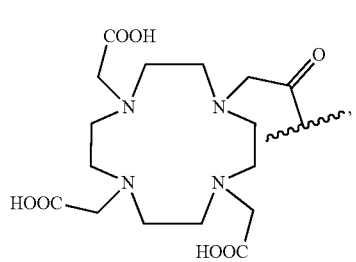 [SMILES: *C(=O)CN1CCN(CC(=O)O)CCN(CC(=O)O)CCN(CC(=O)O)CC1]

the compound has a structure represented by formulas below:

Structure 229:

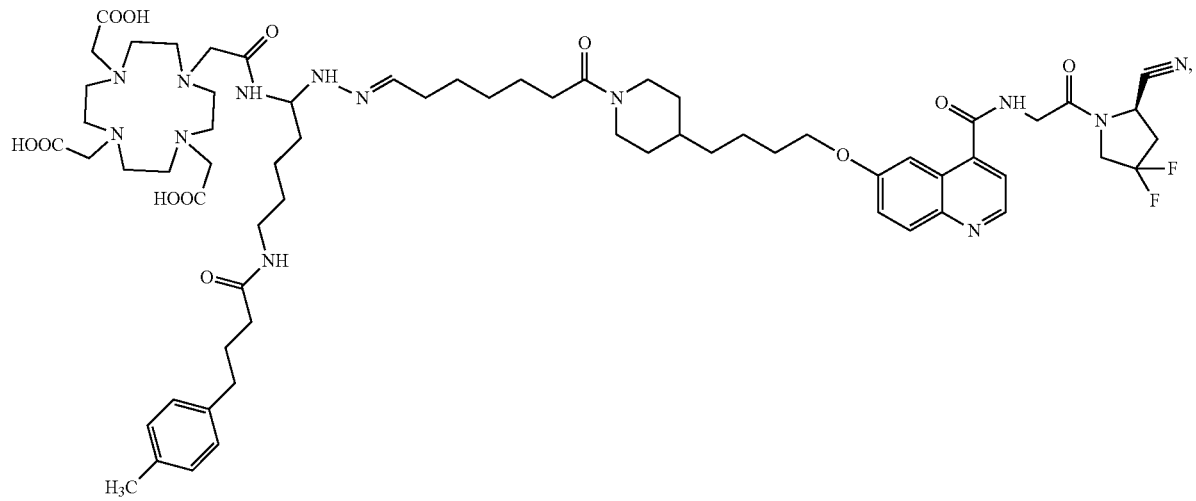

wherein
R1 is selected from R1-V-1, wherein the optical configuration of the optically active carbon is S configuration;
Code: FAPI-INER-1396-S;
Molecular weight: 1286.5;
Molecular formula: $C_{65}H_{93}F_2N_{13}O_{12}$;

Structure 230:

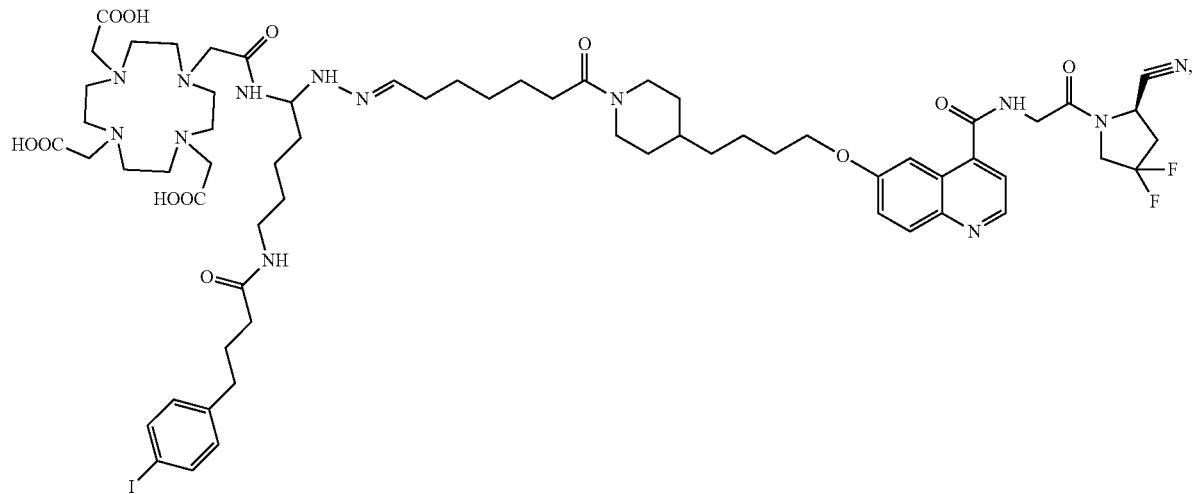

wherein
R1 is selected from R1-V-2, wherein the optical configuration of the optically active carbon is S configuration;

Code: FAPI-INER-1400-S;
Molecular weight: 1398.3;
Molecular formula: $C_{64}H_{90}F_2IN_{13}O_{12}$;

or R2 is selected from R2-V-4 of the set of R2-V and then is an integer of 2, R1 is any structure selected from the set of R1-V, and the D structure is

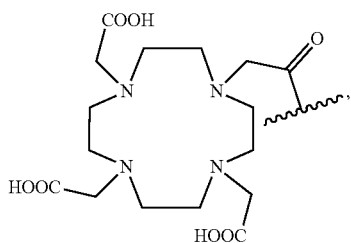 [SMILES: *C(=O)CN1CCN(CC(=O)O)CCN(CC(=O)O)CCN(CC(=O)O)CC1]

and thus the compound has a structure represented by formulas below:

Structure 231:

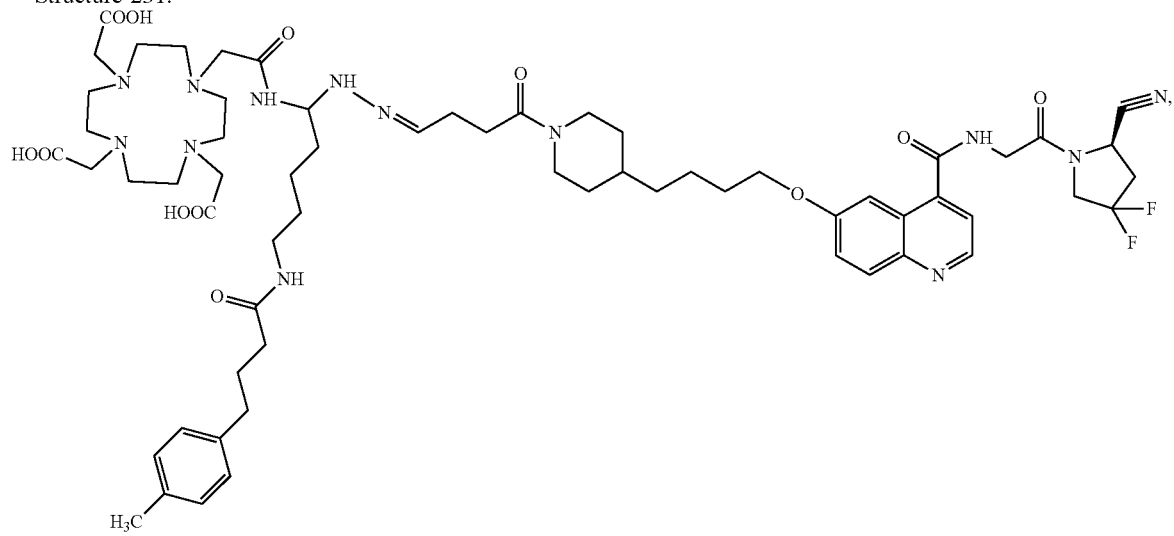

wherein
R1 is selected from R1-V-1, wherein the optical configuration of the optically active carbon is S configuration;
Code: FAPI-INER-1404-S;
Molecular weight: 1244.4;
Molecular formula: $C_{82}H_{87}F_2N_{13}O_{12}$;
Structure 232:

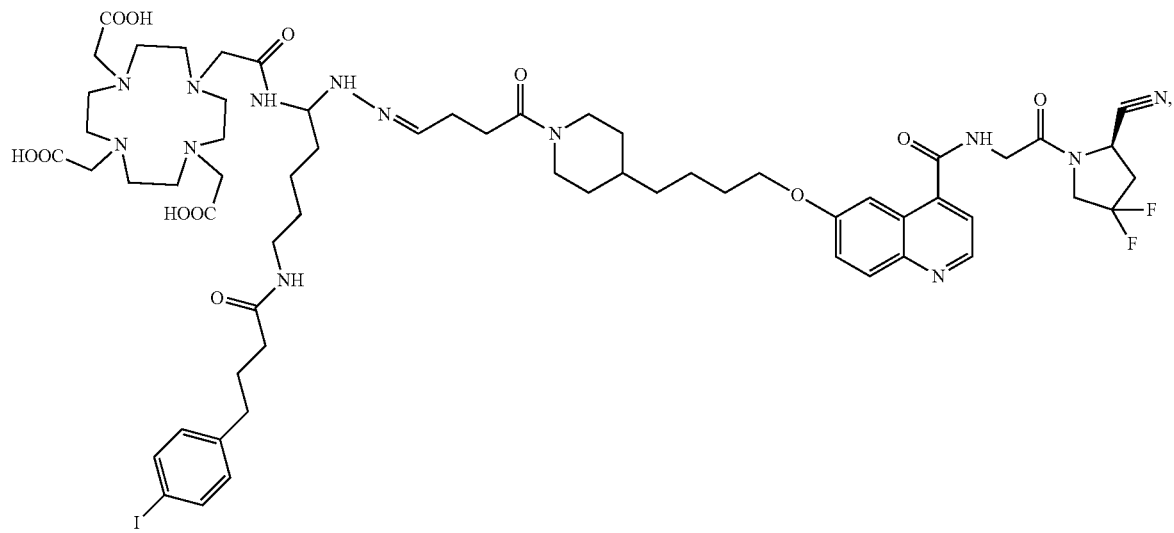

wherein
R1 is selected from R1-V-2, wherein the optical configuration of the optically active carbon is S configuration;
Code: FAPI-INER-1408-S;
Molecular weight: 1356.3;
Molecular formula: $C_{61}H_{84}F_2IN_{13}O_{12}$.

6. A method for preparing a compound represented by formula (I) D-R1-R2-A-R' or its salt thereof according to claim 1, wherein the method comprises a reaction scheme of synthesis shown below:

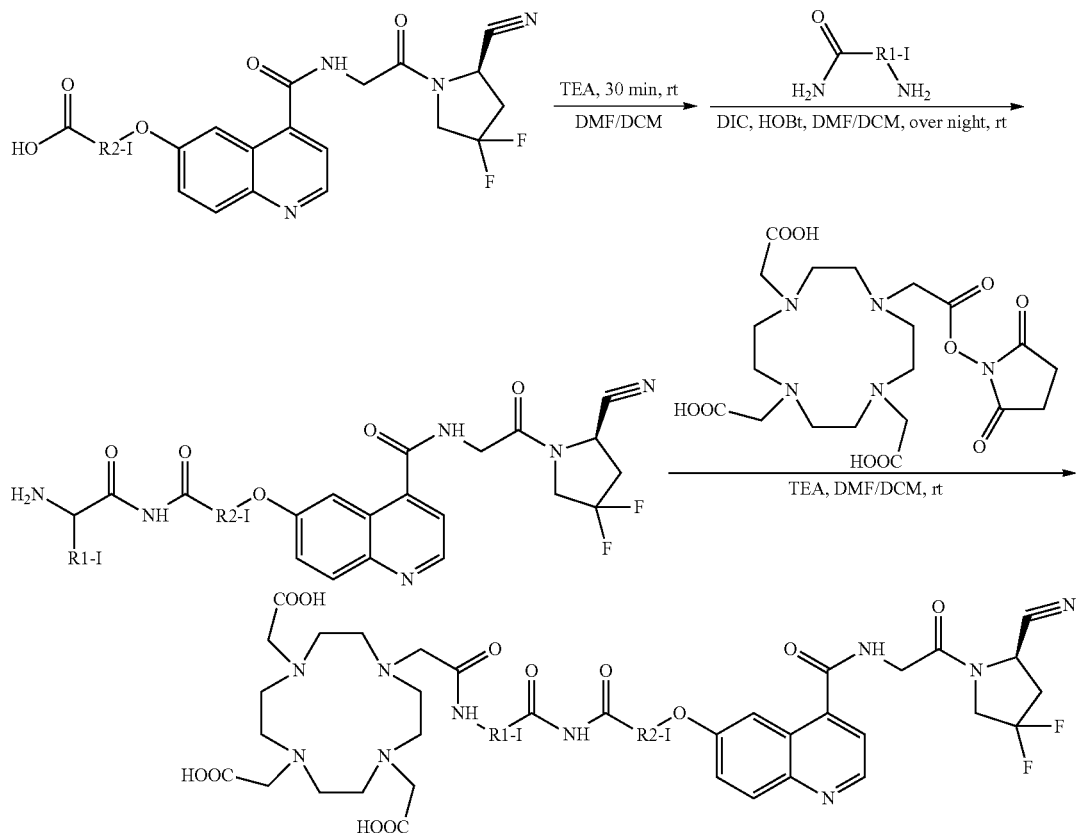

D-R1-R2-A-R' compound or its salt thereof, wherein R' is a cyano group, R2 is any structure selected from the set of R2-I, and the R1 structure is any structure selected from the set of R1-I, a carboxyl group (—COOH) of R2-I reacts with an amide-terminal amino group (—C(O)—NH$_2$) of R1-I to form an amide bond, and then another amino group (—NH$_2$) of R1-I reacts with 1,4,7,10-tetraazacyclododecane-1,4,7,10-tetraacetic acid 1-(2,5-dioxo-1-pyrrolidinyl) ester to produce the D-R1-R2-A-R' compound or salt thereof.

7. A method for preparing a compound represented by formula (I) D-R1-R2-A-R' or its salt thereof according to claim 1, wherein the method comprises a reaction scheme of synthesis shown below:

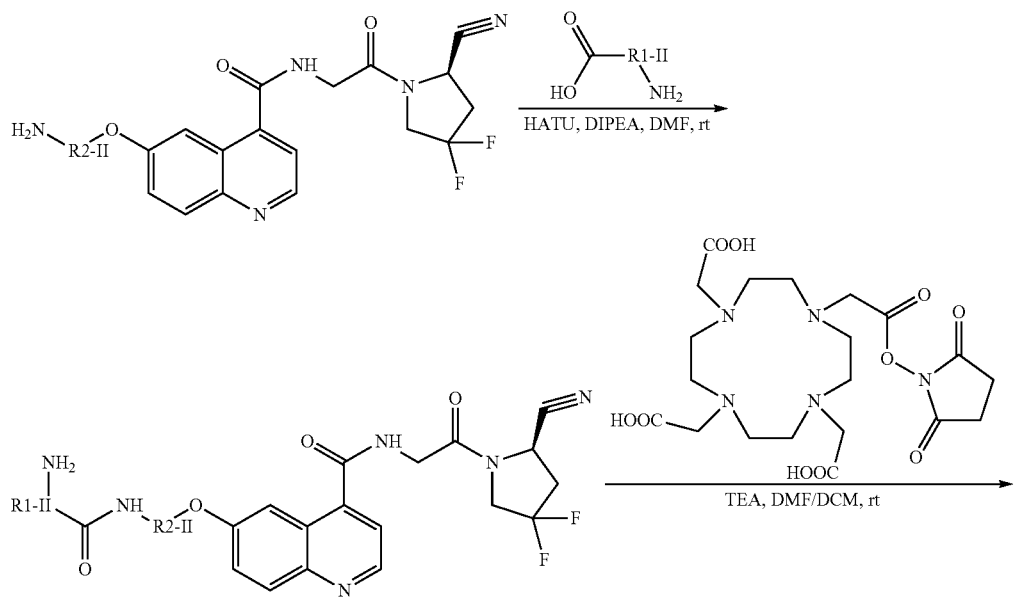

-continued

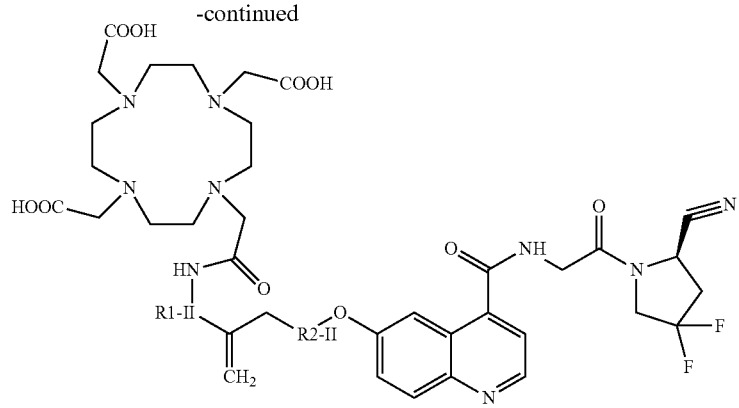

D-R1-R2-A-R' compound or its salt thereof, wherein R' is a cyano group, R2 is any structure selected from the set of R2-II, and R1 structure is any structure selected from the set of R1-II, an amino group of R2-I reacts with an a carboxyl group (—COOH) of R1-II to form an amide bond, and then an amino group of R1-II reacts with 1,4,7,10-tetraazacyclododecane-1,4,7,10-tetraacetic acid 1-(2,5-dioxo-1-pyrrolidinyl) ester to produce the D-R1-R2-A-R' compound or its salt thereof.

8. A method for preparing a compound represented by formula (I) D-R1-R2-A-R' or its salt thereof according to claim 1, wherein the method comprises a reaction scheme of synthesis shown below:

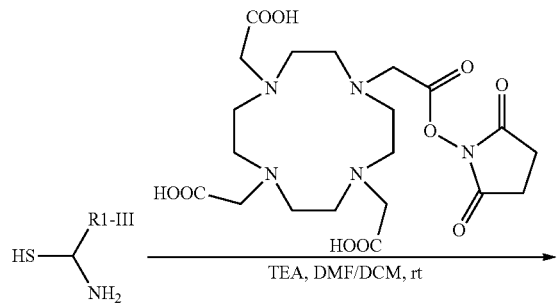

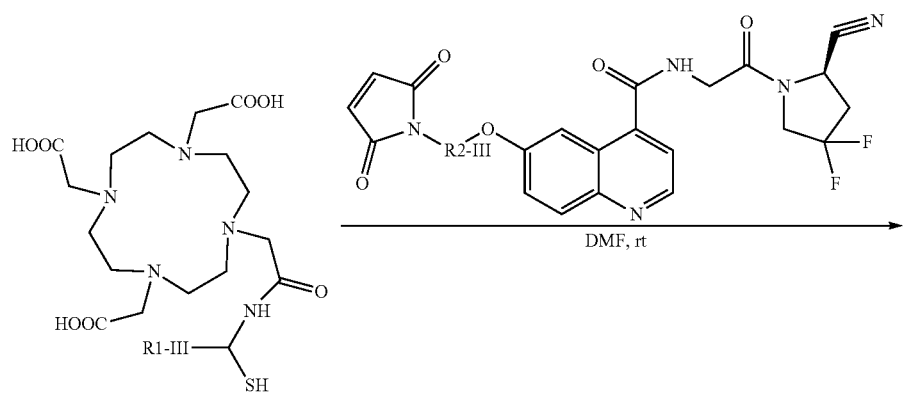

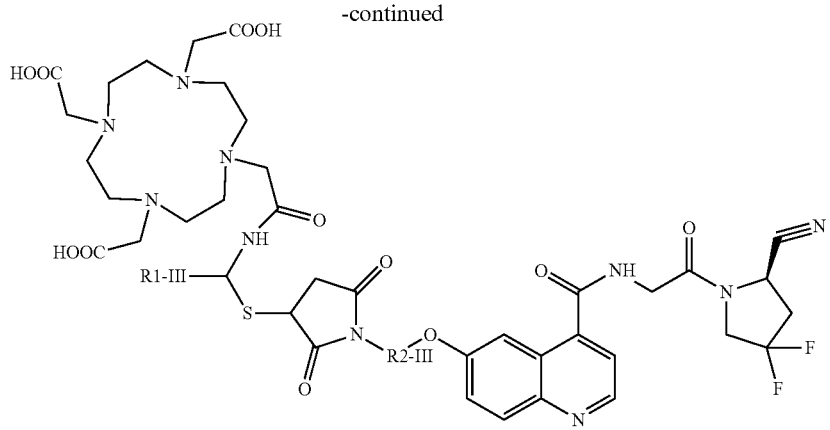

D-R1-R2-A-R' compound or its salt thereof, wherein R' is a cyano group, R2 is any structure selected from the set of R2-III, and R1 structure is any structure selected from the set of R1-III, an amino group of R1-III reacts with 1,4,7,10-Tetraazacyclododecane-1,4,7,10-tetraacetic acid, 1-(2,5-dioxo-1-pyrrolidinyl) ester to form an amide bond, and then a thiol group (—SH) of R1-III reacts with the maleimide group of R2-III to produce the D-R1-R2-A-R' compound or its salt thereof.

9. A method for preparing a compound represented by formula (I) D-R1-R2-A-R' or its salt thereof according to claim 1, wherein the method comprises a reaction scheme of synthesis shown below:

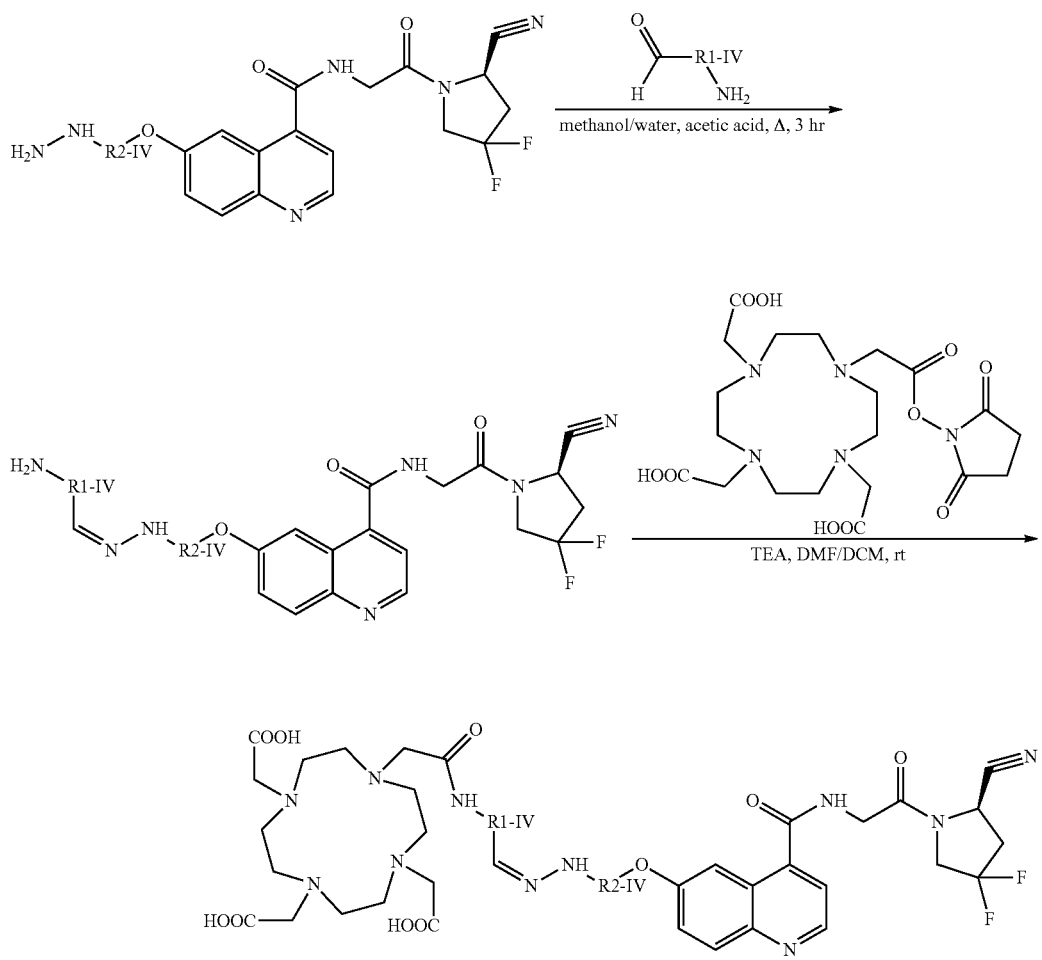

D-R1-R2-A-R' compound or its salt thereof, wherein R' is a cyano group, R2 is any structure selected from the set of R2-IV, and R1 structure is any structure selected from the set of R1-IV, a semicarbazide group (—C(O)NHNH$_2$) of R2-IV reacts with an aldehyde group (—C(O)H) of R1-IV to form a semicarbazone bond, and then an amino group (—NH$_2$) of R1-IV reacts with 1,4,7,10-tetraazacyclododecane-1,4,7,10-tetraacetic acid 1-(2,5-dioxo-1-pyrrolidinyl) ester to produce the D-R1-R2-A-R' compound or its salt thereof.

10. A method for preparing a compound represented by formula (I) D-R1-R2-A-R' or its salt thereof according to claim 1, wherein the method comprises a reaction scheme of synthesis shown below:

11. The compound represented by formula (I) D-R1-R2-A-R' or its salt thereof according to claim 1, wherein the D structure is

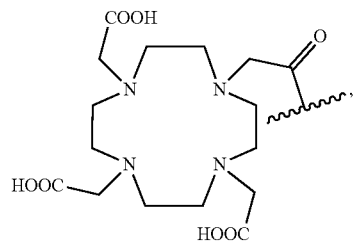 [SMILES: *C(=O)CN1CCN(CC(=O)O)CCN(CC(=O)O)CCN(CC(=O)O)CC1]

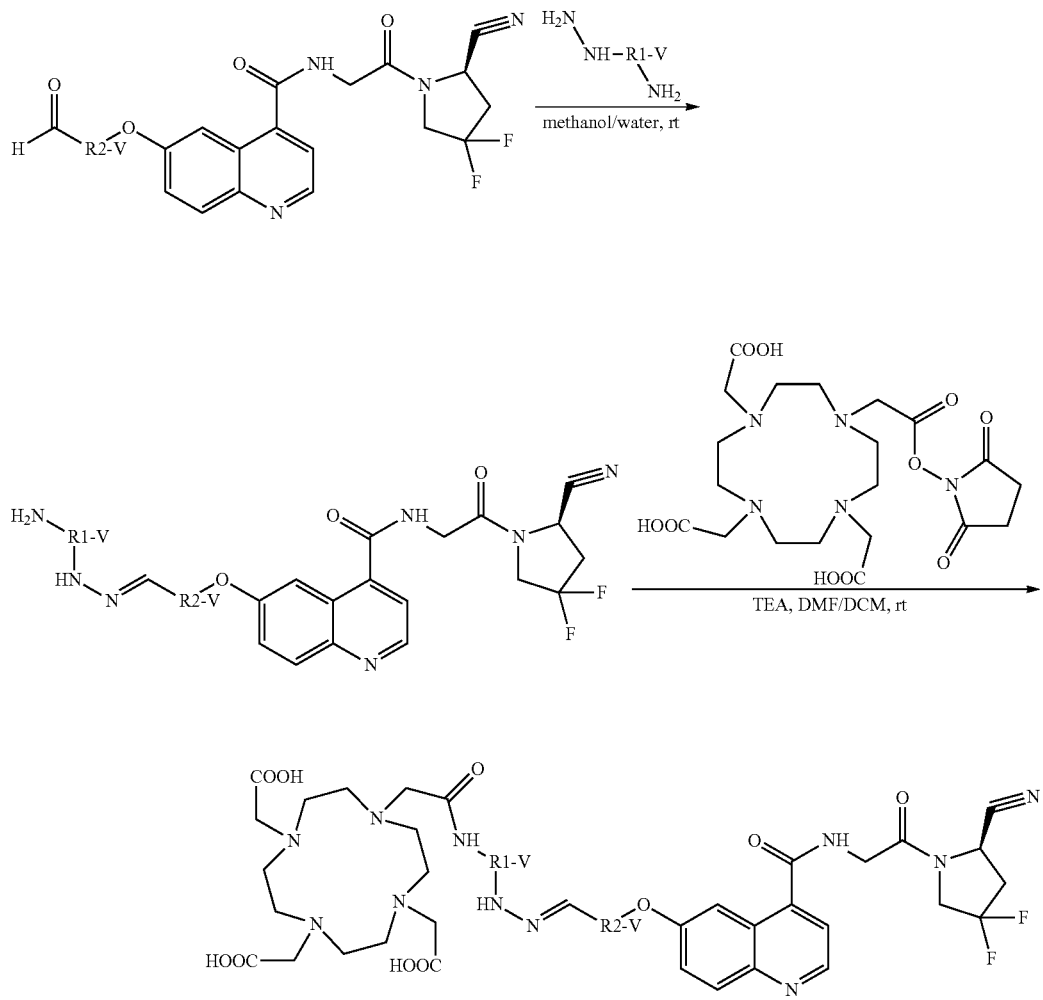

D-R1-R2-A-R' compound or its salt thereof, wherein R' is a cyano group, R2 is any structure selected from the set of R2-IV, and R1 structure is any structure selected from the set of R1-IV, a aldehyde group (—C(O)H) of R2-V reacts with a semicarbazide group (—C(O)NHNH$_2$) of R1-IV to form a semicarbazone bond, and then an amino group (—NH$_2$) of R1-V reacts with 1,4,7,10-tetraazacyclododecane-1,4,7,10-tetraacetic acid 1-(2,5-dioxo-1-pyrrolidinyl) ester to produce the D-R1-R2-A-R' compound or its salt thereof.

and is bonded to a positively charged trivalent metal ion M, wherein M is a positive trivalent metal ion selected from the group consisting of $^{111}$In, $^{68}$Ga, $^{67}$Ga, $^{90}$Y or $^{177}$Lu.

12. The compound represented by formula (I) D-R1-R2-A-R' or its salt thereof that bonded to M according to claim 1, which is used for imaging of fibroblast activation protein, wherein M is a positive trivalent metal ion selected from the group consisting of $^{111}$In, $^{68}$Ga, $^{67}$Ga, $^{90}$Y or $^{177}$Lu.

13. The compound represented by formula (I) D-R1-R2-A-R' or its salt thereof that bonded to M according to claim 1, which is used for preparing a medicine for radiotherapy, wherein M is a positive trivalent metal ion selected from the group consisting of $^{111}$In, $^{68}$Ga, $^{67}$Ga, $^{90}$Y or $^{177}$Lu.

* * * * *